United States Patent
Deshmukh et al.

(10) Patent No.: US 11,684,615 B2
(45) Date of Patent: *Jun. 27, 2023

(54) METHODS OF USING INDAZOLE-3-CARBOXAMIDES AND THEIR USE AS WNT/β-CATENIN SIGNALING PATHWAY INHIBITORS

(71) Applicant: BioSplice Therapeutics, Inc., San Diego, CA (US)

(72) Inventors: Vishal Deshmukh, San Diego, CA (US); Eric Anthony Murphy, San Marcos, CA (US); John Hood, San Diego, CA (US)

(73) Assignee: BioSplice Therapeutics, Inc., San Diego, CA (US)

( * ) Notice: Subject to any disclaimer, the term of this patent is extended or adjusted under 35 U.S.C. 154(b) by 112 days.

This patent is subject to a terminal disclaimer.

(21) Appl. No.: 16/915,316

(22) Filed: Jun. 29, 2020

(65) Prior Publication Data
US 2021/0121448 A1  Apr. 29, 2021

Related U.S. Application Data

(63) Continuation of application No. 15/790,544, filed on Oct. 23, 2017, now Pat. No. 10,806,726.

(60) Provisional application No. 62/411,478, filed on Oct. 21, 2016.

(51) Int. Cl.
| | |
|---|---|
| *A61K 31/444* | (2006.01) |
| *A61P 19/04* | (2006.01) |
| *A61P 17/00* | (2006.01) |
| *A61K 31/5377* | (2006.01) |
| *A61K 31/4439* | (2006.01) |
| *A61K 31/496* | (2006.01) |
| *A61K 31/501* | (2006.01) |
| *A61P 17/06* | (2006.01) |
| *A61K 31/4545* | (2006.01) |
| *A61K 31/5355* | (2006.01) |

(52) U.S. Cl.
CPC ........ *A61K 31/444* (2013.01); *A61K 31/4439* (2013.01); *A61K 31/4545* (2013.01); *A61K 31/496* (2013.01); *A61K 31/501* (2013.01); *A61K 31/5355* (2013.01); *A61K 31/5377* (2013.01); *A61P 17/00* (2018.01); *A61P 17/06* (2018.01); *A61P 19/04* (2018.01)

(58) Field of Classification Search
None
See application file for complete search history.

(56) References Cited

U.S. PATENT DOCUMENTS

| | | |
|---|---|---|
| 4,164,559 A | 8/1979 | Miyata et al. |
| 4,474,752 A | 10/1984 | Haslam et al. |
| 4,603,139 A | 7/1986 | King |
| 5,037,844 A | 8/1991 | Hamminga et al. |
| 5,922,733 A | 7/1999 | Forbes et al. |
| 6,120,484 A | 9/2000 | Silverstein |
| 6,358,978 B1 | 3/2002 | Ritzeler et al. |
| 6,377,849 B1 | 4/2002 | Lenarz et al. |
| 6,440,102 B1 | 8/2002 | Arenberg et al. |
| 6,555,539 B2 | 4/2003 | Reich et al. |
| 6,648,873 B2 | 11/2003 | Arenberg et al. |
| 6,831,175 B2 | 12/2004 | Li et al. |
| 6,884,890 B2 | 4/2005 | Kania et al. |
| 6,897,208 B2 | 5/2005 | Edwards et al. |
| 6,911,211 B2 | 6/2005 | Eini et al. |
| 6,919,461 B2 | 7/2005 | Reich et al. |
| 7,008,953 B2 | 3/2006 | Kephart et al. |
| 7,064,215 B2 | 6/2006 | Renhowe et al. |
| 7,232,912 B2 | 6/2007 | Reich et al. |
| 7,285,565 B2 | 10/2007 | Zhu et al. |
| 7,390,815 B2 | 6/2008 | Davies et al. |
| 7,429,609 B2 | 9/2008 | Ohi et al. |
| 7,452,993 B2 | 11/2008 | Arnold et al. |
| 7,468,376 B2 | 12/2008 | Rosales et al. |
| 7,482,342 B2 | 1/2009 | D'Orchymont et al. |
| 7,488,737 B2 | 2/2009 | Xie et al. |
| 7,491,710 B2 | 2/2009 | Cherrier et al. |
| 7,541,367 B2 | 6/2009 | Chiu et al. |
| 7,626,021 B2 | 12/2009 | Arnold et al. |

(Continued)

FOREIGN PATENT DOCUMENTS

| | | |
|---|---|---|
| CN | 1394205 | 1/2003 |
| CN | 1671710 | 9/2005 |

(Continued)

OTHER PUBLICATIONS

Byrn et al., "Pharmaceutical solids: a strategic approach to regulatory considerations," Pharmaceutical research, Jul. 1995, 12(7):945-954.

Deshmukh et al., A Small Molecule, SM04690, Has Inhibitory Effects on the Wnt Pathway and Inflammation in Vitro, with Potential Implications for the Treatment of Osteoarthritis [abstract]. Arthritis Rheumatol. 2016; 68 (suppl 10). https://acrabstracts.org/abstract/a-small-molecule-sm04690-has-inhibitory-effects-on-the-wnt-pathway-and-inflammation-in-vitro-with-potential-implications-for-the-treatment-of-osteoarthritis/. Accessed Dec. 28, 2020.

(Continued)

*Primary Examiner* — Zinna Northington Davis
(74) *Attorney, Agent, or Firm* — Fish & Richardson P.C.

(57) ABSTRACT

This disclosure features the use of one or more indazole-3-carboxamide compounds or salts or analogs thereof, in the treatment of one or more diseases or conditions independently selected from the group consisting of a tendinopathy, dermatitis, psoriasis, morphea, ichthyosis, Raynaud's syndrome, and Darier's disease; and/or for promoting wound healing. The methods include administering to a subject (e.g., a subject in need thereof) a therapeutically effective amount of one or more indazole-3-carboxamide compounds or salts or analogs thereof as described anywhere herein.

31 Claims, 12 Drawing Sheets

(56) References Cited

U.S. PATENT DOCUMENTS

| | | |
|---|---|---|
| 7,642,278 B2 | 1/2010 | Jansen et al. |
| 7,666,867 B2 | 2/2010 | Makriyannis et al. |
| 7,812,043 B2 | 10/2010 | Lan et al. |
| 7,829,558 B2 | 11/2010 | Arnold et al. |
| 7,842,711 B2 | 11/2010 | D'Orchymont et al. |
| 7,902,217 B2 | 3/2011 | Xie et al. |
| 7,943,616 B2 | 5/2011 | Cox et al. |
| 8,008,481 B2 | 8/2011 | Ericsson et al. |
| 8,088,772 B2 | 1/2012 | Garcia et al. |
| 8,129,519 B2 | 3/2012 | Cholody et al. |
| 8,158,647 B2 | 4/2012 | Blaney et al. |
| 8,252,812 B2 | 8/2012 | Hood et al. |
| 8,288,425 B2 | 10/2012 | Edwards et al. |
| 8,304,408 B2 | 11/2012 | Wrasidlo et al. |
| 8,450,340 B2 | 5/2013 | Hood et al. |
| 8,604,052 B2 | 12/2013 | Hood et al. |
| 8,618,128 B1 | 12/2013 | Hood et al. |
| 8,637,508 B2 | 1/2014 | Badiger et al. |
| 8,664,241 B2 | 3/2014 | Hood et al. |
| 8,673,936 B2 | 3/2014 | Hood et al. |
| 8,697,887 B2 | 4/2014 | Hood et al. |
| 8,703,794 B2 | 4/2014 | Hood et al. |
| 8,815,897 B2 | 8/2014 | Hood et al. |
| 8,822,478 B2 | 9/2014 | Hood et al. |
| 8,846,714 B2 | 9/2014 | Hood et al. |
| 8,883,822 B2 | 11/2014 | Hood et al. |
| 8,901,150 B2 | 12/2014 | Hood et al. |
| 8,987,298 B2 | 3/2015 | Hood et al. |
| 9,012,472 B2 | 4/2015 | Hood et al. |
| 9,056,874 B2 | 6/2015 | Adams et al. |
| 9,067,939 B2 | 6/2015 | Hood et al. |
| 9,090,613 B2 | 7/2015 | Hood et al. |
| 9,174,967 B2 | 11/2015 | Körber et al. |
| 9,199,991 B2 | 12/2015 | Hood et al. |
| 9,221,793 B2 | 12/2015 | Hood et al. |
| 9,233,104 B2 | 1/2016 | Hood et al. |
| 9,381,192 B2 | 7/2016 | Hood et al. |
| 9,538,272 B2 | 1/2017 | Auclair et al. |
| 9,540,398 B2 | 1/2017 | Kc et al. |
| 9,586,977 B2 | 3/2017 | Hood et al. |
| 9,745,271 B2 | 8/2017 | Hood et al. |
| 9,763,927 B2 | 9/2017 | Hood et al. |
| 9,763,951 B2 | 9/2017 | Kc et al. |
| 9,802,916 B2 | 10/2017 | Hood et al. |
| 9,815,854 B2 | 11/2017 | Kc et al. |
| 9,828,372 B2 | 11/2017 | Kc et al. |
| 9,844,536 B2 | 12/2017 | Kc et al. |
| 9,855,272 B2 | 1/2018 | Hood et al. |
| 9,889,140 B2 | 2/2018 | Kc et al. |
| 10,407,425 B2 | 9/2019 | Hood et al. |
| 10,806,726 B2 * | 10/2020 | Deshmukh ........... A61K 31/444 |
| 10,899,757 B2 | 1/2021 | Hood et al. |
| 10,947,228 B2 | 3/2021 | Hood et al. |
| 10,981,909 B2 | 4/2021 | Kc |
| 11,066,388 B2 | 7/2021 | Hood et al. |
| 11,446,288 B2 | 9/2022 | Dellamary |
| 2002/0103229 A1 | 8/2002 | Bhagwat et al. |
| 2002/0161022 A1 | 10/2002 | Reich et al. |
| 2003/0199516 A1 | 10/2003 | Moser et al. |
| 2004/0048868 A1 | 3/2004 | Edwards et al. |
| 2004/0077681 A1 | 4/2004 | Rawlings et al. |
| 2004/0176325 A1 | 9/2004 | Munson et al. |
| 2004/0236101 A1 | 11/2004 | Makriyannis et al. |
| 2005/0009894 A1 | 1/2005 | Babin et al. |
| 2005/0026960 A1 | 2/2005 | Kephart et al. |
| 2005/0070546 A1 | 3/2005 | Arrington et al. |
| 2005/0090529 A1 | 4/2005 | McAlpine et al. |
| 2005/0192262 A1 | 9/2005 | Hagstrom et al. |
| 2005/0208582 A1 | 9/2005 | Ohi et al. |
| 2005/0261339 A1 | 11/2005 | Ohi et al. |
| 2006/0004000 A1 | 1/2006 | D'Orchymont et al. |
| 2006/0014756 A1 | 1/2006 | Edwards et al. |
| 2006/0079564 A1 | 4/2006 | Jansen et al. |
| 2006/0094706 A1 | 5/2006 | Paruch et al. |
| 2006/0111322 A1 | 5/2006 | Reich et al. |
| 2006/0116519 A1 | 6/2006 | Ma et al. |
| 2006/0135589 A1 | 6/2006 | Berdino et al. |
| 2006/0142345 A1 | 6/2006 | Kephart et al. |
| 2006/0167056 A1 | 7/2006 | Rynberg et al. |
| 2006/0264897 A1 | 11/2006 | Lobl |
| 2007/0027140 A1 | 2/2007 | Lan et al. |
| 2007/0049598 A1 | 3/2007 | Billedeau et al. |
| 2007/0060616 A1 | 3/2007 | Bennett et al. |
| 2007/0078147 A1 | 4/2007 | Schumacher et al. |
| 2007/0185187 A1 | 8/2007 | D'Orchymont et al. |
| 2007/0219257 A1 | 9/2007 | Beachy et al. |
| 2007/0282101 A1 | 12/2007 | Ericsson et al. |
| 2008/0004270 A1 | 1/2008 | Gill et al. |
| 2008/0132495 A1 | 6/2008 | Berdini et al. |
| 2008/0255085 A1 | 10/2008 | Arvidsson et al. |
| 2008/0262205 A1 | 10/2008 | Haar et al. |
| 2008/0287452 A1 | 11/2008 | Bursavich et al. |
| 2009/0005356 A1 | 1/2009 | Blaney et al. |
| 2009/0005377 A1 | 1/2009 | Almansa Rosales et al. |
| 2009/0048249 A1 | 2/2009 | Chiu et al. |
| 2009/0054397 A1 | 2/2009 | Ohi et al. |
| 2009/0099062 A1 | 4/2009 | Lee et al. |
| 2009/0203690 A1 | 8/2009 | Akritopoulou-Zanze et al. |
| 2009/0247504 A1 | 10/2009 | Churcher et al. |
| 2009/0264446 A9 | 10/2009 | Rosales et al. |
| 2009/0286983 A1 | 11/2009 | Almansa Rosales et al. |
| 2010/0280063 A1 | 11/2010 | Price et al. |
| 2010/0298377 A1 | 11/2010 | Aletru et al. |
| 2011/0009353 A1 | 1/2011 | Chen-Kiang et al. |
| 2011/0021467 A1 | 1/2011 | D'Orchymont et al. |
| 2011/0034441 A1 | 2/2011 | Hood et al. |
| 2011/0082144 A1 | 4/2011 | Lan et al. |
| 2011/0178075 A1 | 7/2011 | Xie et al. |
| 2011/0190290 A1 | 8/2011 | Hood et al. |
| 2011/0034497 A1 | 10/2011 | Hood et al. |
| 2012/0053345 A1 | 3/2012 | Ericson et al. |
| 2012/0059047 A1 | 3/2012 | Prins et al. |
| 2012/0129837 A1 | 5/2012 | Cholody et al. |
| 2012/0277229 A1 | 11/2012 | Bearss et al. |
| 2013/0039906 A1 | 2/2013 | Do et al. |
| 2013/0079329 A1 | 3/2013 | Hood et al. |
| 2013/0267548 A1 | 10/2013 | Follmann et al. |
| 2014/0194441 A1 | 7/2014 | Kumar Kc et al. |
| 2014/0263319 A1 | 9/2014 | Fazi et al. |
| 2014/0364451 A1 | 12/2014 | John et al. |
| 2015/0087687 A1 | 3/2015 | Brown et al. |
| 2015/0111872 A1 | 4/2015 | Desroy et al. |
| 2015/0152105 A1 | 6/2015 | Hood et al. |
| 2016/0068529 A1 | 3/2016 | Kc et al. |
| 2016/0068547 A1 | 3/2016 | Kc et al. |
| 2016/0068548 A1 | 3/2016 | Kc et al. |
| 2016/0068549 A1 | 3/2016 | Kc et al. |
| 2016/0068550 A1 | 3/2016 | Kc et al. |
| 2016/0068551 A1 | 3/2016 | Kc et al. |
| 2016/0075701 A1 | 3/2016 | Kc |
| 2016/0090380 A1 | 3/2016 | Kc |
| 2016/0101092 A1 | 4/2016 | Hood et al. |
| 2016/0297812 A1 | 10/2016 | Hood et al. |
| 2017/0333409 A1 | 11/2017 | Hood et al. |
| 2017/0349584 A1 | 12/2017 | Kc et al. |
| 2018/0086754 A1 | 3/2018 | Kc et al. |
| 2018/0133199 A1 | 5/2018 | Dellamary |
| 2018/0141963 A1 | 5/2018 | Kc et al. |
| 2018/0148444 A1 | 5/2018 | Kc et al. |
| 2018/0153873 A1 | 6/2018 | Hood et al. |
| 2018/0162840 A1 | 6/2018 | Kc et al. |
| 2018/0177787 A1 | 6/2018 | Kc et al. |
| 2018/0185343 A1 | 7/2018 | Deshmukh et al. |
| 2018/0201624 A1 | 7/2018 | Kc et al. |
| 2018/0207141 A1 | 7/2018 | Kc et al. |
| 2018/0214427 A1 | 8/2018 | Kc et al. |
| 2018/0214428 A1 | 8/2018 | Kc et al. |
| 2018/0214429 A1 | 8/2018 | Kc et al. |
| 2018/0215753 A1 | 8/2018 | Kc et al. |
| 2018/0221341 A1 | 8/2018 | Kc et al. |
| 2018/0221350 A1 | 8/2018 | Kc et al. |
| 2018/0221351 A1 | 8/2018 | Kc et al. |
| 2018/0221352 A1 | 8/2018 | Kc et al. |
| 2018/0221353 A1 | 8/2018 | Kc et al. |

(56) References Cited

U.S. PATENT DOCUMENTS

| | | | |
|---|---|---|---|
| 2018/0221354 A1 | 8/2018 | Kc et al. |
| 2018/0222891 A1 | 8/2018 | Kc et al. |
| 2018/0222923 A1 | 8/2018 | Kc et al. |
| 2018/0228780 A1 | 8/2018 | Kc et al. |
| 2018/0228781 A1 | 8/2018 | Kc et al. |
| 2018/0228782 A1 | 8/2018 | Kc et al. |
| 2018/0228783 A1 | 8/2018 | Kc et al. |
| 2018/0228784 A1 | 8/2018 | Kc et al. |
| 2018/0228785 A1 | 8/2018 | Kc et al. |
| 2018/0230142 A1 | 8/2018 | Kc et al. |
| 2018/0237416 A1 | 8/2018 | Hood et al. |
| 2018/0250269 A1 | 9/2018 | Kc et al. |
| 2018/0256588 A1 | 9/2018 | Hood et al. |
| 2021/0002273 A1 | 1/2021 | Kc |
| 2021/0145807 A1 | 5/2021 | Dellamary |
| 2021/0292318 A1 | 9/2021 | Hood et al. |
| 2021/0292319 A1 | 9/2021 | Hood et al. |
| 2022/0024914 A1 | 1/2022 | Kc |

FOREIGN PATENT DOCUMENTS

| | | |
|---|---|---|
| CN | 1829713 | 9/2006 |
| CN | 101440092 | 5/2009 |
| CN | 103929963 | 7/2014 |
| EA | 200200768 | 2/2003 |
| KR | 20140074943 | 6/2014 |
| KR | 20140143796 | 12/2014 |
| KZ | 20122 | 1/2010 |
| RU | 2331640 | 8/2008 |
| RU | 2350271 | 3/2009 |
| RU | 2416610 | 4/2011 |
| WO | WO1987005297 | 9/1987 |
| WO | WO1996002537 | 2/1996 |
| WO | WO2001002369 | 1/2001 |
| WO | WO2001053268 | 7/2001 |
| WO | WO2003004488 | 1/2003 |
| WO | WO2003035005 | 5/2003 |
| WO | WO2003035065 | 5/2003 |
| WO | WO2003035644 | 5/2003 |
| WO | WO2003051366 | 6/2003 |
| WO | WO2003070236 | 8/2003 |
| WO | WO2003070706 | 8/2003 |
| WO | WO2003097610 | 11/2003 |
| WO | WO2003101968 | 12/2003 |
| WO | WO2003101993 | 12/2003 |
| WO | WO2004014864 | 2/2004 |
| WO | WO2004031158 | 4/2004 |
| WO | WO2004076450 | 9/2004 |
| WO | WO2005009997 | 2/2005 |
| WO | WO2005012301 | 2/2005 |
| WO | WO2005014554 | 2/2005 |
| WO | WO2005047266 | 5/2005 |
| WO | WO2005049019 | 6/2005 |
| WO | WO2005092890 | 10/2005 |
| WO | WO2005099703 | 10/2005 |
| WO | WO2005110410 | 11/2005 |
| WO | WO2006001894 | 1/2006 |
| WO | WO2006015124 | 2/2006 |
| WO | WO2006024945 | 3/2006 |
| WO | WO2006054143 | 5/2006 |
| WO | WO2006054151 | 5/2006 |
| WO | WO2006063302 | 6/2006 |
| WO | WO2006063841 | 6/2006 |
| WO | WO2006130673 | 12/2006 |
| WO | WO2007061360 | 5/2007 |
| WO | WO2007107346 | 9/2007 |
| WO | WO2007117465 | 10/2007 |
| WO | WO2007147874 | 12/2007 |
| WO | WO2008061109 | 5/2008 |
| WO | WO2008071397 | 6/2008 |
| WO | WO2008071398 | 6/2008 |
| WO | WO2008071451 | 6/2008 |
| WO | WO2008124848 | 10/2008 |
| WO | WO2008137408 | 11/2008 |
| WO | WO2008140792 | 11/2008 |
| WO | WO2008147713 | 12/2008 |
| WO | WO2008150914 | 12/2008 |
| WO | WO2008154241 | 12/2008 |
| WO | WO2008156757 | 12/2008 |
| WO | WO2009011850 | 1/2009 |
| WO | WO2009016072 | 2/2009 |
| WO | WO2009029609 | 3/2009 |
| WO | WO2009061345 | 5/2009 |
| WO | WO 2009/152868 | 12/2009 |
| WO | WO2010064875 | 6/2010 |
| WO | WO2010107765 | 9/2010 |
| WO | WO2010111060 | 9/2010 |
| WO | WO2010132725 | 11/2010 |
| WO | WO2011011722 | 1/2011 |
| WO | WO2011019648 | 2/2011 |
| WO | WO2011019651 | 2/2011 |
| WO | WO2011050245 | 4/2011 |
| WO | WO2011079076 | 6/2011 |
| WO | WO2011084486 | 7/2011 |
| WO | WO2011123890 | 10/2011 |
| WO | WO2012068589 | 5/2012 |
| WO | WO2012104388 | 8/2012 |
| WO | WO2012129562 | 9/2012 |
| WO | WO2013024011 | 2/2013 |
| WO | WO2013030138 | 3/2013 |
| WO | WO2013040215 | 3/2013 |
| WO | WO2013113722 | 8/2013 |
| WO | WO 2015143380 | 9/2015 |
| WO | WO2017079765 | 5/2017 |

OTHER PUBLICATIONS

Gudjonsson et al., "Mouse models of psoriasis. Journal of Investigative Dermatology," Jun. 1, 2007, 127(6):1292-1308.

Ator et al., "Overview of Drug Discovery and Development," Current Protocols in Pharmacology, 2006, Unit 9.9, 26 pages.

Deep et al., "New Combination Therapies with Cell Cycle Agents," Curr. Opin. Investig. Drugs, Jun. 2008, 9(6):591-604.

Hengstschlager et al., "Cyclin-dependent kinases at the G1-S transition of the mammalian cell cycle," Mutation Research, 1999, 436:1-9.

Lapenna et al., "Cell cycle kinases as therapeutic targets for cancer," Nature Review—Drug Discovery, Jul. 2009, 8:547-566.

Malumbres et al., "CDK inhibitors in cancer therapy: what is next?" TRENDS in Pharmacological Sciences, Dec. 2007, 29(1):16-21.

Nigg, "Mitotic Kinases as Regulators of Cell Division and its Checkpoints," Nature Reviews—Molecular Cell Biology, Jan. 2001, 2:21-32.

Pharmacology, 10th ed., Kharkevich (ed)., 2010, pp. 73-74 (English Translation).

Pharmacology, Zhulenko (ed)., 2008, pp. 34-35 (English Translation).

Santamaria et al., "Cdk1 is sufficient to drive the mammalian cell cycle," Nature, Aug. 16, 2007, 448:811-815.

Sharma et al., "Inhibitors of Cyclin Dependent Kinases: Useful Targets for Cancer Treatment," Current Cancer Drug Targets, 2008, 8(1):53-75.

"Application +A2:A31of Hamish Christopher Swan Wood, Norman Whittaker, Irene Stirling and Kyuji Ohta.," 582 F.2d 638 (Fed. Cir, 1978), 2 pages.

Adaimy et al., "Mutation in WNT10A Is Associated with an Autosomal Recessive Ectodermal Dysplasia: The Odonto-onychodermal Dysplasia," Am. J. Hum. Genet., (Oct. 2007), 81(4), 821-828.

Adult Brain Tumors Treatment, National Cancer Institute, pp. 1-21 (Jan. 24, 2013), 21 pages.

Ai et al., "Optimal Method to Stimulate Cytokine Producti on and Its Use in Immunotoxicity Assessment," Int J Environ Res Public Health, Sep. 2013, 10(9):3834-3842.

Anastas and Moon, "WNT signalling pathways as therapeutic targets in cancer," *Nat Rev Cancer*, 13(1):11-26, Jan. 2013.

Andres, "Molecular genetics and animal models in autistic disorder," *Brain Research Bulletin*, (2002), 57(1), 109-119.

(56) References Cited

OTHER PUBLICATIONS

Barker and Clevers, "Mining the Wnt pathway for cancer therapeutics," *Nat Rev Drug Discov.*, 5(12):997-1014, Dec. 2006.
Barroga et al., "Discovery of an Intra-Articular Injection Small Molecule Inhibitor of the Wnt Pathway (SM04690) As a Potential Disease Modifying Treatment for Knee Osteoarthritis," 2015 ACR/ARHP Annual Meeting, Abst. No. 2007, Sep. 29, 2015, retrieved on Sep. 27, 2018, URL <https://acrabstracts.org/abstract/discovery-of-an-intra-articular-injection-small-molecule-inhibitor-of-the-wnt-pathway-sm04690-as-a-potential-disease-modifying-treatment-for-knee-osteoarthritis/>, 3 pages.
Bass, "Why the difference between tendinitis and tendinosis matters," International Journal of Therapeutic Massage and Bodywork, vol. 5, No. 1, Mar. 2012.
Bendele, "Animal Models of Arthritis: Relevance to Human Disease" Toxicol Pathol 1999 27: 134-142.
Beyer et al., "Extended report: β-catenin is a central mediator of pro-fibrotic Wnt signaling in systemic sclerosis," *Ann Rheum Dis*, 71:761-767, online Feb. 2012.
Biason-Lauber et al., "A WNT4 Mutation Associated with Mullerian-Duct Regression and Virilization in a 46,XX Woman," *N. Engl. J. Med.*, (Aug. 2004), 351(8), 792-798.
Blaydon et al., "The gene encoding R-spondin 4 (RSPO4), a secreted protein implicated in Wnt signaling, is mutated in inherited anonychia," *Nat. Genet.*, (Nov. 2006), 38(11), 1245-1247.
Blom et al., "Involvement of the Wnt signaling pathway in experimental and human osteoarthritis: prominent role of Wnt-induced signaling protein 1," *Arthritis Rheum.*, 60(2):501-512, Feb. 2009.
Bone fractures—https://my.clevelandclinic.org/health/diseases/15241-bone-fractures-Jun. 2018, 5 pages.
Boyden et al., "High Bone Density Due to a Mutation in LDL-Receptor-Related Protein 5," *N. Engl. J. Med.*, (May 2002), 346(20):1513-1521.
Brack et al., "Increased Wnt signaling during aging alters muscle stem cell fate and increases fibrosis," *Science.*, 317(5839):807-810, Aug. 2007.
Brown et al., "Toxicity and toxicokinetics of the cyclin-dependent kinase inhibitor AG-024322 in cynomolgus monkeys following intravenous infusion," *Cancer Chemother Pharmacol.*, 62(6): 1091-1101, Epub May 2008.
Cancer definition in MedicineNet.com—2005, 1 page.
Cancer Drug Design and Discovery Neidle, Stephen, ed. (Elsevier/Academic Press, 2008), 5 pages.
Cecil Textbook of Medicine, edited by Bennet, J.C., and Plum F., 20th edition, Volunne 1, 1004-1010, 1996.
Chanput et.al., "Transcription profiles of LPS-stimulated THP-1 monocytes and macrophages: a tool to study inflammation modulating effects of food-derived compounds," Food Funct, Dec. 2010, 1(3):254-61.
Chilosi et al., "The pathogenesis of COPD and IPF: Distinct horns of the same devil?," *Respiratory Research*, 13:3, 2012.
Chockalingam et al., "Elevated aggrecanase activity in a rat model of joint injury is attenuated by an aggrecanase specific inhibitor," Osteoarthritis Cartilage, Mar. 2011, 19(3): 315-323.
Chou and Talalay, "Quantitative analysis of dose-effect relationships: the combined effects of multiple drugs or enzyme inhibitors," *Advances in Enzyme Regulation* (1984), 22, 27-55.
Chou, "Drug combination studies and their synergy quantification using the Chou-Talalay method," *Cancer Res.*, 70(2):440-446, Jan. 2010.
Chou, "Graphic rule for drug metabolism systems," *Current Drug Metabolism*, (May 2010) 11(4): 369-378.
Christodoulides et al., "WNT10B mutations in human obesity," *Diabetologia*. (2006) 49(4):678-684.
Clevers and Nusse, "Wnt/β-catenin signaling and disease," *Cell*, (Jun. 2012), 149(6): 1192-1205.
Clevers, "Wnt/beta-catenin signaling in development and disease," *Cell*, (Nov. 2006), 127(3), 469-480.
clinicaltrials.gov' [online]. ClinicalTrials.gov Identifier: NCT02095548, "Phase 1, Dose Escalation Study Evaluating the Safety, Tolerability, Pharmacokinetics and Pharmacodynamics of SM04690 in Moderate to Severe Knee Osteoarthritis (OA)," Mar. 26, 2014, [retreived on Aug. 1, 2018], Retreived from the Internet: URL<https://clinicaltrials.gov/ct2/show/NCT02095548?term=NCT02095548&rank=1>, 7 pages.
clinicaltrials.gov' [online]. ClinicalTrials.gov Identifier: NCT02536833, "A Study Evaluating the Safety, Tolerability, and Efficacy of SM04690 Injected in the Target Knee Joint of Moderately to Severely Symptomatic Osteoarthritis Subjects," Sep. 1, 2015, [retrieved on Aug. 1, 2018], Retrieved from the Internet: URL<https://clinicaltrials.gov/ct2/show/NCT02536833?term=NCT02536833&rank=1>, X pages.
Corr, "Wnt-beta-catenin signaling in the pathogenesis of osteoarthritis," *Nat Clin Pract Rheumatol.*, 4(10):550-556, Oct. 2008.
D'Alessio et al., "Benzodipyrazoles: a new class of potent CDK2 inhibitors," *Bioorganic & Medicinal Chemistry Letters* (2005), 15(5), 1315-1319.
Damia "Contemporary pre-clinical development of anticancer agents—What are the optimal preclinical models?" European Journal of Cancer 2009, 45, 2768-2781 p. 2778.
Dann et al., "Insights into Wnt binding and signaling from the structures of two Frizzled cysteine-rich domains," Nature, (Jul. 2001), 412, pp. 86-90.
Datta et al., "Novel therapeutic approaches for pulmonary fibrosis," *Br J Pharmacol.*, 163(1):141-172, May 2011.
Davidson et al., "Emerging links between CDK cell cycle regulators and Wnt signaling," Trends Cell Biol., Aug. 2010, 20(8):453-460.
De Ferrari and Inestrosa, "Wnt signaling function in Alzheimer's disease," *Brain Research Reviews*, (2000), 33(1): 1-12.
De Ferrari and Moon, "The ups and downs of Wnt signaling in prevalent neurological disorders," Oncogene, (2006) 25(57): 7545-7553.
De Ferrari et al., "Common genetic variation within the Low-Density Lipoprotein Receptor-Related Protein 6 and late-onset Alzheimer's disease," *Proc. Natl. Acad. Sci.* USA, (May 2007), 104(22):9434-9439.
Dermer et al., "Another Anniversary for the War on Cancer," Bio/Technology, Mar. 1994, 12:320.
Dermer, "Another Anniversary for the War on Cancer," *Nature Biotechnology*, 12:320 (1994).
Deshmkukh et al, "Abstract: A Small Molecule Inhibitor of the Wnt Pathway (SM04755) as a Potential Topical Treatment for Tendinopathy," Abstract from the Orthobiologic Institue (TOBI) Annual Symposium, Las Vegas, Nevada, Jun. 7, 2018, 1 page.
Deshmkukh et al, "Abstract: Discovery of a Small Molecule Inhibitor of the Wnt Pathway (SM04755) as a Potential Topical Treatment for Tendinopathy," Abstract from Osteoarthritis Research Society International (OARSI), Las Vegas, Nevada, Apr. 27, 2017, 2 pages.
Deshmkukh et al, "Abstract: Discovery of a Small Molecule Inhibitor of the Wnt Pathway (SM04755) as a Potential Topical Treatment for Tendinopathy," Abstract from the World Congress on Osteoporosis Osteoarthritis and Musculoskeletal Disease, Florence, Italy, Mar. 23, 2017, 2 pages.
Deshmkukh et al, "Abstract: Experimental Tendinopathy Treatment with SM04755, a Topical Small Molecule Inhibitor of the Wnt Pathway," Abstract from Osteoarthritis Research Society International (OARSI), Liverpool, England, Apr. 26, 2018, 3 pages.
Deshmkukh et al, "Abstract: Experimental Tendinopathy Treatment with SM04755, a Topical Small Molecule Wnt Pathway Inhibitor," Abstract from the Orthobiologic Institue (TOBI) Annual Symposium, Las Vegas, Nevada, Jun. 7, 2018, 2 pages.
Deshmkukh et al, "Poster: A Small Molecule Inhibitor of the Wnt Pathway (SM04755) as a Potential Topical Treatment for Tendinopathy," Poster from the Orthobiologic Institue (TOBI) Annual Symposium, Las Vegas, Nevada, Jun. 7, 2018, 1 page.
Deshmkukh et al, "Poster: Discovery of a Small Molecule Inhibitor of the Wnt Pathway (SM04755) as a Potential Topical Treatment for Tendinopathy," Poster from the World Congress on Osteoporosis Osteoarthritis and Musculoskeletal Disease, Florence, Italy, Mar. 23, 2017, 1 page.
Deshmkukh et al, "Poster: Experimental Tendinopathy Treatment with SM04755, a Topical Small Molecule Wnt Pathway Inhibitor," Poster from the Orthobiologic Institue (TOBI) Annual Symposium, Las Vegas, Nevada, Jun. 7, 2018, 2 pages.

(56) References Cited

OTHER PUBLICATIONS

Deshmkukh et al, "Presentation: Experimental Tendinopathy Treatment with SM04755, a Topical Small Molecule Inhibitor of the Wnt Pathway," Presentation from Osteoarthritis Research Society International (OARSI), Liverpool, England, Apr. 26, 2018, 17 pages.
Deshmukh et al, "Abstract #EULAR-6427: Discovery of a Small Molecule Inhibitor of the Wnt Pathway (SM04755) as a Potential Topical Treatment for Tendinopathy," Abstract from Annual European Congress of Rheumatology (EULAR), Madrid, Spain, Jun. 14, 2017, 2 pages.
Deshmukh et al, "Abstract #THU0522: Experimental Tendinopathy Treatment with SM04755, a Topical Small Molecule Inhibitor of the Wnt Pathway," Abstract from Annual European Congress of Rheumatology (EULAR), Amsterdam, Netherlands, Jun. 13-16, 2018, 2 pages.
Deshmukh et al, "Abstract: Discovery of a Small Molecule Inhibitor of the Wnt Pathway (SM04755) as a Potential Topical Treatment for Tendinopathy," Abstract from Orthopaedic Research Society Annual Meeting, New Orleans, Louisiana, Mar. 19, 2017, 1 page.
Deshmukh et al, "Abstract: Discovery of a Small Molecule Inhibitor of the Wnt Pathway (SM04755) as a Potential Topical Treatment for Tendinopathy," Abstract from Regenerative Medicine and Biology From Development to Regeneration, St. Louis, Missouri, May 4, 2017, 2 pages.
Deshmukh et al, "Abstract: Experimental tendinopathy treatment with SM04755, a topical small molecule inhibitor of the Wnt pathway," Abstract from Orthopaedic Research Society Annual Meeting, New Orleans, Louisiana, Mar. 10, 2018, 2 pages.
Deshmukh et al, "Poster # 1459: Experimental tendinopathy treatment with SM04755, a topical small molecule inhibitor of the Wnt pathway," Poster from Orthopaedic Research Society Annual Meeting, New Orleans, Louisiana, Mar. 19, 2018, 1 page.
Deshmukh et al, "Poster #443: Discovery of a Small Molecule Inhibitor of the Wnt Pathway (SM04755) as a Potential Topical Treatment for Tendinopathy," Poster from Osteoarthritis Research Society International (OARSI), Las Vegas, Nevada, Apr. 27, 2017, 1 page.
Deshmukh et al, "Poster #SAT067: Discovery of a Small Molecule Inhibitor of the Wnt Pathway (SM04755) as a Potential Topical Treatment for Tendinopathy," Poster from Annual European Congress of Rheumatology (EULAR), Madrid, Spain, Jun. 14, 2017, 1 page.
Deshmukh et al, "Poster #THU0522: Experimental Tendinopathy Treatment with SM04755, a Topical Small Molecule Inhibitor of the Wnt Pathway," Poster from Annual European Congress of Rheumatology (EULAR), Amsterdam, Netherlands, Jun. 13-16, 2018, 1 page.
Deshmukh et al, "Poster: Discovery of a Small Molecule Inhibitor of the Wnt Pathway (SM04755) as a Potential Topical Treatment for Tendinopathy," Poster from Regenerative Medicine and Biology From Development to Regeneration, St. Louis, Missouri, May 4, 2017, 2 pages.
Deshmukh et al, "Presentation: Discovery of a Small Molecule Inhibitor of the Wnt Pathway (SM04755) as a Potential Topical Treatment for Tendinopathy," Presentation from Orthopaedic Research Society Annual Meeting, New Orleans, Louisiana, Mar. 19, 2017, 19 pages.
Deshmukh et al., "A small-molecule inhibitor of the Wnt pathway (SM04690) as a potential disease modifying agent for the treatment of osteoarthritis of the knee," Osteoarthritis and Cartilage, Jan. 2018, 26(1):48-27.
Deshmukh et al., "Abstract #1104: Discovery of a Small Molecule Inhibitor of the Wnt Pathway(SM04755) As a Potential Topical Treatment for Chronic Tendinopathy," Abstract from 2016 ACR/ARHP Annual Meeting, Nov. 14, 2016, 3 pages.
Deshmukh et al., "Experimental Tendinopathy Treatment with SM04755, a Topical, Small Molecule Inhibitor of the Wnt Pathway," Abstract of Oral Presentation at #1952 at the American College of Rheumatology (ACR) Conference 2018, Chicago, Illinois, Oct. 19-24, 2018, 2 pages.
Deshmukh et al., "Experimental Tendinopathy Treatment with SM04755, a Topical, Small Molecule Inhibitor of the Wnt Pathway," Slides Present at #1952 at the American College of Rheumatology (ACR) Conference 2018, Chicago, Illinois, Oct. 19-24, 2018, 22 pages.
Deshmukh et al., "Poster #1104: Discovery of a Small Molecule Inhibitor of the Wnt Pathway(SM04755) As a Potential Topical Treatment for Chronic Tendinopathy," Poster from 2016 ACR/ARHP Annual Meeting, Nov. 14, 2016, 3 pages.
Dessalew et al., "3D-QSAR CoMFA and CoMSIA study onbenzodipyrazoles as cyclin dependent kinase 2 inhibitors," *Medicinal Chemistry*, (2008), 4(4), 313-321.
Dong et al., "QSAR study of Akt/protein kinase B (PKB) inhibitors using support vector machine," *European Journal of Medicinal Chemistry*, (Oct. 2009), pp. 44(10): 4090-4097.
Doumpas et al., "TCF/LEF dependent and independent transcriptional regulation of Wnt/b-catenin target genes" The EMBO Journal Nov. 13, 2018 1-14.
Du Bois, "Strategies for treating idiopathic pulmonary fibrosis," *Nature Reviews Drug Discovery*, 9(2): 129-140 (Feb 2010).
Edamoto et al., "Alterations of RBI, p53 and Wnt pathways in hepatocellular carcinomas associated with hepatitis C, hepatitis B and alcoholic liver cirrhosis," *Int J Cancer.*, 106(3):334-341, Sep. 1, 2003.
Egloff et al., "Gastrin-releasing peptide receptor expression in non-cancerous bronchial epithelia is associated with lung cancer: a case-control study," *Respiratory Research*, 13:9, Feb. 2012.
Enzo et al., "The Wnt/β-catenin pathway in human fibrotic-like diseases and its eligibility as a therapeutic target," Molecular and Cellular Therapies, 2015, 3(1), 13 pages.
Espada et al., "Wnt signalling and cancer stem cells," *Clin. Transl. Oncol.*, (2009), 11(7), 411-27.
Ewan et al., "A useful approach to identify novel small-molecule inhibitors of Wnt-dependent transcription," *Cancer Res.* (2010), 70(14), 5963-5973.
Florez et al., "TCF7L2 Polymorphisms and Progression to Diabetes in the Diabetes Prevention Program," *N. Engl. J. Med.*, (Jul. 2006), 355(3):241-250.
Forestier et al., "Prevalence of generalized osteoarthritis in a population with knee osteoarthritis," Joint Bone Spine, May 2011, 78(3):275-278.
Freese et al., "Wnt signaling in development and disease," *Neurobiology of Disease*, (2010) 38(2): 148-153.
Freshney et al., Culture of Animal Cells, A Manual of Basic Technique, Alan R. Liss, Inc., 1983, New York, p. 1-6.
Fujii et al., "An antagonist of dishevelled protein-protein interaction suppresses beta-catenin-dependent tumor cell growth," *Cancer Res.*, 67(2):573-579, Jan. 2007.
Fukuzawa et al., "Beckwith-Wiedemann Syndrome-associated Hepatoblastoma: Wnt Signal Activation Occurs Later in Tumorigenesis in Patients with 11p15.5 Uniparental Disomy," *Pediatric and Developmental Pathology* (2003), 6(4): 299-306.
Giles et al., "Caught up in a Wnt storm: Wnt signaling in cancer," *Biochim Biophys Acta.*, Jun. 2003, 1653(1):1-24.
Gitter et al., "Characteristics of human synovial fibroblast activation by IL-1 beta and TNF alpha," Immunology, Feb. 1989, 66(2):496-200.
Golub et al., "Molecular Classification of Cancer: Class Discovery and Class Prediction by Gene Expression Monitoring," Science, Oct. 1999, 286(5439):531-537.
Gunther et al., "Prevalence of generalised osteoarthritis in patients with advanced hip and knee osteoarthritis: the Ulm Osteoarthritis Study," Ann. Rheum. Dis., Dec. 1998, 57(12):717-723.
Handeli and Simon, "A small-molecule inhibitor of Tcf/beta-catenin signaling down-regulates PPARgamma and PPARdelta activities," *Mol Cancer Ther.*, 7(3):521-529, Mar. 2008.
Hayami et al., "Characterization of articular cartilage and subchondral bone changes in the rat anterior cruciate ligament transection and meniscectomized models of osteoarthritis," Bone, Feb. 2006, 38(2):234-243.
Henderson Jr. et al., "Inhibition of Wnt/beta-catenin/CREB binding protein (CBP) signaling reverses pulmonary fibrosis," *Proc Natl Acad Sci U S A.*, 107(32):14309-14314, Epub Jul. 2010.

(56) References Cited

OTHER PUBLICATIONS

Hu et al., "Discovery of indazoles as inhibitors of Tpl2 kinase," *Bioorganic & Medicinal Chemistry Letters*, (Aug. 2011) 21(16): 4758-4761.
Huang et al., "Tankyrase inhibition stabilizes axin and antagonizes Wnt signaling," *Nature*, (Oct. 2009), 461(7264): 614-620.
Huang et al., "Synthesis of 3-(1H-benzimidazol-2-yl)-5-isoquinolin-4-ylpyrazolo[1,2-b]pyridine, a potent cyclin dependent kinase 1 (CDK1) inhibitor," *Bioorganic & Medicinal Chemistry Letters*, (2007) 17(5): 1243-1245.
Hübner et al., "Standardized quantification of pulmonary fibrosis in histological samples," *Biotechniques*, 44(4):507-511, 514-517, Apr. 2008.
Ikejima et al., "Interleukin-1 induces tumor necrosis factor (TNF) in human peripheral blood mononuclear cells in vitro and a circulating TNF-like activity in rabbits," J Infect Dis, Jul. 1990, 162(1):215-23.
Im et al., "Wnt inhibitors enhance chondrogenesis of human mesenchymal stem cells in a long-term pellet culture," *Biotechnol Lett.*, 33(5): 1061-1068, Epub Jan. 2011.
Inestrosa and Toledo, "The role of Wnt signaling in neuronal dysfunction in Alzheimer's Disease," *Mol Neurodegener*, 3:9, doi: 10.1186/1750-1326-3-9, 13 pages, Jul. 2008.
International Preliminary Report on Patentability for Application No. PCT/US2017/057536, dated Apr. 23, 2019, 8 pages.
International Preliminary Report on Patentability in International Application No. PCT/US2017/057536, dated Apr. 23, 2019, 10 pages.
International Search Report and Written Opinion for International Application No. PCT/US2017/057536, dated Feb. 8, 2018, 15 pages.
Invitation to Pay Additional Fees for Application No. PCT/US2017/057536, dated Dec. 14, 2017, 11 pages.
Janssens et al., "The Wnt-dependent signaling pathways as target in oncology drag discovery," *Invest New Drugs.*, 24(4):263-280, Jul. 2006.
Jenkins et al., "Germline mutations in WTX cause a sclerosing skeletal dysplasia but do not predispose to tumorigenesis," *Nat. Genet.* (Jan. 2009), 41(1), 95-100.
Jessen et al., "Peripheral white blood cell toxicity induced by broad spectrum cyclin-dependent kinase inhibitors," *Journal of Applied Toxicology* (Jan. 2007), 27(2), 133-142.
Johnson et al., "A stem cell-based approach to cartilage repair," *Science.*, 336(6082):717-721, Epub Apr, 5, 2012.
Johnson, et. al. "Relationships between drag activity in NCI preclinical in vitro and in vivo models and early clinical trials." British Journal of Cancer 2001, 84, 1424-1431.
Kanazawa et al., "Association of the Gene Encoding Wingless-Type Mammary Tumor Virus Integration-Site Family Member 5B (WNT5B) with Type 2 Diabetes," *Am. J. Hum. Genet.* (2004), 75(5), 832-843.
Karlberg et al., "Structural basis for the interaction between tankyrase-2 and a potent Wnt-signaling inhibitor," *J. Med. Chem.* (2010), 53(14), 5352-5.
Kibar et al., "Mutations in VANGL1 Associated with Neural-Tube Defects," *N. Engl. J. Med.*, (Apr. 2007), 356(14):1432-1437.
King et al., "BUILD-3: a randomized, controlled trial of bosentan in idiopathic pulmonary fibrosis," *Am J Respir Crit Care Med.*, 184(1):92-99, Epub Apr. 2011.
Kishimoto et al.: "Wnt/Beta-Catenin Signaling Suppresses Expressions of Ses, Mkx and Tnmd in Tendon-Derived Cells," Plos One, Jul. 27, 2017, 12(7), E0182051, pp. 1-17.
Kuwajima et al., "Necdin Promotes GABAergic Neuron Differentiation in Cooperation with Dlx Homeodomain Proteins," *Journal of Neuroscience* (May 2006), 26(20), 5383-5392.
Lacy et al., "Generation and characterization of ABT-981, a dual variable domain immunoglobulin (DVD-Ig(TM)) molecule that specifically and potently neutralizes both IL-1α and IL-1β," Mabs, May 2015, 7(3): 605-619.
Lala and Oracevic, "Role of nitric oxide in tumor progression: lessons from experimental tumors," Cancer and Metastasi Review, vol. 17, Mar. 1998, pp. 91-106.

Lammi et al., "Mutations in AXIN2 Cause Familial Tooth Agenesis and Predispose to Colorectal Cancer," *Am. J. Hum. Genet.* (2004), 74(5), 1043-1050.
Ledford "US cancer institute overhauls cell lines" Nature Feb. 25, 2016 vol. 530 p. 391.
Leyns et al., "Frzb-1 Is a Secreted Antagonist of Wnt Signaling Expressed in the Spemann Organizer," *Cell* (Mar. 1997), 88(6), 747-756.
Li et al., "Artesunate attenuates the growth of human colorectal carcinoma and inhibits hyperactive Wnt/beta-catenin pathway," *Int J Cancer.*, 121(6):1360-1365, Sep. 2007.
Lin et al., "Synthesis and evaluation of pyrazolo[3,4-b]pyridine CDK1 inhibitors as anti-tumor agents," *Bioorganic & Medicinal Chemistry Letters*, (Aug. 2007), 17(15): 4297-4302.
Liu, et.al., "Fibrotic lung fibroblasts show blunted inhibition by cAMP due to deficient cAMP response element-binding protein phosphorylation," *J Pharmacol Exp Ther.*, 315(2):678-687, Epub Aug. 3, 2005.
Lories et al., "To Wnt or not to Wnt: the bone and joint health dilemma," *Nat Rev Rheumatol.*, 9(6):328-339, Epub Mar. 2013.
Low et al., "Phenotypic fingerprinting of small molecule cell cycle kinase inhibitors for drug discovery," *Curr Chem Genomics.*, 3:13-21, Mar. 2009.
Lu et al., "Structure-activity relationship studies of small-molecule inhibitors of Wnt response," *Bioorganic & Medicinal Chemistry Letters*, (Jul. 2009), 19(14):3825-3827.
Lui: "Histopathological Changes in Tendinopathypotential Roles of BMPs?" Rheumatology, May 2013, 52:2116-2126.
Luo et al., "Fragile X Mental Retardation Protein Regulates Proliferation and Differentiation of Adult Neural Stem/Progenitor Cells," *PLoS Genetics*, (Apr. 2010), 6(4):e1000898, 15 pages.
Luu et al., "Wnt/beta-catenin signaling pathway as a novel cancer drug target," *Curr Cancer Drug Targets.*, 4(8):653-671, Dec. 2004.
Luyten et al., "Wnt signaling and osteoarthritis," *Bone*, 44(4):522-527, Epub Dec. 14, 2008.
MacDonald et al., "Wnt/beta-catenin signaling: components, mechanisms, and diseases," *Dev. Cell* (Jul. 2009), 17(1), 9-26.
Mandel et al., "SERKAL Syndrome: An Autosomal-Recessive Disorder Caused by a Loss-of-Function Mutation in WNT4," *Am. J. Hum. Genet.*, (Jan. 2008), 82(1), 39-47.
Mani, et al., "LRP6 Mutation in a Family with Early Coronary Disease and Metabolic Risk Factors," *Science*, (Mar. 2007), 315(5816), 1278-1282.
McBride, et al. "Design and structure-activity relationship of 3-benzimidazol-2-yl-1H-indazoles as inhibitors of receptor tyrosine kinases," *Bioorganic & Medicinal Chemistry Letters* (2006), 16(13), 3595-3599.
McMahon et al., "VEGF receptor signaling in tumor angiogenesis," The Oncologist, 2005, pp. 3-10.
Medlineplus, [online] "Cancer," [retrieved on Jul. 6, 2007], Retrieved from the internet, URL http://www.nlnn.nih.govinnedlineplus/cancer.html>.
Misra et al., "1H-Pyrazolo[3,4-b]pyridine inhibitors of cyclin-dependent kinases: highly potent 2,6-Difluorophenacyl analogues," *Bioorganic & Medicinal Chemistry Letters*, (2003), 13:2405-2408.
Monner et al., "Induction of lymphokine synthesis in peripheral blood mononuclear cells with phorbol ester and calcium ionophore allows precise measurement of individual variations in capacity to produce IL 2," Lymphokine Res. 1986;5 Suppl 1:S67-73.
Mora et al., "Emerging therapies for idiopathic pulmonary fibrosis, a progressive age-related disease," Nat Rev Drug Discov. Oct. 30, 2017; 16(11): 810.
Morrisey, "Wnt signaling and pulmonary fibrosis," *Am J Pathol.*, 162(5): 1393-1397, May 2003.
Muddassar et al., "Elucidation of binding mode and three dimensional quantitative structure-activity relationship studies of a novel series of protein kinase B/Akt inhibitors ," *Journal of Molecular Modeling*, (2009), 15(2): 183-192.
Ngkelo et al., "LPS induced inflammatory responses in human peripheral blood mononuclear cells is mediated through NOX4 and Gia dependent PI-3 kinase signaling," Journal of Inflammation, Dec. 2012, 9(1):1, 7 pages.

(56) References Cited

OTHER PUBLICATIONS

Niemann et al., "Homozygous WNT3 Mutation Causes Tetra-Amelia in a Large Consanguineous Family," *Am. J. Hum. Genet.* (2004), 74(3), 558-563.
Nishisho et al., "Mutations of chromosome 5q21 genes in FAP and colorectal cancer patients," *Science*, (Aug. 1991), 253(5020):665-669.
Nusse, "Wnt signaling in disease and in development," *Cell Res.*, 15(1):28-32, Jan. 2005.
Oates et al., "Increased DNA Methylation at the AXIN1 Gene in a Monozygotic Twin from a Pair Discordant for a Caudal Duplication Anomaly," *Am. J. Hum. Genet.* (2006 ), 79(1), 155-162.
Ocana, A. "Preclinical development of molecular targeted agents for cancer" Nat. Rev. Clin. Oncol. 2011, 8, 200-209.
Oduor et al., "Trypanosoma bmcei glycogen synthase kinase-3, a target for anti-trypanosomal drug development: a public-private partnership to identify novel leads," *PLoS Negl Trop Dis.*, 5(4):e1017, Apr. 2011.
Okerlund and Cheyette, "Synaptic Wnt signaling-a contributor to major psychiatric disorders?" *J Neurodev Disord.*, (2011) 3(2):162-174.
Osteoarthritis, https://www.mayoclinic.org/diseases-conditions/osteoarthritis/diagnosis-treatrnent/drc-20351930- Sep. 2018, 8 pages.
Park et. al., "Optimized THP-1 differentiation is required for the detection of responses to weak stimuli," Inflamm Res, Jan. 2007, 56(1):45-50.
Parsons et al., "Benzo[d]imidazole Transient Receptor Potential Vanilloid 1 Antagonists for the Treatment of Pain: Discovery of trans-2-(2-{2-[2-(4-Trifluoromethyl-phenyl)-vinyl]-1H-benzimidazol-5-yl}-phenyl)-propan-2-ol (Mavatrep)," J Med Chem, May 2015, 58(9): 3859-3874.
Patani and Lavoie, "Bioisosterism: A Rational Approach in Drag Design," Chem. Rev, Jul. 25, 1996, vol. 96, p. 3147-3176.
Piersanti et al., "Synthesis of benzo[1,2-d;3,4-d']diimidazole and 1 H-pyrazolo[4,3-b]pyridine as putative A2A receptor antagonists," Organic and Biomolecular Chemistry, Aug. 2007, 5(16):2567-2571.
Pinedo & Slamon, "Translational Research: the role of VEGF in tumor angiogenesis," The Oncologist, 2005, pp. 1-2.
Polakis, "Wnt signaling and cancer," *Genes Dev.*, 14: 1837-1851, 2000.
Pritzker et al., "Osteoarthritis cartilage histopathology: grading and staging," Osteoarthr. Cartil., Jan. 2006, 14(1):13-29.
Pubchem. Substance Record for SID 164345938. Deposit Date: Nov. 4, 2013. [retrieved on Nov. 16, 2015], Retrieved from the Internet. <URL: https://pubchem.ncbi.nlm.nih.gov/substance/164345938#section=Top>, 5 pages.
Qin et al. "Complexity of the genotype-phenotype correlation in familial exudative vitreoretinopathy with mutations in the LRP5 and/or FZD4 genes," *Hum. Mutat.* (2005), 26(2), 104-112.
Reya and Clevers, "Wnt signalling in stem cells and cancer," *Nature* 434: 843-850, Apr. 2005.
Richards et al., "Peripheral blood proteins predict mortality in idiopathic pulmonary fibrosis," *Am J Respir Crit Care Med.*, 185(1):67-76, Jan. 2012.
Rivera et al., "An X Chromosome Gene, WTX, Is Commonly Inactivated in Wilms Tumor," Science, (Feb. 2007), 315(5812):642-645, published online Jan. 4, 2007.
Robitaille et al., "Mutant frizzled-4 disrupts retinal angiogenesis in familial exudative vitreoretinopathy," *Nat. Genet.*, (Sep. 2002), 32(2):326-330.
Rother et al., "Efficacy and safety of epicutaneous ketoprofen in Transfersome (IDEA-033) versus oral celecoxib and placebo in osteoarthritis of the knee: multicentre randomised controlled trial," Annals of the Rheumatic Diseases, Sep. 2007, 66(9): 1178-1183.
Ryu et al., "Natural derivatives of curcumin attenuate the Wnt/beta-catenin pathway through down-regulation of the transcriptional coactivator p300," *Biochem Biophys Res Commun.*, 377(4):1304-1308, print Dec. 2008, Epub Nov. 2008.

Salinas, "Wnt signaling in the vertebrate central nervous system: from axon guidance to synaptic function," *Cold Spring Harb Perspect Biol.*, (2012) 4(2). pii: a008003, 15 pages.
Sato, "Upregulation of the Wnt/beta-catenin pathway induced by transforming growth factor-beta in hypertrophic scars and keloids," *Acta Derm Venereol.*, 86(4):300-307, 2006.
Seah et al., "Neuronal Death Resulting from Targeted Disruption of the Snf2 Protein ATRX Is Mediated by p53," *Journal of Neuroscience* (Nov. 2008), 28(47), 12570-12580.
Shih et al., "Pharmacophore modeling and virtual screening to identify potential RET kinase inhibitors," *Bioorg Med Chem Lett.*, 21(15):4490-4497, Epub Jun. 2011.
Shruster et al., "Wnt signaling enhances neurogenesis and improves neurological function after focal ischemic injury," *PLoS One*, (Jul. 2012), 7(7):e40843, 11 pages.
Silva et al., "Advances in Prodrug Design," *Mini-Revs. In Med. Chem.* (2005), 5: 893-914.
Solowiej et al., "Characterizing the Effects of the Juxtamembrane Domain on Vascular Endothelial Growth Factor Receptor-2 Enzymatic Activity, Autophosphorylation, and Inhibition by Axitinib," *Biochemistry*, (2009), 48(29), 7019-7031.
Sperber et al., "Cytokine secretion induced by superantigens in peripheral blood mononuclear cells, lamina propria lymphocytes, and intraepithelial lymphocytes," Clin Diagn Lab Immunol, Jul. 1995, 2(4):473-477.
Staines et al., "Cartilage development and degeneration: a Wnt situation," *Cell Biochem Funct.*, 30(8):633-642, Epub Jun. 2012.
Sutherland et al., "A robust high-content imaging approach for probing the mechanism of action and phenotypic outcomes of cell-cycle modulators," *Molecular Cancer Therapeutics*, (Feb. 2011), 10(2): 242-254.
Swaney et al., "A novel, orally active LPA(1) receptor antagonist inhibits lung fibrosis in the mouse bleomycin model," *Br J Pharmacol.*, 160(7):1699-1713, Aug. 2010.
Takahashi-Yanaga et al., "Celecoxib-induced degradation of T-cell factors-1 and -4 in human colon cancer cells," *Biochem Biophys Res Commun.*, 377(4):1185-1190, print Dec. 2008, Epub Nov. 2008.
Tamamura et al., "Developmental regulation of Wnt/beta-catenin signals is required for growth plate assembly, cartilage integrity, and endochondral ossification," *J Biol Chem.*, 280(19):19185-95. Epub Mar. 2005.
Thompson et al., "WNT/beta-catenin signaling in liver health and disease," *Hepatology.*, 45(5):4298-1305, May 2007.
Trujillo et al., "2-(6-Phenyl-1H-indazol-3-yl)-1H-benzo[d]imidazoles: design and synthesis of a potent and isoform selective PKC-zeta inhibitor," *Bioorg Med Chem Lett.*, 19(3):908-911, Epub Dec. 6, 2008.
Types of Brain Cancer at http://www.cancercenter.com/brain-cancer/types-of-brain-cancer.cfrn (Mar. 12, 2013), 3 pages.
Types of Breast Cancer, published inbreastcancer.org (Sep. 30, 2012), 1 page.
Ugur et al., "Homozygous WNT10b mutation and complex inheritance in Split-Hand/Foot Malformation," *Hum. Mol. Genet.* (2008), 17(17), 2644-2653.
Vulpetti et al., "Structure-Based Approaches to Improve Selectivity: CDK2-GSK3β Binding Site Analysis," *Journal of Chemical Information and Modeling* (2005), 45(5), 1282-1290.
Wagner et al., "The therapeutic potential of the Wnt signaling pathway in bone disorders," *Curr Mol Pharmacol.*, 4(1):14-25, Jan. 2011.
Walters and Kleeberger, "Mouse models of bleomycin-induced pulmonary fibrosis," *Current Protocols in Pharmacology*, (2008) Chapter 5: Unit 5.46, 1-17.
Wang, et al., "Mutations in X-linked PORCN, a putative regulator of Wnt signaling, cause focal dermal hypoplasia," *Nat. Genet.* (Jul. 2007), 39(7), 836-838.
Wantanabe and Dai, "Winning WNT: race to Wnt signaling inhibitors," *Proc Natl Acad Sci U S A.* 108(15):5929-5930, Epub Mar. 2011.
Watts et.al., "RhoA signaling modulates cyclin D1 expression in human lung fibroblasts; implications for idiopathic pulmonary fibrosis," *Respir Res.*, 7:88, Jun. 15, 2006.

(56) References Cited

OTHER PUBLICATIONS

Weng et al., "Control of Dkk-1 ameliorates chondrocyte apoptosis, cartilage destraction, and subchondral bone deterioration in osteoarthritic knees," *Arthritis Rheum.*, 62(5):1393-1402, May 2010.
Witherington et al., "5-Aryl-pyrazolo[3,4-b]pyridazines: potent inhibitors of glycogen synthase kinase-3 (GSK-3)," *Bioorganic & Medicinal Chemistry Letters*, (May 2003), 13(9):1581-1584.
Woods, S. et al., "Mutations in WNT7A Cause a Range of Limb Malformations, Including Fuhrmann Syndrome and Al-Awadi/Raas-Rothschild/Schinzel Phocomelia Syndrome," *Am. J. Hum. Genet.* (Aug. 2006), 79(2), 402-408.
Yamada et al., "Emergence of TNIK inhibitors in cancer therapeutics," Cancer Sci, May 2017, 108(5):818-823.
Yan et al., "Discovery of small molecule inhibitors of the Wnt/b-catenin signaling pathway by targeting b-catenin/Tcf4 interactions" Experimental Biology and Medicine vol. 242 Jun. 2017 1185-1197.
Yardy and Brewster, "Wnt signalling and prostate cancer," *Prostate Cancer Prostatic Dis*, 8(2):119-126, 2005.
Yazici et al., "Abstract #: 312: Safety, Efficacy and Biomarker Outcomes of a Novel, Intra-Articular, Injectable, Wnt Inhibitor (SM04690) in the Treatment of Osteoarthritis of the Knee: Interim, Exploratory Analysis of Results from a Randomized, Double-Blind, Placebo-Controlled Phase 1 Study," Poster, Presented at 2015 ACR/American College of Rheumatology Annual Meeting, San Francisco CA, Nov. 6-11, 2015; Arthritis Rheumatol. 2015; 67 (suppl 10): 1 page.
Yazici et al., "Abstract #: 313: Magnetic Resonance Imaging Outcomes Using an Intra-Articular Injection (SM04690) in the Treatment of Osteoarthritis of the Knee: Interim, Exploratory Analysis of Results from a Randomized, Double-Blind, Placebo-Controlled, Phase 1 Study," Poster, Presented at 2015 ACR/American College of Rheumatology Annual Meeting, San Francisco CA, Nov. 6-11, 2015; Arthritis Rheumatol. 2015; 67 (suppl 10): 1 page.
Zhan et al., "Wnt signaling in cancer" Oncogene (2017) 36, 1461-1473.
Zhang et al., "Small-molecule synergist of the Wnt/beta-catenin signaling pathway," *Proc Natl Acad Sci U S A.*, 104(18):7444-7448, Epub Apr. 2007 and correction 104(30):12581, Jul. 2007.
Zheng "Small-molecule inhibitors of Wnt signaling pathway: towards novel anticancer therapeutics" Future Med. Chem. (2015) 7(18), 2485-2505.
Zhong et al., "Characterization of in vitro and in vivo metabolism of AG-024322, a novel cyclin-dependent kinase (CDK) inhibitor," *Health* (2009), 1(4): 249-262.
Zhu et al. "Design and synthesis of pyridine-pyrazolopyridine-based inhibitors of protein kinase B/Akt," Bioorganic & Medicinal Chemistiy, Mar. 2007, 15(6):2441-2452.
Lui et al., "Expression of Wnt pathway mediators in metaplasic tissue in animal model and clinical samples of tendinopathy," Rheumatology, Sep. 1, 2013, 52(9):1609-1618.
Shi et al., "Uniaxial mechanical tension promoted osteogenic differentiation of rat tendon-derived stem cells (rTDSCs) via the Wnt5a-RhoA pathway," Journal of cellular biochemistry, Oct. 2012, 113(10):3133-3142.
Blom et al., "Preparative LC-MS Purification: Improved Compound-Specific Method Optimization," Journal of Combinatorial Chemistry, 2004, 6(6), 874-883.
Machova Urdzikova et al., "Human multipotent mesenchymal stem cells improve healing after collagenase tendon injury in the rat," Biomedical engineering online, Dec. 2014, 13(1):1-5.
Menghin et al., "N α-imidazolylalkyl and pyridylalkyl derivatives of histaprodifen: synthesis and in vitro evaluation of highly potent histamine H1-receptor agonists," Journal of medicinal chemistry, Dec. 4, 2003, 46(25):5458-5470.
Pétursson, "Protecting groups in carbohydrate chemistry," Journal of chemical education, Nov. 1997, 74(11):1297-1303.

\* cited by examiner

A

B

METHODS OF USING INDAZOLE-3-CARBOXAMIDES AND THEIR USE AS WNT/β-CATENIN SIGNALING PATHWAY INHIBITORS

RELATED APPLICATIONS

This application is a continuation of U.S. application Ser. No. 15/790,544, filed on Oct. 23, 2017, which claims the benefit of U.S. Provisional Application No. 62/411,478, filed Oct. 21, 2016, which is incorporated herein by reference in its entirety.

BACKGROUND

Technical Field

This disclosure features the use of one or more indazole-3-carboxamide compounds or salts or analogs thereof, in the treatment of one or more diseases or conditions independently selected from the group consisting of a tendinopathy, dermatitis, psoriasis, morphea, ichthyosis, Raynaud's syndrome, and Darier's disease; and/or for promoting wound healing. The methods include administering to a subject (e.g., a subject in need thereof) a therapeutically effective amount of one or more indazole-3-carboxamide compounds or salts or analogs thereof as described anywhere herein.

Background

Pattern formation is the activity by which embryonic cells form ordered spatial arrangements of differentiated tissues. Speculation on the mechanisms underlying these patterning effects usually centers on the secretion of a signaling molecule that elicits an appropriate response from the tissues being patterned. More recent work aimed at the identification of such signaling molecules implicates secreted proteins encoded by individual members of a small number of gene families.

The Wnt growth factor family includes more than 10 genes identified in the mouse and at least 19 genes identified in the human. Members of the Wnt family of signaling molecules mediate many important short- and long-range patterning processes during invertebrate and vertebrate development. The Wnt signaling pathway is known for its important role in the inductive interactions that regulate growth and differentiation, and plays important roles in the homeostatic maintenance of post-embryonic tissue integrity. Wnt stabilizes cytoplasmic β-catenin, which stimulates the expression of genes including c-myc, c jun, fra-1, and cyclin D1. In addition, misregulation of Wnt signaling can cause developmental defects and is implicated in the genesis of several human cancers. More recently, the Wnt pathway has been implicated in the maintenance of stem or progenitor cells in a growing list of adult tissues that now includes skin, blood, gut, prostate, muscle and the nervous system.

Pathological activation of the Wnt pathway is also believed to be the initial event leading to colorectal cancer in over 85% of all sporadic cases in the Western world. Activation of the Wnt pathway has also been extensively reported for hepatocellular carcinoma, breast cancer, ovarian cancer, pancreatic cancer, melanomas, mesotheliomas, lymphomas and leukemias. In addition to cancer, inhibitors of the Wnt pathway can be used for stem cell research or for the treatment of any diseases characterized by aberrant Wnt activation such as diabetic retinopathy, pulmonary fibrosis, rheumatoid arthritis, scleroderma as well as mycotic and viral infections and bone and cartilage diseases. As such, it is a therapeutic target that is of great interest to the field.

In addition to cancer, there are many cases of genetic diseases due to mutations in Wnt signaling components. Examples of some of the many diseases are Alzheimer's disease [*Proc. Natl. Acad. Sci. USA* (2007), 104(22), 9434-9], osteoarthritis, polyposis *coli* [*Science* (1991), 253(5020), 665-669], bone density and vascular defects in the eye (osteoporosis-pseudoglioma syndrome, OPPG) [*N. Engl. J. Med.* (2002), 346(20), 1513-21], familial exudative vitreoretinopathy [*Hum. Mutat.* (2005), 26(2), 104-12], retinal angiogenesis [*Nat. Genet.* (2002), 32(2), 326-30], early coronary disease [*Science* (2007), 315(5816), 1278-82], tetra-amelia syndrome [*Am. J. Hum. Genet.* (2004), 74(3), 558-63], Müllerian-duct regression and virilization [*Engl. J. Med.* (2004), 351(8), 792-8], SERKAL syndrome [*Am. J. Hum. Genet.* (2008), 82(1), 39-47], diabetes mellitus type 2 [*Am. J. Hum. Genet.* (2004), 75(5), 832-43; *N Engl. J. Med.* (2006), 355(3), 241-50], Fuhrmann syndrome [*Am. J. Hum. Genet.* (2006), 79(2), 402-8], Al-Awadi/Raas-Rothschild/ Schinzel phocomelia syndrome [*Am. J. Hum. Genet.* (2006), 79(2), 402-8], odonto-onycho-dermal dysplasia [*Am. J. Hum. Genet.* (2007), 81(4), 821-8], obesity [Diabetologia (2006), 49(4), 678-84], split-hand/foot malformation [*Hum. Mol. Genet.* (2008), 17(17), 2644-53], caudal duplication syndrome [*Am. J. Hum. Genet.* (2006), 79(1), 155-62], tooth agenesis [*Am. J. Hum. Genet.* (2004), 74(5), 1043-50], Wilms tumor [*Science* (2007), 315(5812), 642-5], skeletal dysplasia [*Nat. Genet.* (2009), 41(1), 95-100], focal dermal hypoplasia [*Nat. Genet.* (2007), 39(7), 836-8], autosomal recessive anonychia [*Nat. Genet.* (2006), 38(11), 1245-7], neural tube defects [*N. Engl. J. Med.* (2007), 356(14), 1432-7], alpha-thalassemia (ATRX) syndrome [*The Journal of Neuroscience* (2008), 28(47), 12570-12580], fragile X syndrome [*PLoS Genetics* (2010), 6(4), e1000898], ICF syndrome, Angelman syndrome [*Brain Research Bulletin* (2002), 57(1), 109-119], Prader-Willi syndrome [*Journal of Neuroscience* (2006), 26(20), 5383-5392], Beckwith-Wiedemann Syndrome [*Pediatric and Developmental Pathology* (2003), 6(4), 299-306] and Rett syndrome.

Regulation of cell signaling by the Wnt signaling pathway is critical for the formation of neuronal circuits. Wnt pathway modulates in neural tissue, among other things, axon pathfinding, dendritic development, and synaptic assembly. Through different receptors, Wnt pathway activates and/or regulates diverse signaling pathways and other processes that lead to local changes on the cytoskeleton or global cellular changes involving nuclear function. Recently, a link between neuronal activity, essential for the formation and refinement of neuronal connections, and Wnt signaling has been uncovered. Indeed, neuronal activity regulates the release of various Wnt proteins and the localization of their receptors. Wnt pathway mediates synaptic structural changes induced by neuronal activity or experience. Evidence suggests that dysfunction in Wnt signaling contributes to neurological disorders [*Brain Research Reviews* (2000), 33(1), 1-12; *Oncogene* (2006) 25(57), 7545-7553; *Molecular Neurodegeneration* (2008), 3, 9; Neurobiology of Disease (2010), 38(2), 148-153; *Journal of Neurodevelopmental Disorders* (2011), 3(2), 162-174 and *Cold Spring Harbor Perspectives in Biology February* (2012), 4(2)].

Tendinopathies are chronic disorders or injuries of the tendons, that typically result from gradual wear and tear to the tendon, e.g., from overuse or aging, and leading to is tendon degeneration, weakness, tearing, and pain. Individuals who tend to make multiple, repeated motions in their jobs, sports, or regular daily activities tend to be more likely to develop tendinopathies. Tendinopathy usually causes pain, stiffness, and loss of strength in the affected area.

Skin disorders are common afflictions for many people. Some of the most common are dermatitis (also known as eczema) and psoriasis. Both dermatitis and psoriasis can cause serious physical and/or psychological suffering to the subject regardless of the location on the body that these conditions occur.

WO 2013/040215 describes indazole-3-carboxamides having Formula (I) and their use as Wnt/B-catenin signaling pathway inhibitors.

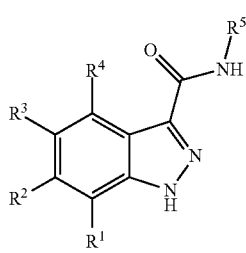

(I)

SUMMARY

This disclosure features the use of one or more indazole-3-carboxamide compounds or salts or analogs thereof, in the treatment of one or more diseases or conditions independently selected from the group consisting of a tendinopathy, dermatitis, psoriasis, morphea, ichthyosis, Raynaud's syndrome, and Darier's disease; and/or for promoting wound healing. The methods include administering to a subject (e.g., a subject in need thereof) a therapeutically effective amount of one or more indazole-3-carboxamide compounds or salts or analogs thereof as described anywhere herein.

One embodiment disclosed herein includes administering an indazole-3-carboxamide compound having the structure of Formula I:

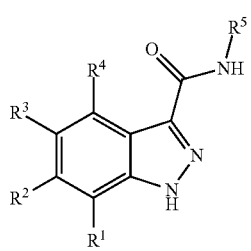

I as well as prodrugs and pharmaceutically acceptable salts thereof.

In some embodiments of Formula (I):

$R^1$, $R^2$ and $R^4$ are independently selected from the group consisting of H, $C_{1-9}$ alkyl, halide, $-N(R^{10})_2$, $-XR^{10}$, CN, $-OCF_3$ and $-CF_3$;

$R^3$ is selected from the group consisting of carbocyclyl$R^6$, heterocyclyl$R^6$, aryl$R^6$ and heteroaryl$R^6$;

$R^5$ is selected from the group consisting of $-(C_{1-9}$ alkyl$)_n$carbocyclyl$R^7$, $-(C_{1-9}$ alkyl$)_n$heterocyclyl$R^7$, $-(C_{1-9}$alkyl$)_n$aryl$R^7$ and $-(C_{1-9}$alkyl$)_n$heteroaryl$R^7$;

each $R^6$ is 1-5 substituents each selected from the group consisting of H, $C_{1-9}$alkyl, halide, amino, $-OCF_3$, $-CF_3$, $-CN$, $-XR^{10}$, $-(C_{1-9}$ alkyl$)_n$carbocyclyl$R^8$, $-(C_{1-9}$ alkyl$)_n$heterocyclyl$R^8$, $-(C_{1-9}$ alkyl$)_n$aryl$R^8$, $-(C_{1-9}$ alkyl$)_n$heteroaryl$R^8$, $-C(=O)R^{11}$, $-N(R^{10})C(=O)R^{11}$, $-(C_{1-9}$ alkyl$)_n$N(R^{10})_2$, $-(C_{1-9}$ alkyl$)_n$N(R^{10})SO_2R^{11}$ and $-SO_2R^{11}$;

each $R^7$ is 1-5 substituents each selected from the group consisting of H, $C_{1-9}$ alkyl, halide, amino, $-OCF_3$, $-CF_3$, $-CN$, $-X^{10}$, $-(C_{1-9}$ alkyl$)_n$carbocyclyl$R^9$, $-(C_{1-9}$ alkyl$)_n$heterocyclyl$R^9$, $-(C_{1-9}$ alkyl$)_n$aryl$R^9$, $-(C_{1-9}$ alkyl$)_n$heteroaryl$R^9$, $-C(=O)R^{11}$, $-N(R^{10})C(=O)R^{11}$, $-(C_{1-9}$ alkyl$)_n$N(R^{10})_2$, $-(C_{1-9}$ alkyl$)_n$ N(R^{10})SO_2R^{11}$ and $-SO_2R^{11}$;

each $R^8$ is 1-5 substituents each selected from the group consisting of H, $C_{1-3}$ alkyl, halide, amino, $OCF_3$, $-CF_3$— CN, $-XR^{12}$, $-C(=O)R^{13}$, $-N(R^{12})C(=O)R^{13}$, $-(C_{1-9}$ alkyl$)_n$N(R^{12})_2$, $-(C_{1-9}$ alkyl$)_n$N(R^{12})SO_2R^{13}$ and $-SO_2R^{13}$;

each $R^9$ is 1-5 substituents each selected from the group consisting of H, $C_{1-3}$ alkyl, halide, amino, $-OCF_3$, $-CF_3$ $-CN$, $-XR^{12}$, $-C(=O)R^{13}$, $-N(R^{12})C(=O)R^{13}$, $-(C_{1-9}$alkyl$)_n$N(R^{12})_2$, $-(C_{1-9}$ alkyl$)_n$N(R^{12})SO_2R^{13}$ and $-SO_2R^{13}$;

each $R^{10}$ is independently selected from the group consisting of H, $C_{1-9}$ alkyl, $-(C_{1-9}$ alkyl$)_n$N(R^{14})_2$, $-(C_{1-9}$ alkyl$)_n$carbocyclyl$R^8$, $-(C_{1-9}$ alkyl$)_n$heterocyclyl$R^8$, $-(C_{1-9}$ alkyl$)_n$aryl$R^8$ and $-(C_{1-9}$alkyl$)_n$heteroaryl$R^8$;

each $R^{11}$ is independently selected from the group consisting of $C_{1-9}$alkyl, $-N(R^{14})_2$, $-(C_{1-9}$ alkyl$)_n$carbocyclyl$R^8$, $-(C_{1-9}$alkyl$)_n$heterocyclyl$R^8$, $-(C_{1-9}$ alkyl$)_n$aryl$R^8$ and $-(C_{1-9}$ alkyl$)_n$heteroaryl$R^8$;

each $R^{12}$ is independently selected from the group consisting of H, $C_{1-9}$ alkyl, $-(C_{1-9}$ alkyl$)_n$N(R^{14})_2$, $-(C_{1-9}$ alkyl$)_n$carbocyclyl, $-(C_{1-9}$ alkyl$)_n$heterocyclyl, $-(C_{1-9}$ alkyl$)_n$aryl and $-(C_{1-9}$ alkyl$)_n$heteroaryl;

each $R^{13}$ is independently selected from the group consisting of $C_{1-9}$ alkyl, $-N(R^{14})_2$, $-(C_{1-9}$ alkyl$)_n$carbocyclyl, $-(C_{1-9}$ alkyl$)_n$heterocyclyl, $-(C_{1-9}$ alkyl$)_n$aryl and $-(C_{1-9}$alkyl$)_n$heteroaryl;

each $R^{14}$ is independently selected from the group consisting of H, $C_{1-3}$ alkyl, carbocyclyl and aryl;

each X is selected from the group consisting of a bond, $-O-$ and $-S-$; and each n is 0 or 1.

In another embodiment of Formula (I):

$R^1$, $R^2$ and $R^4$ are independently selected from the group consisting of H, $C_{1-9}$alkyl, halide, $-N(R^{10})_2$, CN, $-OCF_3$ and $-CF_3$;

$R^3$ is selected from the group consisting of carbocyclyl$R^6$, heterocyclyl$R^6$, aryl$R^6$ and heteroaryl$R^6$;

in some embodiments, it is provided that when $R^3$ is heteroaryl, the heteroaryl is not selected from the group consisting of isoquinoline, 1H-pyrrolo[2,3-c]pyridine and tetrazole;

$R^5$ is selected from the group consisting of $-(C_{1-9}$ alkyl$)_n$carbocyclyl$R^7$, $-(C_{1-9}$ alkyl$)_n$heterocyclyl$R^7$, $-(C_{1-9}$alkyl$)_n$aryl$R^7$ and $-(C_{1-9}$alkyl$)_n$heteroaryl$R^7$;

in some embodiments, it is provided that $R^5$ is not 4-pyridyl$R^7$ when $R^1$, $R^2$ and $R^4$ are H, $R^3$ is selected from the group consisting of 3-pyridyl$R^6$, 4-pyridyl$R^6$, 2-pyridyl$R^6$, phenyl$R^6$, thiazole$R^6$, imidazole$R^6$, pyrimidine$R^6$, oxazole$R^6$,

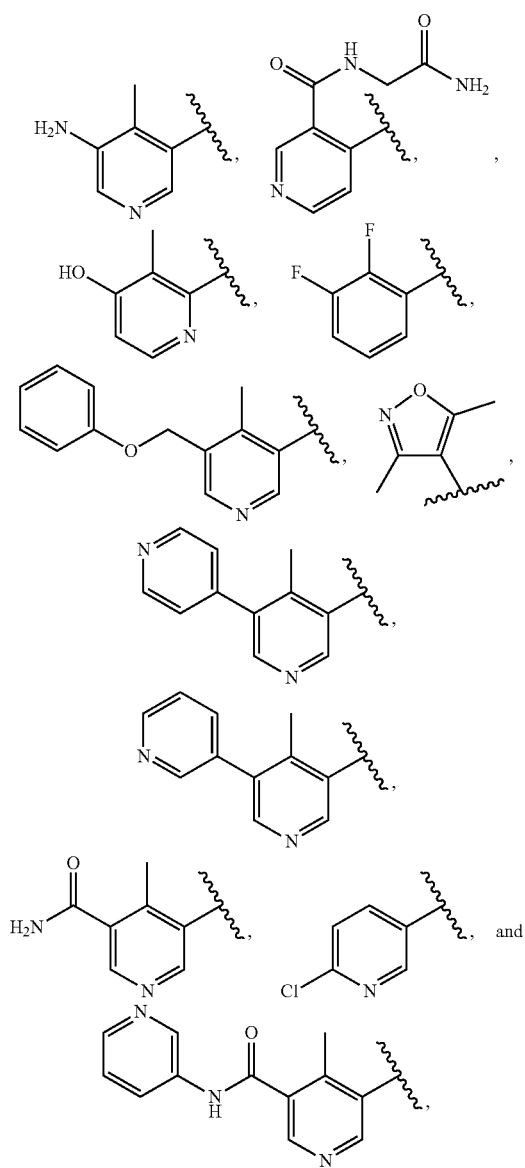

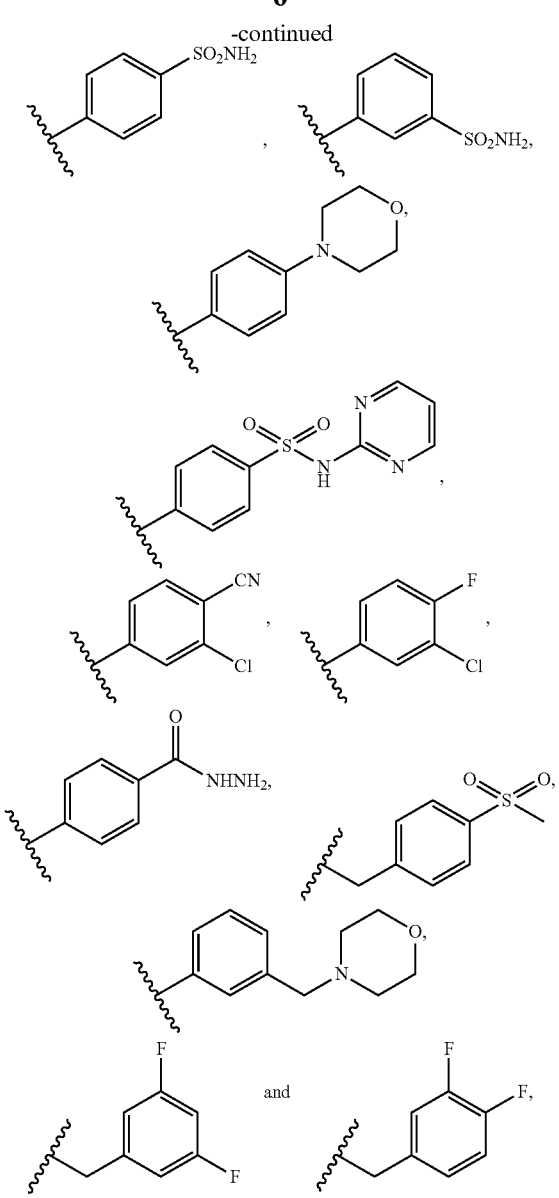

and $R^6$ and $R^7$ are both H.

in some embodiments, it is provided that $R^5$ is not —(CH$_2$)(3-pyridyl)$R^7$ when $R^1$, $R^2$ and $R^4$ are H, $R^3$ is selected from the group consisting of 3-pyridyl$R^6$, 4-pyridyl$R^6$ and thiazole$R^6$, and $R^6$ and $R^7$ are both H;

in some embodiments, it is provided that $R^5$ is not phenyl$R^7$ when $R^1$, $R^2$ and $R^4$ are H, $R^3$ is 4-pyridyl$R^6$ and $R^6$ and $R^7$ are both H;

in some embodiments, it is provided that $R^3$ is not 3-pyridyl$R^6$ when $R^1$, $R^2$ and $R^4$ are H, $R^5$ is selected from the group consisting of phenyl$R^7$,

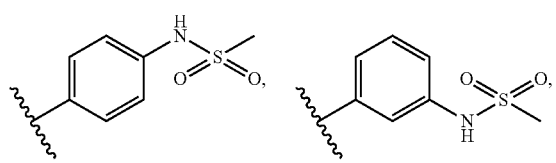

and $R^6$ and $R^7$ are both H;

in some embodiments, it is provided that $R^3$ is not oxazole$R^6$ when $R^1$, $R^2$ and $R^4$ are H, $R^5$ is selected from the group consisting of

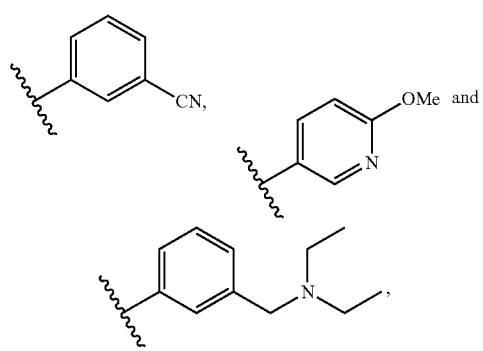

and $R^6$ is H;

in some embodiments, it is provided that $R^3$ is not thiazoleR$^6$ when $R^1$, $R^2$ and $R^4$ are H, $R^5$ is selected from the group consisting of

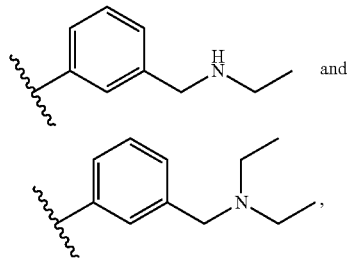

$R^6$ is H;

each $R^6$ is 1-5 substituents each selected from the group consisting of H, $C_{1-9}$ alkyl, halide, amino, —OCF$_3$, —CF$_3$, —CN, —XR$^{10}$, —($C_{1-9}$ alkyl)$_n$carbocyclylR$^8$, —($C_{1-9}$ alkyl)$_n$heterocyclylR$^8$, —($C_{1-9}$ alkyl)$_n$arylR$^8$, —($C_{1-9}$ alkyl)$_n$heteroarylR$^8$, —C(=O)R$^{11}$, —N(R$^{10}$)C(=O)R$^{11}$, —($C_{1-9}$)alkyl)$_n$N(R$^{10}$)$_2$, —($C_{1-9}$) alkyl)$_n$N(R$^{10}$)SO$_2$R$^{11}$ and —SO$_2$R$^{11}$;

each $R^7$ is 1-5 substituents each selected from the group consisting of H, $C_{1-9}$ alkyl, halide, amino, —OCF$_3$, —CF$_3$, —CN, —($C_{1-9}$ alkyl)$_n$carbocyclylR$^9$, —($C_{1-9}$ alkyl)$_n$heterocyclylR$^9$, —($C_{1-9}$ alkyl)$_n$arylR$^9$, —($C_{1-9}$ alkyl)$_n$heteroarylR$^9$, —C(=O)R$^{11}$, —N(R$^{10}$)C(=O)R$^{11}$, —($C_{1-9}$)alkyl)$_n$N(R$^{10}$)$_2$, —($C_{1-9}$) alkyl)$_n$N(R$^{10}$)SO$_2$R$^{11}$ and —SO$_2$R$^{11}$;

each $R^8$ is 1-5 substituents each selected from the group consisting of H, $C_{1-3}$ alkyl, halide, amino, OCF$_3$, —CF$_3$—CN, —C(=O)R$^{13}$, —N(R$^{12}$)C(=O)R$^{13}$, alkyl)$_n$N(R$^{12}$)$_2$, —($C_{1-9}$ alkyl)$_n$N(R$^{12}$)SO$_2$R$^{13}$ and —SO$_2$R$^{13}$;

each $R^9$ is 1-5 substituents each selected from the group consisting of H, $C_{1-3}$ alkyl, halide, amino, —OCF$_3$, —CF$_3$—CN, —C(=O)R$^{13}$, —N(R$^{12}$)C(=O)R$^{13}$, —($C_{1-9}$ alkyl)$_n$N(R$^{12}$)$_2$, —($C_{1-9}$ alkyl)$_n$ N(R$^{12}$)SO$_2$R$^{13}$ and —SO$_2$R$^{13}$;

each $R^{10}$ is independently selected from the group consisting of H, $C_{1-9}$ alkyl, —($C_{1-9}$ alkyl)$_n$N(R$^{14}$)$_2$, —($C_{1-9}$ alkyl)$_n$carbocyclylR$^8$, —($C_{1-9}$ alkyl)$_n$heterocyclylR$^8$, —($C_{1-9}$ alkyl)$_n$arylR$^8$ and —($C_1$-9 alkyl)$_n$heteroarylR$^8$;

each $R^{11}$ is independently selected from the group consisting of $C_{1-9}$ alkyl, —N(R$^{14}$)$_2$, —($C_{1-9}$ alkyl)$_n$carbocyclylR$^8$, —($C_{1-9}$ alkyl)$_n$heterocyclylR$^8$, —($C_{1-9}$ alkyl)$_n$arylR$^8$ and —($C_{1-9}$ alkyl)$_n$heteroarylR$^8$;

each $R^{12}$ is independently selected from the group consisting of H, $C_{1-9}$ alkyl, —($C_{1-9}$ alkyl)$_n$N(R$^{14}$)$_2$, —($C_{1-9}$ alkyl)$_n$carbocyclyl, —($C_{1-9}$ alkyl)$_n$heterocyclyl, —($C_{1-9}$ alkyl)$_n$aryl and —($C_{1-9}$ alkyl)$_n$heteroaryl;

each $R^{13}$ is independently selected from the group consisting of $C_{1-9}$ alkyl, —N(R$^{14}$)$_2$, —($C_{1-9}$ alkyl)$_n$carbocyclyl, —($C_{1-9}$ alkyl)$_n$heterocyclyl, —($C_{1-9}$ alkyl)$_n$aryl and —($C_{1-9}$ alkyl)$_n$heteroaryl;

each $R^{14}$ is independently selected from the group consisting of H, $C_{1-3}$ alkyl, carbocyclyl and aryl;

each X is selected from the group consisting of a bond, —O— and —S—; and each n is 0 or 1.

Some embodiments include administering stereoisomers and pharmaceutically acceptable salts of a compound of general Formula (I).

Some embodiments include administering pro-drugs of a compound of general Formula (I).

Some embodiments include administering pharmaceutical compositions comprising a compound of general Formula (I) or in a pharmaceutically acceptable carrier, diluent, or excipient.

It is to be understood that both the foregoing general description and the following detailed description are exemplary and explanatory only and are not restrictive of the invention, as claimed.

DETAILED DESCRIPTION

Figure 1:
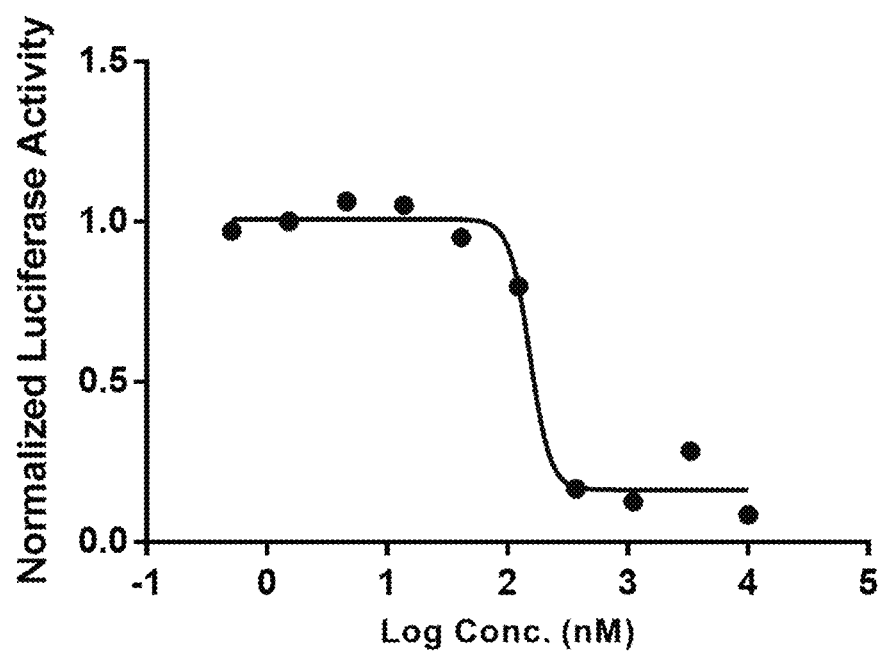
FIG. 1 depicts a plot showing that exposure of a human colorectal cancer cell line (SW480) to compound 175 inhibited Wnt/β-catenin activity in these cells in a dose-dependent manner (EC50=152.9 nM). The human colorectal cancer cell line (SW480) with constitutive activation of the Wnt pathway and engineered to express a Wnt responsive promoter linked to luciferase were treated with compound 175 at test concentrations of 10, 3, 1, 0.3, 0.1, 0.03, 0.01, 0.003, 0.001 and 0.0003 μM.
Figure 2A:
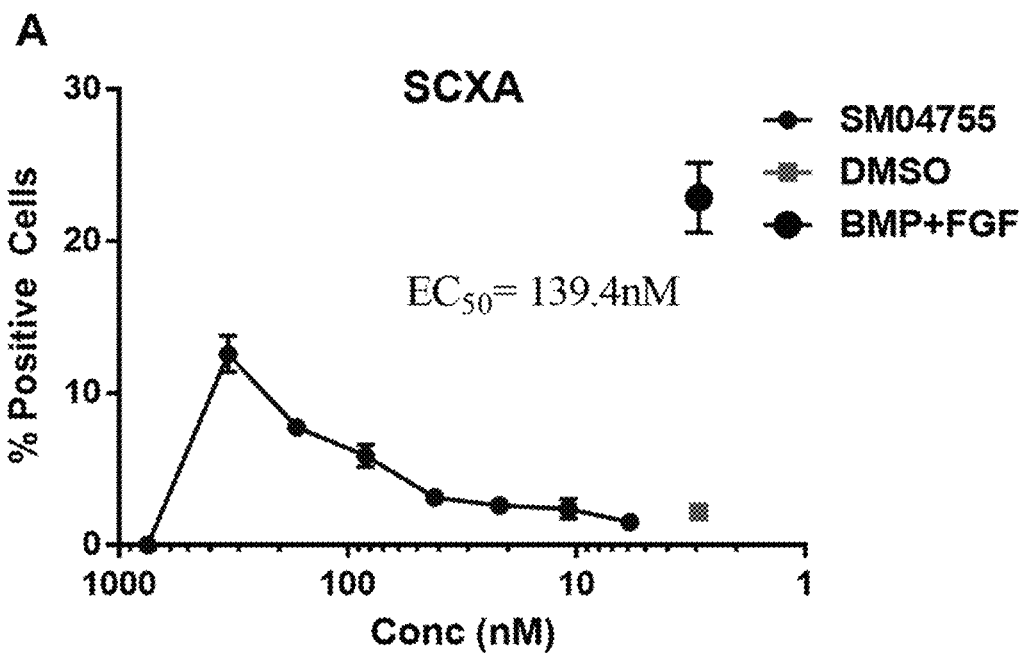
FIGS. 2A-C depict plots of the percentage of human mesenchymal stem cells (hMSC) expressing SCXA, tenacinC, and tenomodulin, respectively vs. concentration of compound 175. Human Mesenchymal Stem Cells were treated with compound 175 at test concentrations of 750, 333.3, 166.6, 83.3, 41.7, 21.7, 10.8 and 5.8 nM. Exposure of the cells to compound 175 for 7 days induced the expression of markers of tenocyte differentiation-SCXA, TenacinC and Tenomodulin in a dose-dependent manner (EC50=139-189 nM).
Figure 2B:
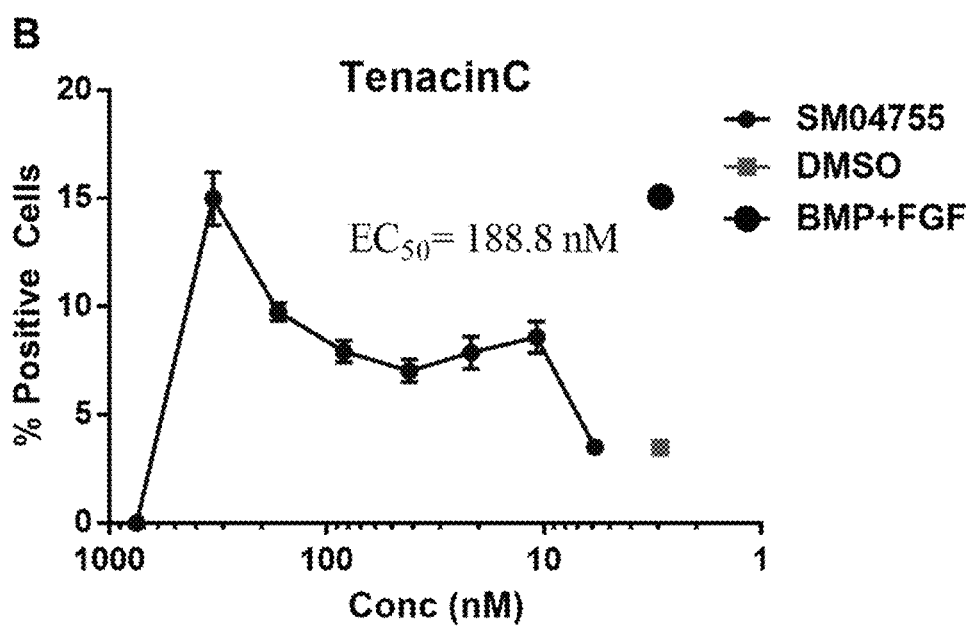
Figure 2C:
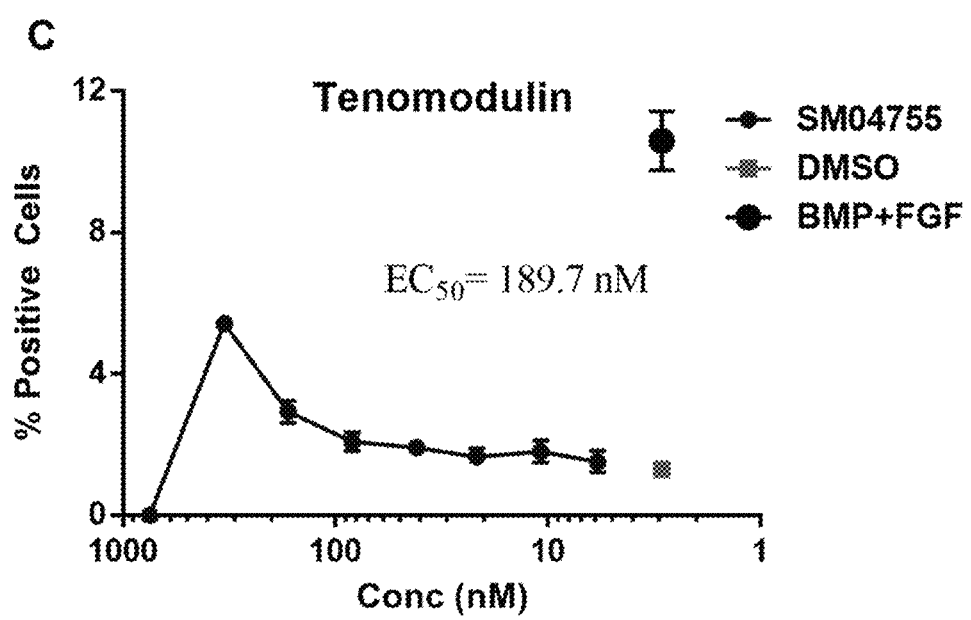
Figure 3:
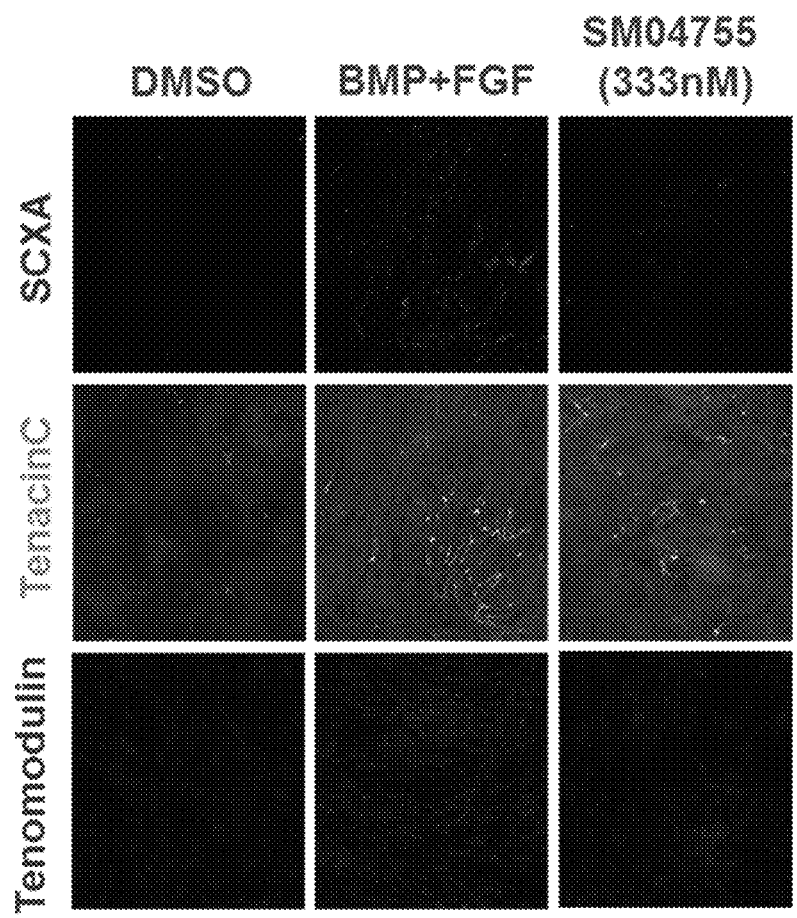
FIG. 3 are images of the expression of SCXA, tenacinC, and tenomodulin in hMSCs treated with DMSO, bone morphogenic protein (BMP) and fibroblast growth factor (FGF), and compound 175 at 333 nM concentration.

This disclosure features the use of one or more indazole-3-carboxamide compounds or salts or analogs thereof, in the treatment of one or more diseases or conditions independently selected from the group consisting of a tendinopathy, dermatitis, psoriasis, morphea, ichthyosis, Raynaud's syndrome, and Darier's disease; and/or for promoting wound healing. The methods include administering to a subject (e.g., a subject in need thereof) a therapeutically effective amount of one or more indazole-3-carboxamide compounds or salts or analogs thereof as described anywhere herein.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

In this specification and in the claims, the following terms have the meanings as defined. As used herein, "alkyl" means a branched, or straight chain chemical group containing only carbon and hydrogen, such as methyl, ethyl, n-propyl, isopropyl, n-butyl, isobutyl, sec-butyl and pentyl. Alkyl groups can either be unsubstituted or substituted with one or more substituents, e.g., halide, alkoxy, acyloxy, amino, amido, cyano, nitro, hydroxyl, mercapto, carboxy, carbonyl, benzyloxy, aryl, heteroaryl, or other functionality that may be suitably blocked, if necessary for purposes of the invention, with a protecting group. Alkyl groups can be saturated or unsaturated (e.g., containing —C=C— or —C≡C— subunits), at one or several positions. Typically, alkyl groups will comprise 1 to 9 carbon atoms, preferably 1 to 6, more preferably 1 to 4, and most preferably 1 to 2 carbon atoms.

As used herein, "carbocyclyl" means a cyclic ring system containing only carbon atoms in the ring system backbone, such as cyclopropyl, cyclobutyl, cyclopentyl, cyclohexyl, and cyclohexenyl. Carbocyclyls may include multiple fused rings. Carbocyclyls may have any degree of saturation provided that at least one ring in the ring system is not aromatic. Carbocyclyl groups can either be unsubstituted or substituted with one or more substituents, e.g., alkyl, halide, alkoxy, acyloxy, amino, amido, cyano, nitro, hydroxyl, mercapto, carboxy, carbonyl, benzyloxy, aryl, heteroaryl, or other functionality that may be suitably blocked, if necessary for purposes of the invention, with a protecting group. Typically, carbocyclyl groups will comprise 3 to 10 carbon atoms, preferably 3 to 6.

As used herein, "lower alkyl" means a subset of alkyl having 1 to 3 carbon atoms, and thus is a hydrocarbon substituent, which is linear, or branched. Examples of lower alkyl include methyl, ethyl, n-propyl and isopropyl. Likewise, radicals using the terminology "lower" refer to radicals preferably with 1 to about 3 carbons in the alkyl portion of the radical.

As used herein, "amido" means a H—CON— or alkyl-CON—, carbocyclyl-CON—, aryl-CON—, heteroaryl-CON— or heterocyclyl-CON group wherein the alkyl, carbocyclyl, aryl or heterocyclyl group is as herein described.

As used herein, "aryl" means an aromatic radical having a single-ring (e.g., phenyl) or multiple condensed rings (e.g., naphthyl or anthryl) with only carbon atoms present in the ring backbone. Aryl groups can either be unsubstituted or substituted with one or more substituents, e.g., alkyl, amino, cyano, hydroxyl, lower alkyl, haloalkyl, alkoxy, nitro, halo, mercapto, and other substituents. A preferred carbocyclic aryl is phenyl.

As used herein, the term "heteroaryl" means an aromatic radical having one or more heteroatom(s) (e.g., N, O, or S) in the ring backbone and may include a single ring (e.g., pyridine) or multiple condensed rings (e.g., quinoline). Heteroaryl groups can either be unsubstituted or substituted with one or more substituents, e.g., amino, cyano, hydroxyl, lower alkyl, haloalkyl, alkoxy, nitro, halo, mercapto, and other substituents. Examples of heteroaryl include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, and others.

In these definitions it is clearly contemplated that substitution on the aryl and heteroaryl rings is within the scope of certain embodiments. Where substitution occurs, the radical is called substituted aryl or substituted heteroaryl. Preferably one to three and more preferably one or two substituents occur on the aryl ring. Though many substituents will be useful, preferred substituents include those commonly found in aryl compounds, such as alkyl, cycloalkyl, hydroxy, alkoxy, cyano, halo, haloalkyl, mercapto and the like.

As used herein, "amide" includes both RNR'CO— (in the case of R=alkyl, alkaminocarbonyl-) and RCONR'— (in the case of R=alkyl, alkyl carbonylamino-).

As used herein, the term "ester" includes both ROCO— (in the case of R=alkyl, alkoxycarbonyl-) and RCOO— (in the case of R=alkyl, alkylcarbonyloxy-).

As used herein, "acyl" means an H—CO— or alkyl-CO—, carbocyclyl-CO—, aryl-CO—, heteroaryl-CO— or heterocyclyl-CO— group wherein the alkyl, carbocyclyl, aryl or heterocyclyl group is as herein described. Preferred acyls contain a lower alkyl. Exemplary alkyl acyl groups include formyl, acetyl, propanoyl, 2-methylpropanoyl, t-butylacetyl, butanoyl and palmitoyl.

As used herein, "halo", "halide" or "halogen" is a chloro, bromo, fluoro or iodo atom radical. Chloro, bromo and fluoro are preferred halides. Most preferred halide is fluorine.

As used herein, "haloalkyl" means a hydrocarbon substituent, which is linear or branched or cyclic alkyl, alkenyl or alkynyl substituted with chloro, bromo, fluoro or iodo atom(s). Most preferred of these are fluoroalkyls, wherein one or more of the hydrogen atoms have been substituted by fluoro. Preferred haloalkyls are of 1 to about 3 carbons in length, more preferred haloalkyls are 1 to about 2 carbons, and most preferred are 1 carbon in length. The skilled artisan will recognize then that as used herein, "haloalkylene" means a diradical variant of haloalkyl, such diradicals may act as spacers between radicals, other atoms, or between the parent ring and another functional group.

As used herein, "heterocyclyl" means a cyclic ring system comprising at least one heteroatom in the ring system backbone. Heterocyclyls may include multiple fused rings. Heterocyclyls may have any degree of saturation provided that at least one ring in the ring system is not aromatic. Heterocyclyls may be substituted or unsubstituted with one or more substituents, e.g., alkyl, halide, alkoxy, acyloxy, amino, amido, cyano, nitro, hydroxyl, mercapto, carboxy, carbonyl, benzyloxy, aryl, heteroaryl, and other substituents, and are attached to other groups via any available valence, preferably any available carbon or nitrogen. More preferred heterocycles are of 5-7 members. In six membered monocyclic heterocycles, the heteroatom(s) are selected from one up to three of 0, N or S, and wherein when the heterocycle is five membered, preferably it has one or two heteroatoms selected from O, N, or S. Examples of heterocyclyl include azirinyl, aziridinyl, azetidinyl, oxetanyl, thietanyl, 1,4,2-dithiazolyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, and others.

As used herein, "substituted amino" means an amino radical which is substituted by one or two alkyl, cycloalkyl, aryl, heteroaryl or heterocyclyl groups, wherein the alkyl, aryl, heteroaryl or heterocyclyl are defined as above.

As used herein, "substituted thiol" means RS— group wherein R is an alkyl, an aryl, heteroaryl or a heterocyclyl group, wherein the alkyl, cycloalkyl, aryl, heteroaryl or heterocyclyl are defined as above.

As used herein, "sulfonyl" means an alkyl$SO_2$, aryl$SO_2$, heteroaryl$SO_2$, carbocyclyl$SO_2$, or heterocyclyl-$SO_2$ group wherein the alkyl, carbocyclyl, aryl, heteroaryl or heterocyclyl are defined as above.

As used herein, "sulfamido" means an alkyl-N—S(O)$_2$N—, aryl-NS(O)$_2$N—, heteroaryl-NS(O)$_2$N—, carbocyclyl-NS(O)$_2$N or heterocyclyl-NS(O)$_2$N— group wherein the alkyl, carbocyclyl, aryl, heteroaryl or heterocyclyl group is as herein described.

As used herein, "sulfonamido" means an alkyl-S(O)$_2$N—, aryl-S(O)$_2$N—, heteroaryl-S(O)$_2$N—, carbocyclyl-S(O)$_2$N— or heterocyclyl-S(O)$_2$N— group wherein the alkyl, carbocyclyl, aryl, heteroaryl or heterocyclyl group is as herein described.

As used herein, "ureido" means an alkyl-NCON—, aryl-NCON—, heteroaryl-NCON—, carbocyclyl-NCON— or heterocyclyl-NCON— group wherein the alkyl, carbocyclyl, aryl, heteroaryl or heterocyclyl group is as herein described.

As used herein, when two groups are indicated to be "linked" or "bonded" to form a "ring," it is to be understood that a bond is formed between the two groups and may involve replacement of a hydrogen atom on one or both groups with the bond, thereby forming a carbocyclyl, heterocyclyl, aryl, or heteroaryl ring. The skilled artisan will recognize that such rings can and are readily formed by routine chemical reactions, and it is within the purview of the skilled artisan to both envision such rings and the methods of their formations. Preferred are rings having from 3-7 members, more preferably 5 or 6 members. As used herein the term "ring" or "rings" when formed by the combination of two radicals refers to heterocyclic, carbocyclic, aryl, or heteroaryl rings.

The skilled artisan will recognize that some structures described herein may be resonance forms or tautomers of compounds that may be fairly represented by other chemical structures, even when kinetically; the artisan recognizes that such structures are only a very small portion of a sample of such compound(s). Such compounds are clearly contemplated within the scope of this invention, though such resonance forms or tautomers may not be explicitly represented herein.

The compounds provided herein may encompass various stereochemical forms. The compounds also encompass diastereomers as well as optical isomers, e.g. mixtures of enantiomers including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art. Unless otherwise indicated, when a disclosed compound is named or depicted by a structure without specifying the stereochemistry and has one or more chiral centers, it is understood to represent all possible stereoisomers of the compound.

The term "administration" or "administering" refers to a method of giving a dosage of a compound or pharmaceutical composition to a vertebrate or invertebrate, including a mammal, a bird, a fish, or an amphibian, where the method is, e.g., orally, subcutaneously, intravenously, intranasally, topically, transdermally, intraperitoneally, intramuscularly, intrapulmonarilly, vaginally, rectally, ontologically, neurootologically, intraocularly, subconjuctivally, via anterior eye chamber injection, intravitreally, intraperitoneally, intrathecally, intracystically, intrapleurally, via wound irrigation, intrabuccally, intra-abdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracistemally, intravascularly, intraventricularly, intraosseously, via irrigation of infected bone, or via application as part of any admixture with a prosthetic devices. The preferred method of administration can vary depending on various factors, e.g., the components of the pharmaceutical composition, the site of the disease, the disease involved, and the severity of the disease.

A "diagnostic" as used herein is a compound, method, system, or device that assists in the identification and characterization of a health or disease state. The diagnostic can be used in standard assays as is known in the art.

The term "mammal" is used in its usual biological sense. Thus, it specifically includes humans, cattle, horses, dogs, and cats, but also includes many other species.

The term "pharmaceutically acceptable carrier" or "pharmaceutically acceptable excipient" includes any and all solvents, co-solvents, complexing agents, dispersion media, coatings, antibacterial and antifungal agents, isotonic and absorption delaying agents and the like which are not biologically or otherwise undesirable. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (2010); *Goodman and Gilman's: The Pharmacological Basis of Therapeutics,* 12th Ed., The McGraw-Hill Companies.

The term "pharmaceutically acceptable salt" refers to salts that retain the biological effectiveness and properties of the compounds of the preferred embodiments and, which are not biologically or otherwise undesirable. In many cases, the compounds of the preferred embodiments are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in World Patent Publication 87/05297, Johnston et al., published Sep. 11, 1987 (incorporated by reference herein).

"Solvate" refers to the compound formed by the interaction of a solvent and a Wnt pathway inhibitor, a metabolite, or salt thereof. Suitable solvates are pharmaceutically acceptable solvates including hydrates.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

By "therapeutically effective amount" or "pharmaceutically effective amount" is one which is sufficient to achieve the desired effect and may vary according to the nature and severity of the disease condition, and the potency of the compound. "Therapeutically effective amount" is also intended to include one or more of the compounds of Formula (I) in combination with one or more other agents that are effective to inhibit Wnt related diseases and/or conditions. The combination of compounds is preferably a synergistic combination. Synergy, as described, for example, by Chou and Talalay, *Advances in Enzyme Regulation* (1984), 22, 27-55, occurs when the effect of the compounds when administered in combination is greater than the additive effect of the compounds when administered alone as a single agent. In general, a synergistic effect is most clearly demonstrated at sub-optimal concentrations of the compounds. It will be appreciated that different concentrations may be employed for prophylaxis than for treatment of an active disease. This amount can further depend upon the patient's height, weight, sex, age and medical history.

A therapeutic effect relieves, to some extent, one or more of the symptoms of the disease, and includes curing a disease. "Curing" means that the symptoms of active disease are eliminated. However, certain long-term or permanent effects of the disease may exist even after a cure is obtained (such as extensive tissue damage).

"Treat," "treatment," or "treating," as used herein refers to administering a pharmaceutical composition for therapeutic purposes. The term "therapeutic treatment" refers to administering treatment to a patient already suffering from a disease thus causing a therapeutically beneficial effect, such as ameliorating existing symptoms, preventing additional symptoms, ameliorating or preventing the underlying metabolic causes of symptoms, postponing or preventing the further development of a disorder and/or reducing the severity of symptoms that will or are expected to develop.

"Morphea" as used herein refers to a skin condition wherein discolored and/or hardened patches appear on the skin (e.g., one or more outer layers of the skin) resulting from excessive collagen deposition.

"Raynaud's syndrome" as used herein refers to a disease in which certain parts of the body (e.g., fingers and/or toes) feel numb and/or cold in response to various stimuli (e.g., cold temperatures and/or stress) due to arterial narrowing.

"Darier's disease" as used herein refers to an autosomal dominant disorder characterized by the appearance of dark crusty patches on the skin (e.g., keratotic papules, keratosis follicularis or dyskeratosis follicularis) that may contain pus.

"Wound healing" as used herein refers to a process by which skin and/or other bodily tissue repairs itself after experiencing, for example, damage and/or trauma.

"Ichthyosis" as used herein refers to a group of genetic skin disorders characterized by the presence of dry, scaly, cracked, and/or flaky skin.

"Tendinopathy" as used herein refers to a disease or disorder of a tendon characterized by inflammation, deterioration, and/or injury of the tendon and/or tissue contacting, near, or associated with the tendon. Tendinopathy includes, for example, inflammation of the tendon (e.g., tendonitis), non-inflammatory degeneration of, for example, the structure and/or composition of a tendon (e.g., tendinosis), inflammation of the paratenon near or in contact with a tendon (e.g., paratenonitis), micro-trauma to the tendon, and rupture of the tendon (e.g., acute, chronic, partial and/or complete rupture). The term also encompasses tenosynovitis, a tendinopathy of the outer lining of the tendon which occurs in certain tendons such as flexor tendons and the Achilles tendon. Symptoms of tendinopathy include pain at rest, upon palpation of the tendon, and/or with movement of, for example, the tendon, tissue, joint, or bone near or associated with the tendon; joint stiffness; difficulty moving; weakness of the joint or muscles surrounding the tendon; redness of the skin near the tendon; swelling of the tendon and/or of tissue near the tendon; and/or crepitus.

"Tendinosis" as used herein, refers to a non-inflammatory injury to the tendon characterized by intratendinous degeneration of the tendon typically in the form of microtears in the tissue in and around the tendon caused by overuse, leading to an increase in the number of tendon repair cells around the area of damage. Degeneration of the tendon is caused by damage to or disorganization of the collagen fibers, cells, and vascular components of the tendon, which can reduce the tendon's tensile strength and can lead to tendon rupture if not treated.

"Tendinitis" as used herein refers to an inflammatory injury to the tendon, characterized by degeneration like that observed in tendinosis, but also accompanied by inflammation of the tendon, vascular disruption and an inflammatory repair response. Tendinitis is often associated with fibroblastic and myofibroblastic proliferation, as well as hemorrhage and organizing granulation tissue. Generally, tendinitis is referred to by the body part involved, such as Achilles tendinitis (affecting the Achilles tendon), or patellar tendinitis (also known as "jumper's knee," affecting the patellar tendon), though there are certain exceptions, such as lateral epicondylitis (also known as "tennis elbow," affecting the Extensor Carpi Radialis Brevis tendon). Symptoms can vary from aches or pains and local stiffness to a burning sensation surrounding the entire joint around the inflamed tendon. In some cases, tendonitis is characterized by swelling, sometimes accompanied by heat and redness; there may also be visible knots surrounding the joint. For many patients, the pain is usually worse during and after activity, and the tendon and joint area can become stiffer the following day as muscles tighten from the movement of the tendon.

"Psoriasis" as used herein refers to an autoimmune disease in which skin cells build up and causes raised, red, scaly patches to appear on the skin.

"Dermatitis" (also known as eczema) as used herein refers to generic inflammation of the skin. Specific types of dermatitis include atopic, contact, nummular, photo-induced, and stasis dermatitis. These diseases are characterized by itchiness, red skin, and a rash.

Compounds

Some embodiments of the present invention include compounds, salts, pharmaceutically acceptable salts or pro-drug thereof of Formula (I):

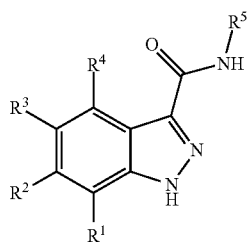

I

In some embodiments of Formula I, $R^1$, $R^2$ and $R^4$ are independently selected from the group consisting of H, $C_{1-9}$ alkyl, halide, $-N(R^{10})_2$, $-XR^{10}$, CN, $-OCF_3$ and $-CF_3$.

In some embodiments of Formula I, $R^3$ is selected from the group consisting of carbocyclyl$R^6$, heterocyclyl$R^6$, aryl$R^6$ and heteroaryl$R^6$.

In some embodiments of Formula I, when $R^3$ is heteroaryl, the heteroaryl is not selected from the group consisting of isoquinoline, $^1$H-pyrrolo[2,3-c]pyridine and tetrazole.

In some embodiments of Formula I, $R^5$ is selected from the group consisting of $-(C_{1-9}$ alkyl$)_n$carbocyclyl$R^7$, $-(C_{1-9}$ alkyl$)_n$heterocyclyl$R^7$, $-(C_{1-9}$ alkyl$)_n$aryl$R^7$ and $-(C_{1-9}$ alkyl$)_n$heteroaryl$R^7$.

In some embodiments of Formula I, $R^5$ is not 4-pyridyl$R^7$ when $R^1$, $R^2$ and $R^4$ are H, $R^3$ is selected from the group consisting of 3-pyridyl$R^6$, 4-pyridyl$R^6$, 2-pyridyl$R^6$, phenyl$R^6$, thiazole$R^6$, imidazole$R^6$, pyrimidine$R^6$, oxazole$R^6$,

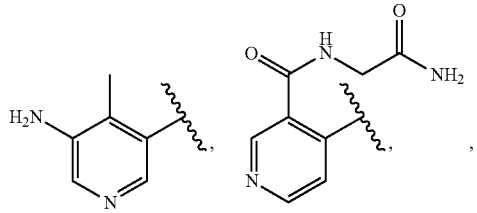

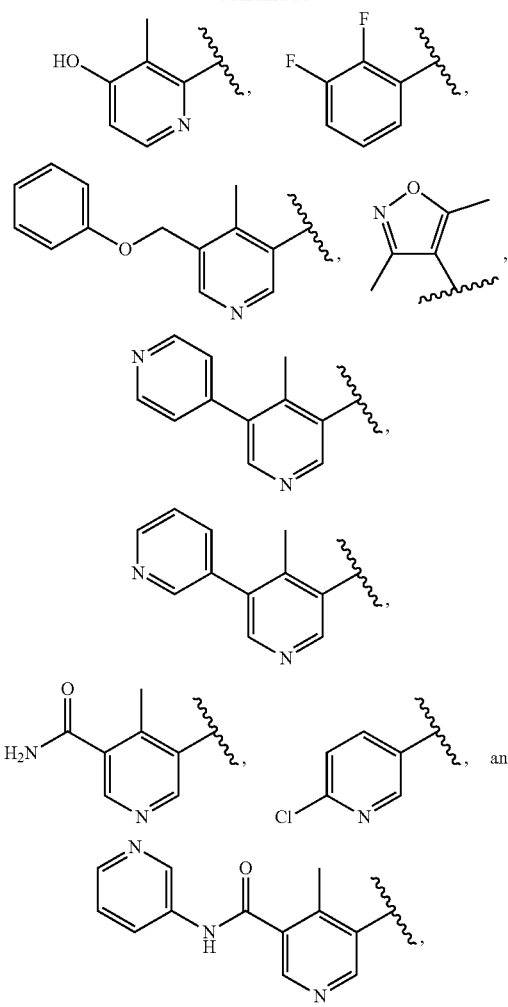

and $R^6$ and $R^7$ are both H.

In some embodiments of Formula I, R' is not $-(CH_2)(3$-pyridyl$)R^7$ when $R^1$, $R^2$ and $R^4$ are H, $R^3$ is selected from the group consisting of 3-pyridyl$R^6$, 4-pyridyl$R^6$ and thiazole$R^6$, and $R^6$ and $R^7$ are both H.

In some embodiments of Formula I, $R^5$ is not phenyl$R^7$ when $R^1$, $R^2$ and $R^4$ are H, $R^3$ is 4-pyridyl$R^6$ and $R^6$ and $R^7$ are both H.

In some embodiments of Formula I, $R^3$ is not 3-pyridyl$R^6$ when $R^1$, $R^2$ and $R^4$ are H, $R^5$ is selected from the group consisting of phenyl$R^7$,

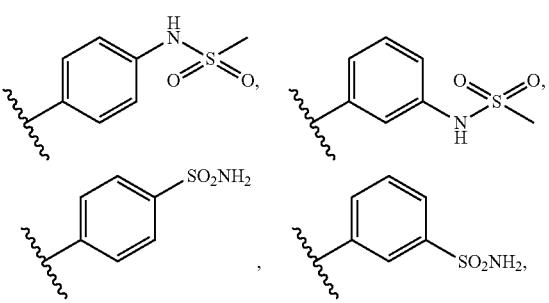

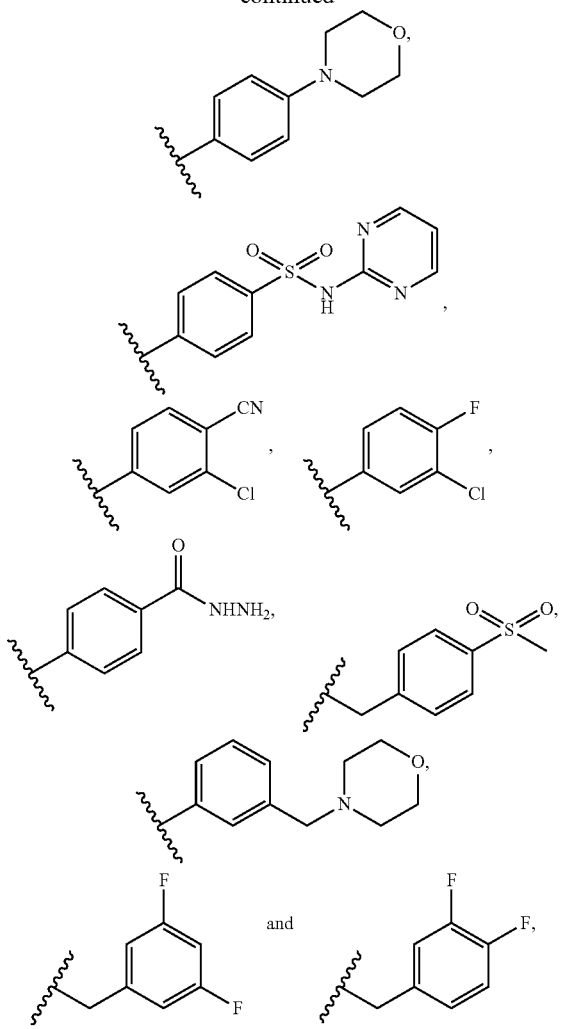

and R[7] are both H.

In some embodiments of Formula I, R[3] is not oxazoleR[6] when R[1], R[2] and R[4] are H, R[5] is selected from the group consisting of

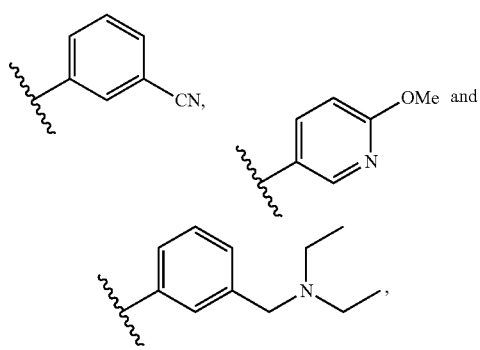

and R[6] is H.

In some embodiments of Formula I, R[3] is not thiazoleR[6] when R[1], R[2] and R[4] are H, R[5] is selected from the group consisting of

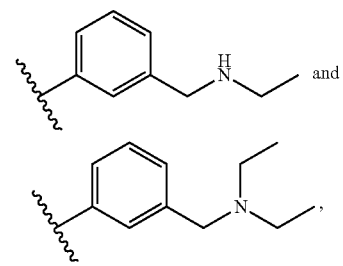

and R[6] is H.

In some embodiments of Formula I, each R[6] is 1-5 substituents each selected from the group consisting of H, $C_{1-9}$ alkyl, halide, amino, —$OCF_3$, —$CF_3$, —CN, —$XR^{10}$, —$(C_{1-9}$ alkyl$)_n$carbocyclylR[8], —$(C_{1-9}$ alkyl$)_n$heterocyclylR[8], —$(C_{1-9}$ alkyl$)_n$arylR[8], —$(C_{1-9}$ alkyl$)_n$heteroarylR[8], —$C(=O)R^{11}$, —$N(R^{10})C(=O)R^{11}$, alkyl$)_n$N(R^{10})_2$, —$(C_{1-9}$ alkyl$)_n$N(R^{10})SO_2R^{11}$ and —$SO_2R^{11}$.

In some embodiments of Formula I, each R[7] is 1-5 substituents each selected from the group consisting of H, $C_{1-9}$ alkyl, halide, amino, —$OCF_3$, —$CF_3$, —CN, —$XR^{10}$, —$(C_{1-9}$ alkyl$)_n$carbocyclylR[9], —$(C_{1-9}$ alkyl$)_n$heterocyclylR[9], —$(C_{1-9}$ alkyl$)_n$arylR[9], —$(C_{1-9}$ alkyl$)_n$heteroarylR[9], —$C(=O)R^{11}$, —$N(R^{10})C(=O)R^{11}$, —$(C_{1-9}$ alkyl$)_n$N(R^{10})_2$, —$(C_{1-9}$alkyl$)_n$N(R^{10})SO_2R^{11}$ and —$SO_2R^{13}$.

In some embodiments of Formula I, each R[8] is 1-5 substituents each selected from the group consisting of H, $C_{1-3}$ alkyl, halide, amino, $OCF_3$, —$CF_3$—CN, —$XR^{12}$, —$C(=O)R^{13}$, —$N(R^{12})C(=O)R^{13}$, —$(C_{1-9}$ alkyl$)_n$N(R^{12})_2$, —$(C_{1-9}$ alkyl$)_n$N(R^{12})SO_2R^{13}$ and —$SO_2R^{13}$.

In some embodiments of Formula I, each R[9] is 1-5 substituents each selected from the group consisting of H, $C_{1-3}$ alkyl, halide, amino, —$OCF_3$, —$CF_3$—CN, —$XR^{12}$, —$C(=O)R^{13}$, —$N(R^{12})C(=O)R^{13}$, —$(C_{1-9}$ alkyl$)_n$N(R^{12})_2$, —$(C_{1-9}$alkyl$)_n$N(R^{12})SO_2R^{13}$ and —$SO_2R^{13}$.

In some embodiments of Formula I, each R[10] is independently selected from the group consisting of H, $C_{1-9}$ alkyl, —$(C_{1-9}$ alkyl$)_n$N(R^{14})_2$, —$(C_{1-9}$ alkyl$)_n$carbocyclylR[8], —$(C_{1-9}$ alkyl$)_n$heterocyclylR[8], —$(C_{1-9}$ alkyl$)_n$arylR[8] and —$(C_{1-9}$ alkyl$)_n$heteroarylR[8].

In some embodiments of Formula I, each R[11] is independently selected from the group consisting of $C_{1-9}$alkyl, —$N(R^{14})_2$, —$(C_{1-9}$alkyl$)_n$carbocyclylR[8], —$(C_{1-9}$ alkyl$)_n$heterocyclylR[8], —$(C_{1-9}$ alkyl$)_n$arylR[8] and —$(C_{1-9}$ alkyl$)_n$heteroarylR[8].

In some embodiments of Formula I, each R[12] is independently selected from the group consisting of H, $C_{1-9}$ alkyl, —$(C_{1-9}$ alkyl$)_n$N(R^{14})_2$, —$(C_{1-9}$ alkyl$)_n$carbocyclyl, —$(C_{1-9}$ alkyl$)_n$heterocyclyl, —$(C_{1-9}$ alkyl$)_n$aryl and —$(C_{1-9}$alkyl$)_n$heteroaryl.

In some embodiments of Formula I, each R[13] is independently selected from the group consisting of $C_{1-9}$ alkyl, —$N(R^{14})_2$, —$(C_{1-9}$ alkyl$)_n$carbocyclyl, —$(C_{1-9}$ alkyl$)_n$heterocyclyl, —$(C_{1-9}$ alkyl$)_n$aryl and —$(C_{1-9}$alkyl$)_n$heteroaryl.

In some embodiments of Formula I, each $R^H$ is independently selected from the group consisting of H, $C_{1-3}$ alkyl, carbocyclyl and aryl.

In some embodiments of Formula I, each X is selected from the group consisting of a bond, —O— and —S—.

In some embodiments of Formula I, each n is 0 or 1.

In some embodiments of Formula I, X is O.

In some embodiments of Formula I, R[1], R[2] and R[4] are H.

Some embodiments of the present invention include compounds, salts, pharmaceutically acceptable salts or pro-drug thereof of Formula (Ia):

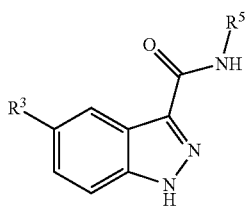

Ia wherein:
$R^3$ is selected from the group consisting of 3-pyridyl$R^6$, 5-pyrimidinyl$R^6$, and 4-pyridazinyl$R^6$;
$R^5$ is selected from the group consisting of -heteroaryl$R^7$;
$R^6$ is a substituent selected from the group consisting of —($C_{1-2}$ alkyl)heterocyclyl$R^8$ and -heterocyclyl$R^8$;
$R^7$ is 1-2 substituents each independently selected from the group consisting of H, $C_{1-3}$ alkyl, halide, —$NH_2$, —$OCF_3$, —$CF_3$, —CN, —$OR^{10}$, —($C_{1-2}$ alkyl)heterocyclyl$R^9$, -heterocyclyl$R^9$, and —$SO_2R^{11}$;
$R^8$ is 1-2 substituents each independently selected from the group consisting of H, $C_{1-3}$ alkyl, halide, and —$OR^{12}$;
each $R^9$ is 1-2 substituents each independently selected from the group consisting of H, $C_{1-3}$ alkyl, halide, amino, —$OCF_3$, —$CF_3$, —CN, and —$OR^{12}$;
$R^{10}$ is selected from the group consisting of H and $C_{1-3}$ alkyl;
$R^{11}$ is $C_{1-3}$ alkyl; and
each $R^{12}$ is independently selected from the group consisting of H and $C_{1-3}$ alkyl.

Some embodiments of the present invention include compounds, salts, pharmaceutically acceptable salts or pro-drug thereof of Formula (Ia):

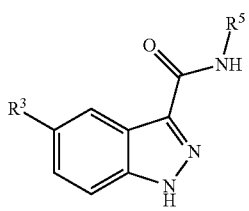

Ia wherein:
$R^3$ is 3-pyridyl$R^6$;
$R^5$ is selected from the group consisting of pyridyl$R^7$, -pyrimidinyl$R^7$, and -pyridazinyl$R^7$; $R^6$ is —$CH_2$heterocyclyl$R^8$;
$R^7$ is 1-2 substituents each independently selected from the group consisting of H, F, methyl, —$NH_2$, —$CF_3$, —CN, —OMe. —$SO_2Me$,

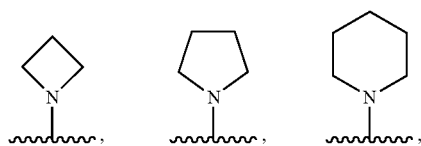

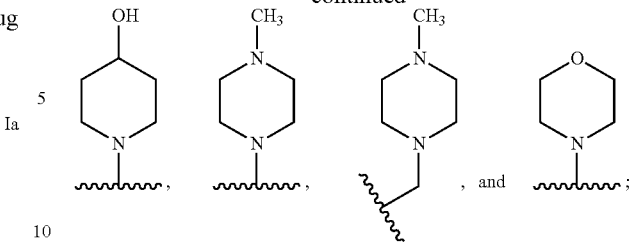

and
$R^8$ is 1-2 substituents each independently selected from the group consisting of H and halide.

In some embodiments of Formula Ia, $R^3$ is selected from the group consisting of 3-pyridyl$R^6$, 5-pyrimidinyl$R^6$, and 4-pyridazinyl$R^6$;

In some embodiments of Formula Ia, $R^5$ is selected from the group consisting of -heteroaryl$R^7$.

In some embodiments of Formula Ia, $R^5$ is selected from the group consisting of -piperazinyl$R^7$, -tetrahydropyranyl$R^7$, -piperidinyl$R^7$, pyrazolyl$R^7$, pyridazinyl$R^7$, benzo[d][1,3]dioxolyl$R^7$, 2,3-dihydrobenzo[b][1,4]dioxinyl$R^7$, pyrazinyl$R^7$, and 3-pyridyl$R^7$.

In some embodiments of Formula Ia, $R^6$ is a substituent selected from the group consisting of —($C_{1-2}$ alkyl)heterocyclyl$R^8$ and -heterocyclyl$R^8$.

In some embodiments of Formula Ia, $R^6$ is each $R^6$ is 1-2 substituents each selected from the group consisting of —($C_{1-2}$ alkyl)heterocyclyl$R^8$, -heterocyclyl$R^8$, —($C_{1-2}$ alkyl)aryl$R^8$, —$N(R^{10})C(=O)R^{11}$ and —($C_{1-2}$ alkyl)$N(R^{10})_2$.

In some embodiments of Formula Ia, $R^7$ is 1-2 substituents each independently selected from the group consisting of H, $C_{1-3}$ alkyl, halide, —$NH_2$, —$OCF_3$, —$CF_3$, —CN, —$OR^{10}$, —($C_{1-2}$ alkyl)heterocyclyl$R^9$, -heterocyclyl$R^9$, and —$SO_2R^{11}$.

In some embodiments of Formula Ia, each $R^7$ is 1-2 substituents each selected from the group consisting of unsubstituted $C_{1-3}$ alkyl, halide, amino, —$OCF_3$, —$CF_3$, —CN, —$OR^{10}$, —C(=O)$R^{11}$, —$N(R^{10})C(=O)R^{11}$, —$N(R^{10})_2$, —($C_{1-2}$ alkyl)$N(R^{10})_2$, and —$N(R^{10})SO_2R^{11}$.

In some embodiments of Formula Ia, $R^8$ is 1-2 substituents each independently selected from the group consisting of H, $C_{1-3}$ alkyl, halide, and —$OR^{12}$.

In some embodiments of Formula Ia, each $R^9$ is 1-2 substituents each independently selected from the group consisting of H, $C_{1-3}$ alkyl, halide, amino, —$OCF_3$, —$CF_3$, —CN, and —$OR^{12}$.

In some embodiments of Formula Ia, $R^{10}$ is selected from the group consisting of H and $C_{1-3}$ alkyl.

In some embodiments of Formula Ia, each $R^{10}$ is independently selected from the group consisting of H, $C_{1-3}$ alkyl, —($C_{1-3}$ alkyl)$N(R^{14})_2$ and -aryl$R^8$.

In some embodiments of Formula Ia, $R^{11}$ is $C_{1-3}$ alkyl.

In some embodiments of Formula Ia, $R^{11}$ is each $R^{11}$ is independently selected from the group consisting of $C_{1-3}$ alkyl, —$N(R^{14})_2$, -carbocyclyl$R^8$ and -heterocyclyl$R^8$.

In some embodiments of Formula Ia, each $R^{12}$ is independently selected from the group consisting of H and $C_{1-3}$ alkyl.

In some embodiments of Formula Ia, $R^3$ is selected from the group consisting of aryl$R^6$ and heteroaryl$R^6$.

In some embodiments of Formula Ia, when $R^3$ is heteroaryl, the heteroaryl is not selected from the group consisting of isoquinoline, 1H-pyrrolo[2,3-c]pyridine and tetrazole.

In some embodiments of Formula Ia, $R^5$ is selected from the group consisting of -carbocyclyl$R^7$, -heterocyclyl$R^7$, -aryl$R^7$, -heteroaryl$R^7$, and —($C_{1-2}$ alkyl)heteroaryl$R^7$.

In some embodiments of Formula Ia, $R^5$ is not 4-pyridyl$R^7$ when $R^3$ is selected from the group consisting of 3-pyridyl$R^6$, 4-pyridyl$R^6$, 2-pyridyl$R^6$, phenyl$R^6$, thiazole$R^6$, imidazole$R^6$, pyrimidine$R^6$, oxazole$R^6$,

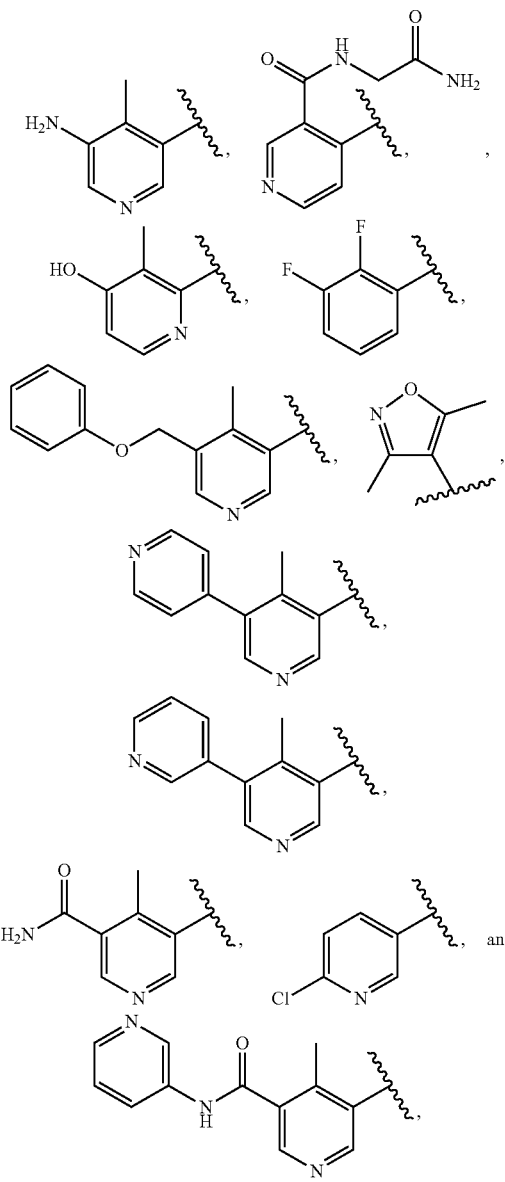

and $R^6$ and $R^7$ are both H.

In some embodiments of Formula Ia, $R^5$ is not —(CH$_2$)(3-pyridyl)$R^7$ when $R^3$ is selected from the group consisting of 3-pyridyl$R^6$, 4-pyridyl$R^6$ and thiazole$R^6$, and $R^6$ and $R^7$ are both H.

In some embodiments of Formula Ia, $R^5$ is not phenyl$R^6$ when $R^3$ is 4-pyridyl$R^6$ and $R^6$ and $R^7$ are both H.

In some embodiments of Formula Ia, $R^3$ is not 3-pyridyl$R^6$ when $R^5$ is selected from the group consisting of phenyl$R^7$,

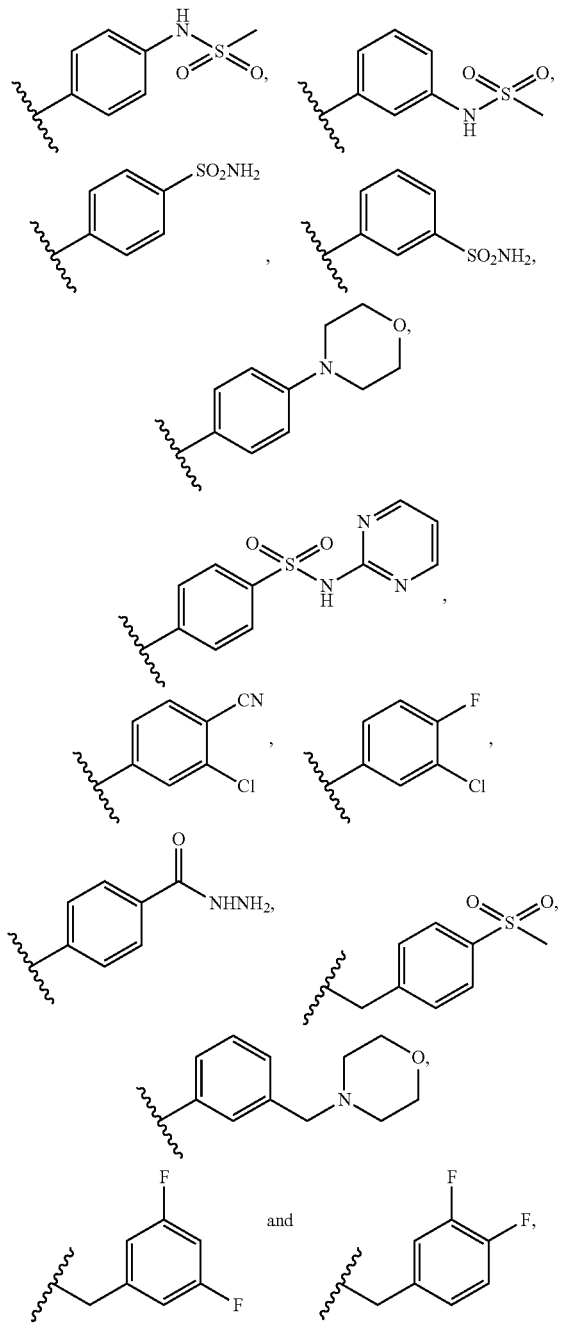

and $R^6$ and $R^7$ are both H.

In some embodiments of Formula Ia, $R^3$ is not oxazole$R^6$ when $R^5$ is selected from the group consisting of

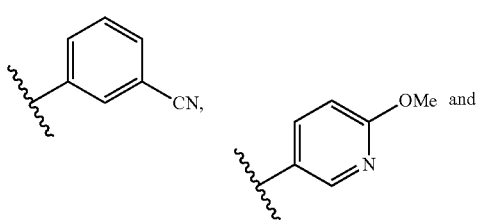

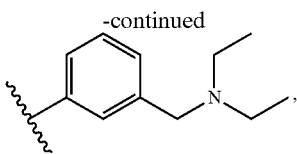

and $R^6$ is H.

In some embodiments of Formula Ia, $R^3$ is not thiazole$R^6$ when $R^5$ is selected from the group consisting of

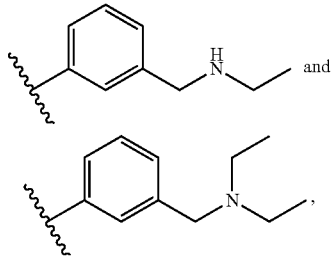

and $R^6$ is H.

In some embodiments of Formula Ia, each $R^6$ is 1-2 substituents each selected from the group consisting of H, $C_{1-3}$ alkyl, halide, amino, —$OCF_3$, —$CF_3$, —CN, —($C_{1-2}$ alkyl)heterocyclyl$R^8$, -heterocyclyl$R^8$, —($C_{1-2}$ alkyl)aryl$R^8$, —C(=O)$R^{11}$, —N($R^{10}$)C(=O)$R^{11}$ and —($C_{1-2}$ alkyl)N($R^{10}$)$_2$.

In some embodiments of Formula Ia, each $R^7$ is 1-2 substituents each selected from the group consisting of H, $C_{1-3}$ alkyl, halide, amino, —$OCF_3$, —$CF_3$, —CN, —$OR^{10}$, —($C_{1-2}$ alkyl)heterocyclyl$R^9$, -heterocyclyl$R^9$, -aryl$R^9$, —($C_{1-2}$ alkyl)aryl$R^9$, —C(=O)$R^{11}$, —N($R^{10}$)C(=O)$R^{11}$, —N($R^{10}$)$_2$, —($C_{1-2}$ alkyl)N($R^{10}$)$_2$, —N($R^{10}$)$SO_2R^{11}$ and —$SO_2R^{11}$.

In some embodiments of Formula Ia, each $R^8$ is 1-2 substituents each selected from the group consisting of H, $C_{1-3}$ alkyl, halide, amino, $OCF_3$, —$CF_3$ —CN and —$OR^{12}$.

In some embodiments of Formula Ia, each $R^9$ is 1-2 substituents each selected from the group consisting of H, $C_{1-3}$ alkyl, halide, amino, —$OCF_3$, —$CF_3$ —CN and —$OR^{11}$.

In some embodiments of Formula Ia, each $R^{10}$ is independently selected from the group consisting of H, $C_{1-3}$ alkyl, —($C_{1-3}$ alkyl)N($R^{14}$)$_2$ and -aryl$R^8$.

In some embodiments of Formula Ia, each $R^{11}$ is independently selected from the group consisting of $C_{1-3}$ alkyl, —N($R^{14}$)$_2$, -carbocyclyl$R^8$ and -heterocyclyl$R^8$.

In some embodiments of Formula Ia, each $R^{12}$ is independently selected from the group consisting of H and $C_{1-3}$ alkyl.

In some embodiments of Formula Ia, each $R^{14}$ is independently selected from the group consisting of H, $C_{1-3}$ alkyl and carbocyclyl.

In some embodiments of Formula I or Formula Ia, halide is fluorine.

In some embodiments of Formula I or Formula Ia, $R^3$ is -aryl$R^6$.

In some embodiments of Formula I or Formula Ia, $R^3$ is -heteroaryl$R^6$.

In some embodiments of Formula I or Formula Ia, $R^5$ is -aryl$R^7$.

In some embodiments of Formula I or Formula Ia, $R^5$ is -heteroaryl$R^7$.

In some embodiments of Formula I or Formula Ia, $R^5$ is -heterocyclyl$R^7$.

In some embodiments of Formula I or Formula Ia, $R^3$ is -heteroaryl$R^6$ and $R^5$ is -heteroaryl$R^7$.

In some embodiments of Formula I or Formula Ia, $R^3$ is -phenyl$R^6$ and $R^5$ is -heteroaryl$R^7$.

In some embodiments of Formula I or Formula Ia, $R^3$ is -heteroaryl$R^6$ and $R^5$ is -phenyl$R^7$.

In some embodiments of Formula I or Formula Ia, $R^3$ is -3-pyridyl$R^6$ and $R^5$ is -3-pyridyl$R^7$.

In some embodiments of Formula I or Formula Ia, $R^3$ is -3-pyridyl$R^6$ and $R^5$ is —$CH_2$-3-pyridyl$R^7$.

In some embodiments of Formula I or Formula Ia, $R^3$ is -3-pyridyl$R^6$ and $R^5$ is -pyridazinyl$R^7$.

In some embodiments of Formula I or Formula Ia, $R^3$ is -3-pyridyl$R^6$ and $R^5$ is -pyrazinyl$R^7$.

In some embodiments of Formula I or Formula Ia, $R^3$ is -3-pyridyl$R^6$ and $R^5$ is -pyrimidinyl$R^7$.

In some embodiments of Formula I or Formula Ia, $R^3$ is -3-pyridyl$R^6$ and $R^5$ is benzo[d][1,3]dioxolyl.

In some embodiments of Formula I or Formula Ia, $R^3$ is -3-pyridyl$R^6$ and $R^5$ is 2,3-dihydrobenzo[b][1,4]dioxinyl In some embodiments of Formula I or Formula Ia, the aryl is phenyl.

In some embodiments of Formula I or Formula Ia, when $R^3$ is heteroaryl, the heteroaryl is 3-pyridyl.

In some embodiments of Formula I or Formula Ia, when $R^5$ is heteroaryl, the heteroaryl is 3-pyridyl.

In some embodiments of Formula I or Formula Ia, when $R^5$ is heteroaryl, the heteroaryl is 5-pyrimidinyl.

In some embodiments of Formula I or Formula Ia, when $R^5$ is heteroaryl, the heteroaryl is 4-pyridazinyl.

In some embodiments of Formula I or Formula Ia, when $R^5$ is heteroaryl, the heteroaryl is pyrazolyl.

In some embodiments of Formula I or Formula Ia, when $R^5$ is heteroaryl, the heteroaryl is benzo[d][1,3]dioxolyl.

In some embodiments of Formula I or Formula Ia, when $R^5$ is heteroaryl, the heteroaryl is 2,3-dihydrobenzo[b][1,4] dioxinyl.

In some embodiments of Formula I or Formula Ia, $R^6$ is a heterocyclyl. For example, the heterocyclyl can be selected from the group consisting of morpholinyl, piperazinyl, piperidinyl, tetrahydropyranyl, azetidinyl and pyrrolidinyl. In certain embodiments, $R^6$ is morpholinyl. In another embodiment, $R^6$ is piperazinyl. In another embodiment, $R^6$ is piperidinyl. In another embodiment, $R^6$ is pyrrolidinyl.

In some embodiments of Formula I or Formula Ia, $R^7$ is a heterocyclyl. For example, the heterocyclyl can be selected from the group consisting of morpholinyl, piperazinyl, piperidinyl, tetrahydropyranyl, azetidinyl and pyrrolidinyl. In certain embodiments, $R^7$ is morpholinyl. In another embodiment, $R^7$ is piperazinyl. In another embodiment, $R^7$ is piperidinyl. In another embodiment, $R^7$ is pyrrolidinyl. In another embodiment, $R^7$ is azetidinyl.

In some embodiments of Formula I or Formula Ia, $R^{10}$ is a carbocyclyl. For example, the carbocyclyl can be selected from the group consisting of cyclopropyl, cyclobutyl, cyclopentyl and cyclohexyl. In certain embodiments, $R^{10}$ is cyclopropyl. In another embodiment, $R^{10}$ is cyclobutyl. In another embodiment, $R^{10}$ is cyclopentyl. In another embodiment, $R^{10}$ is cyclohexyl.

In some embodiments of Formula I or Formula Ia, $R^{11}$ is a heterocyclyl. For example, the heterocyclyl can be selected from the group consisting of morpholinyl, piperazinyl, piperidinyl, tetrahydropyranyl, azetidinyl and pyrrolidinyl. In certain embodiments, $R^{11}$ is morpholinyl. In another embodiment, $R^{11}$ is piperazinyl. In another embodiment, $R^{11}$ is piperidinyl. In another embodiment, $R^{11}$ is pyrrolidinyl. In another embodiment, $R^{11}$ is azetidinyl.

In some embodiments of Formula I or Formula Ia, $R^{11}$ is a carbocyclyl. For example, the carbocyclyl can be selected from the group consisting of cyclopropyl, cyclobutyl, cyclopentyl and cyclohexyl. In certain embodiments, $R^{11}$ is cyclopropyl. In another embodiment, $R^{11}$ is cyclobutyl. In another embodiment, $R^{11}$ is cyclopentyl. In another embodiment, $R^{11}$ is cyclohexyl.

In some embodiments of Formula I or Formula Ia, $R^{12}$ is a carbocyclyl. For example, the carbocyclyl can be selected from the group consisting of cyclopropyl, cyclobutyl, cyclopentyl and cyclohexyl. In certain embodiments, $R^{12}$ is cyclopropyl. In another embodiment, $R^{12}$ is cyclobutyl. In another embodiment, $R^{12}$ is cyclopentyl. In another embodiment, $R^{12}$ is cyclohexyl.

In some embodiments of Formula I or Formula Ia, $R^{13}$ is a heterocyclyl. For example, the heterocyclyl can be selected from the group consisting of morpholinyl, piperazinyl, piperidinyl, tetrahydropyranyl, azetidinyl and pyrrolidinyl. In certain embodiments, $R^{13}$ is morpholinyl. In another embodiment, $R^{13}$ is piperazinyl. In another embodiment, $R^{13}$ is piperidinyl. In another embodiment, $R^{13}$ is pyrrolidinyl. In another embodiment, $R^{11}$ is azetidinyl.

In some embodiments of Formula I or Formula Ia, $R^{13}$ is a carbocyclyl. For example, the carbocyclyl can be selected from the group consisting of cyclopropyl, cyclobutyl, cyclopentyl and cyclohexyl. In certain embodiments, $R^{13}$ is cyclopropyl. In another embodiment, $R^{11}$ is cyclobutyl. In another embodiment, $R^{11}$ is cyclopentyl. In another embodiment, $R^{11}$ is cyclohexyl.

In some embodiments of Formula I or Formula Ia, $R^{6}$ is one substituent.

In some embodiments of Formula I or Formula Ia, $R^{6}$ is 1-2 substituents.

In some embodiments of Formula I, $R^{6}$ is 1-3 substituents.

In some embodiments of Formula I, $R^{6}$ is 1-4 substituents.

In some embodiments of Formula I or Formula Ia, $R^{6}$ is H.

In some embodiments of Formula I or Formula Ia, $R^{6}$ is one substituent and the substituent is a halide.

In some embodiments of Formula I or Formula Ia, $R^{6}$ is one substituent and the substituent is $—NH_2$.

In some embodiments of Formula I or Formula Ia, $R^{6}$ is one substituent and the substituent is $—OCF_3$.

In some embodiments of Formula I or Formula Ia, $R^{6}$ is one substituent and the substituent is $—OCH_3$.

In some embodiments of Formula I or Formula Ia, $R^{6}$ is one substituent and the substituent is $—CF_3$.

In some embodiments of Formula I or Formula Ia, $R^{6}$ is one substituent and the substituent is -heterocyclyl$R^{8}$.

In some embodiments of Formula I or Formula Ia, $R^{6}$ is one substituent and the substituent is $—(CH_2)$heterocycyl$R^{8}$.

In some embodiments of Formula I or Formula Ia, $R^{6}$ is one substituent and the substituent is $—(CH_2)$pyrrolidinyl$R^{8}$.

In some embodiments of Formula I or Formula Ia, $R^{6}$ is one substituent and the substituent is $—(CH_2)$pyrrolidinyl$R^{8}$ where $R^{8}$ is two substituents and both substituents are halides.

In some embodiments of Formula I or Formula Ia, $R^{6}$ is one substituent and the substituent is $—(CH_2)$piperidinyl$R^{8}$.

In some embodiments of Formula I or Formula Ia, $R^{6}$ is one substituent and the substituent is $—(CH_2)$phenyl$R^{8}$.

In some embodiments of Formula I or Formula Ia, $R^{6}$ is one substituent and the substituent is -phenoxy$R^{8}$.

In some embodiments of Formula I or Formula Ia, $R^{6}$ is one substituent and the substituent is

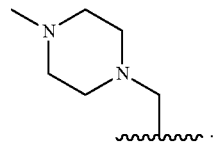 [SMILES: *CN1CCN(C)CC1]

In some embodiments of Formula I or Formula Ia, $R^{6}$ is one substituent and the substituent is $—N(R^{10})_2$.

In some embodiments of Formula I or Formula Ia, $R^{6}$ is one substituent and the substituent is $—N(R^{10})_2$ where each $R^{10}$ is independently selected from $C_{1-3}$ alkyl.

In some embodiments of Formula I or Formula Ia, $R^{6}$ is one substituent and the substituent is $—(CH_2)N(R^{10})_2$.

In some embodiments of Formula I or Formula Ia, $R^{6}$ is one substituent and the substituent is $—(CH_2)N(R^{10})_2$ where each $R^{10}$ is independently selected from $C_{1-3}$ alkyl.

In some embodiments of Formula I or Formula Ia, $R^{6}$ is one substituent and the substituent is $—N(R^{10})SO_2R^{11}$.

In some embodiments of Formula I or Formula Ia, $R^{6}$ is one substituent and the substituent is $—N(R^{10})C(=O)R^{11}$.

In some embodiments of Formula I or Formula Ia, $R^{6}$ is one substituent and the substituent is $—N(R^{10})C(=O)R^{11}$ where $R^{11}$ is a heterocyclyl.

In some embodiments of Formula I or Formula Ia, $R^{6}$ is one substituent and the substituent is $—N(R^{10})C(=O)R^{11}$ where $R^{11}$ is a carbocyclyl.

In some embodiments of Formula I, $R^{6}$ is two substituents and the substituents are fluorine and $—(C_{1-9}$ alkyl$)_n$heterocyclyl$R^{8}$.

In some embodiments of Formula Ia, $R^{6}$ is two substituents and the substituents are fluorine and -heterocyclyl$R^{8}$.

In some embodiments of Formula Ia, $R^{6}$ is two substituents and the substituents are fluorine and $—(C_{1-2}$ alkyl)heterocyclyl$R^{8}$.

In some embodiments of Formula I or Formula Ia, $R^{6}$ is one substituent and the substituent is select from the group consisting of

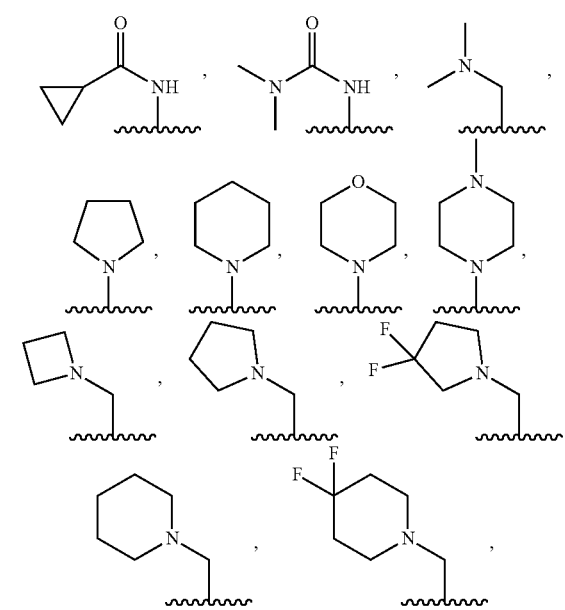

-continued

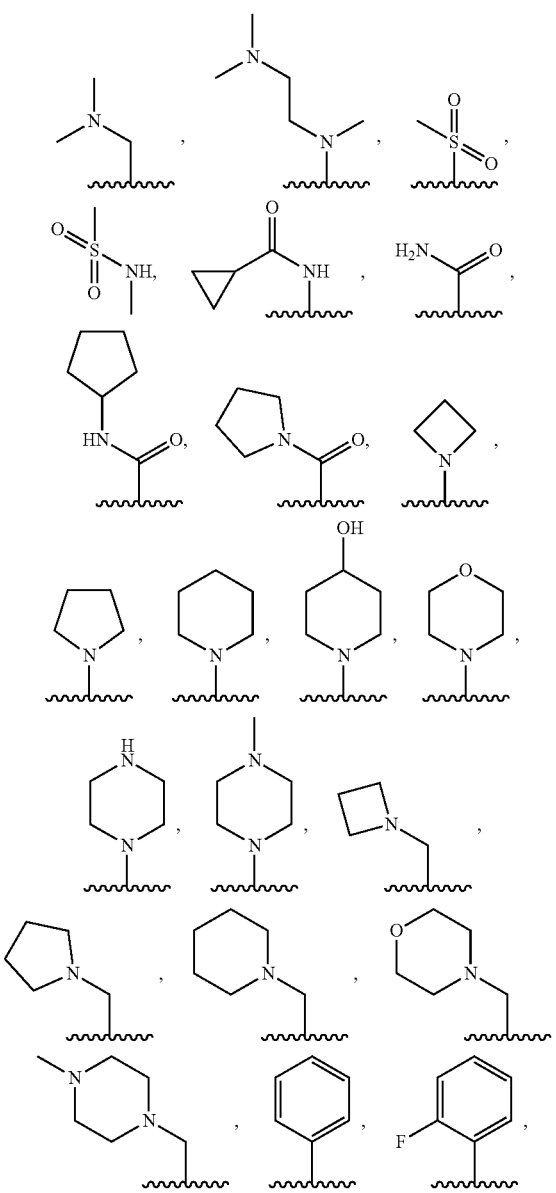

In some embodiments of Formula I or Formula Ia, $R^7$ is one substituent.

In some embodiments of Formula I or Formula Ia, $R^7$ is 1-2 substituents.

In some embodiments of Formula I, $R^7$ is 1-3 substituents.

In some embodiments of Formula I, $R^7$ is 1-4 substituents.

In some embodiments of Formula I or Formula Ia, $R^7$ is one substituent and the substituent is a halide.

In some embodiments of Formula I or Formula Ia, $R^7$ is one substituent and the substituent is —$NH_2$.

In some embodiments of Formula I or Formula Ia, $R^7$ is one substituent and the substituent is —OH.

In some embodiments of Formula I or Formula Ia, $R^7$ is one substituent and the substituent is —$CF_3$.

In some embodiments of Formula I or Formula Ia, $R^7$ is one substituent and the substituent is —CN.

In some embodiments of Formula I, $R^7$ is one substituent and the substituent is —$XR^{10}$ where X is O and $R^{10}$ is $C_{1-3}$ alkyl.

In some embodiments of Formula Ia, $R^7$ is one substituent and the substituent is —$OR^{10}$ and $R^{10}$ is $C_{1-3}$ alkyl.

In some embodiments of Formula I or Formula Ia, $R^7$ is one substituent and the substituent is -phenyl$R^9$.

In some embodiments of Formula I or Formula Ia, $R^7$ is one substituent and the substituent is —$(CH_2)N(R^{10})_2$.

In some embodiments of Formula I or Formula Ia, $R^7$ is one substituent and the substituent is —$(CH_2)N(R^{10})_2$ where each $R^{10}$ is independently selected from $C_{1-3}$ alkyl.

In some embodiments of Formula I or Formula Ia, $R^7$ is one substituent and the substituent is —$(CH_2)$heterocyclyl$R^9$.

In some embodiments of Formula I or Formula Ia, $R^7$ is one substituent and the substituent is —$(CH_2)$pyrrolidinyl$R^9$.

In some embodiments of Formula I or Formula Ia, $R^7$ is one substituent and the substituent is -heterocyclyl$R^9$.

In some embodiments of Formula I or Formula Ia, $R^7$ is one substituent and the substituent is -phenoxy$R^9$.

In some embodiments of Formula I or Formula Ia, $R^7$ is one substituent and the substituent is —$(CH_2)$phenyl$R^9$.

In some embodiments of Formula I or Formula Ia, $R^7$ is one substituent and the substituent is -phenyl$R^9$.

In some embodiments of Formula I or Formula Ia, $R^7$ is one substituent and the substituent is —$N(R^{10})C(=O)R^{11}$.

In some embodiments of Formula I or Formula Ia, $R^7$ is one substituent and the substituent is —$N(R^{10})C(=O)R^{11}$ where $R^{11}$ is a carbocyclyl.

In some embodiments of Formula I or Formula Ia, $R^7$ is one substituent and the substituent is —$N(R^{10})_2$.

In some embodiments of Formula I or Formula Ia, $R^7$ is one substituent and the substituent is —$C(=O)R^{11}$ where $R^{11}$ is select from the group consisting of -heterocyclyl$R^8$ and —$N(R^{10})_2$.

In some embodiments of Formula I or Formula Ia, $R^7$ is one substituent and the substituent is —$SO_2R^{11}$.

In some embodiments of Formula I or Formula Ia, $R^7$ is one substituent and the substituent is —$SO_2R^{11}$; and $R^{11}$ is $C_{1-3}$ alkyl.

In some embodiments of Formula I or Formula Ia, $R^7$ is two substituents and the substituents are $C_{1-3}$ alkyl and -heterocyclyl$R^9$.

In some embodiments of Formula I or Formula Ia, $R^7$ is one substituent and the substituent is select from the group consisting of

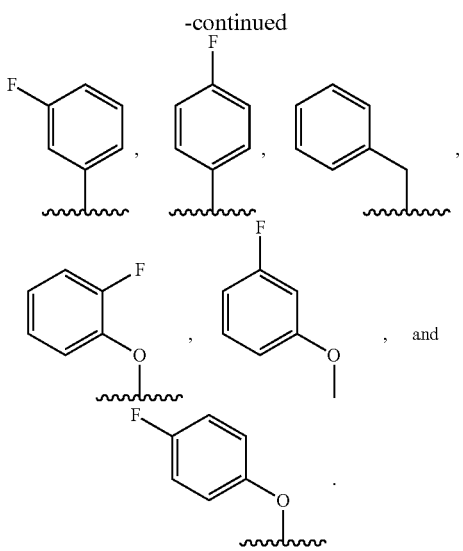

In some embodiments of Formula I or Formula Ia, $R^8$ is one substituent.

In some embodiments of Formula I or Formula Ia, $R^8$ is 1-2 substituents.

In some embodiments of Formula I, $R^8$ is 1-3 substituents.

In some embodiments of Formula I, $R^8$ is 1-4 substituents.

In some embodiments of Formula I or Formula Ia, $R^8$ is H.

In some embodiments of Formula I or Formula Ia, $R^8$ is one substituent and the substituent is $C_{1-3}$ alkyl.

In some embodiments of Formula I or Formula Ia, $R^8$ is one substituent and the substituent is —OH.

In some embodiments of Formula I or Formula Ia, $R^8$ is one substituent and the substituent is a halide.

In some embodiments of Formula I or Formula Ia, $R^8$ is two substituents and the substituents are halides.

In some embodiments of Formula I, $R^8$ is three substituents and the substituents are halides.

In some embodiments of Formula I or Formula Ia, $R^9$ is one substituent.

In some embodiments of Formula I or Formula Ia, $R^9$ is 1-2 substituents.

In some embodiments of Formula I, $R^9$ is 1-3 substituents.

In some embodiments of Formula I, $R^9$ is 1-4 substituents.

In some embodiments of Formula I or Formula Ia, $R^9$ is H.

In some embodiments of Formula I or Formula Ia, $R^9$ is one substituent and the substituent is $C_{1-3}$ alkyl.

In some embodiments of Formula I or Formula Ia, $R^9$ is one substituent and the substituent is —OH.

In some embodiments of Formula I or Formula Ia, $R^9$ is one substituent and the substituent is a halide.

In some embodiments of Formula I or Formula Ia, $R^9$ is two substituents and the substituents are halides.

In some embodiments of Formula I or Formula Ia, $R^8$ is a —$C_{1-3}$ alkyl. For example, the —$C_{1-3}$ alkyl can be selected from the group consisting of methyl, ethyl, n-propyl and isopropyl. In certain embodiments, $R^8$ is methyl. In another embodiment, $R^8$ is ethyl.

In some embodiments of Formula I or Formula Ia, $R^{10}$ is a —$C_{1-3}$ alkyl. For example, the —$C_{1-3}$ alkyl can be selected from the group consisting of methyl, ethyl, n-propyl and iso-propyl. In certain embodiments, $R^{10}$ is methyl. In another embodiment, $R^{10}$ is ethyl. In another embodiment, $R^{10}$ is n-propyl. In another embodiment, $R^{10}$ is iso-propyl.

In some embodiments of Formula I or Formula Ia, $R^{11}$ is a —$C_{1-3}$ alkyl. For example, the —$C_{1-3}$ alkyl can be selected from the group consisting of methyl, ethyl, n-propyl and iso-propyl. In certain embodiments, $R^{11}$ is methyl. In another embodiment, $R^{11}$ is ethyl. In another embodiment, $R^{11}$ is n-propyl. In another embodiment, $R^{11}$ is iso-propyl.

In some embodiments of Formula I or Formula Ia, $R^{14}$ is a —$C_{1-3}$ alkyl. For example, the —$C_{1-3}$ alkyl can be selected from the group consisting of methyl, ethyl, n-propyl and iso-propyl. In certain embodiments, $R^{14}$ is methyl. In another embodiment, $R^{14}$ is ethyl. In another embodiment, $R^{14}$ is n-propyl. In another embodiment, $R^{14}$ is iso-propyl.

In some embodiments of Formula I or Formula Ia, $R^3$ is -3-pyridyl$R^6$ and $R^5$ is -3-pyridyl$R^7$; $R^6$ is one substituent consisting of —$(C_{1-2}$ alkyl$)N(R^{10})_2$; and $R^7$ is one substituent consisting of —$CF_3$; and each $R^{10}$ is —$C_{1-3}$alkyl.

In some embodiments of Formula I or Formula Ia, $R^3$ is -3-pyridyl$R^6$ and $R^5$ is -3-pyridyl$R^7$; $R^6$ is one substituent consisting of —$(C_{1-2}$ alkyl$)$heterocyclyl$R^8$; $R^7$ and $R^8$ are both H; and the heterocycle is a 5-member ring.

In some embodiments of Formula I or Formula Ia, $R^3$ is -3-pyridyl$R^6$ and $R^5$ is -3-pyridyl$R^7$; $R^6$ is one substituent consisting of —$(C_{1-2}$ alkyl$)$heterocyclyl$R^8$; $R^7$ and $R^8$ are both H; and the heterocycle is a 6-member ring.

In some embodiments of Formula I or Formula Ia, $R^3$ is -3-pyridyl$R^6$ and $R^5$ is -3-pyridyl$R^7$; $R^6$ is one substituent consisting of —$(C_{1-2}$ alkyl$)$heterocyclyl$R^8$; $R^7$ is one substituent consisting of CN; $R^8$ is H; and the heterocycle is a 5-member ring.

In some embodiments of Formula I or Formula Ia, $R^3$ is -3-pyridyl$R^6$ and $R^5$ is -3-pyridyl $R^7$; $R^6$ is one substituent consisting of —$(C_{1-2}$alkyl$)$heterocyclyl$R^8$; $R^7$ is one substituent consisting of CN; $R^8$ is H; and the heterocycle is a 6-member ring.

In some embodiments of Formula I or Formula Ia, $R^3$ is -3-pyridyl$R^6$ and $R^5$ is -3-pyridyl$R^7$; $R^6$ is one substituent consisting of —$(C_{1-2}$ alkyl$)$heterocyclyl$R^8$; $R^7$ is one substituent consisting of $CF_3$; $R^8$ is H; and the heterocycle is a 6-member ring.

In some embodiments of Formula I or Formula Ia, $R^3$ is -3-pyridyl$R^6$ and $R^5$ is -3-pyridyl$R^7$; $R^6$ is one substituent consisting of —$(C_{1-2}$ alkyl$)$heterocyclyl$R^8$; $R^7$ is one substituent consisting of -heterocyclyl$R^8$; each $R^8$ is H; and the heterocycles are independently selected from a 5 or 6-member ring.

In some embodiments of Formula I or Formula Ia, $R^3$ is -3-pyridyl$R^6$ and $R^5$ is -3-pyridyl$R^7$; $R^6$ is one substituent consisting of —$(C_{1-2})$alkyl$)N(R^{10})_2$; and $R^7$ is one substituent consisting of —CN; and each $R^{10}$ is —$C_{1-3}$ alkyl.

In some embodiments of Formula I or Formula Ia, $R^3$ is -3-pyridyl$R^6$ and $R^5$ is -3-pyridyl $R^7$; $R^6$ is one substituent consisting of —$(C_{1-2})$alkyl$)N(R^{10})_2$; and $R^7$ is one substituent consisting of —$(C_{1-2}$ alkyl$)$heterocyclyl$R^8$; $R^8$ is H; each $R^{10}$ is —$C_{1-3}$ alkyl; and the heterocycle is a 6-member ring.

In some embodiments of Formula I or Formula Ia, $R^3$ is -3-pyridyl$R^6$ and $R^5$ is -3-pyridyl$R^7$; $R^6$ is one substituent consisting of —$(C_{1-2}$ alkyl$)$heterocyclyl$R^8$; $R^7$ is one substituent consisting of -heterocyclyl$R^8$; each $R^8$ is one substituent independently selected from H and —OH; and the heterocycles are independently selected from a 5 or 6-member ring.

In some embodiments of Formula I or Formula Ia, $R^3$ is -3-pyridyl$R^6$ and $R^5$ is -3-pyridyl$R^7$; $R^6$ is one substituent consisting of —$(C_{1-2}$ alkyl$)$heterocyclyl$R^8$; $R^7$ is one substituent consisting of —$C(=O)R^{11}$; $R^{11}$ is -heterocyclyl$R^8$; each $R^8$ is H; and the heterocycles are independently selected from a 5 or 6-member ring.

In some embodiments of Formula I or Formula Ia, $R^3$ is -3-pyridyl$R^6$ and $R^5$ is -3-pyridyl$R^7$; $R^6$ is one substituent consisting of —($C_{1-2}$ alkyl)heterocyclyl$R^8$; $R^7$ is one substituent consisting of -heterocyclyl$R^8$; each $R^8$ is 1-3 substituents independently selected from H and F with the proviso that at least one substituent on one heterocycle is fluorine; and each heterocycle is a 5-member ring.

In some embodiments of Formula I or Formula Ia, $R^3$ is -3-pyridyl$R^6$ and $R^5$ is -3-pyridyl$R^7$; $R^6$ is one substituent consisting of —($C_{1-2}$ alkyl)heterocyclyl$R^8$; $R^7$ is one substituent consisting of —C(=O)$R^{11}$; $R^{11}$ is —NH$R^{10}$; $R^{10}$ is heterocyclyl$R^8$; each $R^8$ is H; and the heterocycles are independently selected from a 5 or 6-member ring.

In some embodiments of Formula I or Formula Ia, $R^3$ is -3-pyridyl$R^6$ and $R^5$ is -3-pyridyl$R^7$; $R^6$ is one substituent consisting of —($C_{1-2}$alkyl)heterocyclyl$R^8$; $R^7$ is one substituent consisting of —SO$_2$$R^{11}$; $R^8$ is H; $R^{11}$ is —$C_{1-3}$ alkyl; and the heterocycle is a 6-member ring.

In some embodiments of Formula I or Formula Ia, $R^3$ is -3-pyridyl$R^6$ and $R^5$ is -3-pyridyl$R^7$; $R^6$ is one substituent consisting of —($C_{1-2}$ alkyl)heterocyclyl$R^8$; $R^7$ is H; $R^8$ is 1-4 substituents independently selected from H and F with the proviso that at least one substituent is fluorine; and the heterocycle is a 5-member ring.

Illustrative compounds of Formula (I) are shown in Table 1.

TABLE 1

| | |
|---|---|
| 1 | ![structure] |
| 2 | ![structure] |
| 3 | ![structure] |

TABLE 1-continued

| 4 | 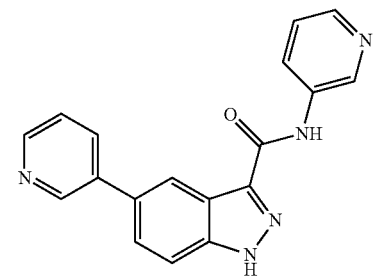 [SMILES: O=C(Nc1cccnc1)c1n[nH]c2ccc(-c3cccnc3)cc12] |
|---|---|
| 5 | 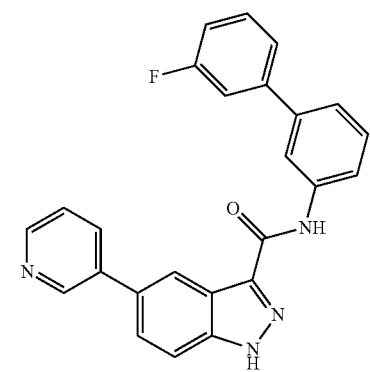 [SMILES: O=C(Nc1cccc(-c2cccc(F)c2)c1)c1n[nH]c2ccc(-c3cccnc3)cc12] |
| 6 | 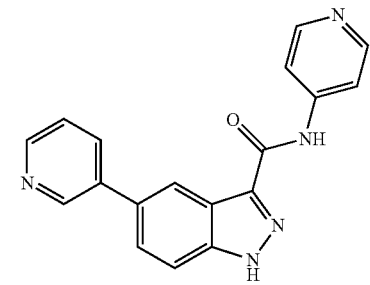 [SMILES: O=C(Nc1ccncc1)c1n[nH]c2ccc(-c3cccnc3)cc12] |
| 7 | 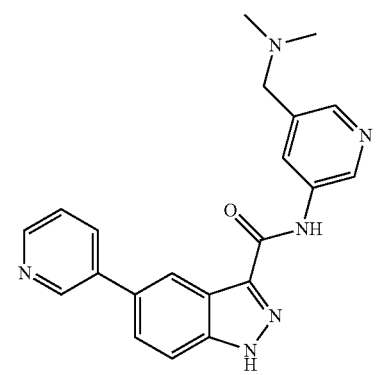 [SMILES: CN(C)Cc1cncc(NC(=O)c2n[nH]c3ccc(-c4cccnc4)cc23)c1] |

TABLE 1-continued
8
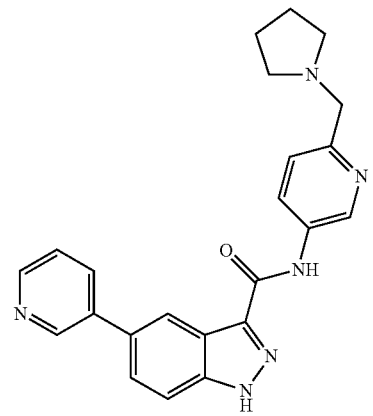 [SMILES: O=C(Nc1ccc(CN2CCCC2)nc1)c1n[nH]c2ccc(-c3cccnc3)cc12]
9
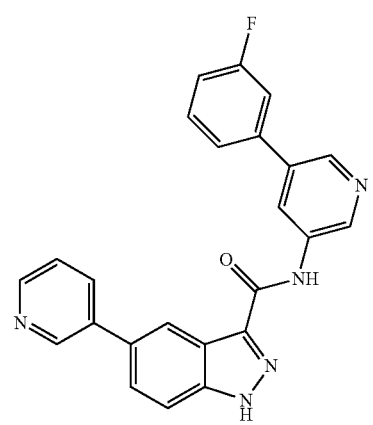 [SMILES: O=C(Nc1cncc(-c2cccc(F)c2)c1)c1n[nH]c2ccc(-c3cccnc3)cc12]
10
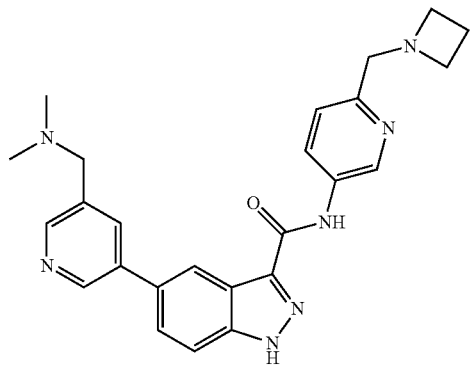 [SMILES: CN(C)Cc1cncc(-c2ccc3[nH]nc(C(=O)Nc4ccc(CN5CCC5)nc4)c3c2)c1]
11
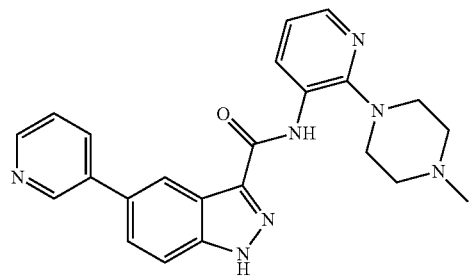 [SMILES: CN1CCN(c2ncccc2NC(=O)c2n[nH]c3ccc(-c4cccnc4)cc23)CC1]
12
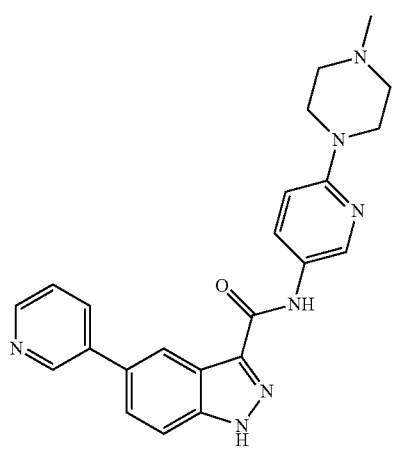 [SMILES: CN1CCN(c2ccc(NC(=O)c3n[nH]c4ccc(-c5cccnc5)cc34)cn2)CC1]
13
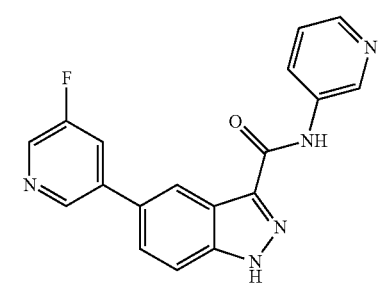 [SMILES: O=C(Nc1cccnc1)c1n[nH]c2ccc(-c3cncc(F)c3)cc12]
14
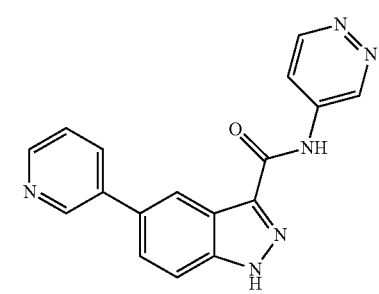 [SMILES: O=C(Nc1ccnnc1)c1n[nH]c2ccc(-c3cccnc3)cc12]
15
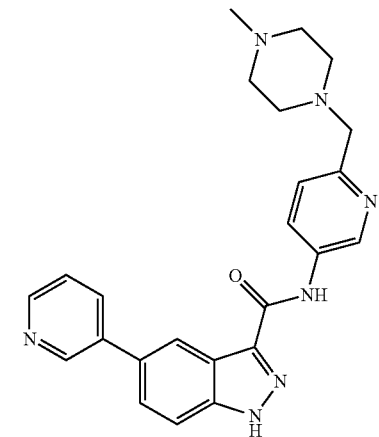 [SMILES: CN1CCN(Cc2ccc(NC(=O)c3n[nH]c4ccc(-c5cccnc5)cc34)cn2)CC1]

TABLE 1-continued
16 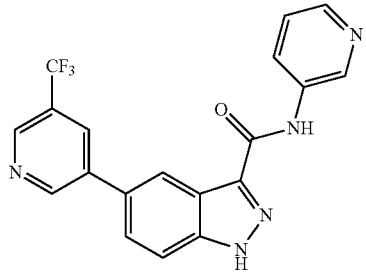 [SMILES: O=C(Nc1cccnc1)c1n[nH]c2ccc(-c3cncc(C(F)(F)F)c3)cc12]
17 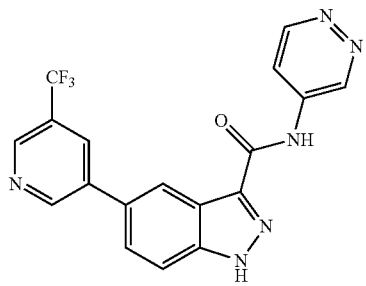 [SMILES: O=C(Nc1ccnnc1)c1n[nH]c2ccc(-c3cncc(C(F)(F)F)c3)cc12]
18 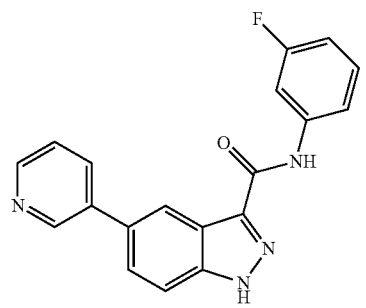 [SMILES: O=C(Nc1cccc(F)c1)c1n[nH]c2ccc(-c3cccnc3)cc12]
19 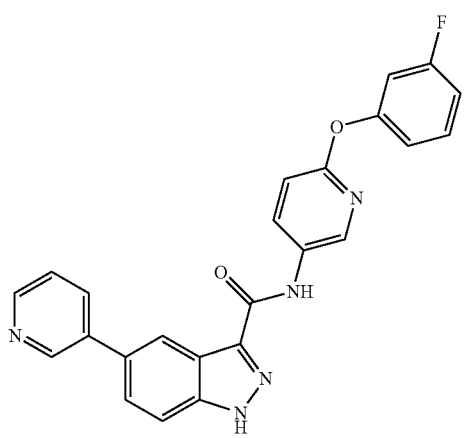 [SMILES: O=C(Nc1ccc(Oc2cccc(F)c2)nc1)c1n[nH]c2ccc(-c3cccnc3)cc12]
TABLE 1-continued
20 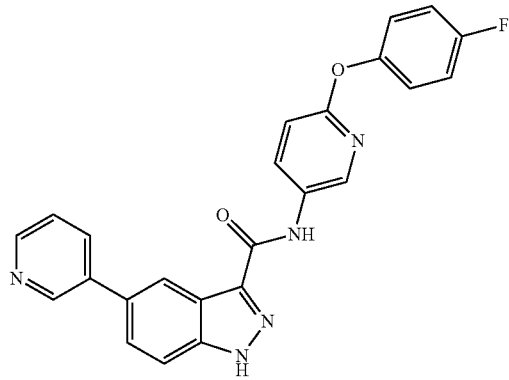 [SMILES: O=C(Nc1ccc(Oc2ccc(F)cc2)nc1)c1n[nH]c2ccc(-c3cccnc3)cc12]
21 
22 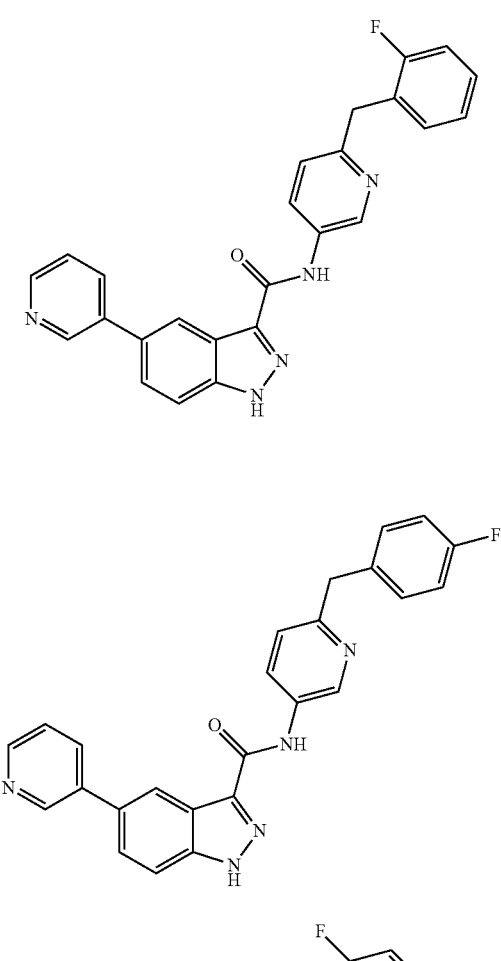
23 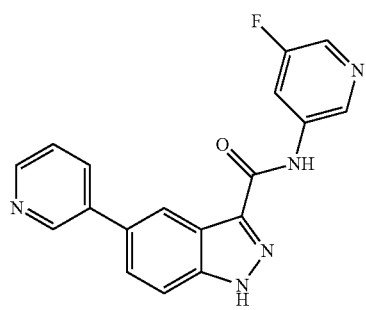 [SMILES: O=C(Nc1cncc(F)c1)c1n[nH]c2ccc(-c3cccnc3)cc12]

TABLE 1-continued
| | |
|---|---|
| 24 | 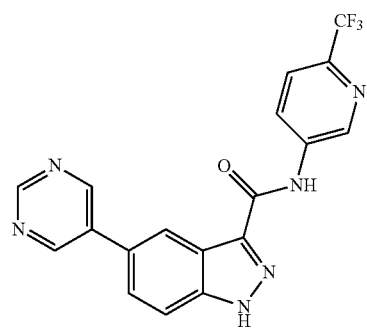 [SMILES: O=C(Nc1ccc(C(F)(F)F)nc1)c1n[nH]c2ccc(-c3cncnc3)cc12] |
| 25 | 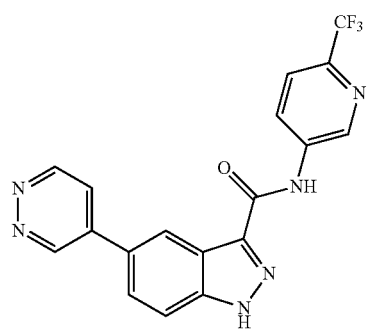 [SMILES: O=C(Nc1ccc(C(F)(F)F)nc1)c1n[nH]c2ccc(-c3ccnnc3)cc12] |
| 26 | 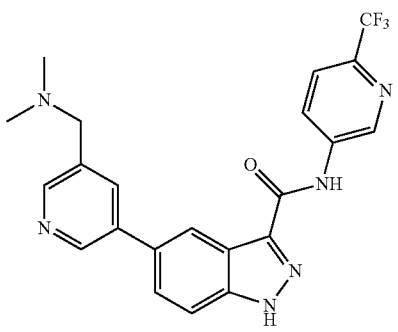 [SMILES: CN(C)Cc1cncc(-c2ccc3[nH]nc(C(=O)Nc4ccc(C(F)(F)F)nc4)c3c2)c1] |
| 27 | 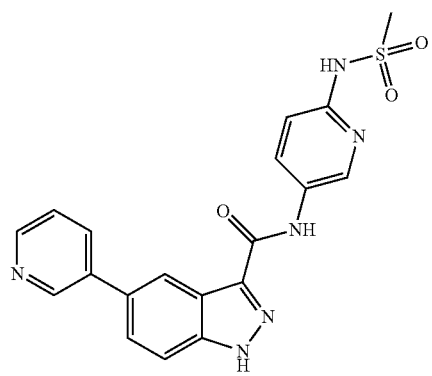 [SMILES: CS(=O)(=O)Nc1ccc(NC(=O)c2n[nH]c3ccc(-c4cccnc4)cc23)cn1] |
| 28 | 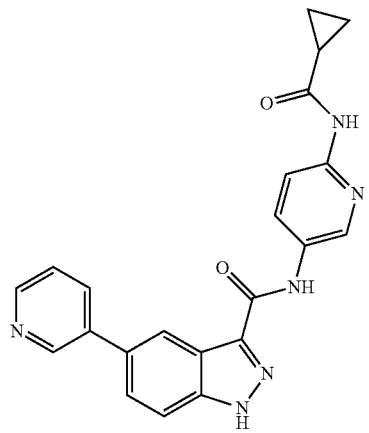 [SMILES: O=C(Nc1ccc(NC(=O)C2CC2)nc1)c1n[nH]c2ccc(-c3cccnc3)cc12] |
| 29 | 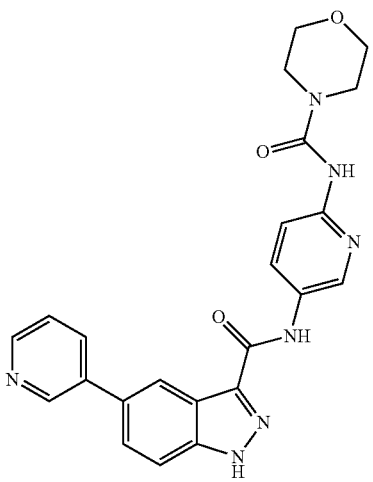 [SMILES: O=C(Nc1ccc(NC(=O)N2CCOCC2)nc1)c1n[nH]c2ccc(-c3cccnc3)cc12] |
| 30 | 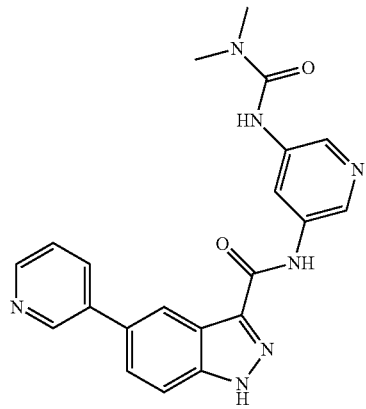 [SMILES: CN(C)C(=O)Nc1cncc(NC(=O)c2n[nH]c3ccc(-c4cccnc4)cc23)c1] |
| 31 | 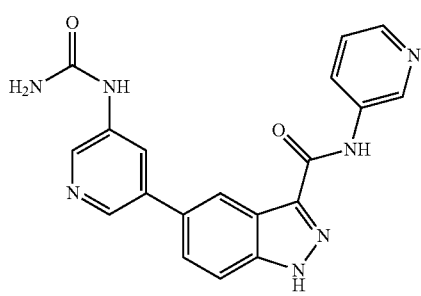 [SMILES: NC(=O)Nc1cncc(-c2ccc3[nH]nc(C(=O)Nc4cccnc4)c3c2)c1] |

TABLE 1-continued
32
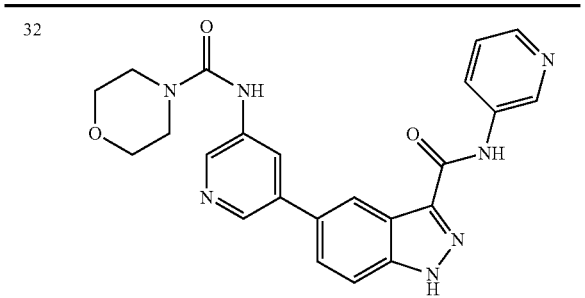
33
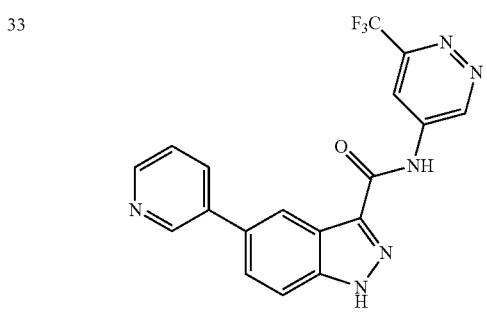
34
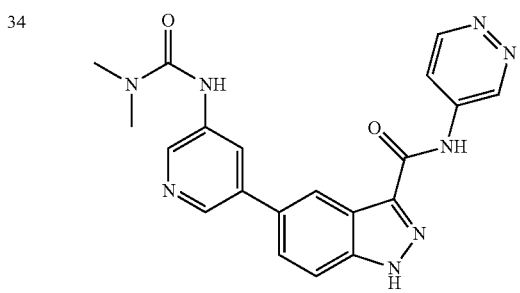
35
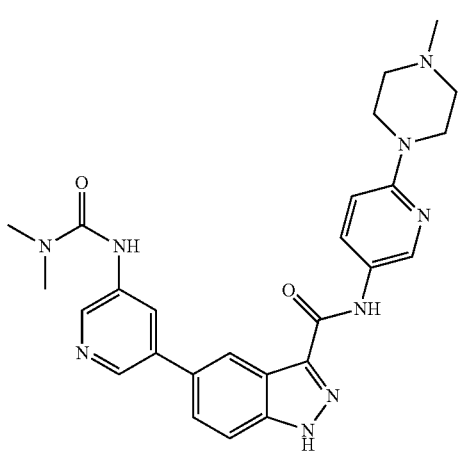 [SMILES: CN1CCN(c2ccc(NC(=O)c3n[nH]c4ccc(-c5cncc(NC(=O)N(C)C)c5)cc34)cn2)CC1]
TABLE 1-continued
36
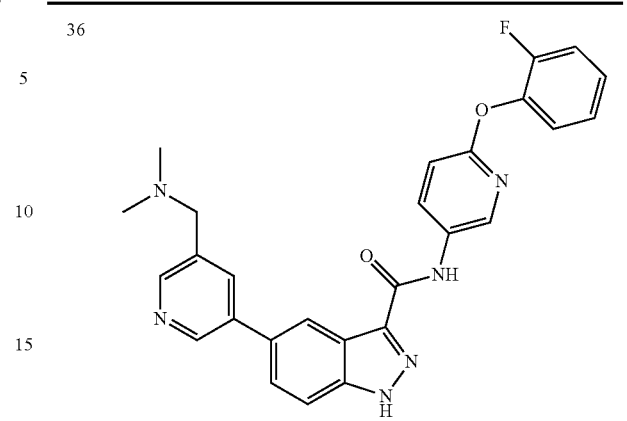
37
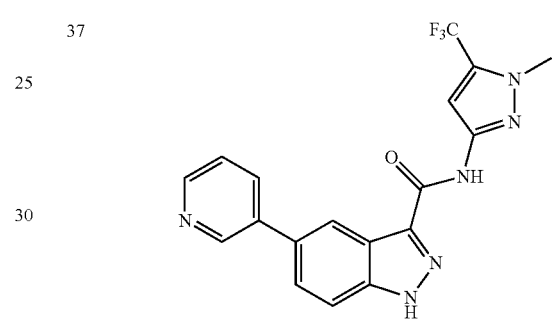
38
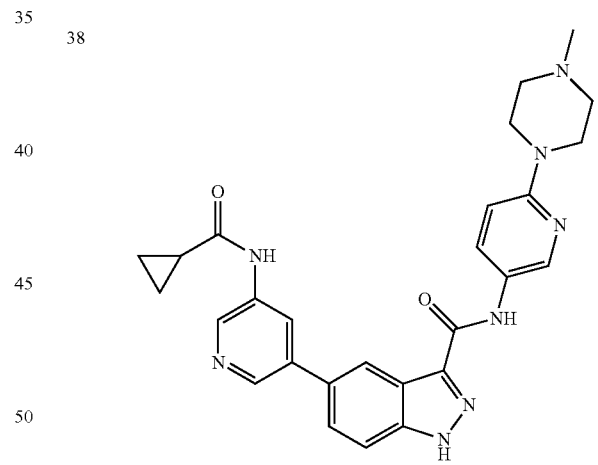
39
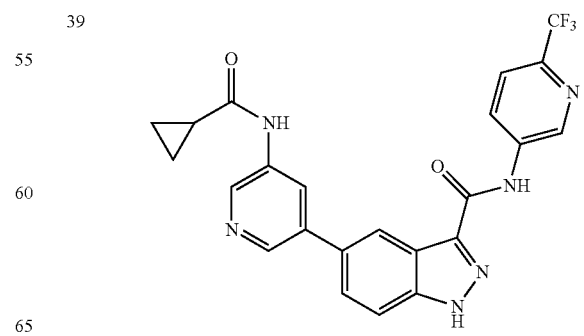

TABLE 1-continued
| 40 | 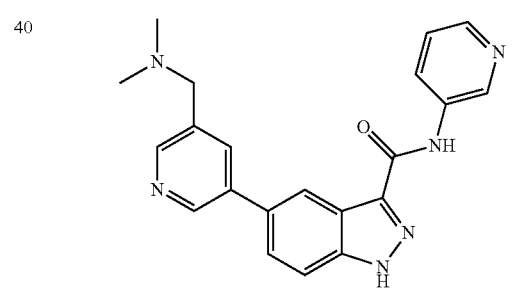 |
| --- | --- |
| 41 | 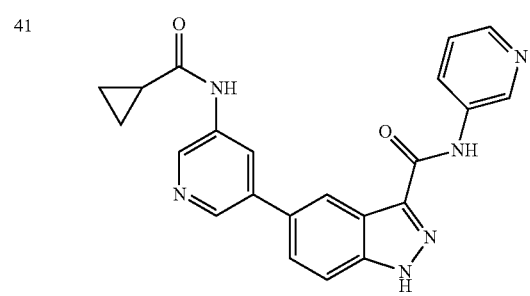 |
| 42 | 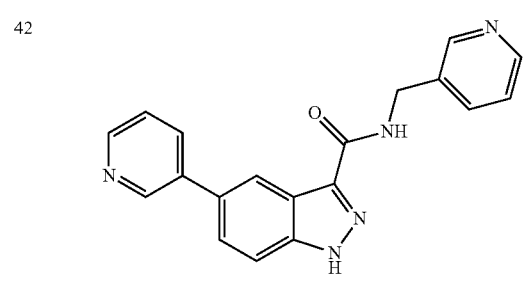 |
| 43 | 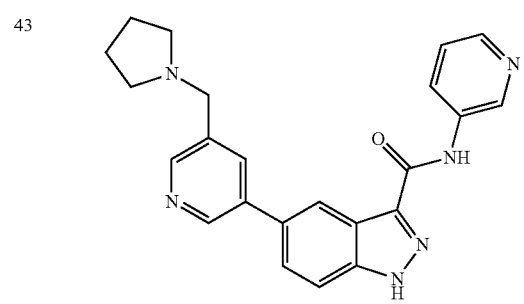 |
| 44 | 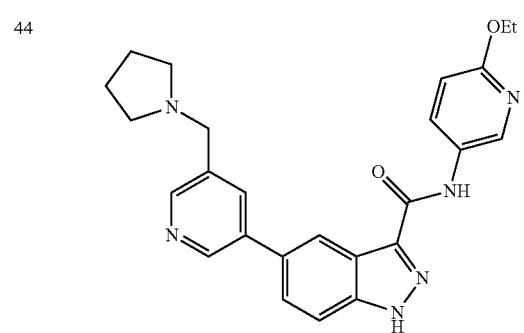 |
| 45 | 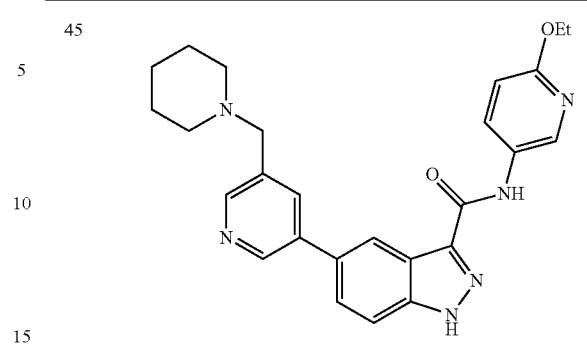 |
| 46 | 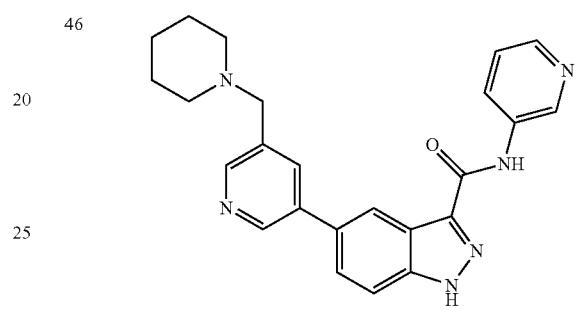 |
| 47 | 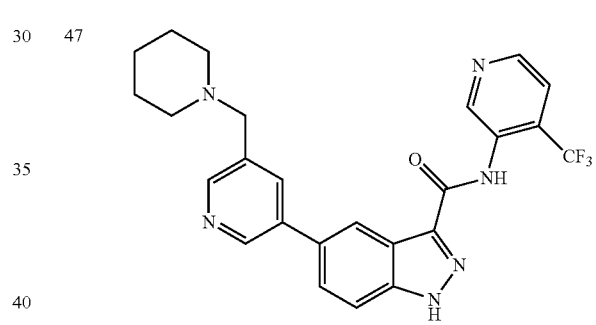 |
| 48 | 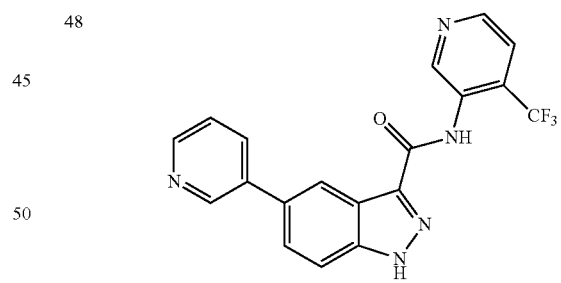 |
| 49 | 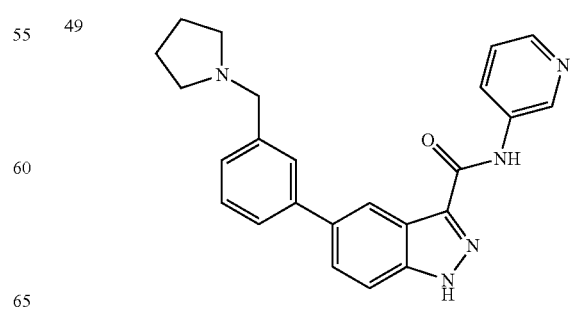 |

TABLE 1-continued
50 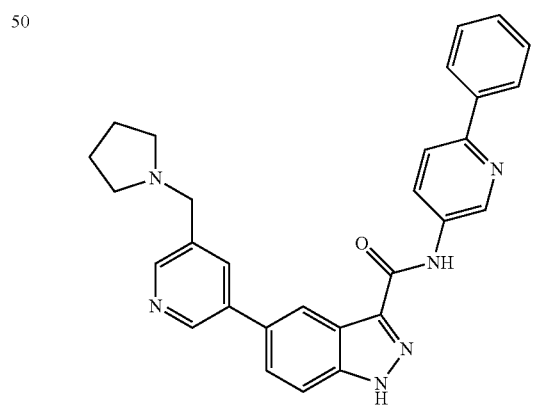
51 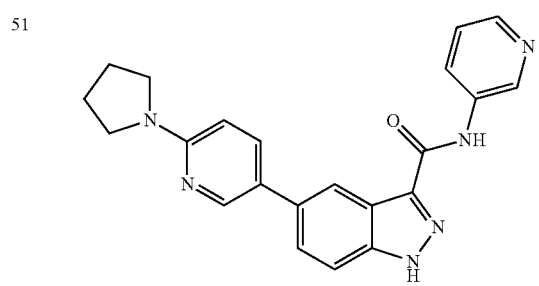
52 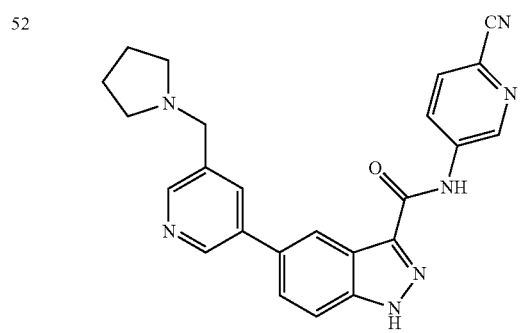
53 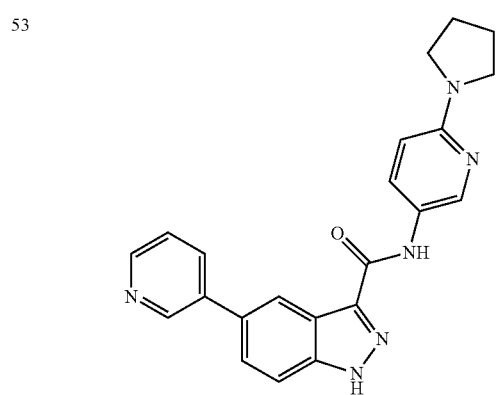
54 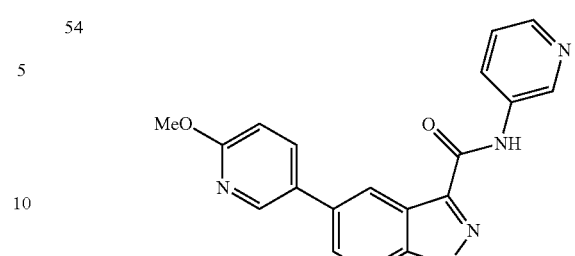
55 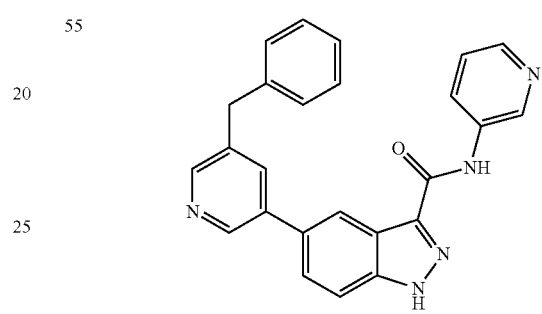
56 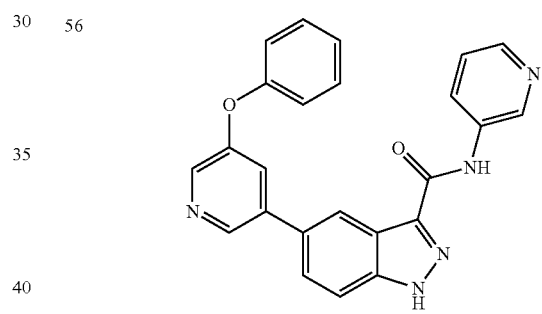
57 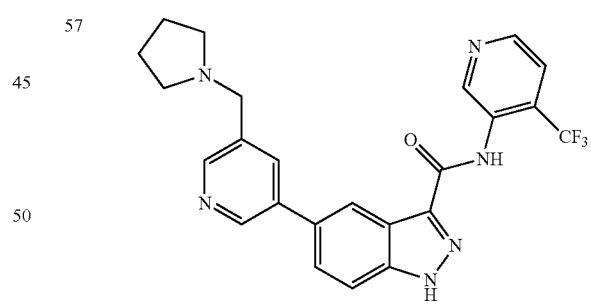
58 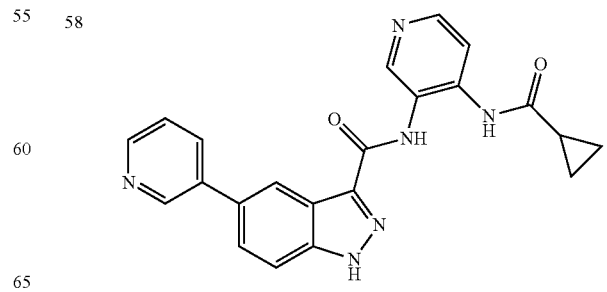

TABLE 1-continued
59 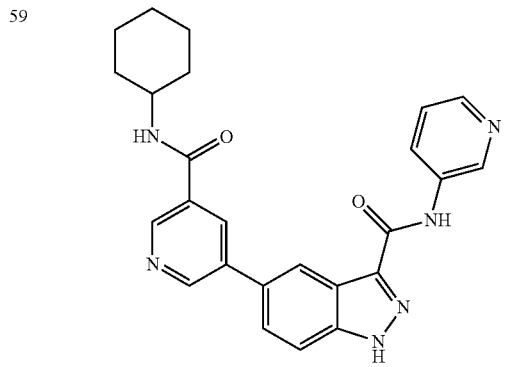
60 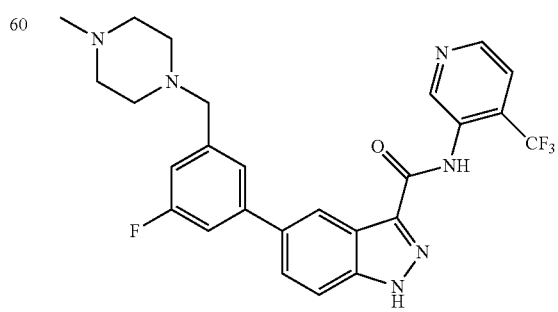
61 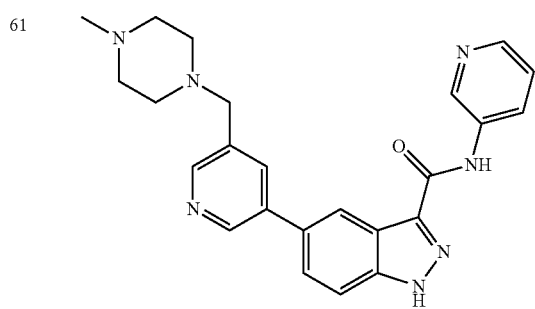
62 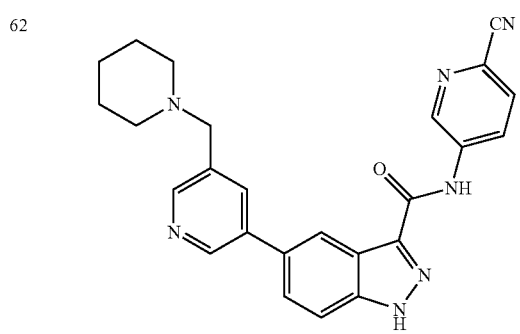
63 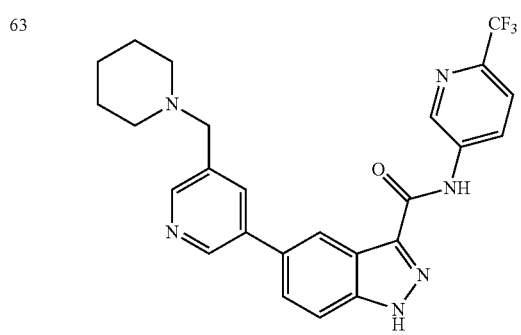
TABLE 1-continued
64 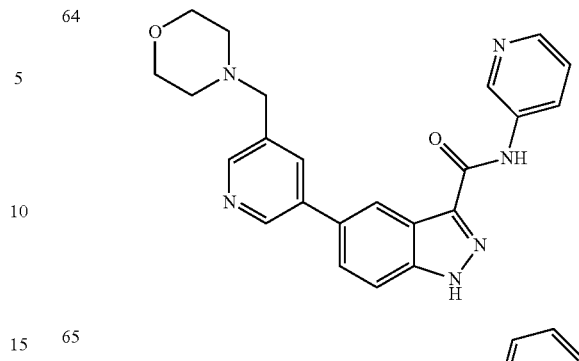
65 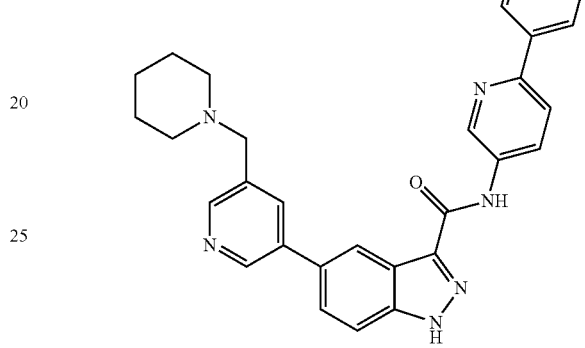
66 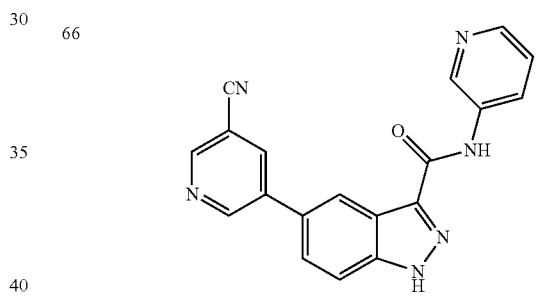
67 
68 

TABLE 1-continued
69
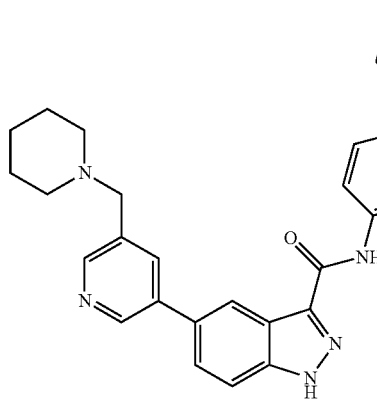
70
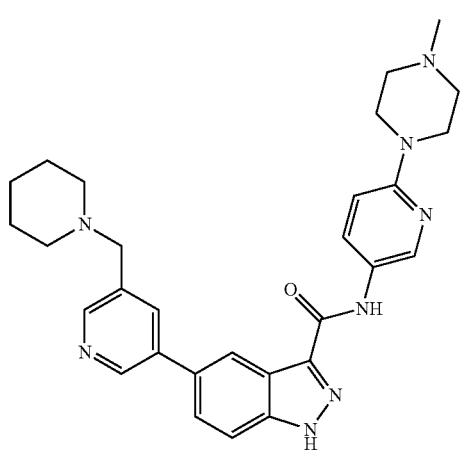 [SMILES: CN1CCN(c2ccc(NC(=O)c3n[nH]c4ccc(-c5cncc(CN6CCCCC6)c5)cc34)cn2)CC1]
71
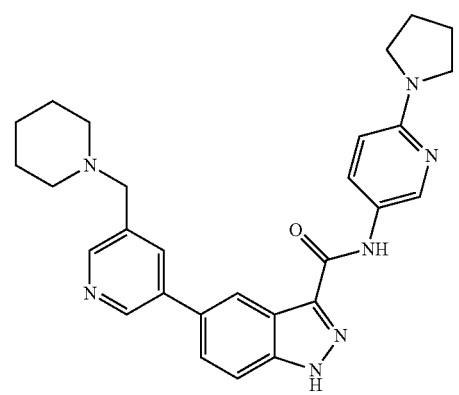 [SMILES: O=C(Nc1ccc(N2CCCC2)nc1)c1n[nH]c2ccc(-c3cncc(CN4CCCCC4)c3)cc12]
TABLE 1-continued
72
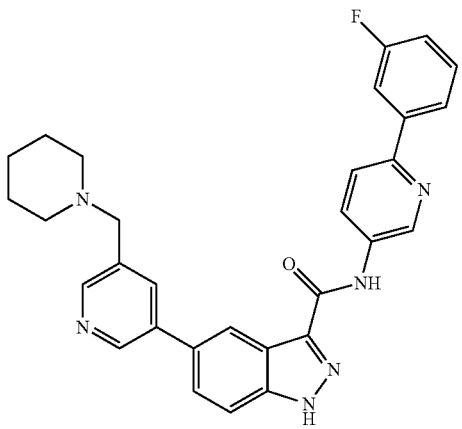 [SMILES: O=C(Nc1ccc(-c2cccc(F)c2)nc1)c1n[nH]c2ccc(-c3cncc(CN4CCCCC4)c3)cc12]
73
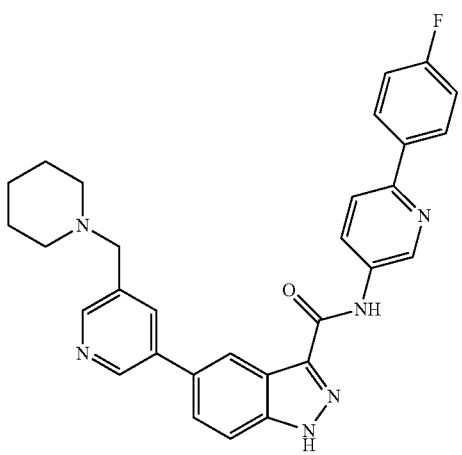 [SMILES: O=C(Nc1ccc(-c2ccc(F)cc2)nc1)c1n[nH]c2ccc(-c3cncc(CN4CCCCC4)c3)cc12]
74
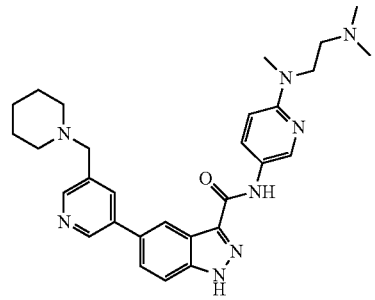 [SMILES: CN(C)CCN(C)c1ccc(NC(=O)c2n[nH]c3ccc(-c4cncc(CN5CCCCC5)c4)cc23)cn1]
75
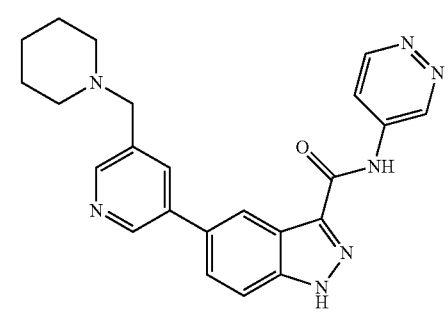 [SMILES: O=C(Nc1ccnnc1)c1n[nH]c2ccc(-c3cncc(CN4CCCCC4)c3)cc12]

TABLE 1-continued
| | |
|---|---|
| 76 | 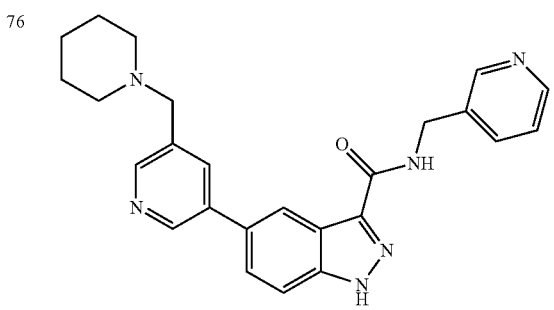 |
| 77 | 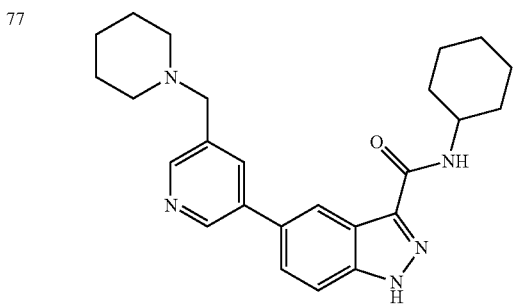 |
| 78 | 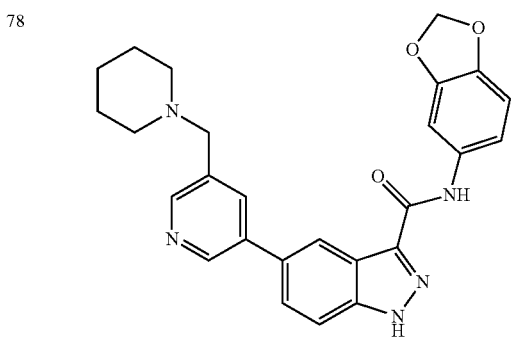 |
| 79 | 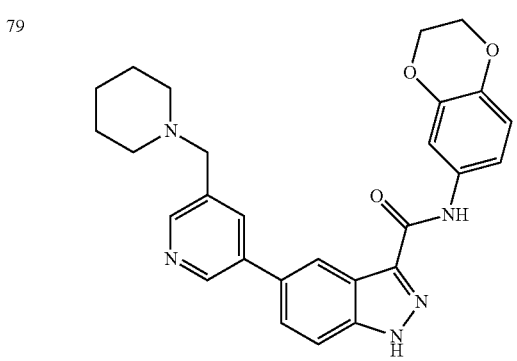 |
| 80 | 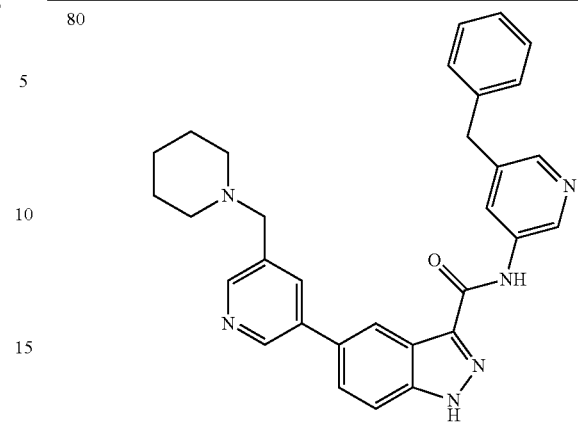 |
| 81 | 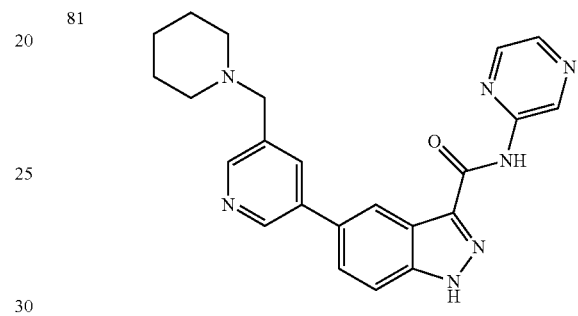 |
| 82 | 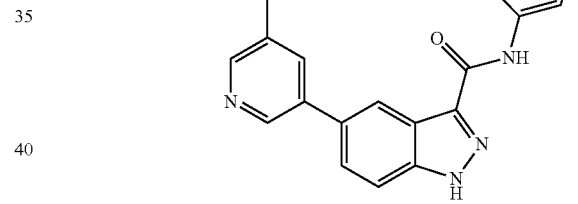 |
| 83 | 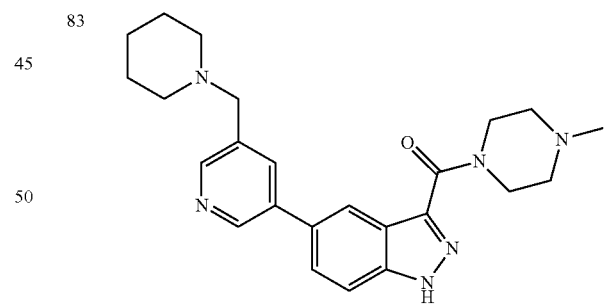 |
| 84 | 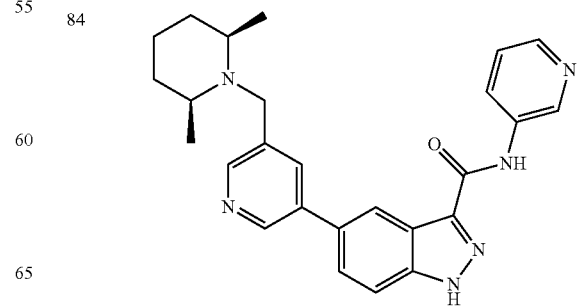 |

TABLE 1-continued
85 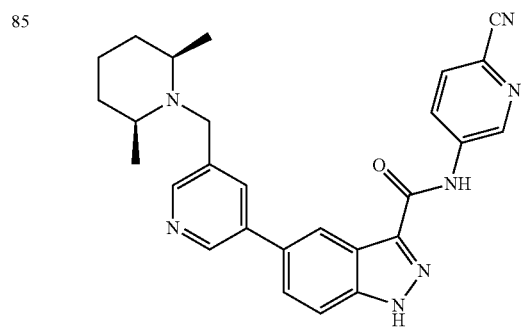
86 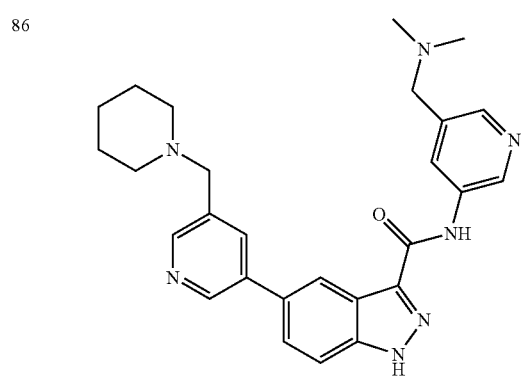
87 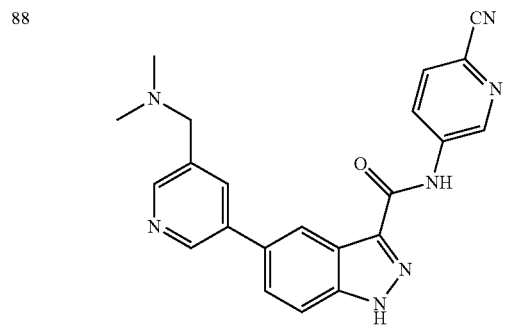
88 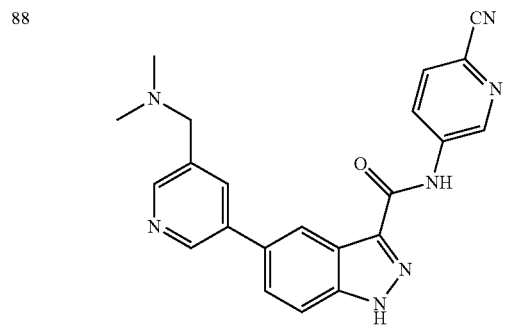
89 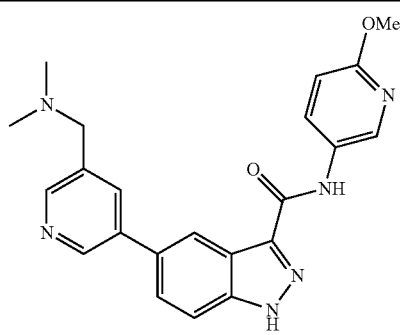
90 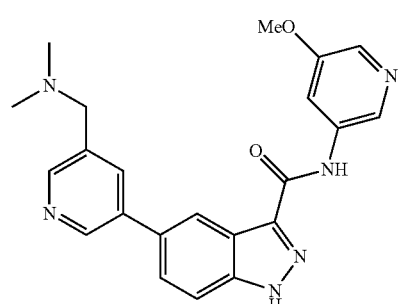
91 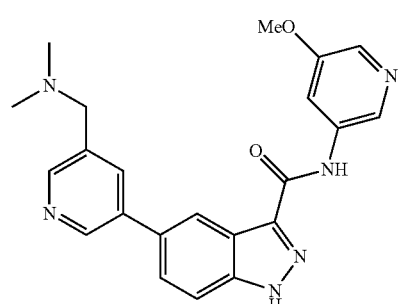
92 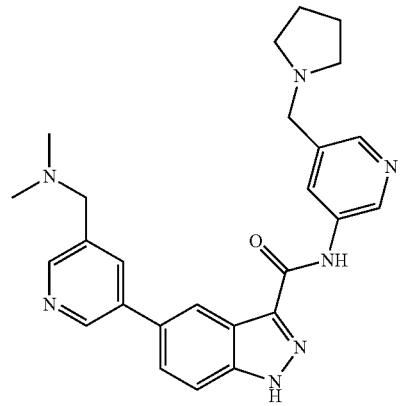 [SMILES: CN(C)Cc1cncc(-c2ccc3[nH]nc(C(=O)Nc4cncc(CN5CCCC5)c4)c3c2)c1]

TABLE 1-continued
93
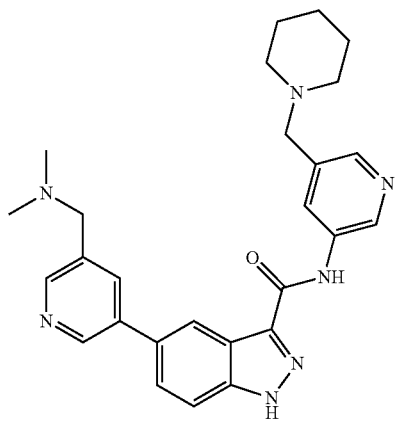 [SMILES: CN(C)Cc1cncc(-c2ccc3[nH]nc(C(=O)Nc4cncc(CN5CCCCC5)c4)c3c2)c1]
94
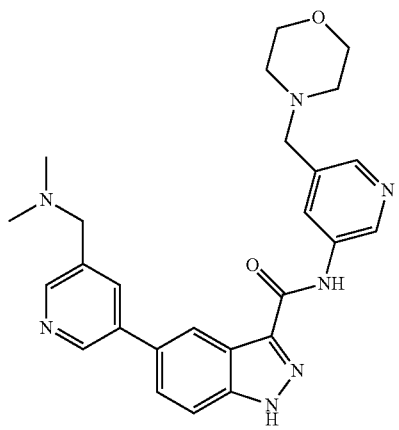 [SMILES: CN(C)Cc1cncc(-c2ccc3[nH]nc(C(=O)Nc4cncc(CN5CCOCC5)c4)c3c2)c1]
95
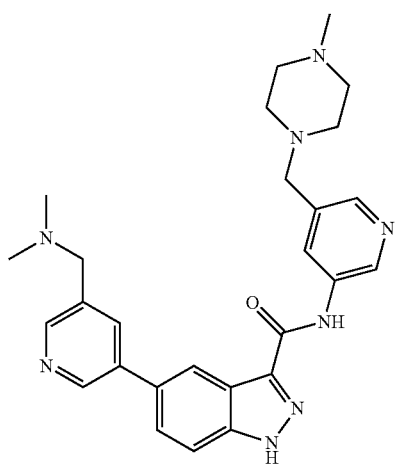 [SMILES: CN(C)Cc1cncc(-c2ccc3[nH]nc(C(=O)Nc4cncc(CN5CCN(C)CC5)c4)c3c2)c1]
96
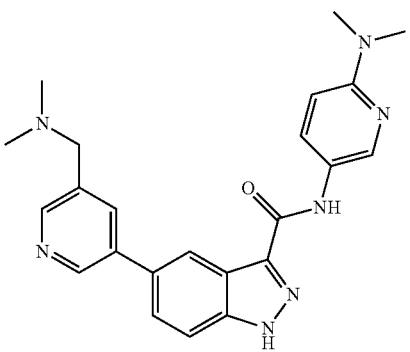
TABLE 1-continued
97
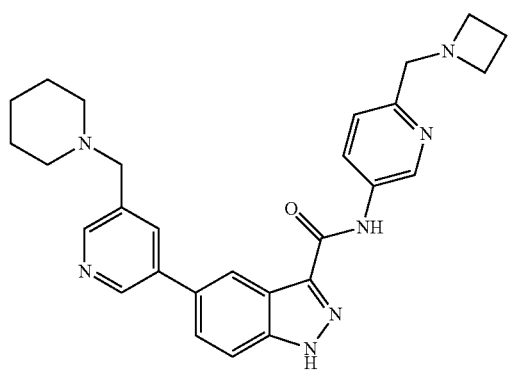 [SMILES: O=C(Nc1ccc(CN2CCC2)nc1)c1n[nH]c2ccc(-c3cncc(CN4CCCCC4)c3)cc12]
98
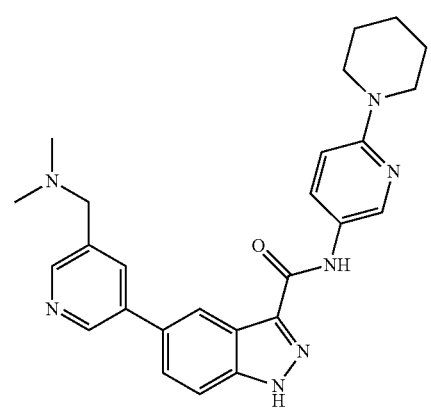 [SMILES: CN(C)Cc1cncc(-c2ccc3[nH]nc(C(=O)Nc4ccc(N5CCCCC5)nc4)c3c2)c1]
99
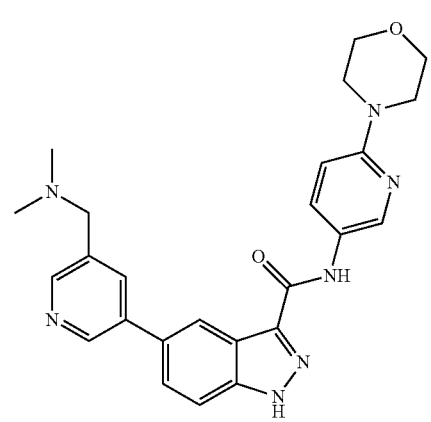 [SMILES: CN(C)Cc1cncc(-c2ccc3[nH]nc(C(=O)Nc4ccc(N5CCOCC5)nc4)c3c2)c1]
100
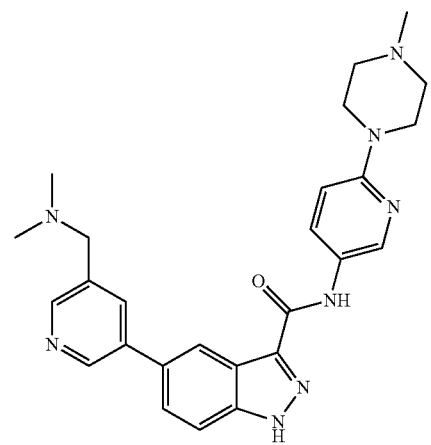 [SMILES: CN(C)Cc1cncc(-c2ccc3[nH]nc(C(=O)Nc4ccc(N5CCN(C)CC5)nc4)c3c2)c1]

TABLE 1-continued
101 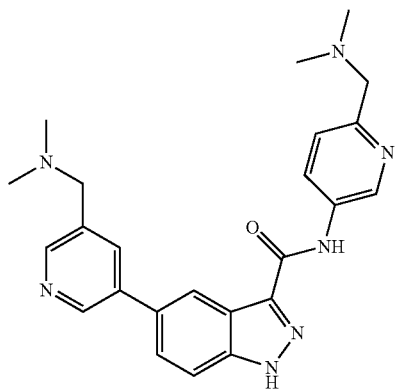 [SMILES: CN(C)Cc1cncc(-c2ccc3[nH]nc(C(=O)Nc4ccc(CN(C)C)nc4)c3c2)c1]
102 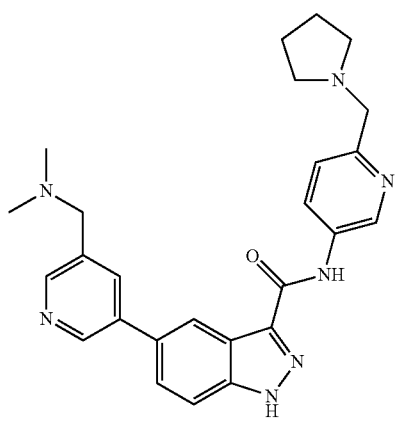 [SMILES: CN(C)Cc1cncc(-c2ccc3[nH]nc(C(=O)Nc4ccc(CN5CCCC5)nc4)c3c2)c1]
103 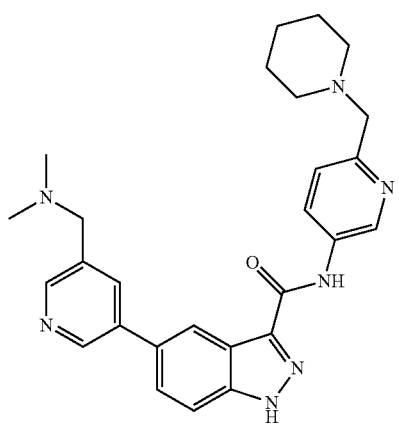 [SMILES: CN(C)Cc1cncc(-c2ccc3[nH]nc(C(=O)Nc4ccc(CN5CCCCC5)nc4)c3c2)c1]
104 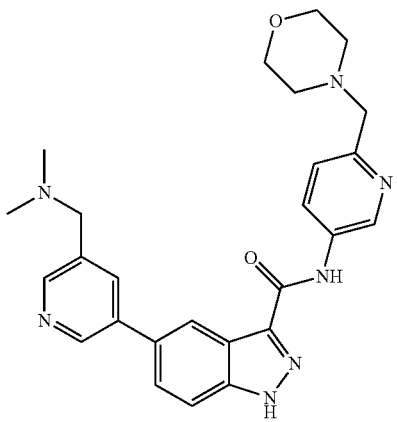 [SMILES: CN(C)Cc1cncc(-c2ccc3[nH]nc(C(=O)Nc4ccc(CN5CCOCC5)nc4)c3c2)c1]
105 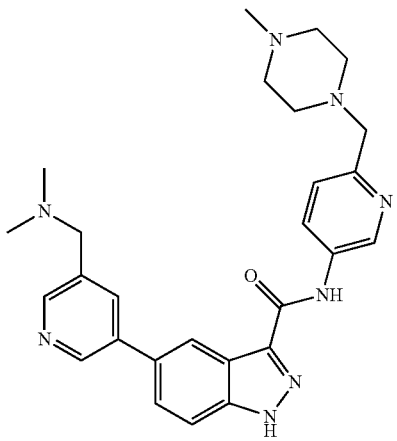 [SMILES: CN(C)Cc1cncc(-c2ccc3[nH]nc(C(=O)Nc4ccc(CN5CCN(C)CC5)nc4)c3c2)c1]
106 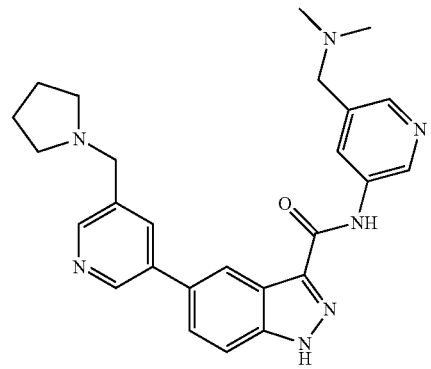 [SMILES: CN(C)Cc1cncc(NC(=O)c2n[nH]c3ccc(-c4cncc(CN5CCCC5)c4)cc23)c1]
107 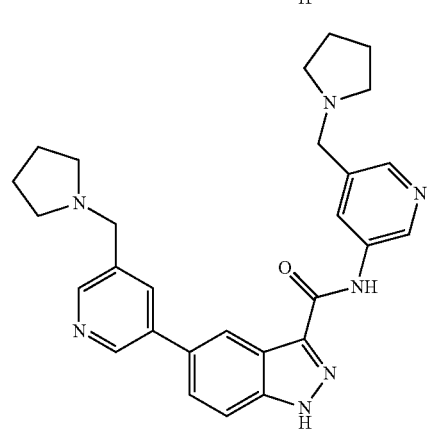

TABLE 1-continued
108 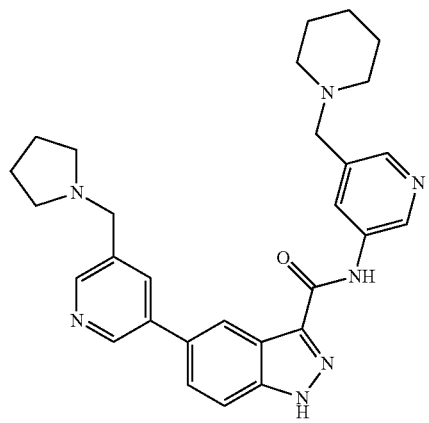 [SMILES: O=C(Nc1cncc(CN2CCCCC2)c1)c1n[nH]c2ccc(-c3cncc(CN4CCCC4)c3)cc12]
109 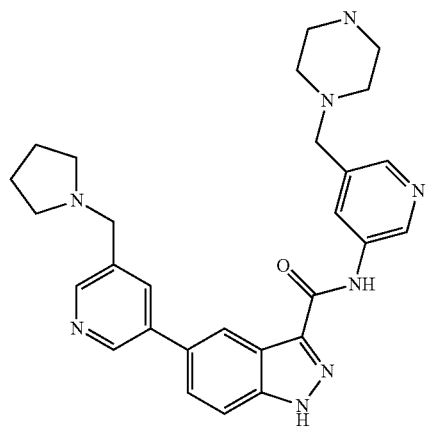 [SMILES: O=C(Nc1cncc(CN2CCNCC2)c1)c1n[nH]c2ccc(-c3cncc(CN4CCCC4)c3)cc12]
110 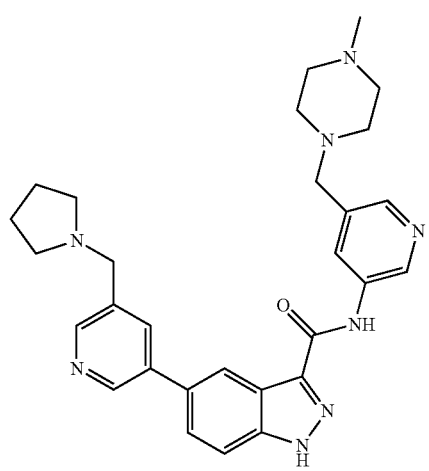 [SMILES: CN1CCN(Cc2cncc(NC(=O)c3n[nH]c4ccc(-c5cncc(CN6CCCC6)c5)cc34)c2)CC1]
111 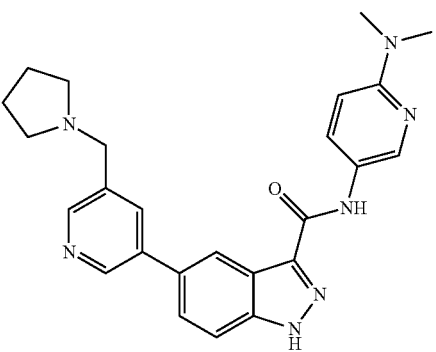 [SMILES: CN(C)c1ccc(NC(=O)c2n[nH]c3ccc(-c4cncc(CN5CCCC5)c4)cc23)cn1]
TABLE 1-continued
112 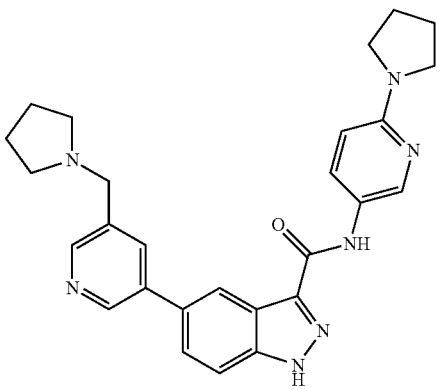 [SMILES: O=C(Nc1ccc(N2CCCC2)nc1)c1n[nH]c2ccc(-c3cncc(CN4CCCC4)c3)cc12]
113 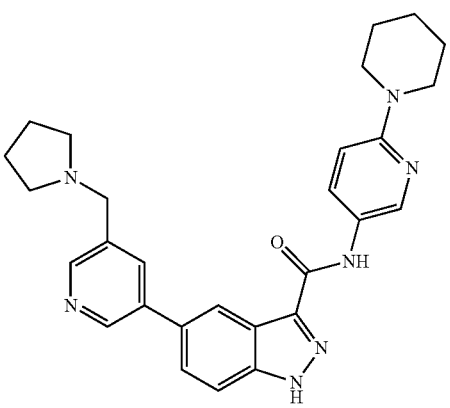 [SMILES: O=C(Nc1ccc(N2CCCCC2)nc1)c1n[nH]c2ccc(-c3cncc(CN4CCCC4)c3)cc12]
114 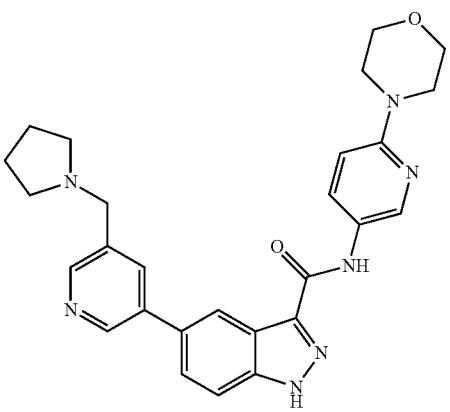 [SMILES: O=C(Nc1ccc(N2CCOCC2)nc1)c1n[nH]c2ccc(-c3cncc(CN4CCCC4)c3)cc12]
115 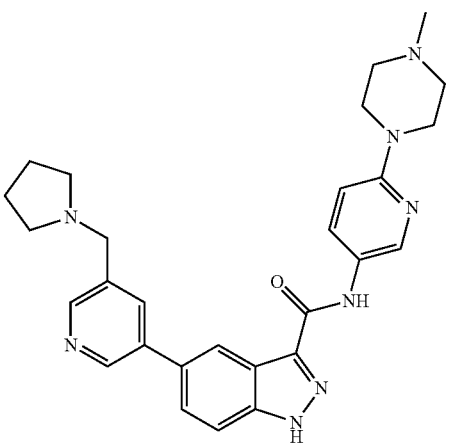 [SMILES: CN1CCN(c2ccc(NC(=O)c3n[nH]c4ccc(-c5cncc(CN6CCCC6)c5)cc34)cn2)CC1]

TABLE 1-continued
116
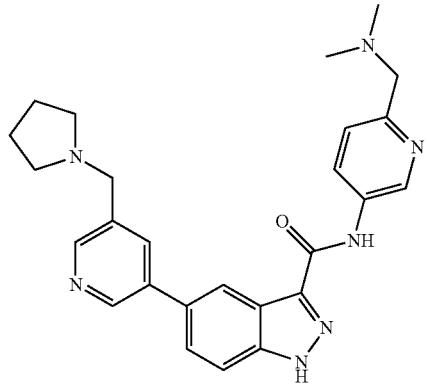 [SMILES: CN(C)Cc1ccc(NC(=O)c2n[nH]c3ccc(-c4cncc(CN5CCCC5)c4)cc23)cn1]
117
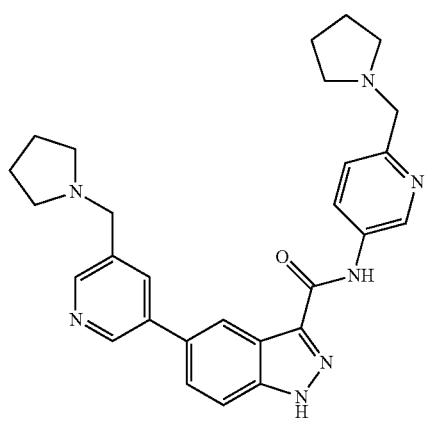 [SMILES: O=C(Nc1ccc(CN2CCCC2)nc1)c1n[nH]c2ccc(-c3cncc(CN4CCCC4)c3)cc12]
118
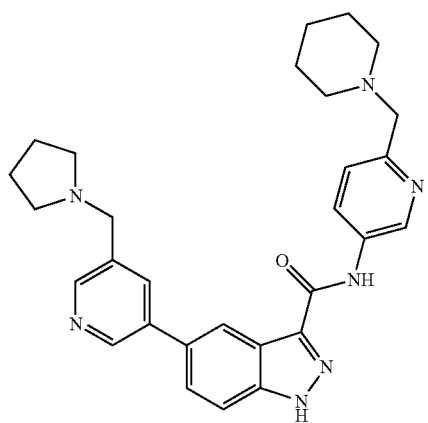 [SMILES: O=C(Nc1ccc(CN2CCOCC2)nc1)c1n[nH]c2ccc(-c3cncc(CN4CCCC4)c3)cc12]
TABLE 1-continued
119
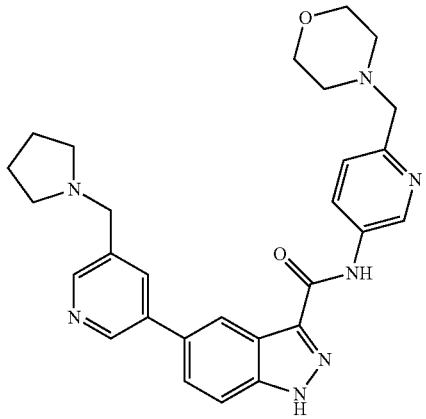
120
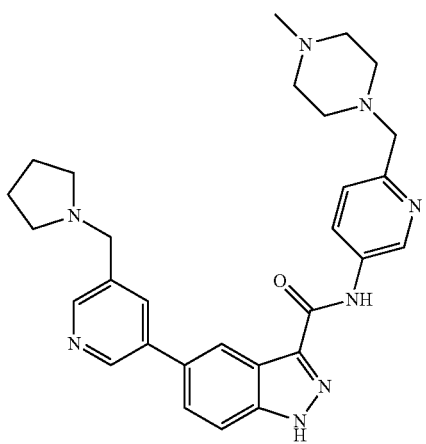 [SMILES: CN1CCN(Cc2ccc(NC(=O)c3n[nH]c4ccc(-c5cncc(CN6CCCC6)c5)cc34)cn2)CC1]
121
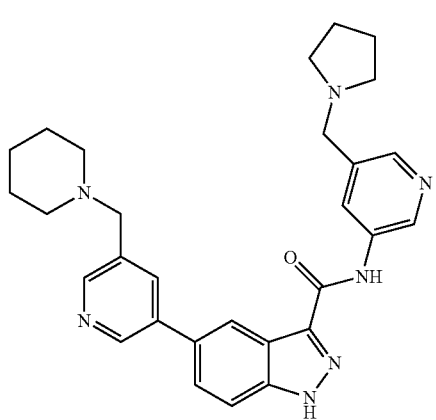 [SMILES: O=C(Nc1cncc(CN2CCCC2)c1)c1n[nH]c2ccc(-c3cncc(CN4CCCCC4)c3)cc12]

TABLE 1-continued
122
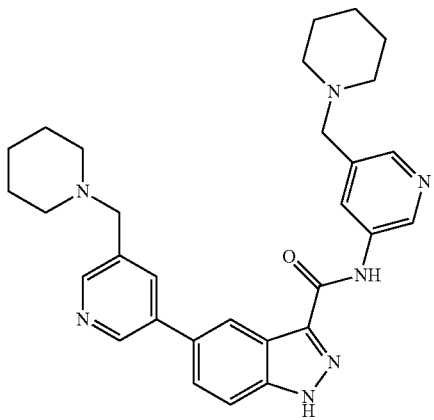 [SMILES: O=C(Nc1cncc(CN2CCCCC2)c1)c1n[nH]c2ccc(-c3cncc(CN4CCCCC4)c3)cc12]
123
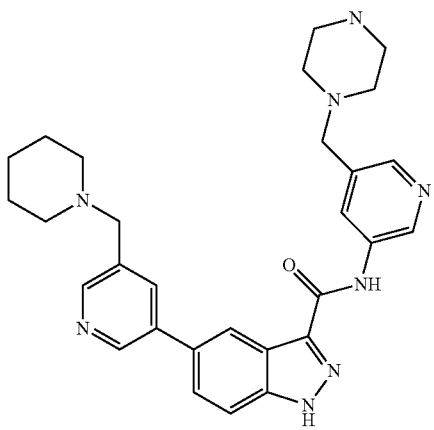 [SMILES: O=C(Nc1cncc(CN2CCNCC2)c1)c1n[nH]c2ccc(-c3cncc(CN4CCCCC4)c3)cc12]
124
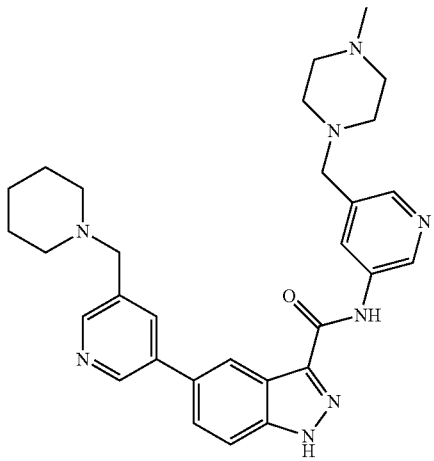 [SMILES: CN1CCN(Cc2cncc(NC(=O)c3n[nH]c4ccc(-c5cncc(CN6CCCCC6)c5)cc34)c2)CC1]
125
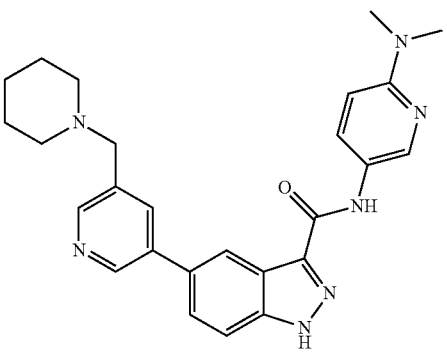 [SMILES: CN(C)c1ccc(NC(=O)c2n[nH]c3ccc(-c4cncc(CN5CCCCC5)c4)cc23)cn1]
TABLE 1-continued
126
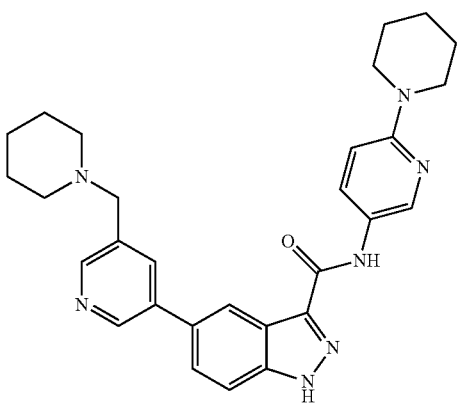 [SMILES: O=C(Nc1ccc(N2CCCCC2)nc1)c1n[nH]c2ccc(-c3cncc(CN4CCCCC4)c3)cc12]
127
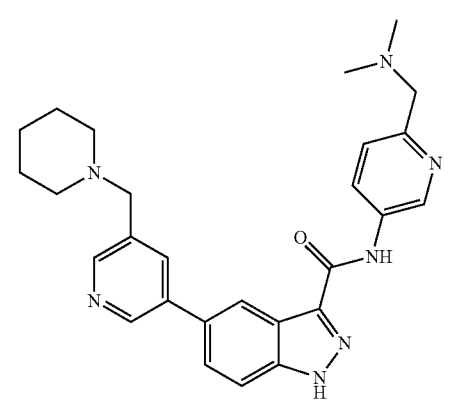 [SMILES: CN(C)Cc1ccc(NC(=O)c2n[nH]c3ccc(-c4cncc(CN5CCCCC5)c4)cc23)cn1]
128
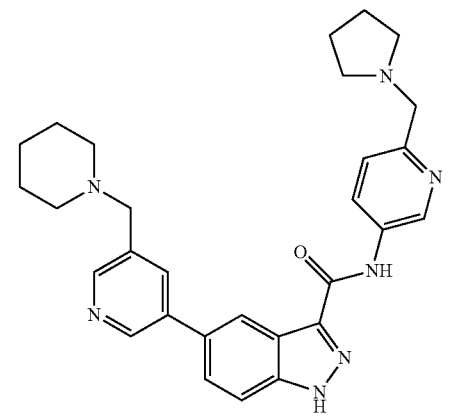 [SMILES: O=C(Nc1ccc(CN2CCCC2)nc1)c1n[nH]c2ccc(-c3cncc(CN4CCCCC4)c3)cc12]
129
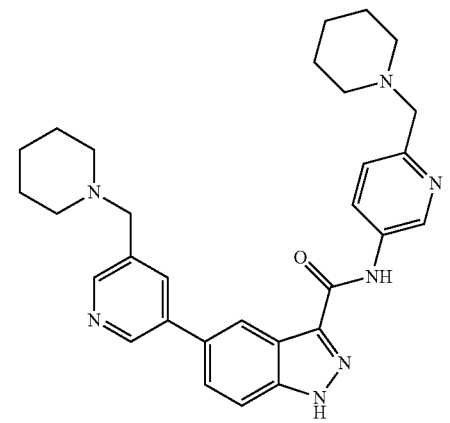 [SMILES: O=C(Nc1ccc(CN2CCCCC2)nc1)c1n[nH]c2ccc(-c3cncc(CN4CCCCC4)c3)cc12]

TABLE 1-continued
130
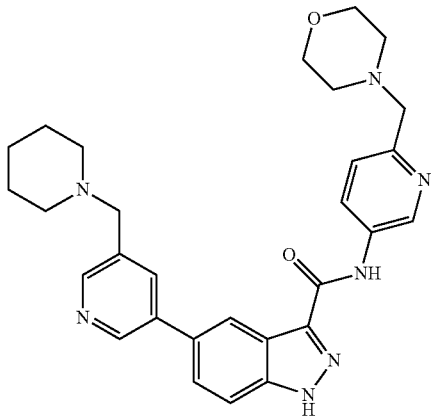
131
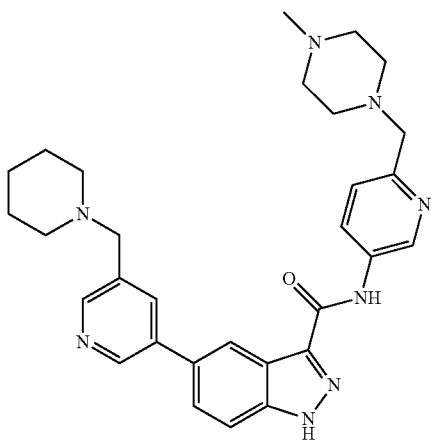 [SMILES: CN1CCN(Cc2ccc(NC(=O)c3n[nH]c4ccc(-c5cncc(CN6CCCCC6)c5)cc34)cn2)CC1]
132
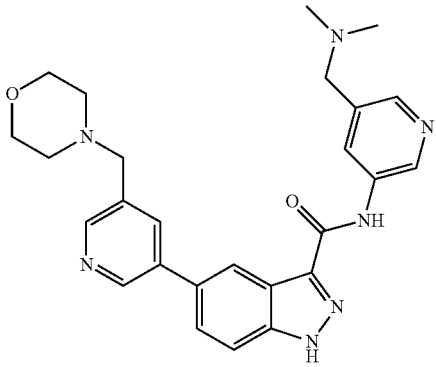 [SMILES: CN(C)Cc1cncc(NC(=O)c2n[nH]c3ccc(-c4cncc(CN5CCOCC5)c4)cc23)c1]
133
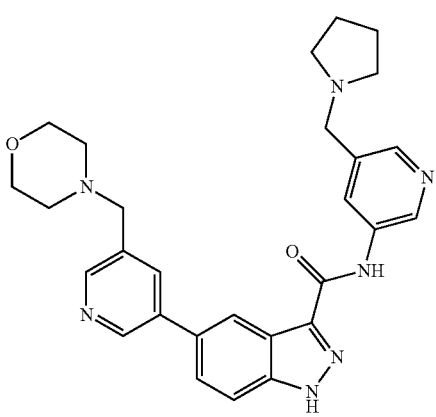 [SMILES: O=C(Nc1cncc(CN2CCCC2)c1)c1n[nH]c2ccc(-c3cncc(CN4CCOCC4)c3)cc12]
TABLE 1-continued
134
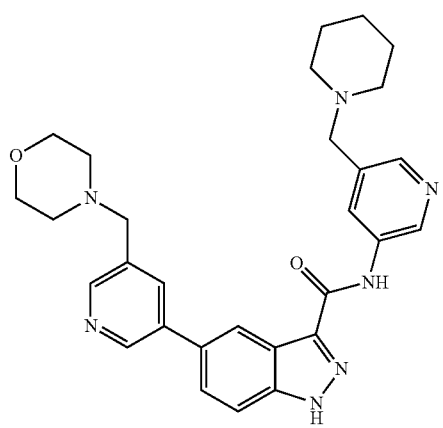 [SMILES: O=C(Nc1cncc(CN2CCCCC2)c1)c1n[nH]c2ccc(-c3cncc(CN4CCOCC4)c3)cc12]
135
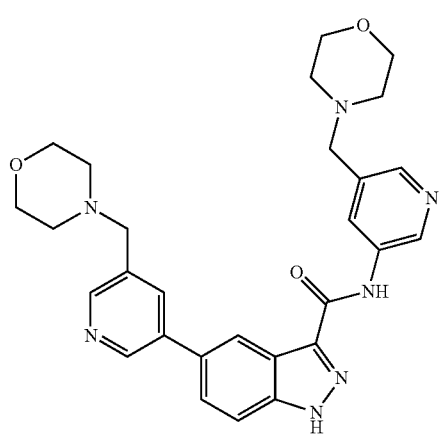 [SMILES: O=C(Nc1cncc(CN2CCOCC2)c1)c1n[nH]c2ccc(-c3cncc(CN4CCOCC4)c3)cc12]
136
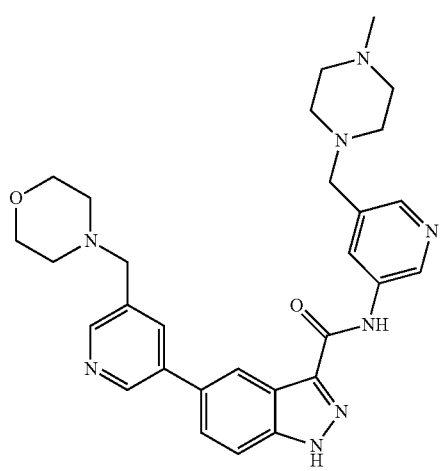 [SMILES: CN1CCN(Cc2cncc(NC(=O)c3n[nH]c4ccc(-c5cncc(CN6CCOCC6)c5)cc34)c2)CC1]

TABLE 1-continued
137
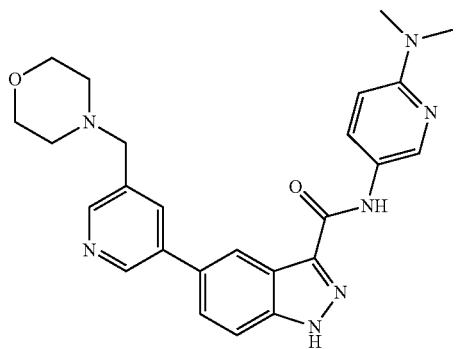 [SMILES: CN(C)c1ccc(NC(=O)c2n[nH]c3ccc(-c4cncc(CN5CCOCC5)c4)cc23)cn1]
138
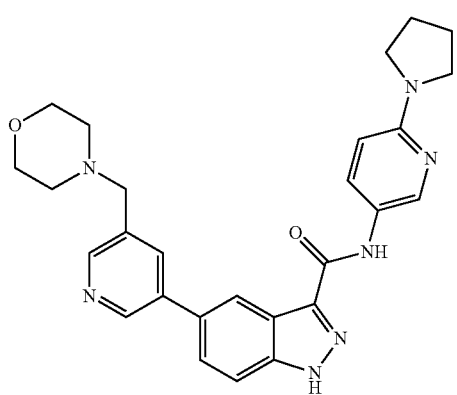 [SMILES: O=C(Nc1ccc(N2CCCC2)nc1)c1n[nH]c2ccc(-c3cncc(CN4CCOCC4)c3)cc12]
139
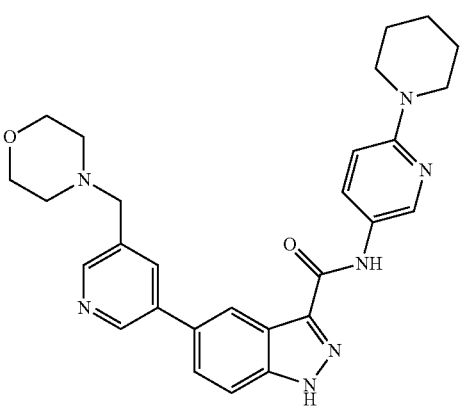 [SMILES: O=C(Nc1ccc(N2CCCCC2)nc1)c1n[nH]c2ccc(-c3cncc(CN4CCOCC4)c3)cc12]
140
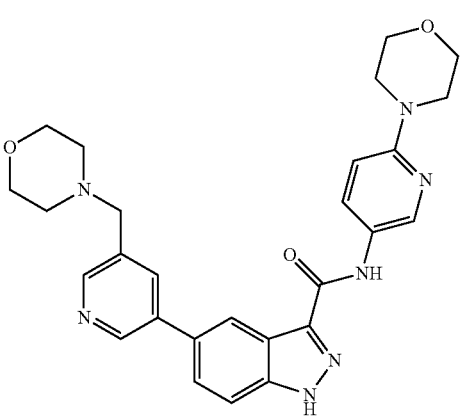 [SMILES: O=C(Nc1ccc(N2CCOCC2)nc1)c1n[nH]c2ccc(-c3cncc(CN4CCOCC4)c3)cc12]
TABLE 1-continued
141
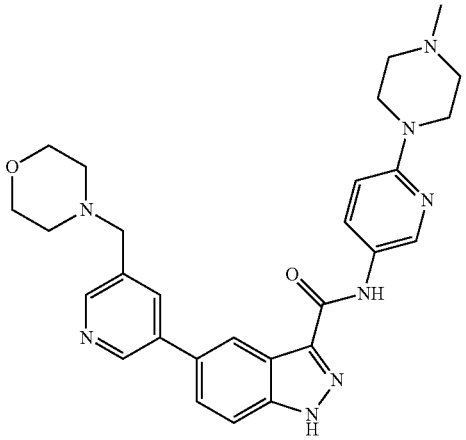 [SMILES: CN1CCN(c2ccc(NC(=O)c3n[nH]c4ccc(-c5cncc(CN6CCOCC6)c5)cc34)cn2)CC1]
142
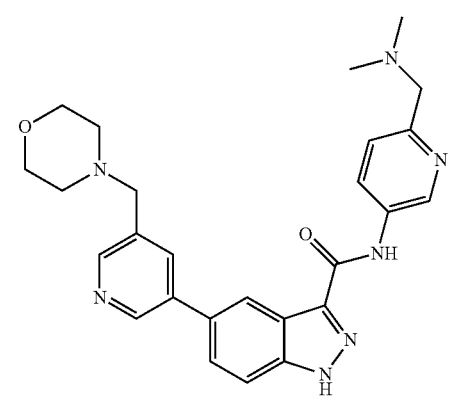 [SMILES: CN(C)Cc1ccc(NC(=O)c2n[nH]c3ccc(-c4cncc(CN5CCOCC5)c4)cc23)cn1]
143
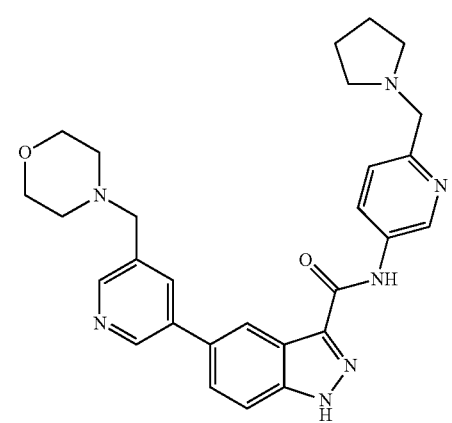 [SMILES: O=C(Nc1ccc(CN2CCCC2)nc1)c1n[nH]c2ccc(-c3cncc(CN4CCOCC4)c3)cc12]

TABLE 1-continued
144
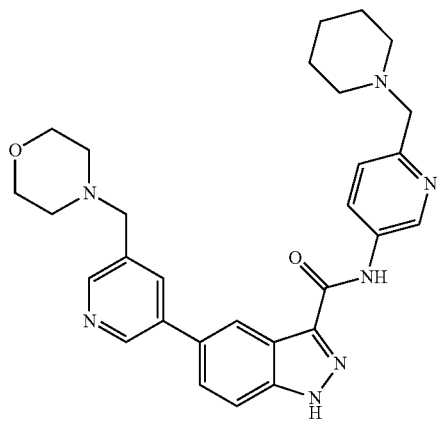
145
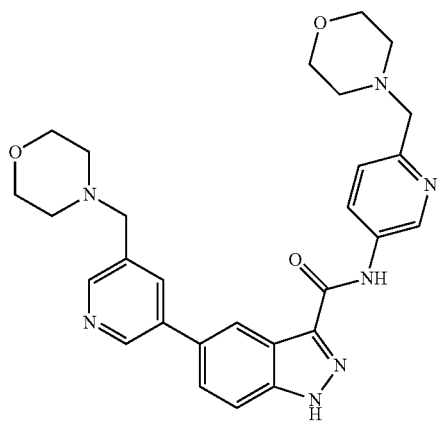 [SMILES: O=C(Nc1ccc(CN2CCCCC2)nc1)c1n[nH]c2ccc(-c3cncc(CN4CCOCC4)c3)cc12]
146
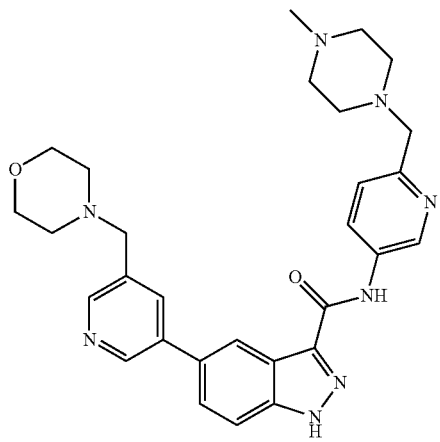 [SMILES: CN1CCN(Cc2ccc(NC(=O)c3n[nH]c4ccc(-c5cncc(CN6CCOCC6)c5)cc34)cn2)CC1]
147
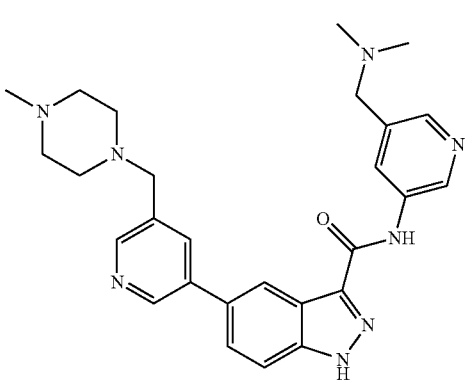 [SMILES: CN(C)Cc1cncc(NC(=O)c2n[nH]c3ccc(-c4cncc(CN5CCN(C)CC5)c4)cc23)c1]
148
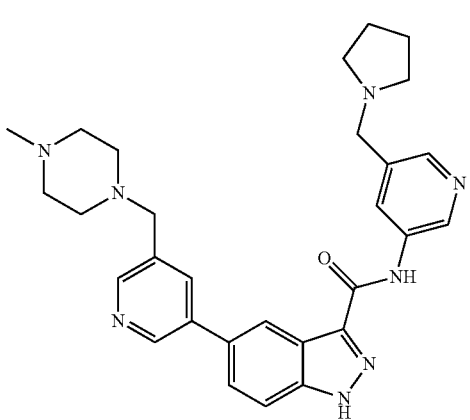 [SMILES: CN1CCN(Cc2cncc(-c3ccc4[nH]nc(C(=O)Nc5cncc(CN6CCCC6)c5)c4c3)c2)CC1]
149
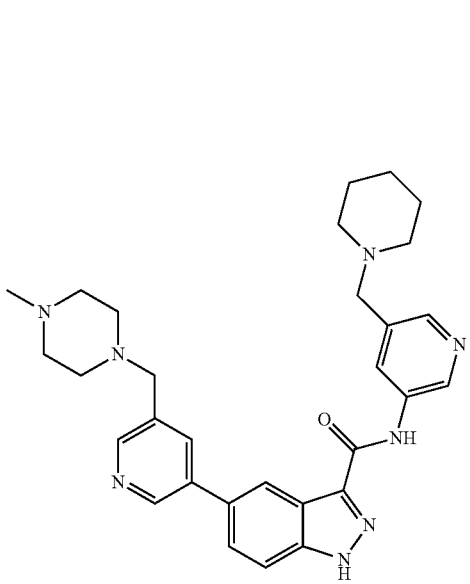 [SMILES: CN1CCN(Cc2cncc(-c3ccc4[nH]nc(C(=O)Nc5cncc(CN6CCCCC6)c5)c4c3)c2)CC1]
150
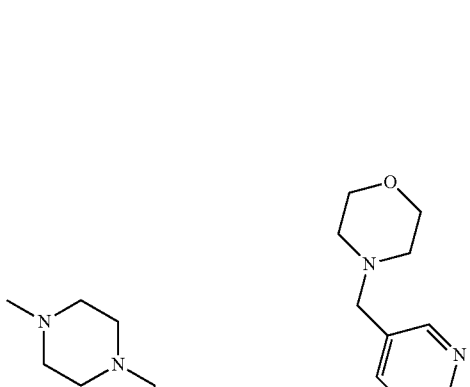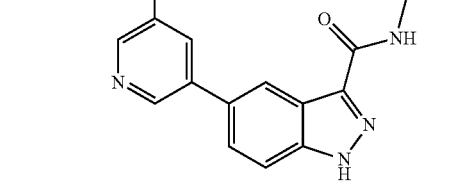

TABLE 1-continued
151
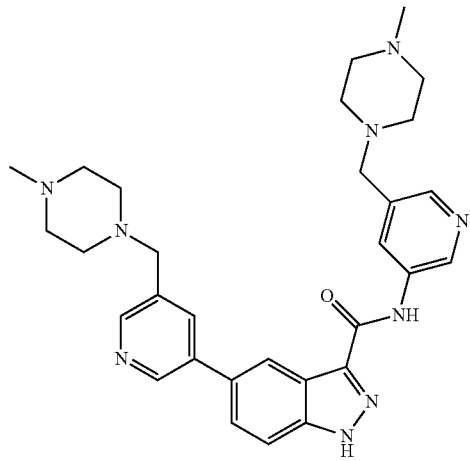 [SMILES: CN1CCN(Cc2cncc(NC(=O)c3n[nH]c4ccc(-c5cncc(CN6CCN(C)CC6)c5)cc34)c2)CC1]
152
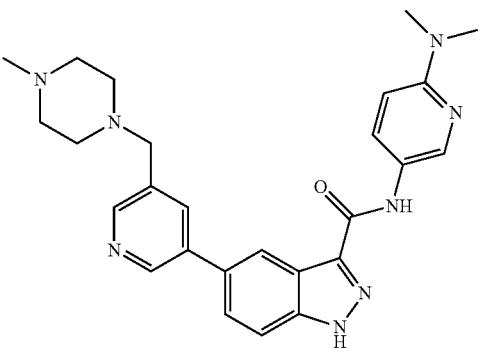
153
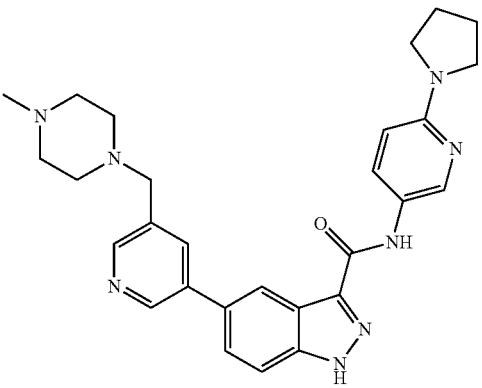 [SMILES: CN1CCN(Cc2cncc(-c3ccc4[nH]nc(C(=O)Nc5ccc(N6CCCC6)nc5)c4c3)c2)CC1]
154
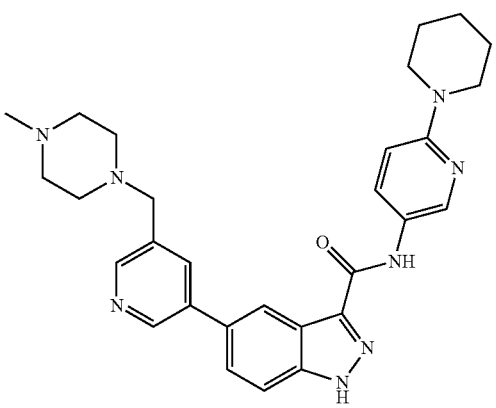 [SMILES: CN1CCN(Cc2cncc(-c3ccc4[nH]nc(C(=O)Nc5ccc(N6CCCCC6)nc5)c4c3)c2)CC1]
TABLE 1-continued
155
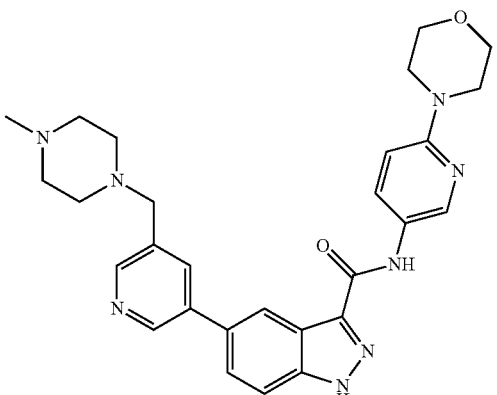
156
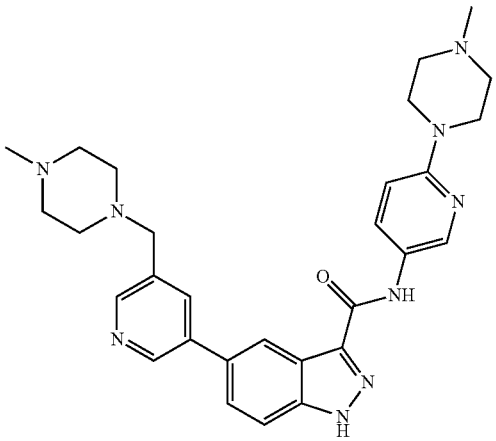 [SMILES: CN1CCN(Cc2cncc(-c3ccc4[nH]nc(C(=O)Nc5ccc(N6CCN(C)CC6)nc5)c4c3)c2)CC1]
157
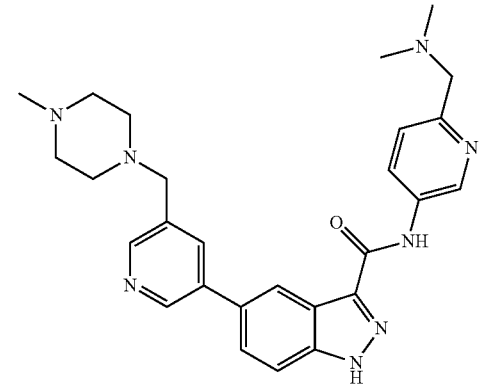 [SMILES: CN(C)Cc1ccc(NC(=O)c2n[nH]c3ccc(-c4cncc(CN5CCN(C)CC5)c4)cc23)cn1]
158
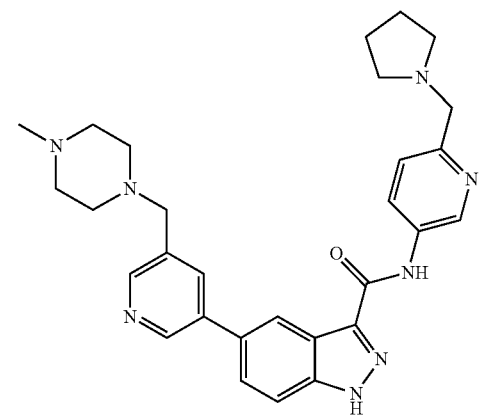 [SMILES: CN1CCN(Cc2cncc(-c3ccc4[nH]nc(C(=O)Nc5ccc(CN6CCCC6)nc5)c4c3)c2)CC1]

TABLE 1-continued
159 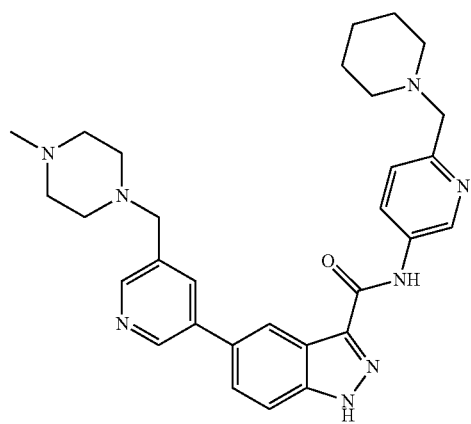 [SMILES: CN1CCN(Cc2cncc(-c3ccc4[nH]nc(C(=O)Nc5ccc(CN6CCOCC6)nc5)c4c3)c2)CC1]
160 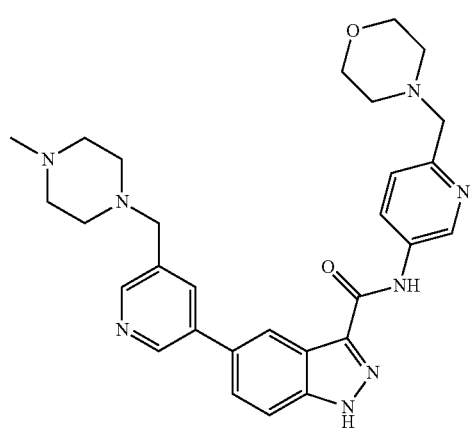
161 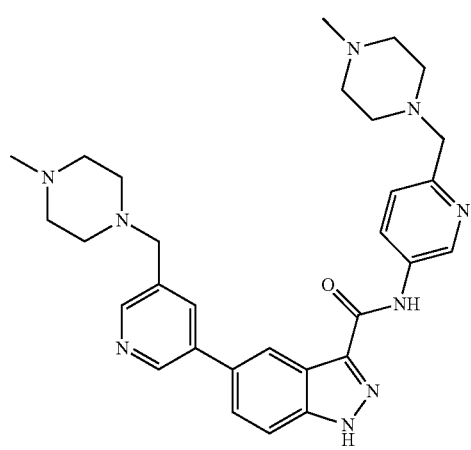 [SMILES: CN1CCN(Cc2cncc(-c3ccc4[nH]nc(C(=O)Nc5ccc(CN6CCN(C)CC6)nc5)c4c3)c2)CC1]
162 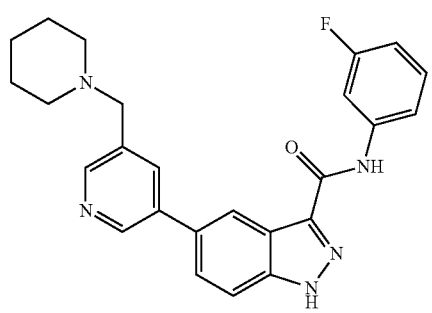 [SMILES: O=C(Nc1cccc(F)c1)c1n[nH]c2ccc(-c3cncc(CN4CCCCC4)c3)cc12]
TABLE 1-continued
163 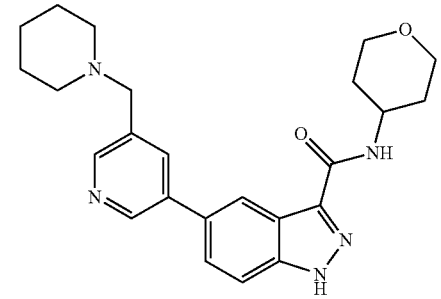 [SMILES: O=C(NC1CCOCC1)c1n[nH]c2ccc(-c3cncc(CN4CCCCC4)c3)cc12]
164 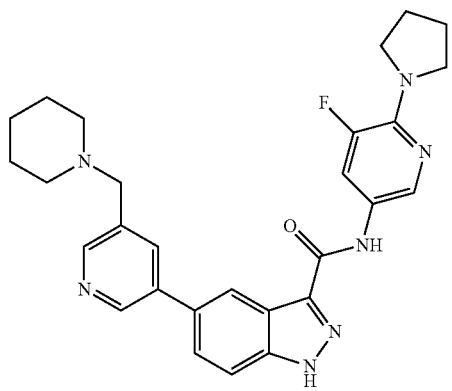 [SMILES: O=C(Nc1cnc(N2CCCC2)c(F)c1)c1n[nH]c2ccc(-c3cncc(CN4CCCCC4)c3)cc12]
165 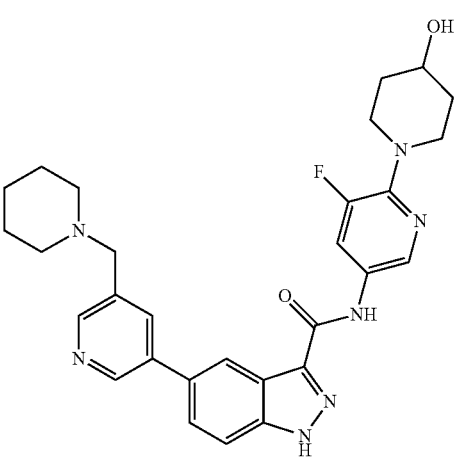 [SMILES: O=C(Nc1cnc(N2CCC(O)CC2)c(F)c1)c1n[nH]c2ccc(-c3cncc(CN4CCCCC4)c3)cc12]
166 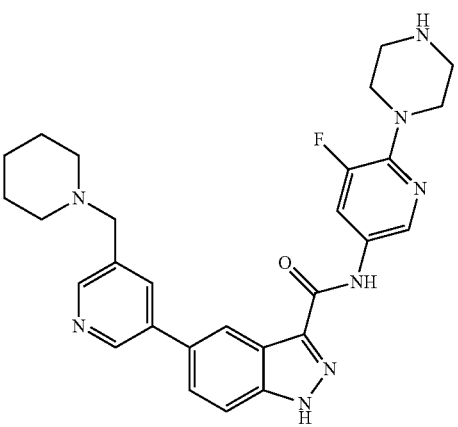 [SMILES: O=C(Nc1cnc(N2CCNCC2)c(F)c1)c1n[nH]c2ccc(-c3cncc(CN4CCCCC4)c3)cc12]

TABLE 1-continued
167 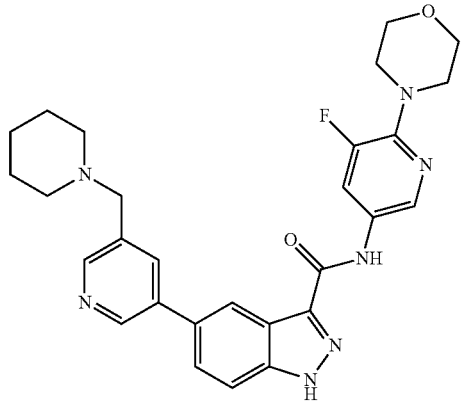 [SMILES: O=C(Nc1cnc(N2CCOCC2)c(F)c1)c1n[nH]c2ccc(-c3cncc(CN4CCCCC4)c3)cc12]
168 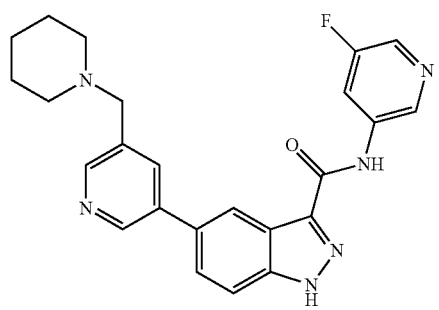 [SMILES: O=C(Nc1cncc(F)c1)c1n[nH]c2ccc(-c3cncc(CN4CCCCC4)c3)cc12]
169 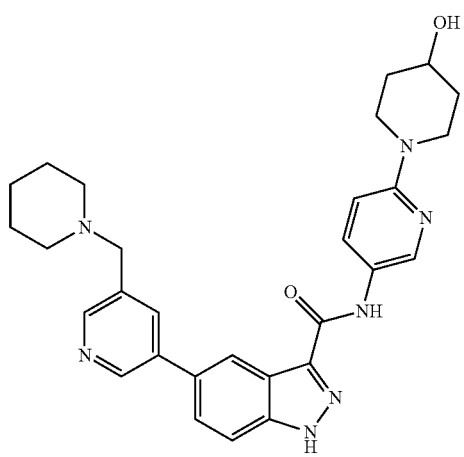 [SMILES: O=C(Nc1ccc(N2CCC(O)CC2)nc1)c1n[nH]c2ccc(-c3cncc(CN4CCCCC4)c3)cc12]
170 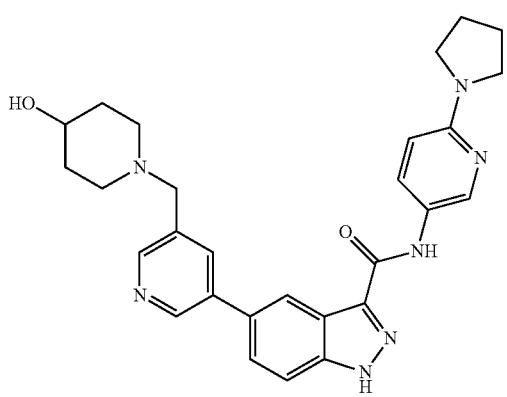 [SMILES: O=C(Nc1ccc(N2CCCC2)nc1)c1n[nH]c2ccc(-c3cncc(CN4CCC(O)CC4)c3)cc12]
TABLE 1-continued
171 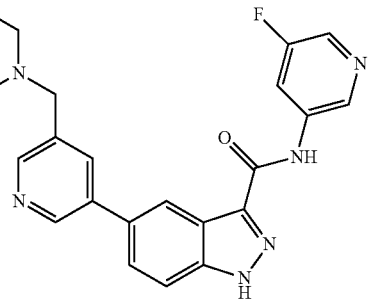
172 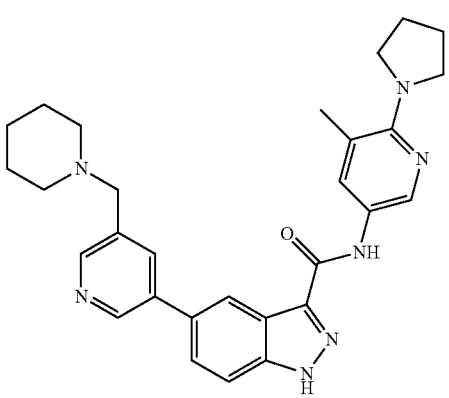 [SMILES: Cc1cc(NC(=O)c2n[nH]c3ccc(-c4cncc(CN5CCCCC5)c4)cc23)cnc1N1CCCC1]
173 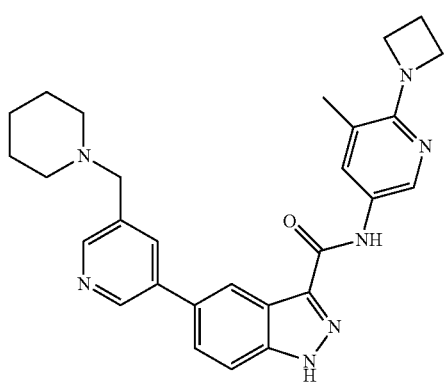 [SMILES: Cc1cc(NC(=O)c2n[nH]c3ccc(-c4cncc(CN5CCCCC5)c4)cc23)cnc1N1CCC1]
174 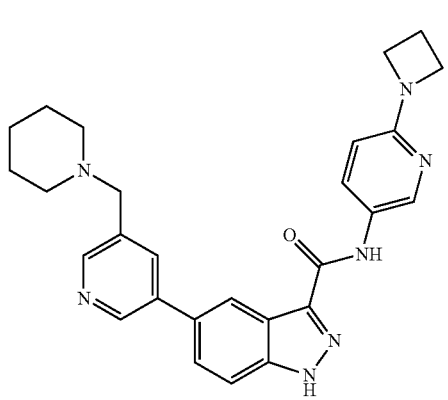 [SMILES: O=C(Nc1ccc(N2CCC2)nc1)c1n[nH]c2ccc(-c3cncc(CN4CCCCC4)c3)cc12]

TABLE 1-continued
| | |
|---|---|
| 175 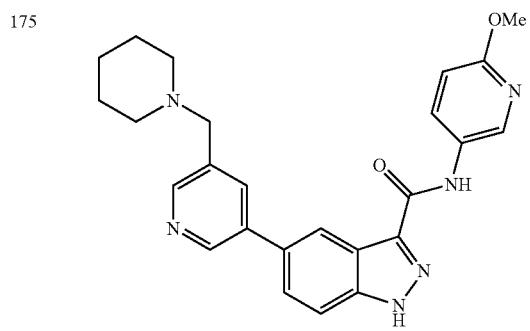 | 179 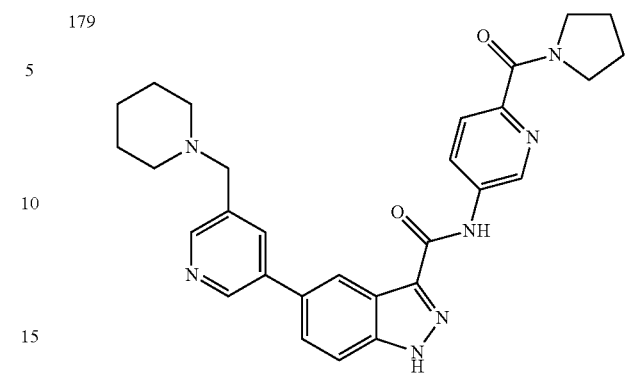 |
| 176 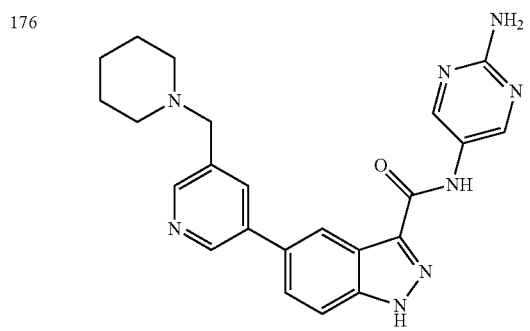 | 180 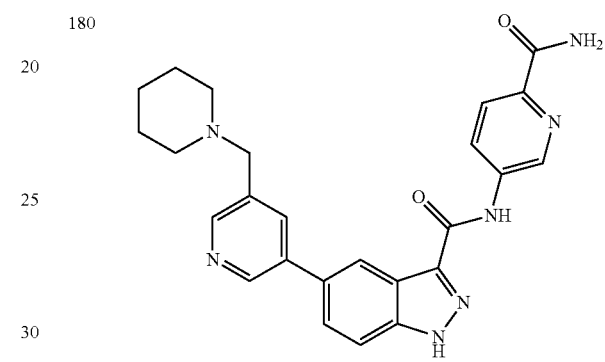 |
| 177 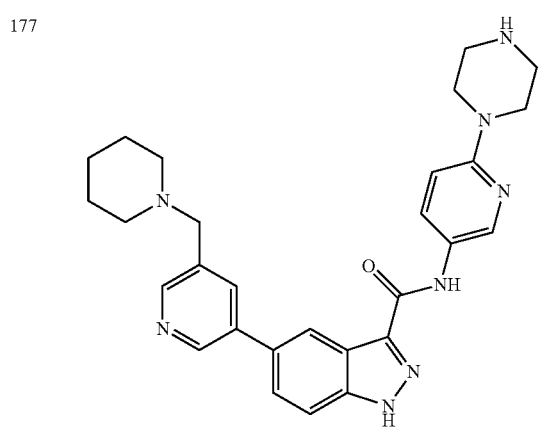 | 181 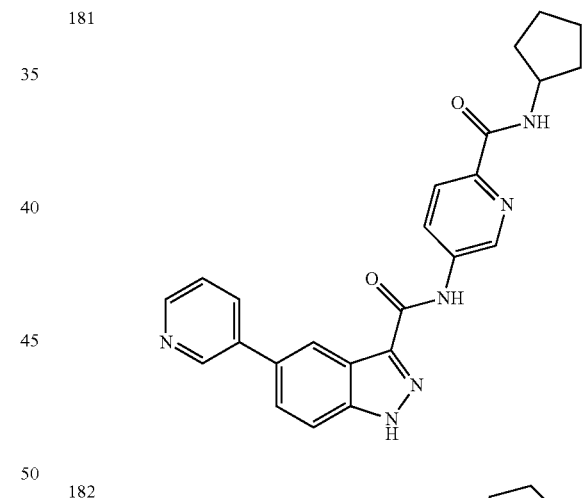 |
| 178 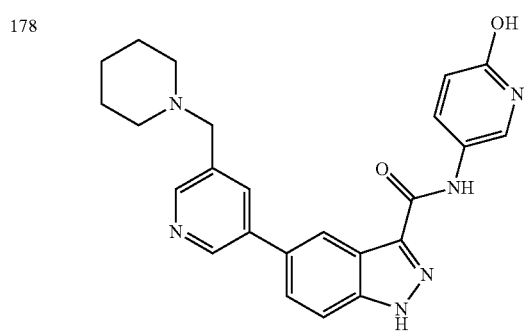 | 182 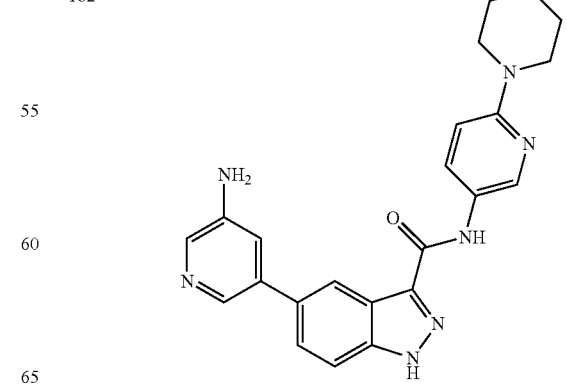 |

TABLE 1-continued
183 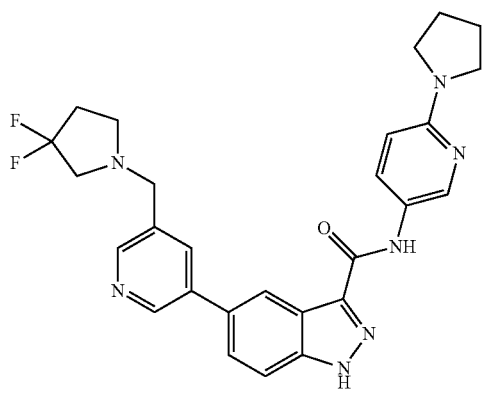 [SMILES: O=C(Nc1ccc(N2CCCC2)nc1)c1n[nH]c2ccc(-c3cncc(CN4CCC(F)(F)C4)c3)cc12]
184 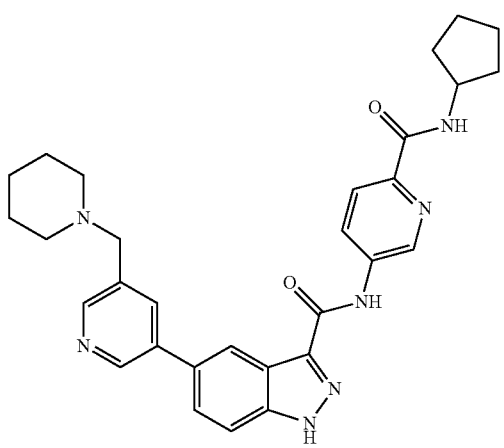 [SMILES: O=C(NC1CCCC1)c1ccc(NC(=O)c2n[nH]c3ccc(-c4cncc(CN5CCCCC5)c4)cc23)cn1]
185 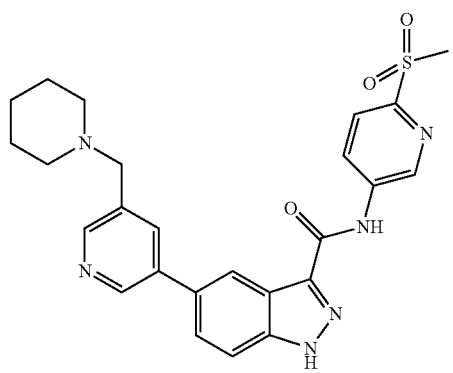 [SMILES: CS(=O)(=O)c1ccc(NC(=O)c2n[nH]c3ccc(-c4cncc(CN5CCCCC5)c4)cc23)cn1]
186 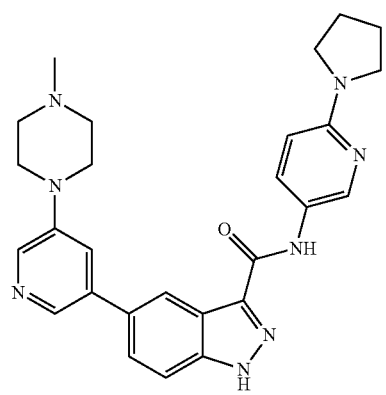 [SMILES: CN1CCN(c2cncc(-c3ccc4[nH]nc(C(=O)Nc5ccc(N6CCCC6)nc5)c4c3)c2)CC1]
TABLE 1-continued
187 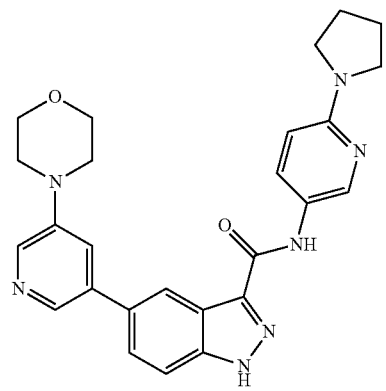 [SMILES: O=C(Nc1ccc(N2CCCC2)nc1)c1n[nH]c2ccc(-c3cncc(N4CCOCC4)c3)cc12]
188 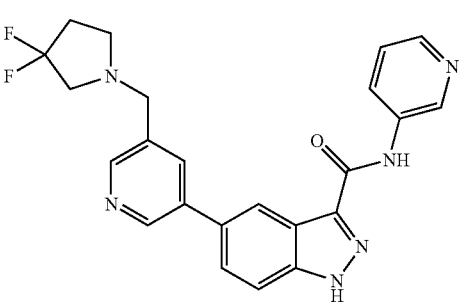 [SMILES: O=C(Nc1cccnc1)c1n[nH]c2ccc(-c3cncc(CN4CCC(F)(F)C4)c3)cc12]
189 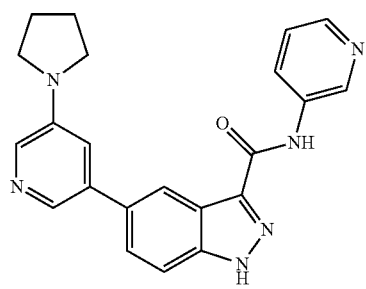
190 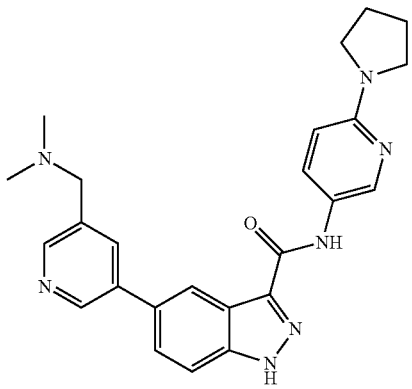 [SMILES: CN(C)Cc1cncc(-c2ccc3[nH]nc(C(=O)Nc4ccc(N5CCCC5)nc4)c3c2)c1]
191 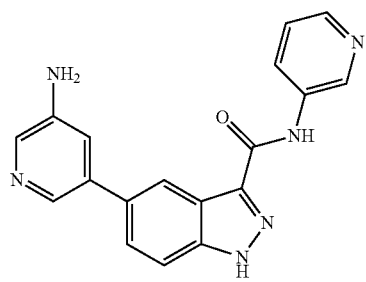

TABLE 1-continued
| 192 | 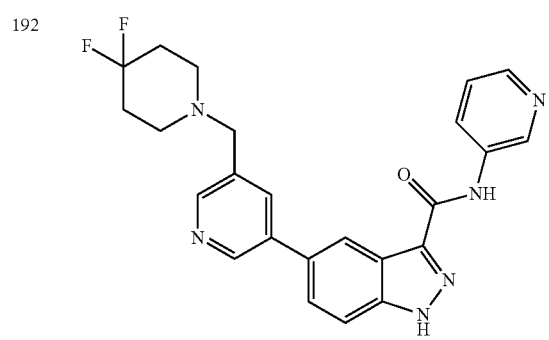 |
| 193 | 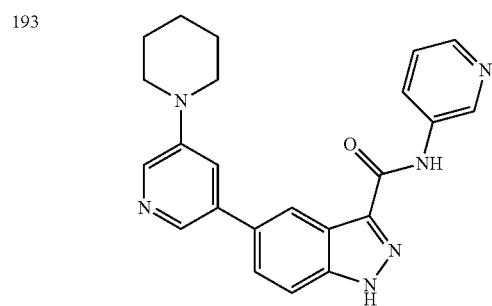 |
| 194 | 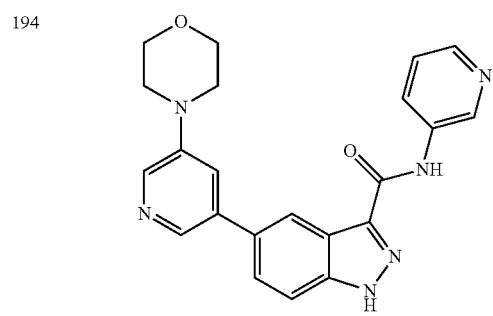 |
| 195 | 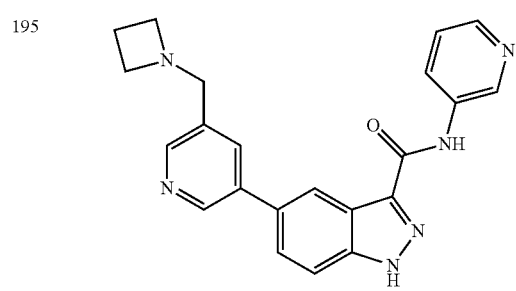 |
| 196 | 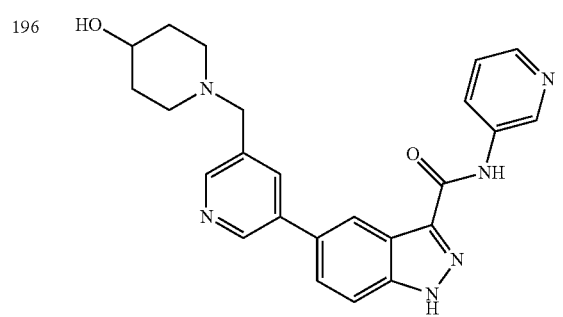 |
TABLE 1-continued
| 197 | 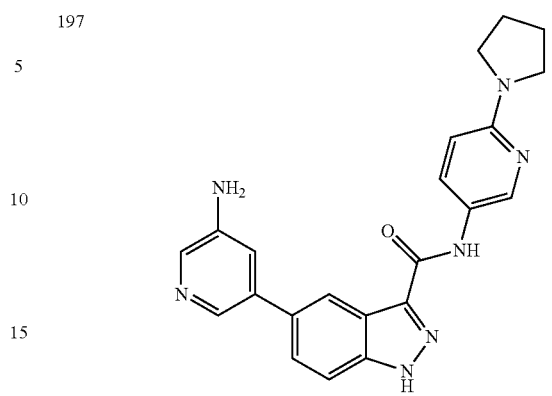 |
| 198 | 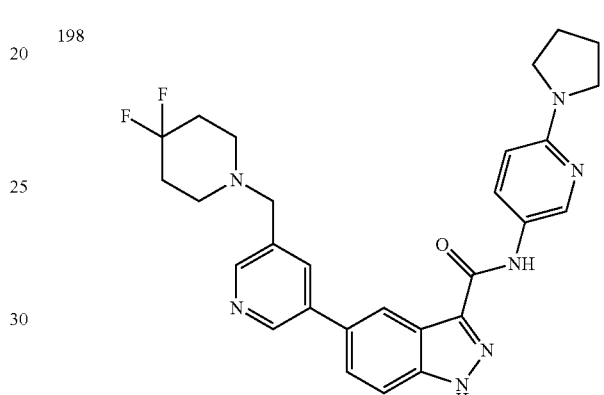 |
| 199 | 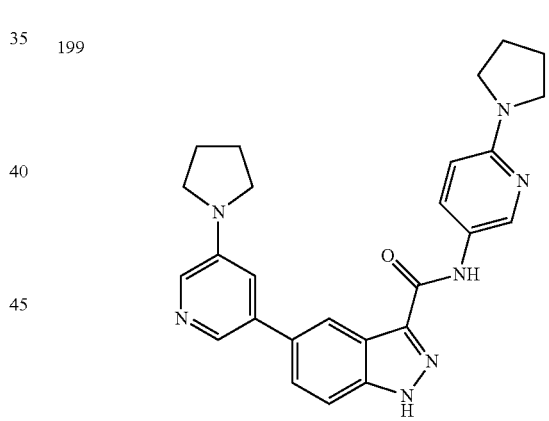 |
| 200 | 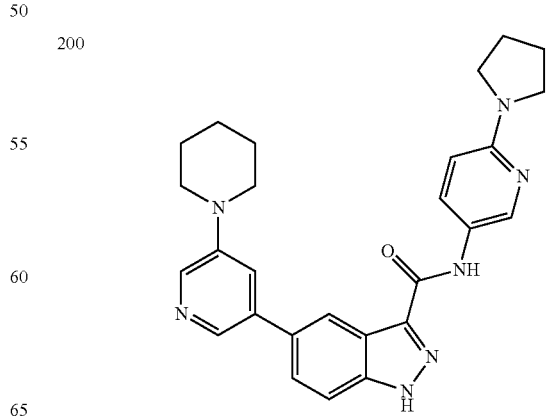 |

TABLE 1-continued
201
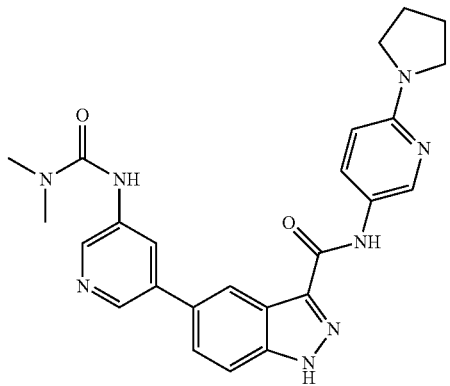 [SMILES: CN(C)C(=O)Nc1cncc(-c2ccc3[nH]nc(C(=O)Nc4ccc(N5CCCC5)nc4)c3c2)c1]
202
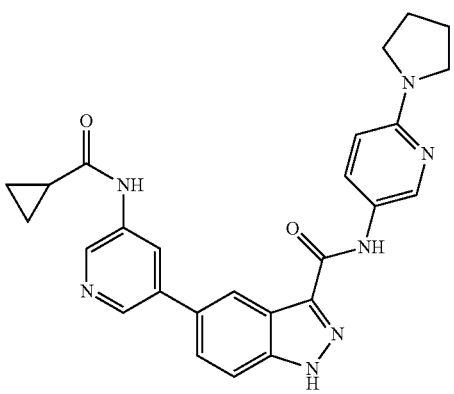 [SMILES: O=C(Nc1ccc(N2CCCC2)nc1)c1n[nH]c2ccc(-c3cncc(NC(=O)C4CC4)c3)cc12]
203
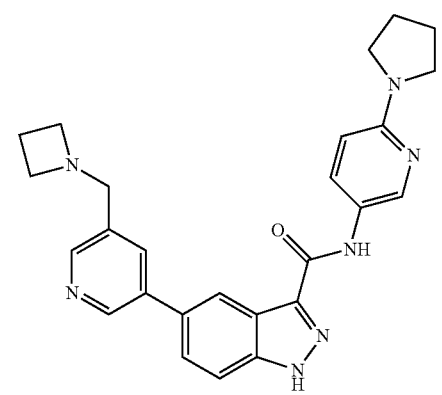 [SMILES: O=C(Nc1ccc(N2CCCC2)nc1)c1n[nH]c2ccc(-c3cncc(CN4CCC4)c3)cc12]
204
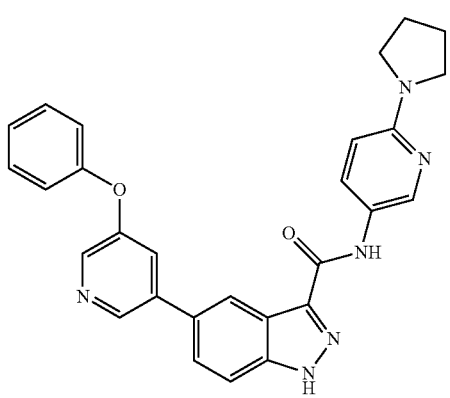 [SMILES: O=C(Nc1ccc(N2CCCC2)nc1)c1n[nH]c2ccc(-c3cncc(Oc4ccccc4)c3)cc12]
TABLE 1-continued
205
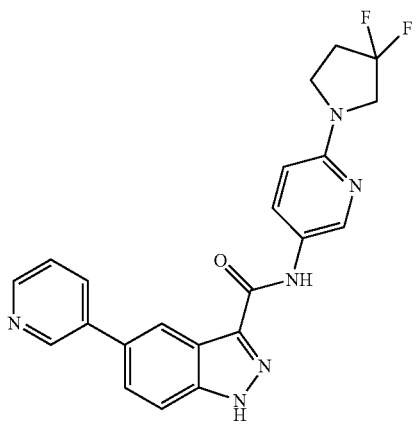 [SMILES: O=C(Nc1ccc(N2CCC(F)(F)C2)nc1)c1n[nH]c2ccc(-c3cccnc3)cc12]
206
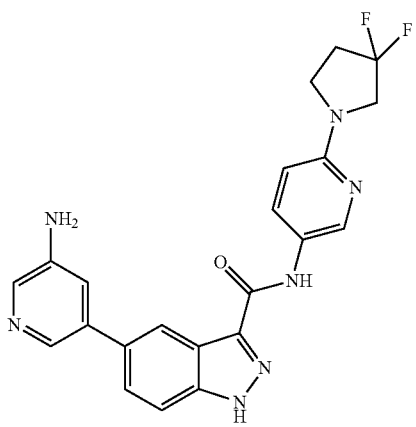 [SMILES: Nc1cncc(-c2ccc3[nH]nc(C(=O)Nc4ccc(N5CCC(F)(F)C5)nc4)c3c2)c1]
207
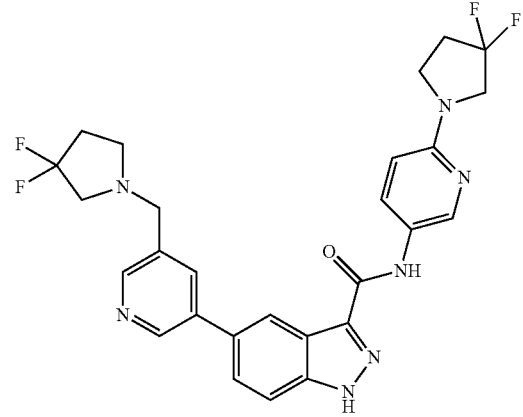 [SMILES: O=C(Nc1ccc(N2CCC(F)(F)C2)nc1)c1n[nH]c2ccc(-c3cncc(CN4CCC(F)(F)C4)c3)cc12]

TABLE 1-continued
208
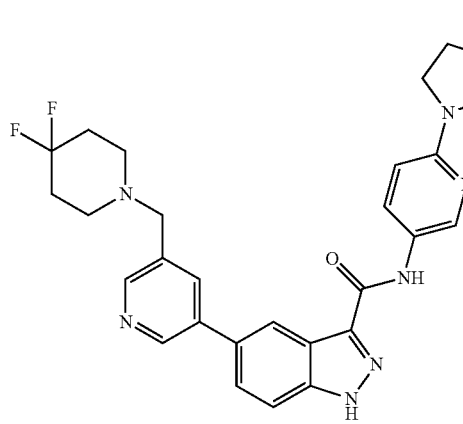
211
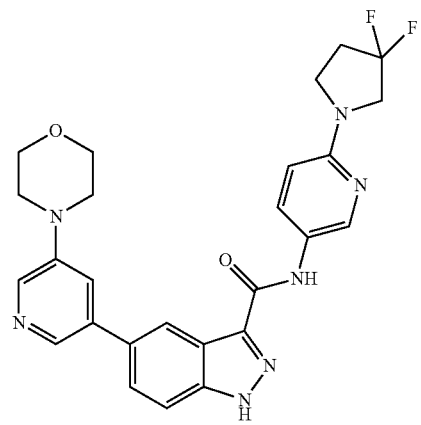
209
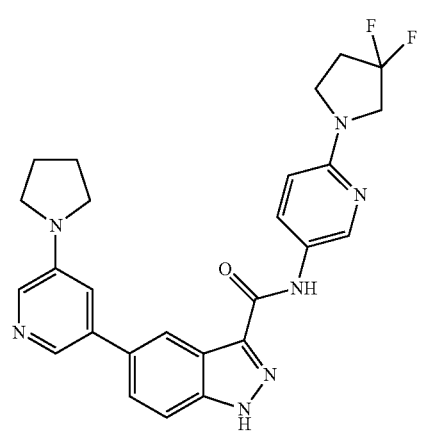 [SMILES: O=C(Nc1ccc(N2CCC(F)(F)C2)nc1)c1n[nH]c2ccc(-c3cncc(N4CCCC4)c3)cc12]
212
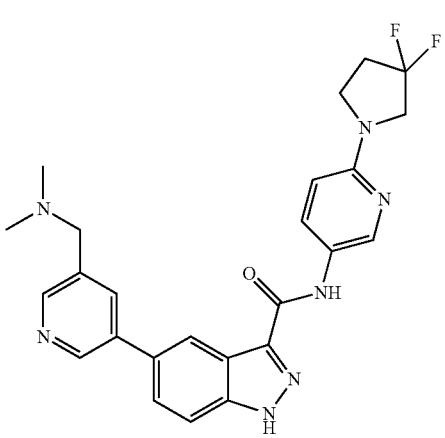
210
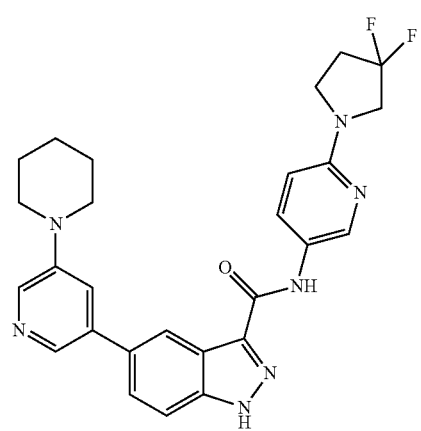 [SMILES: O=C(Nc1ccc(N2CCC(F)(F)C2)nc1)c1n[nH]c2ccc(-c3cncc(N4CCCCC4)c3)cc12]
213
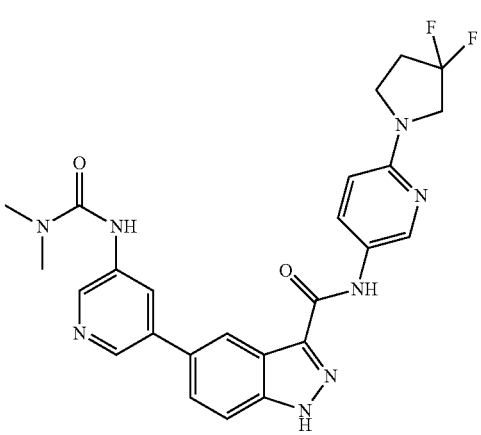 [SMILES: CN(C)C(=O)Nc1cncc(-c2ccc3[nH]nc(C(=O)Nc4ccc(N5CCC(F)(F)C5)nc4)c3c2)c1]

TABLE 1-continued
214
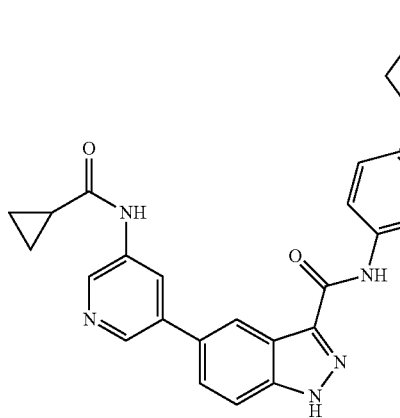
215
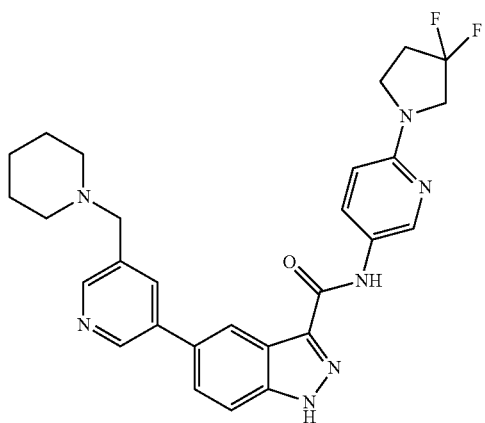 [SMILES: O=C(Nc1ccc(N2CCC(F)(F)C2)nc1)c1n[nH]c2ccc(-c3cncc(CN4CCCCC4)c3)cc12]
216
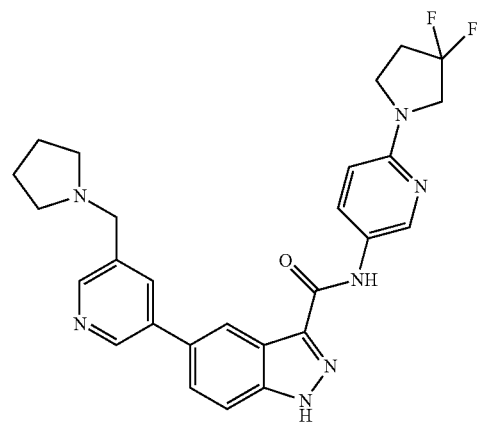 [SMILES: O=C(Nc1ccc(N2CCC(F)(F)C2)nc1)c1n[nH]c2ccc(-c3cncc(CN4CCCC4)c3)cc12]
217
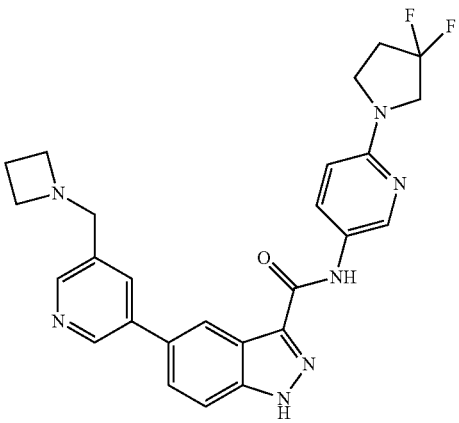 [SMILES: O=C(Nc1ccc(N2CCC(F)(F)C2)nc1)c1n[nH]c2ccc(-c3cncc(CN4CCC4)c3)cc12]
218
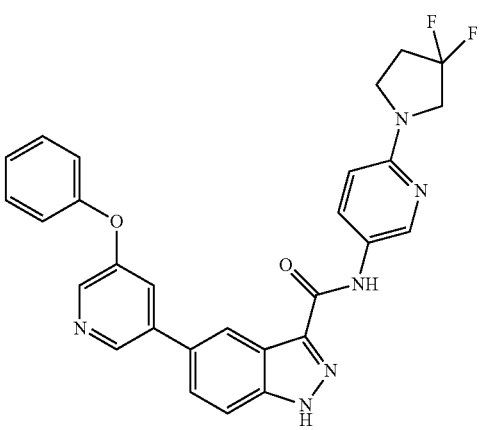 [SMILES: O=C(Nc1ccc(N2CCC(F)(F)C2)nc1)c1n[nH]c2ccc(-c3cncc(Oc4ccccc4)c3)cc12]
219
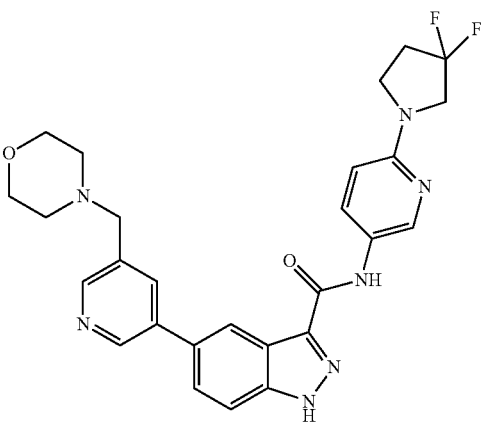 [SMILES: O=C(Nc1ccc(N2CCC(F)(F)C2)nc1)c1n[nH]c2ccc(-c3cncc(CN4CCOCC4)c3)cc12]
220
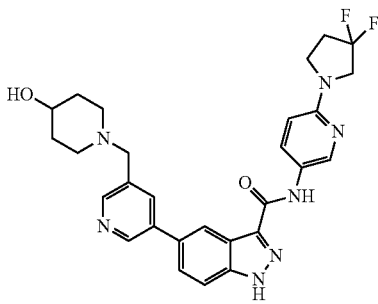 [SMILES: O=C(Nc1ccc(N2CCC(F)(F)C2)nc1)c1n[nH]c2ccc(-c3cncc(CN4CCC(O)CC4)c3)cc12]

TABLE 1-continued
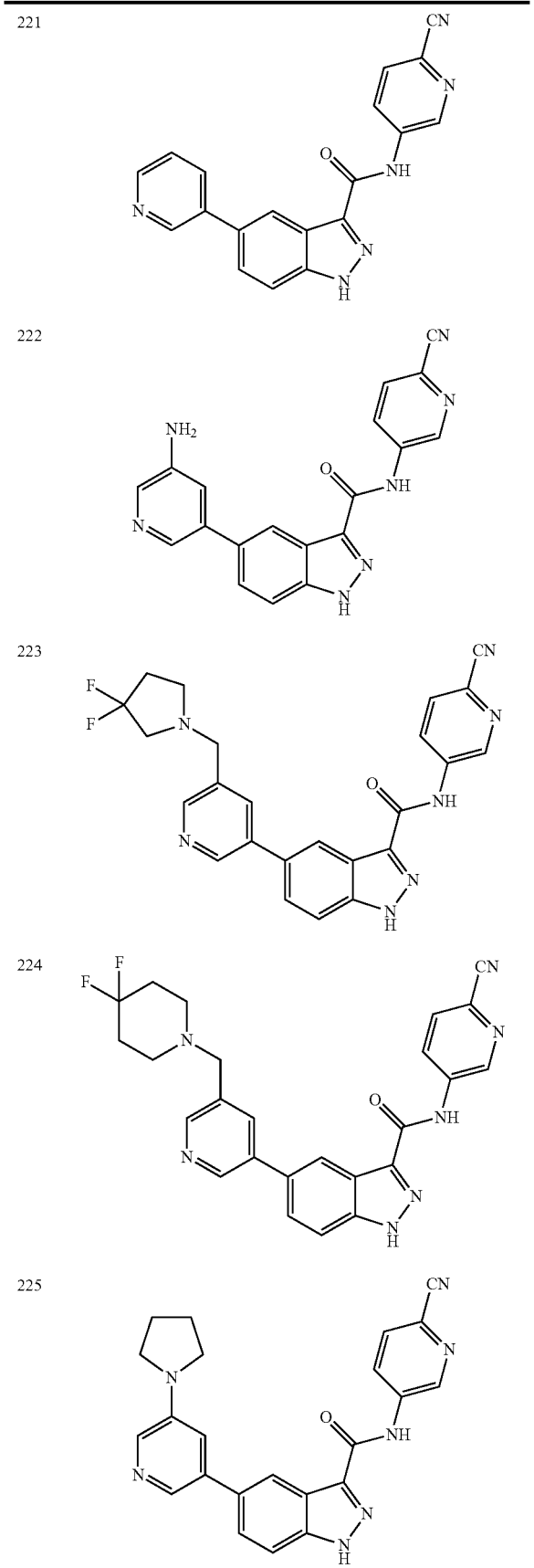
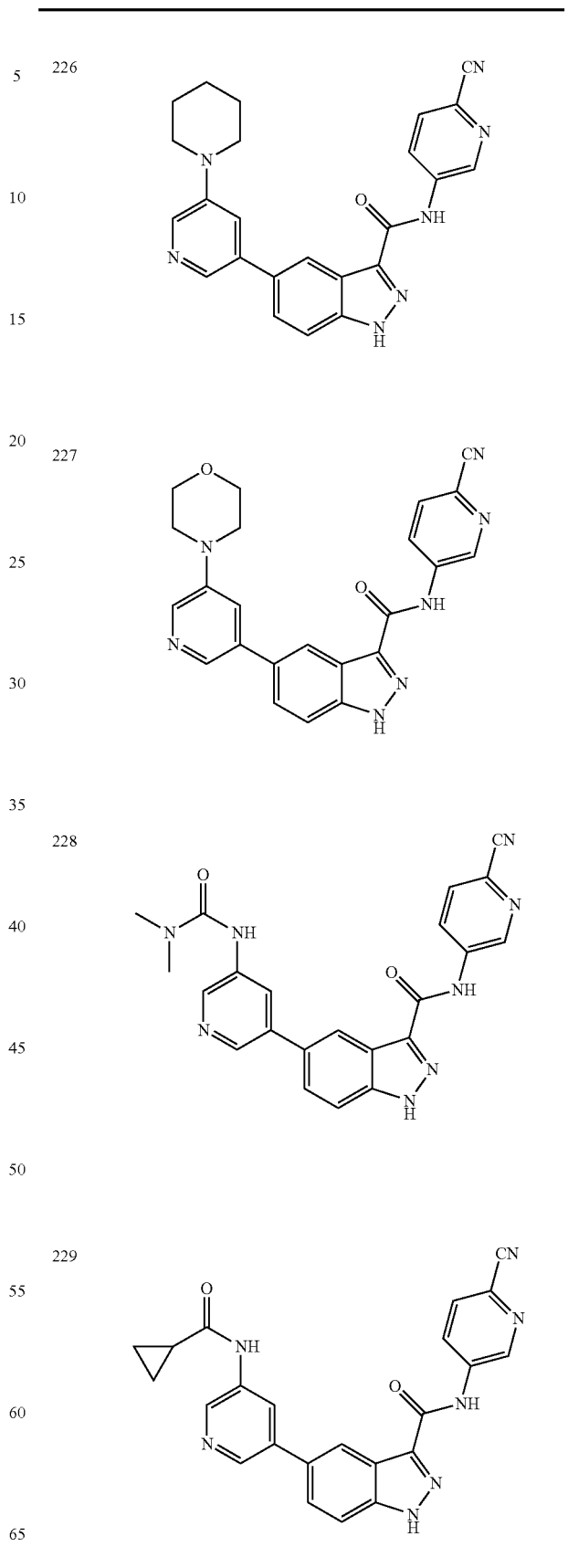

TABLE 1-continued
230 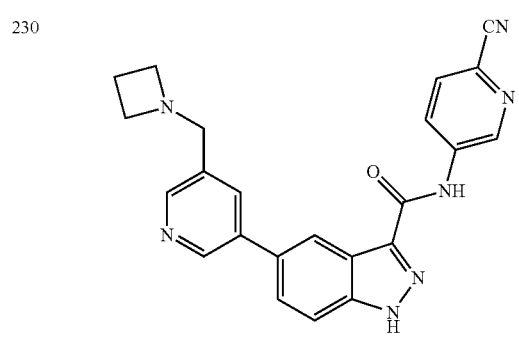
231 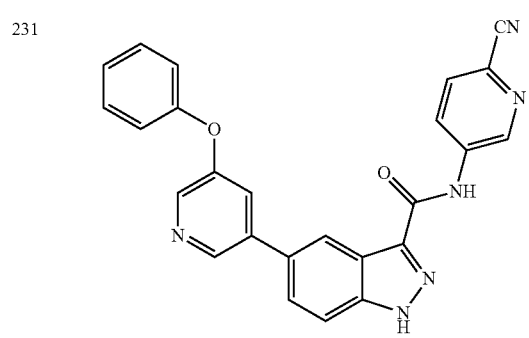
232 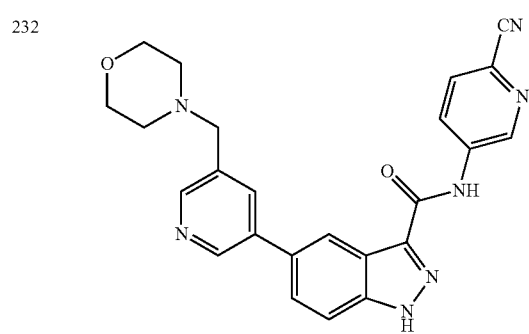
233 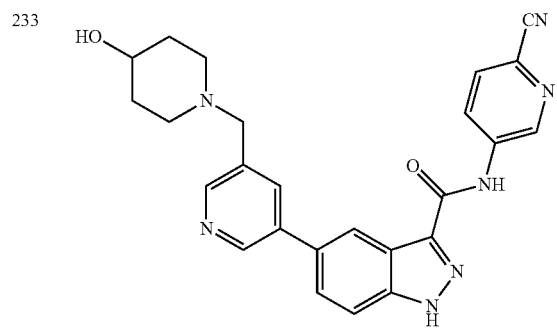
234 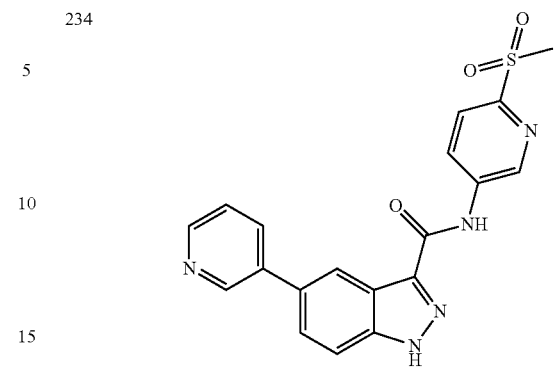
235 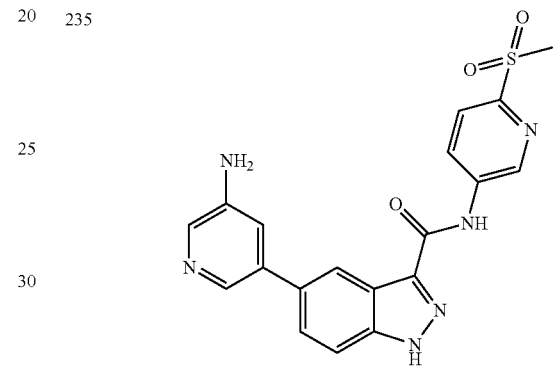
236 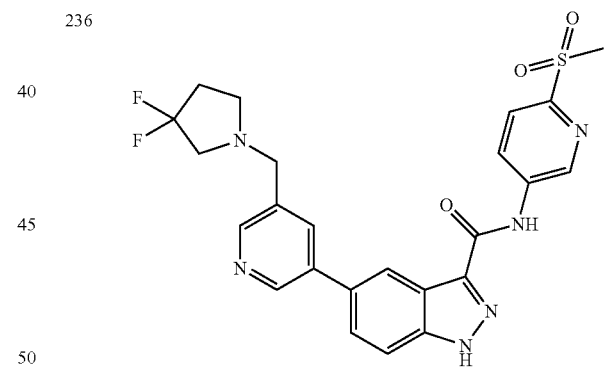
237 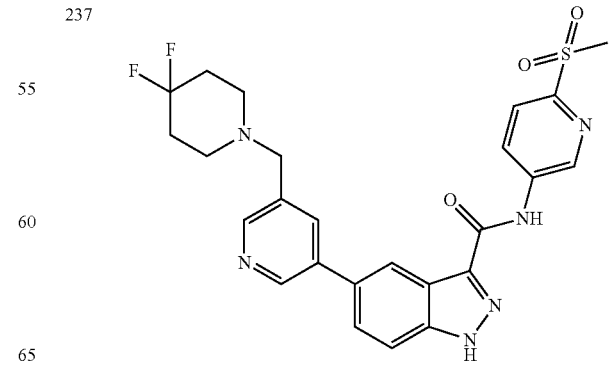

TABLE 1-continued
| 238 | 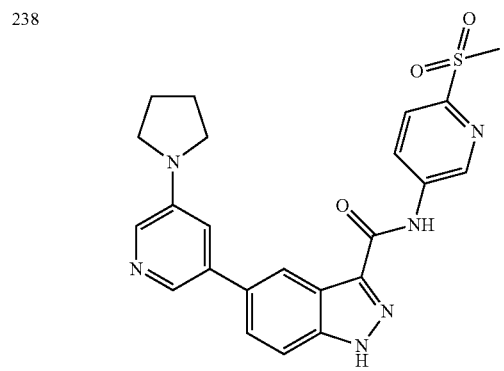 | 242 | 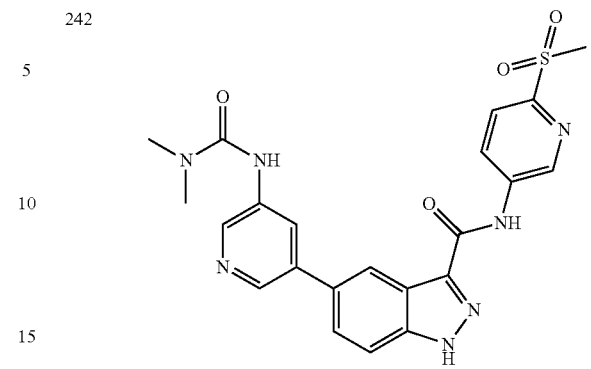 |
| 239 | 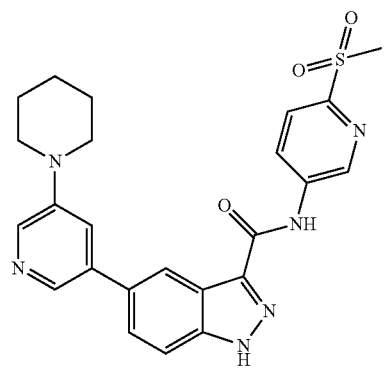 [SMILES: CS(=O)(=O)c1ccc(NC(=O)c2n[nH]c3ccc(-c4cncc(N5CCCCC5)c4)cc23)cn1] | 243 | 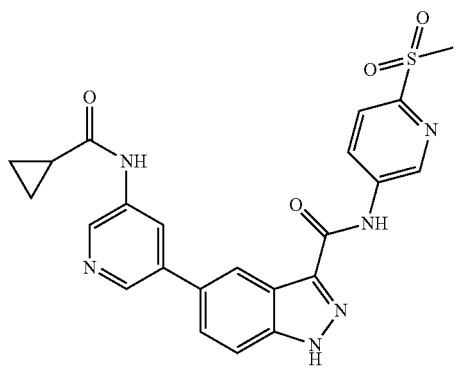 [SMILES: CS(=O)(=O)c1ccc(NC(=O)c2n[nH]c3ccc(-c4cncc(NC(=O)C5CC5)c4)cc23)cn1] |
| 240 | 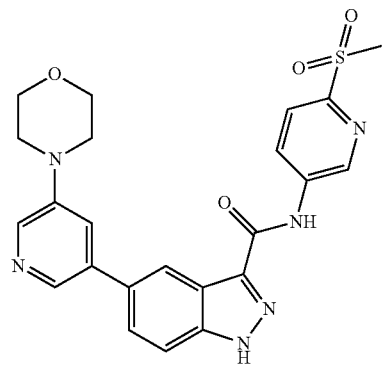 | 244 | 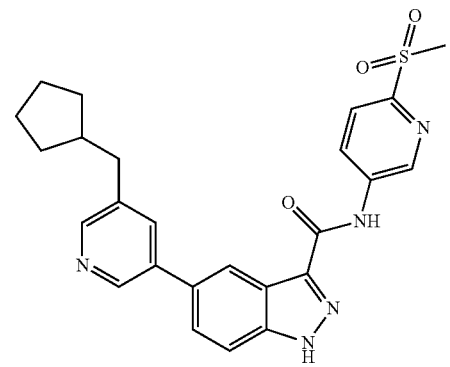 [SMILES: CS(=O)(=O)c1ccc(NC(=O)c2n[nH]c3ccc(-c4cncc(CC5CCCC5)c4)cc23)cn1] |
| 241 | 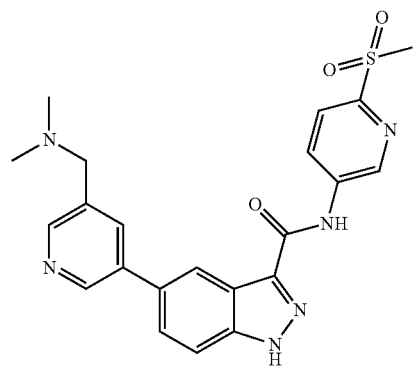 | 245 | 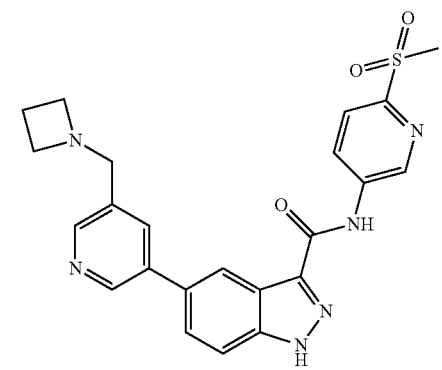 [SMILES: CS(=O)(=O)c1ccc(NC(=O)c2n[nH]c3ccc(-c4cncc(CN5CCC5)c4)cc23)cn1] |

TABLE 1-continued
246 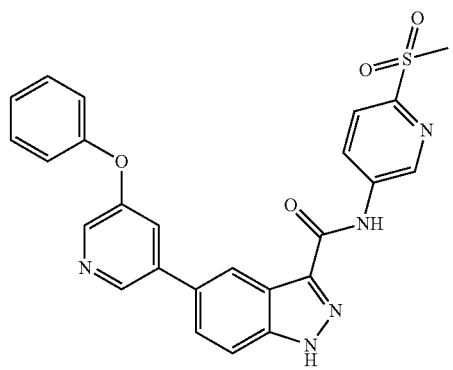 [SMILES: CS(=O)(=O)c1ccc(NC(=O)c2n[nH]c3ccc(-c4cncc(Oc5ccccc5)c4)cc23)cn1]
247 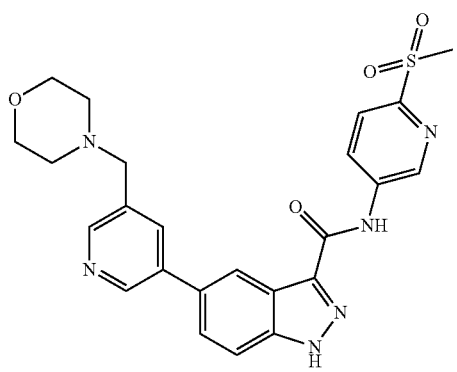 [SMILES: CS(=O)(=O)c1ccc(NC(=O)c2n[nH]c3ccc(-c4cncc(CN5CCOCC5)c4)cc23)cn1]
248 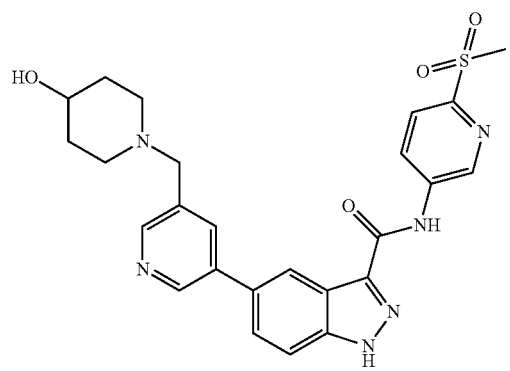 [SMILES: CS(=O)(=O)c1ccc(NC(=O)c2n[nH]c3ccc(-c4cncc(CN5CCC(O)CC5)c4)cc23)cn1]
249 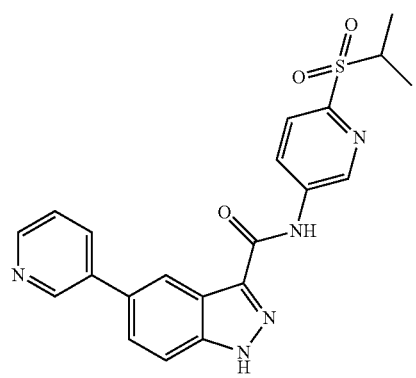 [SMILES: CC(C)S(=O)(=O)c1ccc(NC(=O)c2n[nH]c3ccc(-c4cccnc4)cc23)cn1]
250 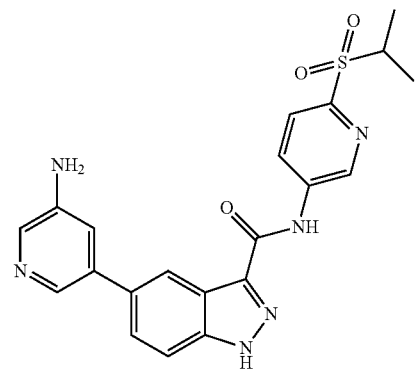 [SMILES: CC(C)S(=O)(=O)c1ccc(NC(=O)c2n[nH]c3ccc(-c4cncc(N)c4)cc23)cn1]
251 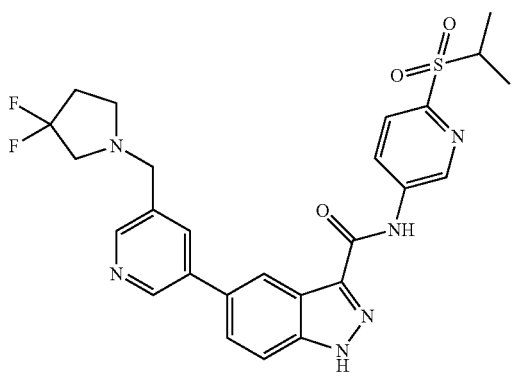 [SMILES: CC(C)S(=O)(=O)c1ccc(NC(=O)c2n[nH]c3ccc(-c4cncc(CN5CCC(F)(F)C5)c4)cc23)cn1]
252 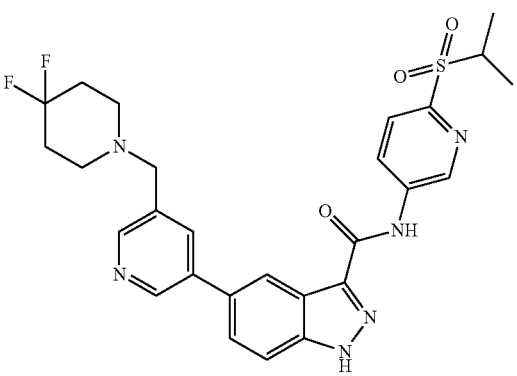 [SMILES: CC(C)S(=O)(=O)c1ccc(NC(=O)c2n[nH]c3ccc(-c4cncc(CN5CCC(F)(F)CC5)c4)cc23)cn1]
253 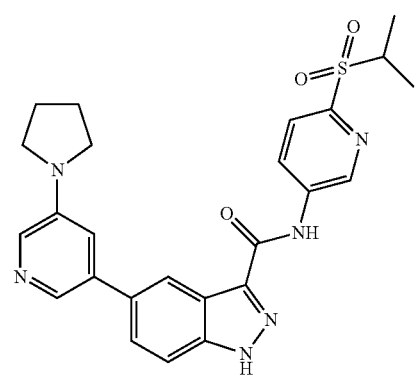 [SMILES: CC(C)S(=O)(=O)c1ccc(NC(=O)c2n[nH]c3ccc(-c4cncc(N5CCCC5)c4)cc23)cn1]

TABLE 1-continued
254 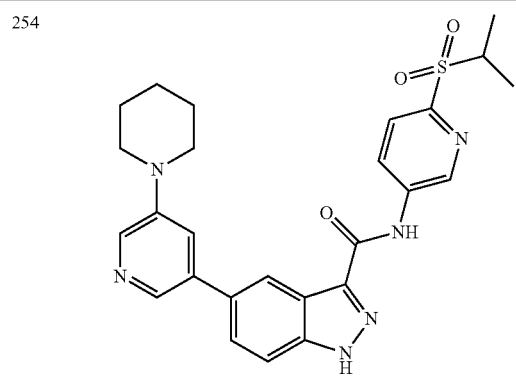
258 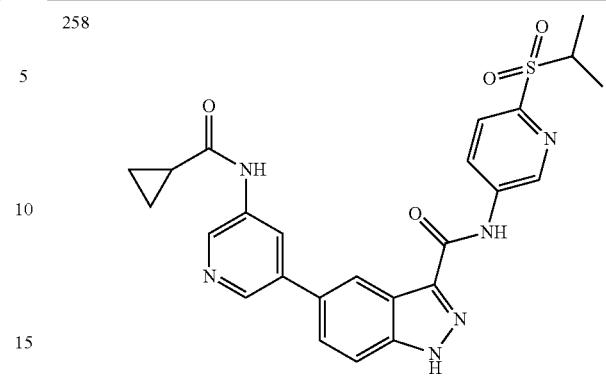
255
259 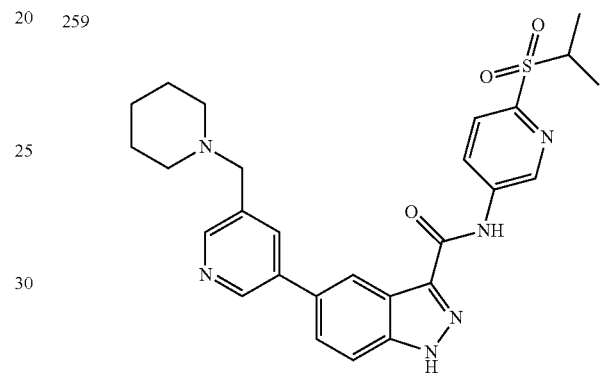
256
260 
257
261 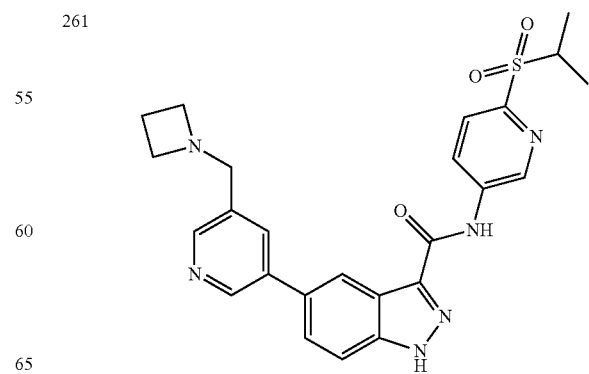

TABLE 1-continued
262 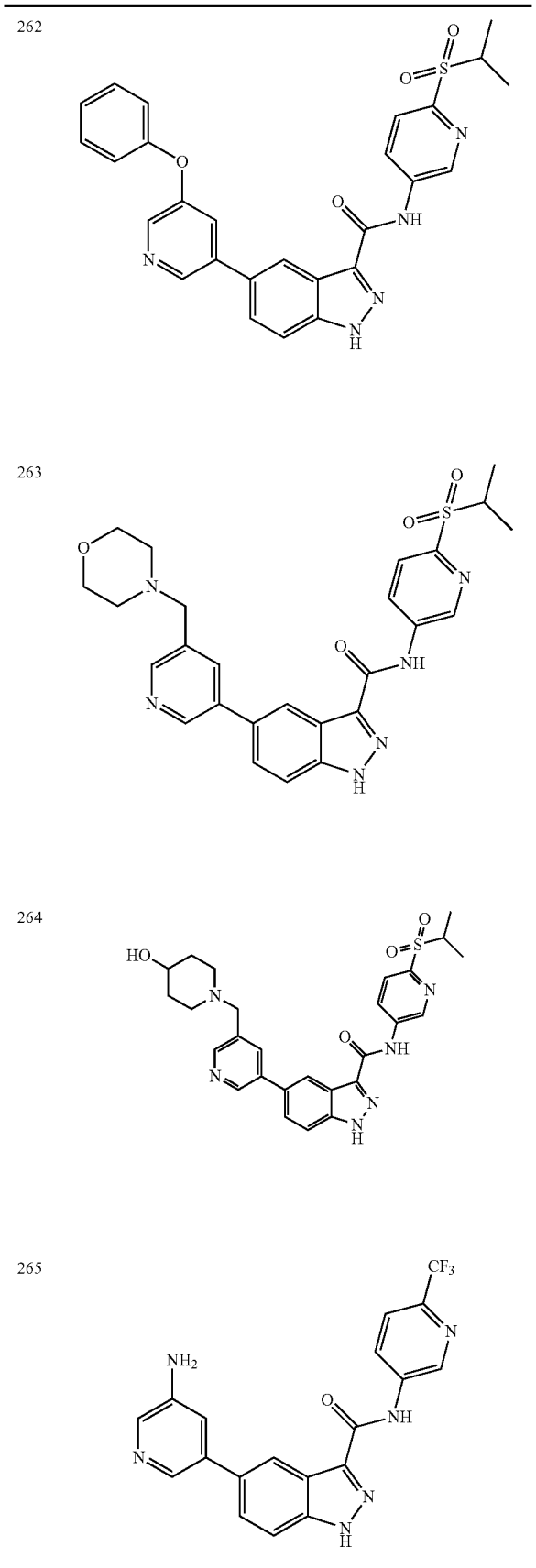
263
264
265
TABLE 1-continued
266 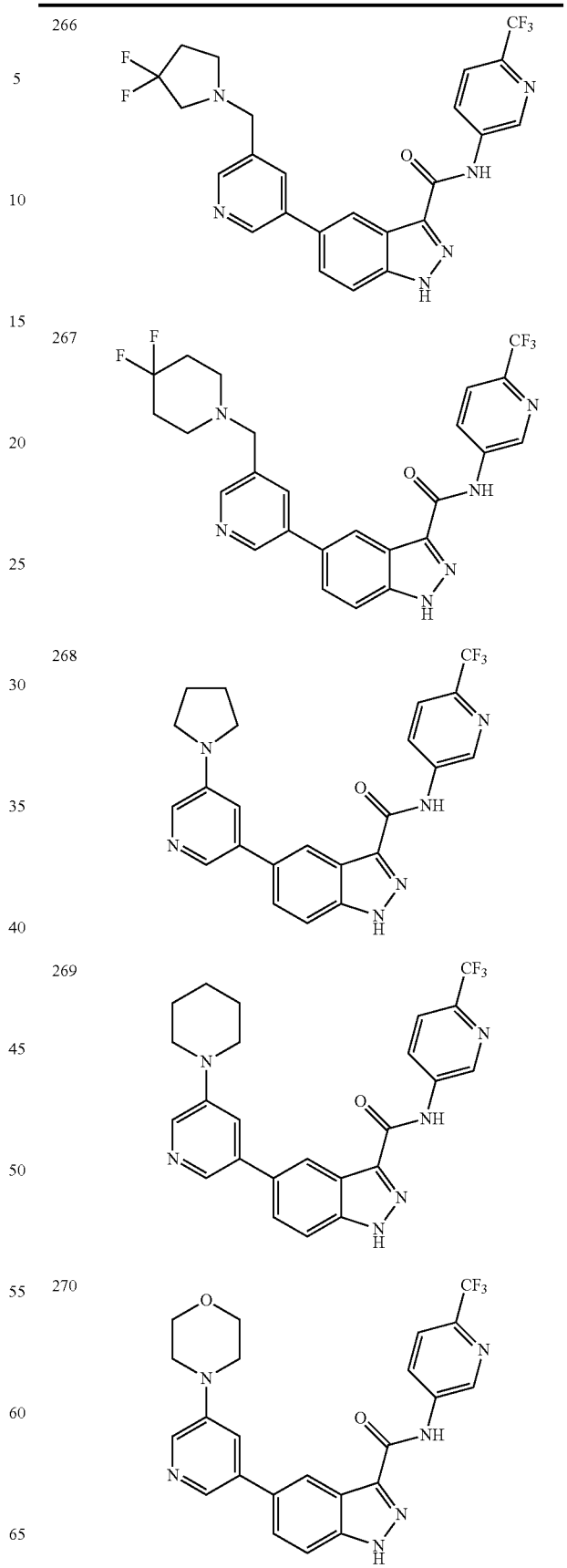
267
268
269
270

TABLE 1-continued
271 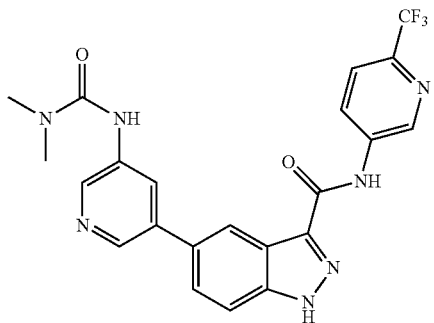
272 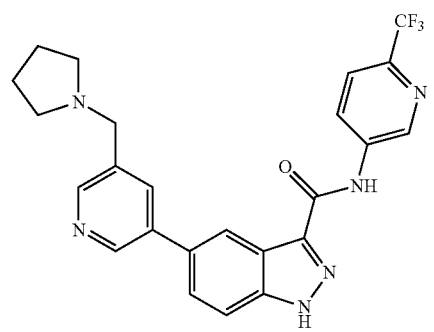 [SMILES: O=C(Nc1ccc(C(F)(F)F)nc1)c1n[nH]c2ccc(-c3cncc(CN4CCCC4)c3)cc12]
273 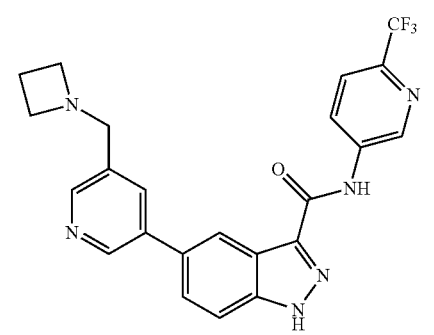 [SMILES: O=C(Nc1ccc(C(F)(F)F)nc1)c1n[nH]c2ccc(-c3cncc(CN4CCC4)c3)cc12]
274 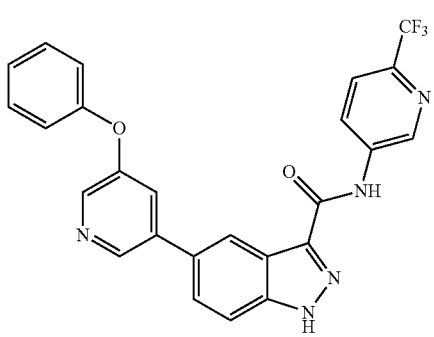
275 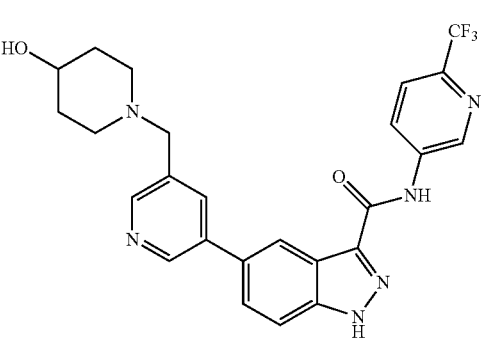 [SMILES: O=C(Nc1ccc(C(F)(F)F)nc1)c1n[nH]c2ccc(-c3cncc(CN4CCC(O)CC4)c3)cc12]
TABLE 1-continued
276 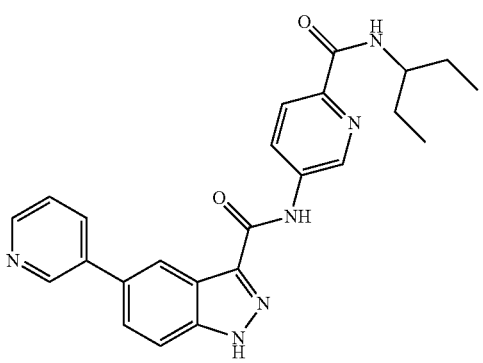 [SMILES: CCC(CC)NC(=O)c1ccc(NC(=O)c2n[nH]c3ccc(-c4cccnc4)cc23)cn1]
277 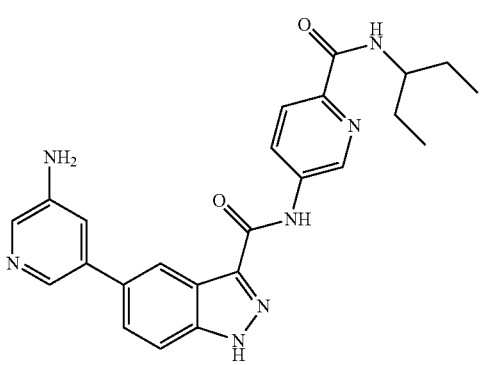 [SMILES: CCC(CC)NC(=O)c1ccc(NC(=O)c2n[nH]c3ccc(-c4cncc(N)c4)cc23)cn1]
278 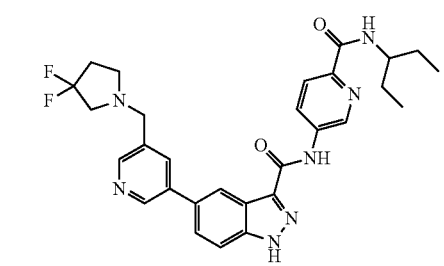 [SMILES: CCC(CC)NC(=O)c1ccc(NC(=O)c2n[nH]c3ccc(-c4cncc(CN5CCC(F)(F)C5)c4)cc23)cn1]
279 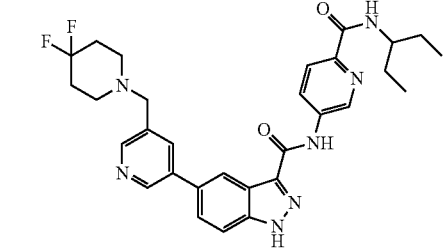 [SMILES: CCC(CC)NC(=O)c1ccc(NC(=O)c2n[nH]c3ccc(-c4cncc(CN5CCC(F)(F)CC5)c4)cc23)cn1]
280 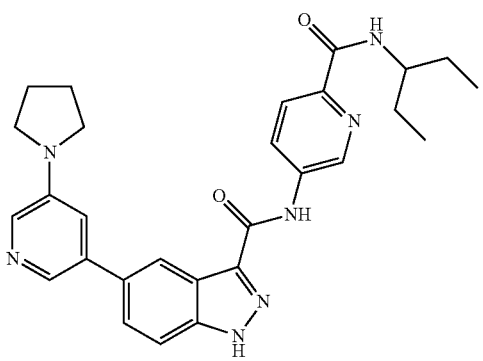 [SMILES: CCC(CC)NC(=O)c1ccc(NC(=O)c2n[nH]c3ccc(-c4cncc(N5CCCC5)c4)cc23)cn1]

TABLE 1-continued
281 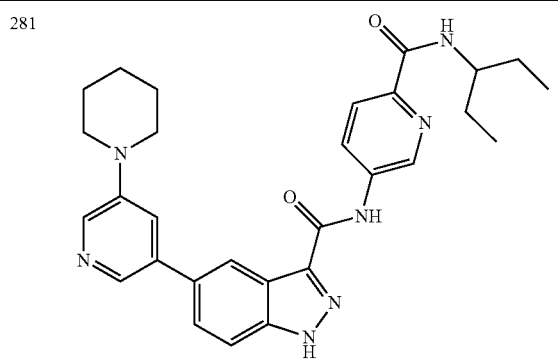
282 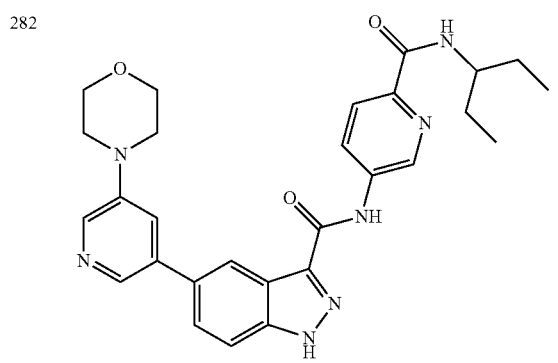
283 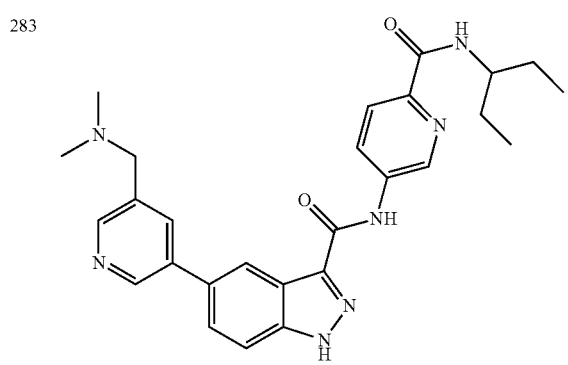
284 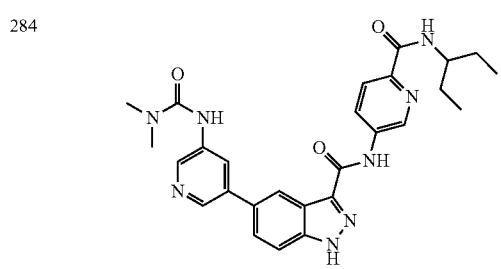
285 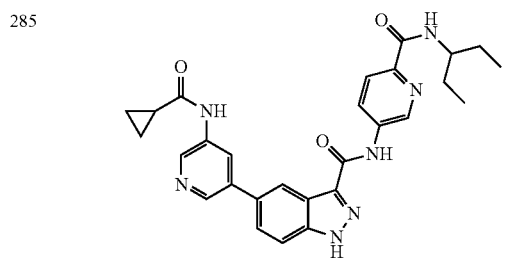
286 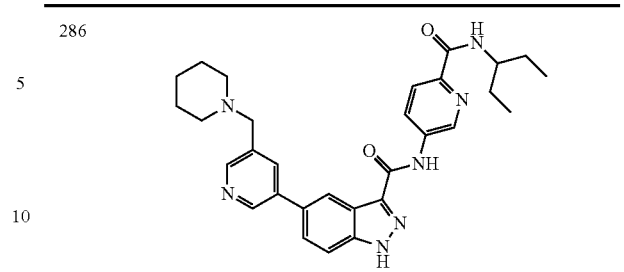
287 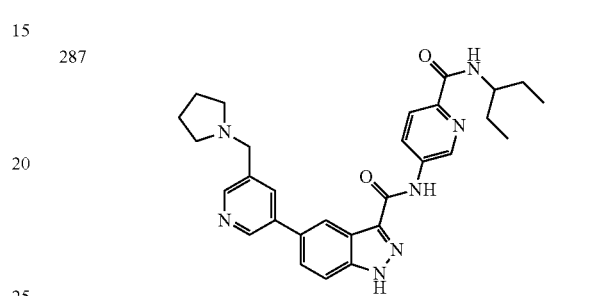
288 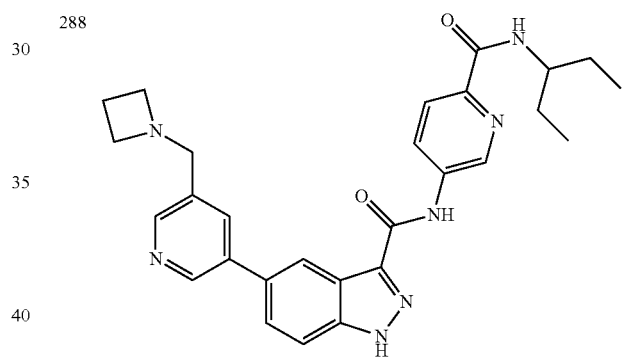
289 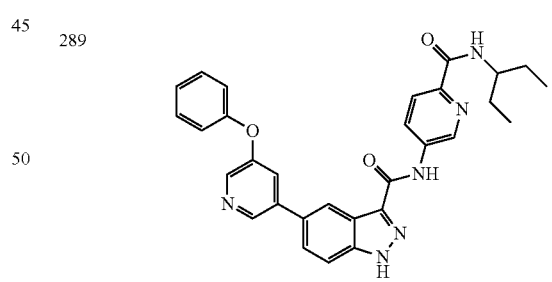
290 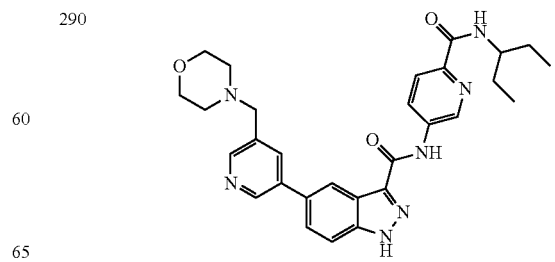

TABLE 1-continued
| | |
|---|---|
| 291 | 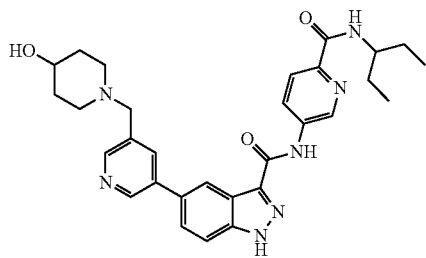 [SMILES: CCC(CC)NC(=O)c1ccc(NC(=O)c2n[nH]c3ccc(-c4cncc(CN5CCC(O)CC5)c4)cc23)cn1] |
| 292 | 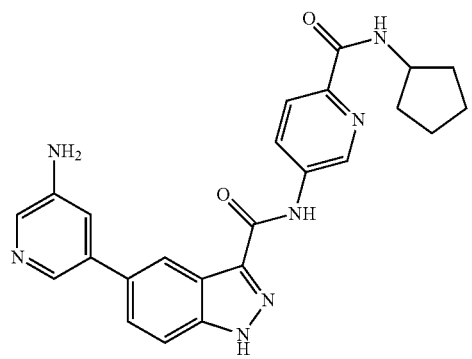 [SMILES: Nc1cncc(-c2ccc3[nH]nc(C(=O)Nc4ccc(C(=O)NC5CCCC5)nc4)c3c2)c1] |
| 293 | 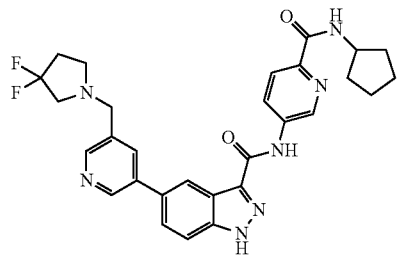 [SMILES: O=C(NC1CCCC1)c1ccc(NC(=O)c2n[nH]c3ccc(-c4cncc(CN5CCC(F)(F)C5)c4)cc23)cn1] |
| 294 | 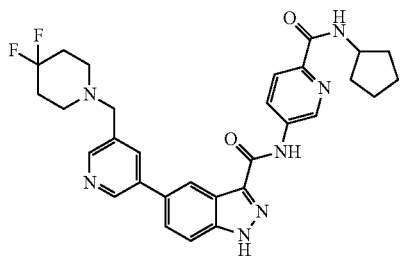 [SMILES: O=C(NC1CCCC1)c1ccc(NC(=O)c2n[nH]c3ccc(-c4cncc(CN5CCC(F)(F)CC5)c4)cc23)cn1] |
| 295 | 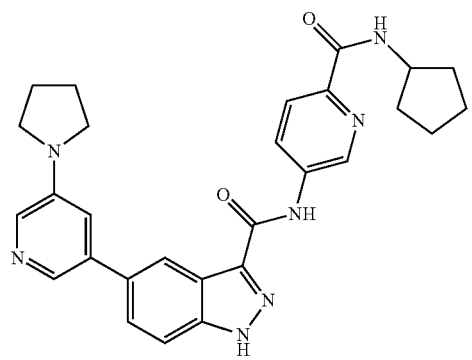 [SMILES: O=C(NC1CCCC1)c1ccc(NC(=O)c2n[nH]c3ccc(-c4cncc(N5CCCC5)c4)cc23)cn1] |
| 296 | 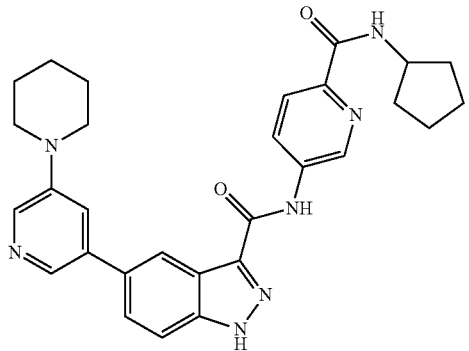 |
| 297 | 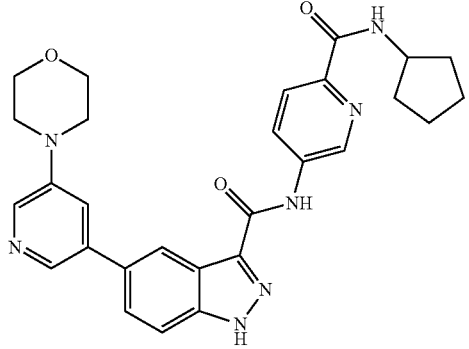 [SMILES: O=C(NC1CCCC1)c1ccc(NC(=O)c2n[nH]c3ccc(-c4cncc(N5CCOCC5)c4)cc23)cn1] |
| 298 | 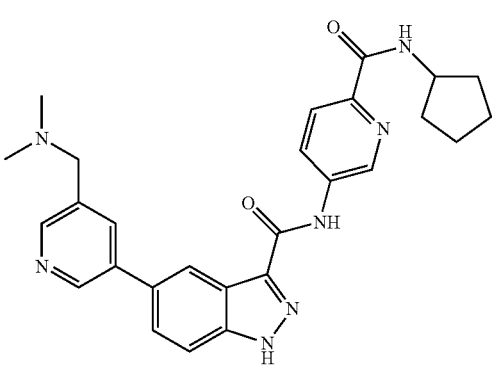 [SMILES: CN(C)Cc1cncc(-c2ccc3[nH]nc(C(=O)Nc4ccc(C(=O)NC5CCCC5)nc4)c3c2)c1] |
| 299 | 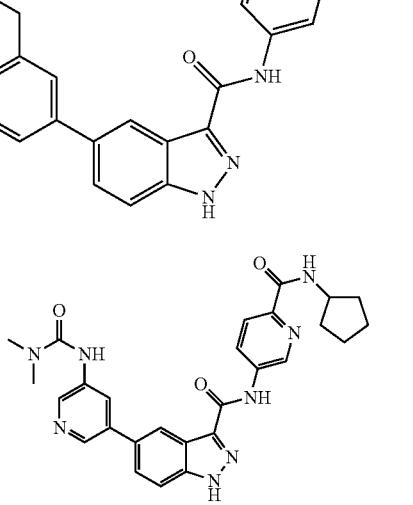 |
| 300 | 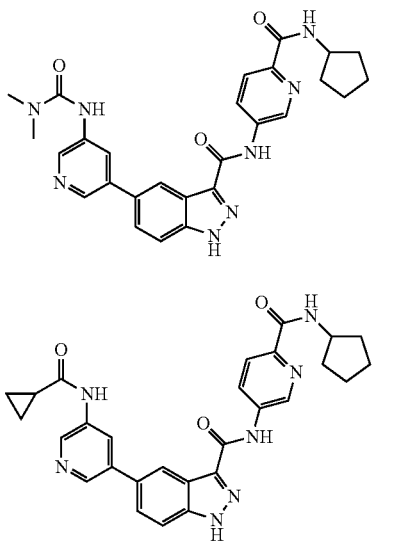 |

TABLE 1-continued
| | |
|---|---|
| 301 | 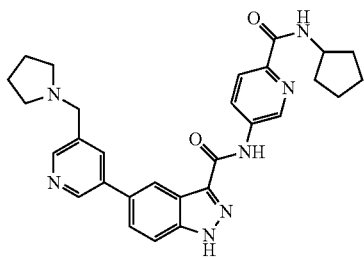 [SMILES: O=C(NC1CCCC1)c1ccc(NC(=O)c2n[nH]c3ccc(-c4cncc(CN5CCCC5)c4)cc23)cn1] |
| 302 | 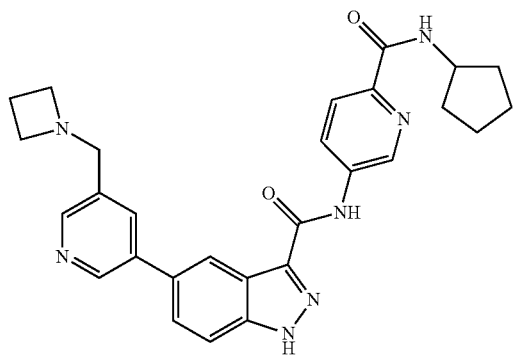 [SMILES: O=C(NC1CCCC1)c1ccc(NC(=O)c2n[nH]c3ccc(-c4cncc(CN5CCC5)c4)cc23)cn1] |
| 303 | 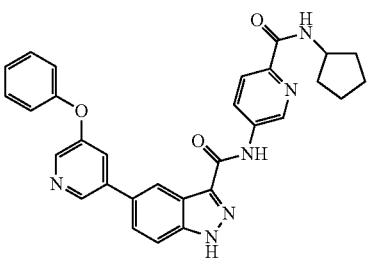 [SMILES: O=C(NC1CCCC1)c1ccc(NC(=O)c2n[nH]c3ccc(-c4cncc(Oc5ccccc5)c4)cc23)cn1] |
| 304 | 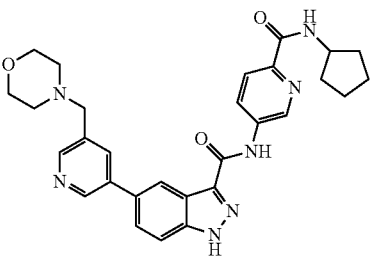 [SMILES: O=C(NC1CCCC1)c1ccc(NC(=O)c2n[nH]c3ccc(-c4cncc(CN5CCOCC5)c4)cc23)cn1] |
| 305 | 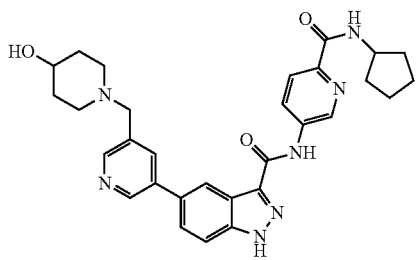 [SMILES: O=C(NC1CCCC1)c1ccc(NC(=O)c2n[nH]c3ccc(-c4cncc(CN5CCC(O)CC5)c4)cc23)cn1] |ऺ
TABLE 1-continued
| | |
|---|---|
| 306 | 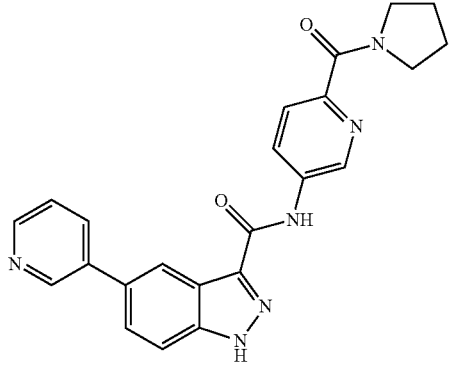 [SMILES: O=C(Nc1ccc(C(=O)N2CCCC2)nc1)c1n[nH]c2ccc(-c3cccnc3)cc12] |
| 307 | 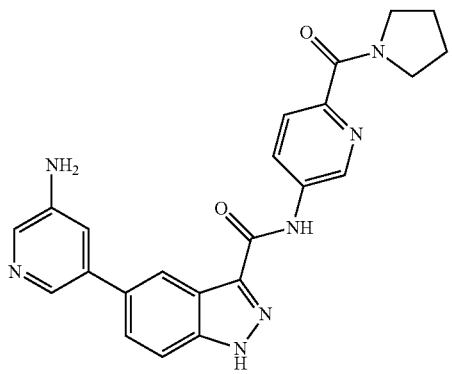 [SMILES: Nc1cncc(-c2ccc3[nH]nc(C(=O)Nc4ccc(C(=O)N5CCCC5)nc4)c3c2)c1] |
| 308 | 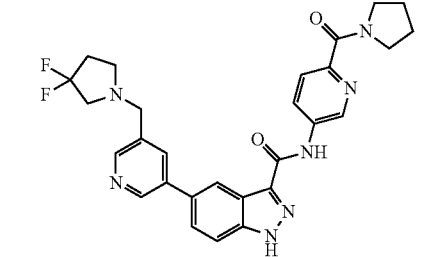 [SMILES: O=C(Nc1ccc(C(=O)N2CCCC2)nc1)c1n[nH]c2ccc(-c3cncc(CN4CCC(F)(F)C4)c3)cc12] |
| 309 | 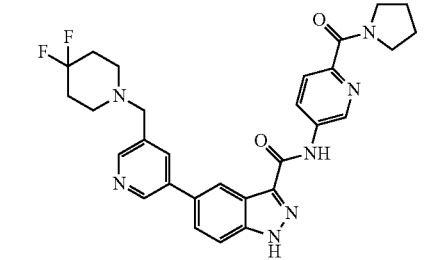 [SMILES: O=C(Nc1ccc(C(=O)N2CCCC2)nc1)c1n[nH]c2ccc(-c3cncc(CN4CCC(F)(F)CC4)c3)cc12] |
| 310 | 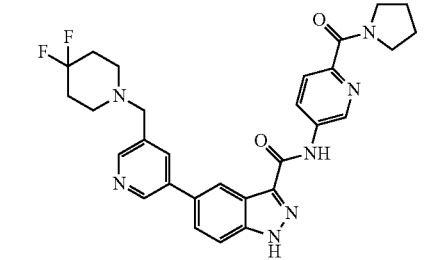 [SMILES: O=C(Nc1ccc(C(=O)N2CCCC2)nc1)c1n[nH]c2ccc(-c3cncc(CN4CCC(F)(F)CC4)c3)cc12] |

TABLE 1-continued
311
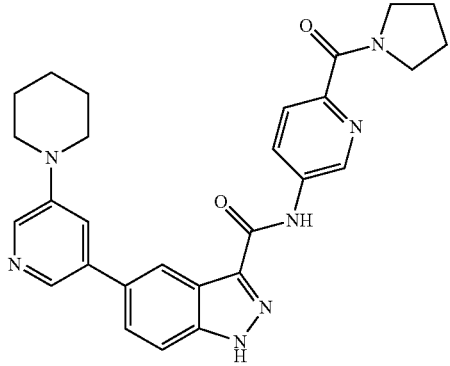 [SMILES: O=C(Nc1ccc(C(=O)N2CCCC2)nc1)c1n[nH]c2ccc(-c3cncc(N4CCOCC4)c3)cc12]
312
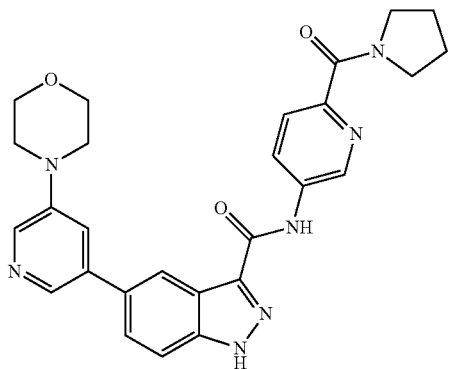
313
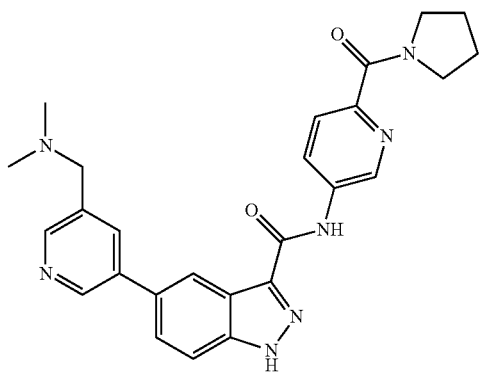 [SMILES: CN(C)Cc1cncc(-c2ccc3[nH]nc(C(=O)Nc4ccc(C(=O)N5CCCC5)nc4)c3c2)c1]
314
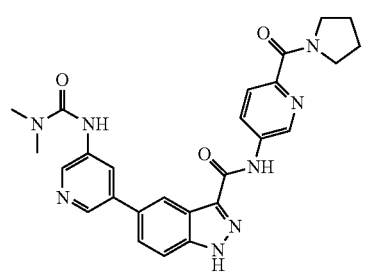 [SMILES: CN(C)C(=O)Nc1cncc(-c2ccc3[nH]nc(C(=O)Nc4ccc(C(=O)N5CCCC5)nc4)c3c2)c1]
TABLE 1-continued
315
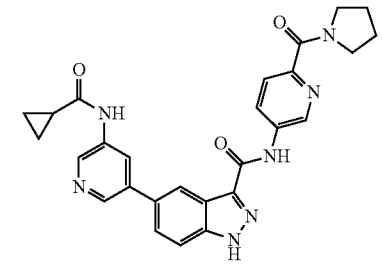 [SMILES: O=C(Nc1ccc(C(=O)N2CCCC2)nc1)c1n[nH]c2ccc(-c3cncc(NC(=O)C4CC4)c3)cc12]
316
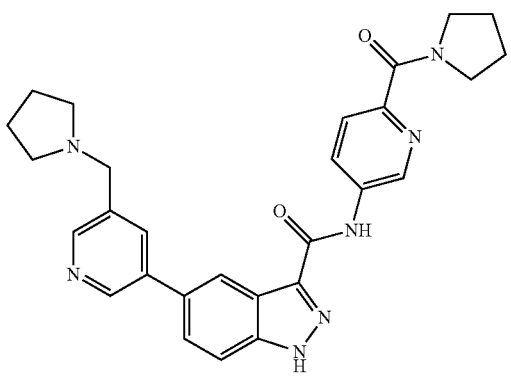 [SMILES: O=C(Nc1ccc(C(=O)N2CCCC2)nc1)c1n[nH]c2ccc(-c3cncc(CN4CCCC4)c3)cc12]
317
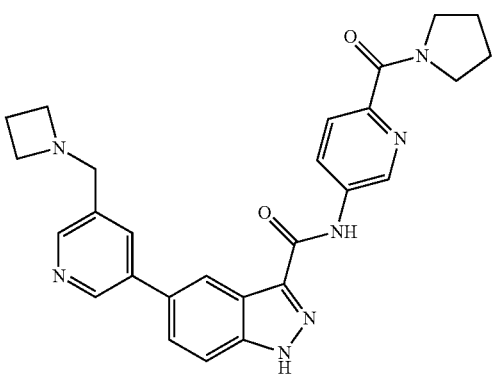 [SMILES: O=C(Nc1ccc(C(=O)N2CCCC2)nc1)c1n[nH]c2ccc(-c3cncc(CN4CCC4)c3)cc12]
318
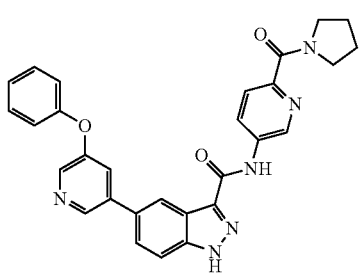 [SMILES: O=C(Nc1ccc(C(=O)N2CCCC2)nc1)c1n[nH]c2ccc(-c3cncc(Oc4ccccc4)c3)cc12]
319
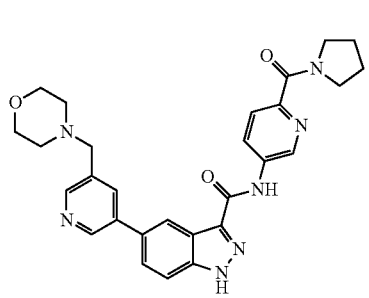 [SMILES: O=C(Nc1ccc(C(=O)N2CCCC2)nc1)c1n[nH]c2ccc(-c3cncc(CN4CCOCC4)c3)cc12]

TABLE 1-continued
| 320 | 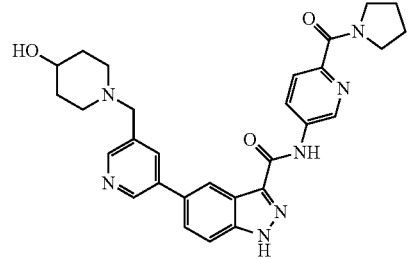 [SMILES: O=C(Nc1ccc(C(=O)N2CCCC2)nc1)c1n[nH]c2ccc(-c3cncc(CN4CCC(O)CC4)c3)cc12] |
| 321 | 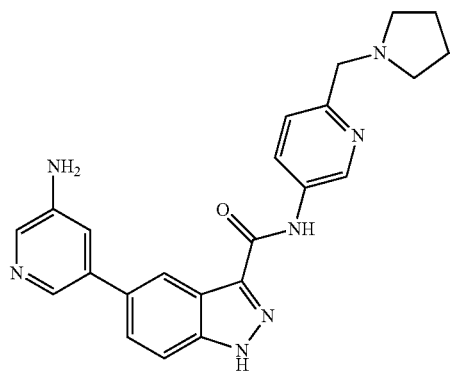 [SMILES: Nc1cncc(-c2ccc3[nH]nc(C(=O)Nc4ccc(CN5CCCC5)nc4)c3c2)c1] |
| 322 | 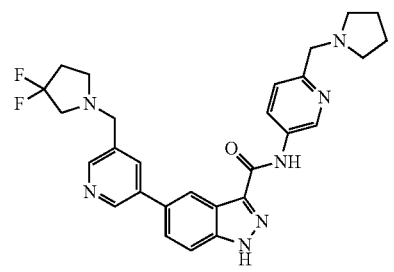 [SMILES: O=C(Nc1ccc(CN2CCCC2)nc1)c1n[nH]c2ccc(-c3cncc(CN4CCC(F)(F)C4)c3)cc12] |
| 323 | 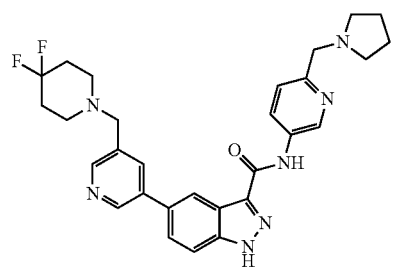 [SMILES: O=C(Nc1ccc(CN2CCCC2)nc1)c1n[nH]c2ccc(-c3cncc(CN4CCC(F)(F)CC4)c3)cc12] |
| 324 | 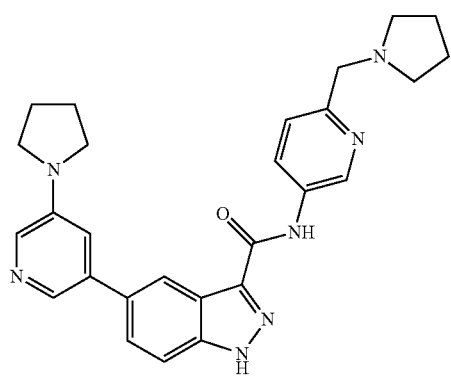 [SMILES: O=C(Nc1ccc(CN2CCCC2)nc1)c1n[nH]c2ccc(-c3cncc(N4CCCC4)c3)cc12] |
TABLE 1-continued
| 325 | 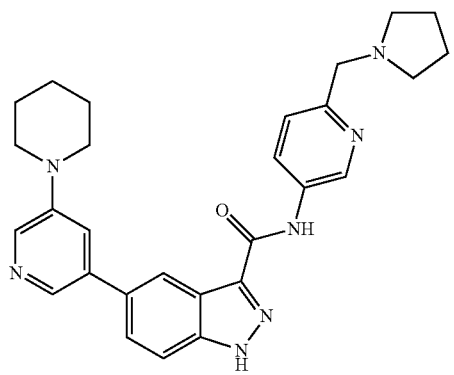 [SMILES: O=C(Nc1ccc(CN2CCCC2)nc1)c1n[nH]c2ccc(-c3cncc(N4CCCCC4)c3)cc12] |
| 326 | 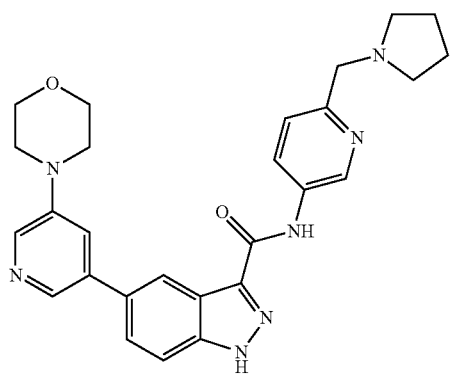 [SMILES: O=C(Nc1ccc(CN2CCCC2)nc1)c1n[nH]c2ccc(-c3cncc(N4CCOCC4)c3)cc12] |
| 327 | 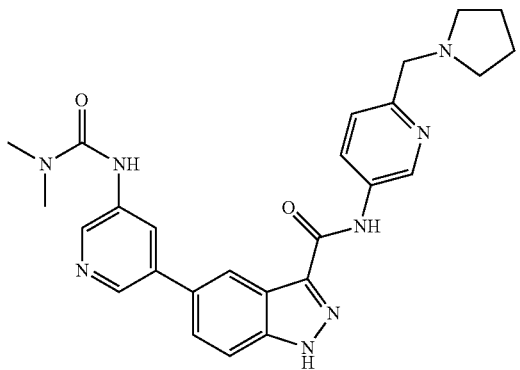 [SMILES: CN(C)C(=O)Nc1cncc(-c2ccc3[nH]nc(C(=O)Nc4ccc(CN5CCCC5)nc4)c3c2)c1] |
| 328 | 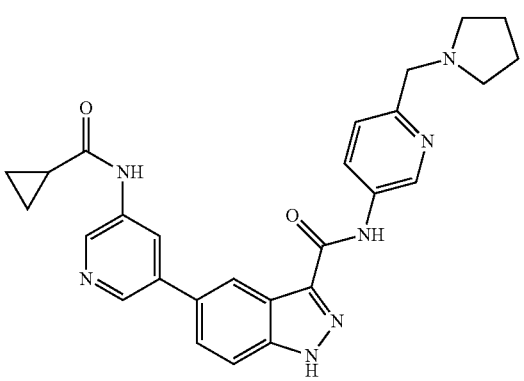 [SMILES: O=C(Nc1ccc(CN2CCCC2)nc1)c1n[nH]c2ccc(-c3cncc(NC(=O)C4CC4)c3)cc12] |

TABLE 1-continued
329
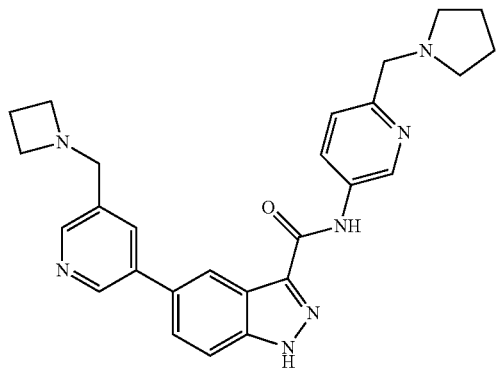 [SMILES: O=C(Nc1ccc(CN2CCCC2)nc1)c1n[nH]c2ccc(-c3cncc(CN4CCC4)c3)cc12]
330
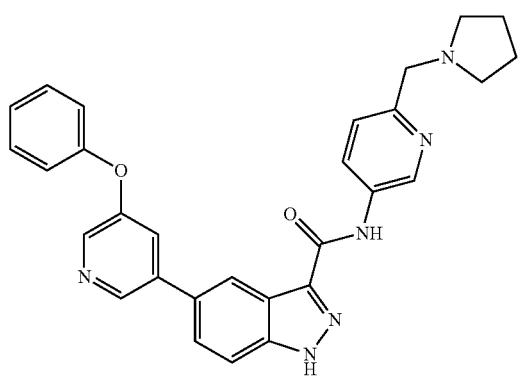 [SMILES: O=C(Nc1ccc(CN2CCCC2)nc1)c1n[nH]c2ccc(-c3cncc(Oc4ccccc4)c3)cc12]
331
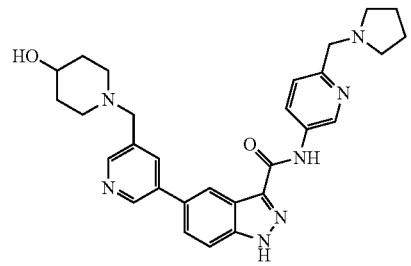 [SMILES: O=C(Nc1ccc(CN2CCCC2)nc1)c1n[nH]c2ccc(-c3cncc(CN4CCC(O)CC4)c3)cc12]
332
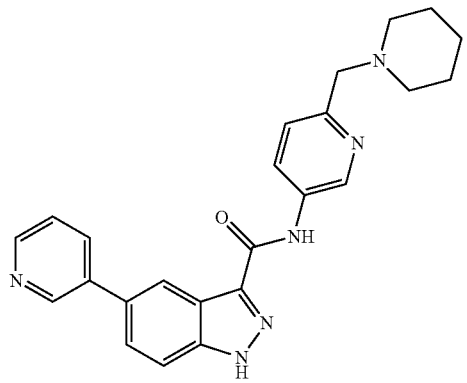 [SMILES: O=C(Nc1ccc(CN2CCCCC2)nc1)c1n[nH]c2ccc(-c3cccnc3)cc12]
333
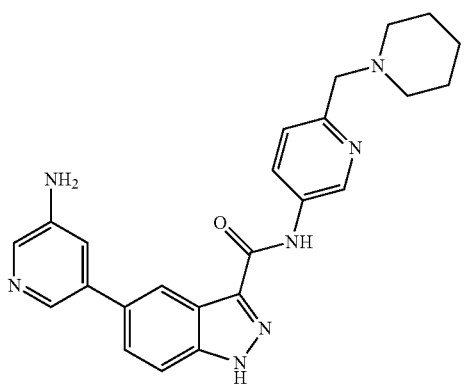 [SMILES: Nc1cncc(-c2ccc3[nH]nc(C(=O)Nc4ccc(CN5CCCCC5)nc4)c3c2)c1]
334
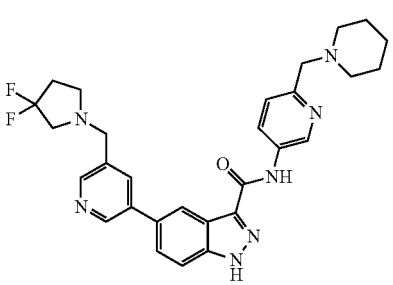 [SMILES: O=C(Nc1ccc(CN2CCCCC2)nc1)c1n[nH]c2ccc(-c3cncc(CN4CCC(F)(F)C4)c3)cc12]
335
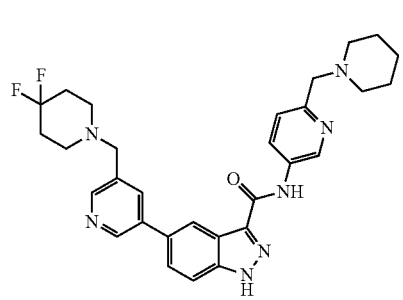 [SMILES: O=C(Nc1ccc(CN2CCCCC2)nc1)c1n[nH]c2ccc(-c3cncc(CN4CCC(F)(F)CC4)c3)cc12]
336
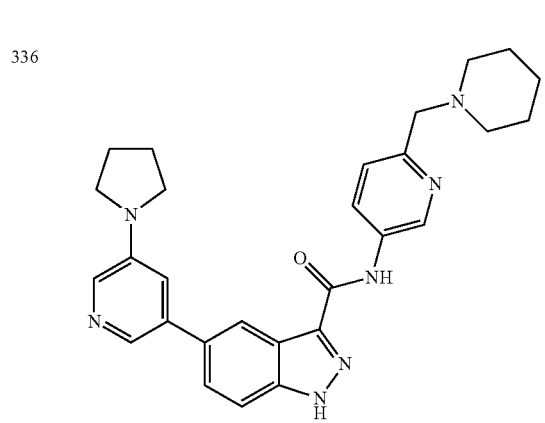

TABLE 1-continued
337 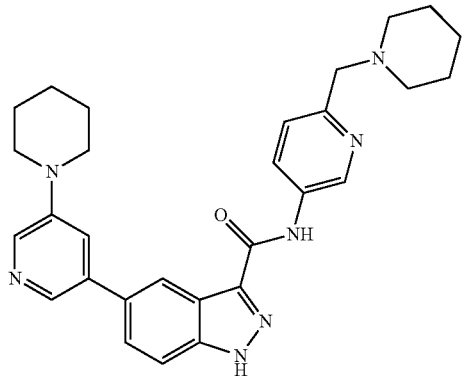
338 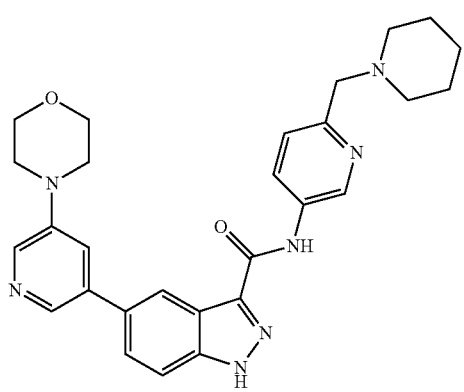 [SMILES: O=C(Nc1ccc(CN2CCCCC2)nc1)c1n[nH]c2ccc(-c3cncc(N4CCOCC4)c3)cc12]
339 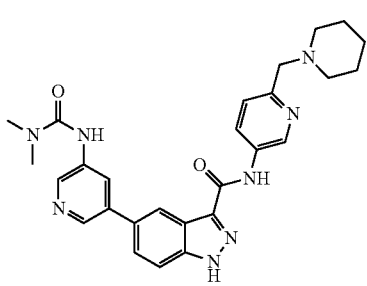 [SMILES: CN(C)C(=O)Nc1cncc(-c2ccc3[nH]nc(C(=O)Nc4ccc(CN5CCCCC5)nc4)c3c2)c1]
340 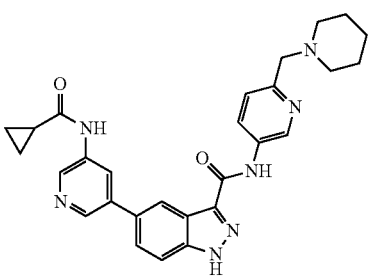 [SMILES: O=C(Nc1ccc(CN2CCCCC2)nc1)c1n[nH]c2ccc(-c3cncc(NC(=O)C4CC4)c3)cc12]
341 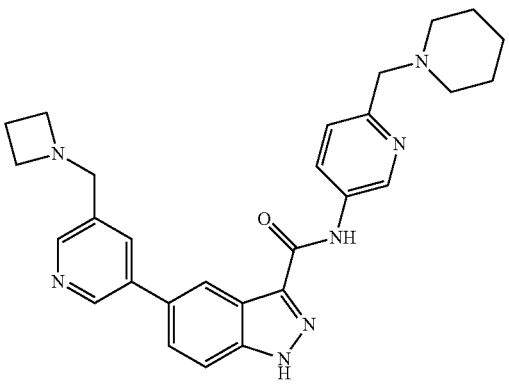 [SMILES: O=C(Nc1ccc(CN2CCCCC2)nc1)c1n[nH]c2ccc(-c3cncc(CN4CCC4)c3)cc12]
342 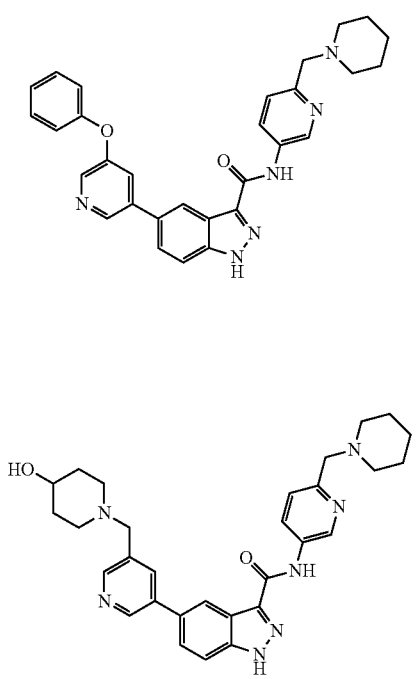
343
344 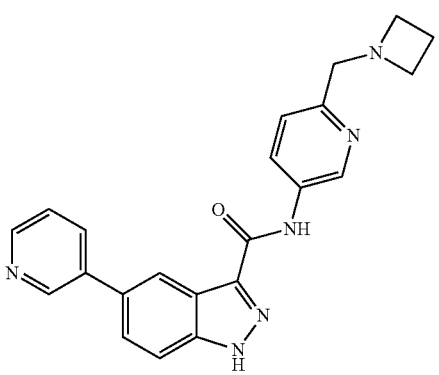 [SMILES: O=C(Nc1ccc(CN2CCC2)nc1)c1n[nH]c2ccc(-c3cccnc3)cc12]

TABLE 1-continued
345 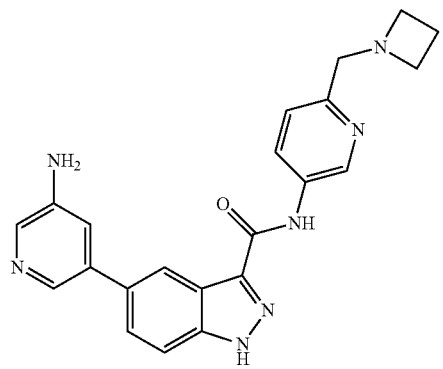 [SMILES: Nc1cncc(-c2ccc3[nH]nc(C(=O)Nc4ccc(CN5CCC5)nc4)c3c2)c1]
346 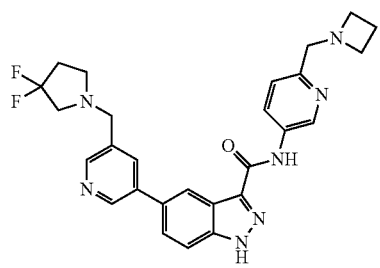 [SMILES: O=C(Nc1ccc(CN2CCC2)nc1)c1n[nH]c2ccc(-c3cncc(CN4CCC(F)(F)C4)c3)cc12]
347 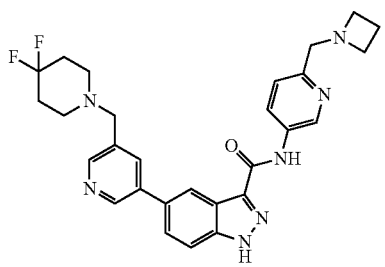 [SMILES: O=C(Nc1ccc(CN2CCC2)nc1)c1n[nH]c2ccc(-c3cncc(CN4CCC(F)(F)CC4)c3)cc12]
348 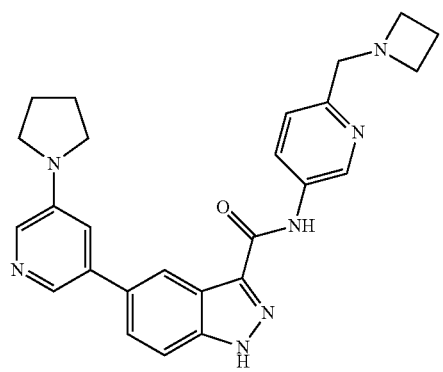 [SMILES: O=C(Nc1ccc(CN2CCC2)nc1)c1n[nH]c2ccc(-c3cncc(N4CCCC4)c3)cc12]
349 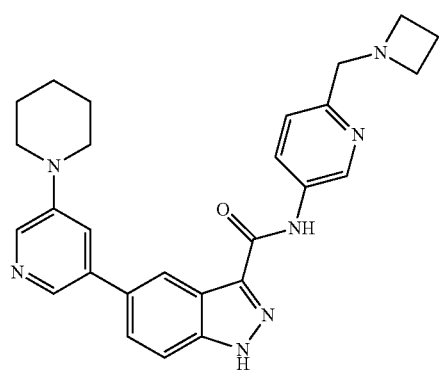
TABLE 1-continued
350 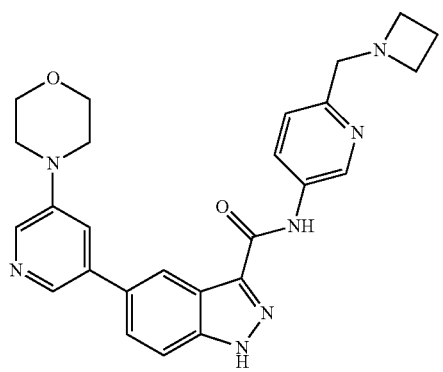 [SMILES: O=C(Nc1ccc(CN2CCC2)nc1)c1n[nH]c2ccc(-c3cncc(N4CCOCC4)c3)cc12]
351 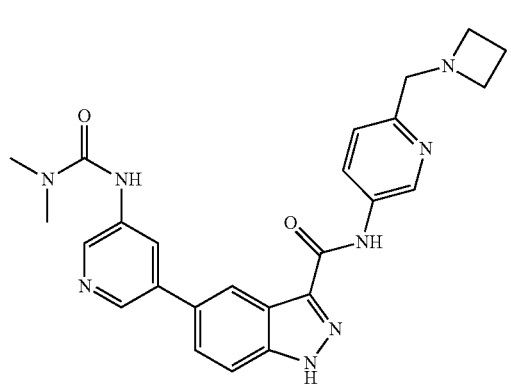 [SMILES: CN(C)C(=O)Nc1cncc(-c2ccc3[nH]nc(C(=O)Nc4ccc(CN5CCC5)nc4)c3c2)c1]
352 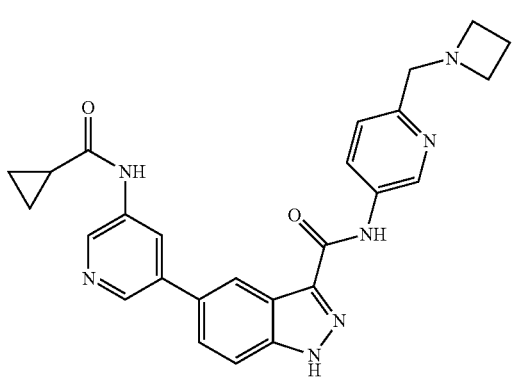 [SMILES: O=C(Nc1ccc(CN2CCC2)nc1)c1n[nH]c2ccc(-c3cncc(NC(=O)C4CC4)c3)cc12]
353 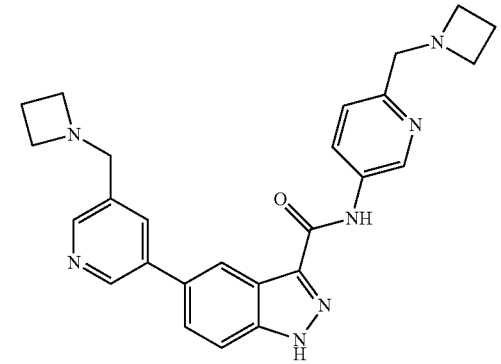 [SMILES: O=C(Nc1ccc(CN2CCC2)nc1)c1n[nH]c2ccc(-c3cncc(CN4CCC4)c3)cc12]

TABLE 1-continued
354
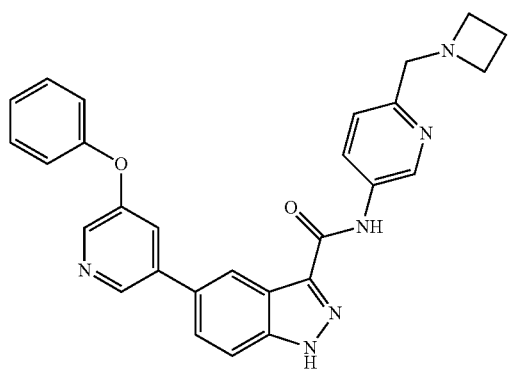 [SMILES: O=C(Nc1ccc(CN2CCC2)nc1)c1n[nH]c2ccc(-c3cncc(Oc4ccccc4)c3)cc12]
355
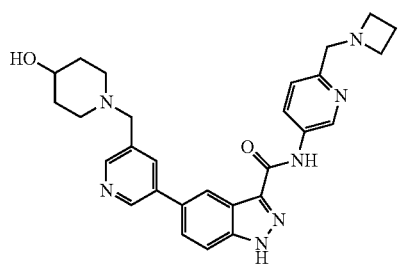 [SMILES: O=C(Nc1ccc(CN2CCC2)nc1)c1n[nH]c2ccc(-c3cncc(CN4CCC(O)CC4)c3)cc12]
356
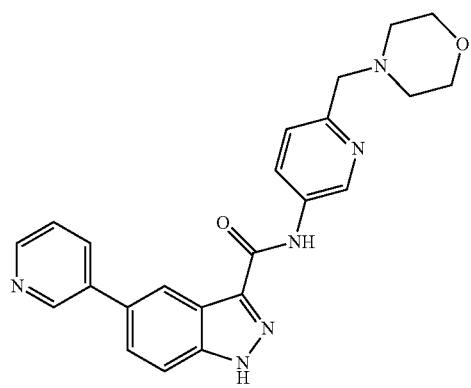 [SMILES: O=C(Nc1ccc(CN2CCOCC2)nc1)c1n[nH]c2ccc(-c3cccnc3)cc12]
357
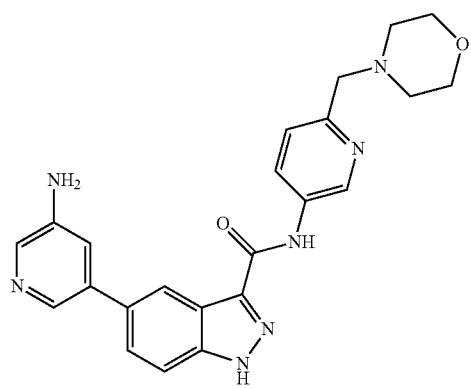 [SMILES: Nc1cncc(-c2ccc3[nH]nc(C(=O)Nc4ccc(CN5CCOCC5)nc4)c3c2)c1]
358
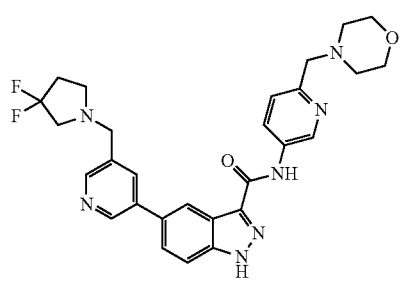 [SMILES: O=C(Nc1ccc(CN2CCOCC2)nc1)c1n[nH]c2ccc(-c3cncc(CN4CCC(F)(F)C4)c3)cc12]
359
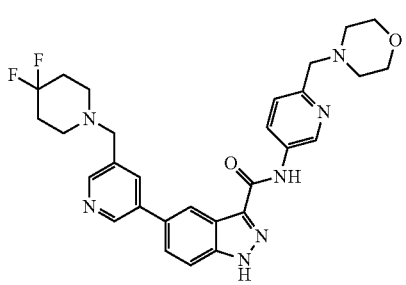 [SMILES: O=C(Nc1ccc(CN2CCOCC2)nc1)c1n[nH]c2ccc(-c3cncc(CN4CCC(F)(F)CC4)c3)cc12]
360
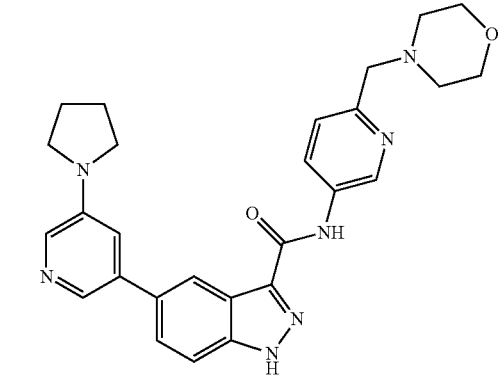 [SMILES: O=C(Nc1ccc(CN2CCOCC2)nc1)c1n[nH]c2ccc(-c3cncc(N4CCCC4)c3)cc12]
361
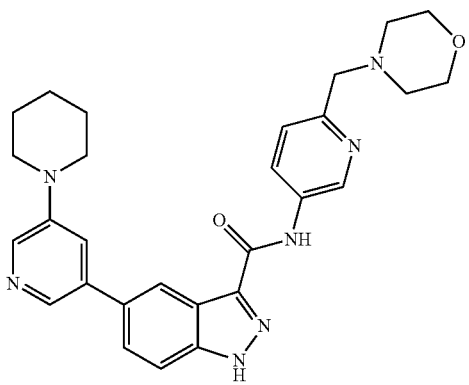 [SMILES: O=C(Nc1ccc(CN2CCOCC2)nc1)c1n[nH]c2ccc(-c3cncc(N4CCCCC4)c3)cc12]

TABLE 1-continued
362 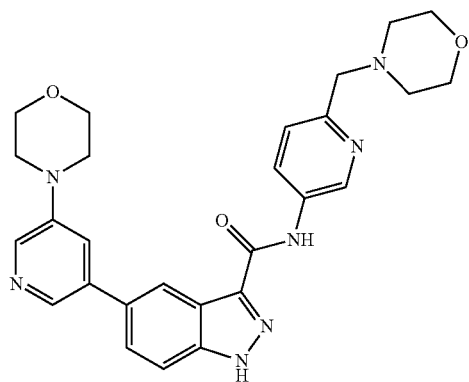
363 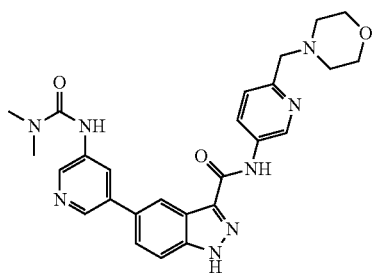 [SMILES: CN(C)C(=O)Nc1cncc(-c2ccc3[nH]nc(C(=O)Nc4ccc(CN5CCOCC5)nc4)c3c2)c1]
364 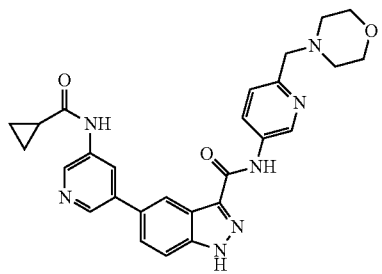 [SMILES: O=C(Nc1ccc(CN2CCOCC2)nc1)c1n[nH]c2ccc(-c3cncc(NC(=O)C4CC4)c3)cc12]
365 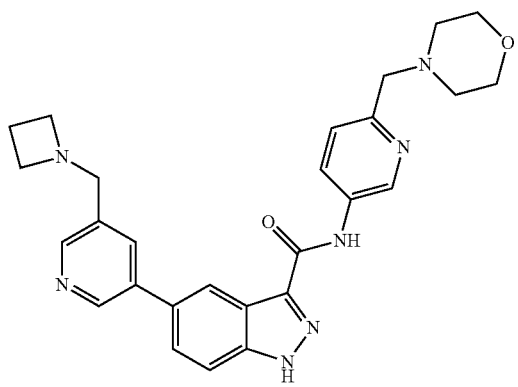 [SMILES: O=C(Nc1ccc(CN2CCOCC2)nc1)c1n[nH]c2ccc(-c3cncc(CN4CCC4)c3)cc12]
366 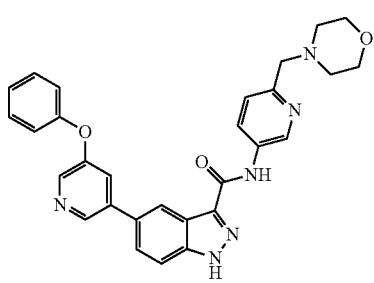 [SMILES: O=C(Nc1ccc(CN2CCOCC2)nc1)c1n[nH]c2ccc(-c3cncc(Oc4ccccc4)c3)cc12]
TABLE 1-continued
367 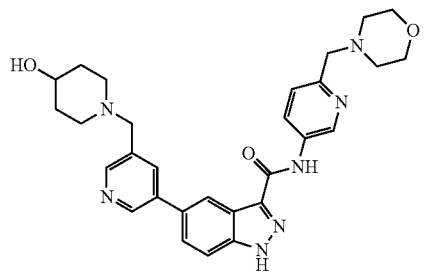 [SMILES: O=C(Nc1ccc(CN2CCOCC2)nc1)c1n[nH]c2ccc(-c3cncc(CN4CCC(O)CC4)c3)cc12]
368 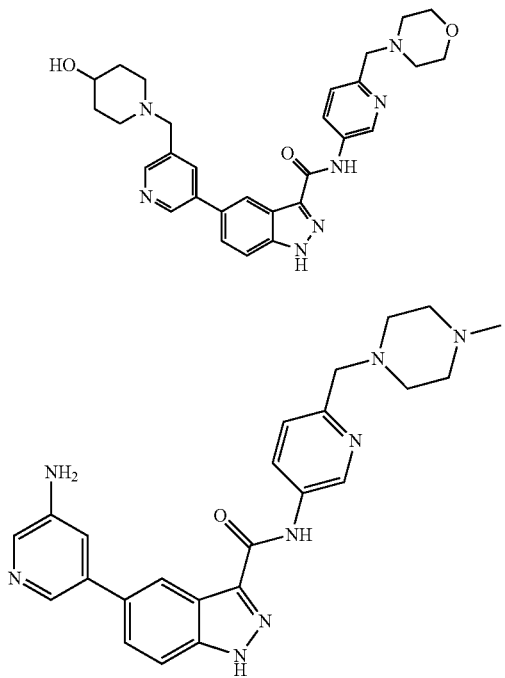
369 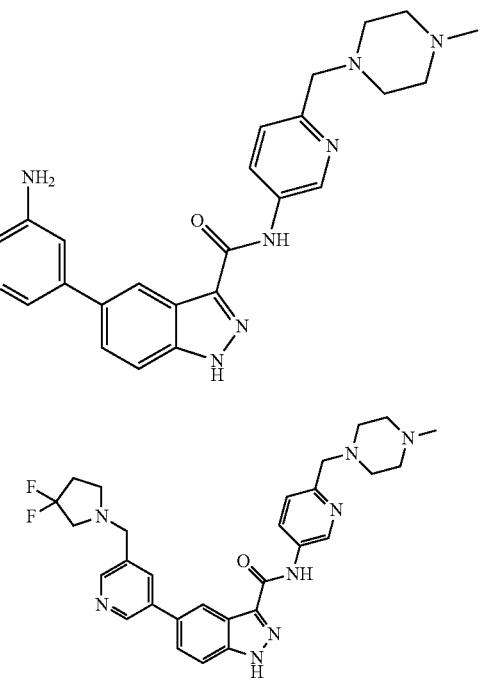
370 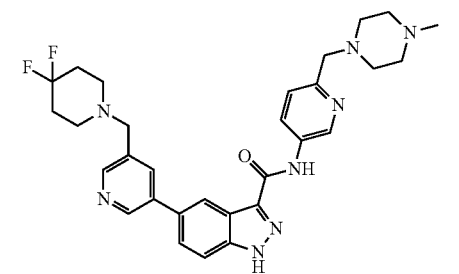 [SMILES: CN1CCN(Cc2ccc(NC(=O)c3n[nH]c4ccc(-c5cncc(CN6CCC(F)(F)CC6)c5)cc34)cn2)CC1]
371 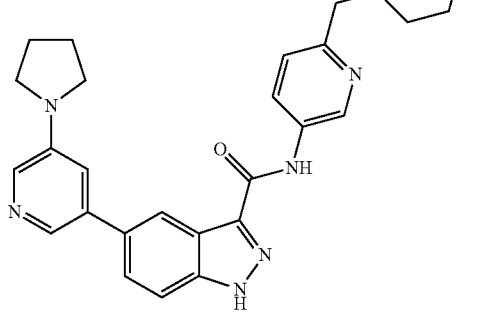

TABLE 1-continued
| | |
|---|---|
| 372 | 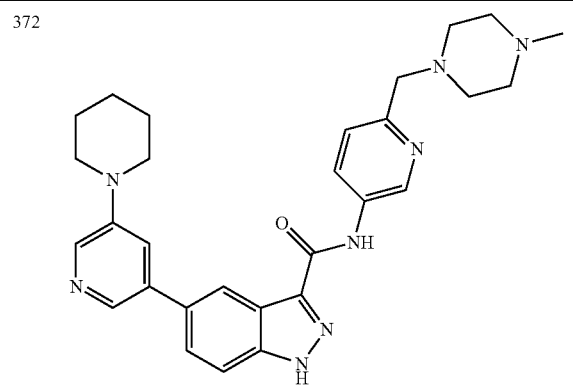 |
| 373 | 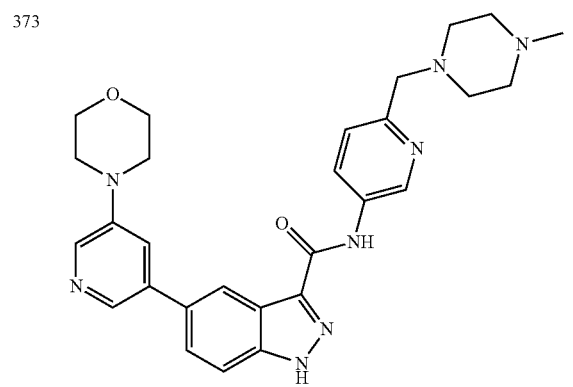 |
| 374 | 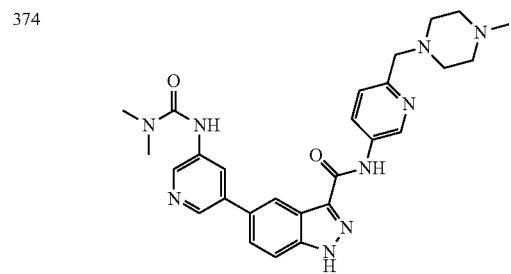 |
| 375 | 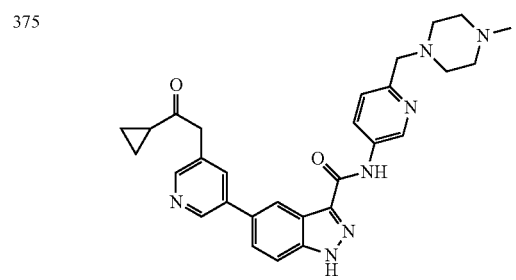 |
| 376 | 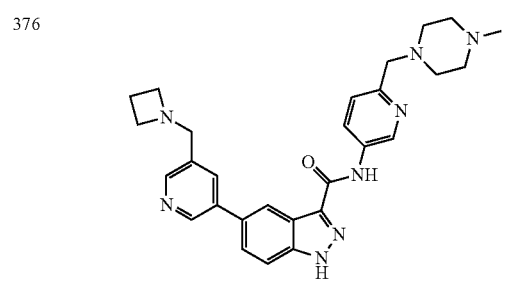 |
| 377 | 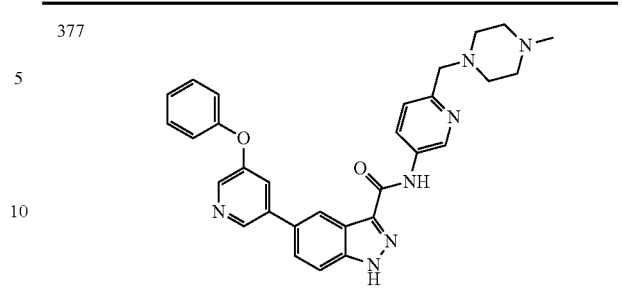 |
| 378 | 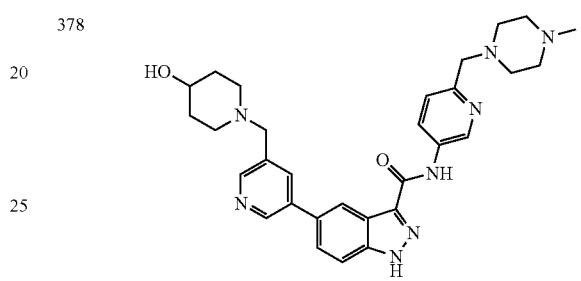 |
| 379 | 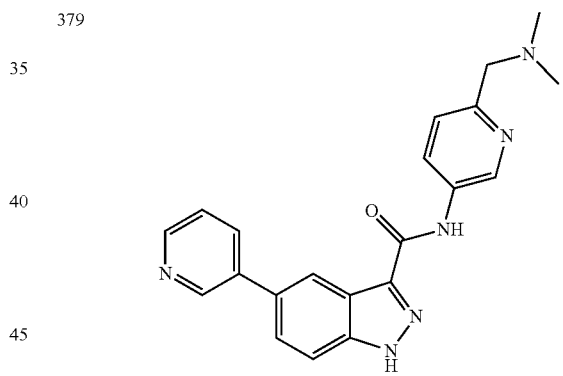 |
| 380 | 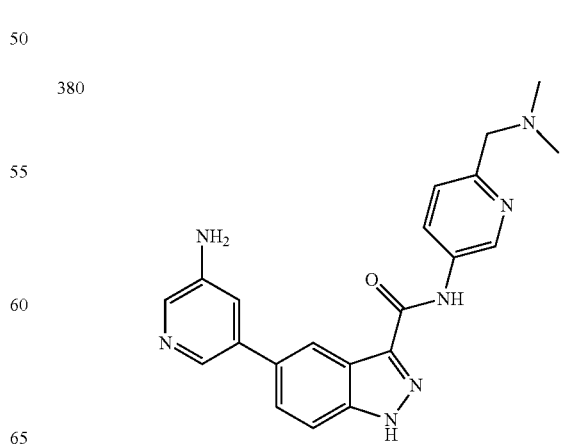 |

TABLE 1-continued
381
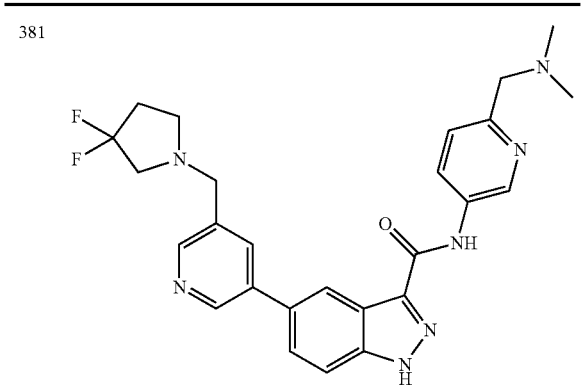
382
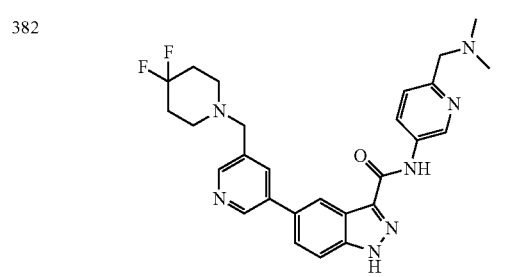
383
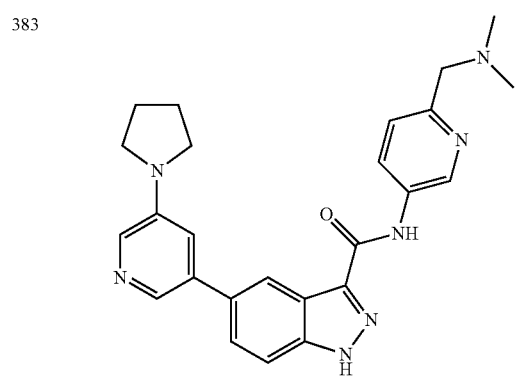
384
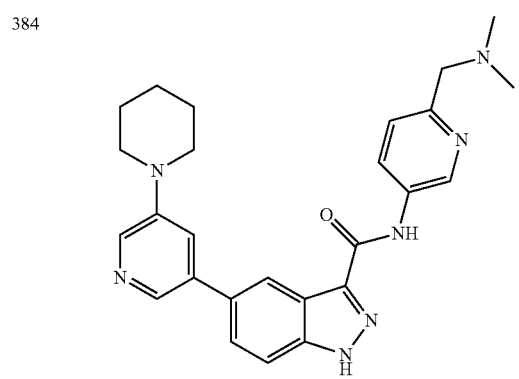
385
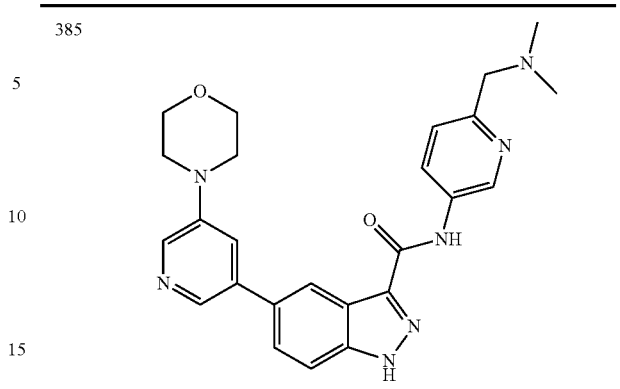
386
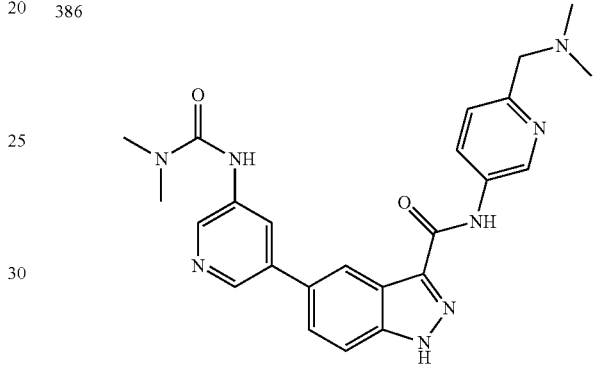
387
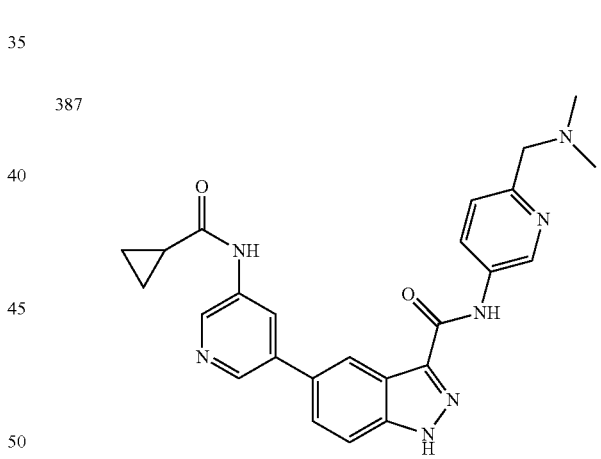
388
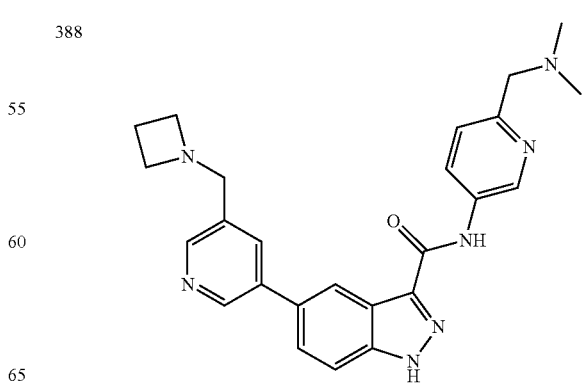

TABLE 1-continued
389
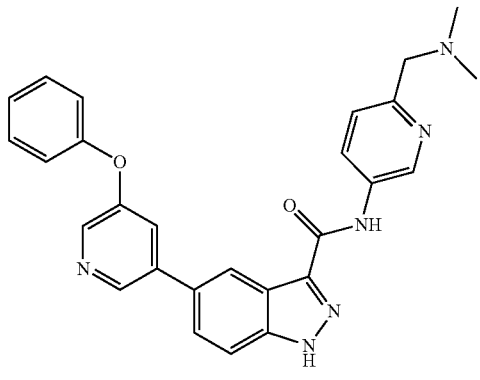 [SMILES: CN(C)Cc1ccc(NC(=O)c2n[nH]c3ccc(-c4cncc(Oc5ccccc5)c4)cc23)cn1]
390
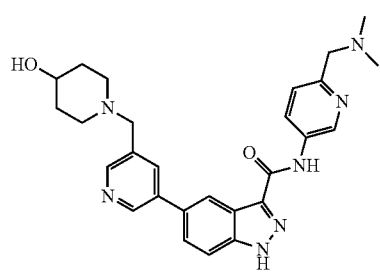 [SMILES: CN(C)Cc1ccc(NC(=O)c2n[nH]c3ccc(-c4cncc(CN5CCC(O)CC5)c4)cc23)cn1]
391
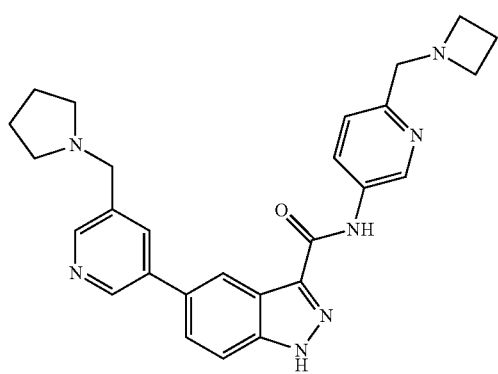 [SMILES: O=C(Nc1ccc(CN2CCC2)nc1)c1n[nH]c2ccc(-c3cncc(CN4CCCC4)c3)cc12]
392
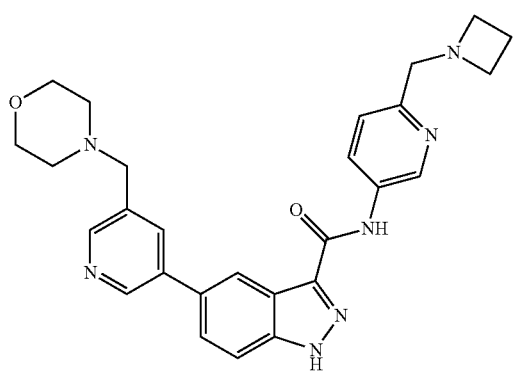 [SMILES: O=C(Nc1ccc(CN2CCC2)nc1)c1n[nH]c2ccc(-c3cncc(CN4CCOCC4)c3)cc12]
TABLE 1-continued
393
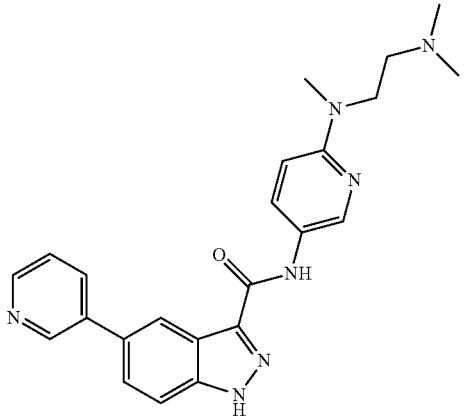 [SMILES: CN(C)CCN(C)c1ccc(NC(=O)c2n[nH]c3ccc(-c4cccnc4)cc23)cn1]
394
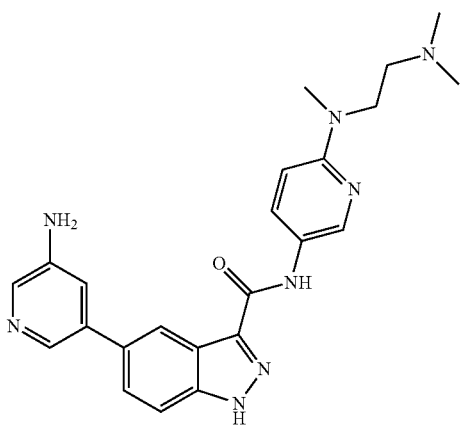 [SMILES: CN(C)CCN(C)c1ccc(NC(=O)c2n[nH]c3ccc(-c4cncc(N)c4)cc23)cn1]
395
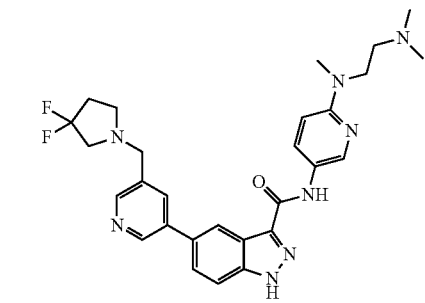 [SMILES: CN(C)CCN(C)c1ccc(NC(=O)c2n[nH]c3ccc(-c4cncc(CN5CCC(F)(F)C5)c4)cc23)cn1]
396
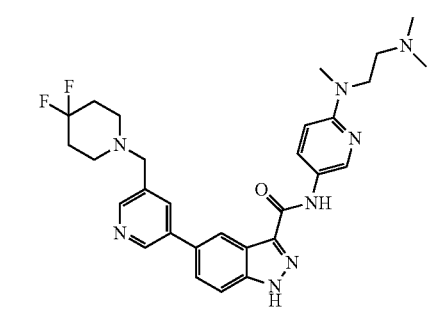 [SMILES: CN(C)CCN(C)c1ccc(NC(=O)c2n[nH]c3ccc(-c4cncc(CN5CCC(F)(F)CC5)c4)cc23)cn1]

TABLE 1-continued
397
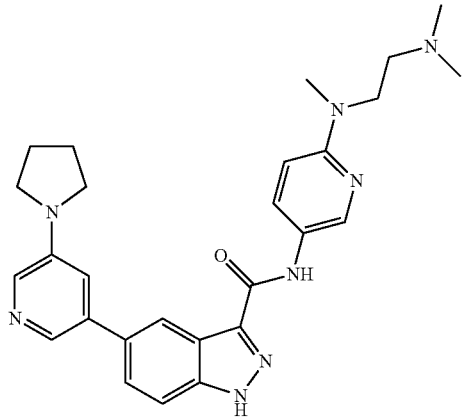 [SMILES: CN(C)CCN(C)c1ccc(NC(=O)c2n[nH]c3ccc(-c4cncc(N5CCCC5)c4)cc23)cn1]
398
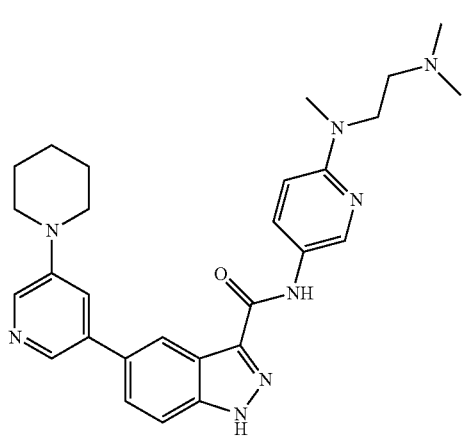 [SMILES: CN(C)CCN(C)c1ccc(NC(=O)c2n[nH]c3ccc(-c4cncc(N5CCCCC5)c4)cc23)cn1]
399
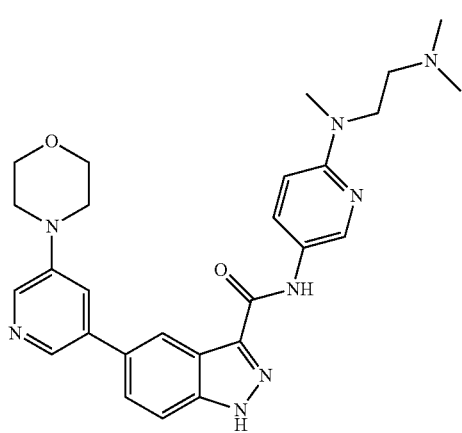
TABLE 1-continued
400
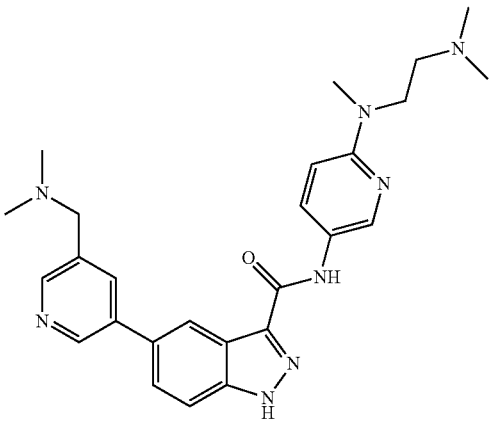
401
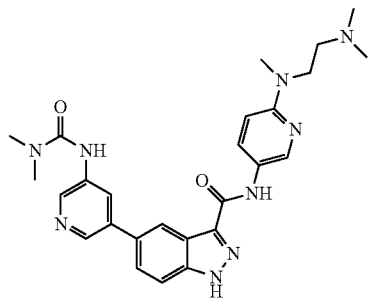
402
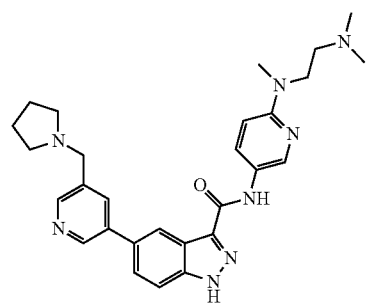 [SMILES: CN(C)CCN(C)c1ccc(NC(=O)c2n[nH]c3ccc(-c4cncc(CN5CCCC5)c4)cc23)cn1]
403

TABLE 1-continued
404
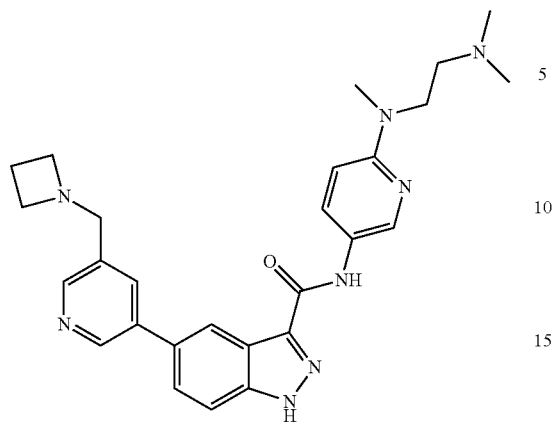
405
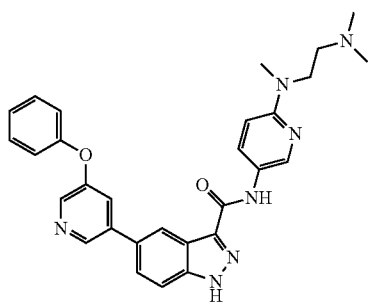 [SMILES: CN(C)CCN(C)c1ccc(NC(=O)c2n[nH]c3ccc(-c4cncc(Oc5ccccc5)c4)cc23)cn1]
406
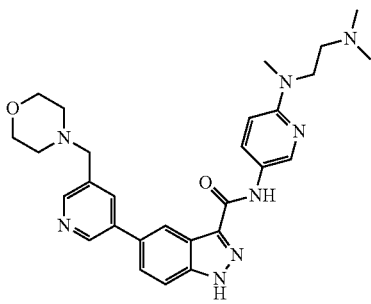 [SMILES: CN(C)CCN(C)c1ccc(NC(=O)c2n[nH]c3ccc(-c4cncc(CN5CCOCC5)c4)cc23)cn1]
407
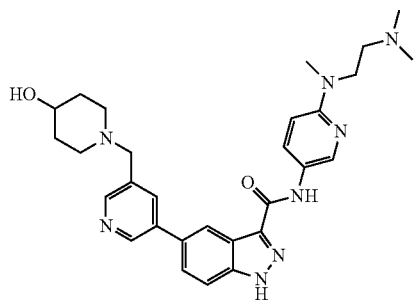 [SMILES: CN(C)CCN(C)c1ccc(NC(=O)c2n[nH]c3ccc(-c4cncc(CN5CCC(O)CC5)c4)cc23)cn1]
408
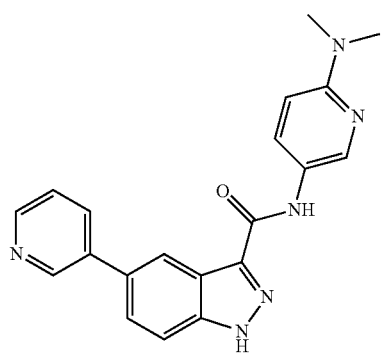 [SMILES: CN(C)c1ccc(NC(=O)c2n[nH]c3ccc(-c4cccnc4)cc23)cn1]
409
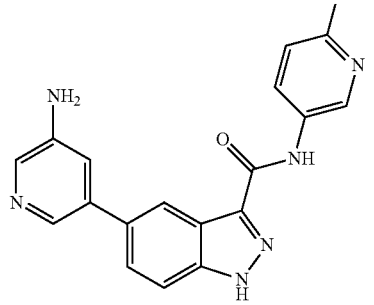
410
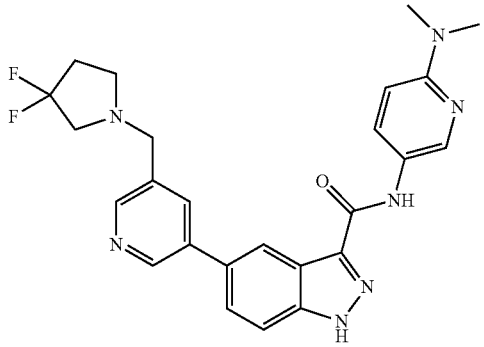 [SMILES: CN(C)c1ccc(NC(=O)c2n[nH]c3ccc(-c4cncc(CN5CCC(F)(F)C5)c4)cc23)cn1]
411
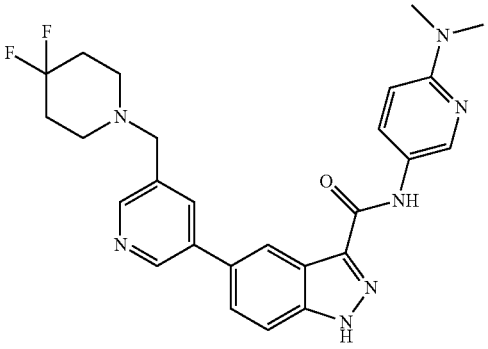 [SMILES: CN(C)c1ccc(NC(=O)c2n[nH]c3ccc(-c4cncc(CN5CCC(F)(F)CC5)c4)cc23)cn1]

TABLE 1-continued
412 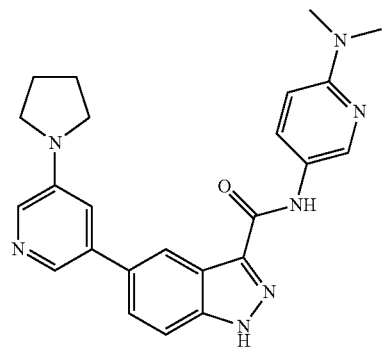 [SMILES: CN(C)c1ccc(NC(=O)c2n[nH]c3ccc(-c4cncc(N5CCCC5)c4)cc23)cn1]
413 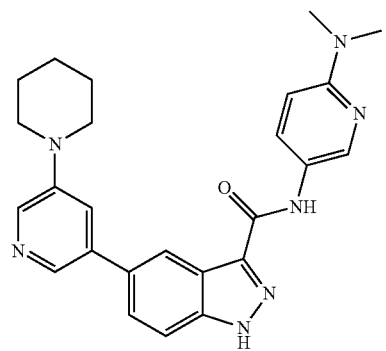 [SMILES: CN(C)c1ccc(NC(=O)c2n[nH]c3ccc(-c4cncc(N5CCCCC5)c4)cc23)cn1]
414 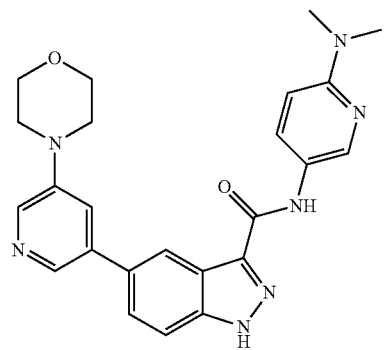 [SMILES: CN(C)c1ccc(NC(=O)c2n[nH]c3ccc(-c4cncc(N5CCOCC5)c4)cc23)cn1]
415 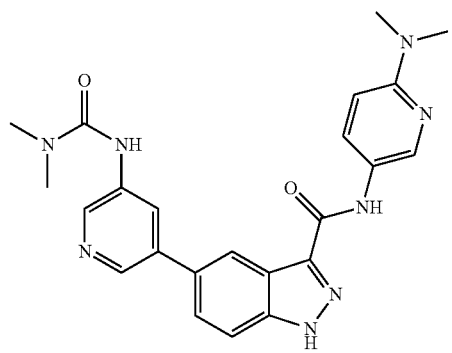
416 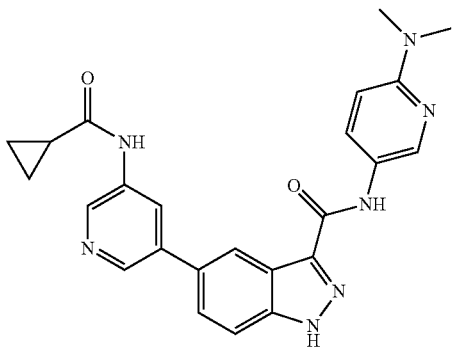 [SMILES: CN(C)c1ccc(NC(=O)c2n[nH]c3ccc(-c4cncc(NC(=O)C5CC5)c4)cc23)cn1]
417 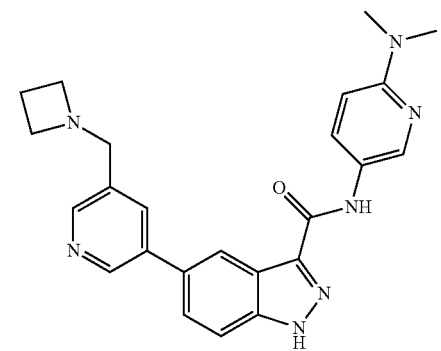 [SMILES: CN(C)c1ccc(NC(=O)c2n[nH]c3ccc(-c4cncc(CN5CCC5)c4)cc23)cn1]
418 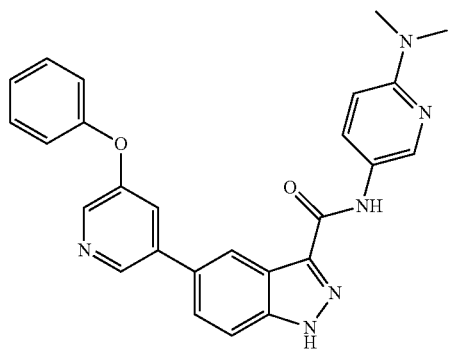 [SMILES: CN(C)c1ccc(NC(=O)c2n[nH]c3ccc(-c4cncc(Oc5ccccc5)c4)cc23)cn1]
419 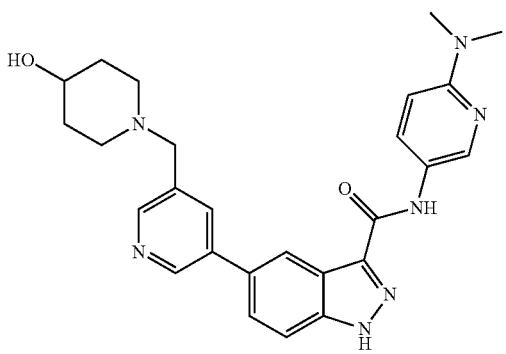 [SMILES: CN(C)c1ccc(NC(=O)c2n[nH]c3ccc(-c4cncc(CN5CCC(O)CC5)c4)cc23)cn1]

TABLE 1-continued
420
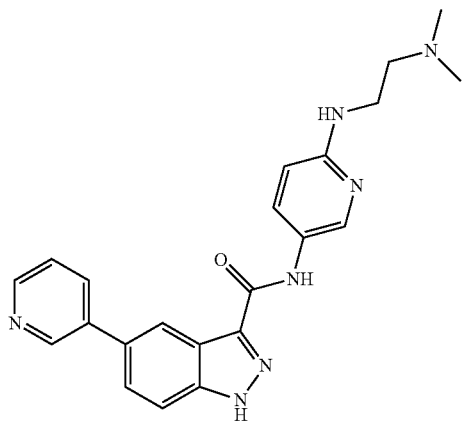 [SMILES: CN(C)CCNc1ccc(NC(=O)c2n[nH]c3ccc(-c4cccnc4)cc23)cn1]
421
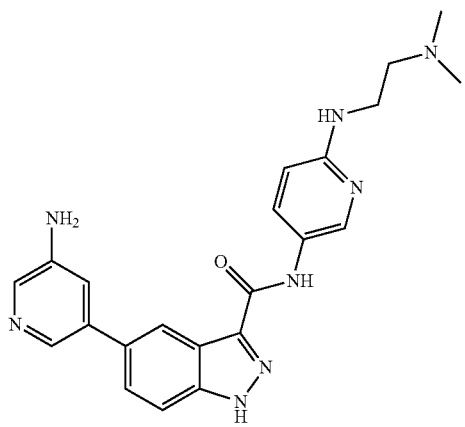 [SMILES: CN(C)CCNc1ccc(NC(=O)c2n[nH]c3ccc(-c4cncc(N)c4)cc23)cn1]
422
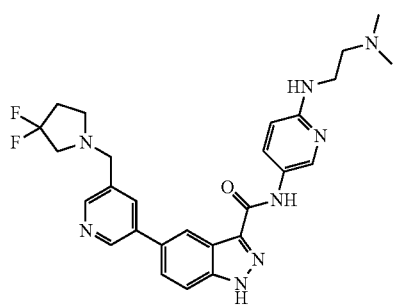 [SMILES: CN(C)CCNc1ccc(NC(=O)c2n[nH]c3ccc(-c4cncc(CN5CCC(F)(F)C5)c4)cc23)cn1]
423
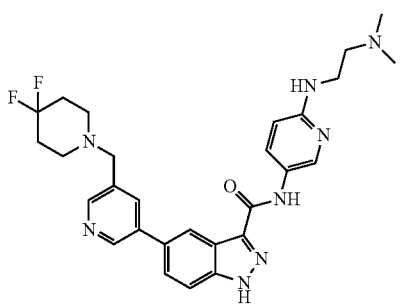 [SMILES: CN(C)CCNc1ccc(NC(=O)c2n[nH]c3ccc(-c4cncc(CN5CCC(F)(F)CC5)c4)cc23)cn1]
424
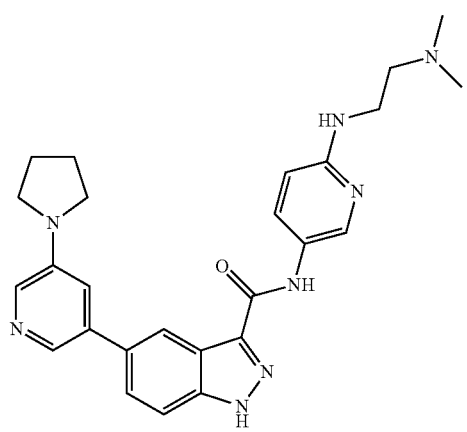 [SMILES: CN(C)CCNc1ccc(NC(=O)c2n[nH]c3ccc(-c4cncc(N5CCCC5)c4)cc23)cn1]
425
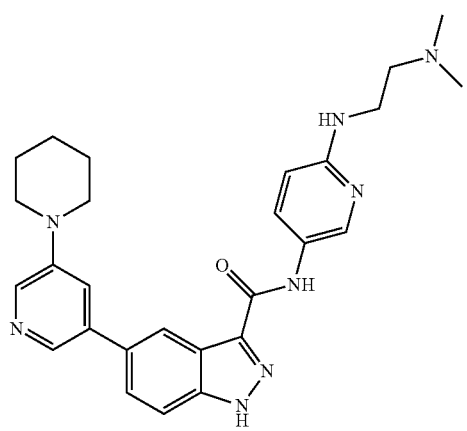 [SMILES: CN(C)CCNc1ccc(NC(=O)c2n[nH]c3ccc(-c4cncc(N5CCCCC5)c4)cc23)cn1]
426
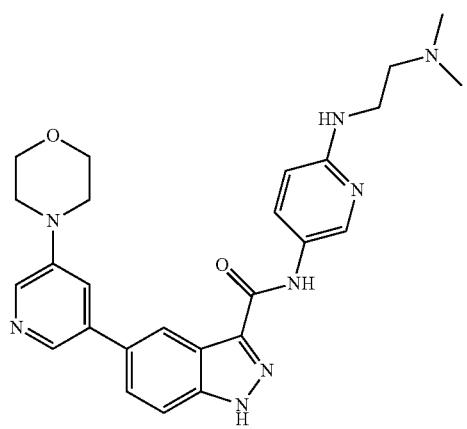 [SMILES: CN(C)CCNc1ccc(NC(=O)c2n[nH]c3ccc(-c4cncc(N5CCOCC5)c4)cc23)cn1]

TABLE 1-continued
427
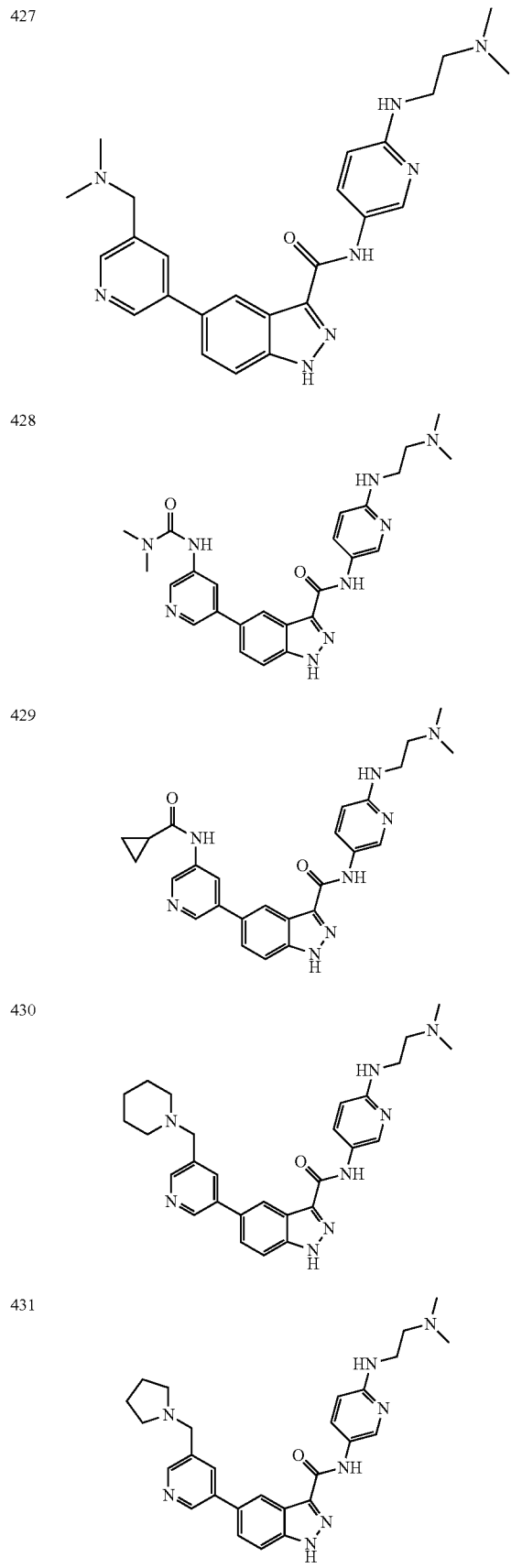
428
429
430
431
TABLE 1-continued
432
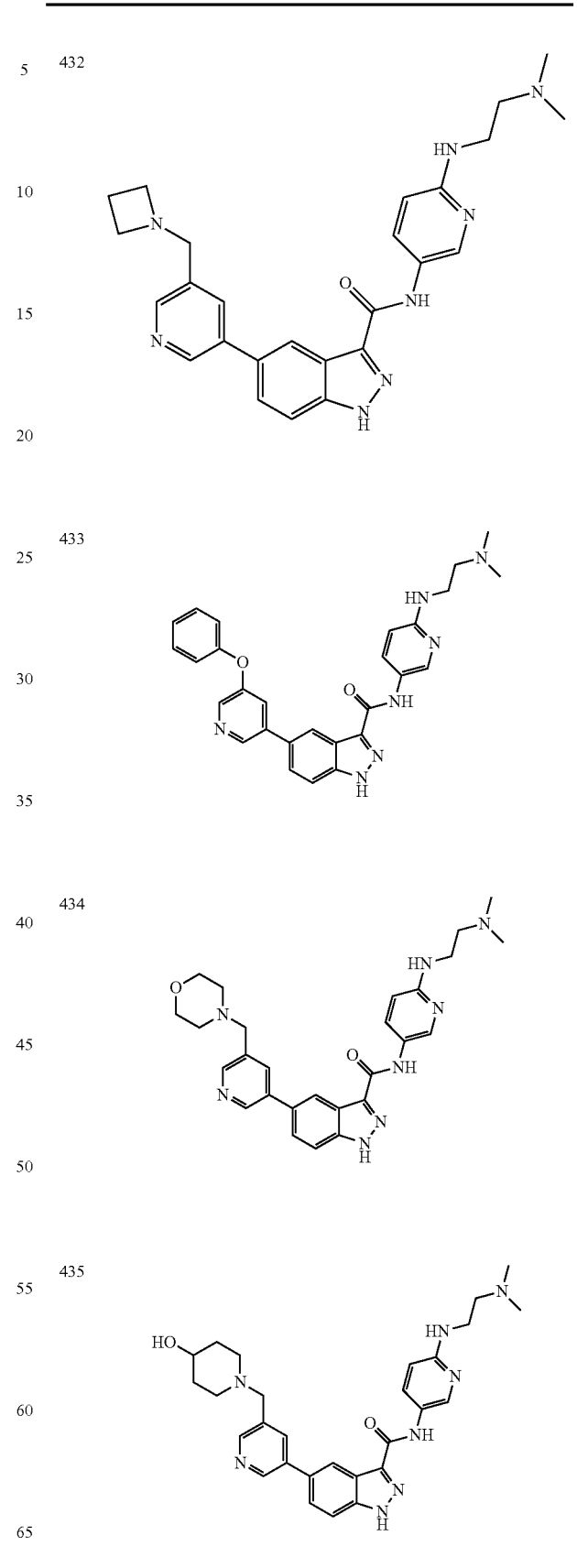
433
434
435

TABLE 1-continued
436
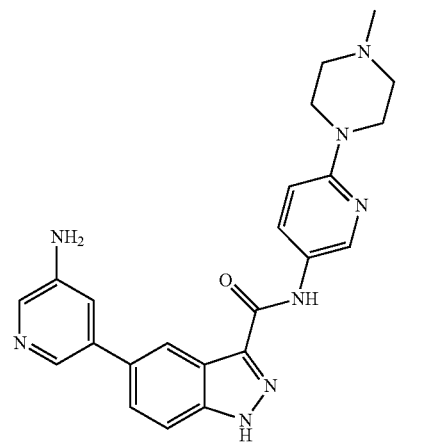 [SMILES: CN1CCN(c2ccc(NC(=O)c3n[nH]c4ccc(-c5cncc(N)c5)cc34)cn2)CC1]
437
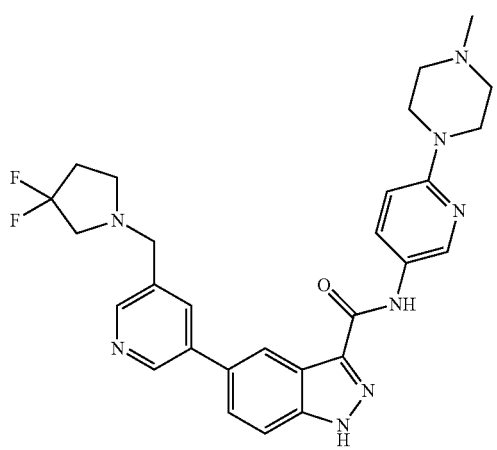 [SMILES: CN1CCN(c2ccc(NC(=O)c3n[nH]c4ccc(-c5cncc(CN6CCC(F)(F)C6)c5)cc34)cn2)CC1]
438
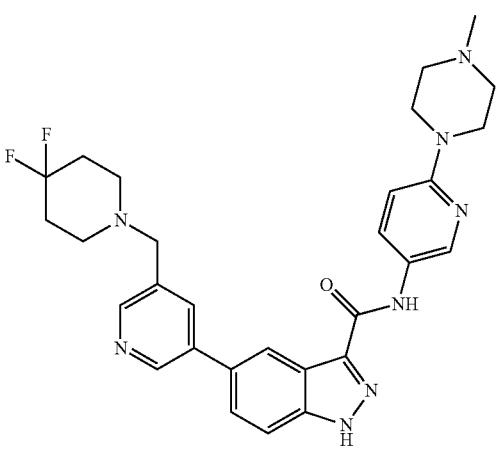 [SMILES: CN1CCN(c2ccc(NC(=O)c3n[nH]c4ccc(-c5cncc(CN6CCC(F)(F)CC6)c5)cc34)cn2)CC1]
439
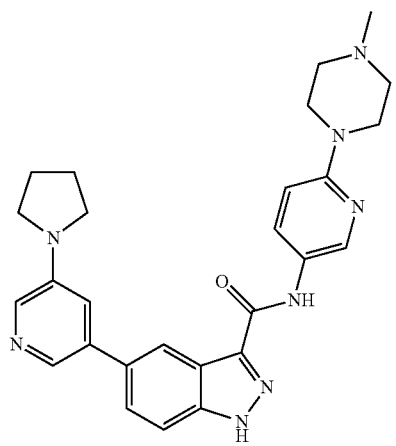 [SMILES: CN1CCN(c2ccc(NC(=O)c3n[nH]c4ccc(-c5cncc(N6CCCC6)c5)cc34)cn2)CC1]
440
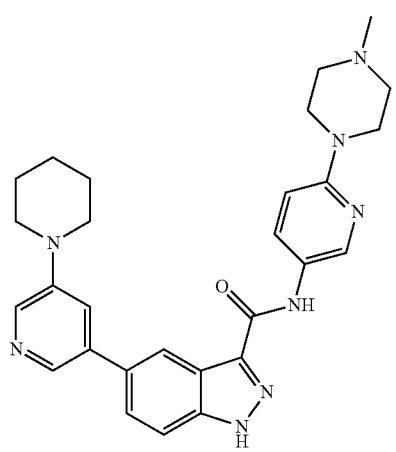
441
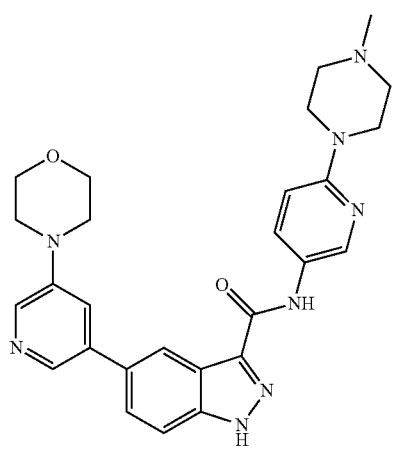 [SMILES: CN1CCN(c2ccc(NC(=O)c3n[nH]c4ccc(-c5cncc(N6CCCCC6)c5)cc34)cn2)CC1]

TABLE 1-continued
442
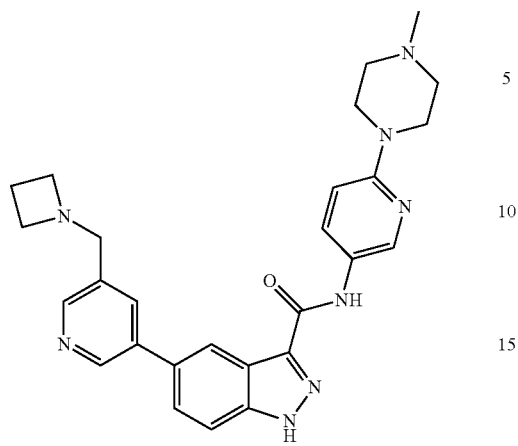
443
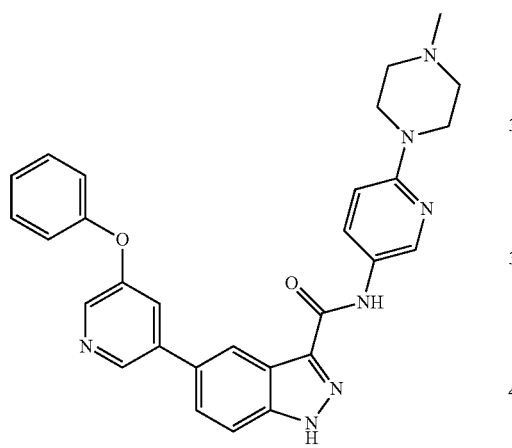
444
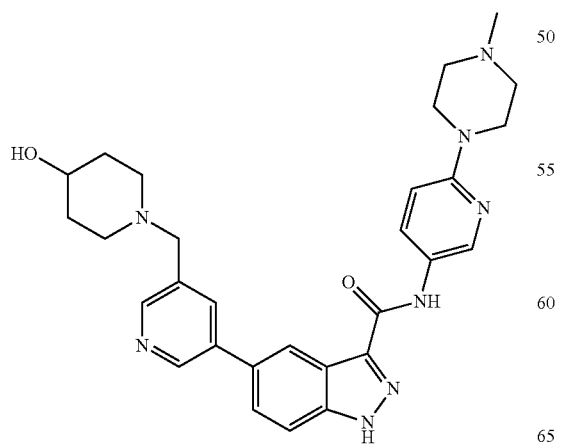
TABLE 1-continued
445
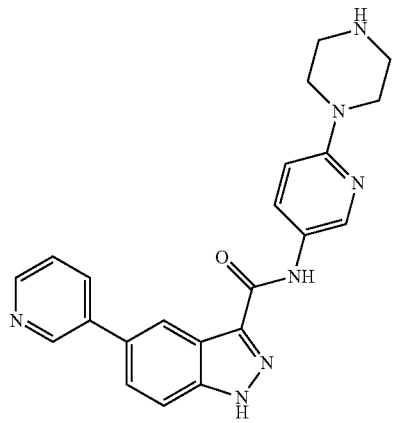 [SMILES: O=C(Nc1ccc(N2CCNCC2)nc1)c1n[nH]c2ccc(-c3cccnc3)cc12]
446
447
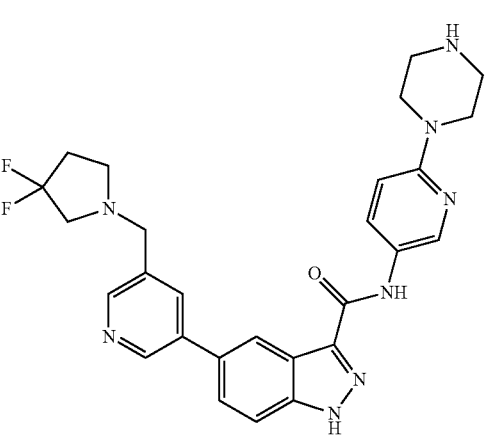 [SMILES: O=C(Nc1ccc(N2CCNCC2)nc1)c1n[nH]c2ccc(-c3cncc(CN4CCC(F)(F)C4)c3)cc12]

TABLE 1-continued
448
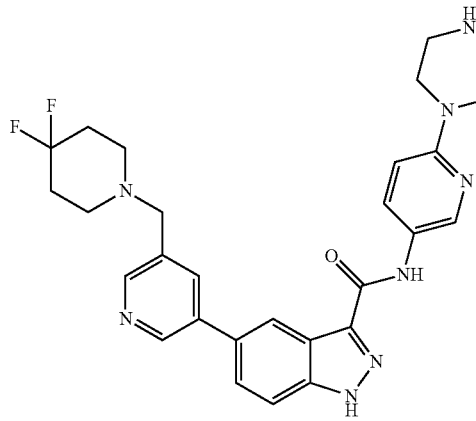
451
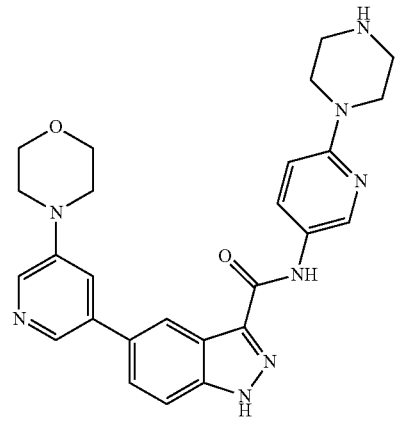
449
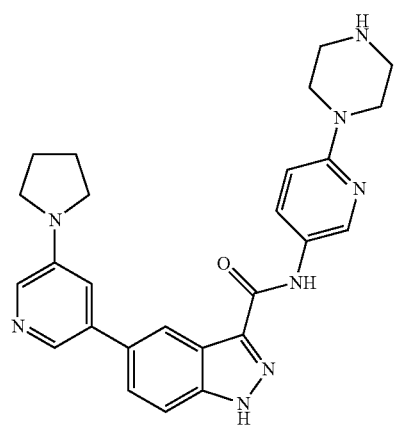 [SMILES: O=C(Nc1ccc(N2CCNCC2)nc1)c1n[nH]c2ccc(-c3cncc(N4CCCC4)c3)cc12]
452
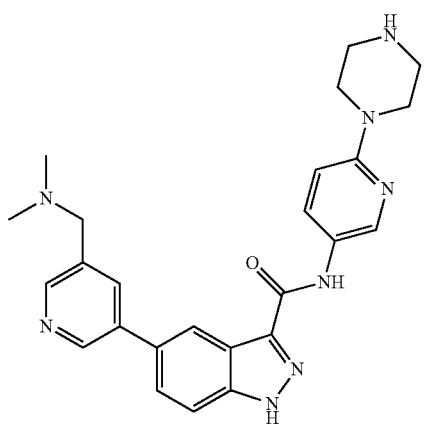
450
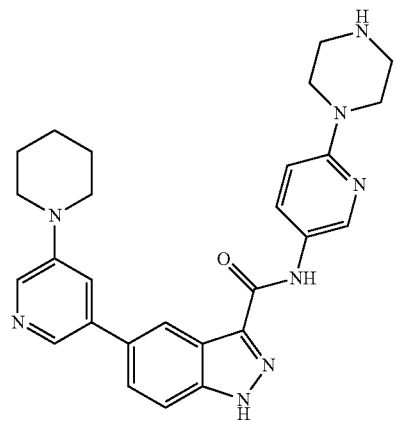 [SMILES: O=C(Nc1ccc(N2CCNCC2)nc1)c1n[nH]c2ccc(-c3cncc(N4CCOCC4)c3)cc12]
453
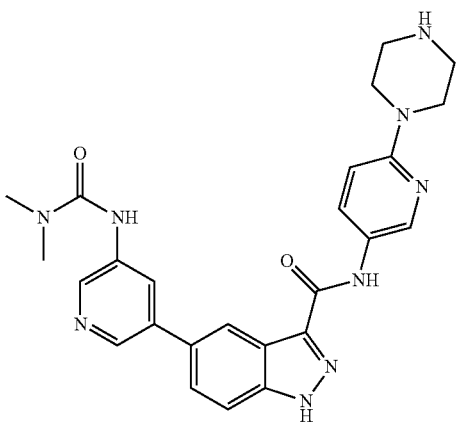 [SMILES: CN(C)C(=O)Nc1cncc(-c2ccc3[nH]nc(C(=O)Nc4ccc(N5CCNCC5)nc4)c3c2)c1]

TABLE 1-continued
454
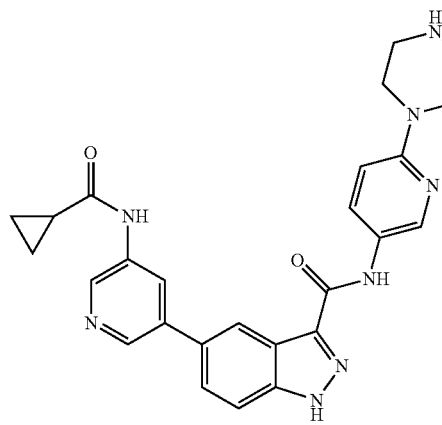
455
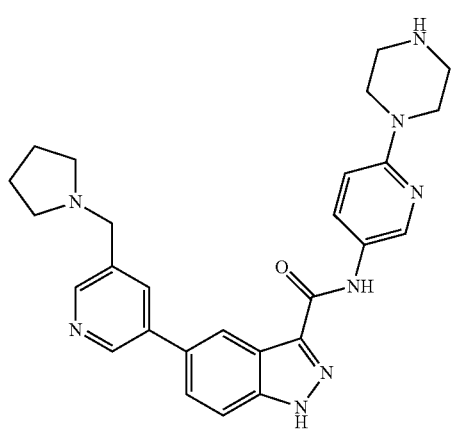 [SMILES: O=C(Nc1ccc(N2CCNCC2)nc1)c1n[nH]c2ccc(-c3cncc(CN4CCCC4)c3)cc12]
456
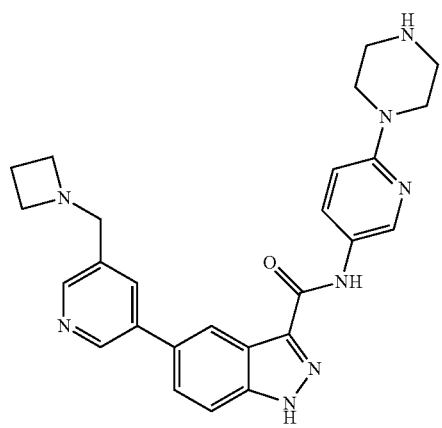 [SMILES: O=C(Nc1ccc(N2CCNCC2)nc1)c1n[nH]c2ccc(-c3cncc(CN4CCC4)c3)cc12]
457
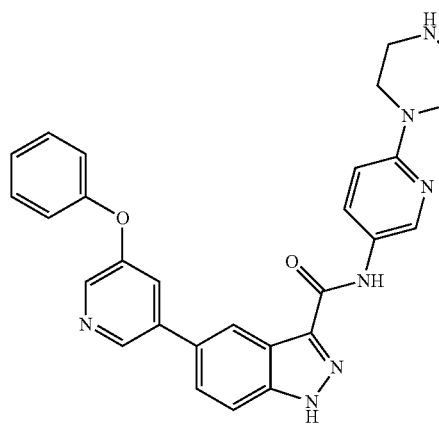
458
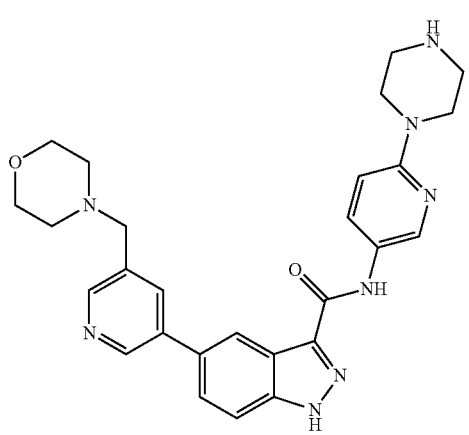 [SMILES: O=C(Nc1ccc(N2CCNCC2)nc1)c1n[nH]c2ccc(-c3cncc(CN4CCOCC4)c3)cc12]
459
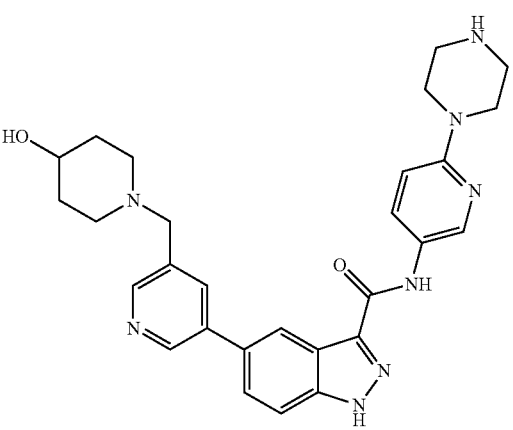 [SMILES: O=C(Nc1ccc(N2CCNCC2)nc1)c1n[nH]c2ccc(-c3cncc(CN4CCC(O)CC4)c3)cc12]

TABLE 1-continued
460
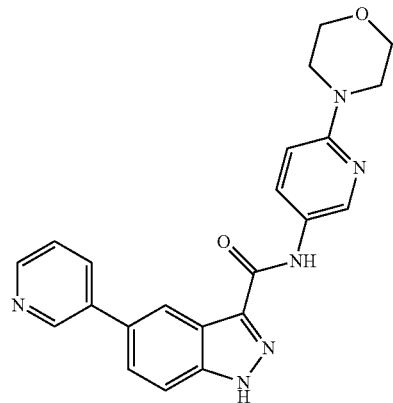 [SMILES: O=C(Nc1ccc(N2CCOCC2)nc1)c1n[nH]c2ccc(-c3cccnc3)cc12]
461
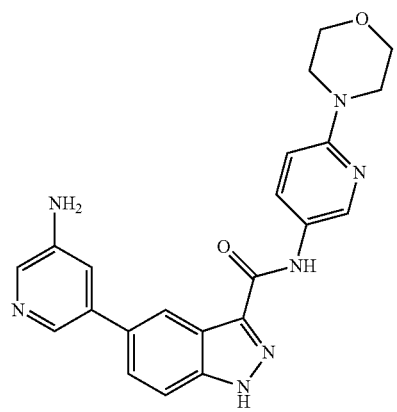 [SMILES: Nc1cncc(-c2ccc3[nH]nc(C(=O)Nc4ccc(N5CCOCC5)nc4)c3c2)c1]
462
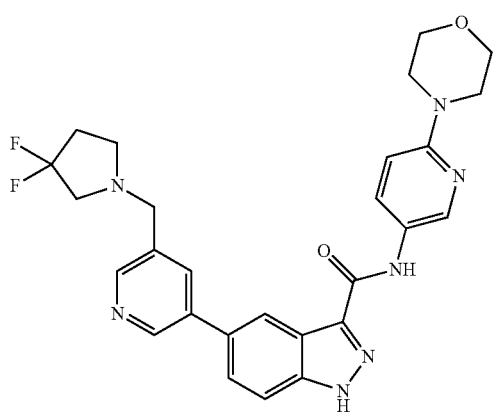 [SMILES: O=C(Nc1ccc(N2CCOCC2)nc1)c1n[nH]c2ccc(-c3cncc(CN4CCC(F)(F)C4)c3)cc12]
463
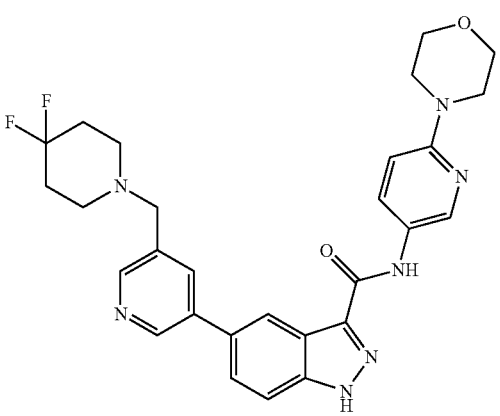 [SMILES: O=C(Nc1ccc(N2CCOCC2)nc1)c1n[nH]c2ccc(-c3cncc(CN4CCC(F)(F)CC4)c3)cc12]
464
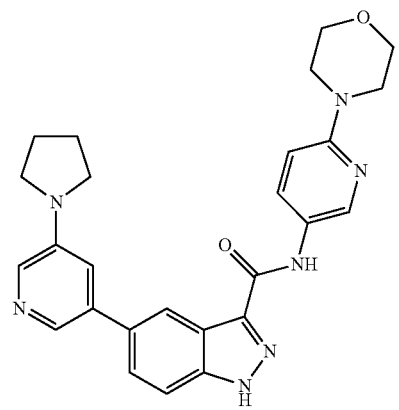 [SMILES: O=C(Nc1ccc(N2CCOCC2)nc1)c1n[nH]c2ccc(-c3cncc(N4CCCC4)c3)cc12]
465
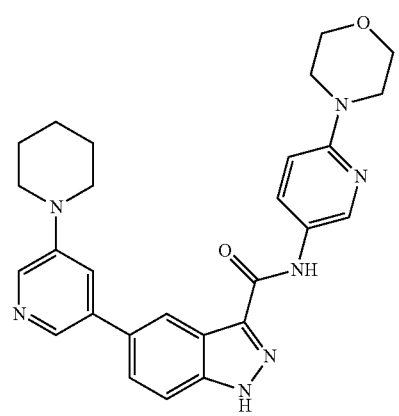 [SMILES: O=C(Nc1ccc(N2CCOCC2)nc1)c1n[nH]c2ccc(-c3cncc(N4CCCCC4)c3)cc12]
466
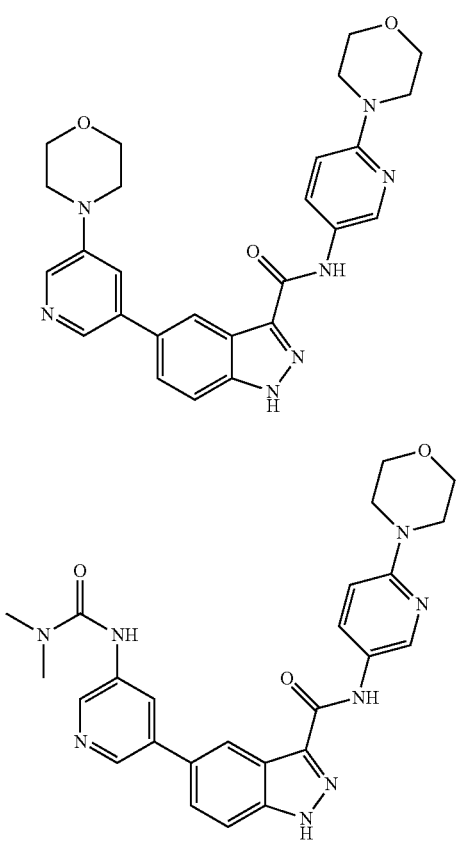
467

TABLE 1-continued
468
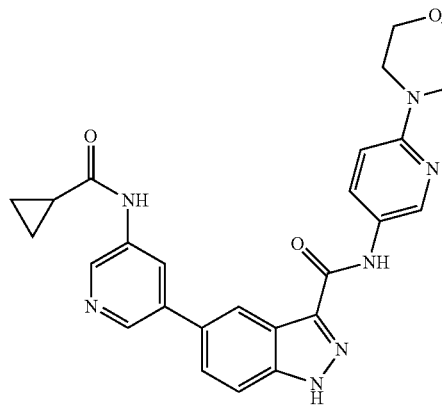
469
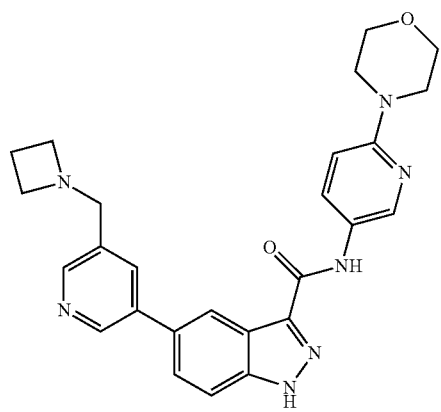 [SMILES: O=C(Nc1ccc(N2CCOCC2)nc1)c1n[nH]c2ccc(-c3cncc(CN4CCC4)c3)cc12]
470
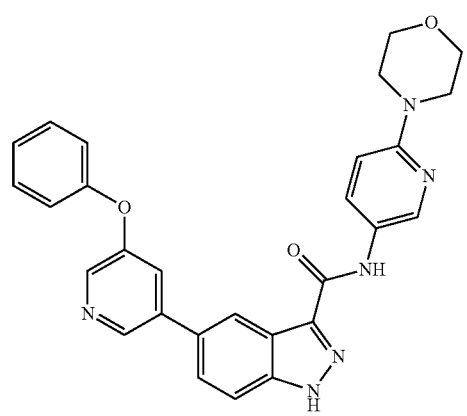 [SMILES: O=C(Nc1ccc(N2CCOCC2)nc1)c1n[nH]c2ccc(-c3cncc(Oc4ccccc4)c3)cc12]
471
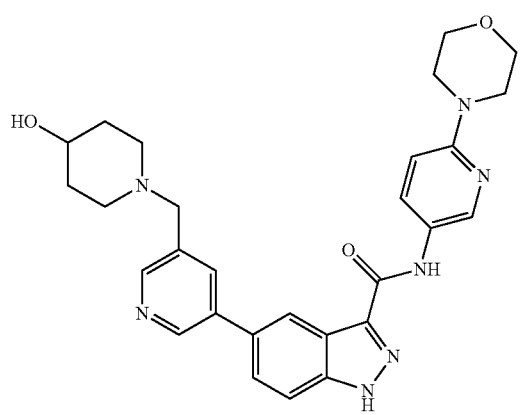 [SMILES: O=C(Nc1ccc(N2CCOCC2)nc1)c1n[nH]c2ccc(-c3cncc(CN4CCC(O)CC4)c3)cc12]
TABLE 1-continued
472
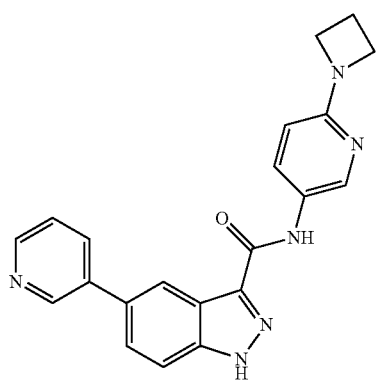 [SMILES: O=C(Nc1ccc(N2CCC2)nc1)c1n[nH]c2ccc(-c3cccnc3)cc12]
473
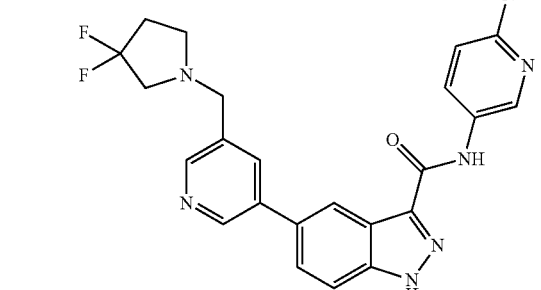
474
475
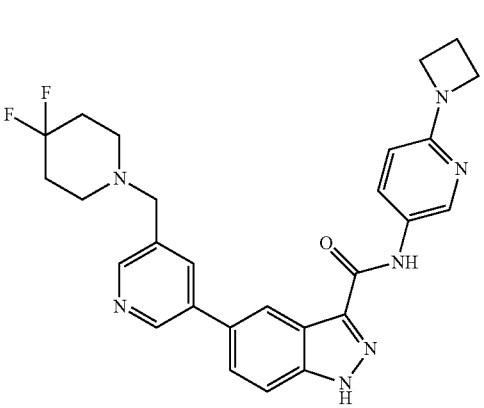 [SMILES: O=C(Nc1ccc(N2CCC2)nc1)c1n[nH]c2ccc(-c3cncc(CN4CCC(F)(F)CC4)c3)cc12]

TABLE 1-continued
476
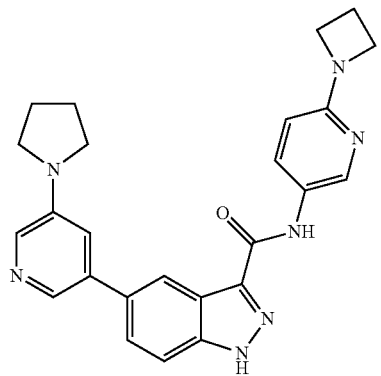 [SMILES: O=C(Nc1ccc(N2CCC2)nc1)c1n[nH]c2ccc(-c3cncc(N4CCCC4)c3)cc12]
477
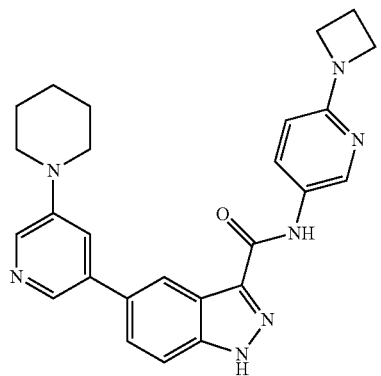 [SMILES: O=C(Nc1ccc(N2CCC2)nc1)c1n[nH]c2ccc(-c3cncc(N4CCCCC4)c3)cc12]
478
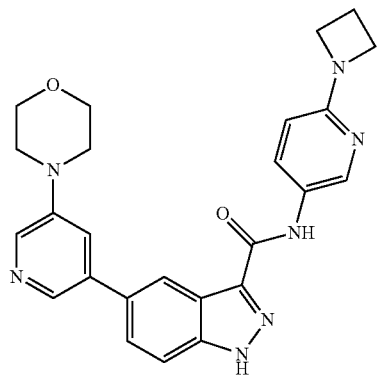
479
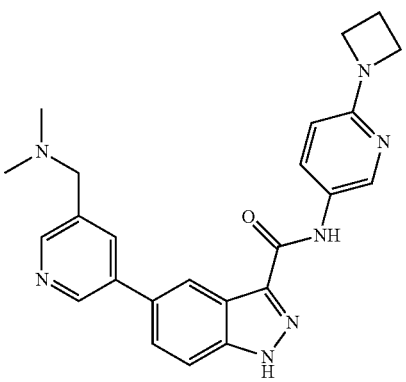 [SMILES: CN(C)Cc1cncc(-c2ccc3[nH]nc(C(=O)Nc4ccc(N5CCC5)nc4)c3c2)c1]
TABLE 1-continued
480
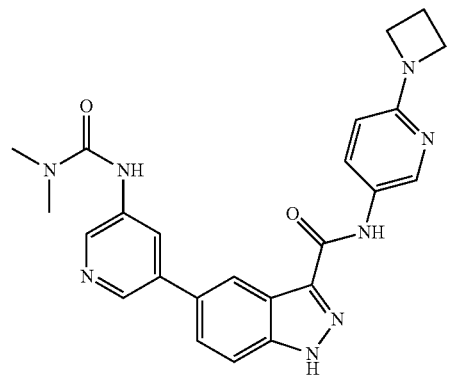 [SMILES: CN(C)C(=O)Nc1cncc(-c2ccc3[nH]nc(C(=O)Nc4ccc(N5CCC5)nc4)c3c2)c1]
481
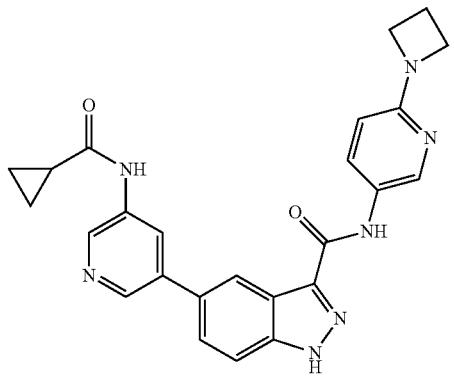 [SMILES: O=C(Nc1ccc(N2CCC2)nc1)c1n[nH]c2ccc(-c3cncc(NC(=O)C4CC4)c3)cc12]
482
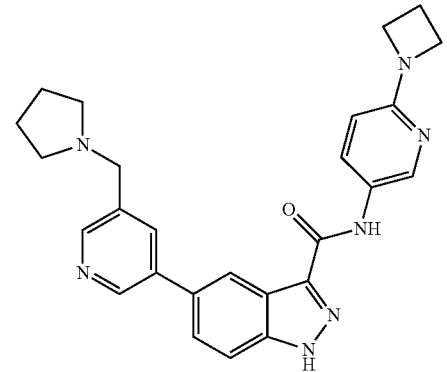 [SMILES: O=C(Nc1ccc(N2CCC2)nc1)c1n[nH]c2ccc(-c3cncc(CN4CCCC4)c3)cc12]
483
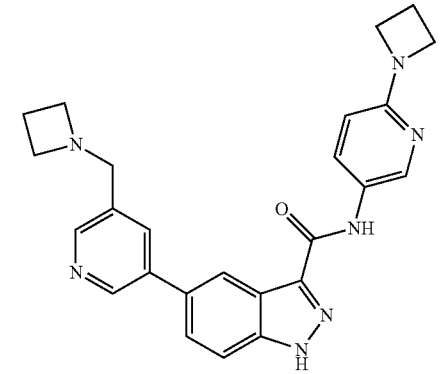 [SMILES: O=C(Nc1ccc(N2CCC2)nc1)c1n[nH]c2ccc(-c3cncc(CN4CCC4)c3)cc12]

TABLE 1-continued
484
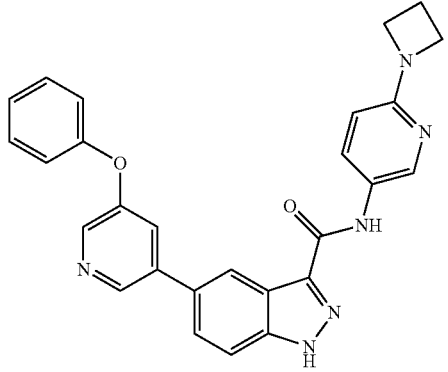 [SMILES: O=C(Nc1ccc(N2CCC2)nc1)c1n[nH]c2ccc(-c3cncc(Oc4ccccc4)c3)cc12]
485
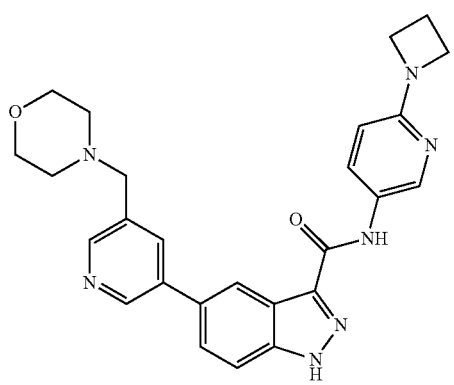 [SMILES: O=C(Nc1ccc(N2CCC2)nc1)c1n[nH]c2ccc(-c3cncc(CN4CCOCC4)c3)cc12]
486
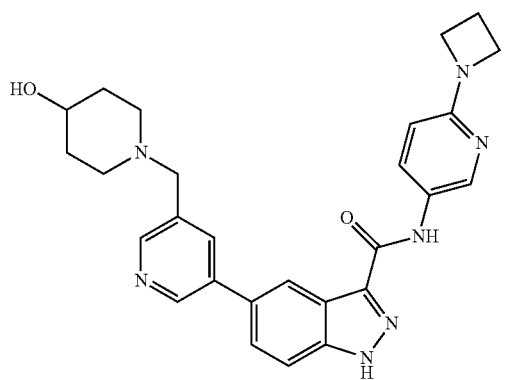 [SMILES: O=C(Nc1ccc(N2CCC2)nc1)c1n[nH]c2ccc(-c3cncc(CN4CCC(O)CC4)c3)cc12]
487
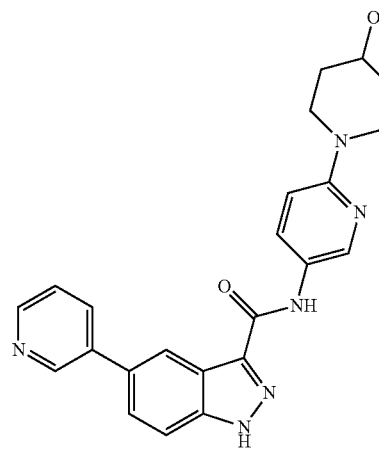
TABLE 1-continued
488
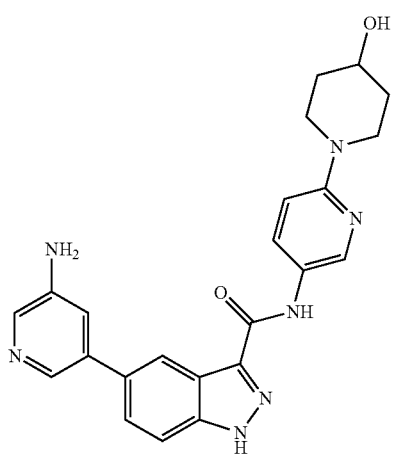 [SMILES: Nc1cncc(-c2ccc3[nH]nc(C(=O)Nc4ccc(N5CCC(O)CC5)nc4)c3c2)c1]
489
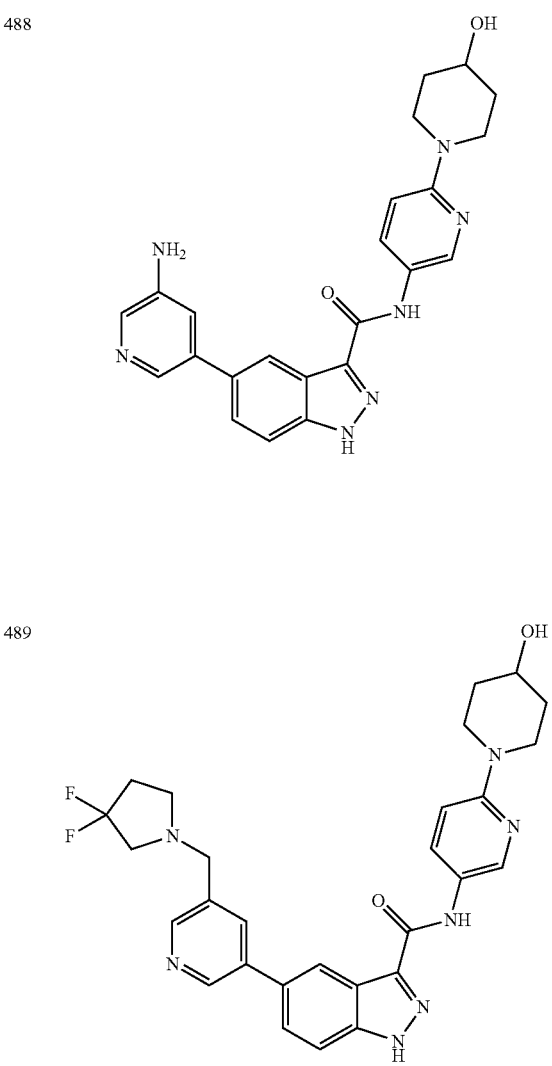
490
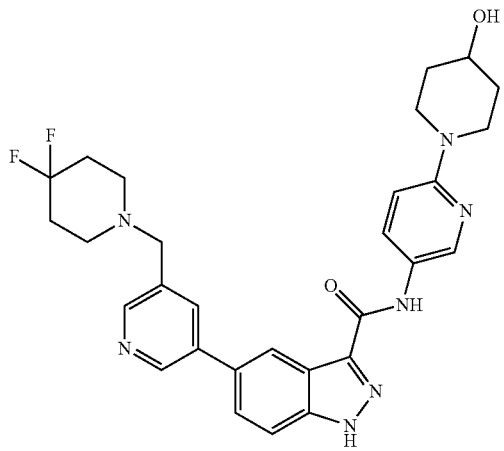 [SMILES: O=C(Nc1ccc(N2CCC(O)CC2)nc1)c1n[nH]c2ccc(-c3cncc(CN4CCC(F)(F)CC4)c3)cc12]

TABLE 1-continued
491 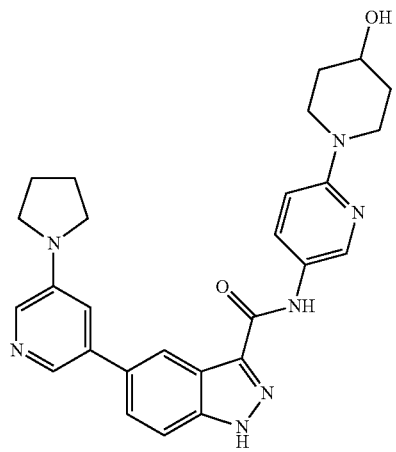 [SMILES: O=C(Nc1ccc(N2CCC(O)CC2)nc1)c1n[nH]c2ccc(-c3cncc(N4CCCC4)c3)cc12]
492 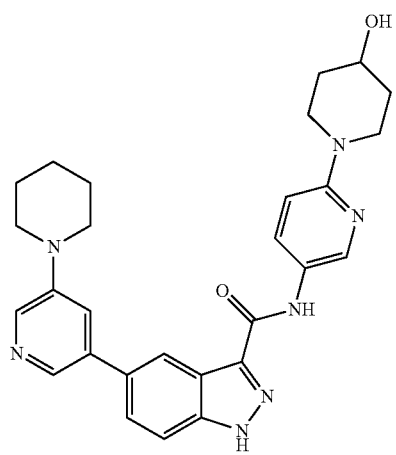 [SMILES: O=C(Nc1ccc(N2CCC(O)CC2)nc1)c1n[nH]c2ccc(-c3cncc(N4CCCCC4)c3)cc12]
493 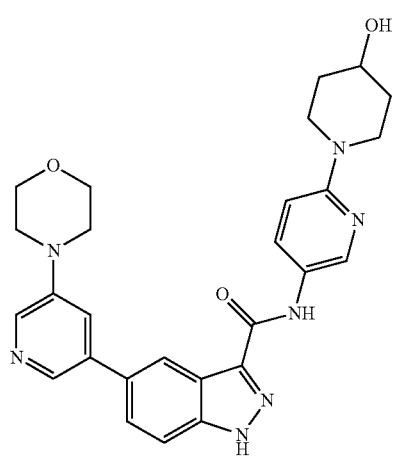 [SMILES: O=C(Nc1ccc(N2CCC(O)CC2)nc1)c1n[nH]c2ccc(-c3cncc(N4CCOCC4)c3)cc12]
TABLE 1-continued
494 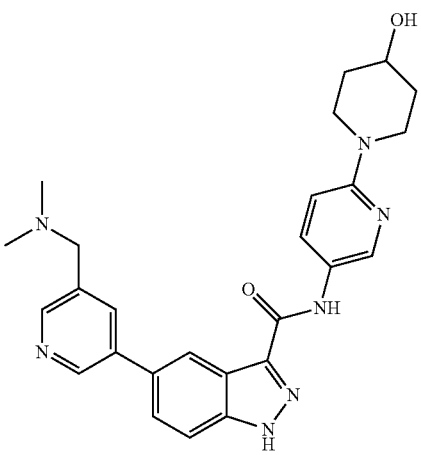 [SMILES: CN(C)Cc1cncc(-c2ccc3[nH]nc(C(=O)Nc4ccc(N5CCC(O)CC5)nc4)c3c2)c1]
495 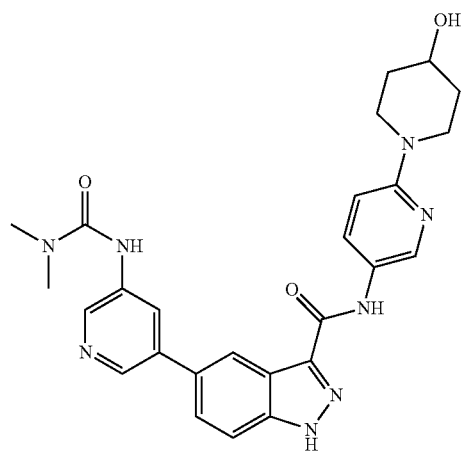 [SMILES: CN(C)C(=O)Nc1cncc(-c2ccc3[nH]nc(C(=O)Nc4ccc(N5CCC(O)CC5)nc4)c3c2)c1]
496 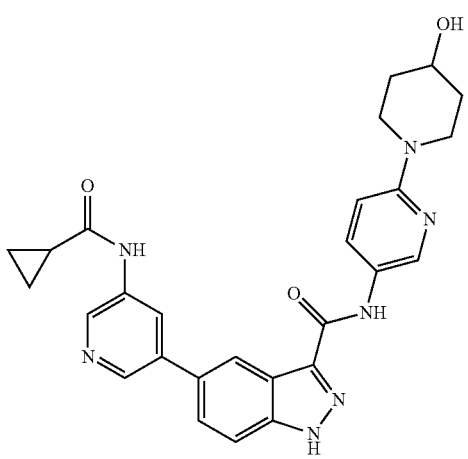 [SMILES: O=C(Nc1ccc(N2CCC(O)CC2)nc1)c1n[nH]c2ccc(-c3cncc(NC(=O)C4CC4)c3)cc12]

TABLE 1-continued
497
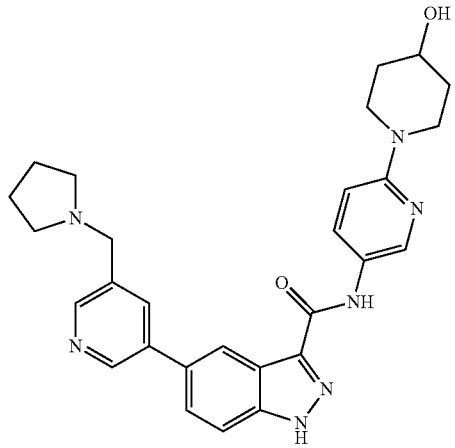 [SMILES: O=C(Nc1ccc(N2CCC(O)CC2)nc1)c1n[nH]c2ccc(-c3cncc(CN4CCCC4)c3)cc12]
498
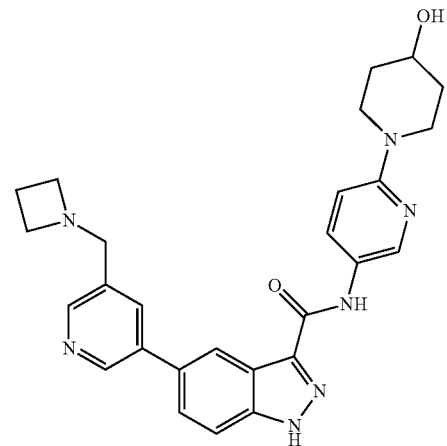 [SMILES: O=C(Nc1ccc(N2CCC(O)CC2)nc1)c1n[nH]c2ccc(-c3cncc(CN4CCC4)c3)cc12]
499
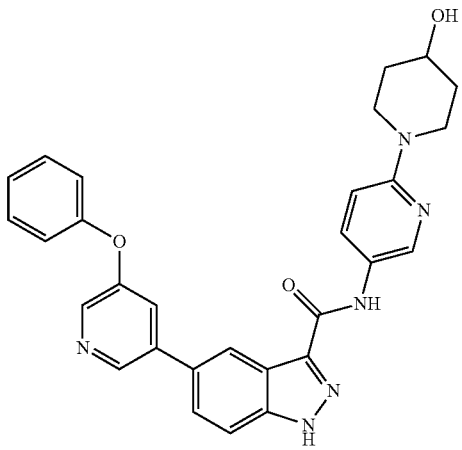 [SMILES: O=C(Nc1ccc(N2CCC(O)CC2)nc1)c1n[nH]c2ccc(-c3cncc(Oc4ccccc4)c3)cc12]
TABLE 1-continued
500
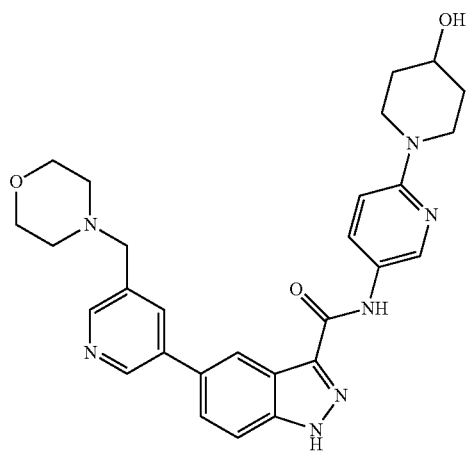 [SMILES: O=C(Nc1ccc(N2CCC(O)CC2)nc1)c1n[nH]c2ccc(-c3cncc(CN4CCOCC4)c3)cc12]
501
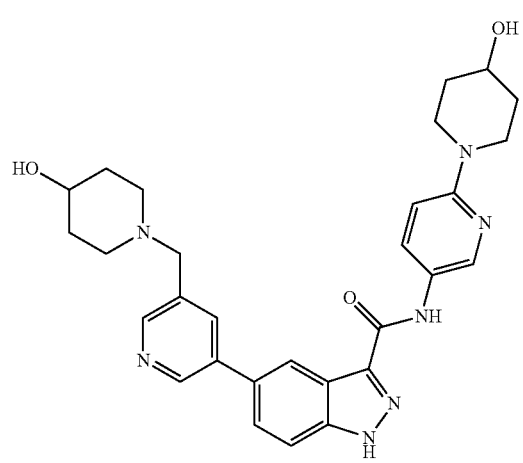 [SMILES: O=C(Nc1ccc(N2CCC(O)CC2)nc1)c1n[nH]c2ccc(-c3cncc(CN4CCC(O)CC4)c3)cc12]
502
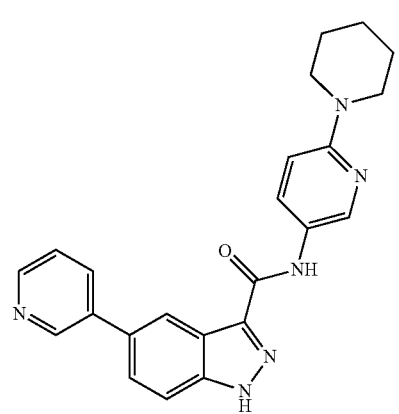 [SMILES: O=C(Nc1ccc(N2CCCCC2)nc1)c1n[nH]c2ccc(-c3cccnc3)cc12]

TABLE 1-continued
503
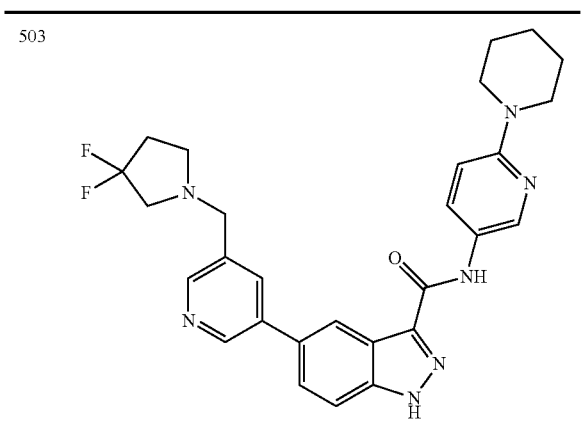
504
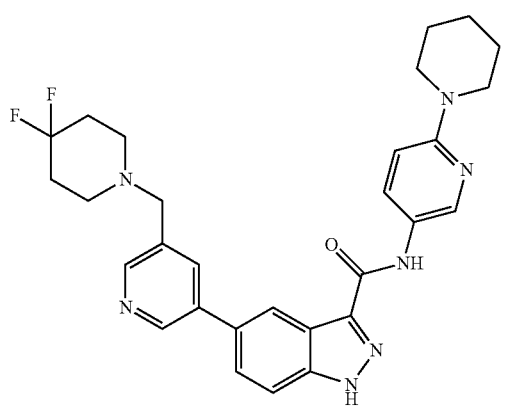 [SMILES: O=C(Nc1ccc(N2CCCCC2)nc1)c1n[nH]c2ccc(-c3cncc(CN4CCC(F)(F)CC4)c3)cc12]
505
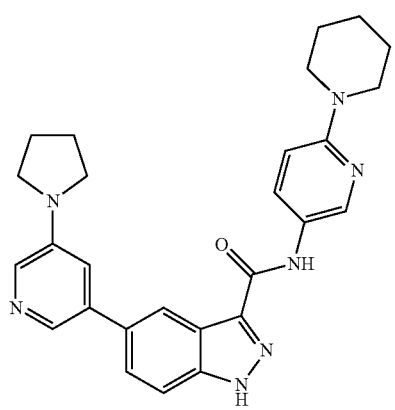 [SMILES: O=C(Nc1ccc(N2CCCCC2)nc1)c1n[nH]c2ccc(-c3cncc(N4CCCC4)c3)cc12]
506
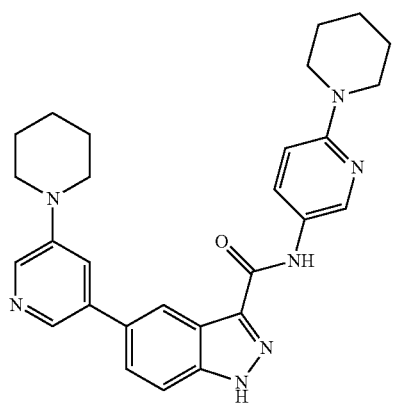 [SMILES: O=C(Nc1ccc(N2CCCCC2)nc1)c1n[nH]c2ccc(-c3cncc(N4CCCCC4)c3)cc12]
TABLE 1-continued
507
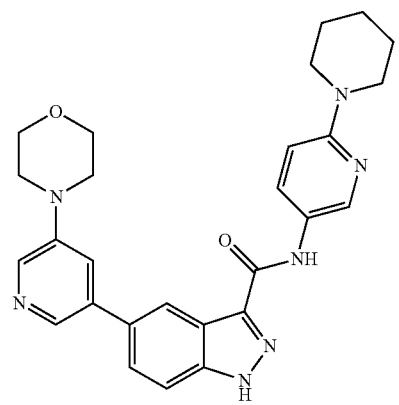 [SMILES: O=C(Nc1ccc(N2CCCCC2)nc1)c1n[nH]c2ccc(-c3cncc(N4CCOCC4)c3)cc12]
508
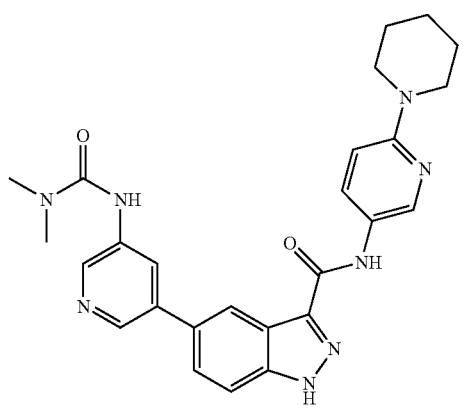 [SMILES: CN(C)C(=O)Nc1cncc(-c2ccc3[nH]nc(C(=O)Nc4ccc(N5CCCCC5)nc4)c3c2)c1]
509
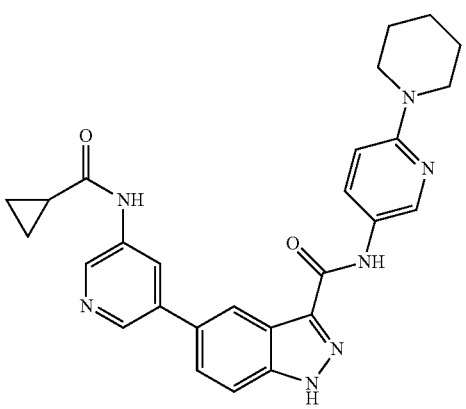 [SMILES: O=C(Nc1ccc(N2CCCCC2)nc1)c1n[nH]c2ccc(-c3cncc(NC(=O)C4CC4)c3)cc12]
510
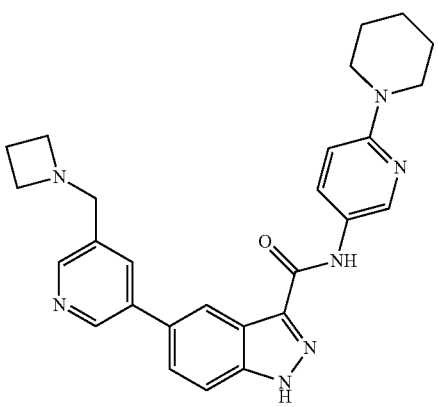 [SMILES: O=C(Nc1ccc(N2CCCCC2)nc1)c1n[nH]c2ccc(-c3cncc(CN4CCC4)c3)cc12]

TABLE 1-continued
511
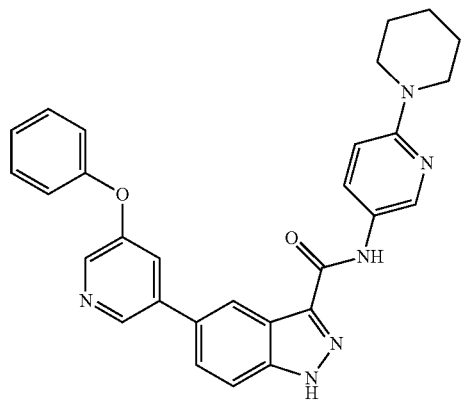 [SMILES: O=C(Nc1ccc(N2CCCCC2)nc1)c1n[nH]c2ccc(-c3cncc(Oc4ccccc4)c3)cc12]
512
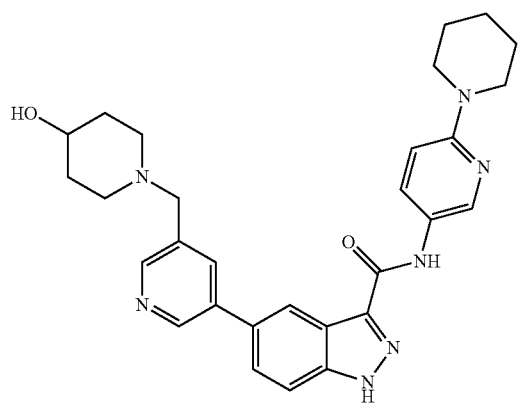 [SMILES: O=C(Nc1ccc(N2CCCCC2)nc1)c1n[nH]c2ccc(-c3cncc(CN4CCC(O)CC4)c3)cc12]
513
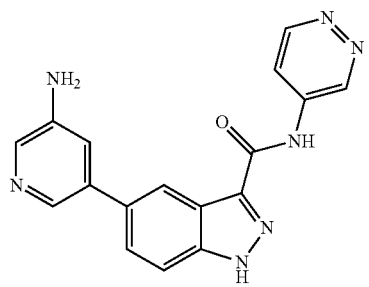 [SMILES: Nc1cncc(-c2ccc3[nH]nc(C(=O)Nc4ccnnc4)c3c2)c1]
514
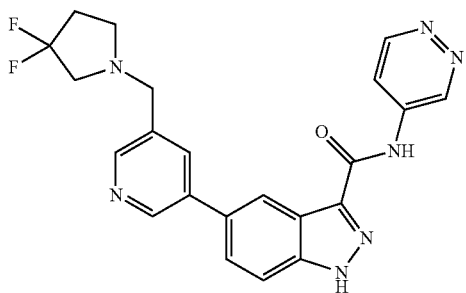 [SMILES: O=C(Nc1ccnnc1)c1n[nH]c2ccc(-c3cncc(CN4CCC(F)(F)C4)c3)cc12]
TABLE 1-continued
515
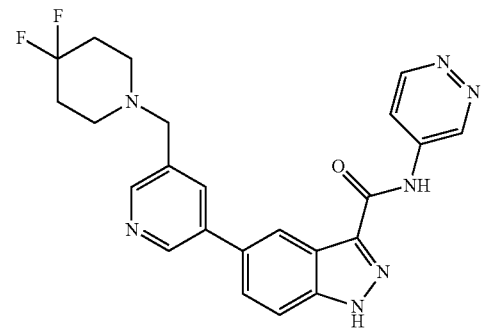
516
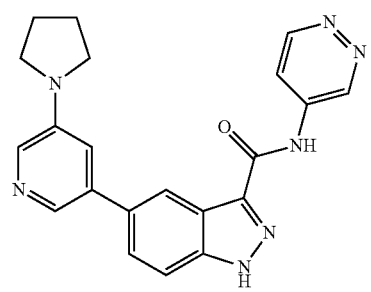 [SMILES: O=C(Nc1ccnnc1)c1n[nH]c2ccc(-c3cncc(N4CCCC4)c3)cc12]
517
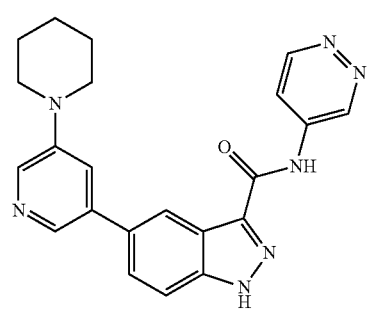 [SMILES: O=C(Nc1ccnnc1)c1n[nH]c2ccc(-c3cncc(N4CCCCC4)c3)cc12]
518
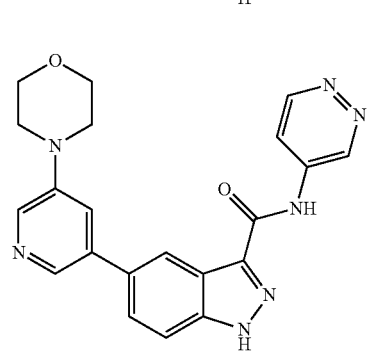
519
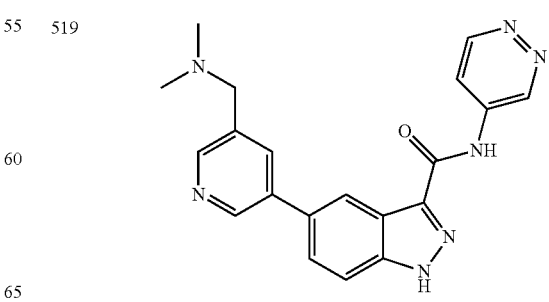

TABLE 1-continued
| 520 | 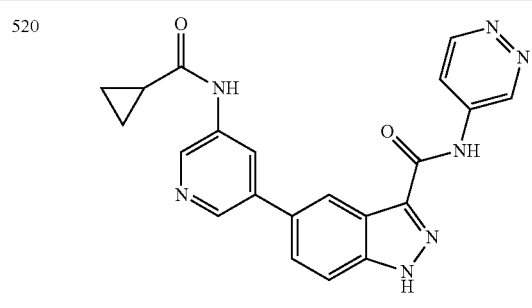 |
| 521 | 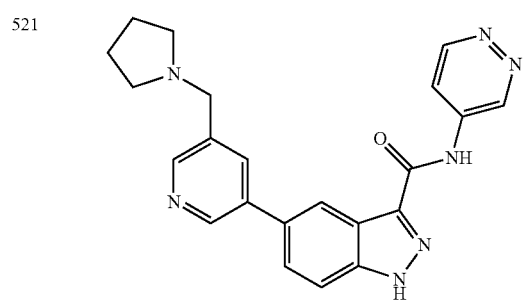 |
| 522 | 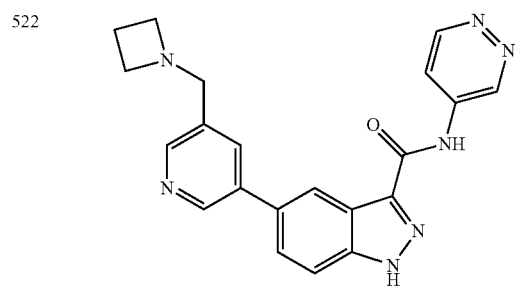 |
| 523 | 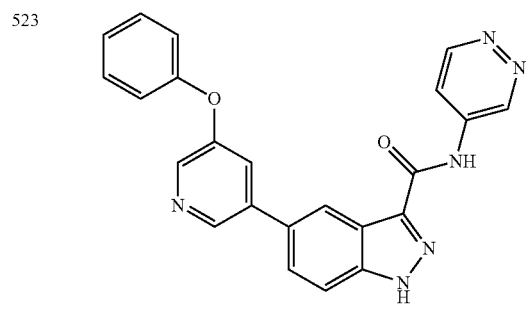 |
| 524 | 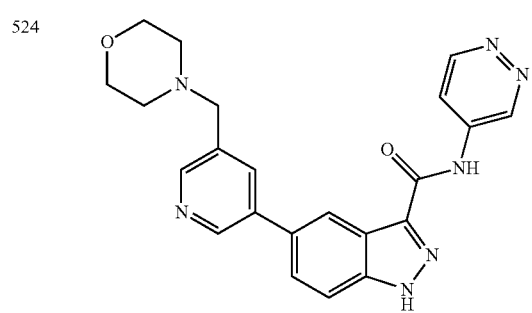 |
TABLE 1-continued
| 525 | 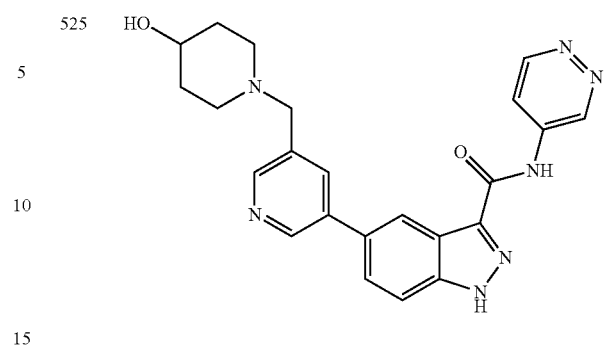 |
| 526 | 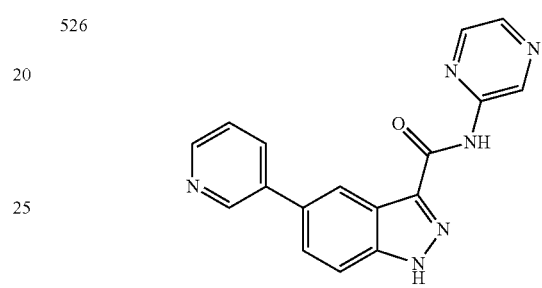 |
| 527 | 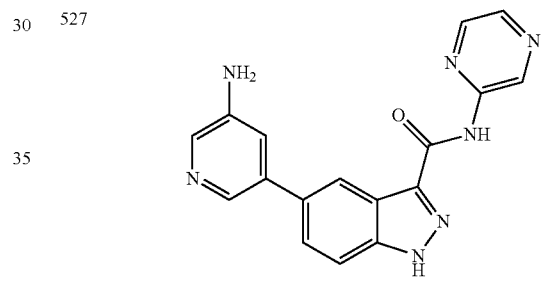 |
| 528 | 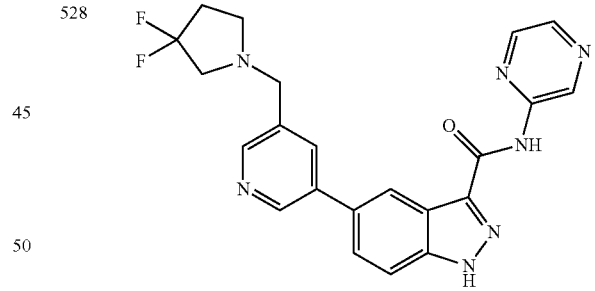 |
| 529 | 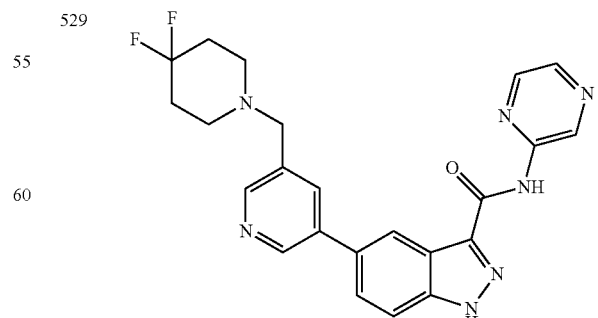 |

TABLE 1-continued
| | |
|---|---|
| 530 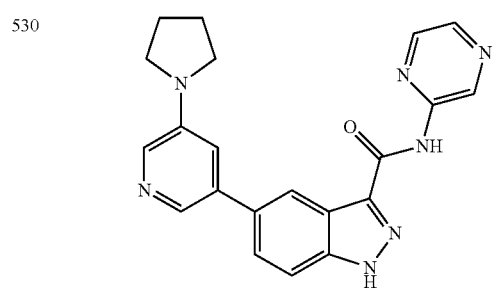 | 535 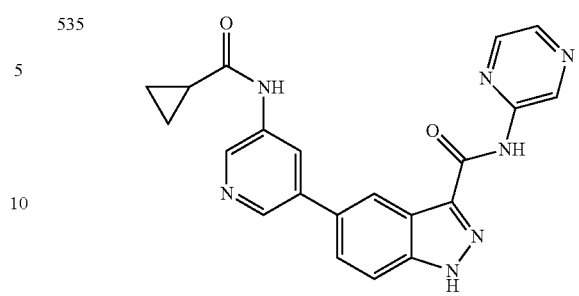 |
| 531 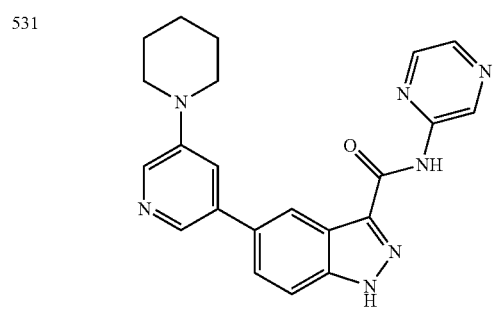 | 536 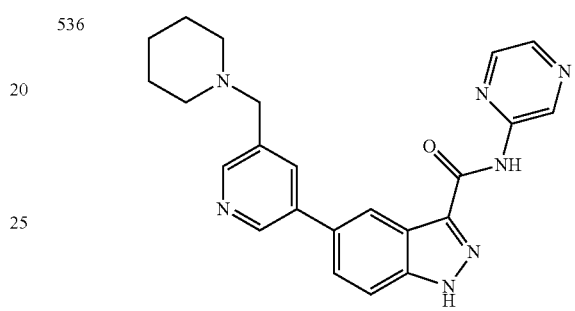 |
| 532 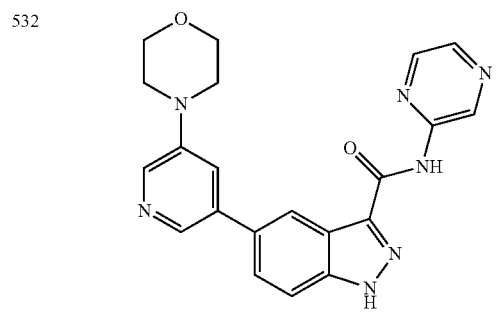 | 537 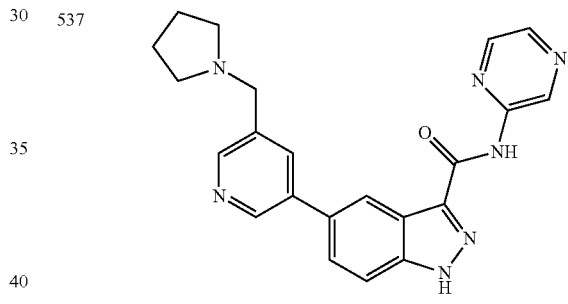 |
| 533 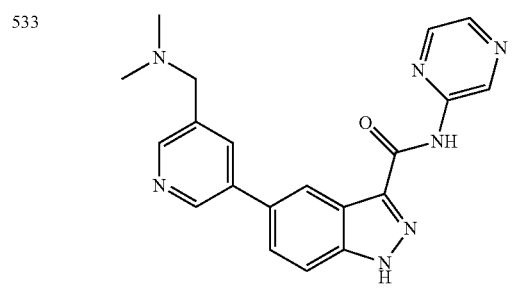 | 538 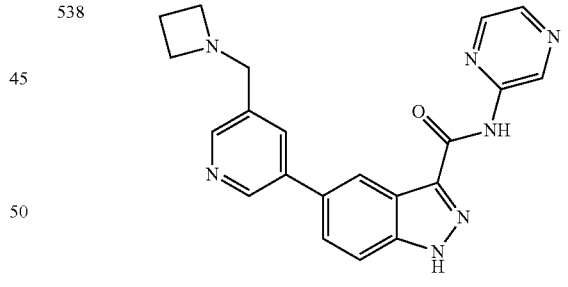 |
| 534 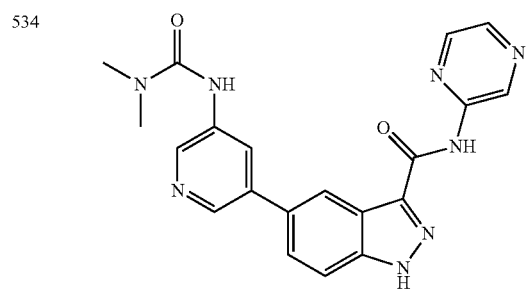 | 539 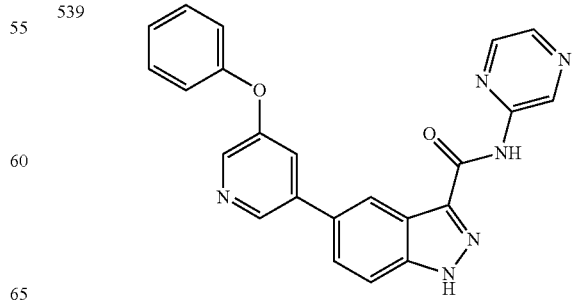 |

TABLE 1-continued
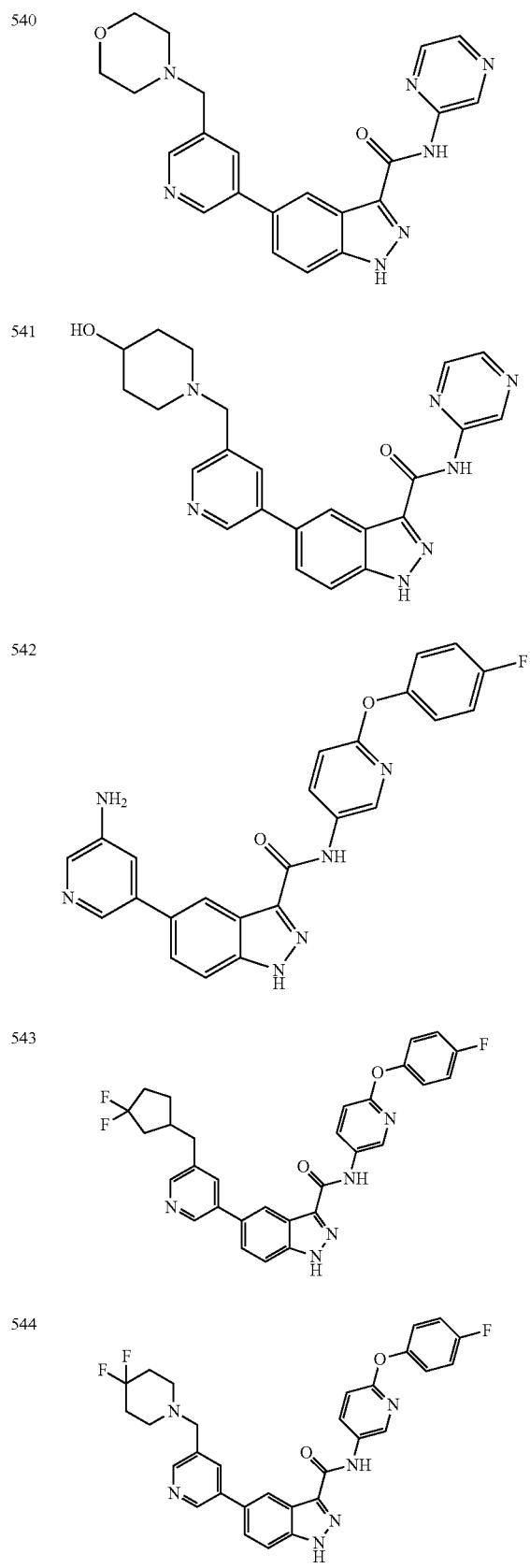
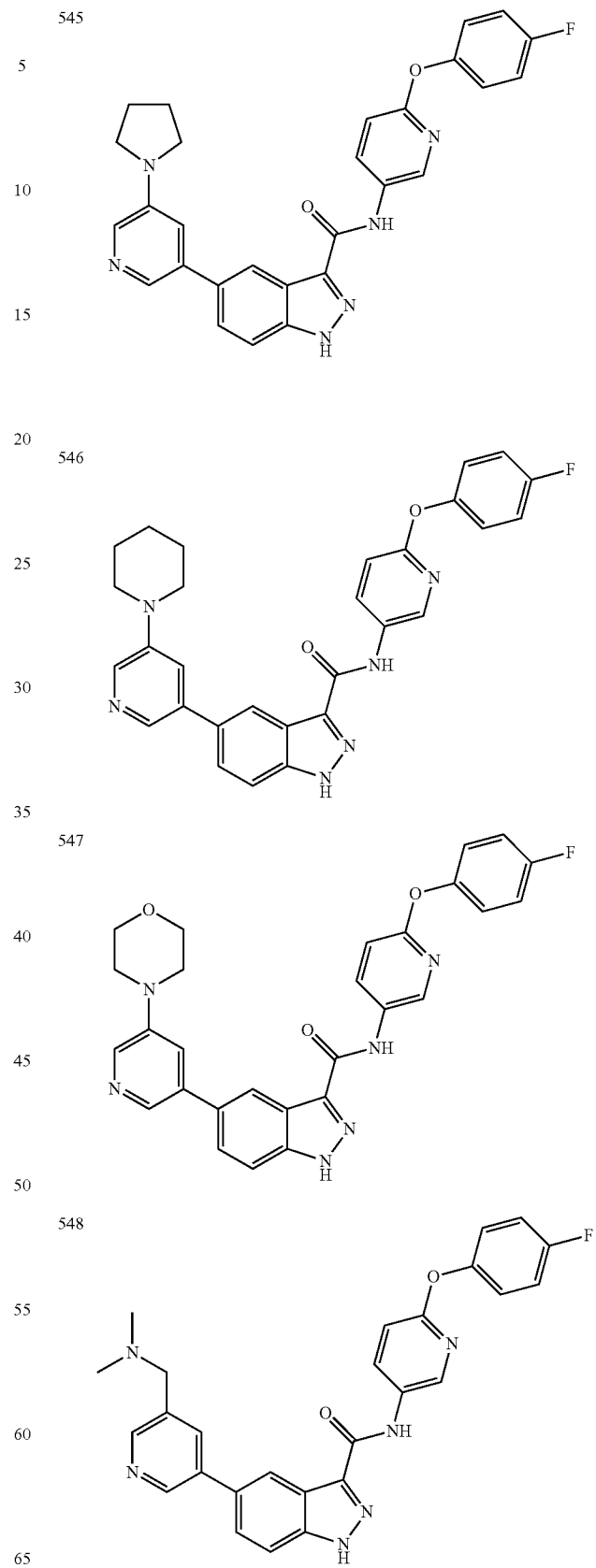

TABLE 1-continued
549 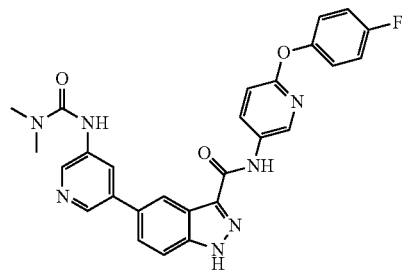 [SMILES: CN(C)C(=O)Nc1cncc(-c2ccc3[nH]nc(C(=O)Nc4ccc(Oc5ccc(F)cc5)nc4)c3c2)c1]
550 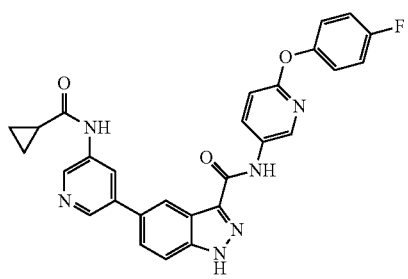 [SMILES: O=C(Nc1ccc(Oc2ccc(F)cc2)nc1)c1n[nH]c2ccc(-c3cncc(NC(=O)C4CC4)c3)cc12]
551 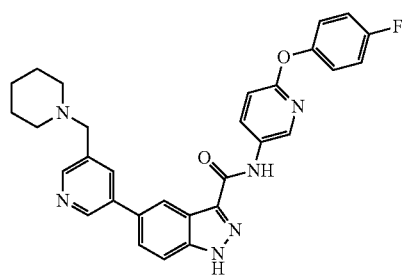 [SMILES: O=C(Nc1ccc(Oc2ccc(F)cc2)nc1)c1n[nH]c2ccc(-c3cncc(CN4CCCCC4)c3)cc12]
552 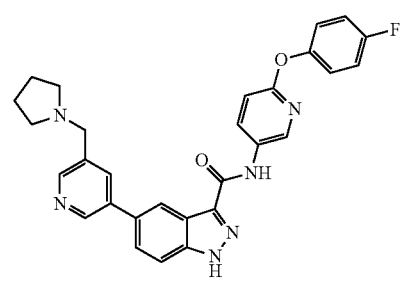 [SMILES: O=C(Nc1ccc(Oc2ccc(F)cc2)nc1)c1n[nH]c2ccc(-c3cncc(CN4CCCC4)c3)cc12]
553 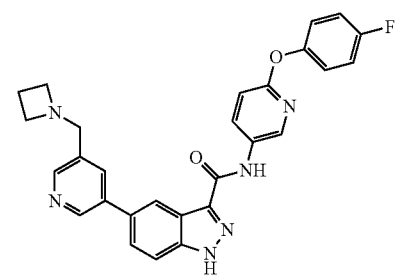 [SMILES: O=C(Nc1ccc(Oc2ccc(F)cc2)nc1)c1n[nH]c2ccc(-c3cncc(CN4CCC4)c3)cc12]
TABLE 1-continued
554 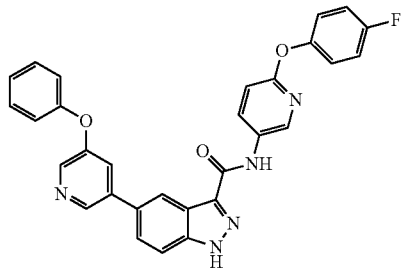 [SMILES: O=C(Nc1ccc(Oc2ccc(F)cc2)nc1)c1n[nH]c2ccc(-c3cncc(Oc4ccccc4)c3)cc12]
555 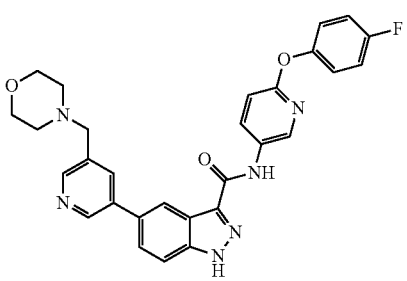 [SMILES: O=C(Nc1ccc(Oc2ccc(F)cc2)nc1)c1n[nH]c2ccc(-c3cncc(CN4CCOCC4)c3)cc12]
556 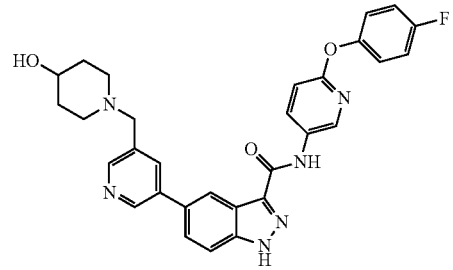 [SMILES: O=C(Nc1ccc(Oc2ccc(F)cc2)nc1)c1n[nH]c2ccc(-c3cncc(CN4CCC(O)CC4)c3)cc12]
557 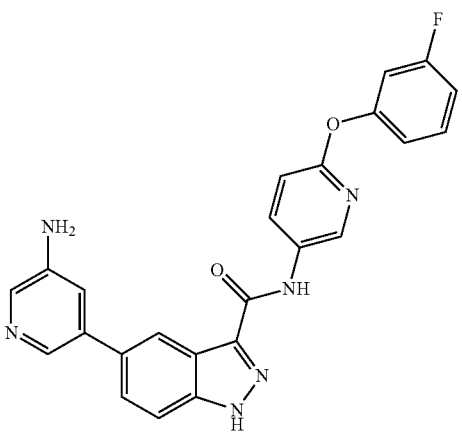 [SMILES: Nc1cncc(-c2ccc3[nH]nc(C(=O)Nc4ccc(Oc5cccc(F)c5)nc4)c3c2)c1]
558 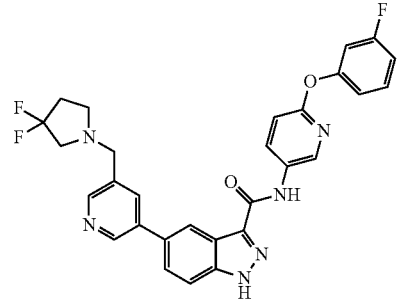 [SMILES: O=C(Nc1ccc(Oc2cccc(F)c2)nc1)c1n[nH]c2ccc(-c3cncc(CN4CCC(F)(F)C4)c3)cc12]

TABLE 1-continued
559
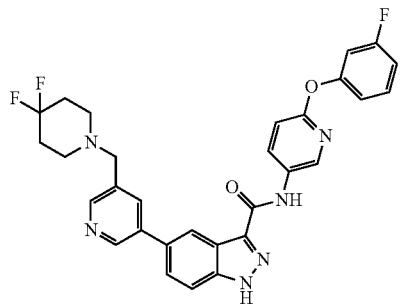 [SMILES: O=C(Nc1ccc(Oc2cccc(F)c2)nc1)c1n[nH]c2ccc(-c3cncc(CN4CCC(F)(F)CC4)c3)cc12]
560
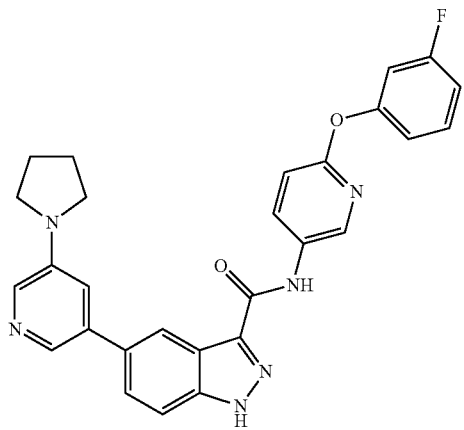 [SMILES: O=C(Nc1ccc(Oc2cccc(F)c2)nc1)c1n[nH]c2ccc(-c3cncc(N4CCCC4)c3)cc12]
561
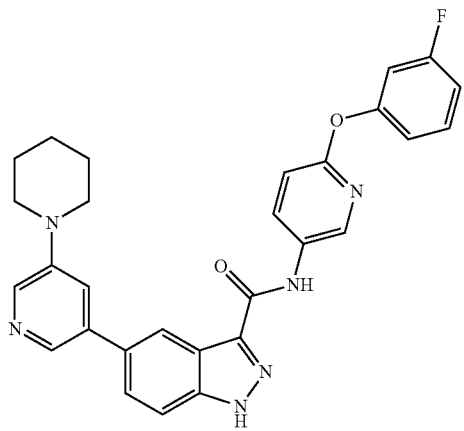 [SMILES: O=C(Nc1ccc(Oc2cccc(F)c2)nc1)c1n[nH]c2ccc(-c3cncc(N4CCCCC4)c3)cc12]
562
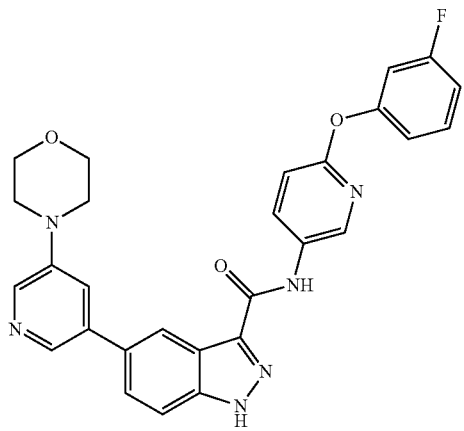
TABLE 1-continued
563
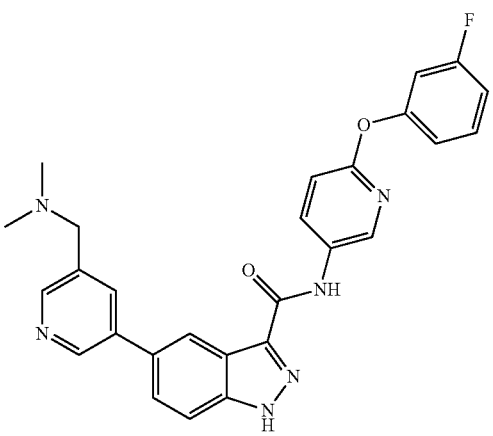 [SMILES: CN(C)Cc1cncc(-c2ccc3[nH]nc(C(=O)Nc4ccc(Oc5cccc(F)c5)nc4)c3c2)c1]
564
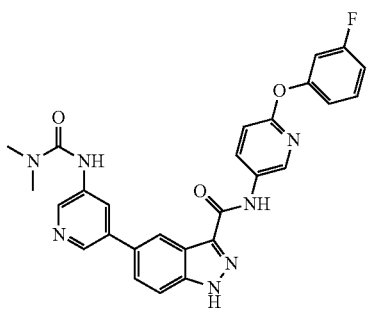 [SMILES: CN(C)C(=O)Nc1cncc(-c2ccc3[nH]nc(C(=O)Nc4ccc(Oc5cccc(F)c5)nc4)c3c2)c1]
565
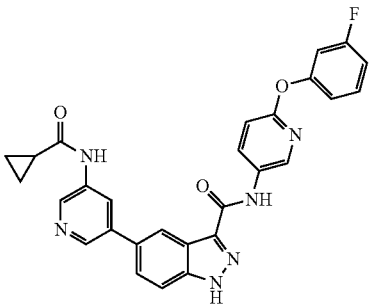 [SMILES: O=C(Nc1ccc(Oc2cccc(F)c2)nc1)c1n[nH]c2ccc(-c3cncc(NC(=O)C4CC4)c3)cc12]
566
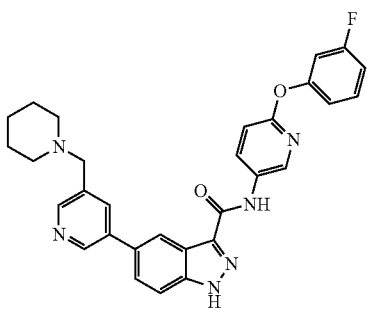 [SMILES: O=C(Nc1ccc(Oc2cccc(F)c2)nc1)c1n[nH]c2ccc(-c3cncc(CN4CCCCC4)c3)cc12]

TABLE 1-continued
567
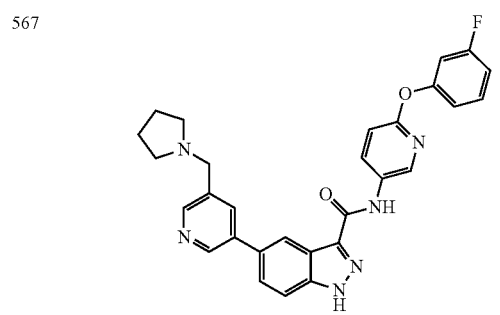
568
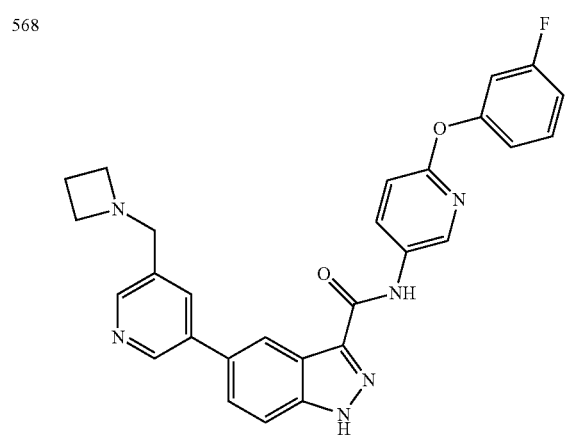
569
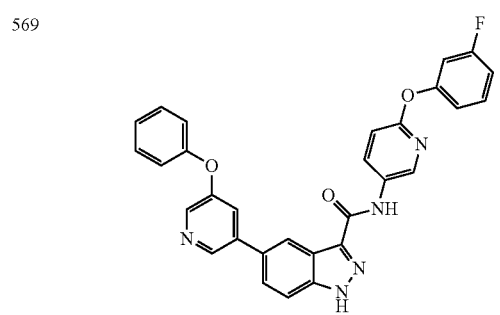
570
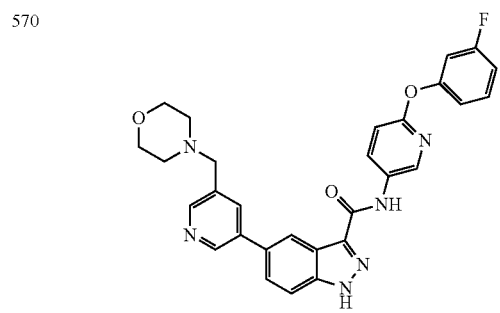
TABLE 1-continued
571
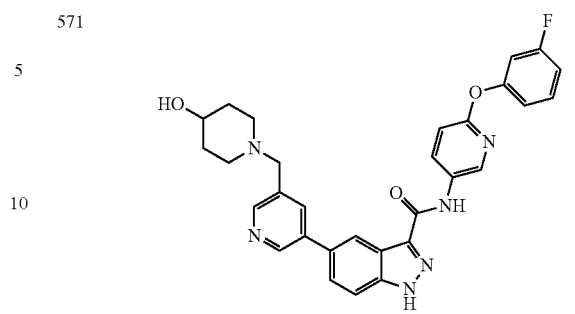
572
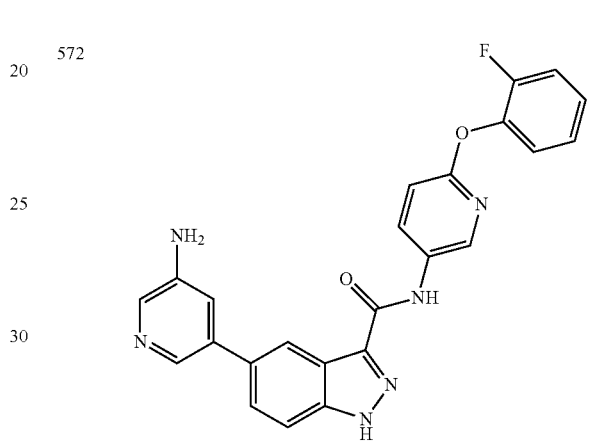
573
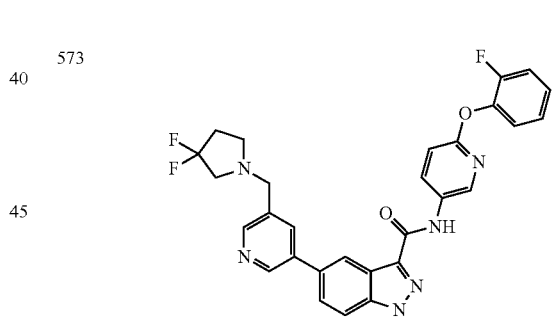
574
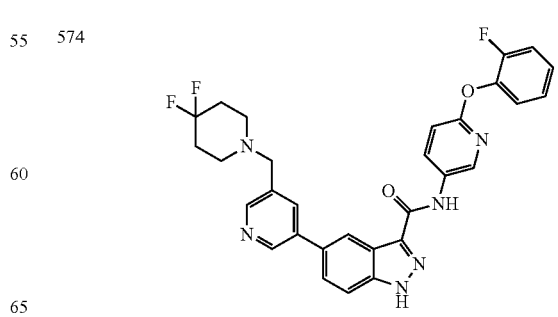

TABLE 1-continued
575 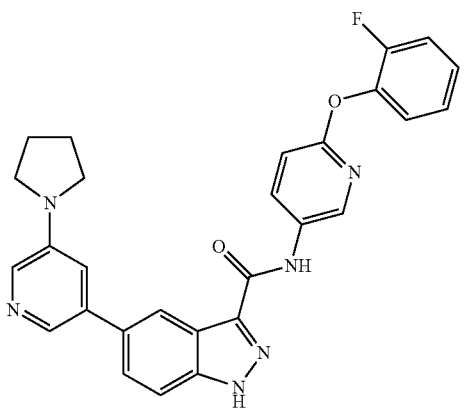 [SMILES: O=C(Nc1ccc(Oc2ccccc2F)nc1)c1n[nH]c2ccc(-c3cncc(N4CCCC4)c3)cc12]
576 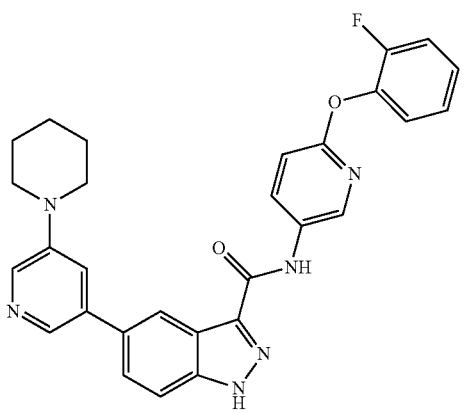 [SMILES: O=C(Nc1ccc(Oc2ccccc2F)nc1)c1n[nH]c2ccc(-c3cncc(N4CCCCC4)c3)cc12]
577 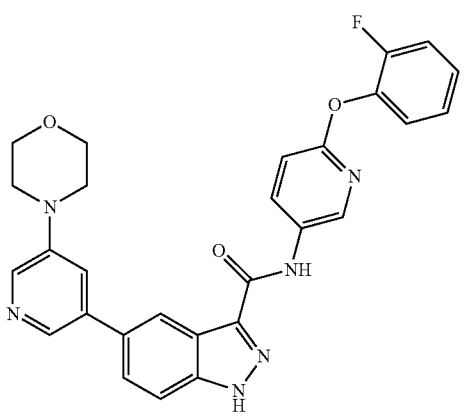 [SMILES: O=C(Nc1ccc(Oc2ccccc2F)nc1)c1n[nH]c2ccc(-c3cncc(N4CCOCC4)c3)cc12]
578 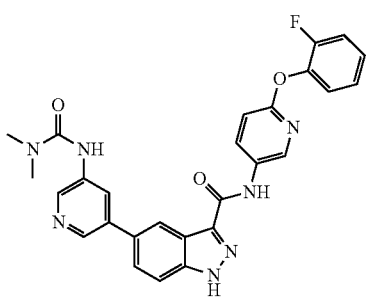 [SMILES: CN(C)C(=O)Nc1cncc(-c2ccc3[nH]nc(C(=O)Nc4ccc(Oc5ccccc5F)nc4)c3c2)c1]
579 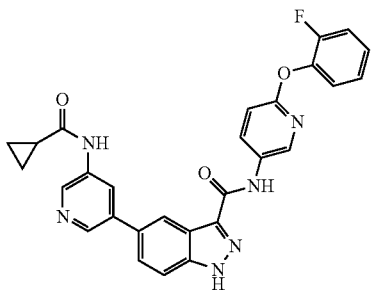 [SMILES: O=C(Nc1ccc(Oc2ccccc2F)nc1)c1n[nH]c2ccc(-c3cncc(NC(=O)C4CC4)c3)cc12]
580 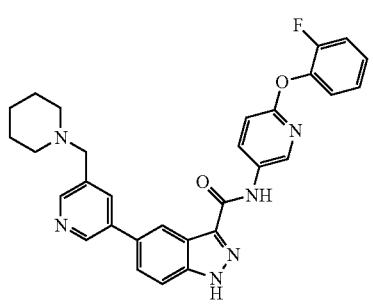 [SMILES: O=C(Nc1ccc(Oc2ccccc2F)nc1)c1n[nH]c2ccc(-c3cncc(CN4CCCCC4)c3)cc12]
581 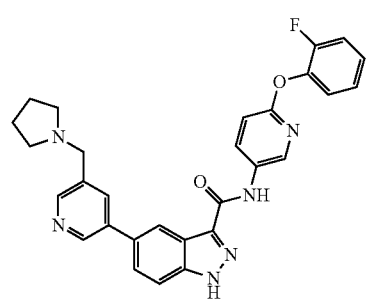 [SMILES: O=C(Nc1ccc(Oc2ccccc2F)nc1)c1n[nH]c2ccc(-c3cncc(CN4CCCC4)c3)cc12]
582 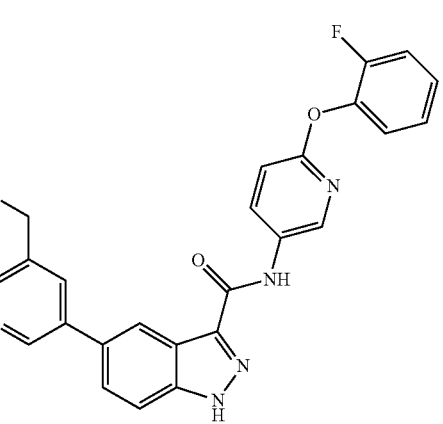
583 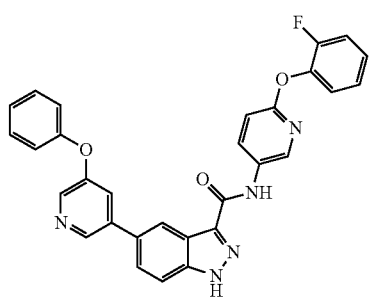 [SMILES: O=C(Nc1ccc(Oc2ccccc2F)nc1)c1n[nH]c2ccc(-c3cncc(Oc4ccccc4)c3)cc12]

TABLE 1-continued
584 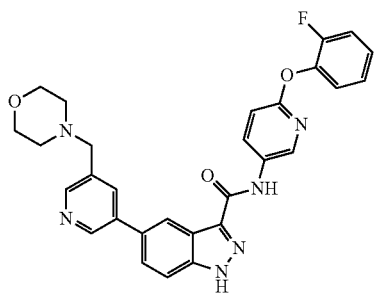 [SMILES: O=C(Nc1ccc(Oc2ccccc2F)nc1)c1n[nH]c2ccc(-c3cncc(CN4CCOCC4)c3)cc12]
585 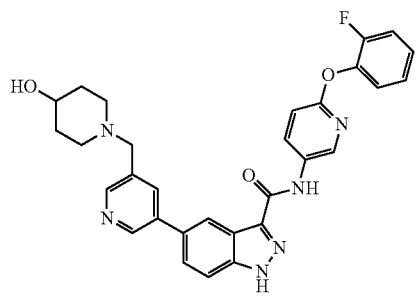 [SMILES: O=C(Nc1ccc(Oc2ccccc2F)nc1)c1n[nH]c2ccc(-c3cncc(CN4CCC(O)CC4)c3)cc12]
586 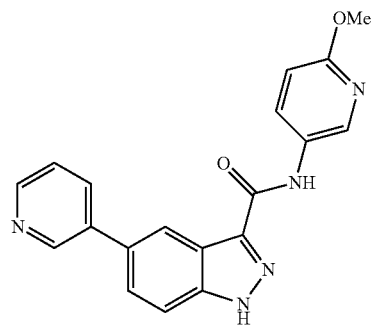 [SMILES: COc1ccc(NC(=O)c2n[nH]c3ccc(-c4cccnc4)cc23)cn1]
587 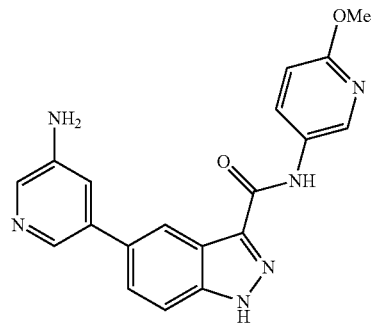 [SMILES: COc1ccc(NC(=O)c2n[nH]c3ccc(-c4cncc(N)c4)cc23)cn1]
588 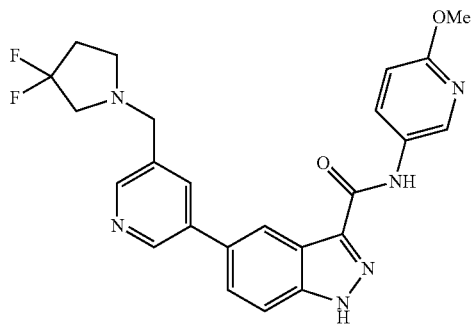 [SMILES: COc1ccc(NC(=O)c2n[nH]c3ccc(-c4cncc(CN5CCC(F)(F)C5)c4)cc23)cn1]
TABLE 1-continued
589 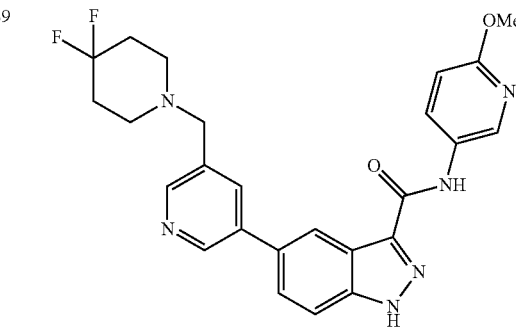
590 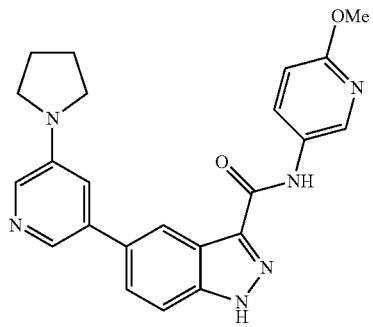 [SMILES: COc1ccc(NC(=O)c2n[nH]c3ccc(-c4cncc(N5CCCC5)c4)cc23)cn1]
591 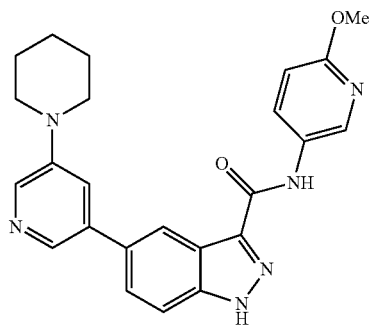 [SMILES: COc1ccc(NC(=O)c2n[nH]c3ccc(-c4cncc(N5CCCCC5)c4)cc23)cn1]
592 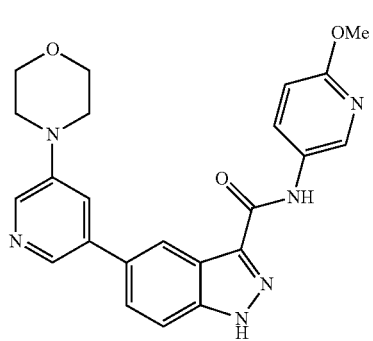 [SMILES: COc1ccc(NC(=O)c2n[nH]c3ccc(-c4cncc(N5CCOCC5)c4)cc23)cn1]
593 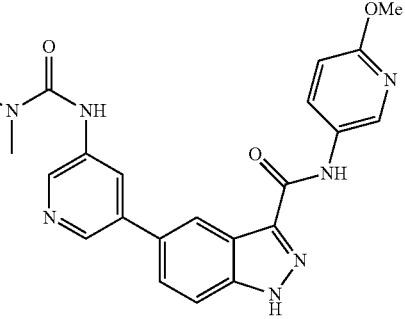

TABLE 1-continued
594 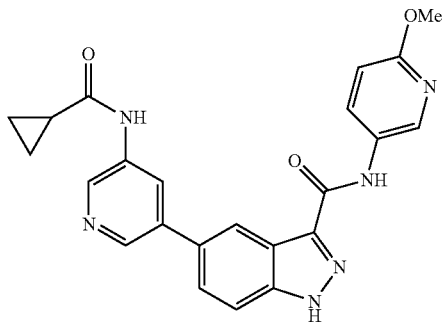 [SMILES: COc1ccc(NC(=O)c2n[nH]c3ccc(-c4cncc(NC(=O)C5CC5)c4)cc23)cn1]
595 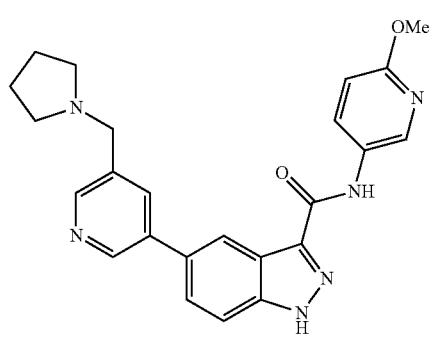 [SMILES: COc1ccc(NC(=O)c2n[nH]c3ccc(-c4cncc(CN5CCCC5)c4)cc23)cn1]
596 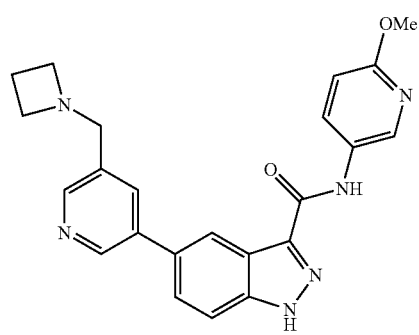 [SMILES: COc1ccc(NC(=O)c2n[nH]c3ccc(-c4cncc(CN5CCC5)c4)cc23)cn1]
597 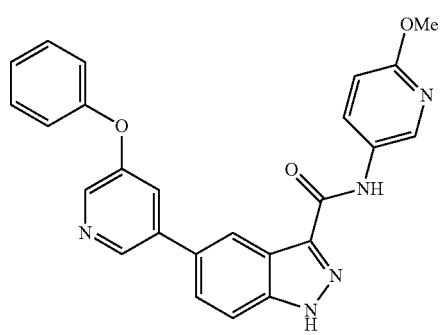 [SMILES: COc1ccc(NC(=O)c2n[nH]c3ccc(-c4cncc(Oc5ccccc5)c4)cc23)cn1]
598 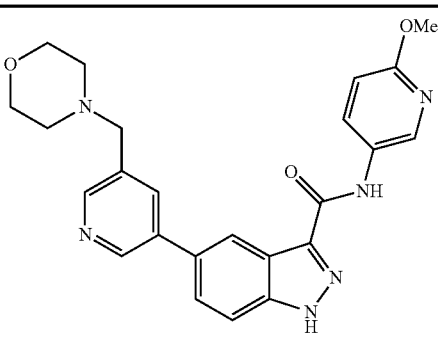
599 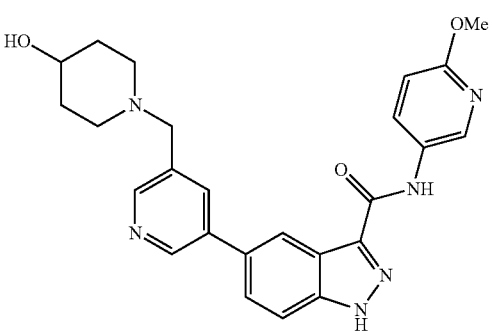 [SMILES: COc1ccc(NC(=O)c2n[nH]c3ccc(-c4cncc(CN5CCC(O)CC5)c4)cc23)cn1]
600 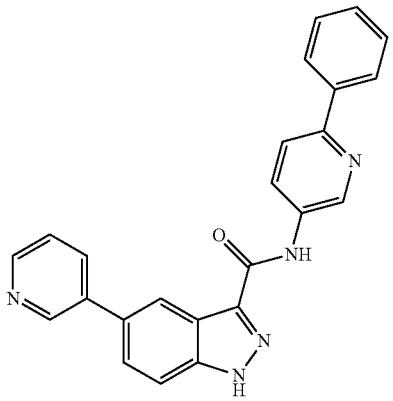 [SMILES: O=C(Nc1ccc(-c2ccccc2)nc1)c1n[nH]c2ccc(-c3cccnc3)cc12]
601 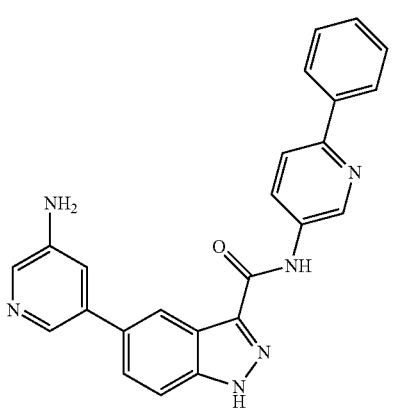 [SMILES: Nc1cncc(-c2ccc3[nH]nc(C(=O)Nc4ccc(-c5ccccc5)nc4)c3c2)c1]

TABLE 1-continued
602
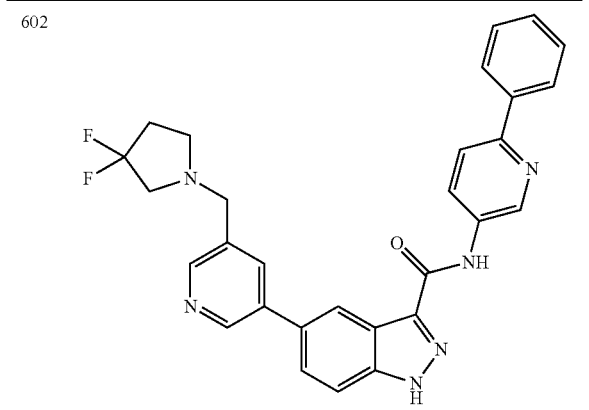
603
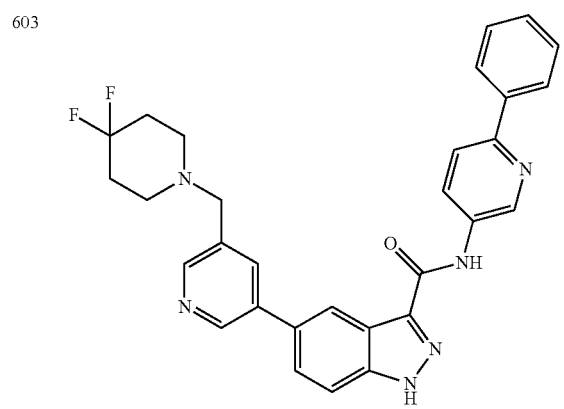
604
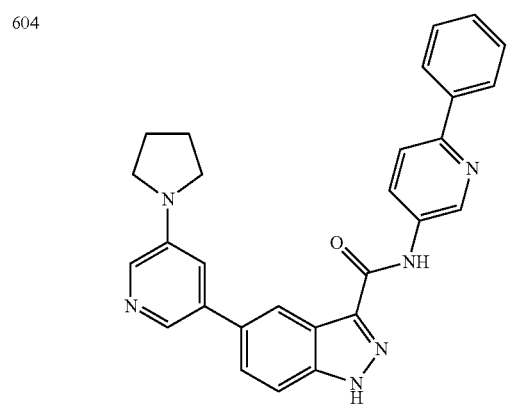
605
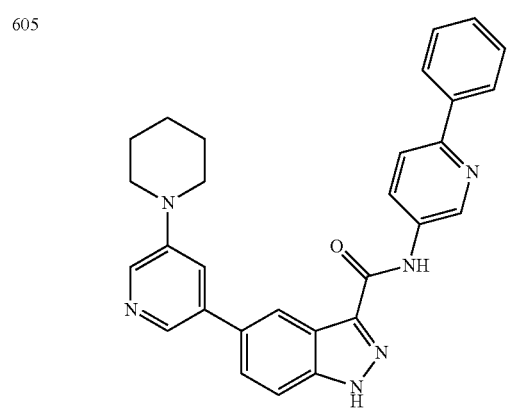
606
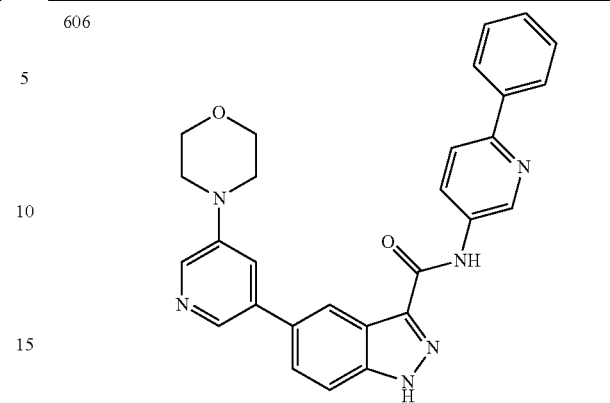
607
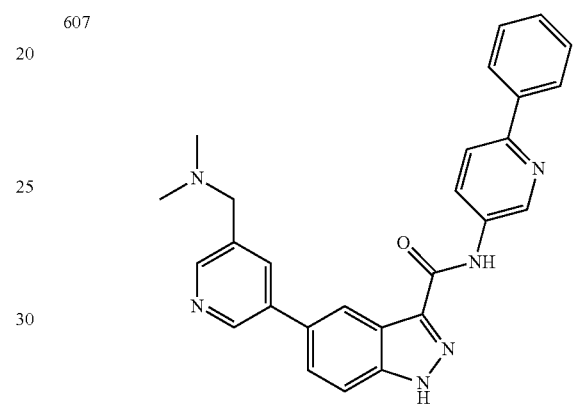
608

609
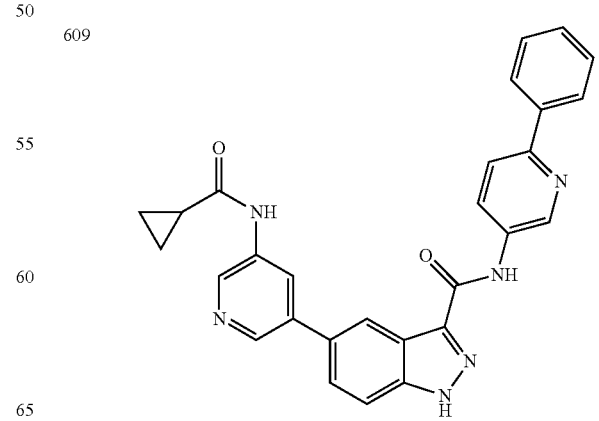

TABLE 1-continued
610
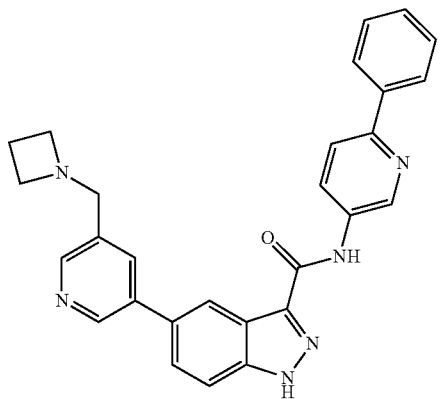 [SMILES: O=C(Nc1ccc(-c2ccccc2)nc1)c1n[nH]c2ccc(-c3cncc(CN4CCC4)c3)cc12]
611
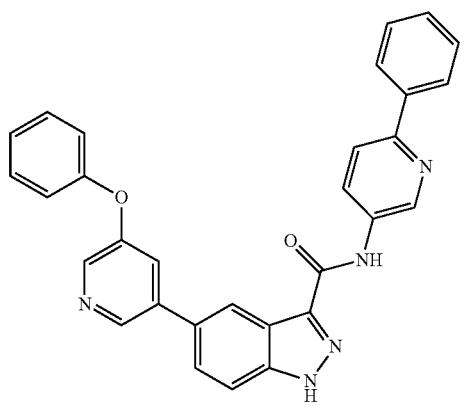 [SMILES: O=C(Nc1ccc(-c2ccccc2)nc1)c1n[nH]c2ccc(-c3cncc(Oc4ccccc4)c3)cc12]
612
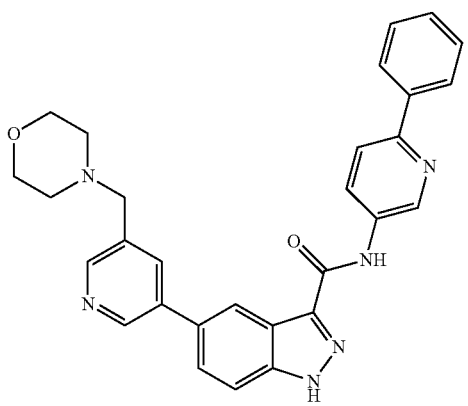 [SMILES: O=C(Nc1ccc(-c2ccccc2)nc1)c1n[nH]c2ccc(-c3cncc(CN4CCOCC4)c3)cc12]
613
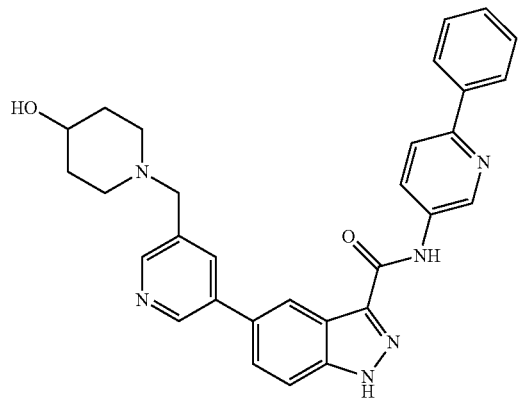 [SMILES: O=C(Nc1ccc(-c2ccccc2)nc1)c1n[nH]c2ccc(-c3cncc(CN4CCC(O)CC4)c3)cc12]
TABLE 1-continued
614
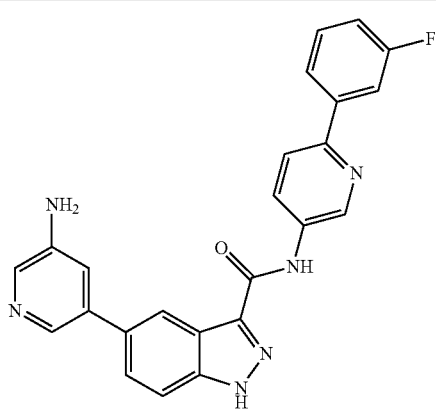 [SMILES: Nc1cncc(-c2ccc3[nH]nc(C(=O)Nc4ccc(-c5cccc(F)c5)nc4)c3c2)c1]
615
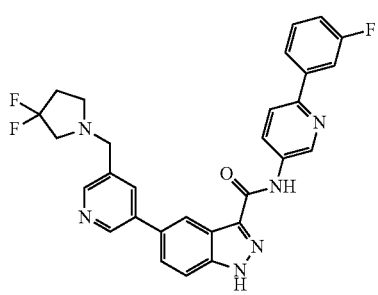 [SMILES: O=C(Nc1ccc(-c2cccc(F)c2)nc1)c1n[nH]c2ccc(-c3cncc(CN4CCC(F)(F)C4)c3)cc12]
616
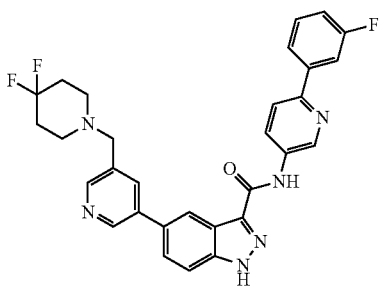 [SMILES: O=C(Nc1ccc(-c2cccc(F)c2)nc1)c1n[nH]c2ccc(-c3cncc(CN4CCC(F)(F)CC4)c3)cc12]
617
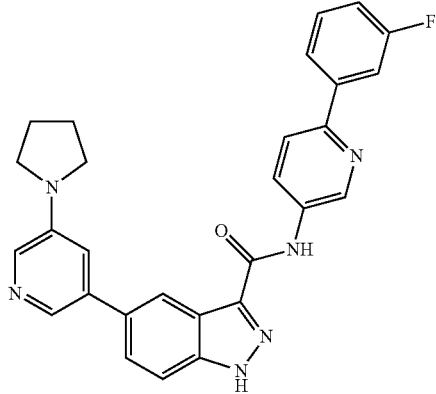 [SMILES: O=C(Nc1ccc(-c2cccc(F)c2)nc1)c1n[nH]c2ccc(-c3cncc(N4CCCC4)c3)cc12]

TABLE 1-continued
618
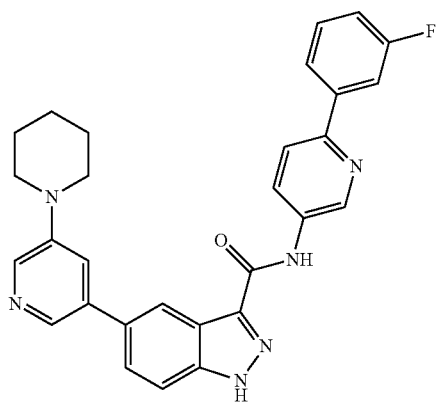
619
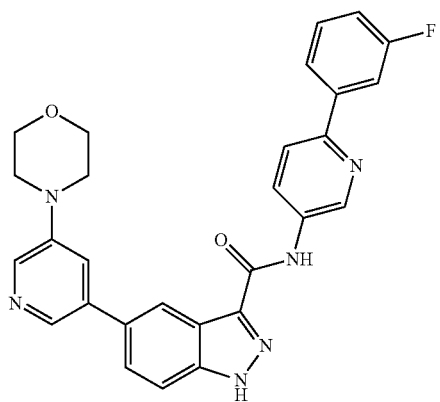 [SMILES: O=C(Nc1ccc(-c2cccc(F)c2)nc1)c1n[nH]c2ccc(-c3cncc(N4CCCCC4)c3)cc12]
620
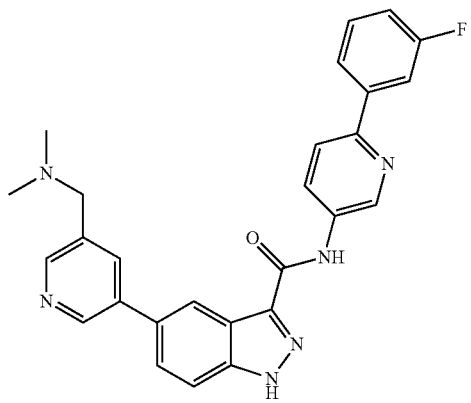 [SMILES: CN(C)Cc1cncc(-c2ccc3[nH]nc(C(=O)Nc4ccc(-c5cccc(F)c5)nc4)c3c2)c1]
621
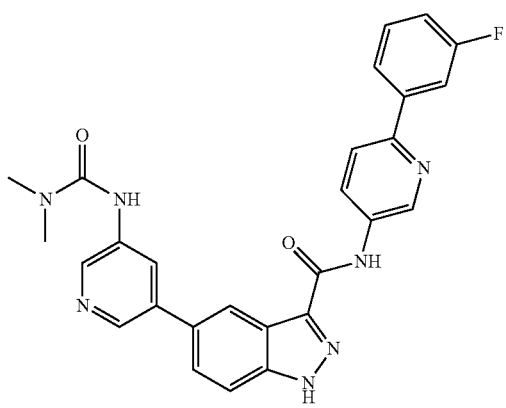 [SMILES: CN(C)C(=O)Nc1cncc(-c2ccc3[nH]nc(C(=O)Nc4ccc(-c5cccc(F)c5)nc4)c3c2)c1]
622
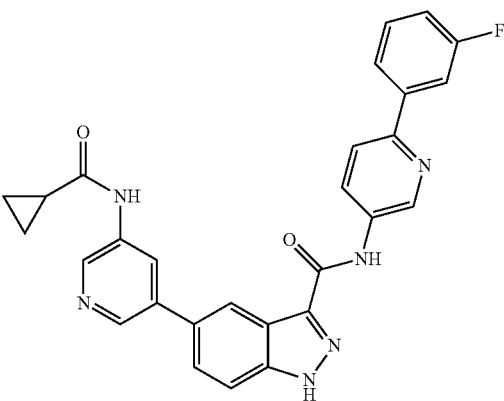 [SMILES: O=C(Nc1ccc(-c2cccc(F)c2)nc1)c1n[nH]c2ccc(-c3cncc(NC(=O)C4CC4)c3)cc12]
623
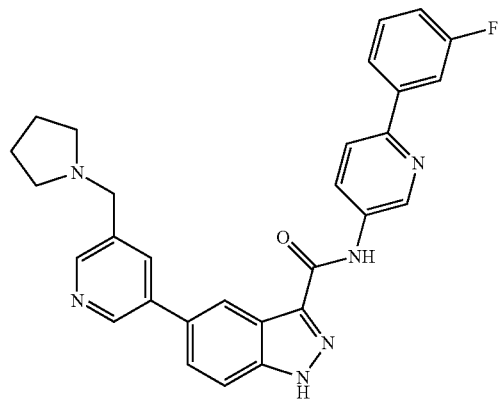 [SMILES: O=C(Nc1ccc(-c2cccc(F)c2)nc1)c1n[nH]c2ccc(-c3cncc(CN4CCCC4)c3)cc12]
624
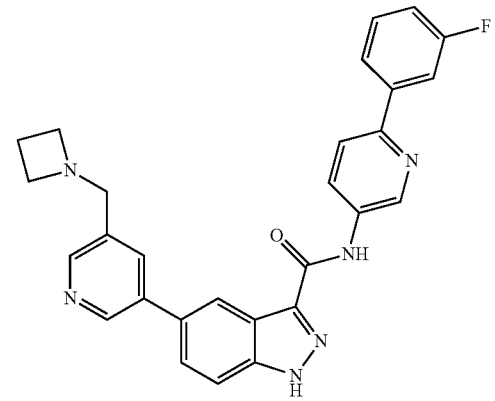 [SMILES: O=C(Nc1ccc(-c2cccc(F)c2)nc1)c1n[nH]c2ccc(-c3cncc(CN4CCC4)c3)cc12]
625
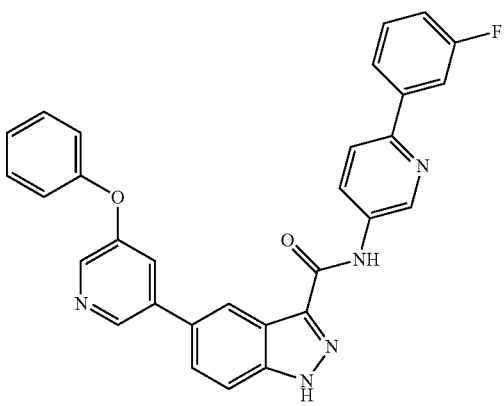 [SMILES: O=C(Nc1ccc(-c2cccc(F)c2)nc1)c1n[nH]c2ccc(-c3cncc(Oc4ccccc4)c3)cc12]

TABLE 1-continued
626
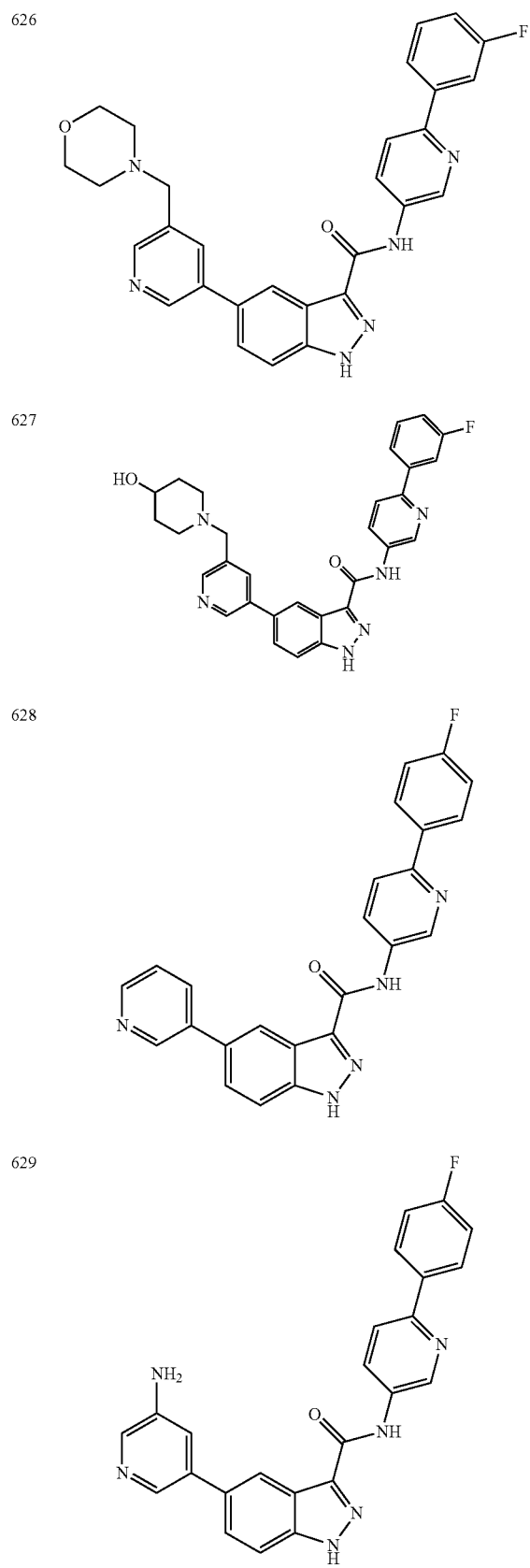
627
628
629
TABLE 1-continued
630
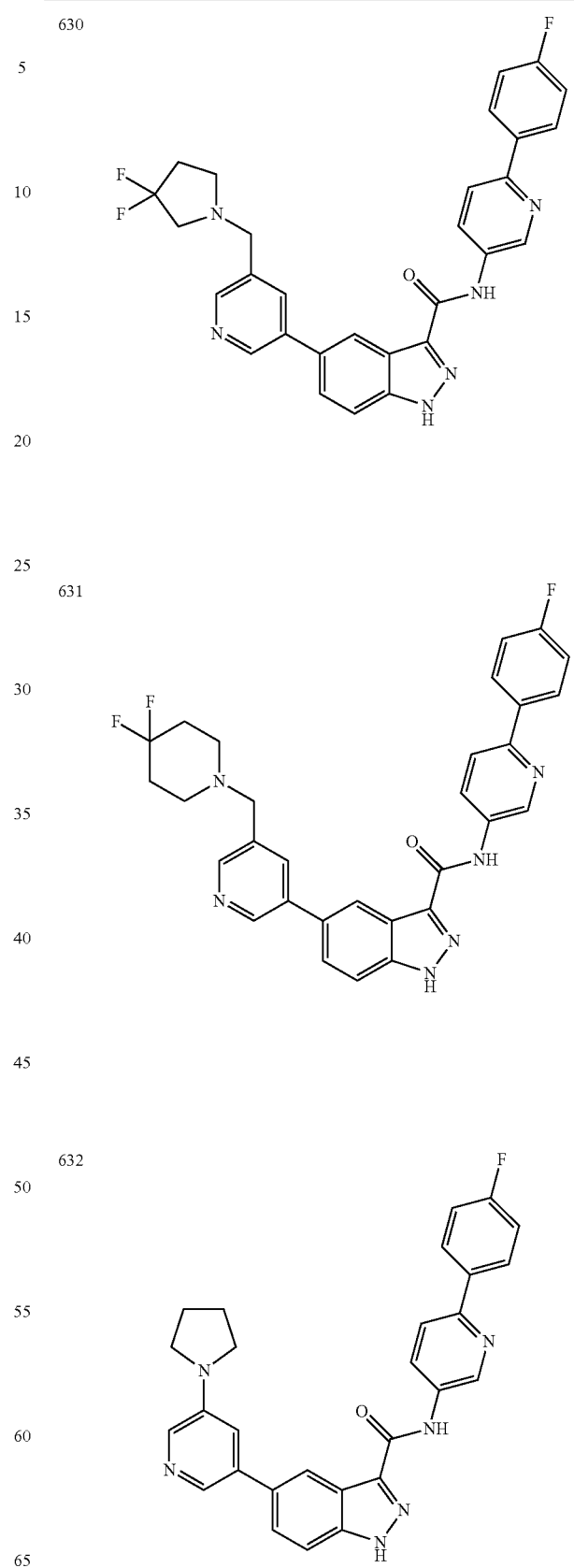
631
632

189
TABLE 1-continued
633
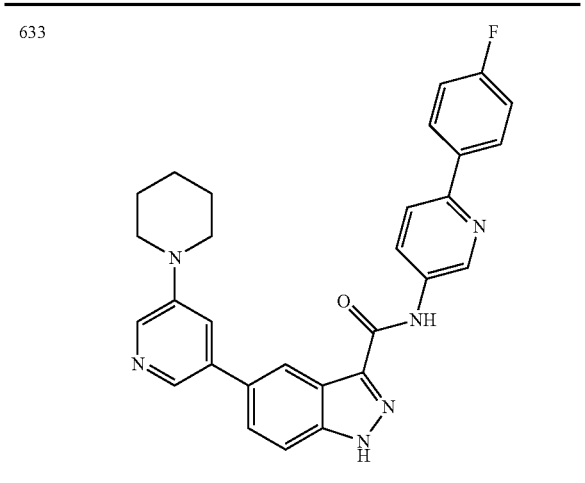
634
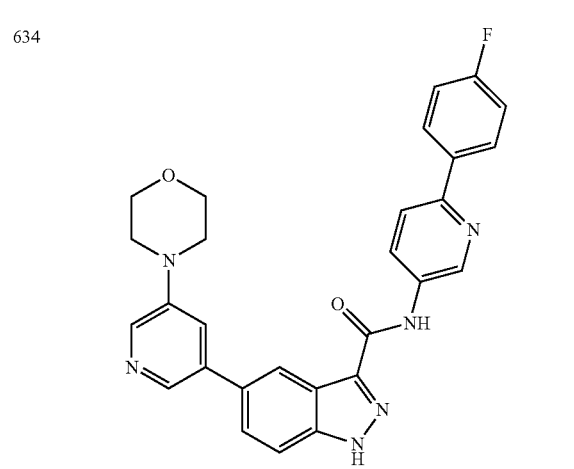
635
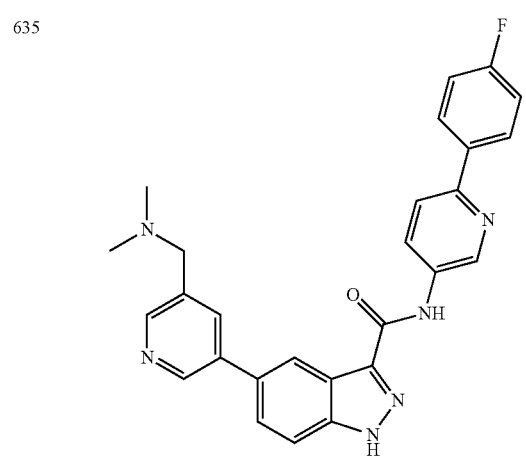
190
TABLE 1-continued
636
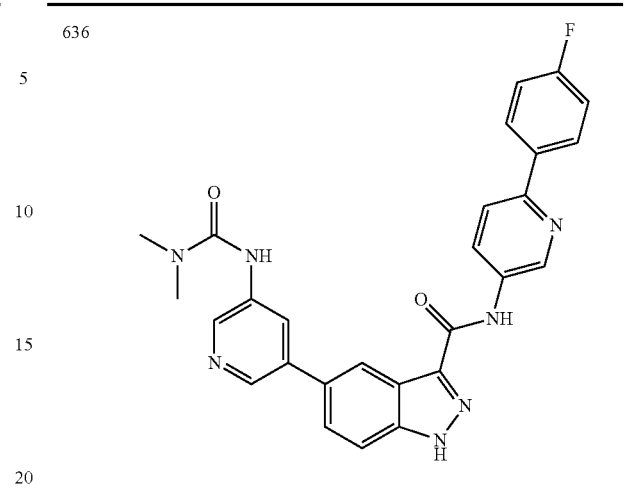
637
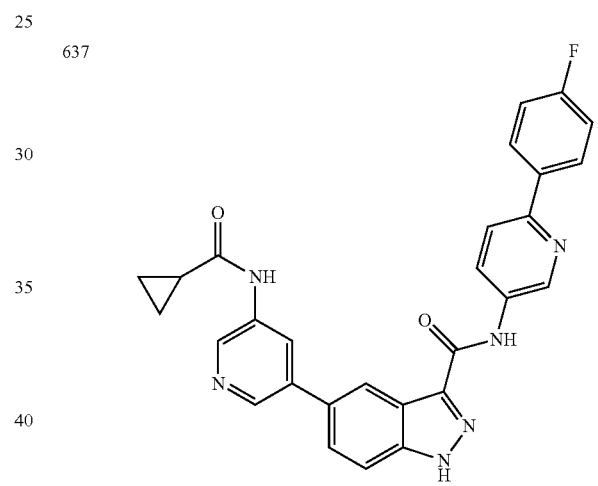
638
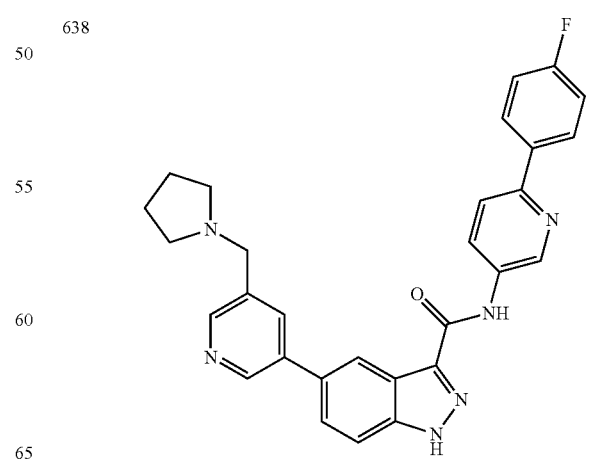

TABLE 1-continued
639
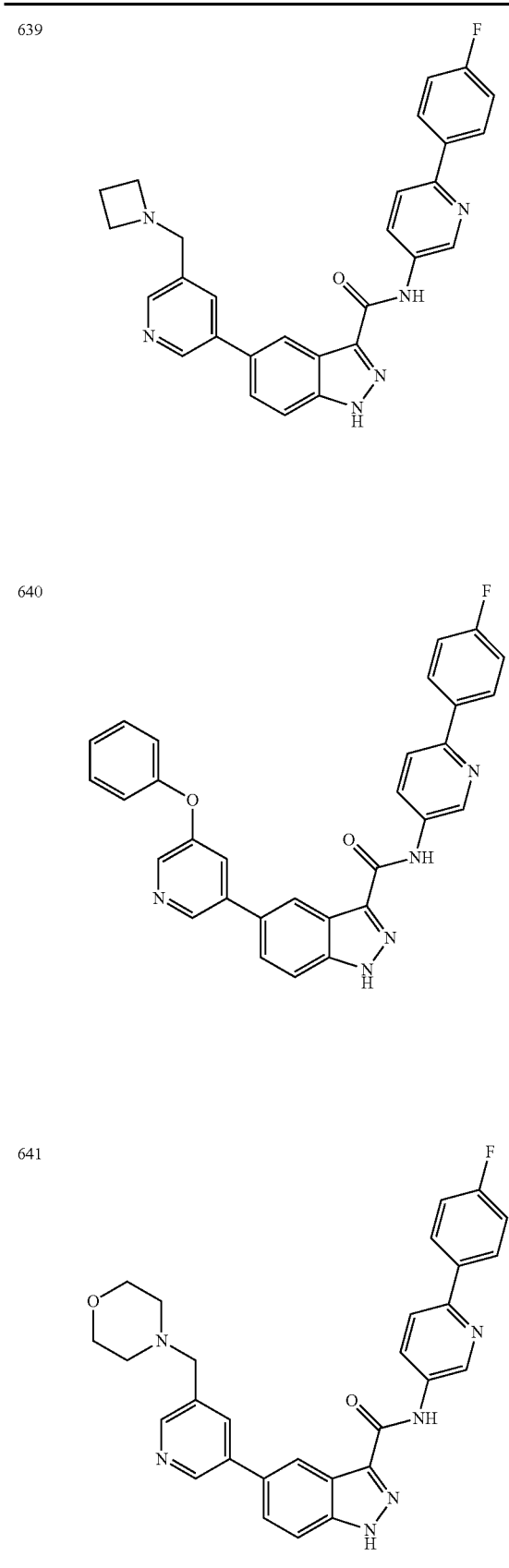
640
641
TABLE 1-continued
642
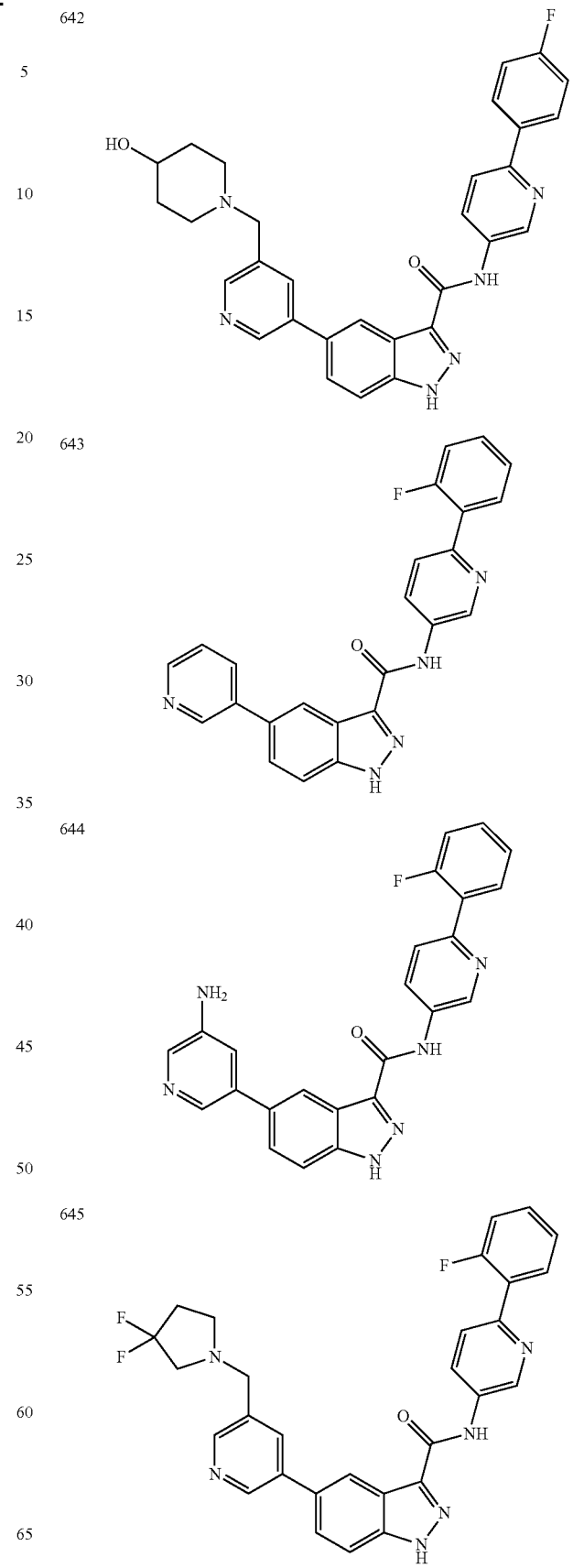
643
644
645

TABLE 1-continued
646
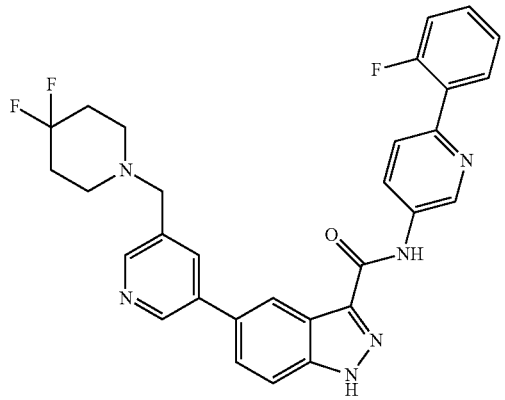 [SMILES: O=C(Nc1ccc(-c2ccccc2F)nc1)c1n[nH]c2ccc(-c3cncc(CN4CCC(F)(F)CC4)c3)cc12]
647
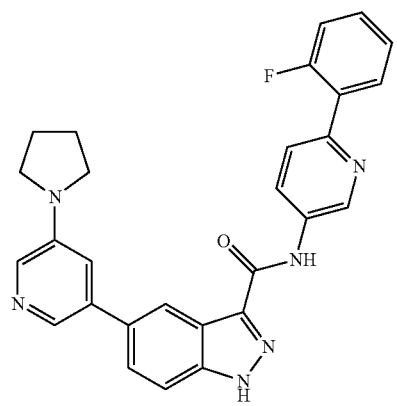 [SMILES: O=C(Nc1ccc(-c2ccccc2F)nc1)c1n[nH]c2ccc(-c3cncc(N4CCCC4)c3)cc12]
648
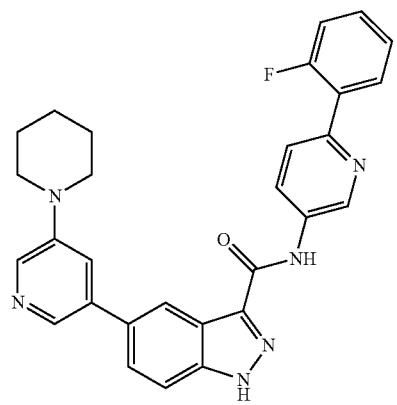 [SMILES: O=C(Nc1ccc(-c2ccccc2F)nc1)c1n[nH]c2ccc(-c3cncc(N4CCCCC4)c3)cc12]
649
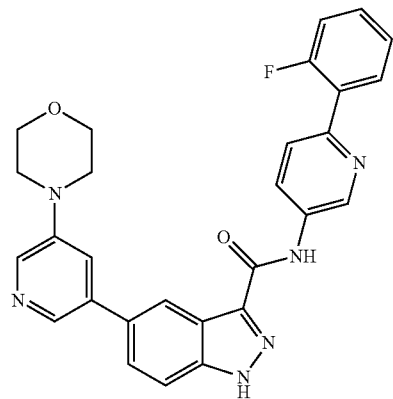 [SMILES: O=C(Nc1ccc(-c2ccccc2F)nc1)c1n[nH]c2ccc(-c3cncc(N4CCOCC4)c3)cc12]
650
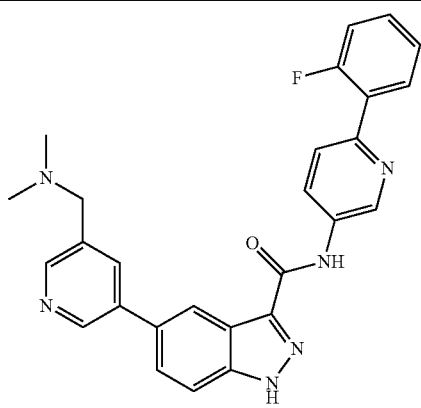
651
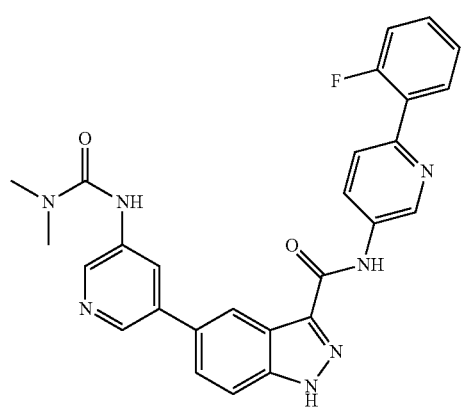 [SMILES: CN(C)C(=O)Nc1cncc(-c2ccc3[nH]nc(C(=O)Nc4ccc(-c5ccccc5F)nc4)c3c2)c1]
652
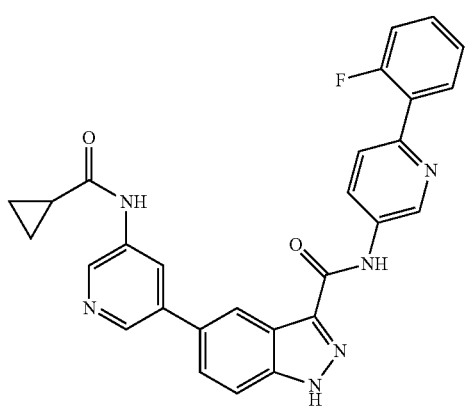 [SMILES: O=C(Nc1ccc(-c2ccccc2F)nc1)c1n[nH]c2ccc(-c3cncc(NC(=O)C4CC4)c3)cc12]
653
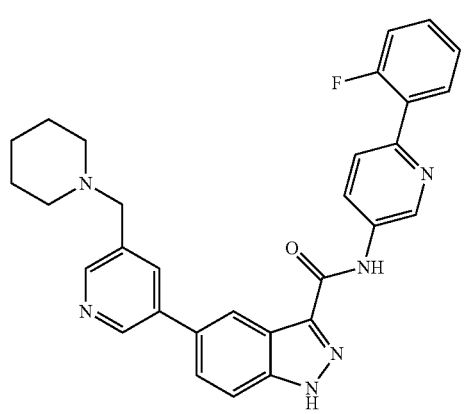 [SMILES: O=C(Nc1ccc(-c2ccccc2F)nc1)c1n[nH]c2ccc(-c3cncc(CN4CCCCC4)c3)cc12]

TABLE 1-continued
654 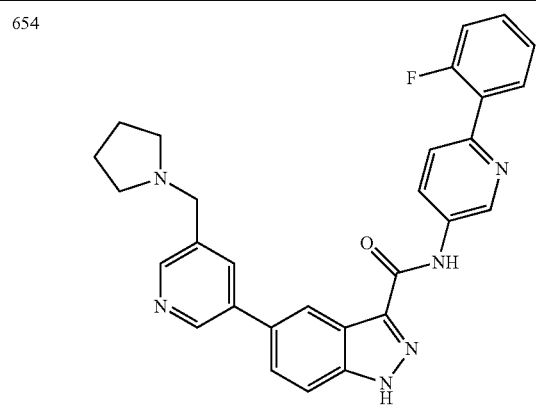
655 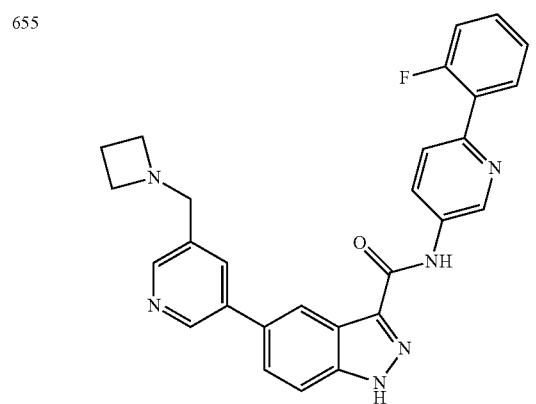
656 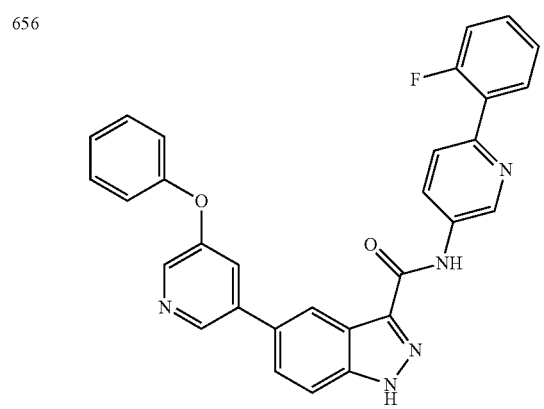
657 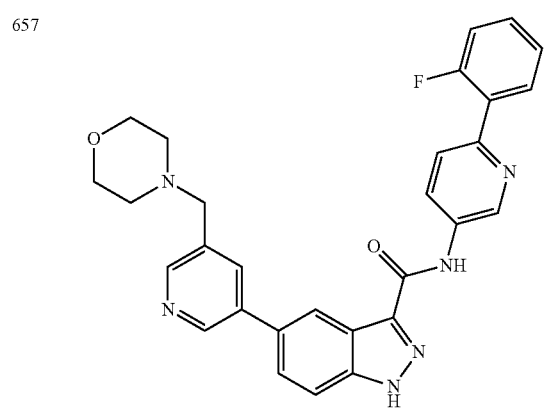
TABLE 1-continued
658 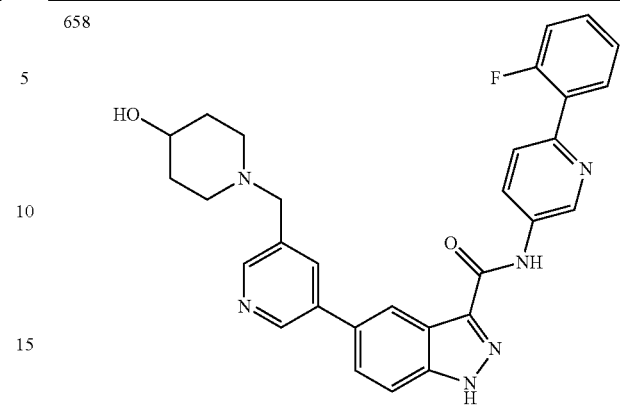
659 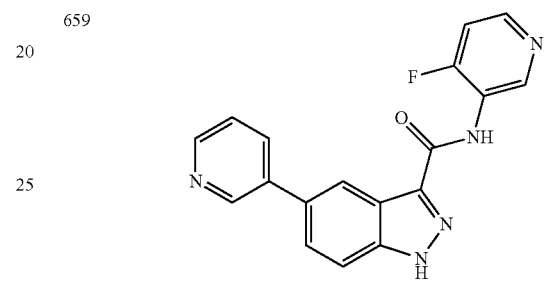
660 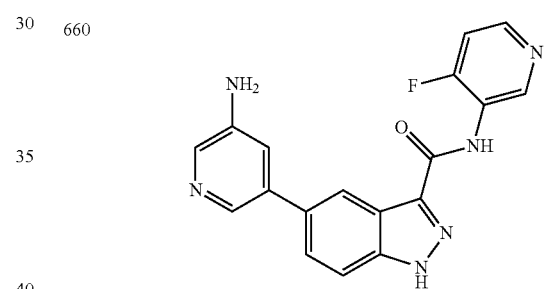
661 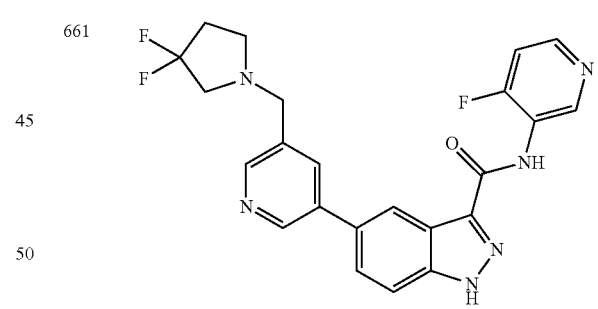
662 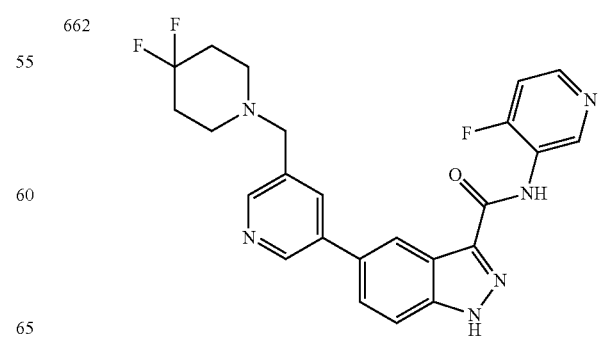

TABLE 1-continued
| 663 | 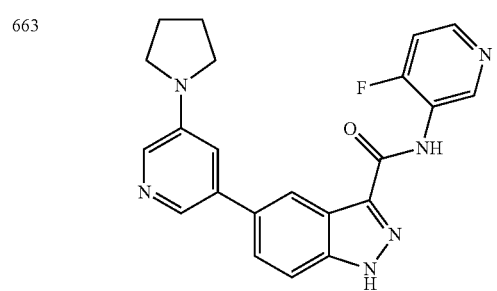 | 668 | 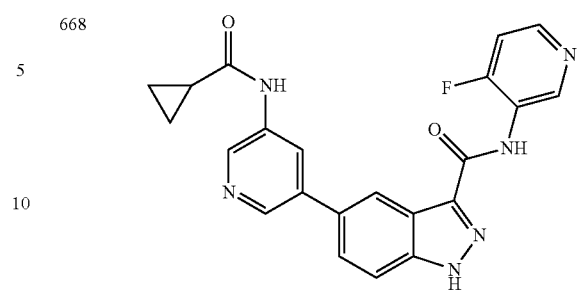 |
| 664 | 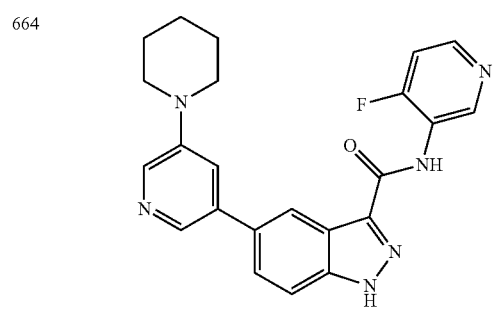 | 669 | 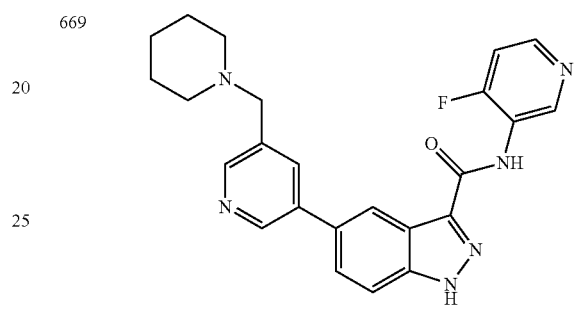 |
| 665 | 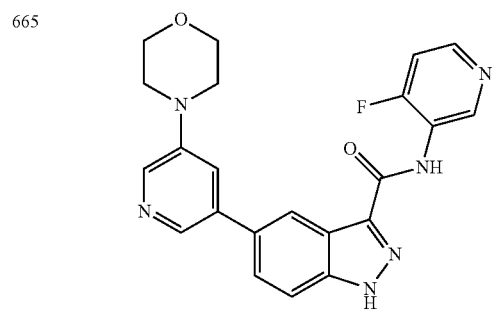 | 670 |  |
| 666 | 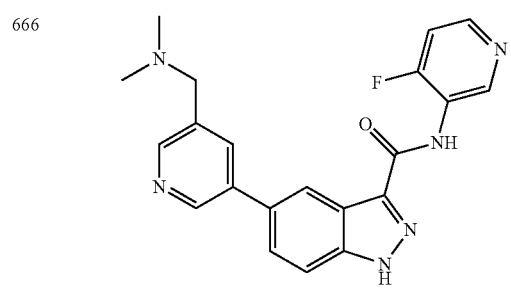 | 671 | 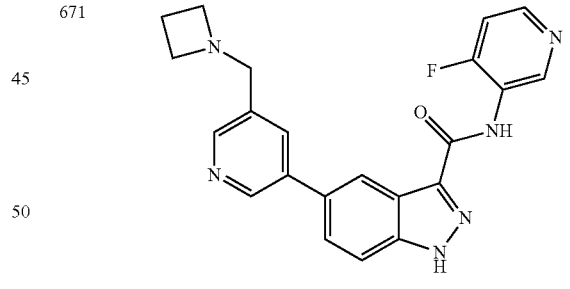 |
| 667 | 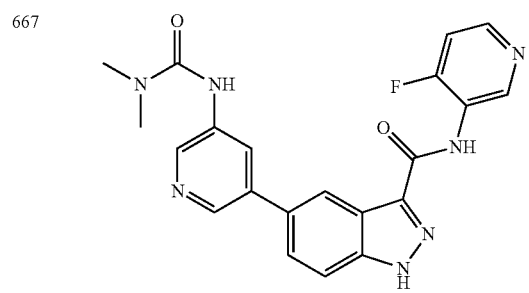 | 672 | 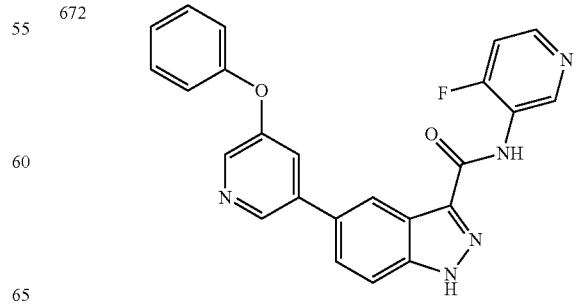 |

TABLE 1-continued
| | |
|---|---|
| 673 | 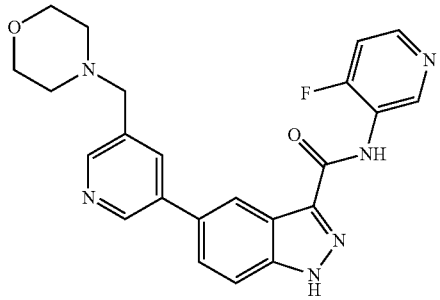 [SMILES: O=C(Nc1cnccc1F)c1n[nH]c2ccc(-c3cncc(CN4CCOCC4)c3)cc12] |
| 674 | 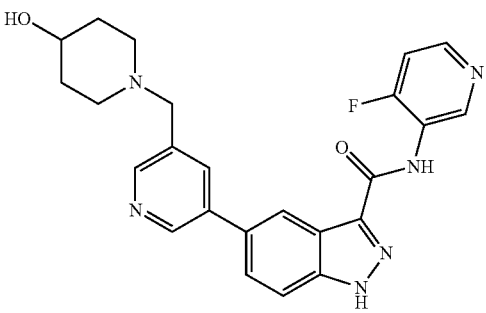 [SMILES: O=C(Nc1cnccc1F)c1n[nH]c2ccc(-c3cncc(CN4CCC(O)CC4)c3)cc12] |
| 675 | 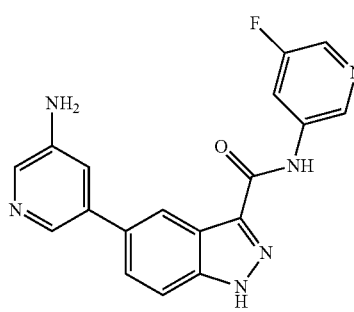 |
| 676 | 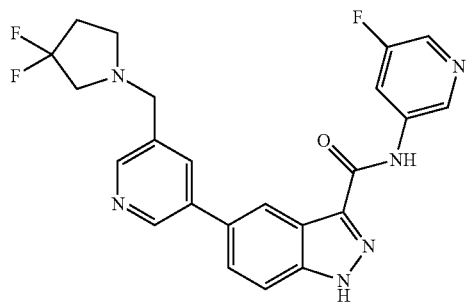 [SMILES: O=C(Nc1cncc(F)c1)c1n[nH]c2ccc(-c3cncc(CN4CCC(F)(F)C4)c3)cc12] |
| 677 | 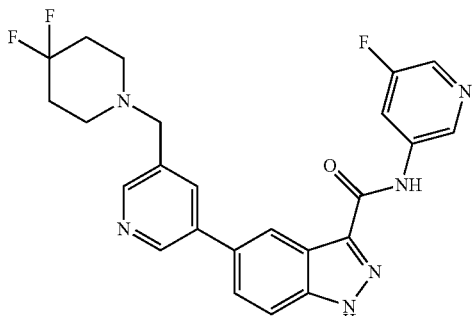 |
| 678 | 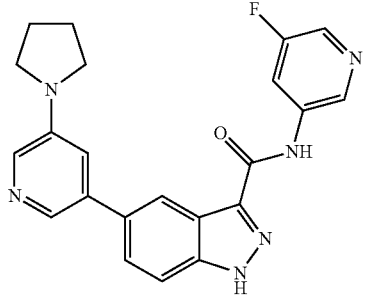 [SMILES: O=C(Nc1cncc(F)c1)c1n[nH]c2ccc(-c3cncc(N4CCCC4)c3)cc12] |
| 679 | 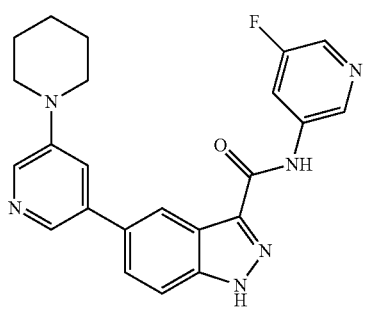 [SMILES: O=C(Nc1cncc(F)c1)c1n[nH]c2ccc(-c3cncc(N4CCCCC4)c3)cc12] |
| 680 | 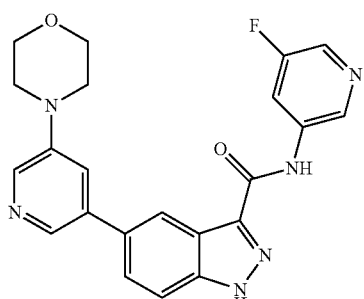 |
| 681 | 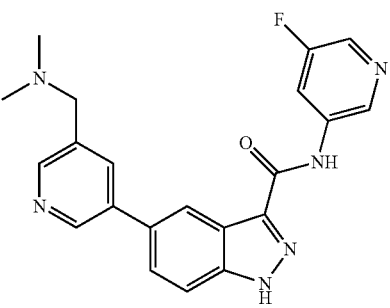 [SMILES: CN(C)Cc1cncc(-c2ccc3[nH]nc(C(=O)Nc4cncc(F)c4)c3c2)c1] |
| 682 | 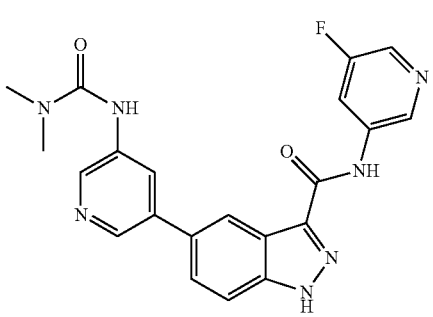 [SMILES: CN(C)C(=O)Nc1cncc(-c2ccc3[nH]nc(C(=O)Nc4cncc(F)c4)c3c2)c1] |

TABLE 1-continued
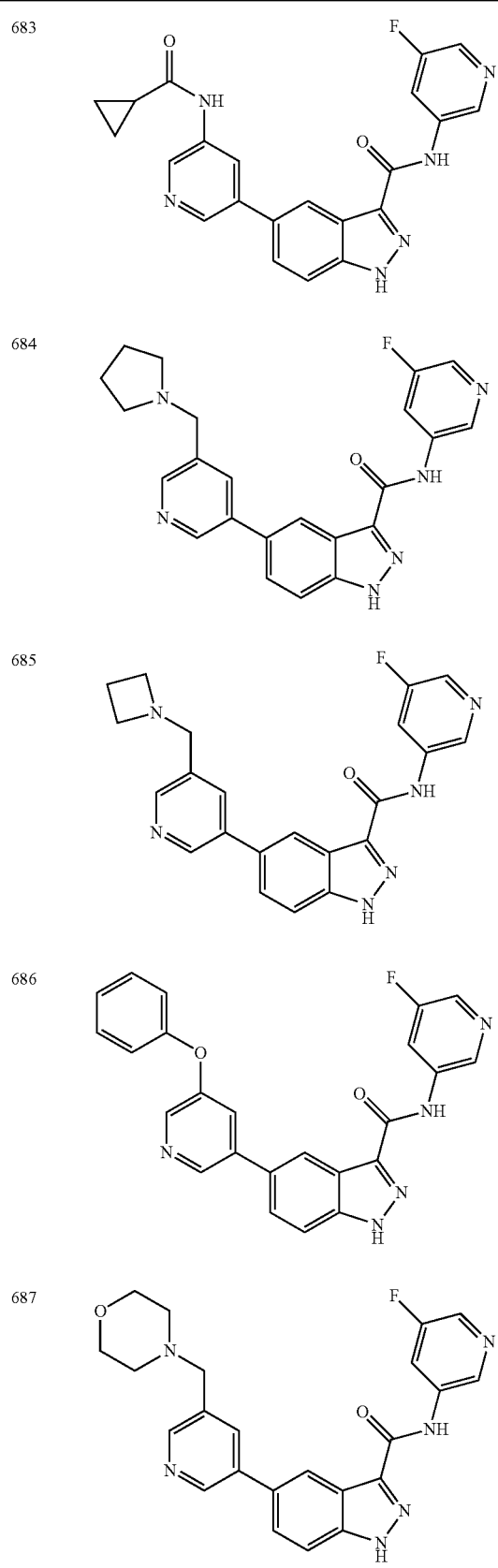
TABLE 1-continued
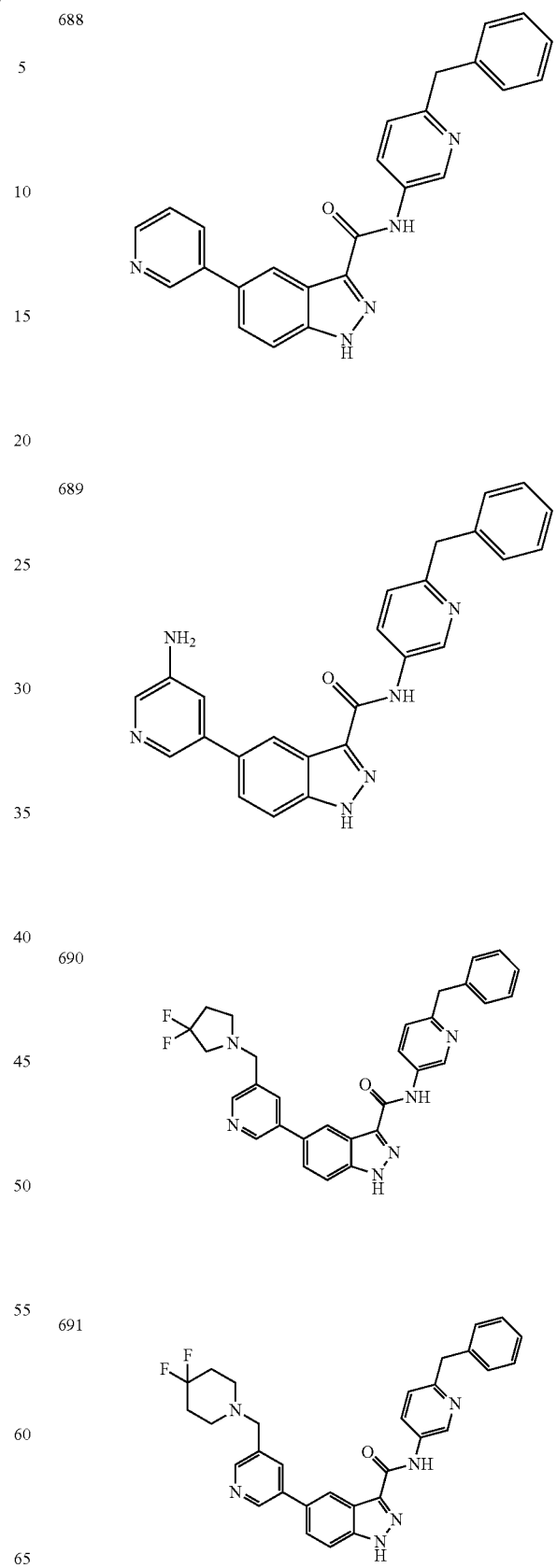

TABLE 1-continued
692
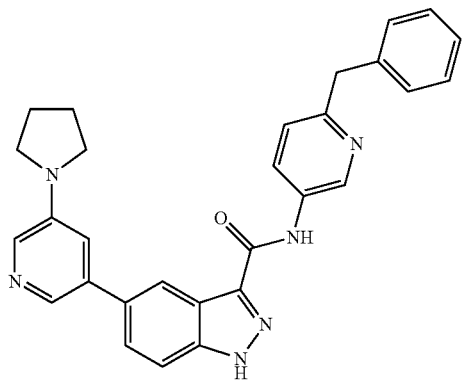 [SMILES: O=C(Nc1ccc(Cc2ccccc2)nc1)c1n[nH]c2ccc(-c3cncc(N4CCCC4)c3)cc12]
693
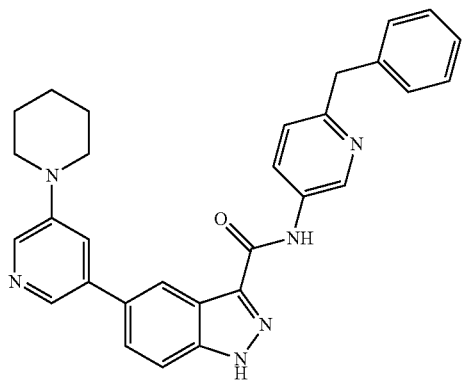 [SMILES: O=C(Nc1ccc(Cc2ccccc2)nc1)c1n[nH]c2ccc(-c3cncc(N4CCCCC4)c3)cc12]
694
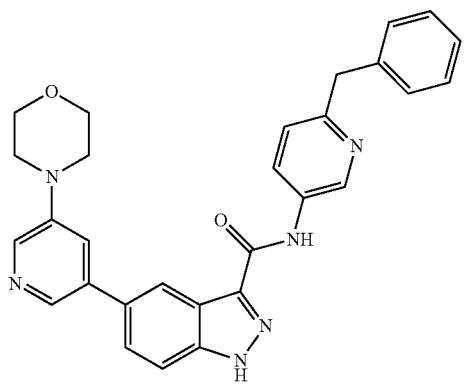
695
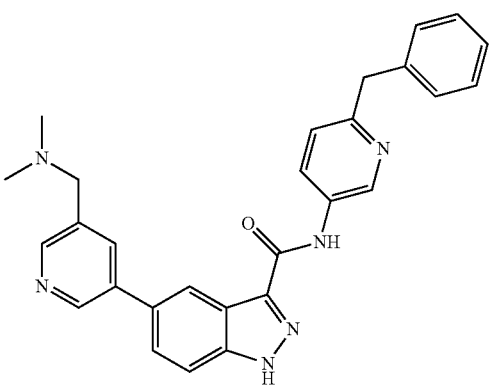 [SMILES: CN(C)Cc1cncc(-c2ccc3[nH]nc(C(=O)Nc4ccc(Cc5ccccc5)nc4)c3c2)c1]
TABLE 1-continued
696
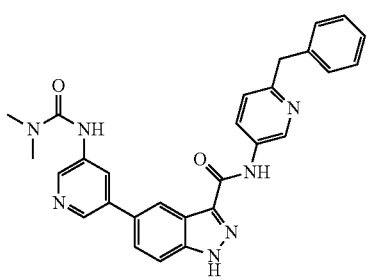 [SMILES: CN(C)C(=O)Nc1cncc(-c2ccc3[nH]nc(C(=O)Nc4ccc(Cc5ccccc5)nc4)c3c2)c1]
697
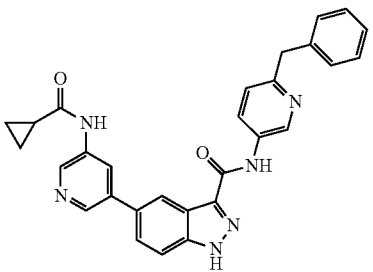 [SMILES: O=C(Nc1ccc(Cc2ccccc2)nc1)c1n[nH]c2ccc(-c3cncc(NC(=O)C4CC4)c3)cc12]
698
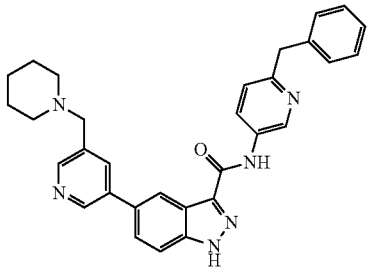 [SMILES: O=C(Nc1ccc(Cc2ccccc2)nc1)c1n[nH]c2ccc(-c3cncc(CN4CCCCC4)c3)cc12]
699
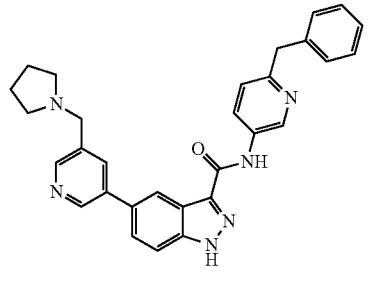 [SMILES: O=C(Nc1ccc(Cc2ccccc2)nc1)c1n[nH]c2ccc(-c3cncc(CN4CCCC4)c3)cc12]
700
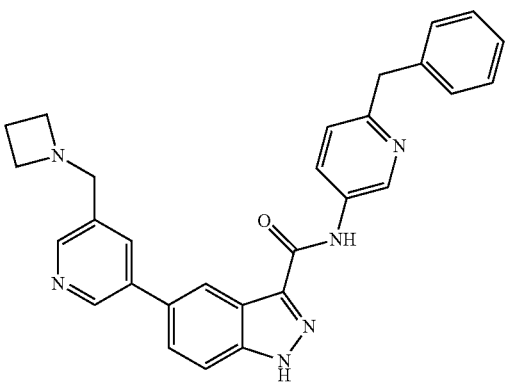 [SMILES: O=C(Nc1ccc(Cc2ccccc2)nc1)c1n[nH]c2ccc(-c3cncc(CN4CCC4)c3)cc12]

TABLE 1-continued
701 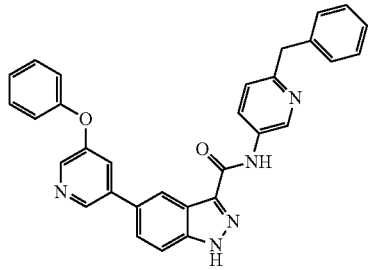 [SMILES: O=C(Nc1ccc(Cc2ccccc2)nc1)c1n[nH]c2ccc(-c3cncc(Oc4ccccc4)c3)cc12]
702 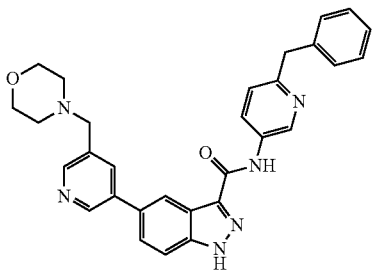 [SMILES: O=C(Nc1ccc(Cc2ccccc2)nc1)c1n[nH]c2ccc(-c3cncc(CN4CCOCC4)c3)cc12]
703 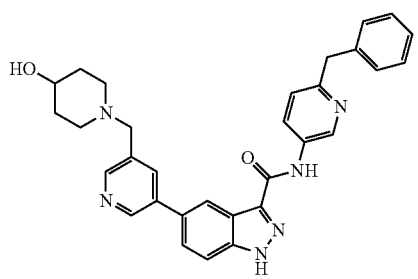 [SMILES: O=C(Nc1ccc(Cc2ccccc2)nc1)c1n[nH]c2ccc(-c3cncc(CN4CCC(O)CC4)c3)cc12]
704 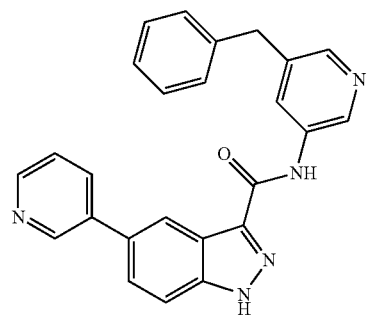 [SMILES: O=C(Nc1cncc(Cc2ccccc2)c1)c1n[nH]c2ccc(-c3cccnc3)cc12]
705 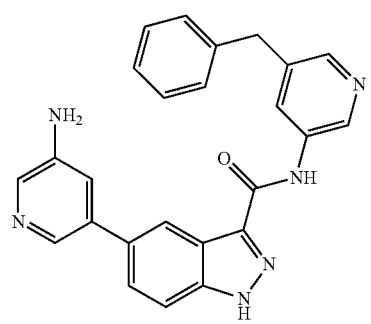 [SMILES: Nc1cncc(-c2ccc3[nH]nc(C(=O)Nc4cncc(Cc5ccccc5)c4)c3c2)c1]
706 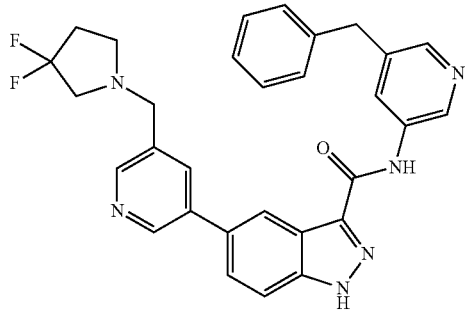 [SMILES: O=C(Nc1cncc(Cc2ccccc2)c1)c1n[nH]c2ccc(-c3cncc(CN4CCC(F)(F)C4)c3)cc12]
707 
708 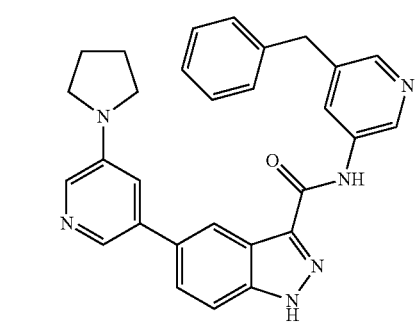 [SMILES: O=C(Nc1cncc(Cc2ccccc2)c1)c1n[nH]c2ccc(-c3cncc(N4CCCC4)c3)cc12]
709 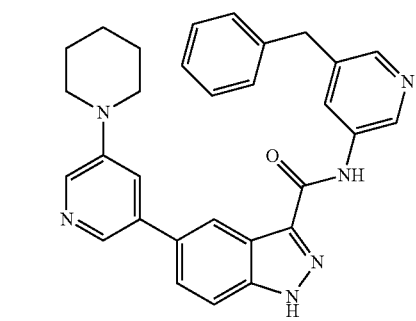
710 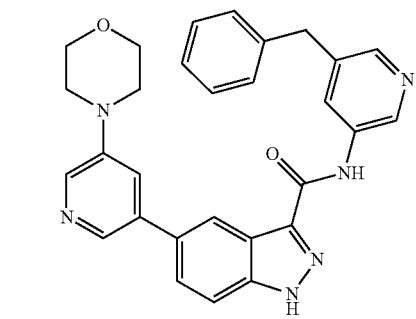 [SMILES: O=C(Nc1cncc(Cc2ccccc2)c1)c1n[nH]c2ccc(-c3cncc(N4CCOCC4)c3)cc12]

TABLE 1-continued
| | |
|---|---|
| 711 | 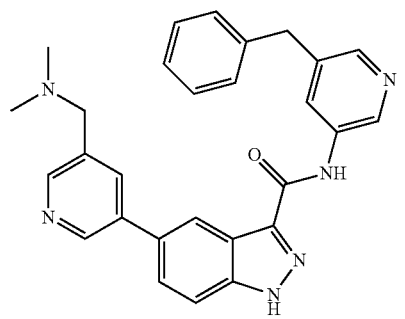 [SMILES: CN(C)Cc1cncc(-c2ccc3[nH]nc(C(=O)Nc4cncc(Cc5ccccc5)c4)c3c2)c1] |
| 712 | 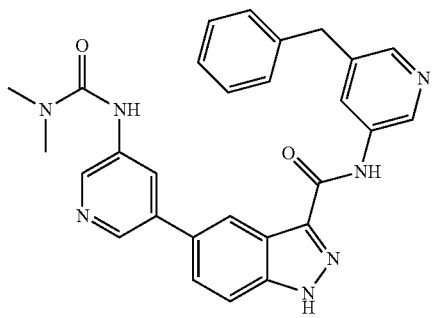 [SMILES: CN(C)C(=O)Nc1cncc(-c2ccc3[nH]nc(C(=O)Nc4cncc(Cc5ccccc5)c4)c3c2)c1] |
| 713 | 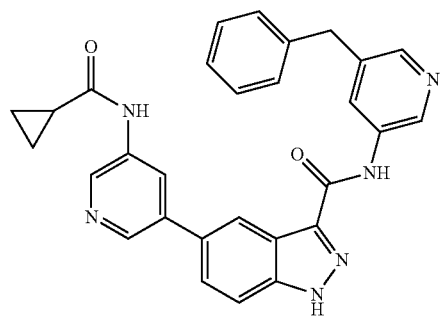 [SMILES: O=C(Nc1cncc(Cc2ccccc2)c1)c1n[nH]c2ccc(-c3cncc(NC(=O)C4CC4)c3)cc12] |
| 714 | 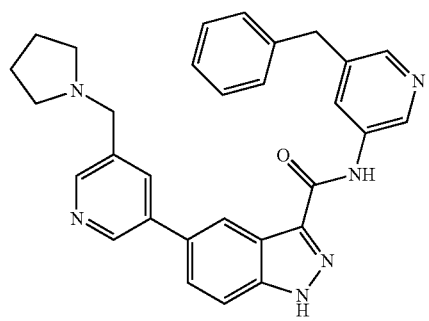 [SMILES: O=C(Nc1cncc(Cc2ccccc2)c1)c1n[nH]c2ccc(-c3cncc(CN4CCCC4)c3)cc12] |
| 715 | 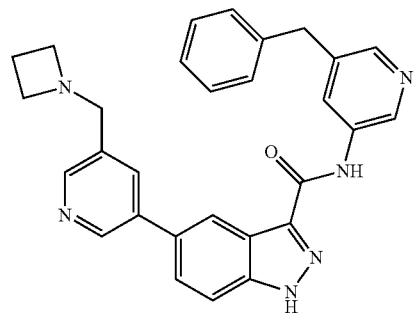 [SMILES: O=C(Nc1cncc(Cc2ccccc2)c1)c1n[nH]c2ccc(-c3cncc(CN4CCC4)c3)cc12] |
| 716 | 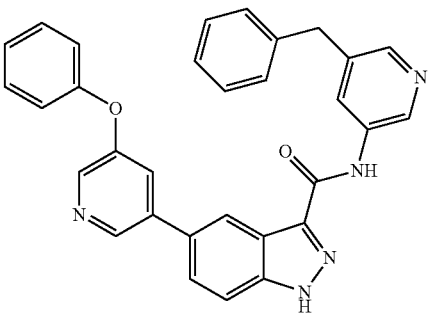 [SMILES: O=C(Nc1cncc(Cc2ccccc2)c1)c1n[nH]c2ccc(-c3cncc(Oc4ccccc4)c3)cc12] |
| 717 | 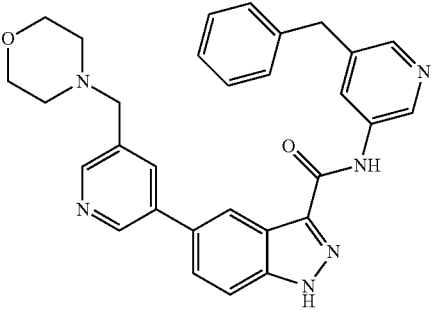 [SMILES: O=C(Nc1cncc(Cc2ccccc2)c1)c1n[nH]c2ccc(-c3cncc(CN4CCOCC4)c3)cc12] |
| 718 | 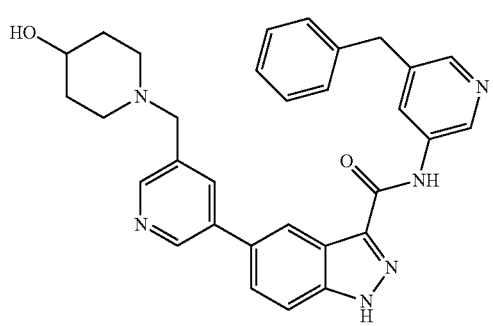 [SMILES: O=C(Nc1cncc(Cc2ccccc2)c1)c1n[nH]c2ccc(-c3cncc(CN4CCC(O)CC4)c3)cc12] |
| 719 | 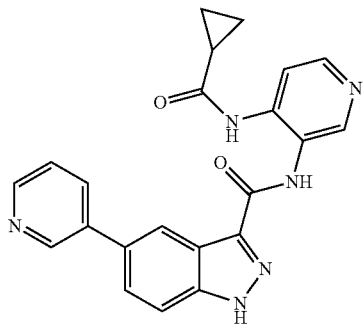 [SMILES: O=C(Nc1cnccc1NC(=O)C1CC1)c1n[nH]c2ccc(-c3cccnc3)cc12] |
| 720 | 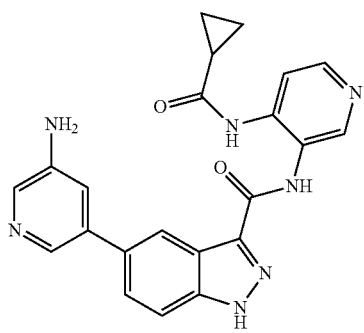 [SMILES: Nc1cncc(-c2ccc3[nH]nc(C(=O)Nc4cnccc4NC(=O)C4CC4)c3c2)c1] |

TABLE 1-continued
721 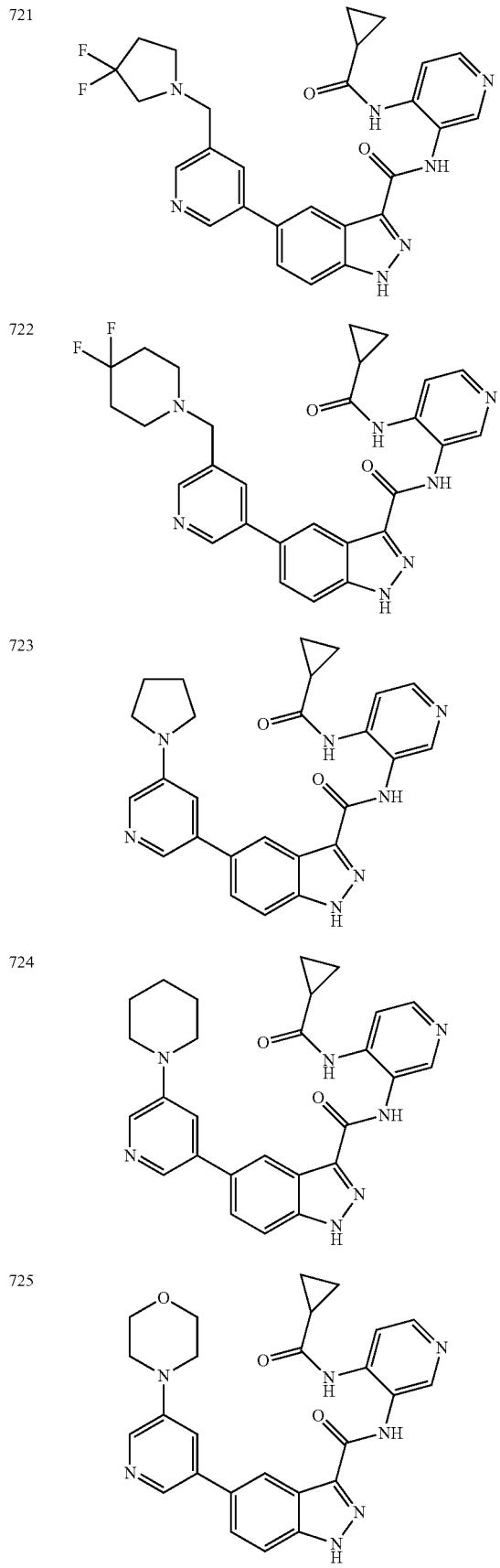
722
723
724
725
TABLE 1-continued
726 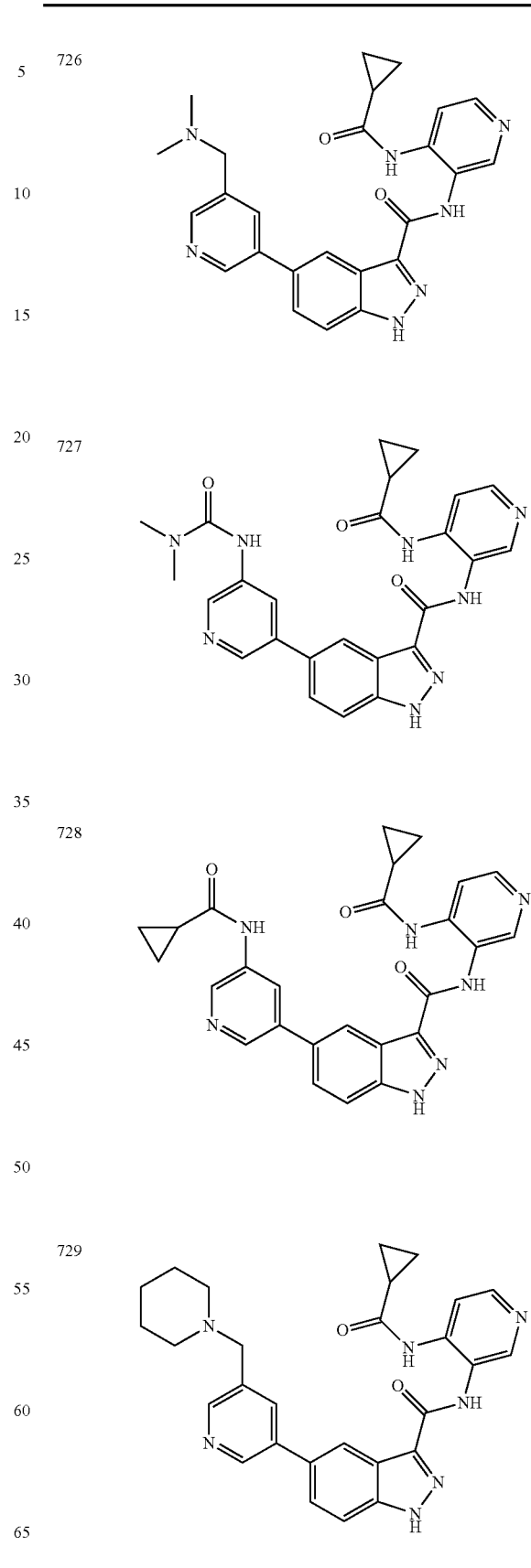
727
728
729

TABLE 1-continued
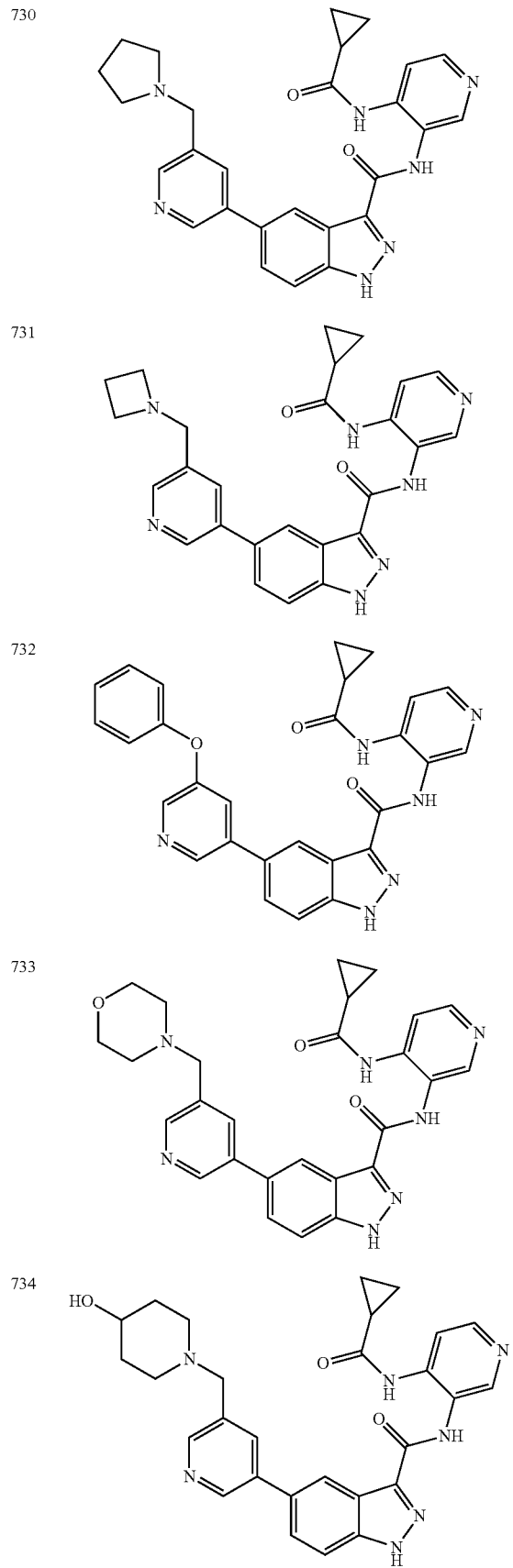
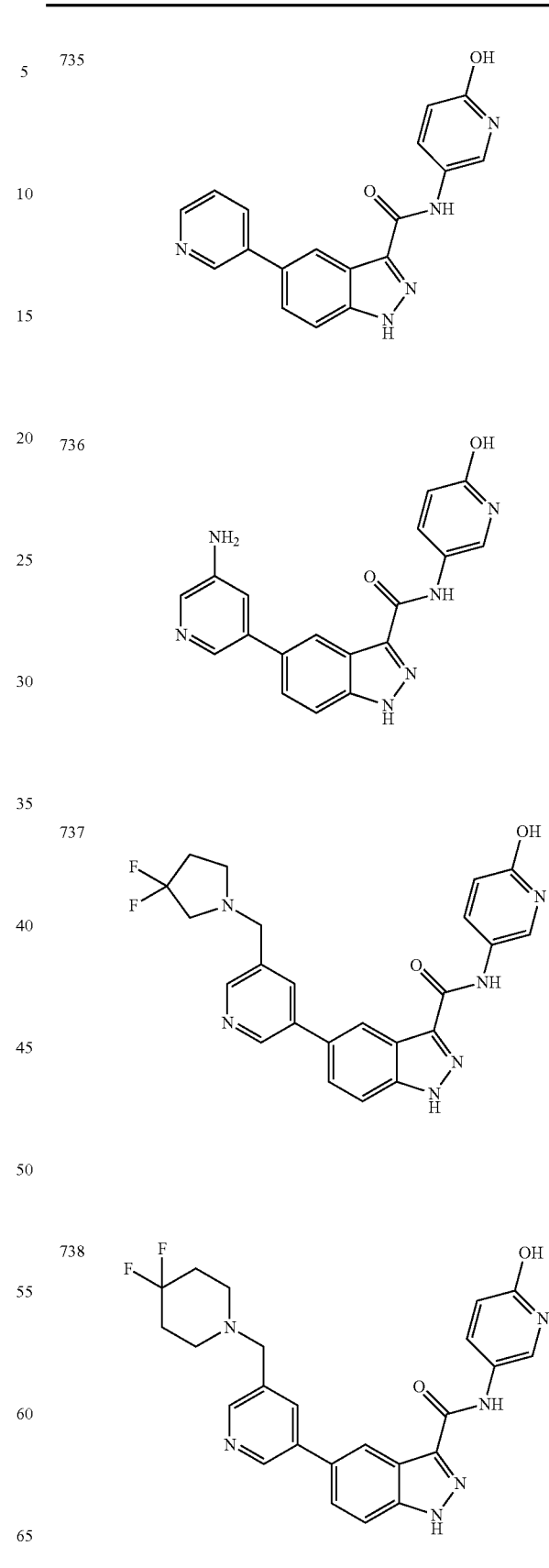

TABLE 1-continued
739 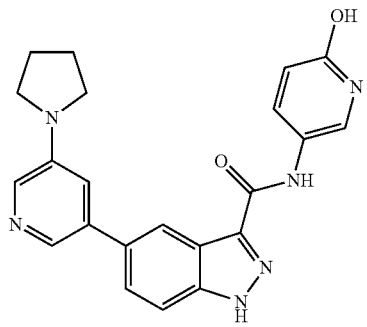 [SMILES: O=C(Nc1ccc(O)nc1)c1n[nH]c2ccc(-c3cncc(N4CCCC4)c3)cc12]
740 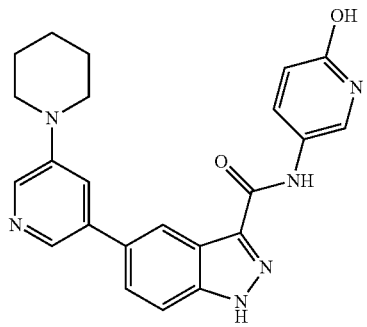
741 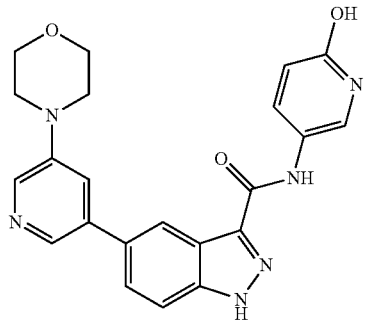 [SMILES: O=C(Nc1ccc(O)nc1)c1n[nH]c2ccc(-c3cncc(N4CCOCC4)c3)cc12]
742 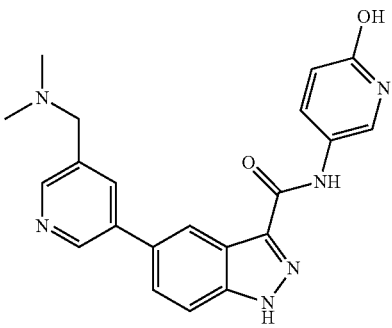
743 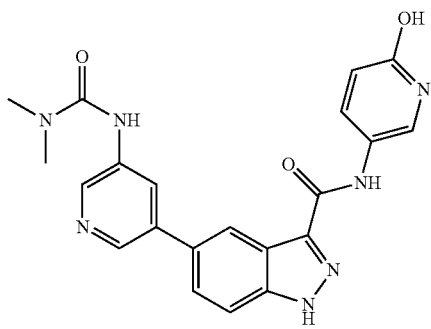
TABLE 1-continued
744 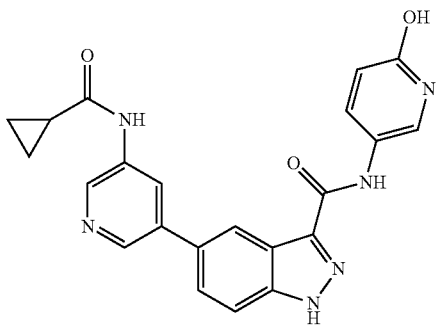
745 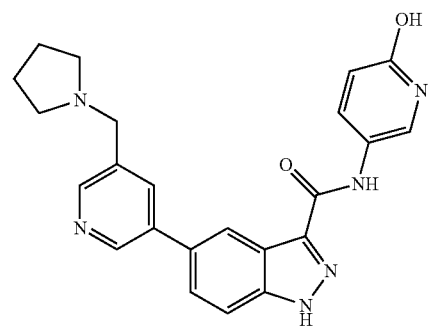
746 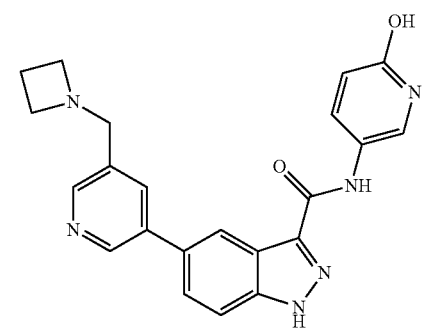
747 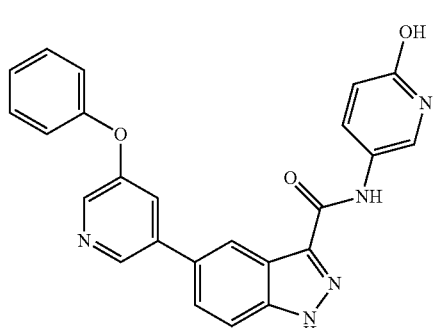
748 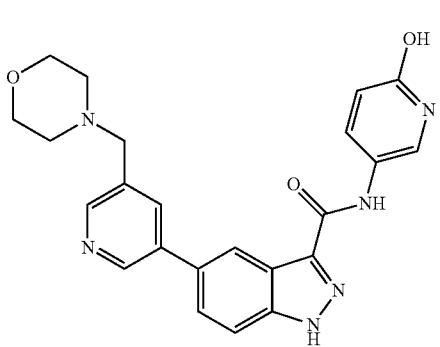

TABLE 1-continued
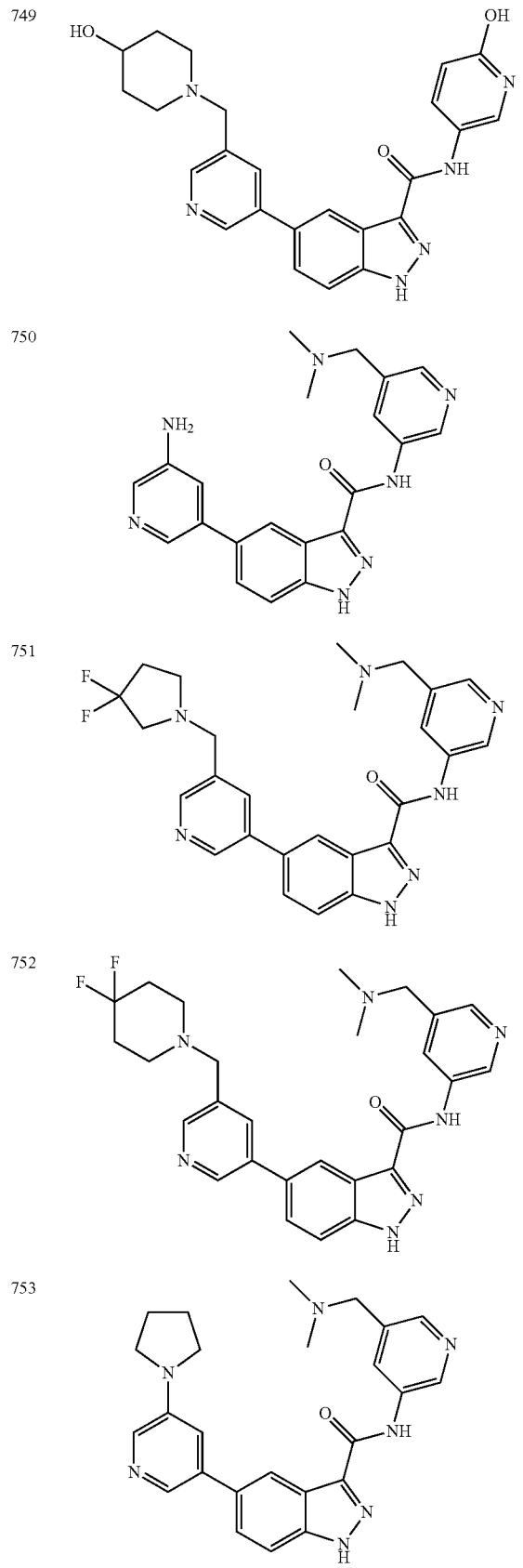
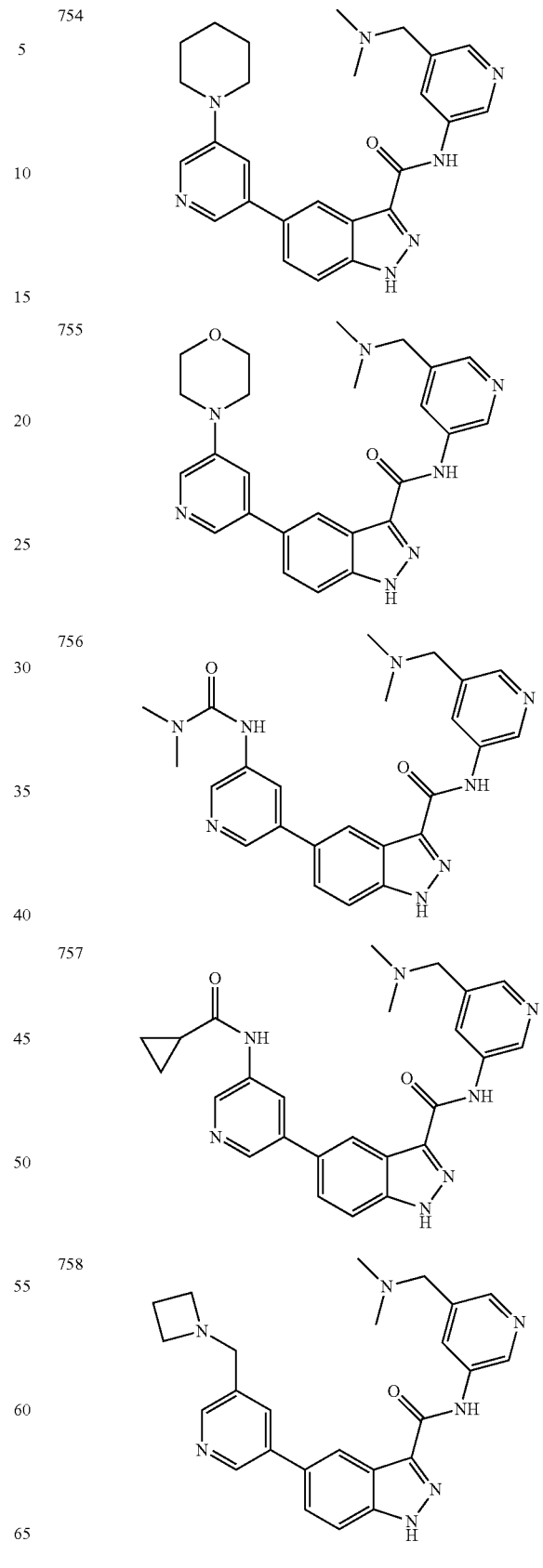

TABLE 1-continued
759 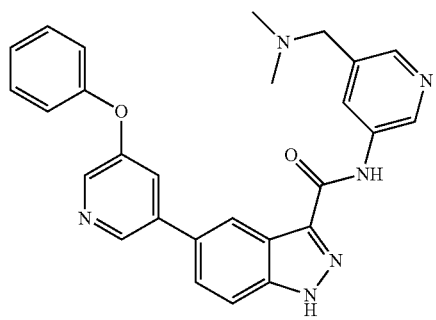 [SMILES: CN(C)Cc1cncc(NC(=O)c2n[nH]c3ccc(-c4cncc(Oc5ccccc5)c4)cc23)c1]
760 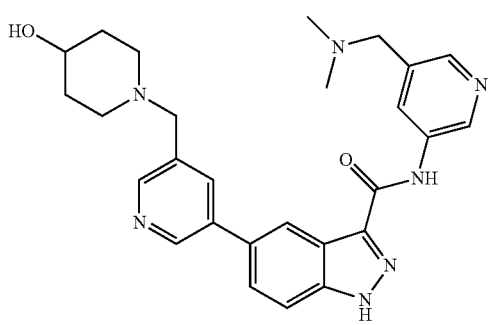 [SMILES: CN(C)Cc1cncc(NC(=O)c2n[nH]c3ccc(-c4cncc(CN5CCC(O)CC5)c4)cc23)c1]
761 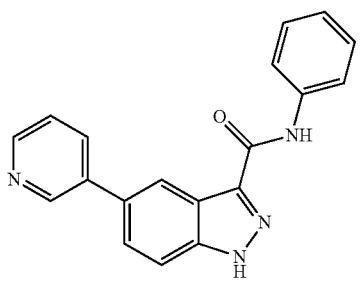 [SMILES: O=C(Nc1ccccc1)c1n[nH]c2ccc(-c3cccnc3)cc12]
762 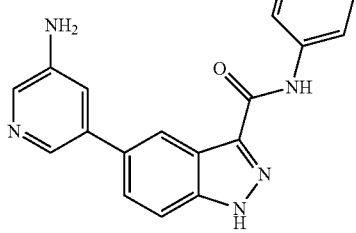
763 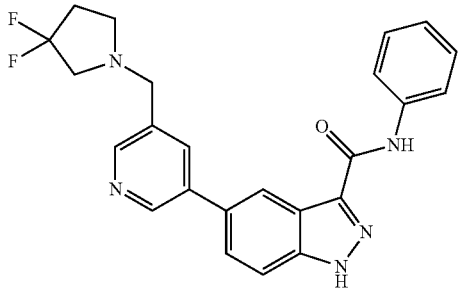 [SMILES: O=C(Nc1ccccc1)c1n[nH]c2ccc(-c3cncc(CN4CCC(F)(F)C4)c3)cc12]
TABLE 1-continued
764 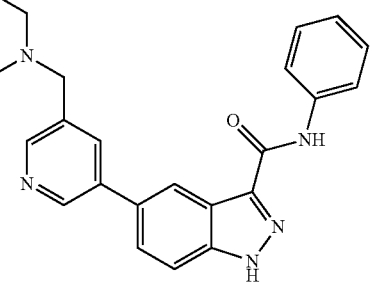
765 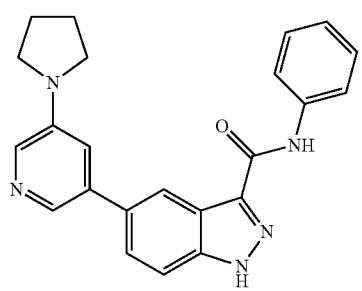 [SMILES: O=C(Nc1ccccc1)c1n[nH]c2ccc(-c3cncc(N4CCCC4)c3)cc12]
766 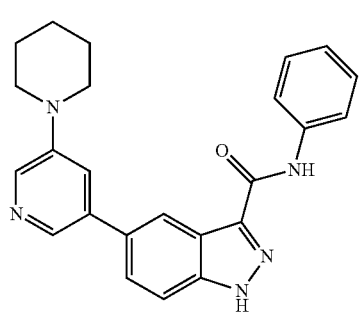 [SMILES: O=C(Nc1ccccc1)c1n[nH]c2ccc(-c3cncc(N4CCCCC4)c3)cc12]
767 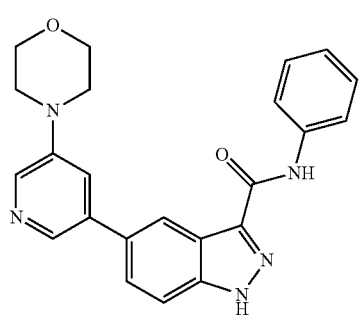
768 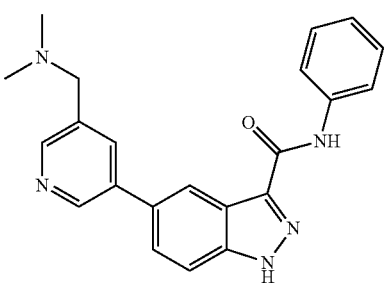 [SMILES: CN(C)Cc1cncc(-c2ccc3[nH]nc(C(=O)Nc4ccccc4)c3c2)c1]

TABLE 1-continued
769 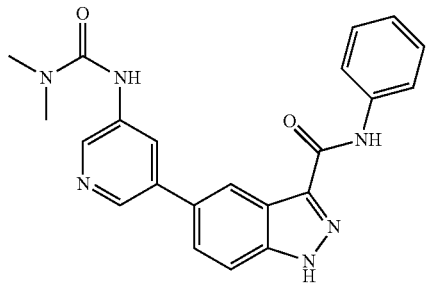 [SMILES: CN(C)C(=O)Nc1cncc(-c2ccc3[nH]nc(C(=O)Nc4ccccc4)c3c2)c1]
770 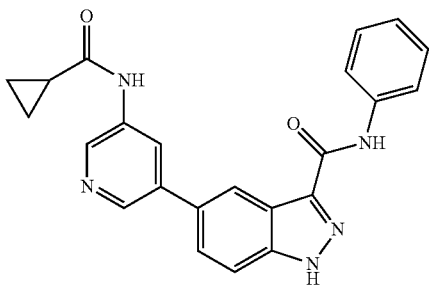 [SMILES: O=C(Nc1ccccc1)c1n[nH]c2ccc(-c3cncc(NC(=O)C4CC4)c3)cc12]
771 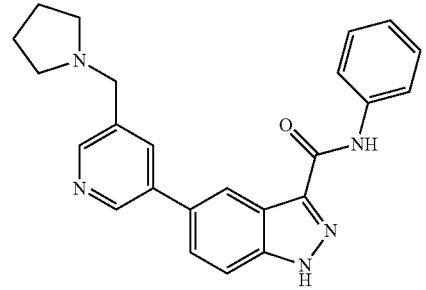 [SMILES: O=C(Nc1ccccc1)c1n[nH]c2ccc(-c3cncc(CN4CCCC4)c3)cc12]
772 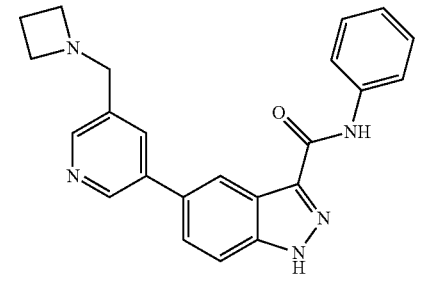 [SMILES: O=C(Nc1ccccc1)c1n[nH]c2ccc(-c3cncc(CN4CCC4)c3)cc12]
773 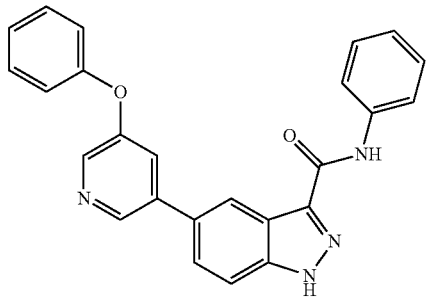 [SMILES: O=C(Nc1ccccc1)c1n[nH]c2ccc(-c3cncc(Oc4ccccc4)c3)cc12]
TABLE 1-continued
774 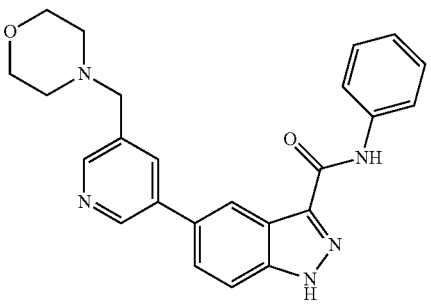 [SMILES: O=C(Nc1ccccc1)c1n[nH]c2ccc(-c3cncc(CN4CCOCC4)c3)cc12]
775 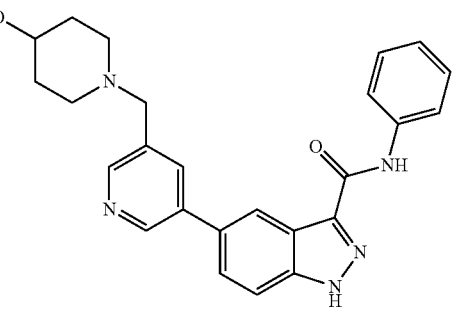
776 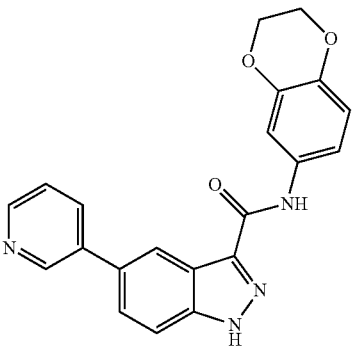 [SMILES: O=C(Nc1ccc2c(c1)OCCO2)c1n[nH]c2ccc(-c3cccnc3)cc12]
777 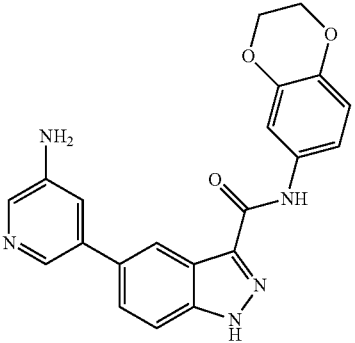 [SMILES: Nc1cncc(-c2ccc3[nH]nc(C(=O)Nc4ccc5c(c4)OCCO5)c3c2)c1]

TABLE 1-continued
| 778 | 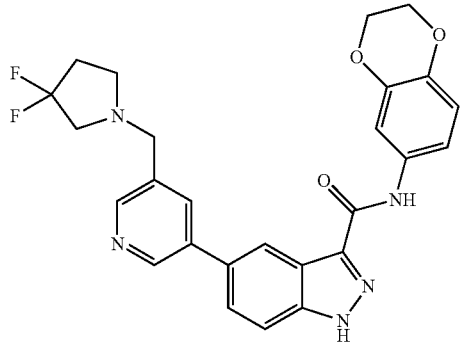 [SMILES: O=C(Nc1ccc2c(c1)OCCO2)c1n[nH]c2ccc(-c3cncc(CN4CCC(F)(F)C4)c3)cc12] |
| --- | --- |
| 779 | 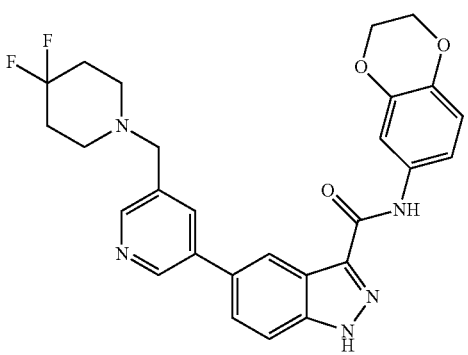 [SMILES: O=C(Nc1ccc2c(c1)OCCO2)c1n[nH]c2ccc(-c3cncc(CN4CCC(F)(F)CC4)c3)cc12] |
| 780 | 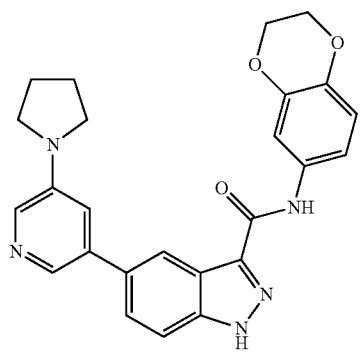 [SMILES: O=C(Nc1ccc2c(c1)OCCO2)c1n[nH]c2ccc(-c3cncc(N4CCCC4)c3)cc12] |
| 781 | 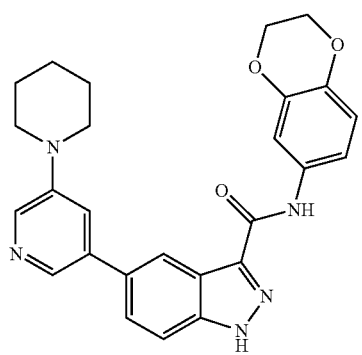 |
TABLE 1-continued
| 782 | 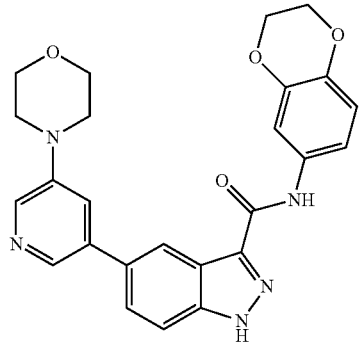 [SMILES: O=C(Nc1ccc2c(c1)OCCO2)c1n[nH]c2ccc(-c3cncc(N4CCOCC4)c3)cc12] |
| --- | --- |
| 783 | 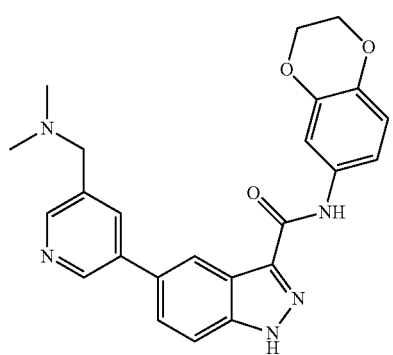 [SMILES: CN(C)Cc1cncc(-c2ccc3[nH]nc(C(=O)Nc4ccc5c(c4)OCCO5)c3c2)c1] |
| 784 | 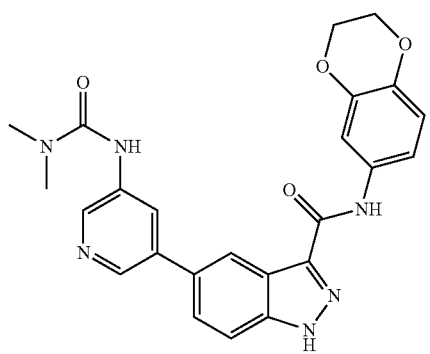 [SMILES: CN(C)C(=O)Nc1cncc(-c2ccc3[nH]nc(C(=O)Nc4ccc5c(c4)OCCO5)c3c2)c1] |
| 785 | 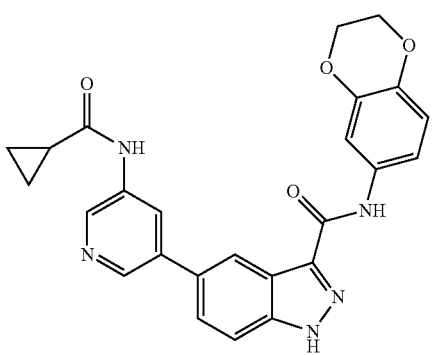 [SMILES: O=C(Nc1ccc2c(c1)OCCO2)c1n[nH]c2ccc(-c3cncc(NC(=O)C4CC4)c3)cc12] |

TABLE 1-continued
786 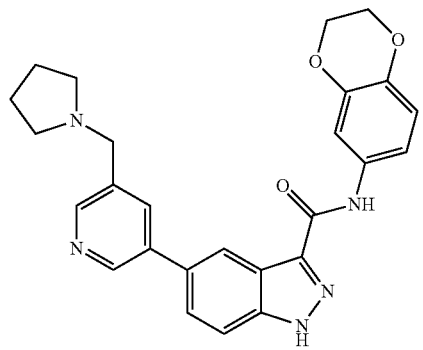 [SMILES: O=C(Nc1ccc2c(c1)OCCO2)c1n[nH]c2ccc(-c3cncc(CN4CCCC4)c3)cc12]
787 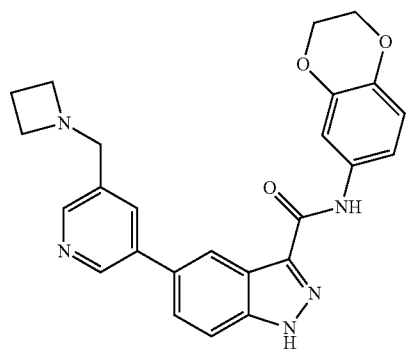 [SMILES: O=C(Nc1ccc2c(c1)OCCO2)c1n[nH]c2ccc(-c3cncc(CN4CCC4)c3)cc12]
788 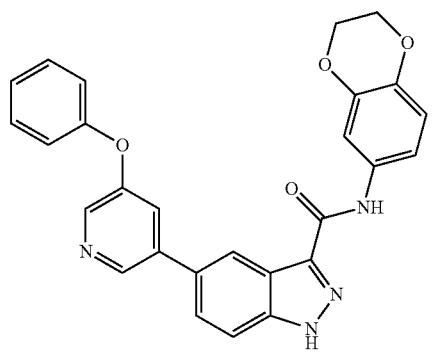 [SMILES: O=C(Nc1ccc2c(c1)OCCO2)c1n[nH]c2ccc(-c3cncc(Oc4ccccc4)c3)cc12]
789 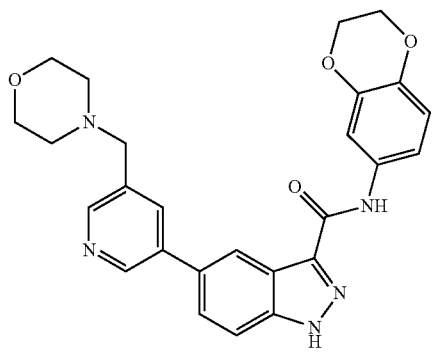 [SMILES: O=C(Nc1ccc2c(c1)OCCO2)c1n[nH]c2ccc(-c3cncc(CN4CCOCC4)c3)cc12]
790 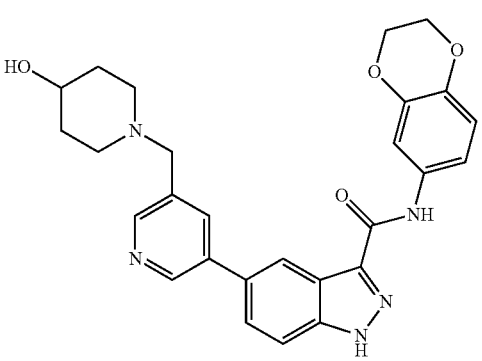 [SMILES: O=C(Nc1ccc2c(c1)OCCO2)c1n[nH]c2ccc(-c3cncc(CN4CCC(O)CC4)c3)cc12]
791 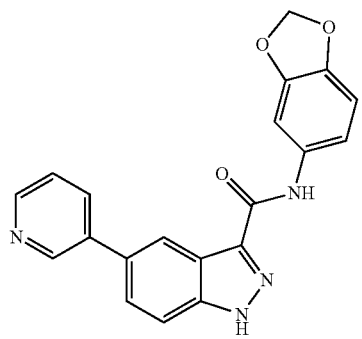 [SMILES: O=C(Nc1ccc2c(c1)OCO2)c1n[nH]c2ccc(-c3cccnc3)cc12]
792 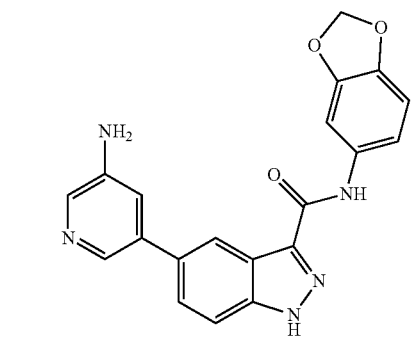 [SMILES: Nc1cncc(-c2ccc3[nH]nc(C(=O)Nc4ccc5c(c4)OCO5)c3c2)c1]
793

TABLE 1-continued
794 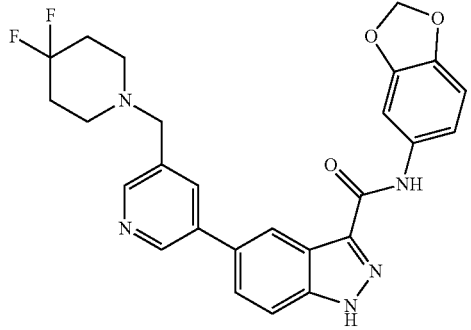 [SMILES: O=C(Nc1ccc2c(c1)OCO2)c1n[nH]c2ccc(-c3cncc(CN4CCC(F)(F)CC4)c3)cc12]
795 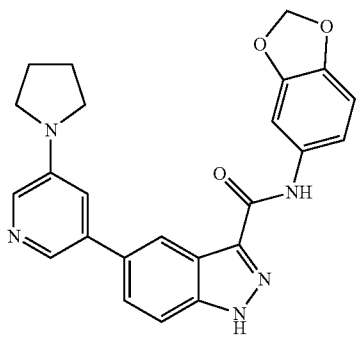 [SMILES: O=C(Nc1ccc2c(c1)OCO2)c1n[nH]c2ccc(-c3cncc(N4CCCC4)c3)cc12]
796 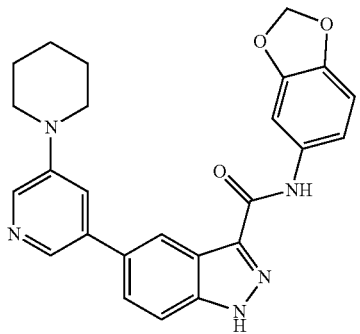
797 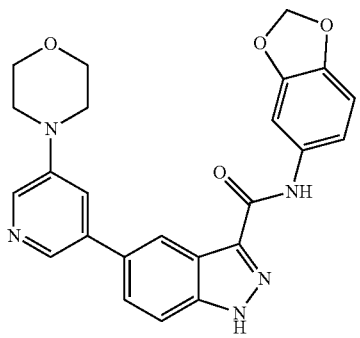 [SMILES: O=C(Nc1ccc2c(c1)OCO2)c1n[nH]c2ccc(-c3cncc(N4CCCCC4)c3)cc12]
TABLE 1-continued
798 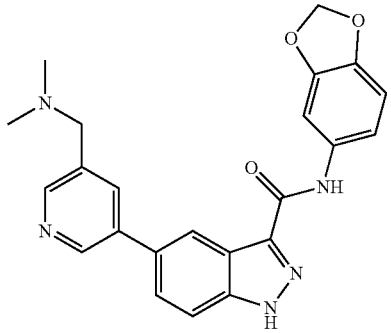 [SMILES: CN(C)Cc1cncc(-c2ccc3[nH]nc(C(=O)Nc4ccc5c(c4)OCO5)c3c2)c1]
799 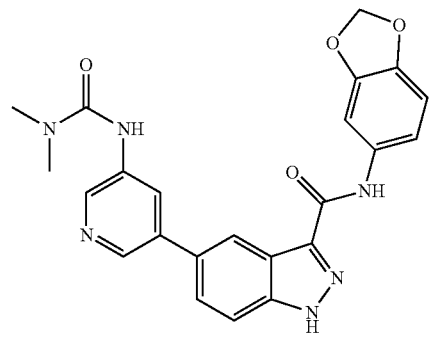 [SMILES: CN(C)C(=O)Nc1cncc(-c2ccc3[nH]nc(C(=O)Nc4ccc5c(c4)OCO5)c3c2)c1]
800 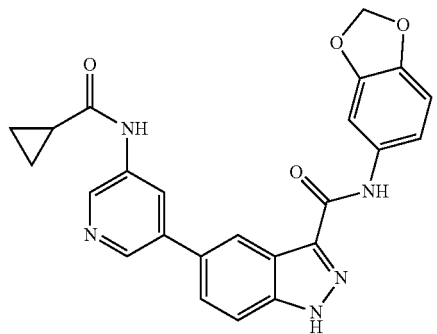 [SMILES: O=C(Nc1ccc2c(c1)OCO2)c1n[nH]c2ccc(-c3cncc(NC(=O)C4CC4)c3)cc12]
801 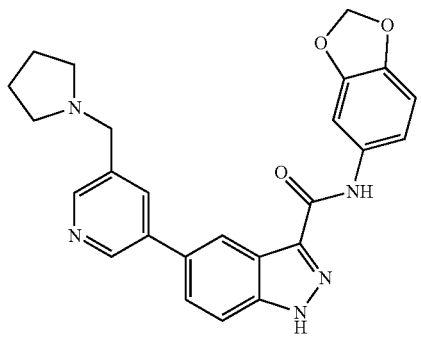 [SMILES: O=C(Nc1ccc2c(c1)OCO2)c1n[nH]c2ccc(-c3cncc(CN4CCCC4)c3)cc12]

TABLE 1-continued
802 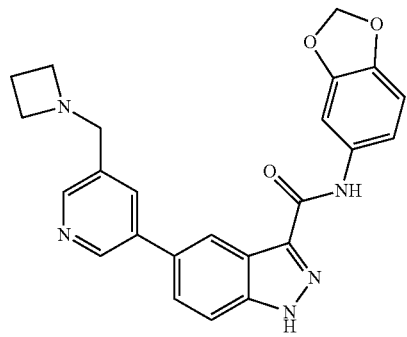 [SMILES: O=C(Nc1ccc2c(c1)OCO2)c1n[nH]c2ccc(-c3cncc(CN4CCC4)c3)cc12]
803 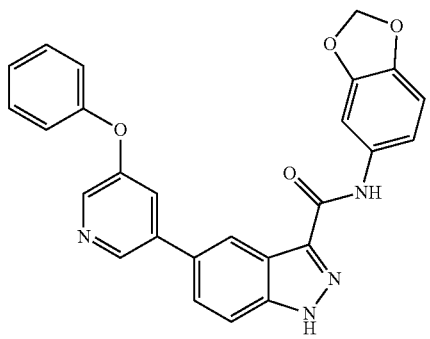 [SMILES: O=C(Nc1ccc2c(c1)OCO2)c1n[nH]c2ccc(-c3cncc(Oc4ccccc4)c3)cc12]
804 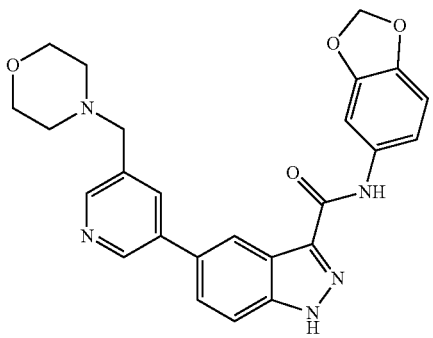 [SMILES: O=C(Nc1ccc2c(c1)OCO2)c1n[nH]c2ccc(-c3cncc(CN4CCOCC4)c3)cc12]
805 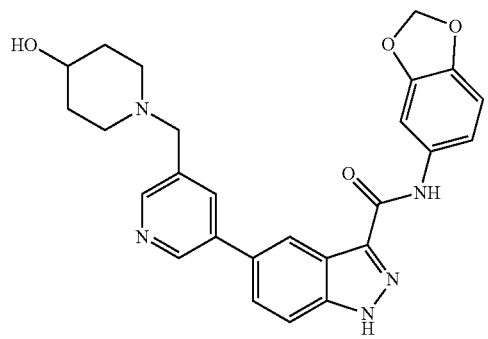 [SMILES: O=C(Nc1ccc2c(c1)OCO2)c1n[nH]c2ccc(-c3cncc(CN4CCC(O)CC4)c3)cc12]
806 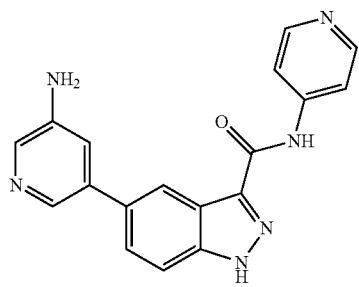 [SMILES: Nc1cncc(-c2ccc3[nH]nc(C(=O)Nc4ccncc4)c3c2)c1]
TABLE 1-continued
807 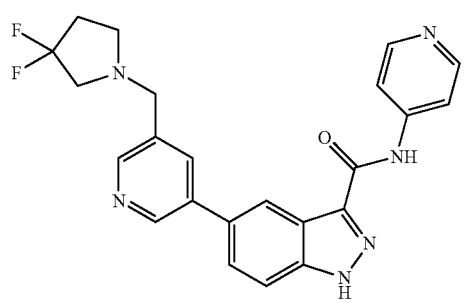 [SMILES: O=C(Nc1ccncc1)c1n[nH]c2ccc(-c3cncc(CN4CCC(F)(F)C4)c3)cc12]
808 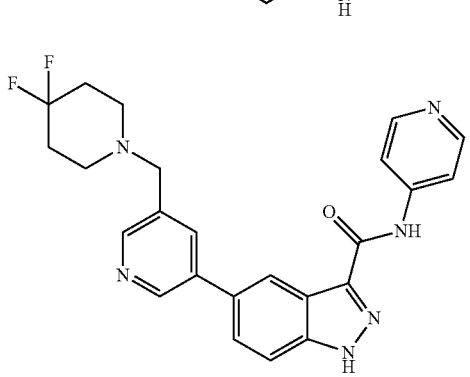
809 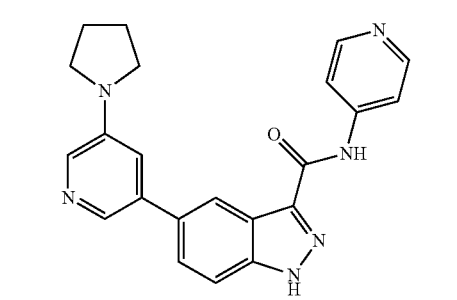 [SMILES: O=C(Nc1ccncc1)c1n[nH]c2ccc(-c3cncc(N4CCCC4)c3)cc12]
810 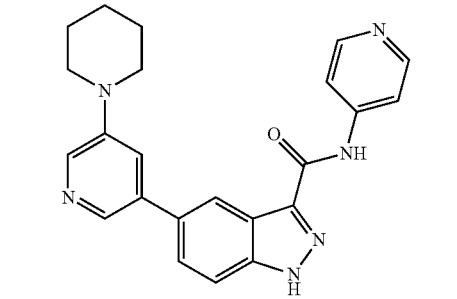 [SMILES: O=C(Nc1ccncc1)c1n[nH]c2ccc(-c3cncc(N4CCCCC4)c3)cc12]
811 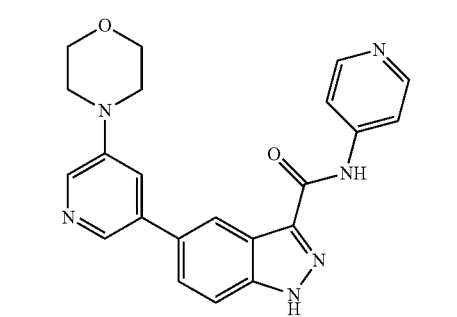 [SMILES: O=C(Nc1ccncc1)c1n[nH]c2ccc(-c3cncc(N4CCOCC4)c3)cc12]

TABLE 1-continued
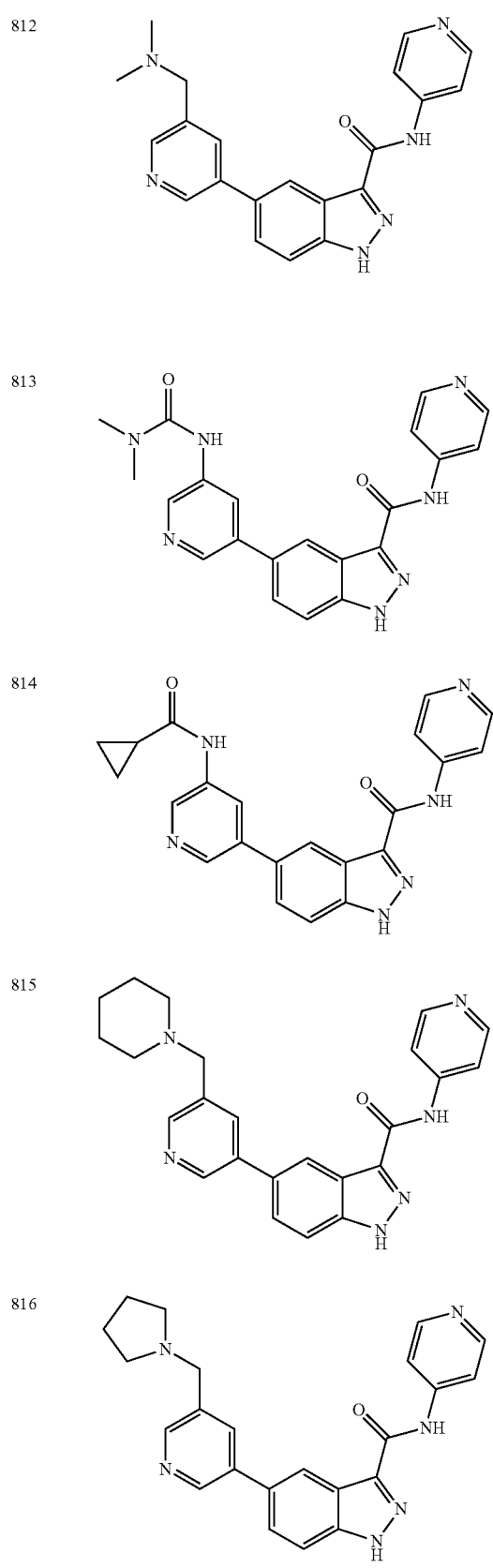
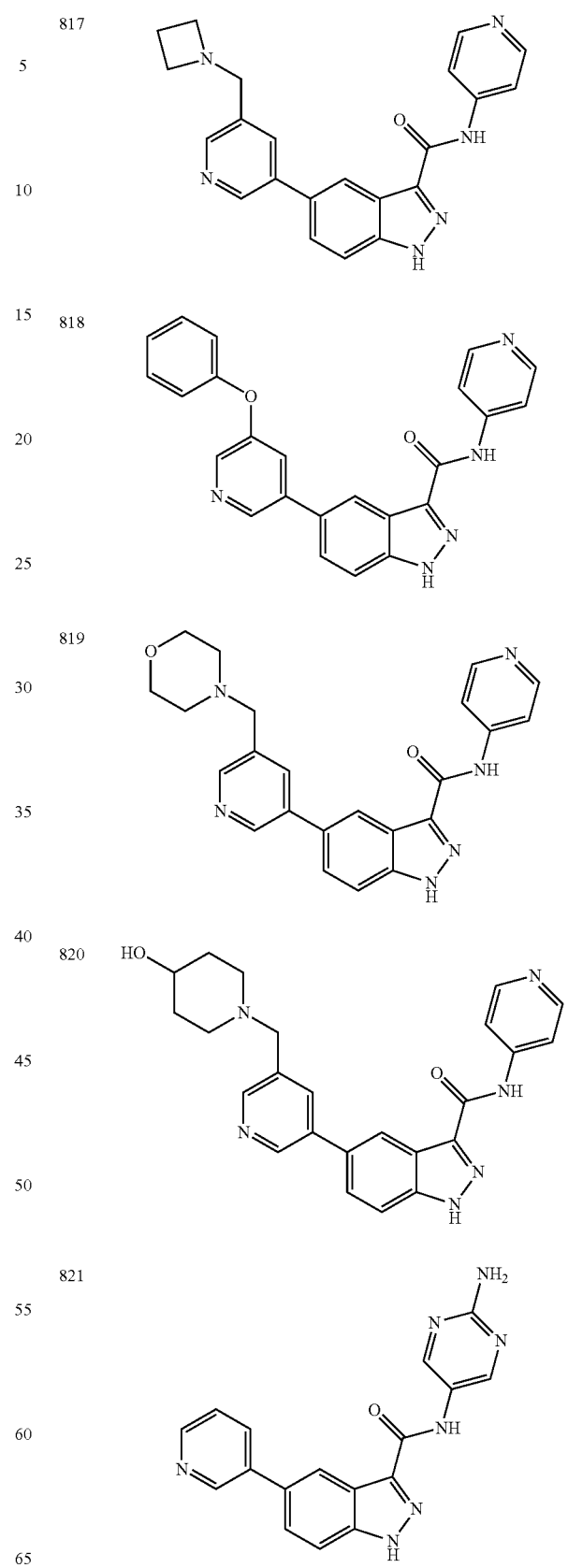

TABLE 1-continued
| 822 | 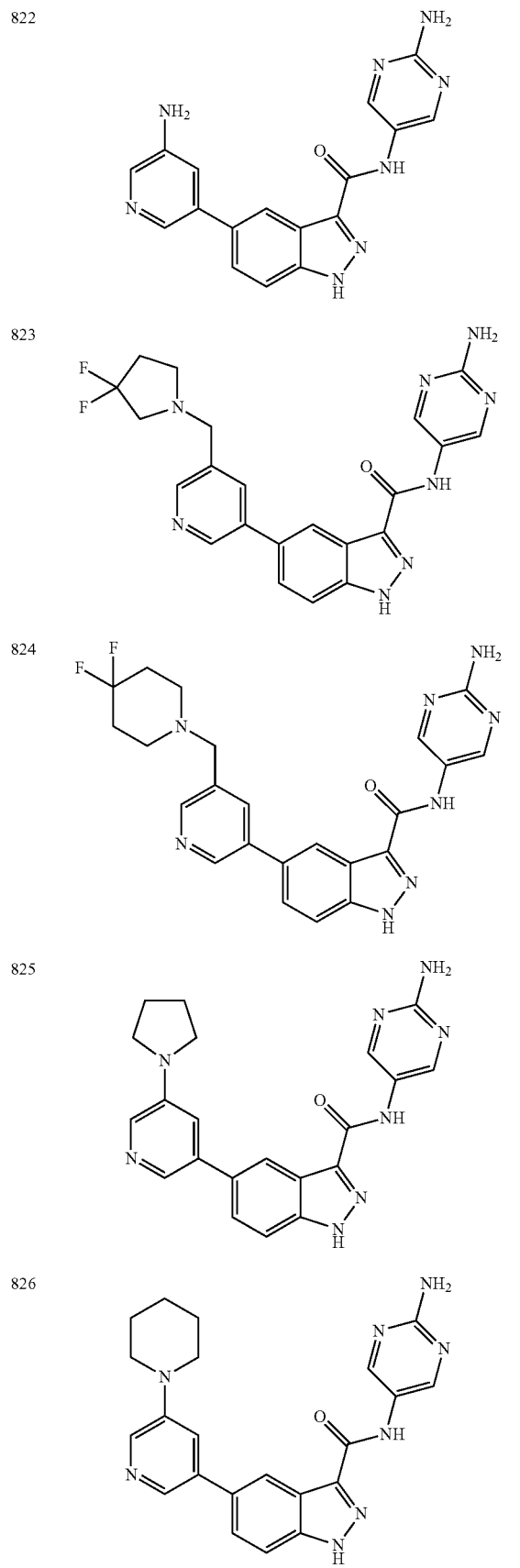 |
| 823 | |
| 824 | |
| 825 | |
| 826 | |
TABLE 1-continued
| 827 | 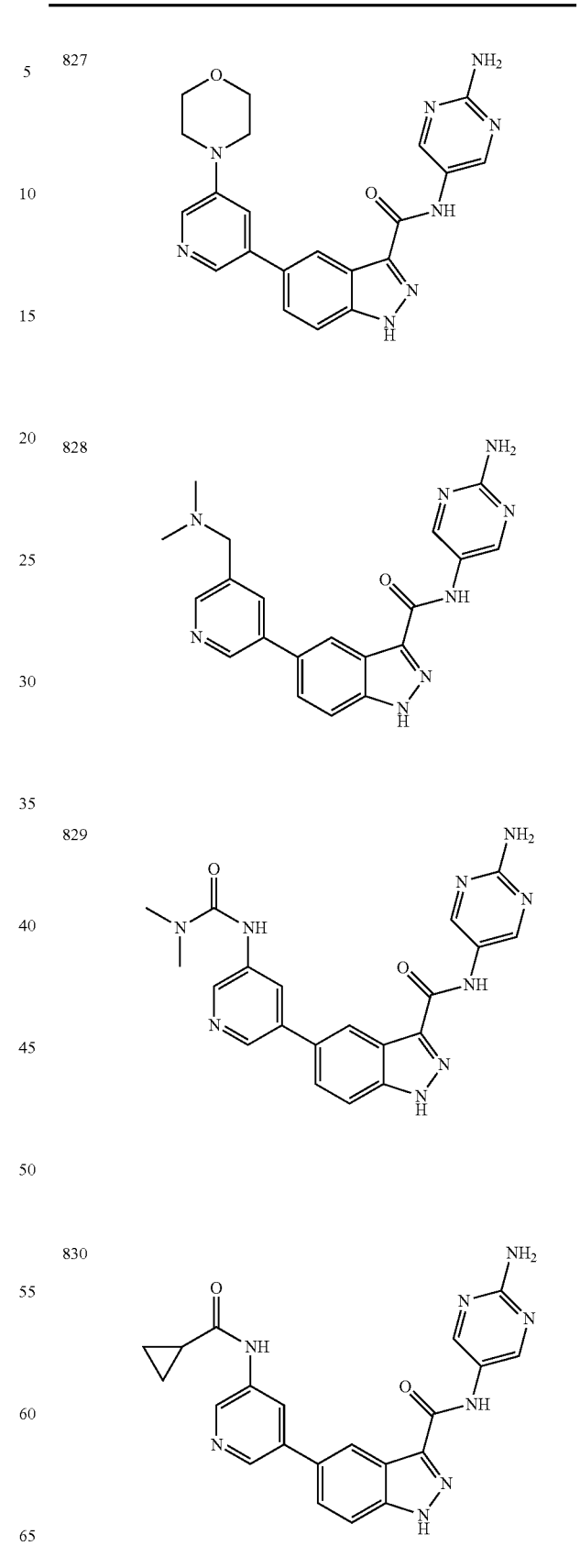 |
| 828 | |
| 829 | |
| 830 | |

TABLE 1-continued
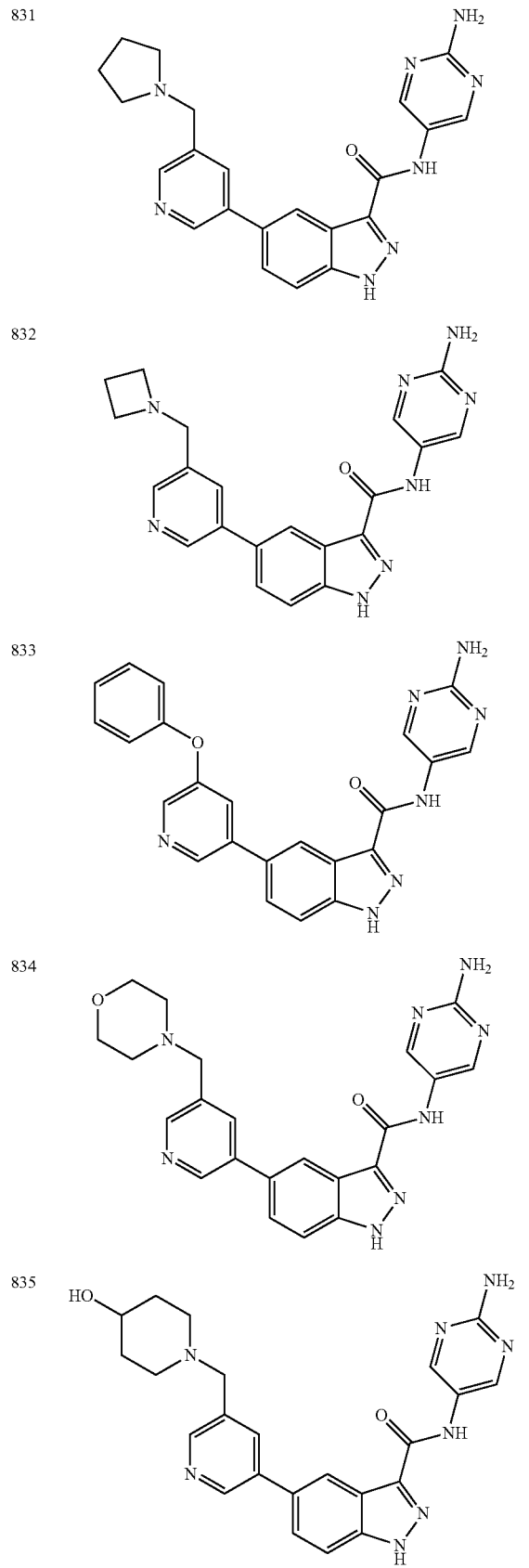
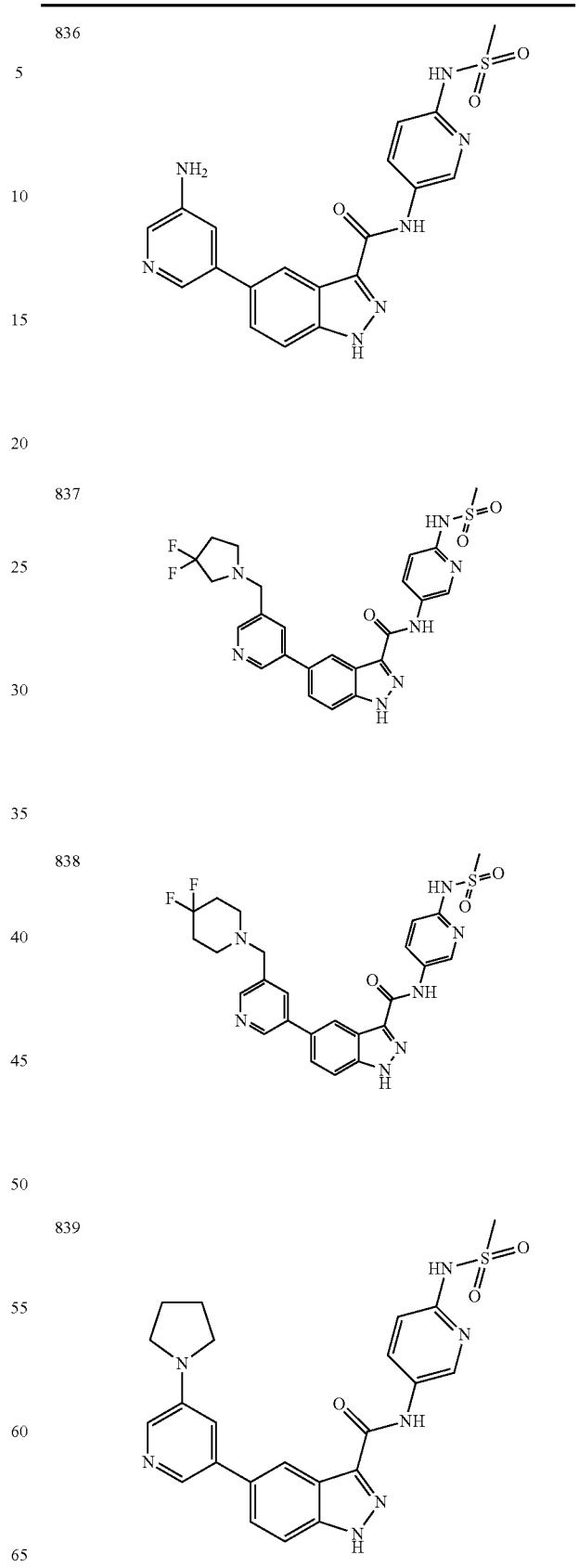

TABLE 1-continued
840
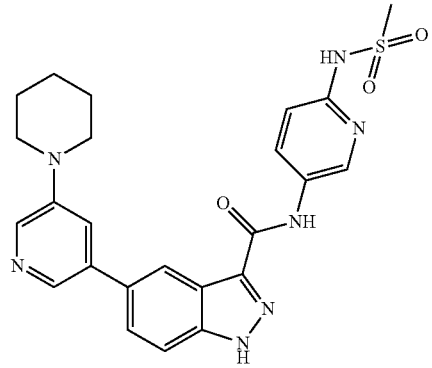 [SMILES: CS(=O)(=O)Nc1ccc(NC(=O)c2n[nH]c3ccc(-c4cncc(N5CCCCC5)c4)cc23)cn1]
841
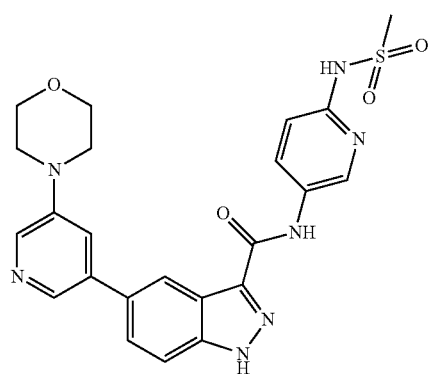 [SMILES: CS(=O)(=O)Nc1ccc(NC(=O)c2n[nH]c3ccc(-c4cncc(N5CCOCC5)c4)cc23)cn1]
842
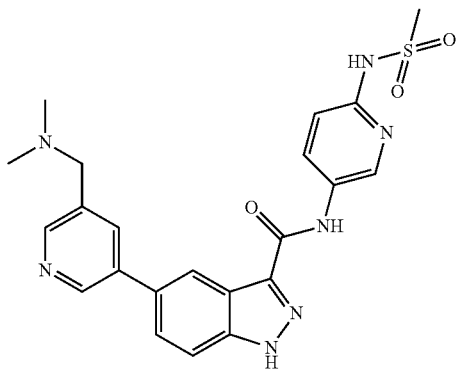 [SMILES: CN(C)Cc1cncc(-c2ccc3[nH]nc(C(=O)Nc4ccc(NS(C)(=O)=O)nc4)c3c2)c1]
843
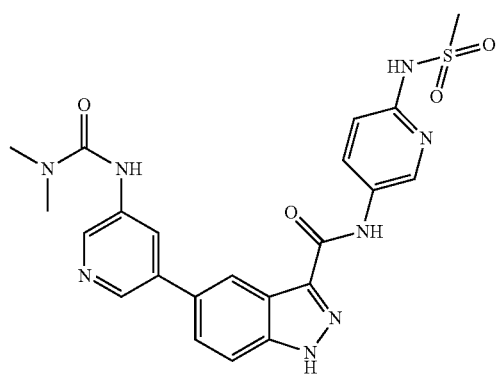 [SMILES: CN(C)C(=O)Nc1cncc(-c2ccc3[nH]nc(C(=O)Nc4ccc(NS(C)(=O)=O)nc4)c3c2)c1]
844
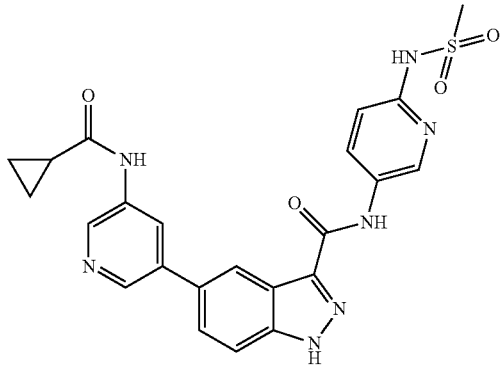 [SMILES: CS(=O)(=O)Nc1ccc(NC(=O)c2n[nH]c3ccc(-c4cncc(NC(=O)C5CC5)c4)cc23)cn1]
845
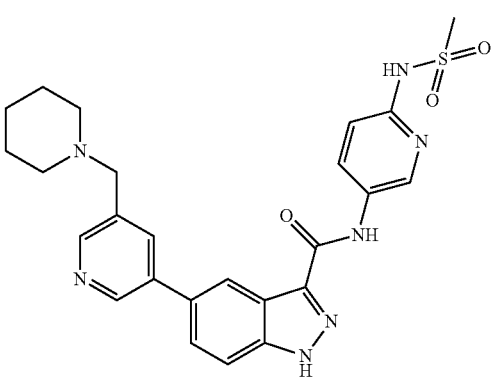 [SMILES: CS(=O)(=O)Nc1ccc(NC(=O)c2n[nH]c3ccc(-c4cncc(CN5CCCCC5)c4)cc23)cn1]
846
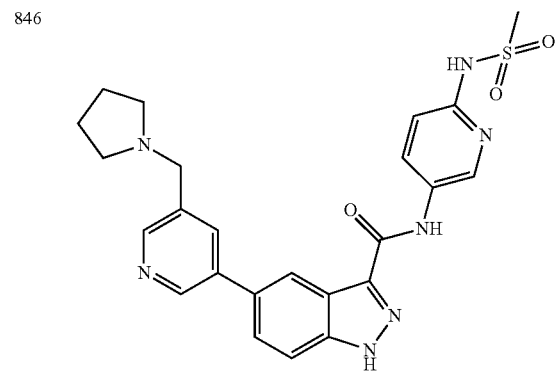
847
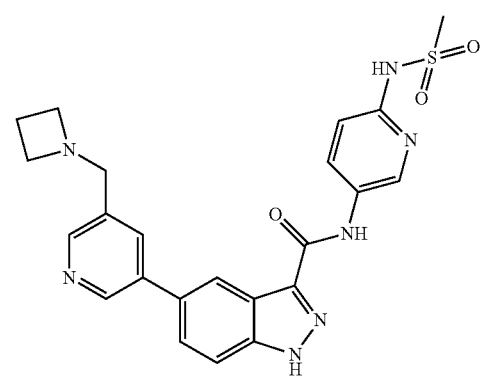 [SMILES: CS(=O)(=O)Nc1ccc(NC(=O)c2n[nH]c3ccc(-c4cncc(CN5CCC5)c4)cc23)cn1]

TABLE 1-continued

848

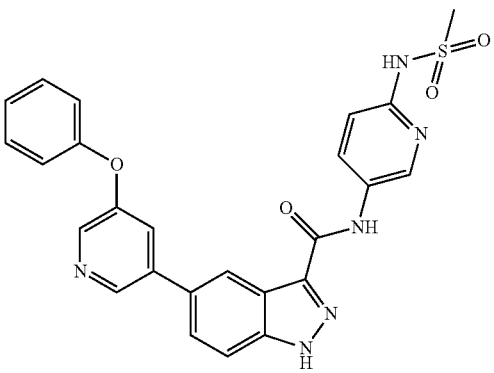 [SMILES: CS(=O)(=O)Nc1ccc(NC(=O)c2n[nH]c3ccc(-c4cncc(Oc5ccccc5)c4)cc23)cn1]

849

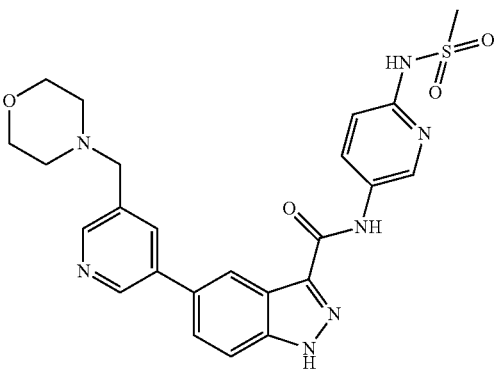 [SMILES: CS(=O)(=O)Nc1ccc(NC(=O)c2n[nH]c3ccc(-c4cncc(CN5CCOCC5)c4)cc23)cn1]

850

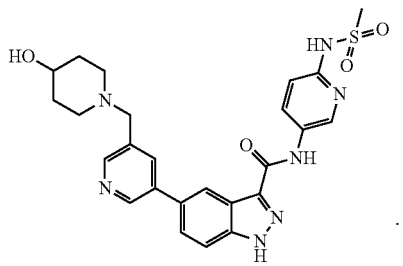 [SMILES: CS(=O)(=O)Nc1ccc(NC(=O)c2n[nH]c3ccc(-c4cncc(CN5CCC(O)CC5)c4)cc23)cn1]

Compound Preparation

The starting materials used in preparing the compounds of the invention are known, made by known methods, or are commercially available. It will be apparent to the skilled artisan that methods for preparing precursors and functionality related to the compounds claimed herein are generally described in the literature. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as *March's Advanced Organic Chemistry*: Reactions, Mechanisms, and Structure 6$^{th}$ Ed., John Wiley & Sons (2007), Carey and Sundberg, *Advanced Organic Chemistry* 5$^{th}$ Ed., Springer (2007), *Comprehensive Organic Transformations: A Guide to Functional Group Transformations*, 2$^{nd}$ Ed., John Wiley & Sons (1999) (incorporated herein by reference in its entirety) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts *Protecting Groups in Organic Synthesis,* 4th Ed., John Wiley & Sons (2007), incorporated herein by reference in its entirety.

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

($^1$H) nuclear magnetic resonance spectra (NMR) were measured in the indicated solvents on a Bruker NMR spectrometer (Avance TM DRX300, 300 MHz for $^1$H or Avance TM DRX500, 500 MHz for $^1$H) or Varian NMR spectrometer (Mercury 400BB, 400 MHz for $^1$H). Peak positions are expressed in parts per million (ppm) downfield from tetramethylsilane. The peak multiplicities are denoted as follows, s, singlet; d, doublet; t, triplet; q, quartet; ABq, AB quartet; quin, quintet; sex, sextet; sep, septet; non, nonet; dd, doublet of doublets; d/ABq, doublet of AB quartet; dt, doublet of triplets; td, triplet of doublets; m, multiplet.

The following abbreviations have the indicated meanings:
brine=saturated aqueous sodium chloride
CDCl$_3$=deuterated chloroform
DCE=dichloroethane
DCM=dichloromethane
DHP=dihydropyran
DIPEA=diisopropylethylamine
DMF=N,N-dimethylformamide
DMSO-d$_6$=deuterated dimethylsulfoxide
ESIMS=electron spray mass spectrometry
EtOAc=ethyl acetate
EtOH=ethanol
h=hour
HATU=2-(1H-7-azabenzotriazol-1-yl)-1,1,3,3-tetramethyluronium hexafluorophosphate
HCl=hydrochloric acid
HOAc=acetic acid
H$_2$SO$_4$=sulfuric acid
iPrOH=iso-propyl alcohol
KOAc=potassium acetate
K$_3$PO$_4$=potassium phosphate
LAH=lithium aluminum hydride
mCPBA=meta-Chloroperoxybenzoic acid
MeOH=methanol
MgSO$_4$=magnesium sulfate
min, =minute MW=microwave
NaBH(OAc)$_3$=sodium triacetoxyborohydride
NaHCO$_3$=sodium bicarbonate
NaHSO$_3$=sodium bisulfite
NaHSO$_4$=sodium bisulfate
NaOH=sodium hydroxide
NH$_4$OH=ammonium hydroxide
NMR=nuclear magnetic resonance
Pd/C=palladium(0) on carbon
PdCl$_2$(dppf)$_2$=1,1'-bis(diphenylphosphino)ferrocene]palladium(II) chloride
Pd$_2$(dba)$_3$=tris(dibenzylideneacetone)dipalladium(0)
Pd(PPh$_3$)$_4$=tetrakis(triphenylphosphine)palladium(0)
PPTS=pyridinium p-toluenesulfonate
r.t.=room temperature
sat$^d$.=saturated
sol$^n$.=solution
Reflx.=heated to reflux
TEA=triethylamine
TFA=trifluoroacetic acid
THF=tetrahydrofuran
TLC=thin layer chromatography
Tr-Cl=trityl chloride or triphenylmethyl chloride The following example schemes are provided for the guidance of the reader, and collectively represent an example method for making the compounds provided herein. Furthermore, other methods for preparing compounds of the invention will be readily apparent to the person of ordinary skill in the art in light of the following reaction schemes and examples. The skilled artisan is thoroughly equipped to prepare these compounds by those methods given the literature and this disclosure. The compound numberings used in the synthetic schemes depicted below are meant for those specific schemes only, and should not be construed as or confused with same numberings in other sections of the application. Unless otherwise indicated, all variables are as defined above.

General Procedures

Compounds of Formula I of the present invention can be prepared as depicted in Scheme 1.

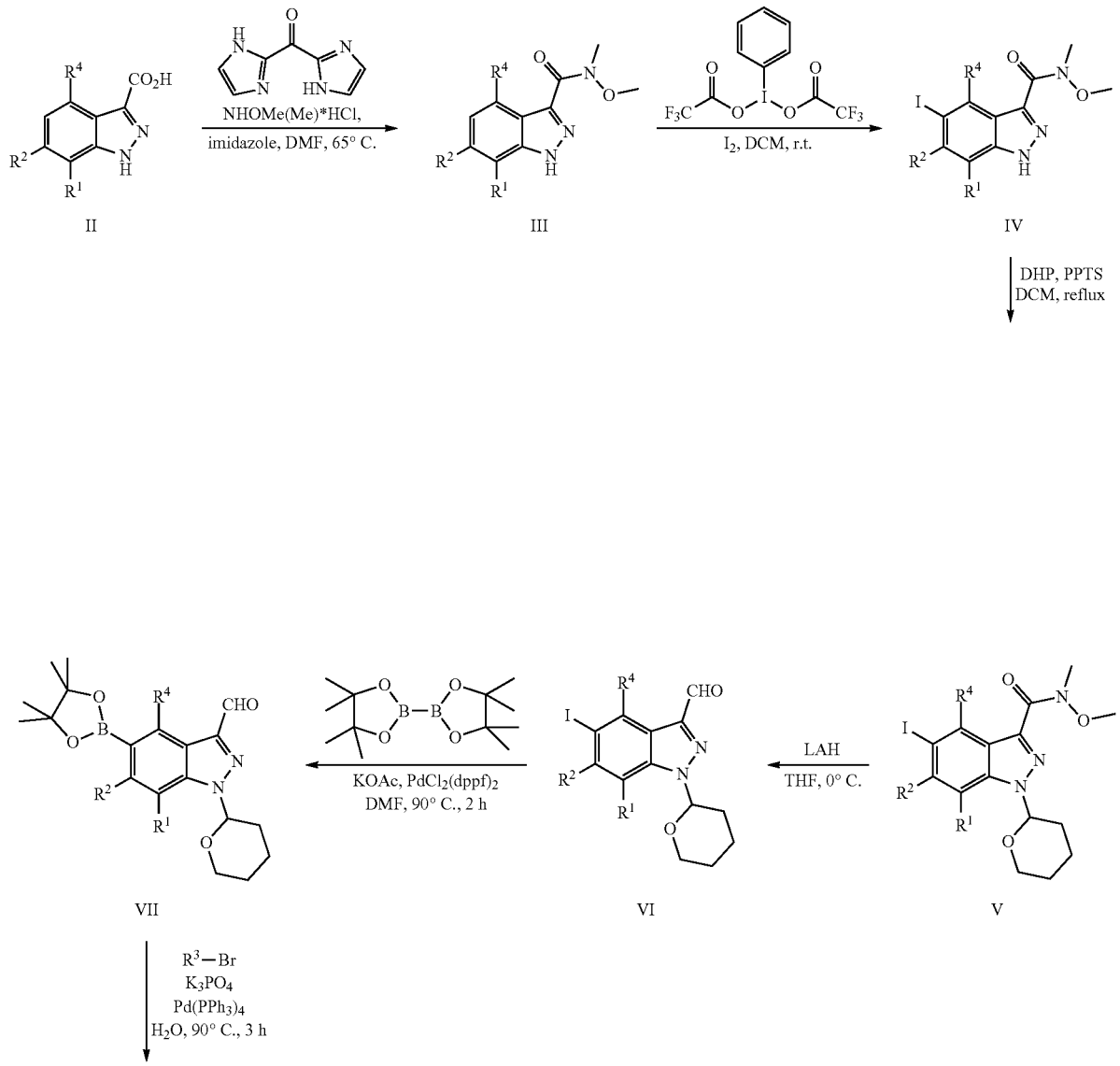

Scheme 1

-continued

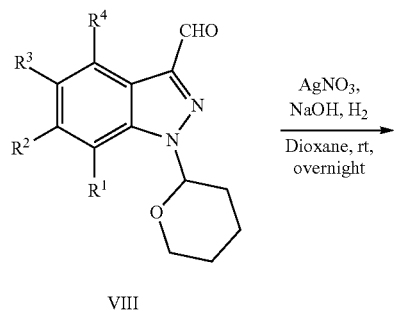 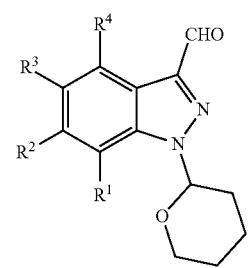 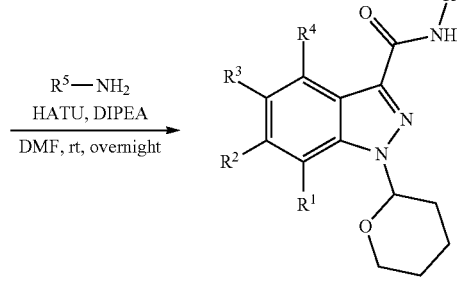

VIII      IX      X

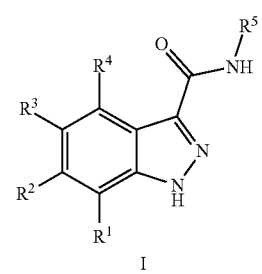

I

Scheme 1 describes a method for preparation of indazole-3-carboxamide derivatives (I) by first forming the Weinreb amide (III) of a 1H-indazole-3-carboxylic acid (II). The Weinreb amide (III) is reacted with (bis(trifluoroacetoxy)iodo)benzene to produce the 5-iodo-1H-indazole-3-carboxylic acid (IV) followed by THP protection of the indazole nitrogen. The Weinreb amide of protected indazole V is reduced to aldehyde VI followed by reaction with bis(pinacolato)diboron to give the pinacol ester (VII). Suzuki coupling with a variety of aromatic and nonaromatic bromides yields the $R^3$ substituted indazole VIII. Oxidation of the aldehyde to the acid (IX) followed by HATU mediated coupling of a variety of amines and sequent deprotection produces the desired indazole-3-carboxamide derivatives (I).

Compounds of Formula I of the present invention can also be prepared as depicted in Scheme 2.

Scheme 2

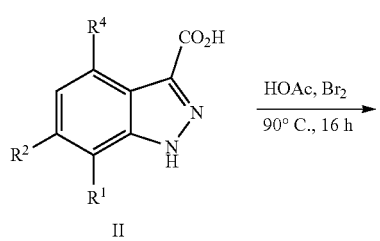 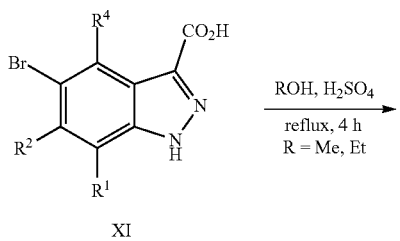 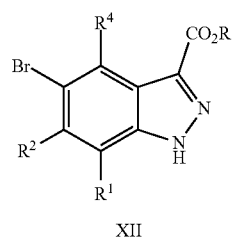

II      XI      XII

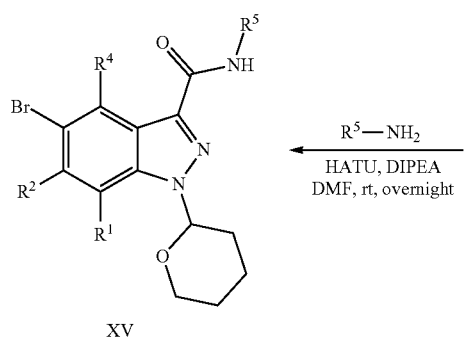

XV

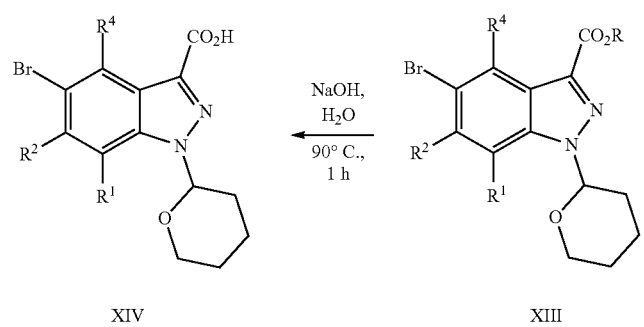

XIV            XIII

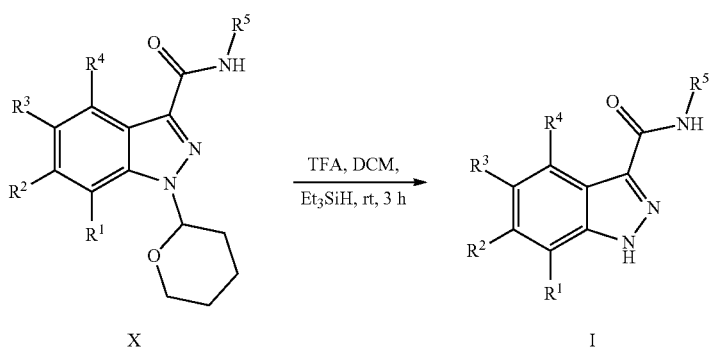

X            I

Scheme 2 describes an alternative method for preparation of indazole-3-carboxamide derivatives (I) by bromination of the indazole 5-position followed by esterification to form ester XII. The indazole nitrogen is THP protected and the ester is hydrolyzed to acid XIV. The acid is coupled with a variety of amines to produce amide XV which is then coupled with a variety of boronic acids (Route 1) to give X. Alternatively, XV can be converted to the boronate ester and then couple to a variety of bromides (Route 2) to yield X. Final deprotection of the indazole nitrogen yields the desired indazole-3-carboxamide derivatives (I).

Compounds of Formula I of the present invention can also be prepared as depicted in Scheme 3.

Scheme 3

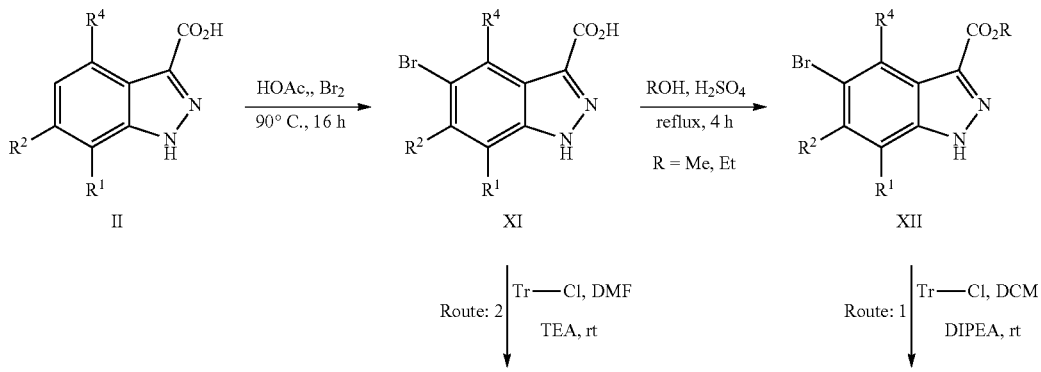

II            XI            XII

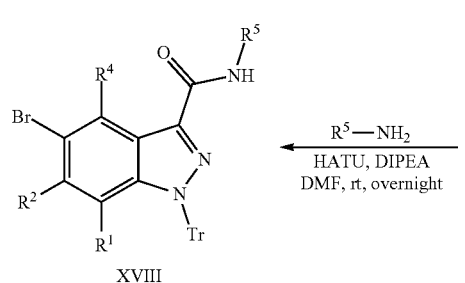
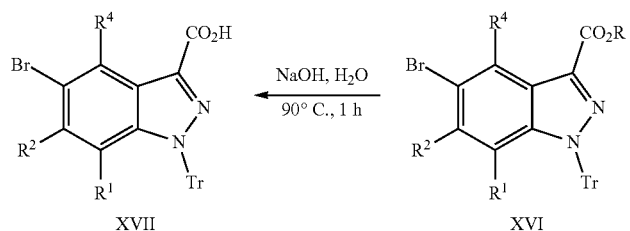
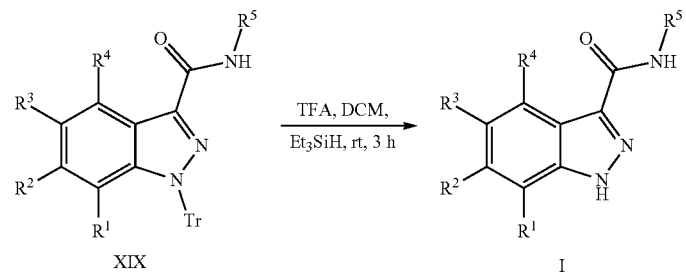

Scheme 3 describes another alternative method for preparation of indazole-3-carboxamide derivatives (I) by bromination of the indazole 5-position followed by either Route 1: esterification to form ester XII, then trityl protection of the indazole nitrogen and then finally hydrolyzed of the ester to acid XVII; or Route 2: trityl protection of the indazole nitrogen directly to acid XVII. The acid is coupled with a variety of amines to produce amide XVIII which is then coupled with a variety of boronic acids (Route 3) to give XIX. Alternatively, XVIII can be converted to the boronate ester and then couple to a variety of bromides (Route 4) to yield XIX. Final deprotection of the indazole nitrogen yields the desired indazole-3-carboxamide derivatives (I).

ILLUSTRATIVE COMPOUND EXAMPLES

Preparation of Intermediate 3-(5-bromopyridin-3-yl)-1,1-dimethylurea (XXII) is Depicted Below in Scheme 4

Scheme 4

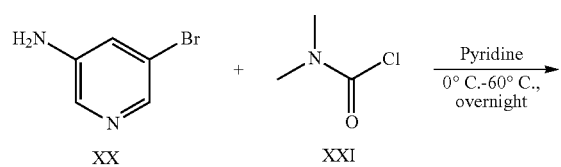

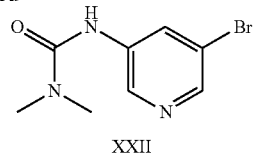

Step 1

3-Amino-5-bromo pyridine (XX) (1.0 g, 5.78 mmol) was dissolved in pyridine and cooled to 0° C. before adding dimethyl carbamyl chloride (XXI) (0.683 g, 6.35 mmol). The reaction mixture was stirred at room temperature for 2 h and then heated overnight at 60° C. under argon. The solution was cooled to room temperature, poured into ice water and extracted with EtOAc. The organic extract was dried over MgSO$_4$, filtered and concentrated to a residue to afford 3-(5-bromopyridin-3-yl)-1,1-dimethylurea (XXII) as a brown solid, (1.24 g, 5.09 mmol, 88% yield). $^1$H NMR (DMSO-d$_6$) δ ppm 8.67-8.64 (m, 2H), 8.23 (d, J=7.8 Hz, 1H), 2.93 (s, 6H); ESIMS found for C$_8$H$_{10}$BrN$_3$O m/z 245.05 (M+H).

The following intermediates were prepared in accordance with the procedure described in the above Scheme 4.

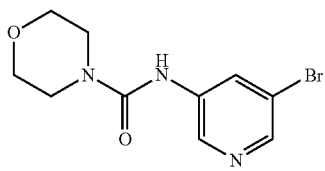

N-(5-bromopyridin-3-yl)morpholine-4-carboxamide (XXIII): Tan solid (0.82 g, 48%). $^1$H NMR (DMSO-$d_6$) 3.43-3.45 (m, 4H), 3.60-3.62 (m, 4H), 8.21 (t, J=2.0 Hz, 1H), 8.26 (d, J=2.0 Hz, 1H), 8.62 (d, J=2.2 Hz, 1H), 8.91 (s, 1H); ESIMS found for $C_{10}H_{12}BrN_3O_2$ m/z 286 (M+H).

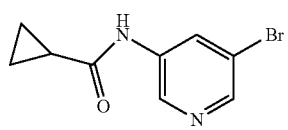

N-(5-bromopyridin-3-yl)cyclopropanecarboxamide (XXIV): Off white solid, (83% yield), $^1$H NMR (CDCl$_3$, 400 MHz) δ ppm 8.46-8.39 (m, 3H), 7.54 (bs, 1H), 1.56-1.50 (m, 1H), 1.13-1.07 (m, 2H), 0.96-0.90 (m, 2H); ESIMS found for $C_9H_9BrN_2O$ m/z 240.85 (M+H).

Preparation of Intermediate (XXVI) is Depicted Below in Scheme 5

Scheme 5

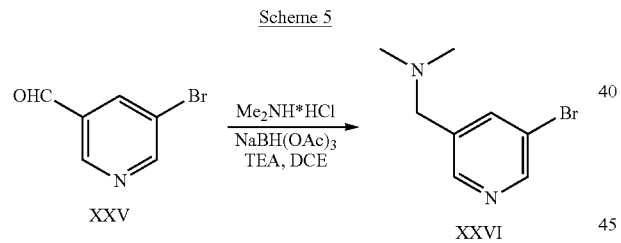

Step 1

To a solution of 5-bromonicotinaldehyde (XXV) (5.0 g, 26.9 mmol) in DCE (108 mL) was added dimethylamine-HCl (4.39 g, 53.8 mmol) and TEA (7.5 g, 53.8 mmol). The reaction was stirred at room temperature for 1 h. NaBH(OAc)$_3$ was added and the reaction was stirred overnight at room temperature. The reaction was diluted with DCM and sat. aq. NaHCO$_3$. The organic layer was separated, washed with water, brine, dried and concentrated under vacuum to produce 1-(5-bromopyridin-3-yl)-N,N-dimethylmethanamine (XXVI) as a brown liquid (92.6% yield). $^1$H NMR (CDCl$_3$) δ ppm 2.15 (s, 6H), 3.43 (s, 2H), 7.94 (s, 1H), 8.47 (d, J=2 Hz, 1H), 8.59 (d, J=3 Hz, 1H); ESIMS found for $C_8H_{11}BrN_2$ m/z 215 ($M^{Br79}$+H) and 217 ($M^{Br81}$+H).

The following intermediates were prepared in accordance with the procedure described in the above Scheme 5.

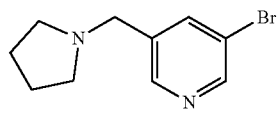

3-Bromo-5-(pyrrolidin-1-ylmethyl)pyridine (XXVII): Golden liquid (1.35 g, 97% yield). $^1$H NMR (DMSO-$d_6$) 1.68-1.71 (m, 4H), 2.42-2.44 (m, 4H), 3.60 (s, 2H), 7.96 (s, 1H), 8.48 (d, J=2 Hz, 1H), 8.58 (d, J=3 Hz, 1H); ESIMS found for $C_{10}H_{13}BrN_2$ m/z 242 (M+H).

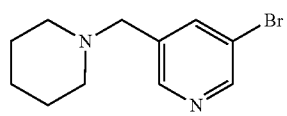

3-Bromo-5-(piperidin-1-ylmethyl)pyridine (XXVIII): Brown liquid (13.1 g, 94% yield). $^1$H NMR (DMSO-$d_6$) 1.36-1.39 (m, 2H), 1.46-1.51 (m, 4H), 2.31-2.32 (m, 4H), 3.46 (s, 2H), 7.94 (s, 1H), 8.47 (d, J=2 Hz, 1H), 8.58 (d, J=3 Hz, 1H); ESIMS found for $C_{11}H_{15}BrN_2$ m/z 257 (M+H).

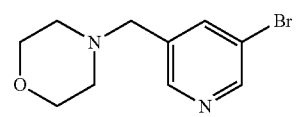

4-((5-Bromopyridin-3-yl)methyl)morpholine (XXIX): Brown oil (1.02 g, 35.6% yield). ESIMS found for $C_{10}H_{13}BrN_2O$ m/z 258 (M+H).

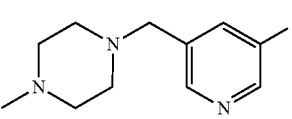

1-((5-Bromopyridin-3-yl)methyl)-4-methylpiperazine (XXX): Brown oil (0.93 g, 64% yield). $^1$H NMR (DMSO-$d_6$) 2.14 (s, 3H), 2.27-2.37 (m, 8H), 3.49 (s, 2H), 7.95 (s, 1H), 8.47 (d, J=1.7 Hz, 1H), 8.59 (d, J=2.2 Hz, 1H); ESIMS found for $C_{11}H_{16}BrN_3$ m/z 272 (M+H).

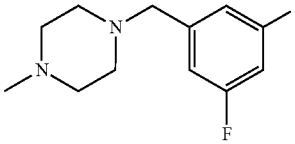

1-(3-Bromo-5-fluorobenzyl)-4-methylpiperazine (XXXI): Light yellow oil (2.07 g, 68% yield). $^1$H NMR (DMSO-$d_6$) 2.14 (s, 3H), 2.28-2.40 (m, 8H), 3.46 (s, 2H), 7.15-7.17 (m, 1H), 7.35 (s, 1H), 7.40-7.42 (m, 1H); ESIMS found for $C_{12}H_{16}BrFN_2$ m/z 288 (M+H).

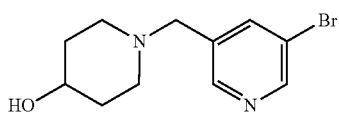

1-(5-Bromopyridin-3-yl)piperidin-4-ol (XXXII): Brown oil (2.15 g, 7.93 mmol, 72.7% yield). $^1$H NMR (DMSO-$d_6$) 1.34-1.41 (m, 2H), 1.67-1.71 (m, 2H), 2.03-2.07 (m, 2H), 2.62-2.64 (m, 2H), 3.42-3.46 (m, 1H), 3.47 (s, 2H), 4.55 (d, J=4.2 Hz, 1H), 7.93-7.94 (m, 1H), 8.46 (d, J=1.6 Hz, 1H), 8.58 (d, J=2.2 Hz, 1H); ESIMS found for $C_{11}H_{15}BrN_2O$ m/z 272 (M+H).

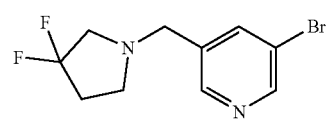

3-Bromo-5-((3,3-difluoropyrrolidin-1-yl)methyl)pyridine (XXXIII): Brown liquid (7.38 g, 26.64 mmol, 94.9% yield). $^1$H NMR (DMSO-$d_6$) 2.21-2.30 (m, 2H), 2.70 (t, J=7 Hz, 2H), 2.89 (t, J=13 Hz, 2H), 3.66 (s, 2H), 7.95-7.98 (m, 1H), 8.57 (d, J=1.7 Hz, 1H), 8.61 (d, J=2.2 Hz, 1H); ESIMS found for $C_{10}H_{11}BrF_2N_2$ m/z 276 (M+H).

Preparation of 3-benzyl-5-bromopyridine (XXXVI) is Depicted Below in SCHEME 6

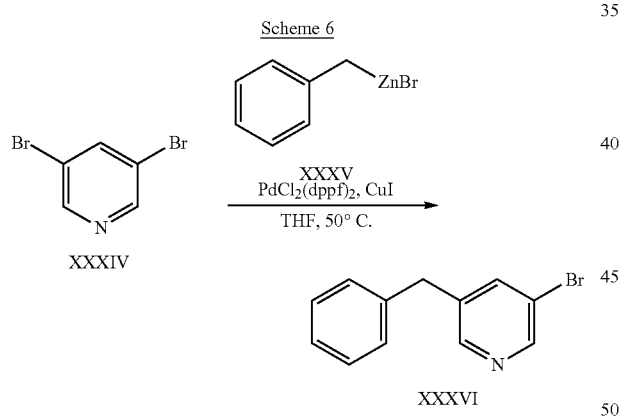

Step 1

To a solution of 3,5-dibromopyridine (XXXIV) (1.03 g, 4.36 mmol) in THF (7 mL) under argon was added CuI (50 mg, 0.26 mmol) and PdCl$_2$(dppf)$_2$ (178 mg, 0.22 mmol). Benzylzinc(II) bromide (XXXV) (0.5M in THF) (13.09 mL, 6.55 mmol) was slowly added by syringe. The reaction was heated at 50° C. over the weekend. The reaction was quenched with water and extracted with EtOAc. The EtOAc was separated, washed with water, brine, dried over MgSO$_4$ and concentrated under vacuum. The residue was purified on a silica gel column (100% hexanes→5:95 EtOAc:hexanes) to afford 3-benzyl-5-bromopyridine (XXXVI) (0.614 g, 2.47 mmol, 57% yield) as a light brown oil. $^1$H NMR (DMSO-$d_6$) δ ppm 3.98 (s, 2H), 7.19-7.23 (m, 1H), 7.27-7.32 (m, 4H), 7.92-7.93 (m, 1H), 8.51 (d, J=2 Hz, 1H), 8.54 (d, J=3 Hz, 1H); ESIMS found for $C_{12}H_{10}BrN$ m/z 248 (M+H).

Preparation of 3-bromo-5-phenoxypyridine (XXXIX) is Depicted Below in Scheme 7

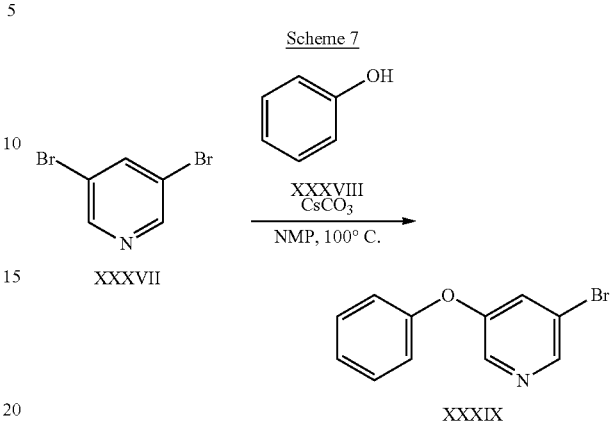

Step 1

To a solution of 3,5-dibromopyridine (XXXVII) (1.00 g, 4.24 mmol) in NMP (11 mL) was added phenol (XXXVIII) (398 mg, 4.24 mmol) and CsCO$_3$ (1.38 g, 4.24 mmol). The reaction was heated at 100° C. over the weekend. The reaction was then partitioned between Et$_2$O/water. The Et$_2$O was separated, washed with 2× water, brine, dried over MgSO$_4$ and concentrated under vacuum. The residue was purified on a silica gel column (100% hexanes 2:98 EtOAc:hexanes) to afford 3-bromo-5-phenoxypyridine (XXXIX) (535 mg, 2.14 mmol, 50% yield) as a clear oil. $^1$H NMR (DMSO-$d_6$) δ ppm 7.13-7.15 (m, 2H), 7.23-7.26 (m, 1H), 7.43-7.46 (m, 2H), 7.69-7.70 (m, 1H), 8.37 (d, J=3 Hz, 1H), 8.49 (d, J=2 Hz, 1H); ESIMS found for $C_{11}H_8BrNO$ m/z 250 (M+H).

Preparation of 1-(5-bromopyridin-3-yl)-4-methylpiperazine (XL) is Depicted Below in Scheme 8

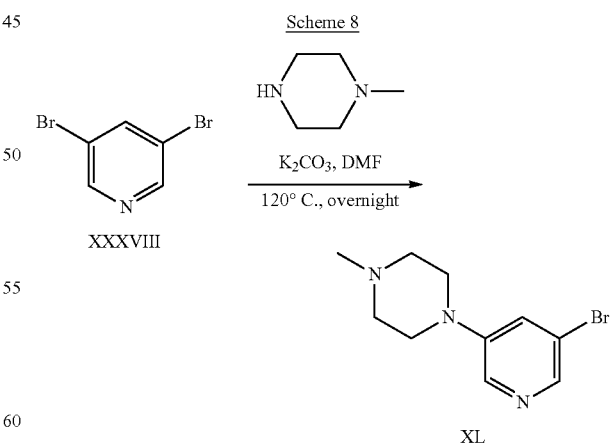

Step 1

To a solution of 3,5-dibromopyridine (XXXVIII) (2.90 g, 12.24 mmol) in dry DMF (20 mL) was added 1-methylpiperazine (2.987 mL, 26.93 mmol) and K$_2$CO$_3$ (5.58 g, 40.39 mmol). The reaction was heated at 120° C. overnight. An additional portion of 1-methylpiperazine (6 mL) was added and heating was continued for another 24 h. The reaction was poured into ice water and filtered. The filtrate was extracted with 66% MeOH/CHCl₃. The organic layer was dried over MgSO4, filtered and concentrated under vacuum to yield 1-(5-bromopyridin-3-yl)-4-methylpiperazine (XL) as a brown viscous oil (2.49 g, 9.76 mmol, 79.8% yield). ESIMS found for $C_{10}H_{14}BrN_3$ m/z 256 (M+H).

The following intermediate was prepared in accordance with the procedure described in the above Scheme 8.

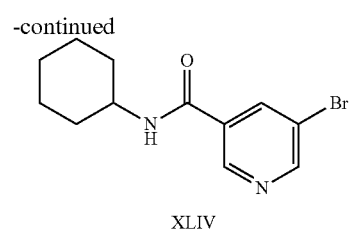

XLIV

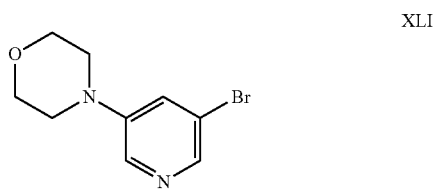 [SMILES: Brc1cncc(N2CCOCC2)c1]

XLI 4-(5-Bromopyridin-3-yl)morpholine (XLI): Yellow solid (1.12 g, 4.61 mmol, 64.9% yield). ESIMS found for $C_9H_{11}BrN_2O$ m/z 244.1 (M+H).

Preparation of 5-bromo-N-cyclohexylnicotinamide (XLIV) is Depicted Below in Scheme 9

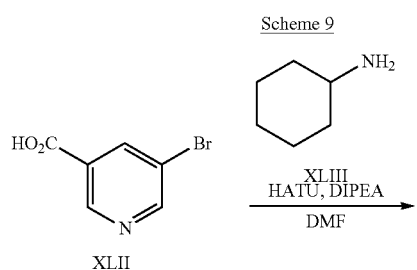

Step 1

To a solution of 5-bromonicotinic acid (XLII) (500 mg, 2.49 mmol) in DMF (8 mL) was added cyclohexanamine (XLIII) (247 mg, 2.49 mmol) and DIPEA (643 mg, 4.98 mmol). The reaction was cooled at 0° C. before adding HATU (947 mg, 2.49 mmol). The reaction was warmed to room temperature and stirred for 4 hrs. The reaction was diluted with EtOAc, washed with 2×water, brine, dried over MgSO₄ and concentrated under vacuum to yield crude 5-bromo-N-cyclohexylnicotinamide (XLIV). The product was used without further purification. ESIMS found for $C_{12}H_{15}BrN_2O$ m/z 283 (M+H).

Preparation of 3-bromo-5-(((2R,6S)-2,6-dimethylpiperidin-1-yl)methyl)pyridine (XLVII) is Depicted Below in Scheme 10

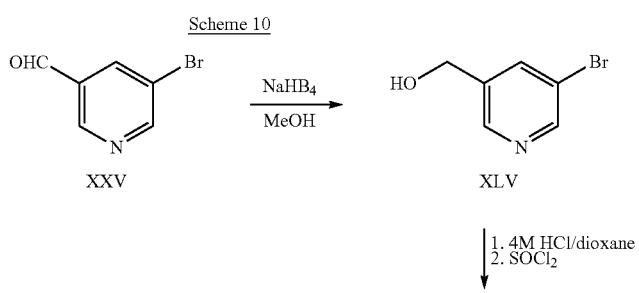

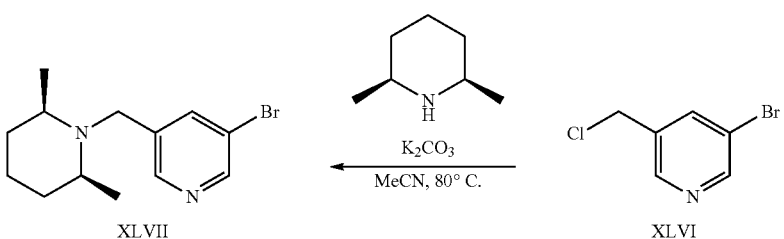

Step 1

To a solution of 5-bromonicotinaldehyde (XXV) (2.05 g, 11.0 mmol) in MeOH (85 mL) was added NaBH$_4$ (832 mg, 21.99 mmol). The reaction was stirred at room temperature for 1 h. The reaction was quenched with saturated aqueous NH$_4$Cl (5 mL). The reaction was concentrated under vacuum and the residue was partitioned between saturated aqueous NH$_4$Cl/EtOAc. The organic layer was separated, washed with water, brine, dried over MgSO$_4$ and concentrated under vacuum to yield crude (5-bromopyridin-3-yl)methanol (XLV) as a golden oil (1.54 g, 8.2 mmol, 74% yield). The product was used without further purification. ESIMS found for C$_6$H$_6$BrNO m/z 188 (M+H).

Step 2

(5-Bromopyridin-3-yl)methanol (XLV) (1.54 g, 8.2 mmol) was treated with 4M HCl in dioxane (10 mL) at 0° C. and then evaporated. The residue was dissolved in SOCl$_2$ (4 mL) and refluxed for 2 hrs. The SOCl$_2$ was removed and the residue was triturated with hexane to produce HCl salt of 3-bromo-5-(chloromethyl)pyridine (XLVI) as a brown solid (1.30 g, 5.4 mmol, 66% yield). The product was used without further purification. ESIMS found for C$_6$H$_5$BrClN m/z 206 (M+H).

Step 3

To a solution of 3-bromo-5-(chloromethyl)pyridine (XLVI) (1.17 g, 4.8 mmol) in MeCN (0.2 mL) and (2S,6R)-2,6-dimethylpiperidine (2.6 mL, 19.3 mmol) was added K$_2$CO$_3$ (667 mg, 4.8 mmol). The reaction was refluxed for 5 hrs. TLC showed the presence of starting material so additional (2S,6R)-2,6-dimethylpiperidine (2.0 mL, 14.8 mmol) was added and the reaction was refluxed for an additional 5 hrs. The solvent was removed and the residue was partitioned between EtOAc/water. The EtOAc was separated and washed with brine, dried over MgSO$_4$ and concentrated under vacuum. The residue was purified on a silica gel column (100% hexanes→6:94 EtOAc:hexanes) to afford 3-bromo-5-(((2R,6S)-2,6-dimethylpiperidin-1-yl)methyl)pyridine (XLVII) as a clear oil (728 mg, 2.57 mmol, 53% yield). $^1$H NMR (DMSO-d$_6$) δ ppm 0.92 (d, J=8 Hz, 6H), 1.21-1.32 (m, 3H), 1.52-1.55 (m, 2H), 1.59-1.63 (m, 1H), 2.42-2.46 (m, 2H), 3.73 (s, 2H), 7.97-7.98 (m, 1H), 8.50 (d, J=3 Hz, 1H), 8.55-8.56 (m, 1H); ESIMS found for C$_{13}$H$_{19}$BrN$_2$ m/z 283 (M+H).

Preparation of Intermediate
3'-fluorobiphenyl-3-amine (LI) is Depicted Below in Scheme 11

Scheme 11

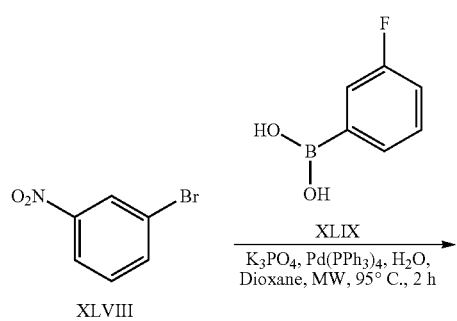

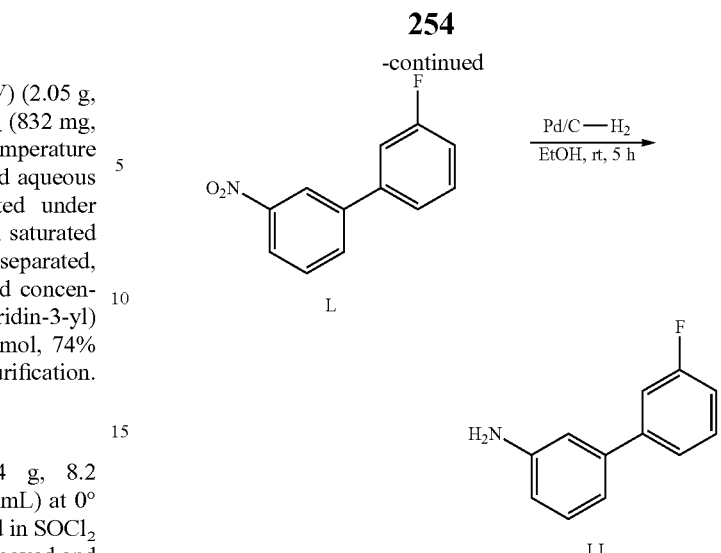

Step 1

A 25 mL microwave vessel was charged with 1-bromo-3-nitrobenzene (XLVIII) (0.61 g, 3.0 mmol), 3-fluorophenylboronic acid (XLIX) (0.46 g, 3.3 mmol), potassium phosphate tribasic (0.95 g, 4.5 mmol), 1,4-dioxane (15.0 mL), and water (3.0 mL). Tetrakis(triphenylphosphine)palladium(0) (0.17 g, 0.15 mmol) was added, and the reaction was placed in a microwave reactor for 1 h at 95° C. An additional 3-fluorophenylboronic acid (0.20 g) and tetrakis(triphenylphosphine)palladium(0) (0.05 g) were added, and the reaction was heated for another 1 h at 95° C. in a microwave reactor. The organic solvent was separated from the water and concentrated to a residue. The residue was then purified by flash chromatography using a 25 g Thomson normal phase silica gel cartridge (100% hexanes→1:99 EtOAc:hexanes) to afford 3'-fluoro-3-nitrobiphenyl (L) (0.63 g, 2.91 mmol, 97% yield) as a white solid. $^1$H NMR (DMSO-d$_6$) δ ppm 8.48 (t, J=2.0 Hz, 1H), 8.26-8.24 (m, 1H), 8.20-8.18 (m, 1H), 7.78 (t, J=8 Hz, 1H), 7.70-7.68 (m, 1H), 7.67-7.65 (m, 1H), 7.59-7.56 (m, 1H), 7.32-7.28 (m, 1H).

Step 2

10% Palladium on carbon (0.095 g) was added to a solution of 3'-fluoro-3-nitrobiphenyl (L) (0.63 g, 2.88 mmol) in EtOH (20.0 mL). The flask was evacuated and replaced with a hydrogen atmosphere. The solution was stirred at room temperature for 5 h under hydrogen. The catalyst was filtered through a pad of Celite, and the solvent was removed under reduced pressure. The residue was purified by flash chromatography using a 40 g Thomson normal phase silica gel cartridge (100% hexanes 15:85 EtOAc:hexanes) to afford 3'-fluorobiphenyl-3-amine (LI) (0.34 g, 1.81 mmol, 63% yield) as a light yellow oil. $^1$H NMR (DMSO-d$_6$) δ ppm 7.47-7.44 (m, 1H), 7.40-7.39 (m, 1H), 7.36-7.33 (m, 1H), 7.15-7.14 (m, 1H), 7.10 (t, J=7.7 Hz, 1H), 6.85-6.84 (m, 1H), 6.80-6.79 (m, 1H), 6.60-6.58 (m, 1H), 5.18 (s, 2H); ESIMS found for C$_{12}$H$_{10}$FN m/z 188 (M+H).

Preparation of Intermediate 5-(3-fluorophenyl)pyridin-3-amine (LIII) is Depicted Below in Scheme 12

Scheme 12

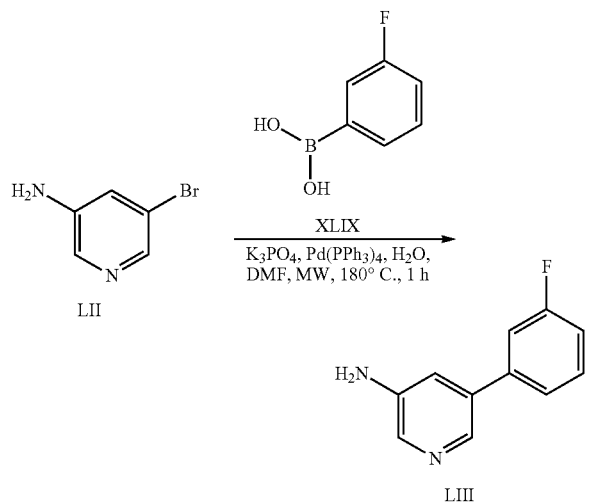

LIII

Step 1

To a microwave vial was added 3-amino-5-bromopyridine (LII) (0.400 g, 2.31 mmol), 3-fluorophenyl boronic acid (XLIX) (0.356 g, 2.54 mmol), tetrakis(triphenylphosphine)palladium(0) (0.133 g, 0.116 mmol), potassium phosphate (0.736 g, 3.47 mmol), water (1 mL), and DMF (5 mL). The reaction vial was capped, purged with argon and heated under microwave irradiation for 1 h at 180° C. The solution was filtered through a pad of Celite and concentrated under vacuum. The residue was purified by column chromatography (4:6 EtOAc:hexanes→7:3 EtOAc:hexanes) to afford the 5-(3-fluorophenyl)pyridin-3-amine (LIII) (0.360 g, 1.92 mmol, 83% yield) as a yellow-white solid. ESIMS found for $C_{11}H_9FN_2$ m/z 189.1 (M+H).

Preparation of Intermediate 5-((dimethylamino)methyl)pyridin-3-amine (LVII) is Depicted Below in Scheme 13

Scheme 13

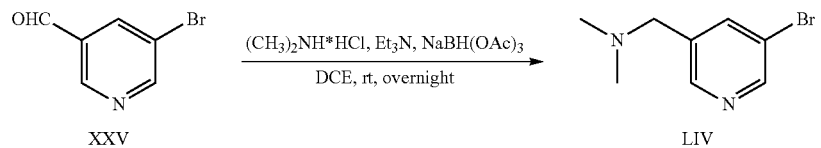

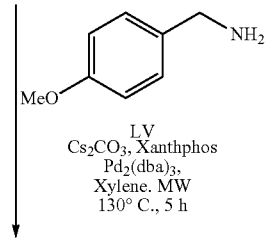

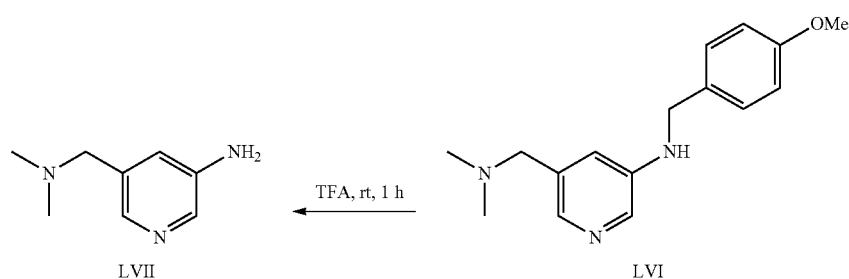

Step 1

5-Bromonicontinaldehyde (XXV) (5.01 g, 26.9 mmol) and dimethylamine hydrochloride (4.39 g, 53.8 mmol) were suspended in 1,2-dichloroethane (108 mL). Triethylamine (7.50 mL, 53.8 mmol) was added, and the reaction was stirred at room temperature for 1 h. Sodium triacetoxyborohydride (8.56 g, 40.4 mmol) was added, and the reaction was further stirred at room temperature overnight. The reaction was diluted with saturated sodium bicarbonate solution and DCM. The organic layer was separated, washed sequentially with water and brine, dried over $MgSO_4$, filtered and concentrated to give 1-(5-bromopyridin-3-yl)-N,N-dimethylmethanamine (LIV) (1.19 g, 23.9 mmol, 89% yield) as a brown oil: $^1$H NMR (DMSO-$d_6$) δ ppm 8.59 (d, J=3 Hz, 1H), 8.47 (d, J=2 Hz, 1H), 7.94 (s, 1H), 3.43 (s, 2H), 2.15 (s, 6H); ESIMS found for $C_8H_{11}BrN_2$ m/z 215 (M+H).

Step 2

In a 25 mL microwave vessel, 1-(5-bromopyridin-3-yl)-N,N-dimethylmethanamine (LIV) (1.27 g, 5.92 mmol), 4-methoxybenzylamine (LV) (0.77 mL, 5.92 mmol), cesium carbonate (2.70 g, 8.29 mmol) and xanthphos (0.17 g, 0.30 mmol) were suspended in xylenes (12.0 mL). The solvent was degassed, and tris(dibenzylideneacetone)dipalladium (0) (0.27 g, 0.30 mmol) was added. The vessel was sealed, and the reaction was heated to 130° C. for 5 h in a microwave reactor. The solvent was decanted away from the solid material and concentrated to a residue. The residue was purified by silica gel chromatography using a 40 g Thomson normal-phase silica gel cartridge (100% $CHCl_3$→3:97 MeOH[7N $NH_3$]:$CHCl_3$) to afford 5-((dimethylamino)methyl)-N-(4-methoxybenzyl)pyridin-3-amine (LVI) (0.68 g, 2.49 mmol, 42% yield) as a yellow solid. $^1$H NMR (DMSO-$d_6$) δ ppm 7.84 (d, J=3 Hz, 1H), 7.64 (d, J=2 Hz, 1H), 7.27 (d, J=11 Hz, 2H), 6.88 (d, J=11 Hz, 2H), 6.83-6.82 (m, 1H), 6.35 (t, J=8 Hz, 1H), 4.20 (d, J=8 Hz, 2H), 3.72 (s, 3H), 3.24 (s, 2H), 2.08 (s, 6H); ESIMS found for $C_{16}H_{21}N_3O$ m/z 272 (M+H).

Step 3

5-((dimethylamino)methyl)-N-(4-methoxybenzyl)pyridin-3-amine (LVI) (0.15 g, 0.56 mmol) was dissolved in TFA (2.0 mL) and stirred at room temperature for 1 h. The TFA was removed, and the residue was treated with 7N ammonia in MeOH/chloroform mixture (7/93) to neutralize the TFA and concentrated again to a residue. The residue was purified by flash silica gel chromatography utilizing a 4 g Thomson normal-phase silica gel cartridge (100% $CHCl_3$→3:97 MeOH[7N $NH_3$]:$CHCl_3$) to afford 5-((dimethylamino)methyl)pyridin-3-amine (LVII) (0.044 g, 0.29 mmol, 52% yield) as a brown oil. ESIMS found for $C_8H_{13}N_3$ m/z 152 (M+H).

The following intermediate was prepared in accordance with the procedure described in the above Scheme 13.

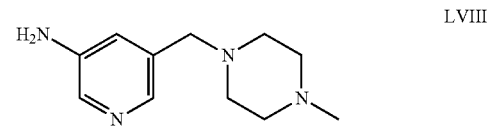

LVIII 5-((4-Methylpiperazin-1-yl)methyl)pyridin-3-amine (LVIII): Dark yellow solid (138 mg, 0.67 mmol, 71% yield). ESIMS found for $C_{11}H_{18}N_4$ m/z 207 (M+H).

Preparation of Intermediate 6-(pyrrolidin-1-ylmethyl)pyridin-3-amine (LXIII) is Depicted Below in Scheme 14

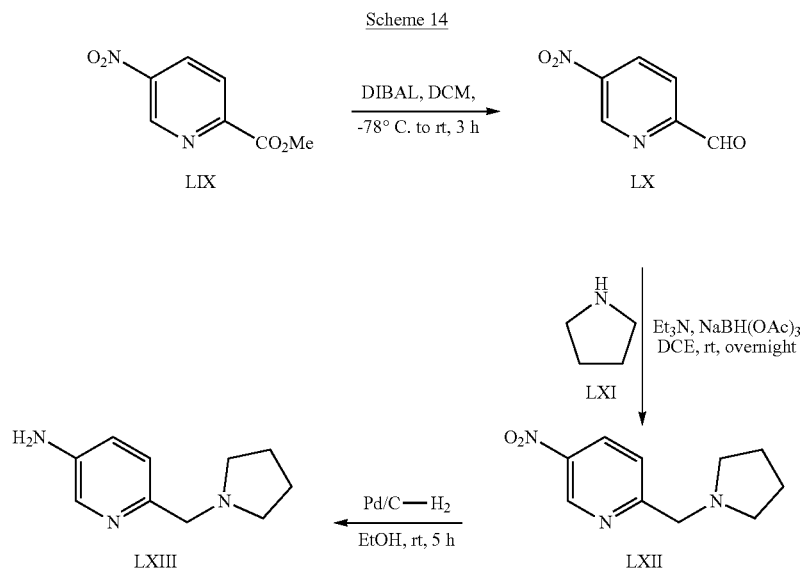

Scheme 14

Step 1

To a suspension of methyl 5-nitropicolinate (LIX) (1.282 g, 7.03 mmol) in DCM (25 mL) stirred at −78° C. under argon was slowly added DIBAL (1M in toluene) (9.14 mL, 9.14 mmol). The solution was allowed to warm to room temperature over 3 h. An aqueous solution of potassium sodium tartrate was added, diluted further with water and DCM. The solution was stirred at room temperature for another 30 min before the organic layer was separated. The aqueous layer was extracted 2×DCM, combined with the organic layer, dried over MgSO4, filtered and evaporated under reduced pressure. The residue was purified by column chromatography to produce 5-nitropicolinaldehyde (LX) as a brown oil (0.64 g, 4.2 mmol, 60% yield). $^1$H NMR (DMSO-$d_6$) δ ppm 8.17 (d, J=9 Hz, 1H), 8.81 (dd, J=9 Hz, J=2 Hz, 1H), 9.56 (d, J=2 Hz, 1H), 10.08 (s, 1H).

Step 2

Preparation of 5-nitro-2-(pyrrolidin-1-ylmethyl)pyridine (LXII) was performed following the procedure listed in Scheme 5, Step 1. Purple oil (0.41 g, 1.98 mmol, 86% yield). $^1$H NMR (DMSO-$d_6$) δ ppm 9.28 (d, J=3 Hz, 1H), 8.56 (dd, J=11 Hz, 3 Hz, 1H), 7.72 (d, J=11 Hz, 1H), 3.85 (s, 2H), 2.53-2.50 (m, 4H), 1.75-1.70 (m, 4H).

Step 3

Preparation of intermediate 6-(pyrrolidin-1-ylmethyl)pyridin-3-amine (LXIII) was performed following the procedure listed in Scheme 11, Step 2. Dark brown oil (0.35 g, 1.97 mmol, quantitative). ESIMS found for $C_{10}H_{15}N_3$ m/z 178 (M+H).

The following intermediate was prepared in accordance with the procedure described in the above Scheme 14.

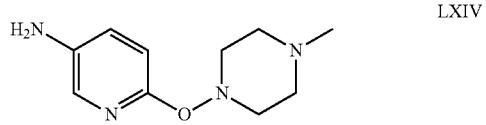

6-((4-Methylpiperazin-1-yl)methyl)pyridin-3-amine (LXIV): Brown oil (120 mg, 0.58 mmol, 100% yield). ESIMS found for $C_{11}H_{18}N_4$ m/z 207 (M+H).

Preparation of Intermediate
6-(3-fluorophenoxy)pyridin-3-amine (LXVIII) is Depicted Below in Scheme 15

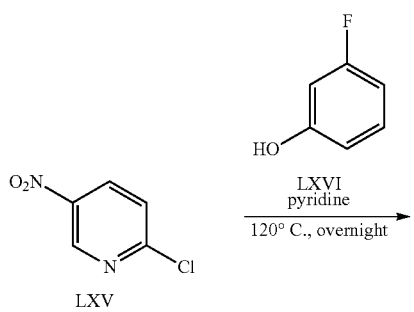

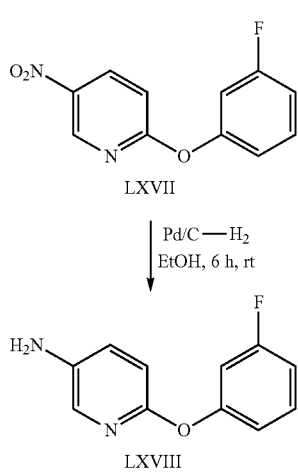

Step 1

A solution of 2-chloro-5-nitropyridine (LXV) (1.98 g, 12.5 mmol) and 3-fluorophenol (LXVI) (1.4 g, 12.5 mmol) in pyridine (20 mL) was heated at 120° C. overnight under argon. The solution was cooled to room temperature and concentrated under vacuum. The residue was dissolved in EtOAc, washed with water, brine, dried over MgSO$_4$ and evaporated. The residue was purified by silica gel column chromatography (100% hexane 2:98 EtOAc:hexane) to give 2-(3-fluorophenoxy)-5-nitropyridine (LXVII) as a yellow viscous oil (2.27 g, 9.7 mmol, 77% yield). $^1$H NMR (DMSO-$d_6$) δ ppm 7.11 (dd, J=8 Hz, J=2 Hz, 1H), 7.17 (dt, J=8 Hz, J=6 Hz, 1H), 7.23 (td, J=10 Hz, J=2 Hz, 1H), 7.31 (d, J=9 Hz, 1H), 7.52 (q, J=9 Hz, 1H), 8.64 (dd, J=9 Hz, J=3 Hz, 1H), 9.05 (d, J=3 Hz, 1H); ESIMS found for $C_{11}H_7FN_2O_3$ m/z 234.9 (M+H).

Step 2

Preparation of intermediate 6-(3-fluorophenoxy)pyridin-3-amine (LXVIII) was performed following the procedure listed in Scheme 11, Step 2. Black green viscous oil (1.90 g, 9.3 mmol, 96% yield). $^1$H NMR (DMSO-$d_6$) δ ppm 5.18 (brs, 2H), 6.74-6.83 (m, 3H), 6.90 (dt, 1H), 7.09 (dd, J=9 Hz, J=3 Hz, 1H), 7.34 (q, J=7 Hz, 1H), 7.57 (d, J=3 Hz, 1H); ESIMS found for $C_{11}H_9FN_2O$ m/z 204.4 (M+).

The following intermediates were prepared in accordance with the procedure described in the above Scheme 15.

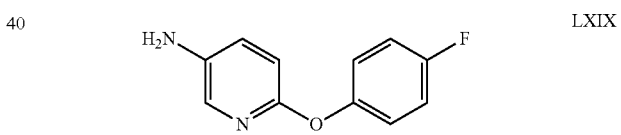

6-(4-Fluorophenoxy)pyridin-3-amine (LXIX): Dark brown oil (870 mg, 4.3 mmol, 100% yield). $^1$H NMR (DMSO-$d_6$) δ ppm 5.08 (brs, 2H), 6.75 (d, J=15 Hz, 1H), 6.90-7.01 (m, 2H), 7.07 (dd, J=9 Hz, J=3 Hz, 1H), 7.16 (t, 9 Hz, 1H), 7.26-7.30 (m, 1H), 7.73 (d, J=3 Hz, 1H); ESIMS found for $C_{11}H_9FN_2O$ m/z 204.9 (M+H).

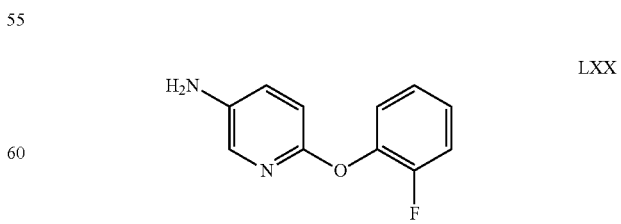

6-(2-Fluorophenoxy)pyridin-3-amine (LXX): Dark brown oil (611 mg, 3.0 mmol, 91% yield). ESIMS found for $C_{11}H_9FN_2O$ m/z 204.9 (M+H).

Preparation of Intermediate
6-phenylpyridin-3-amine (LXXIV) is Depicted
Below in Scheme 16

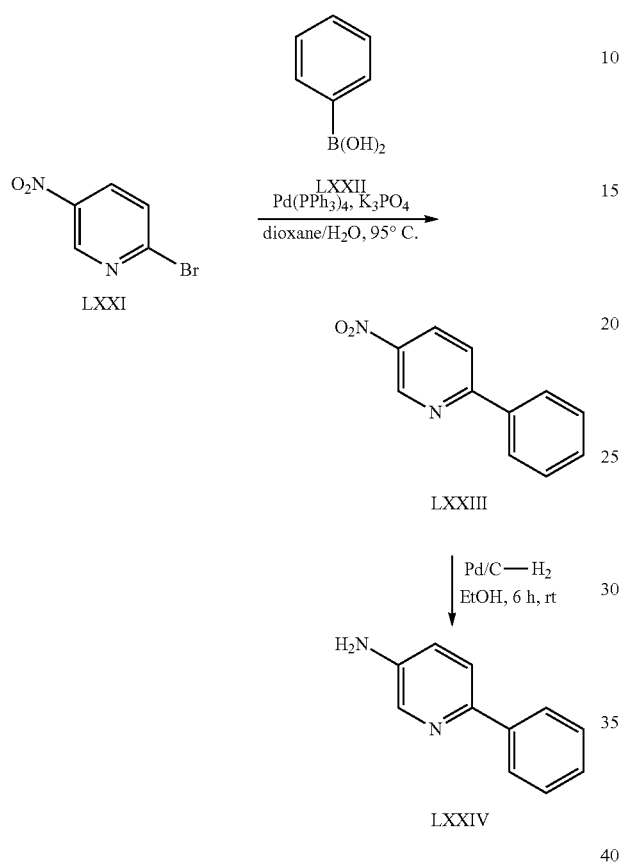

Step 1

To a solution of 2-bromo-5-nitropyridine (LXXI) (302 mg, 1.49 mmol) in a mixture of dioxane (14 mL) and water (3 mL) was added phenylboronic acid (LXXII) (199 mg, 1.64 mmol), Pd(PPh$_3$)$_4$ (86 mg, 0.74 mmol) and K$_3$PO$_4$ (473 mg, 2.23 mmol). The reaction was microwaved at 95° C. for 1 h. The reaction was cooled and the organic phase was separated, dried over MgSO$_4$ and evaporated under vacuum. The residue was purified by silica gel column chromatography (100% hexane→+5:95 EtOAc:hexane) to give 5-nitro-2-phenylpyridine (LXXIII) as off-white needles (254 mg, 1.27 mmol, 85% yield). ESIMS found for C$_{11}$H$_8$N$_2$O$_2$ m/z 200.9 (M+H).

Step 2

Preparation of intermediate 6-phenylpyridin-3-amine (LXXIV) was performed following the procedure listed in Scheme 11, Step 2. Black green viscous oil (211 mg, 1.24 mmol, 98% yield). $^1$H NMR (DMSO-d$_6$) δ ppm 5.45 (s, 2H), 6.99 (dd, J=11 Hz, J=3 Hz, 1H), 7.25-7.28 (m, 1H), 7.38-7.40 (m, 2H), 7.62 (d, J=11 Hz, 1H0, 7.89-7.91 (m, 1H), 8.02 (d, J=3 Hz, 1H); ESIMS found for C$_{11}$H$_{10}$N$_2$ m/z 171 (M+H).

The following intermediates were prepared in accordance with the procedure described in the above Scheme 16.

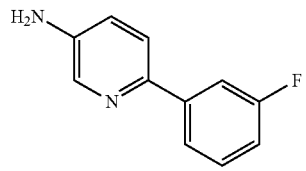

6-(3-Fluorophenyl)pyridin-3-amine (LXXV): Brown oil (252 mg, 1.34 mmol, 98% yield). ESIMS found for C$_{11}$H$_9$FN$_2$ m/z 189 (M+H).

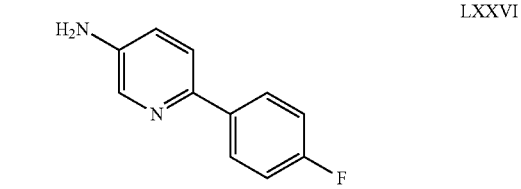 [SMILES: Nc1ccc(-c2ccc(F)cc2)nc1]

6-(4-Fluorophenyl)pyridin-3-amine (LXXVI): Deep purple oil (202 mg, 1.07 mmol, 98% yield). ESIMS found for C$_1$H9FN$_2$ m/z 189 (M+H).

Preparation of Intermediate
5-benzylpyridin-3-amine (LXXX) is Depicted
Below in Scheme 17

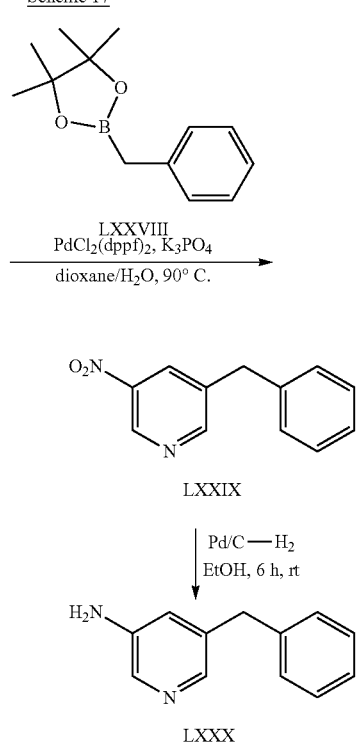

Step 1

To a solution of 3-bromo-5-nitropyridine (LXXVII) (295 mg, 1.45 mmol) in dioxane (14 mL) was added 2-benzyl-4,4,5,5-tetramethyl-1,3,2-dioxaborolane (LXXVIII) (420

µL, 1.89 mmol), PdCl$_2$(dppf)$_2$, (120 mg, 0.15 mmol) and 2M aqueous K$_3$PO$_4$ (2.2 mL, 4.36 mmol). The reaction was microwaved at 90° C. for 2 h. The reaction was cooled and the organic phase was separated, dried over MgSO$_4$ and evaporated under vacuum. The residue was purified by silica gel column chromatography (100% hexane 6:94 EtOAc: hexane) to give 3-benzyl-5-nitropyridine (LXXIX) as brown oil (117 mg, 0.54 mmol, 37% yield). $^1$H NMR (DMSO-d$_6$) δ ppm 4.16 (s, 2H), 7.21-7.25 (m, 1H), 7.31-7.33 (m, 4H), 8.45-8.46 (m, 1H), 8.93 (d, J=2 Hz, 1H), 9.21 (d, J=3 Hz, 1H); ESIMS found for C$_{12}$H$_{10}$N$_2$O$_2$ m/z 215 (M+H).

Step 2

Preparation of 5-benzylpyridin-3-amine (LXXX) was performed following the procedure listed in Scheme 11, Step 2. Black green viscous oil (139 mg, 0.75 mmol, 98% yield). ESIMS found for C$_{12}$H$_{12}$N$_2$ m/z 185 (M+H).

Preparation of Intermediate 2-(4-methylpiperazin-1-yl)pyridin-3-amine (LXXXIV) is Depicted Below in Scheme 18

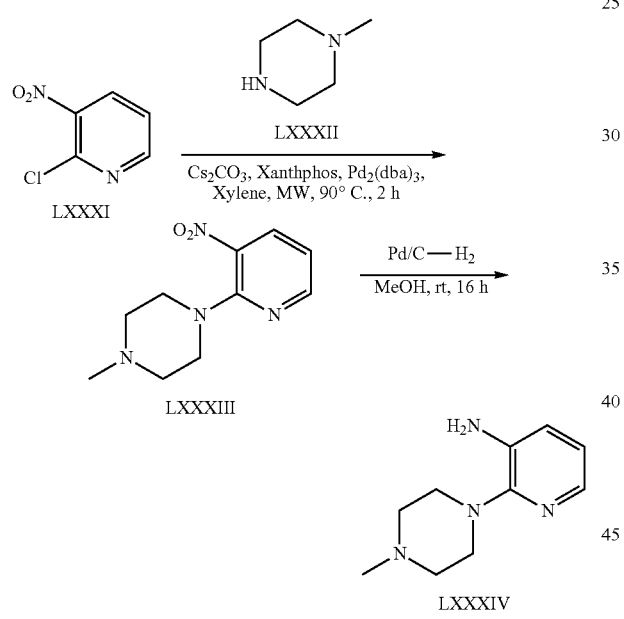

Step 1

To a microwave vial was added 2-chloro-3-nitropyridine (LXXXI) (1.00 g, 6.31 mmol), 1-methylpiperazine (LXXXII) (0.758 g, 7.57 mmol), cesium carbonate (2.88 g, 8.83 mmol), Pd$_2$(dba)$_3$ (0.173 g, 0.189 mmol), xanthphos (0.109 g, 0.189 mmol), and dioxane (5 mL). The reaction vial was capped and purged with argon. The solution into the reaction vial was heated under microwave irradiation for 2 h at 90° C. The solution was filtered through a pad of Celite and concentrated to a residue under vacuum. The residue was purified by column chromatography (1:99 MeOH: CHCl$_3$→8:92 MeOH:CHCl$_3$) to afford 1-methyl-4-(3-nitro-pyridin-2-yl)-piperazine (LXXXIII) (1.30 g, 5.85 mmol, 93% yield) as a brown oil.

Step 2

To a stirring solution of 1-methyl-4-(3-nitro-pyridin-2-yl)-piperazine (LXXXIII) (1.30 g, 5.85 mmol) in MeOH (15 mL) was added 10% Pd/C. The solution was purged with hydrogen. The solution was stirred at room temperature for 16 h under hydrogen. The solution was filtered through a pad of Celite and concentrated to a residue under vacuum. The residue was purified by column chromatography (100% CHCl$_3$→2:98 MeOH[7N NH$_3$]:CHCl$_3$) to afford 2-(4-methylpiperazin-1-yl)pyridin-3-amine (LXXXIV) (0.466 g, 2.42 mmol, 52% yield) as a tan solid. ESIMS found for C$_{10}$H$_{16}$N$_4$ m/z 192.4 (M+H).

The following intermediates were prepared in accordance with the procedure described in the above Scheme 18.

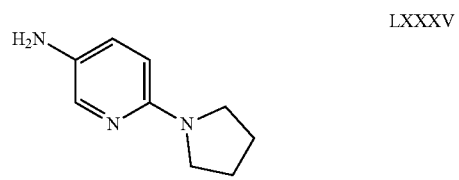 [SMILES: Nc1ccc(N2CCCC2)nc1]

6-(Pyrrolidin-1-yl)pyridin-3-amine (LXXXV): Deep purple oil (1.43 g, 8.77 mmol, 100% yield). ESIMS found for C$_9$H$_{13}$N$_3$ m/z 164 (M+H).

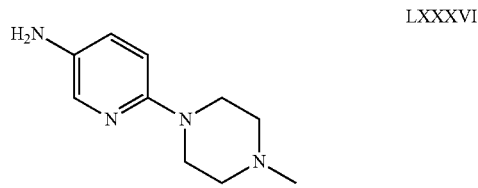

6-(4-Methylpiperazin-1-yl)pyridin-3-amine (LXXXVI): Purple solid (598 mg, 3.11 mmol, 32% yield). ESIMS found for C$_{10}$H$_{16}$N$_4$ m/z 193 (M+H).

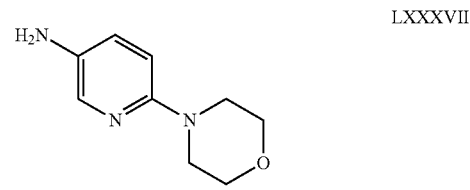 [SMILES: Nc1ccc(N2CCOCC2)nc1]

6-Morpholinopyridin-3-amine (LXXXVII): Purple solid (782 mg, 4.36 mmol, 95% yield). ESIMS found for C$_9$H$_{13}$N$_3$O m/z 180 (M+H).

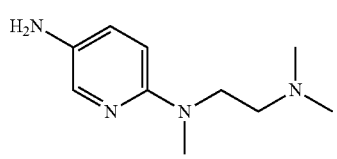

N$^2$-(2-(Dimethylamino)ethyl)-N$^2$-methylpyridine-2,5-diamine (LXXXVIII): Deep purple oil (1.55 g, 7.98 mmol, 96% yield). ESIMS found for C$_{10}$H$_{18}$N$_4$ m/z 195 (M+H).

Preparation of Intermediate 1-(5-aminopyridin-2-yl)piperidin-4-ol (XCI) is Depicted Below in Scheme 19

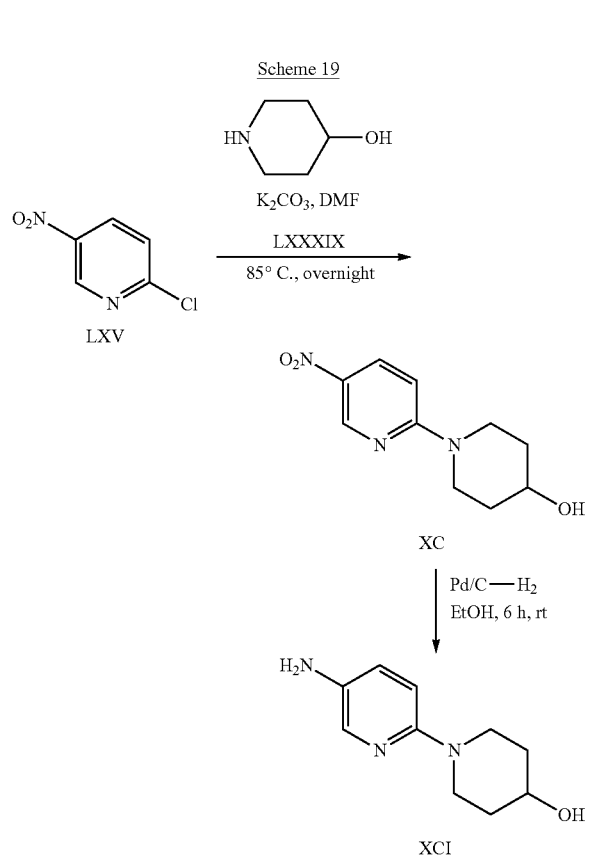

Step 1

To a solution of 2-chloro-5-nitropyridine (LXV) (5.0 g, 31.5 mmol) in DMF (50 mL) was added piperidin-4-ol (LXXXIX) (3.5 g, 34.65 mmol) and $K_2CO_3$ (8.7 g, 63.0 mmol). The reaction was headed at 85° C. overnight. The solution was poured into ice water, stirred for 15 min and then filtered. The solid was washed with cold water and dried under vacuum to produce 1-(5-aminopyridin-2-yl)piperidin-4-ol (XC) as a yellow solid (6.62 g, 29.67 mmol, 94.2% yield). NMR (DMSO-$d_6$) δ ppm 1.34-1.42 (m, 2H), 1.77-1.83 (m, 2H), 3.40-3.56 (m, 2H), 3.76-3.83 (m, 1H), 4.12 (brd, 2H), 4.81 (d, J=4 Hz, 1H), 6.94 (d, J=10 Hz, 1H), 8.17 (dd, 0.1=10 Hz, J=3 Hz, 1H), 8.94 (d, J=3 Hz, 1H); ESIMS found for $C_{10}H_{13}N_3O_3$ m/z 224.1 (M+H).

Step 2

Preparation of intermediate 1-(5-aminopyridin-2-yl)piperidin-4-ol (XCI) was performed following the procedure listed in Scheme 11, Step 2. Dark brown oil (5.7 g, 29.5 mmol, 99.5% yield). $^1$H NMR (DMSO-$d_6$) δ ppm 1.36 (tq, J=13 Hz, J=4 Hz, 2H), 1.72-1.76 (m, 2H), 2.79 (dt, J=13 Hz, J=3 Hz, 2H), 3.54-3.61 (m, 1H), 3.70-3.78 (m, 2H), 4.49 (s, 2H), 4.61 (d, J=4 Hz, 1H), 6.61 (d, J=9 Hz, 1H), 6.88 (dd, J=9 Hz, J=3 Hz, 1H), 7.57 (d, J=3 Hz, 1H); ESIMS found for $C_{10}H_{15}N_3O$ m/z 194.1 (M+H).

The following intermediates were prepared in accordance with the procedure described in the above Scheme 19.

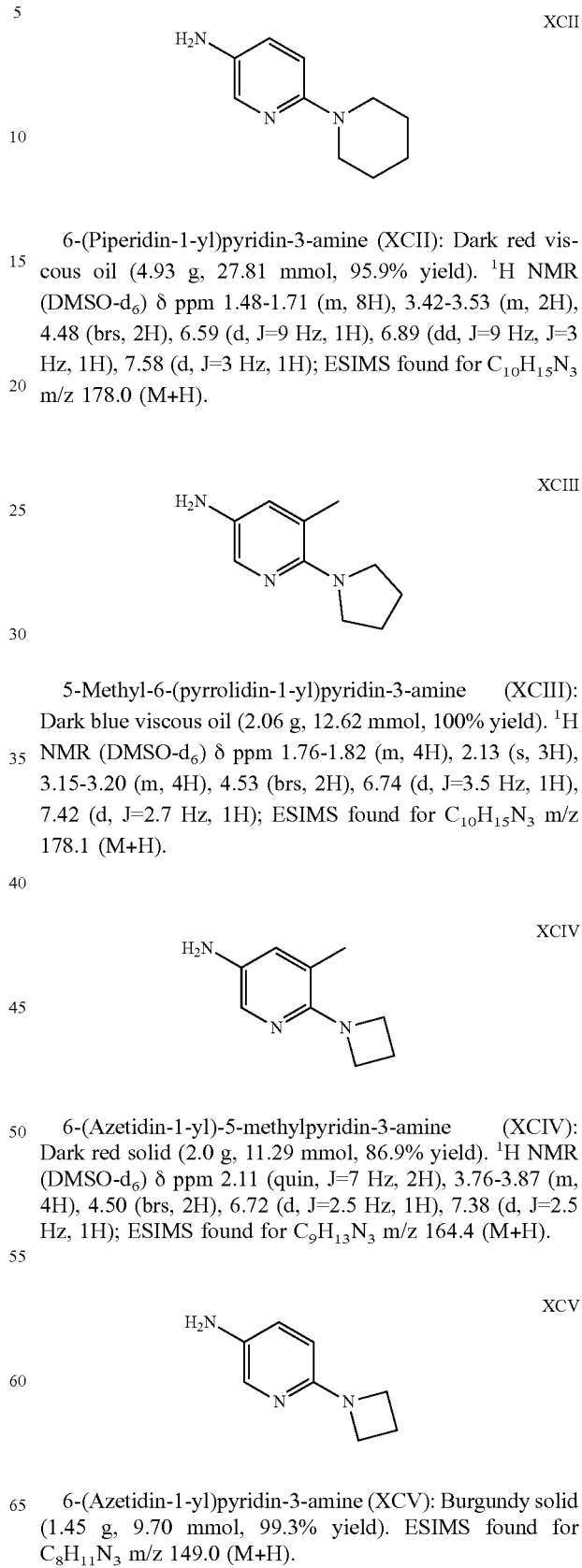

6-(Piperidin-1-yl)pyridin-3-amine (XCII): Dark red viscous oil (4.93 g, 27.81 mmol, 95.9% yield). $^1$H NMR (DMSO-$d_6$) δ ppm 1.48-1.71 (m, 8H), 3.42-3.53 (m, 2H), 4.48 (brs, 2H), 6.59 (d, J=9 Hz, 1H), 6.89 (dd, J=9 Hz, J=3 Hz, 1H), 7.58 (d, J=3 Hz, 1H); ESIMS found for $C_{10}H_{15}N_3$ m/z 178.0 (M+H).

5-Methyl-6-(pyrrolidin-1-yl)pyridin-3-amine (XCIII): Dark blue viscous oil (2.06 g, 12.62 mmol, 100% yield). $^1$H NMR (DMSO-$d_6$) δ ppm 1.76-1.82 (m, 4H), 2.13 (s, 3H), 3.15-3.20 (m, 4H), 4.53 (brs, 2H), 6.74 (d, J=3.5 Hz, 1H), 7.42 (d, J=2.7 Hz, 1H); ESIMS found for $C_{10}H_{15}N_3$ m/z 178.1 (M+H).

6-(Azetidin-1-yl)-5-methylpyridin-3-amine (XCIV): Dark red solid (2.0 g, 11.29 mmol, 86.9% yield). $^1$H NMR (DMSO-$d_6$) δ ppm 2.11 (quin, J=7 Hz, 2H), 3.76-3.87 (m, 4H), 4.50 (brs, 2H), 6.72 (d, J=2.5 Hz, 1H), 7.38 (d, J=2.5 Hz, 1H); ESIMS found for $C_9H_{13}N_3$ m/z 164.4 (M+H).

6-(Azetidin-1-yl)pyridin-3-amine (XCV): Burgundy solid (1.45 g, 9.70 mmol, 99.3% yield). ESIMS found for $C_8H_{11}N_3$ m/z 149.0 (M+H).

Preparation of Intermediate tert-butyl 4-(5-amino-pyridin-2-yl)piperazine-1-carboxylate (XCVIII) is Depicted Below in Scheme 20

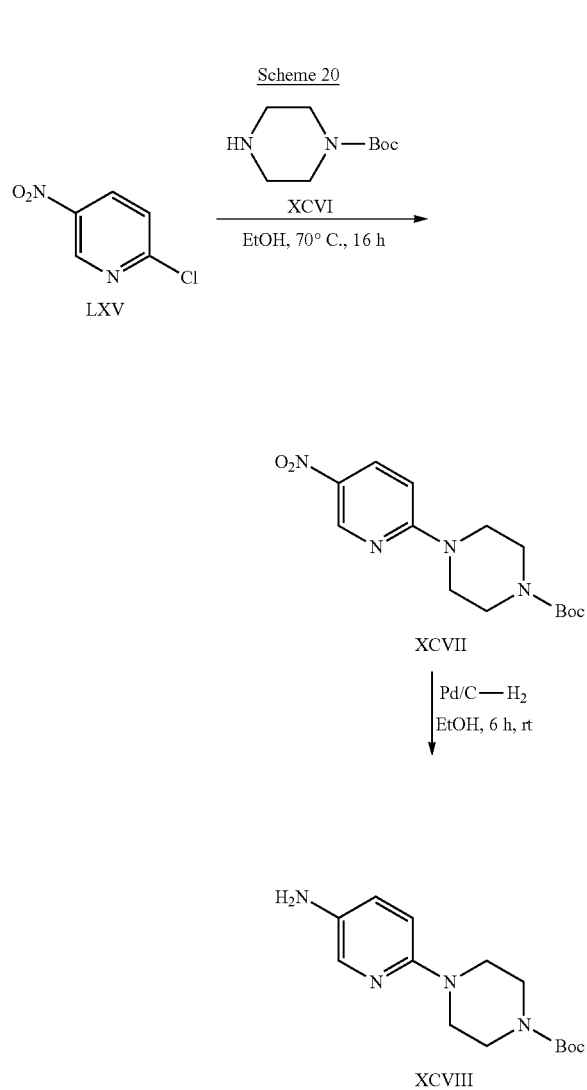

Preparation of Intermediate N-(3-aminopyridin-4-yl) cyclopropanecarboxamide (CII) is Depicted Below in Scheme 21

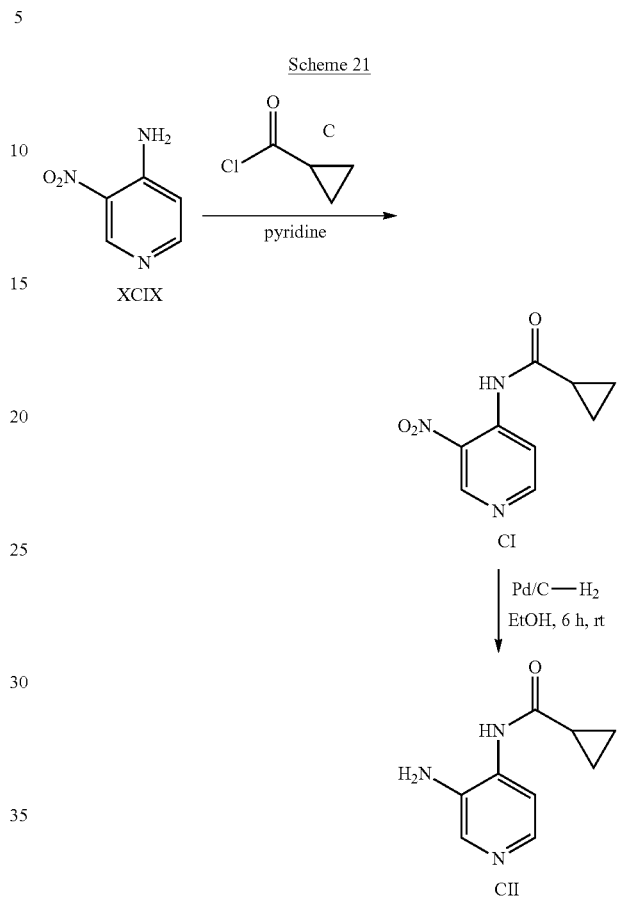

Step 1

To a solution of 2-chloro-5-nitropyridine (LXV) (2.0 g, 12.6 mmol) in EtOH (20 mL) was added tert-butyl piperazine-1-carboxylate (XCVI) (7.05 g, 37.9 mmol). The reaction was heated at 70° C. for 16 h. The reaction was concentrated under vacuum and then dissolved in EtOAc. The EtOAc was washed with 1 M NaOH, brine and then dried over MgSO4 to give tert-butyl 4-(5-nitropyridin-2-yl)piperazine-1-carboxylate (XCVII) as a yellow solid (4.94 g). ESIMS found for $C_{14}H_{20}N_4O_4$ m/z 309.0 (M+H).

Step 2

Preparation of intermediate tert-butyl 4-(5-aminopyridin-2-yl)piperazine-1-carboxylate (XCVIII) was performed following the procedure listed in Scheme 11, Step 2. Purple solid (990 mg, 3.56 mmol, quantitative). ESIMS found for $C_{14}H_{22}N_4O_2$ m/z 278.8 (M+H).

Step 1

Preparation of N-(3-nitropyridin-4-yl)cyclopropanecarboxamide (CI) was performed following the procedure listed in Scheme 4, Step 1. Orange solid (130 mg, 0.93 mmol, 13% yield). ESIMS found for $C_9H_9N_3O_3$ m/z 207.8 (M+H).

Step 2

Preparation of intermediate N-(3-aminopyridin-4-yl) cyclopropanecarboxamide (CII) was performed following the procedure listed in Scheme 11, Step 2. Dark grey solid (100 mg, 0.56 mmol, quantitative). ESIMS found for $C_9H_{11}N_3O$ m/z 178.3 (M+H).

Preparation of Intermediate (5-aminopyridin-2-yl) (pyrrolidin-1-yl)methanone (CV) is Depicted Below in Scheme 22

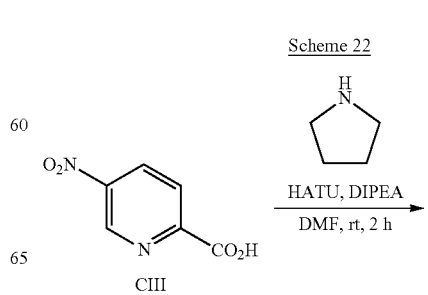

269

-continued

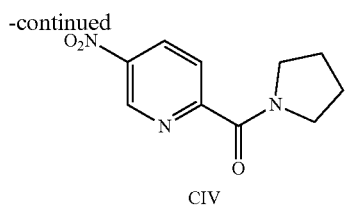
CIV

Pd/C—H₂
EtOH, 6 h, rt ↓

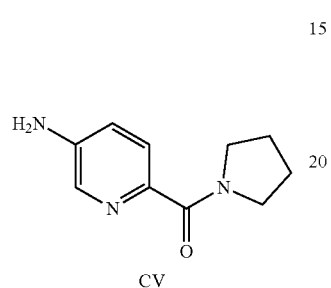
CV

Step 1

To a solution of 5-nitropicolinic acid (CIII) (500 mg, 2.97 mmol) in DMF (15 mL) was added pyrrolidine (244 μl, 2.47 mmol) and DIPEA (1.03 mL, 5.95 mmol). The reaction was cooled at 0° C. before adding HATU (1.13 g, 2.47 mmol). The reaction was warmed to room temperature and stirred for 2 hrs. The reaction was concentrated under vacuum and then dissolved in a mixture of water and 10% iPrOH/CHCl₃. The organic layer was separated and the aqueous phase was washed again with 10% iPrOH/CHCl₃. The combined organic phases were washed with brine, dried over MgSO4 and evaporated to yield (5-nitropyridin-2-yl)(pyrrolidin-1-yl)methanone (CIV) as a red solid (849 mg). ESIMS found for $C_{10}H_{11}N_3O_3$ m/z 222.1 (M+H).

Step 2

Preparation of intermediate (5-aminopyridin-2-yl)(pyrrolidin-1-yl)methanone (CV) was performed following the procedure listed in Scheme 11, Step 2. Yellow solid (708 mg, 7.3 mmol, 96.4% yield). ESIMS found for $C_{10}H_{13}N_3O$ m/z 191.4 (M+H).

The following intermediate was prepared in accordance with the procedure described in the above Scheme 22.

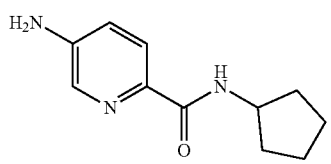
CVI

5-Amino-N-cyclopentylpicolinamide (CVI): Yellow solid (450 mg, 2.19 mmol, 93.7% yield). ESIMS found for $C_{11}H_{15}N_3O$ m/z 206.1 (M+H).

270

Preparation of Intermediate 6-(methylsulfonyl)pyridin-3-amine (CIX) is Depicted Below in Scheme 23

Scheme 23

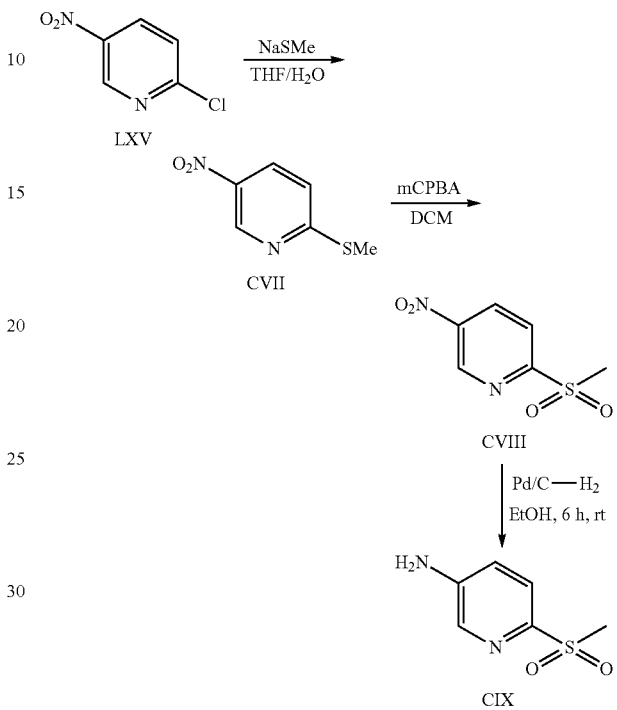

Step 1

To a solution of sodium thiomethoxide in THF (53 mL) and H₂O (20 mL) cooled to 0° C. was added 2-chloro-5-nitropyridine (LXV) (5.09 g, 32.09 mmol). The reaction was warmed to room temperature and stirred for 2 hrs. The reaction was poured into ice water and stirred for 10 minutes, filtered, washed with water, dried under vacuum to yield 2-(methylthio)-5-nitropyridine (CVII) as a yellow solid (5.14 g, 30.20 mmol, 94.1%). $^1H$ NMR (DMSO-d₆) δ ppm 2.62 (s, 3H), 7.57 (d, J=8.9 Hz, 1H), 8.38 (d, J=8.9 Hz, 1H), 9.22 (d, J=2.7 Hz, 1H); ESIMS found for $C_6H_6N_2O_2S$ m/z 171.1 (M+H).

Step 2

To a solution of 2-(methylthio)-5-nitropyridine (CVII) (502 mg, 2.95 mmol) in DCM (60 mL) was mCPBA (1.33 g, 5.90 mmol). The reaction was stirred at room temperature for 1 hr. Two additional portions of mCPBA (2×250 mg) were added at 1 hr intervals for a total reaction time of 4 hr. The reaction was poured into saturated aqueous NaHCO₃. The organic phase was separated and washed with water, brine and then dried over MgSO₄. The solvent was removed under vacuum to produce crude 2-(methylsulfonyl)-5-nitropyridine (CVIII) (854 mg) which was used without purification for step 3. ESIMS found for $C_6H_6N_2O_4S$ m/z 203.0 (M+H).

Step 3

Preparation of intermediate 6-(methylsulfonyl)pyridin-3-amine (CIX) was performed following the procedure listed in Scheme 11, Step 2. The crude product was used as is without purification. ESIMS found for $C_6H_8N_2O_2S$ m/z 173.0 (M+H).

Preparation of Intermediate 5-iodo-1-(tetrahydro-2H-pyran-2-yl)-1H-indazole-3-carbaldehyde (CXIV) is Depicted Below in Scheme 24

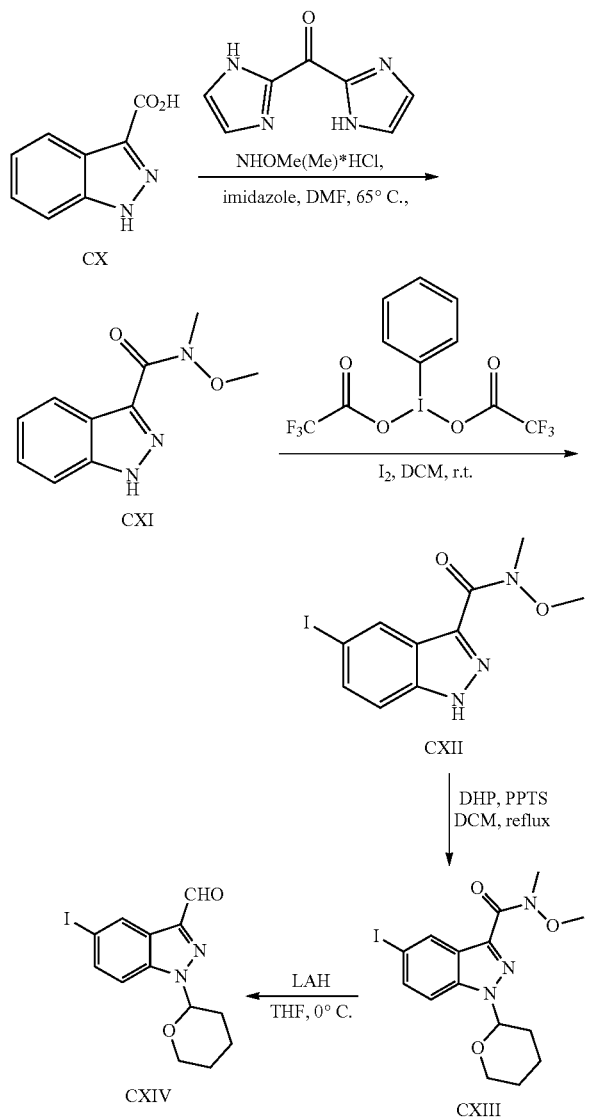

Step 1

1H-indazole-3-carboxylic acid (CX) (100 g, 617 mmol) in DMF was treated with carbonyldiimidazole (110 g, 678 mmol) at room temperature until the evolution of gas ceased (ca. 15 minutes). The reaction was heated to 60-65° C. for 2 h and then allowed to cool to room temperature. N,O-Dimethylhydroxylamine-HCl (66.2 g, 678 mmol) was added as a solid and the mixture was heated to 65° C. for 3 h. The reaction was concentrated to a paste, taken up in DCM and washed subsequently with water and 2 N HCl. The product could be seen coming out of solution. The solid was filtered and rinsed separately with EtOAc. The EtOAc and DCM layers were separately washed with sodium bicarbonate followed by brine, dried over MgSO₄ and concentrated under reduced pressure. The resulting solids were combined, triturated with 1:1 mixture of DCM-ether, filtered, and dried to produce N-methoxy-N-methyl-1H-indazole-3-carboxamide (CXI) as a white solid (100 g, 487 mmol, 79% yield). $^1$H NMR (DMSO-d$_6$) δ ppm 3.46 (s, 3H), 3.69-3.85 (m, 3H), 7.13-7.31 (m, 1H), 7.41 (t, J=7.25 Hz, 1H), 7.56-7.65 (m, 1H), 7.93-8.08 (m, 1H); ESIMS found for $C_{10}H_{11}N_3O_2$ m/z 206 (M+H).

Step 2

To N-methoxy-N-methyl-1H-indazole-3-carboxamide (CXI) (20 g, 97.4 mmol) in DCM (1 L) was added (Bis (trifluoroacetoxy)iodo)benzene (46 g, 107 mmol) followed by portionwise addition of iodine (14.84 g, 58.5 mmol) at room temperature. After 1 h, saturated aqueous NaHSO₃ (600 mL) was added and a solid began to precipitate which was filtered and rinsed with excess DCM. The filtrate was washed with brine, dried over MgSO₄, concentrated and the remaining solid was triturated with a minimal amount of DCM. The combined solids were dried under vacuum over KOH to produce 5-iodo-N-methoxy-N-methyl-1H-indazole-3-carboxamide (CXII) as a white solid (23.2 g, 70 mmol, 72% yield). $^1$H NMR (DMSO-d$_6$) δ ppm 3.45 (s, 3H), 3.77 (s, 3H), 7.45-7.54 (m, 1H), 7.66 (dd, J=8.81, 1.51 Hz, 1H), 8.40 (d, J=1.01 Hz, 1H); ESIMS found for $C_{10}H_{10}IN_3O_2$ m/z 331 (M+H).

Step 3

A mixture of 5-iodo-N-methoxy-N-methyl-1H-indazole-3-carboxamide (CXII) (16.5 g, 50 mmol), 3,4-dihydro-2H-pyran (10.3 mL, 113 mmol) and PPTS (0.12 g, 0.6 mmol) in DCM was heated to reflux for 5 h. The solution was poured into a saturated aqueous NaHCO₃ solution, the layers were separated, and the aqueous layer was extracted with DCM. The combined organic layers were washed with 5% aqueous citric acid and brine, dried over MgSO₄, and concentrated. The crude product was purified on a silica gel column (100% EtOAc 3:97 MeOH:DCM) to provide 5-iodo-N-methoxy-N-methyl-1-(tetrahydro-2H-pyran-2-yl)-1H-indazole-3-carboxamide (CXIII) as a white viscous oil (19.1 g, 46 mmol, 92% yield). NMR (DMSO-d$_6$) δ ppm 1.28-1.84 (m, 6H), 3.43 (s, 3H), 3.60-4.04 (s, 5H), 5.86-6.08 (m, 1H), 7.45-7.87 (m, 2H), 8.39 (s, 1H); ESIMS found for $C_{131}H_{18}IN_3O_3$ m/z 416 (M+H).

Step 4

Lithium aluminum hydride (160 mg, 4.21 mmol) was added in portions to a cooled (0° C.) solution of 5-iodo-N-methoxy-N-methyl-1-(tetrahydro-2H-pyran-2-yl)-1H-indazole-3-carboxamide (CXIII) (1.46 g, 3.5 mmol) in THF. Stirring was continued at 0° C. until the reaction was completed, approximately 30 min. The reaction was quenched by the slow addition of EtOAc at 0° C., and the whole mixture was poured into 0.4 N aqueous NaHSO₄. The organic layer was washed with brine, dried over MgSO₄, concentrated, and purified on a silica gel column (100% EtOAc→3:97 MeOH:DCM) to give 5-iodo-1-(tetrahydro-2H-pyran-2-yl)-1H-indazole carbaldehyde (CXIV) as a white solid (0.90 g, 3.15 mmol, 72% yield). $^1$H NMR (DMSO-d$_6$) δ ppm 1.50-1.71 (m, 2H), 1.71-1.87 (m, 1H), 1.97-2.15 (m, 2H), 2.31-2.42 (m, 1H), 3.66-3.99 (m, 2H), 5.96-6.17 (m, 1H), 7.78 (d, J=6 Hz, 1H), 7.84 (d, J=6 Hz, 1H), 8.50 (s, 1H), 10.13 (s, 1H); ESIMS found for $C_{13}H_{13}IN_2O_2$ m/z 357 (M+H).

Preparation of Intermediate 5-bromo-1-(tetrahydro-2H-pyran-2-yl)-1H-indazole-3-carboxylic acid (CXVIII) is Depicted Below in Scheme 25

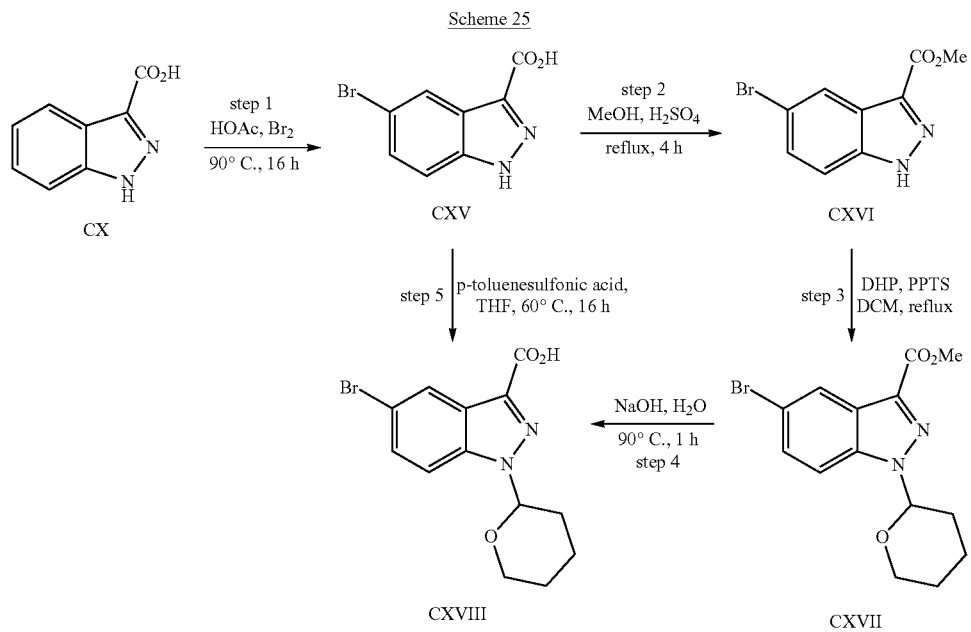

Scheme 25

Step 1

A suspension of indazole-3-carboxylic acid (CX) (1.0 g, 6.16 mmol) in glacial acetic acid (60 mL) was heated at 120° C. to get a clear solution. The solution was cooled to 90° C. A solution of bromine (0.633 mL, 12.33 mmol) in glacial acetic acid (2 mL) was added slowly to the solution while heating at 90° C. The solution was further heated 16 h at 90° C. The solution was cooled to room temperature, poured into ice water and further stirred at room temperature for 15 min. The solids formed were filtered, washed with cold water and dried under vacuum at room temperature to get 5-bromo-1H-indazole-3-carboxylic acid (CXV) as a white solid (1.30 g, 5.39 mmol, 87.5% yield). NMR (DMSO-$d_6$) δ ppm 13.95 (s, 1H), 13.18 (br s, 1H), 8.21 (d, J=1.2 Hz, 1H), 7.65 (d, J=7.0 Hz, 1H), 7.56 (dd, J=7.0, 1.2 Hz, 1H); ESIMS found for $C_8H_4BrN_2O_2$ m/z 242.0 (M+H).

Step 2

Concentrated sulfuric acid (1 mL) was added to a suspension of 5-bromo-1H-indazole-3-carboxylic acid (CXV) (1.30 g, 5.39 mmol) in dry MeOH (50 mL) and heated to reflux for 4 h under argon. The solution was cooled to room temperature and the MeOH was evaporated under vacuum. The residue was dissolved in EtOAc and washed with water. The organic phase was dried over $Na_2SO_4$, filtered and concentrated to afford methyl 5-bromo-1H-indazole carboxylate (CXVI) as a white solid (1.35 g, 5.29 mmol, 98% yield). $^1$H NMR (DMSO-$d_6$) δ ppm 14.13 (s, 1H), 8.21 (d, J=1.6 Hz, 1H), 7.67 (d, J=7.2 Hz, 1H), 7.59 (dd, J=7.2, 1.2 Hz, 1H), 3.92 (s, 3H); ESIMS found for $C_9H_7BrN_2O_2$ m/z 256.0 (M+H).

Step 3

A suspension of methyl 5-bromo-1H-indazole-3-carboxylate (CXVI) (1.35 g, 5.29 mmol), pyridinium p-toluenesulfonate (0.143 g, 0.56 mmol) and 3,4 dihydro-2H-pyran (1.02 mL, 11.90 mmol) in anhydrous dichloroethane (20 mL) was refluxed 5 h under argon. The suspension was turned into the clear solution. The solution was cooled and the excess solvent was evaporated under vacuum. The residue was dissolved in EtOAc and washed with dilute $NaHCO_3$ solution (sat$^d$. $NaHCO_3$ sol$^n$/$H_2O$: 1:9). The organic layer was dried over $Na_2SO_4$, filtered and concentrated. The residue was purified by column chromatography (100% hexanes 5:95 EtOAc:hexanes) to get methyl 5-bromo-1-(tetrahydro-2H-pyran-2-yl)-1H-indazole-3-carboxylate (CXVII) as a white solid (1.47 g, 4.34 mmol, 82% yield). $^1$H NMR (DMSO-$d_6$) δ ppm 8.22 (d, J=1.4 Hz, 1H), 7.89 (d, J=7.2 Hz, 1H), 7.68 (dd, J=7.2, 1.6 Hz, 1H),), 6.02 (dd, J=8.0, 2.4 Hz, 1H), 3.94 (s, 3H), 3.88 (m, 1H), 3.79 (m, 1H), 2.37-2.31 (m, 1H), 2.05-1.96 (m, 2H), 1.77-1.73 (m, 1H). 1.60-1.58 (m, 2H); ESIMS found for $C_{14}H_{15}BrN_2O_3$ m/z 340.0 (M+H).

Step 4

2 N Aqueous NaOH solution (10 mL) was added to a suspension of methyl 5-bromo-1-(tetrahydro-2H-pyran-2-yl)-1H-indazole-3-carboxylate (CXVII) (1.30 g, 3.83 mmol)

in water (20 mL) and heated at 90° C. for 1 h. The solution was cooled to room temperature, diluted with ice water and acidified to pH 3.0 with 10% aqueous HCl. The solids formed were filtered, washed with cold water and dried under vacuum at room temperature to get 5-bromo-1-(tetrahydro-2H-pyran-2-yl)-1H-indazole-3-carboxylic acid (CXVIII) as a white solid (0.87 g, 2.68 mmol, 70% yield). ESIMS found for $C_{13}H_{13}BrN_2O_3$ m/z 326.0 (M+H).

Step 5

To a solution of 5-bromo-1H-indazole-3-carboxylic acid (CXV) (59.8 g, 248 mmol) in THF (800 mL) under argon was added 3,4 dihydro-2H-pyran (50.6 mL, 558 mmol) and p-TsOH (4.72 g, 24.8 mmol). The reaction was heated to reflux at 60° C. for 16 h. An additional portion of p-TsOH (0.025 eq) and 3,4 dihydro-2H-pyran (0.56 eq) was added and the reflux continued for 5 h. The solution was concentrated under vacuum. EtOAc was added to the residue and the suspension was filtered and dried under high vacuum overnight to produce 5-bromo (tetrahydro-2H-pyran-2-yl)-1H-indazole-3-carboxylic acid (CXVIII) as a white solid (49.07 g, 150.9 mmol, 60.8% yield). ESIMS found for $C_{13}H_{13}BrN_2O_3$ m/z 326.3 (M+H).

Preparation of Intermediate
5-bromo-1-trityl-1H-indazole-3-carboxylic acid
(CXXI) is Depicted Below in Scheme 26

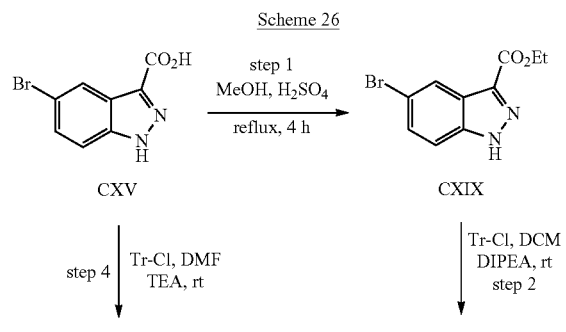

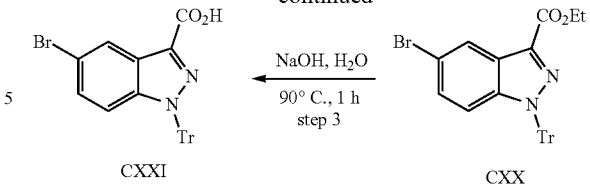

Step 1

Preparation of intermediate ethyl 5-bromo-1H-indazole-3-carboxylate (CXIX) was performed following the procedure listed in Scheme 25, Step 2. White solid. (3.60 g, 13.38 mmol, 64.5% yield). $^1$H NMR (DMSO-$d_6$) δ ppm 1.37 (t, J=7 Hz, 3H), 4.40 (q, J=7 Hz, 2H), 7.57 (dd, J=9 Hz, J=2 Hz, 1H), 7.66 (d, J=9 Hz, 1H), 8.20 (d, J=2 Hz, 1H), 14.11 (brs, 1H); ESIMS found for $C_{10}H_9BrN_2O_2$ m/z 269.0 (M+H).

Step 2

To a solution of ethyl 5-bromo-1H-indazole-3-carboxylate (CXIX) and trityl chloride in DCM was slowly added DIPEA. The solution was stirred at room temperature overnight. The reaction was poured into water and stirred for 5 min. The organic layer was separated, dried over MgSO$_4$ and concentrated under vacuum. The residue was purified by column chromatography using a ISCO 200RF system with a SiO$_2$ column (12 g) (100% hexanes 10:90 EtOAc:hexanes) to produce a white solid. (357 mg, 0.70 mmol, 69.8% yield). $^1$H NMR (DMSO-$d_6$) δ ppm 1.34 (t, J=7 Hz, 3H), 4.38 (q, J=7 Hz, 2H), 6.43 (d, J=9.5 Hz, 1H), 7.11-7.14 (m, 6H), 7.31-7.35 (m, 10H), 8.23 (d, J=2 Hz, 1H); ESIMS found for $C_{29}H_{23}BrN_2O_2$ m/z 511.0 (M+H).

Step 3

Preparation of intermediate 5-bromo-1-trityl-1H-indazole-3-carboxylic acid (CXXI) by hydrolysis of ethyl 5-bromo-1-trityl-1H-indazole-3-carboxylate (CXX) can be performed following the procedure listed in Scheme 25, Step 3.

Step 4

Preparation of intermediate 5-bromo-1-trityl-1H-indazole-3-carboxylic acid (CXXI) by tritylation of 5-bromo-1H-indazole-3-carboxylic acid (CXV) can be performed following the procedure listed in the *Journal of Medicinal Chemistry* (2003), 46(25), 5458-5470.

Example 1

Preparation of 5-(5-(3,3-dimethylureido)pyridin-3-yl)-N-(pyridin-3-yl)-1H-indazole-3-carboxamide (1) is Depicted Below in Scheme 27

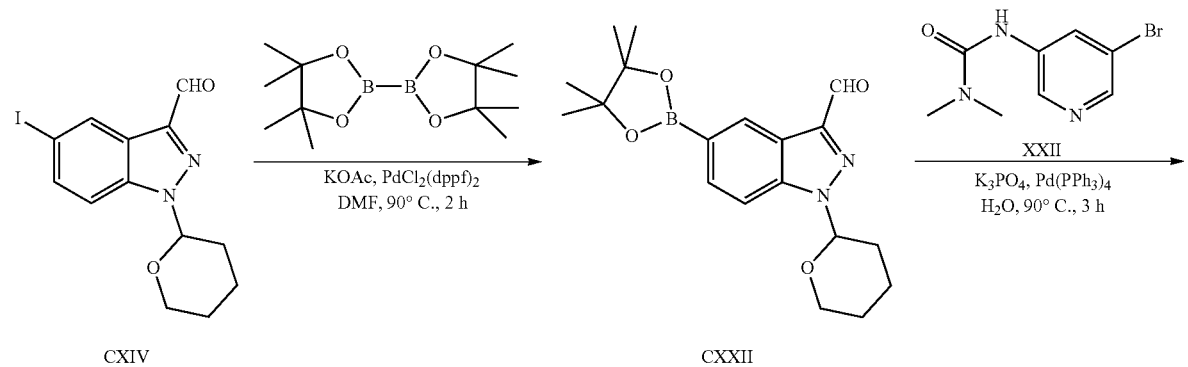

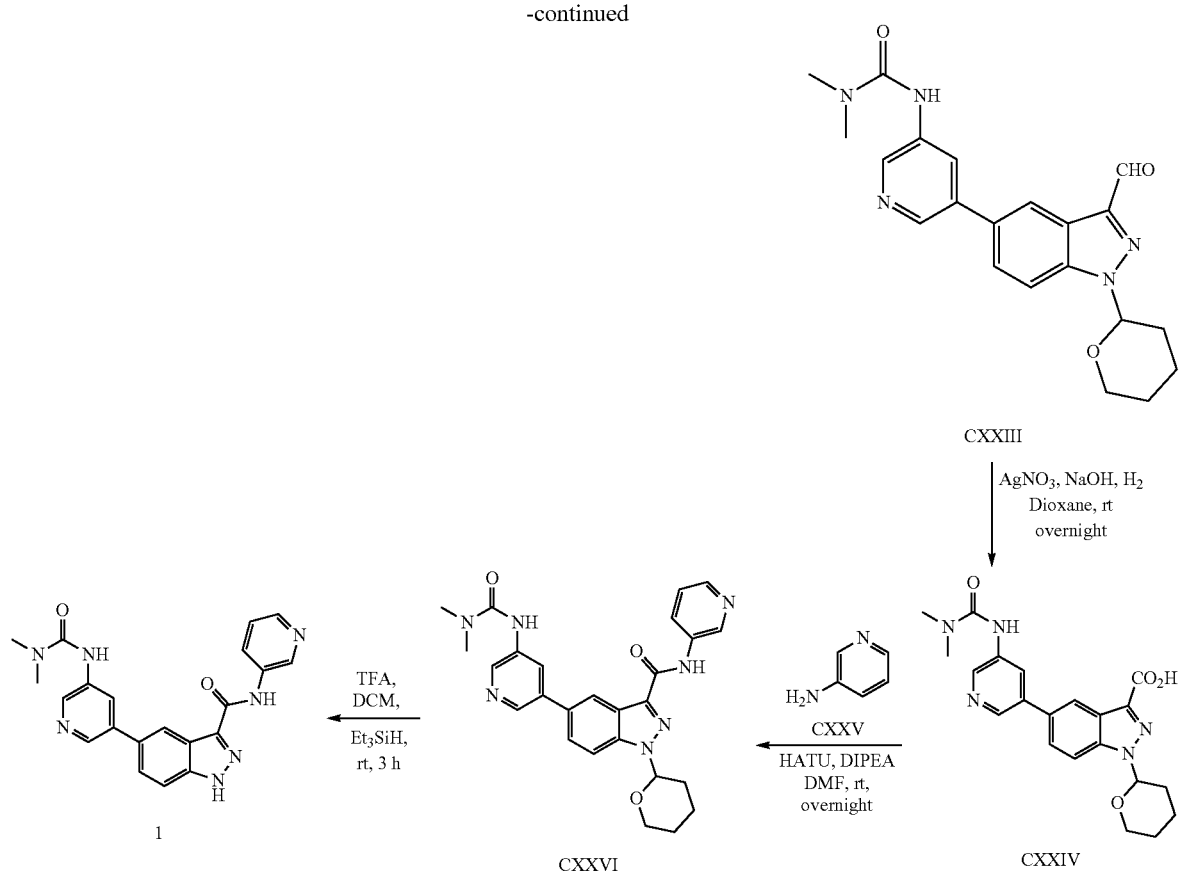

Step 1-2

A solution of 5-iodo-1-(tetrahydro-2H-pyran-2-yl)-1H-indazole carbaldehyde (CXIV) (1.780 g, 5.0 mmol), bis(pinacolato)diboron (1.523 g, 6.0 mmol), KOAc (1.471 g, 15 mmol) and dry DMF (20 mL) was purged with argon. PdCl$_2$(dppf)$_2$ (0.245 g, 0.3 mmol) was added to the reaction and purged again with argon. The solution was heated at 90° C. for 2 h. Once TLC showed the disappearance of (CXIV), the solution was cooled to room temperature. To this solution was added K$_3$PO$_4$ (1.592 g, 7.5 mmol), 3-(5-bromopyridin-3-yl)-1,1-dimethylurea (XXII) (1.220 g, 5.0 mmol), Pd(PPh$_3$)$_4$ (173 mg, 0.15 mmol) and water (2 mL). The solution was purged with argon and heated at 90° C. for 3 h. The solution was cooled to room temperature and then concentrated under reduced pressure. The residue was dissolved in DCM and washed with water, dried over MgSO$_4$, filtered and then evaporated under vacuum. The residue was purified on a silica gel column (100% DCM 2:98 MeOH:DCM) to give 3-(5-(3-formyl-1-(tetrahydro-2H-pyran-2-yl)-1H-indazol-5-yl)pyridin-3-yl)-1,1-dimethylurea (CXXIII) as a brown viscous oil which solidified under vacuum at room temperature (354 mg, 0.90 mmol, 18% yield for 2 steps). NMR (DMSO-d$_6$) δ ppm 10.22 (s, 1H), 8.76 (d, J=1.6 Hz, 1H), 8.63 (s, 1H), 8.52 (d, J=1.6 Hz, 1H), 8.36 (s, 1H), 8.24 (m, 1H), 8.05 (d, J=7.2 Hz, 1H), 7.91 (dd, J=7.2, 1.4 Hz, 1H), 6.13 (dd, J=7.6, 2.0 Hz, 1H), 3.93 (m, 1H), 3.85 (m, 1H), 2.98 (s, 6H), 2.47-2.42 (m, 1H), 2.11-2.06 (m, 2H), 1.82-1.79 (m, 1H) 1.64 (m, 2H); ESIMS found for C$_{21}$H$_{23}$N$_5$O$_3$ m/z 394.0 (M+H).

Step 3

A solution of sodium hydroxide (0.173 g, 4.33 mmol) in water (5 mL) was added to a solution of silver nitrate (0.367 g, 2.16 mmol) in water (5 mL) to give a brown precipitate. 3-(5-(3-formyl-1-(tetrahydro-2H-pyran-2-yl)-1H-indazol-5-yl) pyridin-3-yl)-1,1-dimethylurea (CXXIII) (0.340 g. 0.86 mmol) was dissolved in 1,4-dioxane (10 mL) and added to the reaction which was stirred overnight at room temperature. The solution was diluted with water and then extracted with diethyl ether. The aqueous layer was separated and carefully brought to pH=3 with aqueous HCl. The aqueous layer was then extracted with 10% iPrOH/chloroform. The combined organic layers were then dried (Na$_2$SO$_4$), filtered and concentrated to give 5-(5-(3,3-dimethylureido)pyridin-3-yl)-1-(tetrahydro-2H-pyran-2-yl)-1H-indazole-3-carboxylic acid (CXXIV) as a brownish white solid (246 mg, 0.60 mmol, 70% yield). $^1$H NMR (DMSO-d$_6$) δ ppm 13.26 (br. s, 1H), 8.87 (s, 1H), 8.63 (s, 1H), 8.41 (s, 1H), 8.34 (s, 1H), 8.03 (d, J=7.1 Hz, 1H), 7.86 (dd, J=7.2, 1.3 Hz, 1H), 6.06 (dd, J=8.0, 4.0 Hz, 1H), 3.92 (m, 1H), 3.80 (m, 1H), 2.98 (s, 6H), 2.42-2.39 (m, 1H), 2.03-2.02 (m, 2H), 1.79-1.77 (m, 1H) 1.61 (m, 2H); ESIMS found for C$_{21}$H$_{23}$N$_5$O$_4$ m/z 410.0 (M+H).

Step 4

HATU (0.190 g, 0.5 mmol) was added to a solution of 5-(5-(3,3-dimethylureido)pyridin-3-yl)-1-(tetrahydro-2H-pyran-2-yl)-1H-indazole-3-carboxylic acid (CXXIV) (0.39 g, 1.21 mmol) and diisopropylethylamine (0.174 mL, 1.0 mmol) in DMF stirred at room temperature under argon. After stirring 5 min, the solution was added with 3-aminopyridine (CXXV) (0.047 g, 0.5 mmol). The solution was stirred overnight at room temperature under argon. The DMF was removed under reduced pressure, and the residue was treated with water, sonicated briefly and filtered. The solids were washed with cold water and dried at room temperature. The product was purified by column chromatography using a 4 g Thomson normal phase silica gel cartridge (100% DCM→5:95 MeOH:DCM) to afford 5-(5-(3,3-dimethylureido)pyridin-3-yl)-N-(pyridin-3-yl)-1-(tetrahydro-2H-pyran-2-yl)-1H-indazole-3-carboxamide (CXXVI) as an off white solid (323 mg, 0.67 mmol, 55% yield). $^1$H NMR (DMSO-d$_6$) δ ppm 10.56 (s, 1H), 9.06 (d, J=2.0 Hz, 1H), 8.75 (d, 0.1=1.6 Hz, 1H), 8.64 (s, 1H), 8.53 (d, J=1.6 Hz, 1H), 8.46 (s, 1H), 8.34-8.29 (m, 2H), 8.26 (m, 1H), 8.03 (d, J=7.0 Hz, 1H), 7.88 (dd, J=7.0, 1.2 Hz, 1H), 7.43 (dd, J=6.64, 3.84 Hz, 1H), 6.07 (dd, J=8.0, 1.8 Hz, 1H), 3.98 (m, 1H), 3.82 (m, 1H), 2.98 (s, 6H), 2.63-2.60 (m, 1H), 2.11-2.06 (m, 2H), 1.83-1.81 (m, 1H) 1.52 (m, 2H); ESIMS found for $C_{21}H_{23}N_5O_4$ m/z 410.0 (M+H).

Step 5

TFA (5 mL) was added to a solution of 5-(5-(3,3-dimethylureido)pyridin-3-yl)-N-(pyridin-3-yl)-1-(tetrahydro-2H-pyran-2-yl)-1H-indazole-3-carboxamide (CXXVI) (0.134 g, 0.27 mmol) and triethylsilane (0.110 mL, 0.69 mmol) in DCM (5 mL) and stirred 3 h at room temperature. The solvent was removed under vacuum. The residue was treated with water, sonicated briefly to disperse the solids, basified to pH 9.0 with 5 N NH$_4$OH and sonicated again. The solids were filtered, washed with cold water and purified by column chromatography (100% DCM 5:95 MeOH[7N NH$_3$]:DCM) to afford 5-(5-(3,3-dimethylureido)pyridin-3-yl)-N-(pyridin-3-yl)-1H-indazole-3-carboxamide (1) as a white solid (35.8 mg, 0.09 mmol, 33% yield). $^1$H NMR (DMSO-d$_6$) δ ppm 13.99 (s, 1H), 10.69 (s, 1H), 9.08 (d, J=1.2 Hz, 1H), 8.74 (d, J=1.8 Hz, 1H), 8.63 (s, 1H), 8.51 (d, J=1.5 Hz, 1H), 8.47 (s, 1H), 8.33-8.30 (m, 2H), 8.26 (m, 1H), 7.80 (s, 2H), 7.41 (dd, J=6.6, 3.6 Hz, 1H), 2.98 (s, 6H); ESIMS found for $C_{21}H_{19}N_7O_2$ m/z 402.3 (M+H).

The following compound was prepared in accordance with the procedure described in the above Example 1.

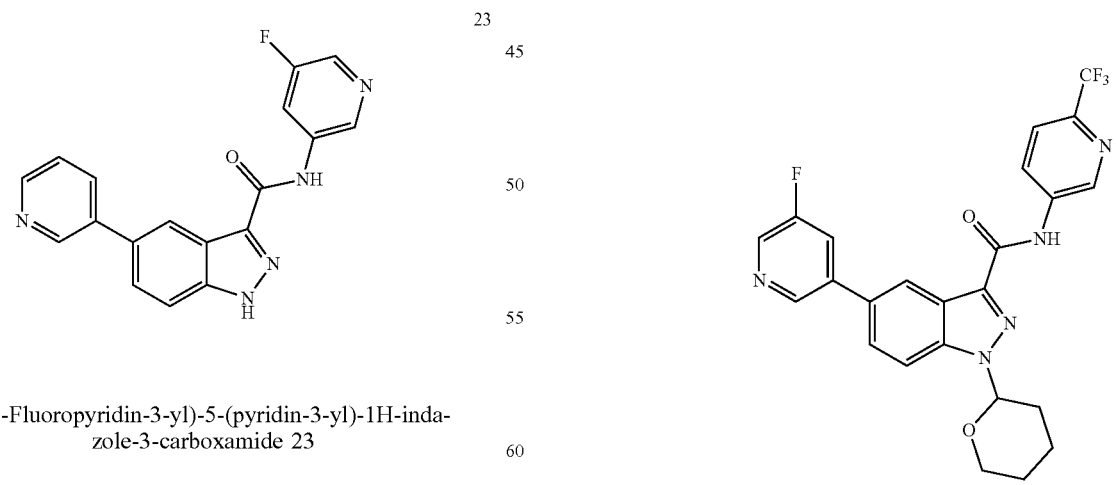

N-(5-Fluoropyridin-3-yl)-5-(pyridin-3-yl)-1H-indazole-3-carboxamide 23

Light tan solid. NMR (DMSO-d$_6$) δ ppm 7.53 (dd, J=8 Hz, J=5 Hz, 1H), 7.82-7.86 (m, 2H), 8.13-8.15 (m, 1H), 8.31-8.34 (m, 2H), 8.47-8.48 (m, 1H), 8.60 (dd, J=5 Hz, J=2 Hz, 1H), 894 (d, J=2 Hz, 1H), 8.99 (d, J=2 Hz, 1H), 10.97 (s, 1H), 14.05 (s, 1H); ESIMS found for $C_{18}H_{12}FN_5O$ m/z 334 (M+1).

Example 2

Preparation of 5-(5-fluoropyridin-3-yl)-N-(6-(trifluoromethyl)pyridin-3-yl)-1H-indazole-3-carboxamide (2) is Depicted Below in Scheme 28

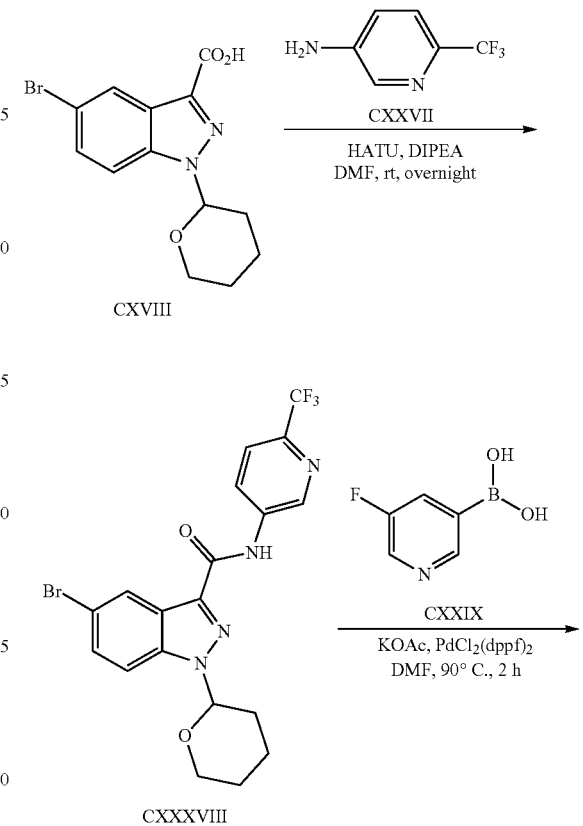

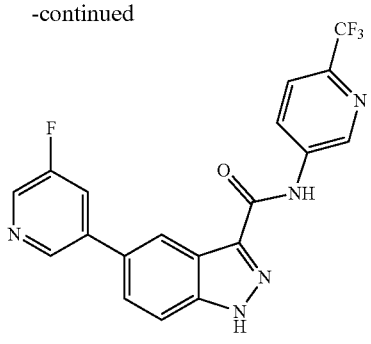

2

Step 1

HATU (1.125 g, 2.96 mmol) was added to a solution of 5-bromo (tetrahydro-2H-pyran-2-yl)-1H-indazole-3-carboxylic acid (CXVIII) (0.876 g, 2.69 mmol) and diisopropylethylamine (1.03 mL, 5.92 mmol) in DMF stirred at room temperature under argon. After stirring 5 min, the solution was added with 5-amino-2-trifluoromethyl pyridine (CXXVII) (0.479 g, 2.96 mmol). The solution was stirred 24 h at room temperature under argon. The DMF was removed under reduced pressure, and the residue was treated with water, sonicated briefly and filtered. The solids were washed with cold water and dried at room temperature. The product was purified by silica gel column chromatography (100% hexanes→7:93 EtOAc:hexanes) to afford 5-bromo-1-(tetrahydro-2H-pyran-2-yl)-N-(6-(trifluoromethyl)pyridin-3-yl)-1H-indazole-3-carboxamide (CXXVIII) as a white solid (1.17 g, 2.50 mmol, 93% yield). $^1$H NMR (DMSO-$d_6$) δ ppm 10.93 (s, 1H), 9.23 (d, J=1.9 Hz, 1H), 8.60 (dd, J=6.8, 1.4 Hz, 1H), 8.38 (d, J=4.4 Hz, 1H), 7.95 (m, 2H), 7.70 (dd, J=7.1, 1.5 Hz, 1H),), 6.04 (dd, J=8.1, 1.9 Hz, 1H), 3.98 (m, 1H), 3.82 (m, 1H), 2.59-2.54 (m, 1H), 2.08-2.03 (m, 2H), 1.81-1.77 (m, 1H). 1.66-1.61 (m, 2H); ESIMS found for $C_{19}H_{16}BrF_3N_4O_2$ m/z 470.0 (M+H).

Step 2

A solution of 5-bromo-1-(tetrahydro-2H-pyran-2-yl)-N-(6-(trifluoromethyl) pyridin-3-yl)-1H-indazole-3-carboxamide (CXXVIII) (0.469 g, 1 mmol), 5-fluoro-pyridyl-3-boronic acid (CXXIX) (0.156 g, 1.1 mmol), potassium phosphate tribasic (0.318 g, 1.5 mmol) and water (degassed, 1 mL) in DMF (10 mL) was purged with argon. Tetrakis(triphenylphosphine)palladium(0) (0.034 g, 0.03 mmol) was added and the solution was purged again with argon. The reaction was heated to 90° C. for 3 h when TLC showed disappearance of starting material. The solution was cooled to room temperature and excess solvent was removed under vacuum. The residue was treated with water, sonicated briefly and the solids formed were filtered. The solids were washed with cold water and dried under vacuum at room temperature which was purified by silica gel column chromatography (2:8 EtOAc:hexanes 3:7 EtOAc:hexanes) to afford 5-(5-fluoropyridin-3-yl)-1-(tetrahydro-2H-pyran-2-yl)-N-(6-(trifluoromethyl) pyridin-3-yl)-1H-indazole-3-carboxamide (CXXX) as a white solid (427 mg, 0.88 mmol, 88% yield). $^1$H NMR (DMSO-$d_6$) δ ppm 10.95 (d, J=1.8 Hz, 1H), 8.85 (m, 1H), 8.63 (d, J=1.8 Hz, 1H), 8.61 (d, J=2.1 Hz, 1H), 8.53 (m, 1H), 8.16-8.13 (m, 1H), 8.08 (d, J=7.1 Hz, 1H), 7.97-7.94 (m, 2H), 6.11 (dd, J=8.1, 1.8 Hz, 1H), 4.01 (m, 1H), 3.88-3.83 (m, 1H), 2.63-2.60 (m, 1H), 2.11-2.07 (m, 2H), 1.83-1.80 (m, 1H). 1.69-1.65 (m, 2H); ESIMS found for $C_{24}H_{19}F_4N_5O_2$ m/z 486.0 (M+H).

Step 3

TFA (10 mL) was added to a solution of 5-(5-fluoropyridin-3-yl) (tetrahydro-2H-pyran-2-yl)-N-(6-(trifluoromethyl) pyridin-3-yl)-1H-indazole-3-carboxamide (CXXX) (0.420 g, 0.86 mmol) and triethylsilane (0.345 mL, 2.16 mmol) in DCM (10 mL) and stirred 5 h at room temperature. The solvent was removed under vacuum. The residue was treated with water, sonicated briefly to disperse the solids, basified to pH 9.0 with 5 N NH$_4$OH and sonicated again. The solids were filtered, washed with cold water and air dried at room temperature. The solids were suspended in DCM:MeOH (1:1) mixture and boiled to get a clear solution. The solution was cooled to room temperature. The solids formed were filtered washed with DCM and dried under vacuum at room temperature to get 5-(5-fluoropyridin-3-yl)-N-(6-(trifluoromethyl)pyridin-3-yl)-1H-indazole-3-carboxamide (2) as a white solid (72.9 mg, 0.18 mmol, 21% yield). $^1$H NMR (DMSO-$d_6$) δ ppm 14.13 (br. s, 1H), 11.11 (s, 1H), 9.27 (d, J=1.8 Hz, 1H), 8.84 (m, 1H), 8.63 (dd, J=6.8, 1.8 Hz, 1H), 8.60 (d, J=2.0 Hz, 1H), 8.53 (m, 1H), 8.14-8.11 (m, 1H), 7.94 (d, J=6.9 Hz, 1H), 7.90-7.83 (m, 2H); ESIMS found for $C_{19}H_{11}F_4N_5O$ m/z 402.30 (M+H).

The following compound was prepared in accordance with the procedure described in the above Example 2.

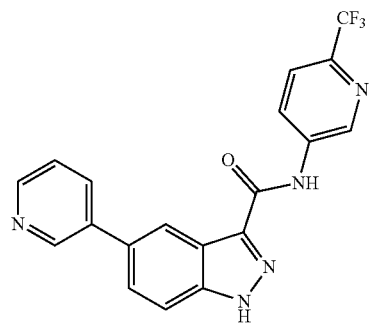

5-(Pyridin-3-yl)-N-(6-(trifluoromethyl)pyridin-3-yl)-1H-indazole-3-carboxamide 3

White solid (19% yield). $^1$H NMR (DMSO-$d_6$) δ ppm 14.03 (br. s, 1H), 11.10 (s, 1H), 9.27 (d, J=1.8 Hz, 1H), 8.94 (d, J=1.6 Hz, 1H), 8.63 (dd, J=6.8, 1.7 Hz, 1H), 8.60 (m, 1H), 8.48 (s, 1H), 8.15-8.13 (m, 1H), 7.93 (d, J=6.9 Hz, 1H), 7.85 (s, 2H), 7.54 (m, 1H); ESIMS found for $C_{19}H_{12}F_3N_5O$ m/z 384.0 (M+H).

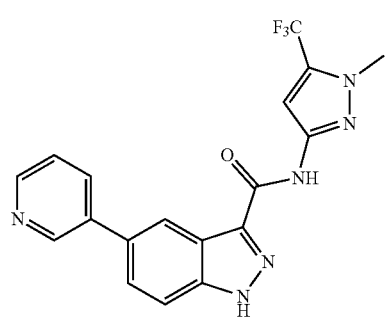

N-(1-Methyl-5-(trifluoromethyl)-1H-pyrazol-3-yl)-5-(pyridin-3-yl)-1H-indazole-3-carboxamide 37

Light green solid (76.7 mg, 0.20 mmol, 48.4% yield). NMR (DMSO-$d_6$) ppm 3.93 (s, 3H), 7.18 (s, 1H), 7.55 (dt, J=8 Hz, J=3 Hz, 1H), 7.81 (dd, J=15 Hz, J=9 Hz, 2H), 8.16 (d, J=8 Hz, 1H), 8.45 (s, 1H), 8.61 (d, J=4 Hz, 1H), 8.95 (s, 1H), 10.81 (s, 1H), 13.96 (s, 1H); ESIMS found for $C_{18}H_{13}F_3N_6O$ m/z 387.1 (M+H).

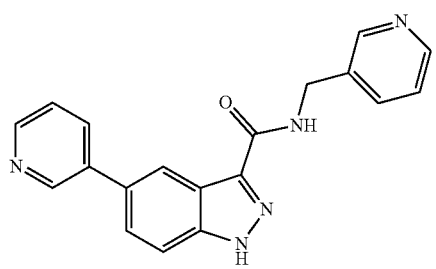

5-(Pyridin-3-yl)-N-(pyridin-3-ylmethyl)-1H-indazole-3-carboxamide 42

White solid (54.5 mg, 0.17 mmol, 78% yield). $^1$H NMR (DMSO-$d_6$) δ ppm 4.53 (d, J=6 Hz, 2H), 7.35 (dd, J=8 Hz, J=5 Hz, 1H), 7.49-7.52 (m, 1H), 7.74-7.78 (m, 3H), 8.09-8.11 (m, 1H), 8.41-8.42 (m, 1H), 8.45 (dd, J=5 Hz, J=2 Hz, 1H), 8.57 (dd, J=5 Hz, J=2 Hz, 1H), 8.59 (d, J=2 Hz, 1H), 8.90 (d, J=2 Hz, 1H), 9.16 (t, 1H), 13.77 (s, 1H); ESIMS found for $C_{19}H_{15}N_5O$ m/z 330 (M+H).

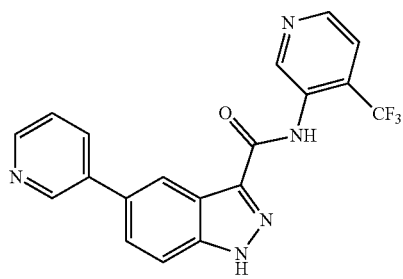

5-(Pyridin-3-yl)-N-(4-(trifluoromethyl)pyridin-3-yl)-1H-indazole carboxamide 48

White solid (67 mg, 0.17 mmol, 62% yield). $^1$H NMR (DMSO-$d_6$) δ ppm 7.52 (dd, J=8 Hz, J=5 Hz, 1H), 7.83-7.87 (m, 3H), 8.12 (td, J=8 Hz, J=2 Hz, 1H), 8.41 (t, J=1 Hz, 1H), 8.59 (dd, J=5 Hz, J=2 Hz, 1H), 8.75 (d, J=5 Hz, 1H), 8.92 (d, J=3 Hz, 1H), 9.08 (s, 1H), 10.21 (s, 1H), 14.06 (brs, 1H); ESIMS found for $C_{19}H_{12}F_3N_5O$ m/z 384.0 (M+H).

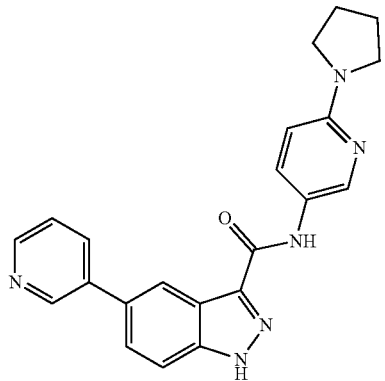

5-(Pyridin-3-yl)-N-(6-(pyrrolidin-1-yl)pyridin-3-yl)-1H-indazole-3-carboxamide 53

Beige solid (23.8 mg, 0.06 mmol, 44.5% yield). $^1$H NMR (DMSO-$d_6$) δ ppm 1.92-1.97 (m, 4H), 3.38 (t, J=7 Hz, 4H), 6.46 (d, J=9 Hz, 1H), 7.52 (dd, J=8 Hz, J=5 Hz, 1H), 7.80 (dq, J=9 Hz, J=2 Hz, 2H), 7.97 (dd, J=9 Hz, J=3 Hz, 1H), 8.12 (dd, J=8 Hz, J=4 Hz, 1H), 8.47 (s, 1H), 8.50 (d, J=3 Hz, 1H), 8.59 (dd, J=5 Hz, J=2 Hz, 1H), 8.92 (d, J=2 Hz, 1H), 10.22 (s, 1H), 13.86 (s, 1H); ESIMS found for $C_{22}H_{20}N_6O$ m/z 385.1 (M+H).

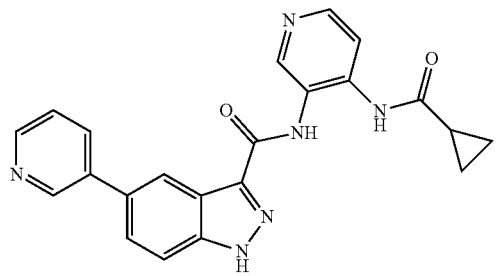

N-(4-(Cyclopropanecarboxamido)pyridin-3-yl)-5-(pyridin-3-yl)-1H-indazole-3-carboxamide 58

White solid (32.7 mg, 0.08 mmol, 37.0% yield). $^1$H NMR (DMSO-$d_6$) δ ppm 0.84-0.88 (m, 2H), 0.88-0.92 (m, 2H), 1.91-1.99 (m, 1H), 7.52 (dd, J=8 Hz, J=5 Hz, 1H), 7.73 (d, J=6 Hz, 1H), 7.82 (dd, J=12 Hz, J=9 Hz, 2H), 8.12 (dt, J=9 Hz, J=4 Hz, 1H), 8.34 (d, J=6 Hz, 1H), 8.44 (s, 1H), 8.59 (dd, J=5 Hz, J=2 Hz, 1H), 8.80 (s, 1H), 8.92 (d, J=2 Hz, 1H), 10.03 (s, 1H), 10.31 (s, 1H), 13.98 (s, 1H); ESIMS found for $C_{22}H_{18}N_6O_2$ m/z 399.0 (M+H).

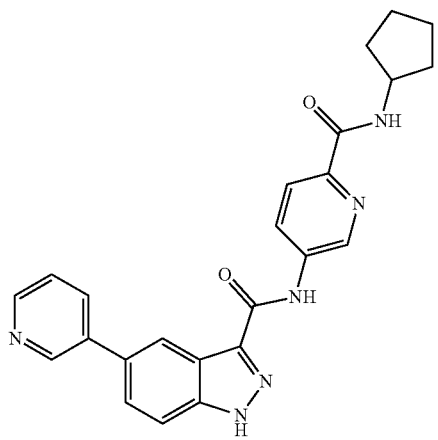

181

N-(6-(Cyclopentylcarbamoyl)pyridin-3-yl)-5-(pyridin-3-yl)-1H-indazole-3-carboxamide 181

Light yellow solid (18 mg, 0.04 mmol, 16.6% yield). $^1$H NMR (DMSO-$d_6$) ppm 1.50-1.64 (m, 4H), 1.67-1.76 (m, 2H), 1.85-1.94 (m, 4H), 4.24 (quin, J=8 Hz, 1H), 7.53 (dd, J=8 Hz, J=5 Hz, 1H), 7.84 (ABq, 2H), 8.03 (d, J=9 Hz, 1H), 8.14 (d, J=8 Hz, 1H), 8.45 (d, J=8 Hz, 1H), 8.48 (s, 1H), 8.54 (dd, J=9 Hz, J=2.5 Hz, 1H), 8.60 (d, J=4 Hz, 1H), 8.94 (d, J=2 Hz, 1H), 9.16 (d, J=2 Hz, 1H), 10.97 (s, 1H), 14.08 (brs, 1H); ESIMS found for $C_{24}H_{22}N_6O_2$ m/z 427.1 (M+H).

Example 3

Preparation of N,5-di(pyridin-3-yl)-1H-indazole-3-carboxamide (4) is Depicted Below in Scheme 29

Scheme 29

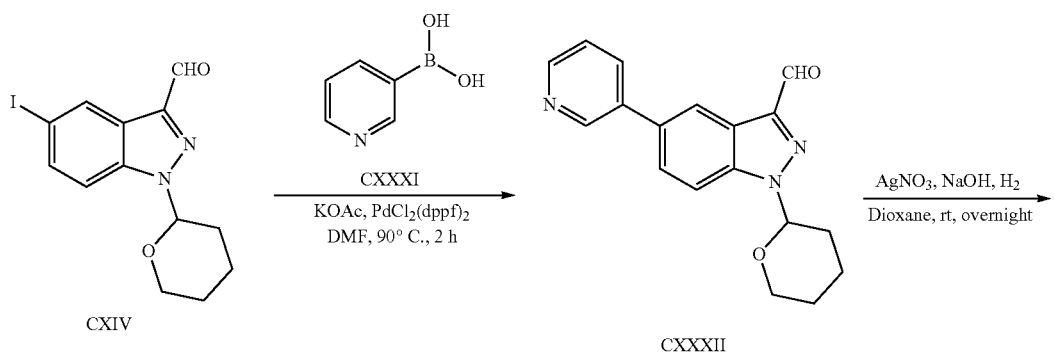

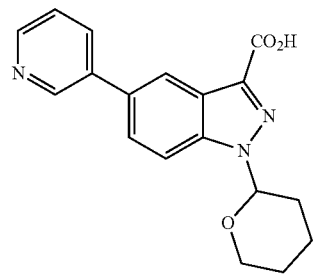

CXXXIII

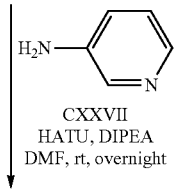

CXXVII
HATU, DIPEA
DMF, rt, overnight

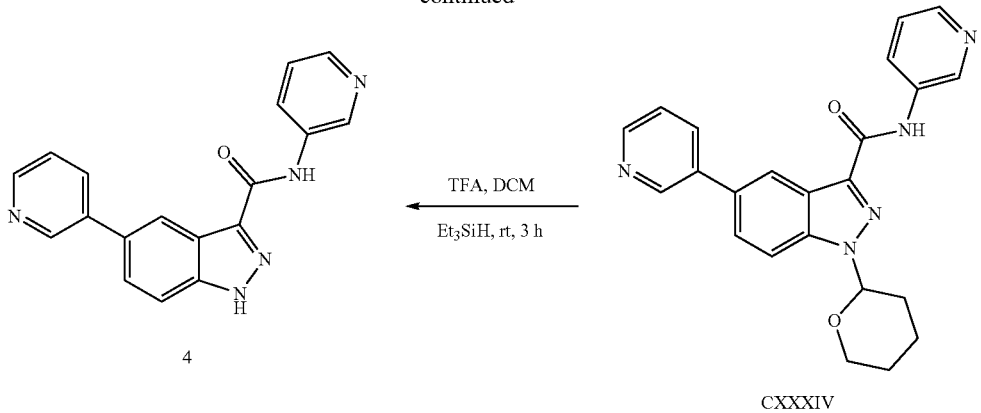

Step 1

5-Iodo-1-(tetrahydro-2H-pyran-2-yl)-1H-indazole-3-carbaldehyde (CXIV) (1.53 g, 4.30 mmol), pyridine-3-boronic acid (CXXXI) (0.58 g, 4.73 mmol), and potassium phosphate tribasic (1.37 g, 6.45 mmol) was dissolved in 1,4-dioxane (43.0 mL) and water (9.0 mL). Tetrakis(triphenylphosphine)palladium(0) (0.50 g, 0.4301 mmol) was added, and the reaction was heated to 95° C. for 2.5 h. The solvent was removed, and the residue was partitioned between EtOAc and water. The organic phase was separated and washed sequentially with water and brine. The material was dried (MgSO$_4$), concentrated, and purified by flash chromatography using a 40 g Thomson normal phase silica gel cartridge (100% hexanes→1:1 EtOAc:hexanes) to afford 5-(pyridin-3-yl)-1-(tetrahydro-2H-pyran-2-yl)-1H-indazole-3-carbaldehyde (CXXXII) (0.62 g, 2.02 mmol, 47% yield) as a tan amorphous solid. $^1$H NMR (DMSO-d$_6$) δ ppm 10.23 (s, 1H), 8.95 (d, J=2.3 Hz, 1H), 8.61 (dd, J=4.8, 1.5 Hz, 1H), 8.39 (d, J=0.98 Hz, 1H), 8.17-8.14 (m, 1H), 8.06 (d, J=8.8 Hz, 1H), 7.95-7.93 (m, 1H), 7.64-7.60 (m, 1H), 6.13 (dd, =9.4, 2.4 Hz, 1H), 3.93-3.90 (m, 1H), 3.86-3.81 (m, 1H), 2.45-2.41 (m, 1H), 2.11-2.07 (m, 2H), 1.82-1.78 (m, 1H), 1.66-1.62 (m, 2H); ESIMS found for C$_{18}$H$_{17}$N$_3$O$_2$ m/z 308 (M+H).

Step 2

To a solution of silver nitrate (0.55 g, 3.25 mmol) in water (10 mL) was added a solution of sodium hydroxide (0.26 g, 6.50 mmol) in water (5 mL) to give a brown precipitate. 5-(pyridin-3-yl)-1-(tetrahydro-2H-pyran-2-yl)-1H-indazole-3-carbaldehyde (CXXXII) (0.40 g, 1.30 mmol) dissolved in 1,4-dioxane (3 mL) was added to the reaction which was stirred at room temperature for 2 h. The reaction was then extracted with diethyl ether. The aqueous layer was separated and carefully brought to pH=3 with 10% aqueous HCl. The aqueous layer was then extracted five times with iPrOH/chloroform (1/9). The combined organic layers were then dried (MgSO$_4$) and concentrated to afford 5-(pyridin-3-yl)-1-(tetrahydro-2H-pyran-2-yl)-1H-indazole-3-carboxylic acid (CXXXIII) (0.30 g, 0.93 mmol, 70% yield) as a white solid. $^1$H NMR (DMSO-d$_6$) δ ppm 13.28 (br, 1H), 8.93 (s, 1H), 8.60 (d, J=4.1 Hz, 1H), 8.32 (d, J=0.83 Hz, 1H), 8.14-8.12 (m, 1H), 8.00 (d, J=8.8 Hz, 1H), 7.86 (dd, J=8.8, 1.7 Hz, 1H), 7.52 (dd, J=7.8, 4.7 Hz, 1H), 6.04 (dd, J=9.3, 2.3 Hz, 1H), 3.92-3.90 (m, 1H), 3.83-3.78 (m, 1H), 2.44-2.37 (m, 1H), 2.08-2.02 (m, 2H), 1.79-1.76 (m, 1H), 1.63-1.61 (m, 2H).

Step 3

To a solution of 5-(pyridin-3-yl)-1-(tetrahydro-2H-pyran-2-yl)-1H-indazole-3-carboxylic acid (CXXXIII) (0.39 g, 1.21 mmol) and 3-aminopyridine (CXXVII) (0.11 g, 1.21 mmol) in DMF (4.0 mL) was added N,N-diisopropylethylamine (0.42 mL, 1.21 mmol). The solution was cooled to 0° C. before adding HATU (0.46 g, 1.21 mmol). The ice bath was removed, and the reaction warmed to room temperature and stirred for 2 h. The DMF was removed under reduced pressure, and the residue was partitioned between chloroform and water. The organic phase was separated and washed sequentially with water and brine, dried over MgSO$_4$, filtered, and concentrated. The product was purified by column chromatography using a 25 g Thomson normal phase silica gel cartridge (100% CHCl$_3$→2:98 MeOH:CHCl$_3$) to afford N,5-di(pyridin-3-yl)-1-(tetrahydro-2H-pyran-2-yl)-1H-indazole-3-carboxamide (CXXXIV) (0.36 g, 0.90 mmol, 75% yield) as an off-white solid. $^1$H NMR (DMSO-d$_6$) δ ppm 10.56 (s, 1H), 9.06 (d, J=2.4 Hz, 1H), 8.94 (d, J=2.3 Hz, 1H), 8.60 (dd, J=4.8, 1.5 Hz, 1H), 8.47 (d, =1.1 Hz, 1H), 8.34-8.33 (m, 1H), 8.31-8.29 (m, 1H), 8.16-8.14 (m, 1H), 8.04 (d, J=8.8 Hz, 1H), 7.90 (dd, J=8.8, 1.8 Hz, 1H), 7.54-7.52 (m, 1H), 7.43-7.41 (m, 1H), 7.43-7.41 (m, 1H), 6.08-6.06 (m, 1H), 4.01-3.99 (m, 1H), 3.87-3.82 (m, 1H), 2.64-2.57 (m, 1H), 2.11-2.06 (m, 2H), 1.84-1.80 (m, 1H), 1.69-1.65 (m, 2H); ESIMS found for C$_{23}$H$_{21}$N$_5$O$_2$ m/z 400 (M+H).

Step 4

TFA (5.0 mL) was added to a solution of N,5-di(pyridin-3-yl)-1-(tetrahydro-2H-pyran-2-yl)-1H-indazole-3-carboxamide (CXXXIV) (0.36 g, 0.90 mmol) and triethylsilane (0.29 mL, 1.81 mmol) in DCM (5.0 mL). The solution was stirred overnight at room temperature. An additional 5.0 mL of TFA was added, and the solution was again stirred overnight. The solvents were removed, and the residue was treated with 7 N ammonia in MeOH. The solvents were again removed, and the product was purified by flash chromatography using a 12 g Thomson normal phase silica gel cartridge (100% CHCl$_3$→5:95 MeOH[7N NH$_3$]:CHCl$_3$) to afford N,5-di(pyridin-3-yl)-1H-indazole-3-carboxamide (4) (0.23 g, 0.73 mmol, 82% yield) as a white solid. $^1$H NMR (DMSO-d$_6$) δ ppm 14.00 (s, 1H), 10.69 (s, 1H), 9.08 (d, J=2.0 Hz, 1H), 8.93 (d, J=2.0 Hz, 1H), 8.60 (dd, J=4.8, 1.3 Hz, 1H), 8.48-8.47 (m, 1H), 8.33-8.31 (m, 2H), 8.15-8.12 (m, 1H), 7.85-7.81 (m, 2H), 7.54-7.51 (m, 1H), 7.41-7.39 (m, 1H); ESIMS found for C$_{18}$H$_{13}$N$_5$O m/z 316 (M+H).

The following compounds were prepared in accordance with the procedure described in the above Example 3.

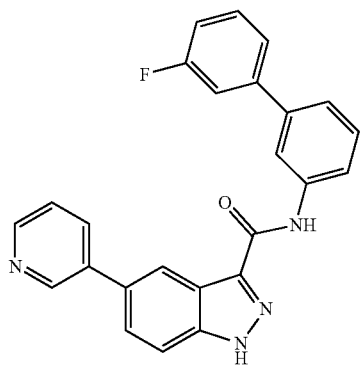

5

N-(3'-Fluorobiphenyl-3-yl)-5-(pyridin-3-yl)-1H-indazole-3-carboxamide 5

White solid (77 mg, 0.19 mmol, 69% yield). $^1$H NMR (DMSO-d$_6$) δ ppm 13.95 (s, 1H), 10.50 (s, 1H), 8.94 (d, J=2.3 Hz, 1H), 8.59 (dd, J=4.6, 1.5 Hz, 1H), 8.51 (d, J=1.0 Hz, 1H), 8.31-8.30 (m, 1H), 8.15-8.13 (m, 1H), 7.99-7.97 (m, 1H), 7.83-7.82 (m, 2H), 7.55-7.45 (m, 6H), 7.24-7.22 (m, 1H); ESIMS found for C$_{25}$H$_{17}$FN$_4$O m/z 409 (M+H).

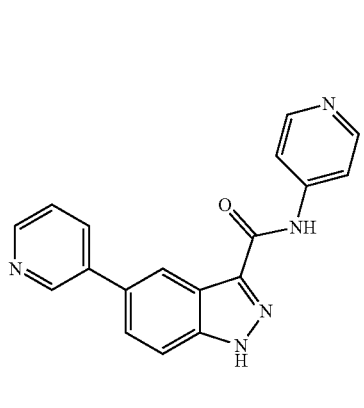

6

5-(Pyridin-3-yl)-N-(pyridin-4-yl)-1H-indazole-3-carboxamide 6

Off-white solid (52 mg, 0.16 mmol, 77% yield). $^1$H NMR (DMSO-d$_6$) δ ppm 14.05 (br, 1H), 10.83 (s, 1H), 8.94 (d, J=2.0 Hz, 1H), 8.60 (dd, J=4.6, 1.2 Hz, 1H), 8.48-8.47 (m, 3H), 8.15-8.13 (m, 1H), 7.94 (dd, 5.0, 1.4 Hz, 2H), 7.86-7.82 (m, 2H), 7.54-7.52 (m, 1H); ESIMS found for C$_{18}$H$_{13}$N$_5$O m/z 316 (M+H).

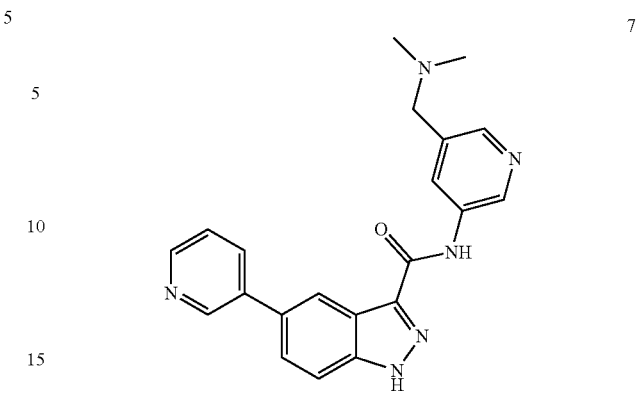

7

N-(5-((Dimethylamino)methyl)pyridin-3-yl)-5-(pyridin-3-yl)-1H-indazole carboxamide 7

Off-white solid (37 mg, 0.10 mmol, 47% yield). $^1$H NMR (DMSO-d$_6$) δ ppm 14.00 (s, 1H), 10.68 (s, 1H), 8.94 (d, J=2.0 Hz, 1H), 8.91 (d, J=2.3 Hz, 1H), 8.60 (dd, J=4.7, 1.2 Hz, 1H), 8.49-8.48 (m, 1H), 8.38-8.37 (m, 1H), 8.21 (d, J=2.2 Hz, 1H), 8.16-8.13 (m, 1H), 7.85-7.81 (m, 2H), 7.52 (dd, J=7.9, 4.9 Hz, 1H), 3.44 (s, 2H), 2.19 (s, 6H); ESIMS found for C$_{21}$H$_{120}$N$_6$O m/z 373 (M+H).

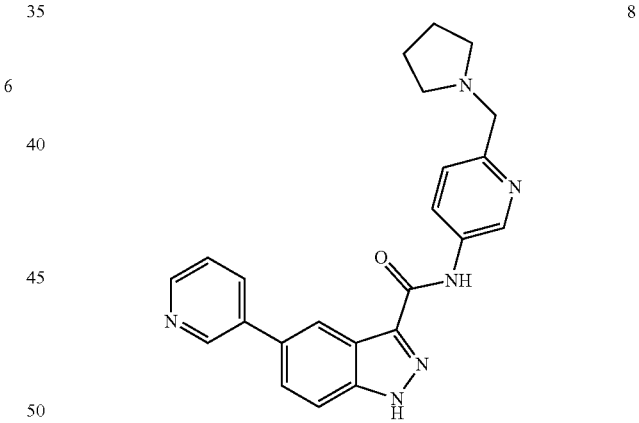

8

5-(Pyridin-3-yl)-N-(6-(pyrrolidin-1-ylmethyl)pyridin-3-yl)-1H-indazole-3-carboxamide 8

Off-white solid (38 mg, 0.10 mmol, 77% yield). $^1$H NMR (DMSO-d$_6$) δ ppm 13.99 (br, 1H), 10.64 (s, 1H), 8.96 (d, J=2.5 Hz, 1H), 8.93 (d, J=2.4 Hz, 1H), 8.59 (dd, J=4.8, 1.5 Hz, 1H), 8.48 (d, J=1.2 Hz, 1H), 8.27 (dd, J=8.5, 2.5 Hz, 1H), 8.16-8.12 (m, 1H), 7.84-7.80 (m. 2H), 7.54-7.51 (m, 1H), 7.41 (d, J=8.5 Hz, 1H), 2.37 (s, 2H), 2.50-2.47 (m, 4H), 1.72-1.70 (m, 4H); ESIMS found for C$_{23}$H$_{22}$N$_6$O m/z 399 (M+H).

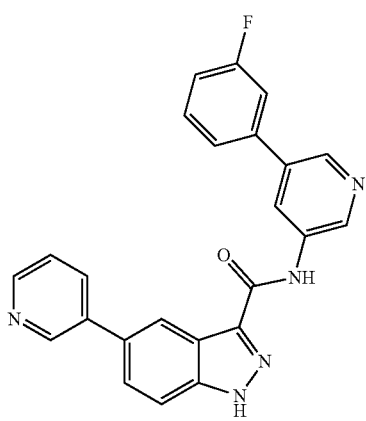

N-(5-(3-Fluorophenyl)pyridin-3-yl)-5-(pyridin-3-yl)-1H-indazole-3-carboxamide 9

White solid (35 mg, 0.09 mmol, 47% yield). $^1$H NMR (DMSO-d$_6$) δ ppm 14.05 (br s, 1H), 10.79 (s, 1H), 9.13 (d, J=2.0 Hz, 1H), 8.94 (d, J=1.9 Hz, 1H), 8.68-8.65 (m, 2H), 8.60 (dd, J=4.83, 4.83 Hz, 1H), 8.52-8.49 (m, 1H), 8.16-8.12 (m, 1H), 7.85-7.81 (m, 2H), 7.62-7.56 (m, 3H), 7.54-7.50 (m, 1H), 7.31-7.26 (m, 1H). ESIMS found for C$_{24}$H$_{16}$FN$_5$O m/z 410.5 (M+H).

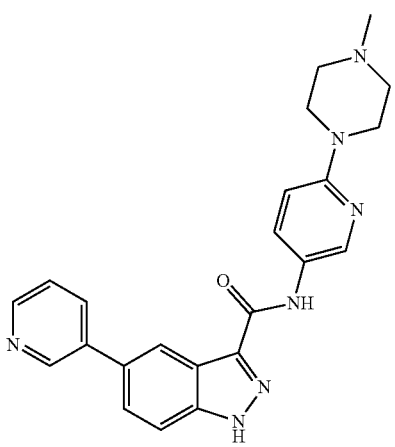

N-(6-(4-Methylpiperazin-1-yl)pyridin-3-yl)-5-(pyridin-3-yl)-1H-indazole-3-carboxamide 12

White solid (31 mg, 0.07 mmol, 39% yield). $^1$H NMR (DMSO-d$_6$) δ ppm 13.86 (br s, 1H), 10.33 (s, 1H), 8.92 (d, J=2.1 Hz, 1H), 8.60-8.58 (m, 2H), 8.46 (s, 1H), 8.14-8.11 (m, 1H), 8.10-8.02 (m, 1H), 7.83-7.78 (m, 2H), 7.54-7.50 (m, 1H), 6.86 (d, J=9.1 Hz, 1H), 3.45-3.42 (m, 4H), 2.42-2.39 (m, 4H), 2.21 (s, 3H). ESIMS found for C$_{23}$H$_{23}$N$_7$O m/z 414.3 (M+H).

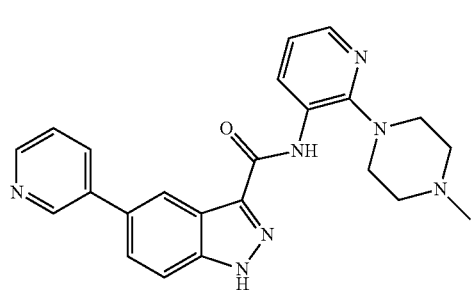

N-(2-(4-Methylpiperazin-1-yl)pyridin-3-yl)-5-(pyridin-3-yl)-1H-indazole-3-carboxamide 11

White solid (11 mg, 0.03 mmol, 65% yield). $^1$H NMR (DMSO-d$_6$) δ ppm 14.10 (s, 1H), 9.63 (s, 1H), 8.93 (d, J=2.1 Hz, 1H), 8.65-8.59 (m, 2H), 8.48 (s, 1H), 8.16-8.12 (m, 1H), 8.11-8.09 (m, 1H), 7.87-7.80 (m, 2H), 7.55-7.51 (m, 1H), 7.20-7.17 (m, 1H), 3.10-3.06 (m, 4H), 2.80-2.40 (m, 4H), 2.30 (s, 3H). ESIMS found for C$_{23}$H$_{23}$N$_7$O m/z 414.0 (M+H).

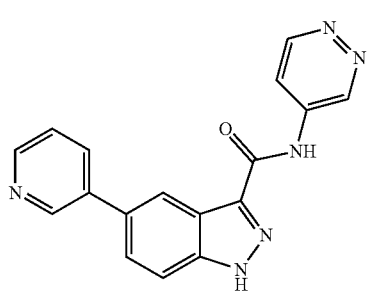

N-(Pyridazin-4-yl)-5-(pyridin-3-yl)-1H-indazole-3-carboxamide 14

Off-white solid (50 mg, 0.16 mmol, 99% yield). $^1$H NMR (DMSO-d$_6$) δ ppm 14.20-13.90 (br, 1H), 11.15 (s, 1H), 9.71-9.70 (m, 1H), 9.09-9.08 (m, 1H), 8.94 (d, J=2.0 Hz, 1H), 8.61-8.60 (m, 1H), 8.47-8.46 (m, 1H), 8.25 (dd, J=5.9, 2.8 Hz, 1H), 8.16-8.13 (m, 1H), 7.86-7.85 (m, 2H), 7.53 (dd, J=7.8, 5.0 Hz, 1H); ESIMS found for C$_{17}$H$_{12}$N$_6$O m/z 317 (M+H).

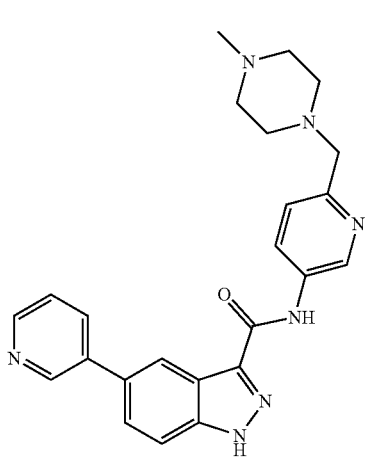

N-(6-((4-Methylpiperazin-1-yl)methyl)pyridin-3-yl)-5-(pyridin-3-yl)-1H-indazole-3-carboxamide 15

White solid (42 mg, 0.10 mmol, 81% yield). $^1$H NMR (DMSO-d$_6$) δ ppm 13.97 (br, 1H), 10.65 (s, 1H), 8.97 (d, J=2.4 Hz, 1H), 8.93 (d, J=2.1 Hz, 1H), 8.59 (dd, J=4.7, 1.5 Hz, 1H), 8.48-8.47 (m, 1H), 8.28 (dd, J=8.5, 2.5 Hz, 1H), 8.15-8.12 (m, 1H), 7.85-7.81 (m, 2H), 7.54-7.51 (m, 1H), 7.40 (d, J=8.5 Hz, 1H), 3.55 (s, 2H), 2.42-2.28 (m, 8H), 2.15 (s, 3); ESIMS found for C$_{24}$H$_{25}$N$_7$O m/z 428 (M+H).

Example 4

Preparation of 5-(5-fluoropyridin-3-yl)-N-(pyridin-3-yl)-1H-indazole-3-carboxamide (13) is Depicted Below in Scheme 30

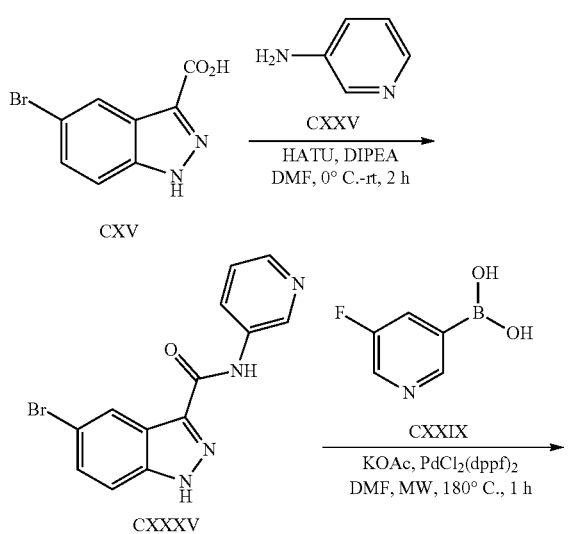

Scheme 30

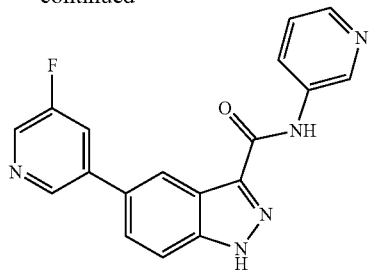

13

Step 1

To a stirring solution of 3-aminopyridine (CXXV) (0.195 g, 0.2.07 mmol) in DMF (10 mL) was added 5-bromo-1H-indazole-3-carboxylic acid (CXV) (0.500 g, 0.2.07 mmol) and N,N-diisopropylethylamine (0.723 mL, 4.15 mmol). The reaction mixture was cooled to 0° C. and added with HATU (0.787 g, 2.07 mmol). The reaction mixture was allowed to warm to room temperature and stirred for an additional 2 h. The solution was concentrated under vacuum. The residue was purified by column chromatography (1:99 MeOH[7N NH$_3$]:CHCl$_3$→4:96 MeOH[7N NH$_3$]:CHCl$_3$) to afford 5-bromo-N-(pyridin-3-yl)-1H-indazole-3-carboxamide (CXXXV) (0.200 g, 0.63 mmol, 30% yield) as a white solid. ESIMS found for C$_{13}$H$_9$BrN$_4$O m/z 318.0 (M+H).

Step 2

To a microwave vial was added 5-bromo-N-(pyridin-3-yl)-1H-indazole-3-carboxamide (CXXXV) (0.200 g, 0.63 mmol), 5-fluoropyridine-3-boronic acid (CXXIX) (0.098 g, 0.694 mmol), tetrakis(triphenylphosphine)palladium(0) (0.036 g, 0.032 mmol), potassium phosphate (0.201 g, 0.947 mmol), water (1 mL), and DMF (5 mL). The reaction vial was capped, purged with argon and heated under microwave irradiation for 1 h at 180° C. The solution was filtered through a pad of Celite and concentrated under vacuum. The crude product was purified by column chromatography (100% CHCl$_3$→2:98 MeOH[7N NH$_3$]: CHCl$_3$) to afford 5-(5-fluoropyridin-3-yl)-N-(pyridin-3-yl)-1H-indazole-3-carboxamide (13) (4 mg, 0.01 mmol, 2% yield) as a white solid. $^1$H NMR (DMSO-d$_6$) δ ppm 14.02 (br s, 1H), 10.70 (s, 1H), 9.08 (d, J=2.5 Hz, 1H), 8.83 (t, J=1.8 Hz, 1H), 8.60 (d, J=2.7 Hz, 1H), 8.53-8.52 (m, 1H), 8.34-8.29 (m, 2H), 8.14-8.09 (m, 1H), 7.89-7.81 (m, 2H), 7.42-7.38 (m, 1H). ESIMS found for C$_{18}$H$_{12}$FN$_5$O m/z 334.0 (M+H).

Example 5
Preparation of N-(pyridin-3-yl)-5-(5-(trifluoromethyl)pyridin-3-yl)-1H-indazole-3-carboxamide (16) is Depicted Below in Scheme 31
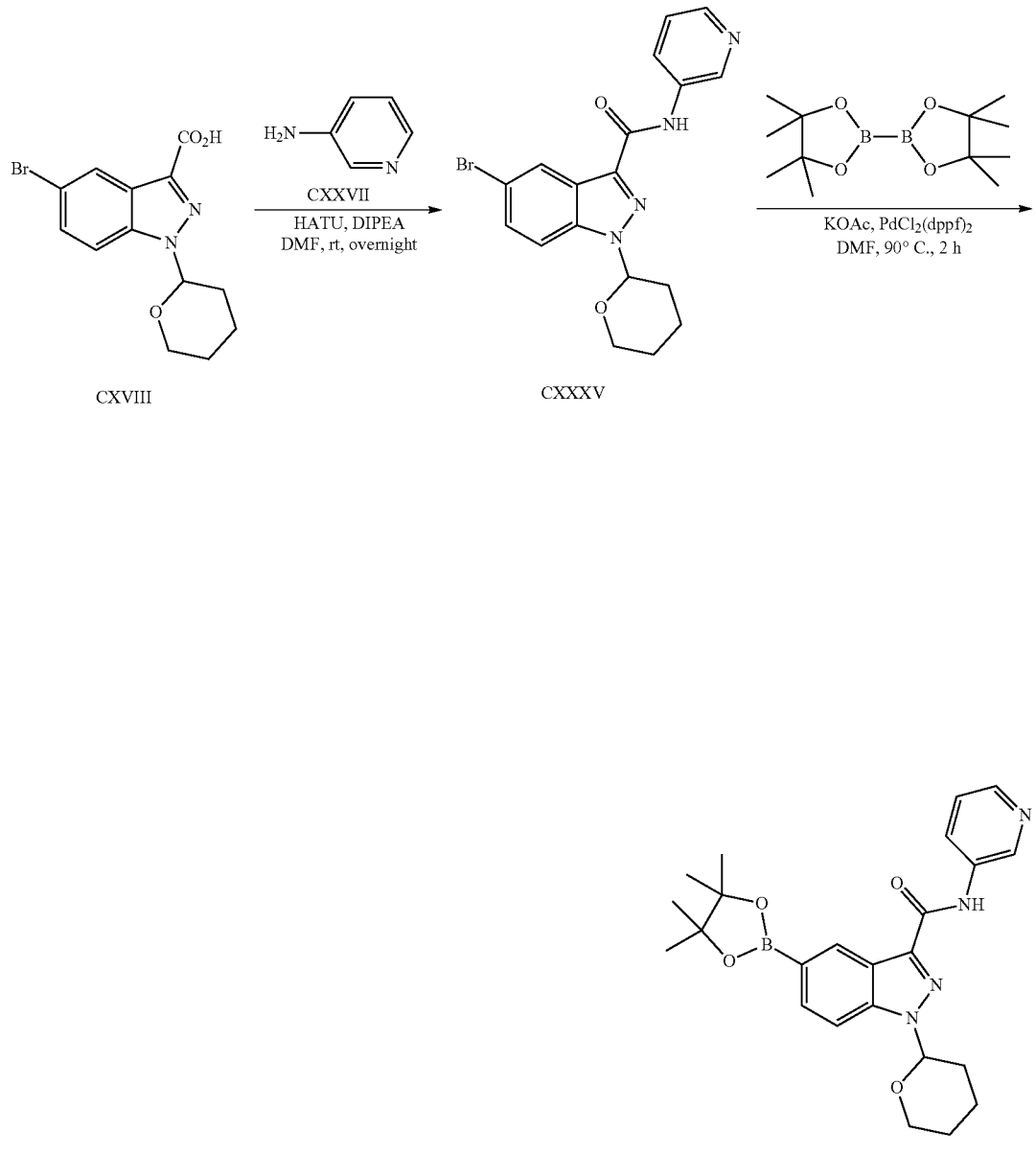
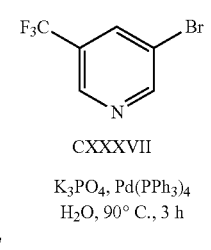

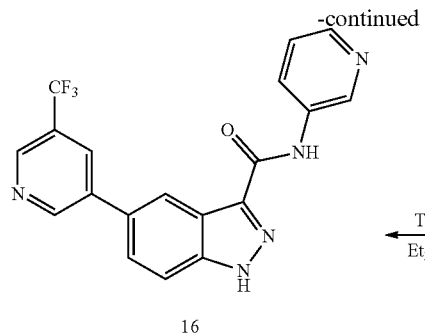

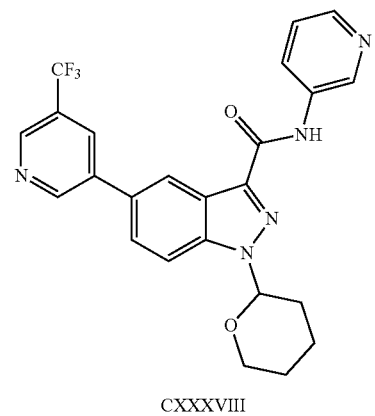

TFA, DCM,
Et₃SiH, rt, 3 h

16

CXXXVIII

Step 1

Preparation of intermediate 5-bromo-N-(pyridin-3-yl)-1-(tetrahydro-2H-pyran-2-yl)-1H-indazole-3-carboxamide (CXXXV) was performed following the procedure listed in Scheme 19, Step 4. Light yellow solid (5.5 g, 13.7 mmol, 88% yield). ESIMS found for $C_{18}H_{17}BrN_4O_2$ m/z 401.1 ($M^{79Br}$+H) and 403.1 ($M^{81Br}$+H).

Steps 2-3

Preparation of intermediate N-(pyridin-3-yl)-1-(tetrahydro-2H-pyran-2-yl)-5-(5-(trifluoromethyl)pyridin-3-yl)-1H-indazole-3-carboxamide (CXXXVIII) was performed following the procedure listed in Scheme 26, Steps 1-2. Tan solid (295 mg, 0.63 mmol, 84% yield). ESIMS found for $C_{24}H_{20}F_3N_5O_2$ m/z 468.1 (M+H).

Step 4

Preparation of N-(pyridin-3-yl)-5-(5-(trifluoromethyl)pyridin-3-yl)-1H-indazole-3-carboxamide (16) was performed following the procedure listed in Scheme 28, Step 4. White solid (95 mg, 0.25 mmol, 39.3% yield). ¹H NMR (DMSO-d₆) δ ppm 7.40 (dd, J=2.2 Hz, J=2 Hz, 1H), 7.84 (d, J=6.7 Hz, 1H), 7.93 (dd, J=1.5 Hz, J=7 Hz, 1H), 8.29-8.34 (m, 2H), 8.50 (s, 1H), 8.57 (s, 1H), 8.99 (s, 1H), 9.09 (d, J=2 Hz, 1H), 9.25 (d, J=1.6 Hz, 1H), 10.72 (brs, 1H); ESIMS found for $C_{19}H_{12}F_3N_5O$ m/z 383.9 (M+H).

The following compounds were prepared in accordance with the procedure described in the above Example 5.

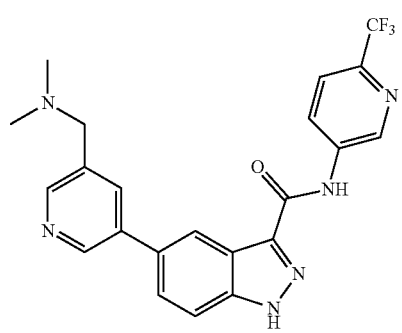

5-(5-((Dimethylamino)methyl)pyridin-3-yl)-N-(6-(trifluoromethyl) pyridin-3-yl)-1H-indazole-3-carboxamide 26

White solid (93 mg, 0.21 mmol, 78% yield). ¹H NMR (DMSO-d₆) δ ppm 2.24 (s, 6H), 3.57 (s, 2H), 7.86 (Abq, J=8 Hz, 2H), 7.93 (d, J=9 Hz, 1H), 8.04 (brs, 1H), 8.50 (d, J=7 Hz, 1H), 8.63 (dd, J=9 Hz, J=2 Hz, 1H), 8.85 (d, J=2 Hz, 1H), 9.27 (d, J=2 Hz, 1H), 11.11 (s, 1H), 14.11 (s, 1H); ESIMS found for $C_{22}H_{19}F_3N_6O$ m/z 441.0 (M+H)

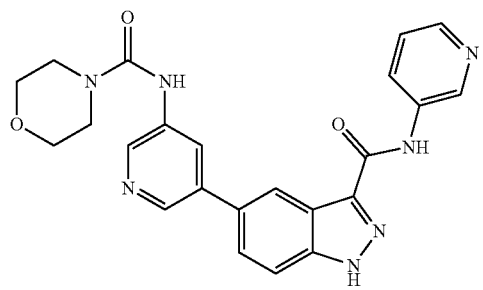

N-(5-(3-(Pyridin-3-ylcarbamoyl)-1H-indazol-5-yl)pyridin-3-yl) morpholine-4-carboxamide 32

White solid (132 mg, 0.30 mmol, 56% yield). ¹H NMR (DMSO-d₆) δ ppm 3.49 (t, J=5 Hz, 4H), 3.64 (t, J=5 Hz, 4H), 7.40 (dd, J=8 Hz, J=5 Hz, 1H), 7.82 (d, J=1 Hz, 1H), 8.26 (t, J=2 Hz, 1H), 8.30-8.34 (m, 2H), 8.47 (s, 1H), 8.54 (d, J=2 Hz, 1H), 8.72 (d, J=2 Hz, 1H), 8.87 (s, 1H), 9.09 (d, 2 Hz, 1H), 10.71 (s, 1H), 14.01 (s, 1H); ESIMS found for $C_{23}H_{21}N_7O_3$ m/z 444.3 (M+H).

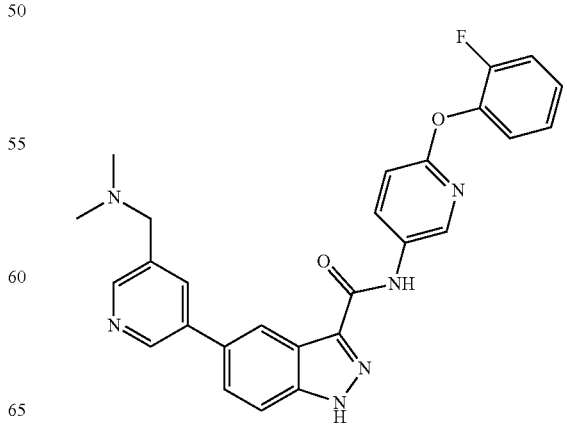

5-(5-((Dimethylamino)methyl)pyridin-3-yl)-N-(6-(2-fluorophenoxy) pyridin-3-yl)-1H-indazole-3-carboxamide 36

White solid (137 mg, 0.28 mmol, 53% yield). $^1$H NMR (DMSO-d$_6$) δ ppm 2.20 (s, 6H), 3.53 (s, 2H), 7.16 (d, J=9 Hz, 1H), 7.22-7.40 (m, 4H), 7.82 (d/Abq, J=9 Hz, J=1 Hz, 2H), 8.00 (t, J=2 Hz, 1H), 8.38 (dd, J=9 Hz, J=3 Hz, 1H), 8.47 (s, 1H), 8.49 (d, J=2 Hz, 1H), 8.55 (d, J=3 Hz, 1H), 8.83 (d, J=2 Hz, 1H), 10.67 (s, 1H), 13.97 (brs, 1H); ESIMS found for C$_{27}$H$_{23}$FN$_6$O$_2$ m/z 383.1 (M+H).

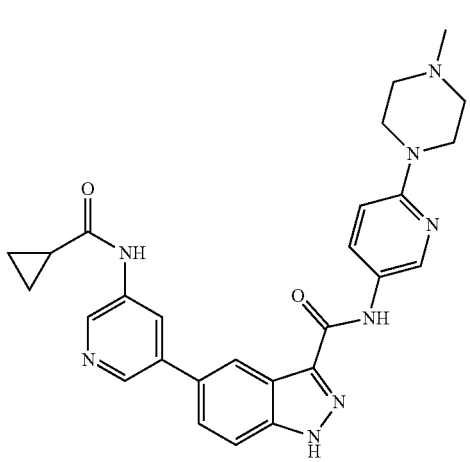

5-(5-(Cyclopropanecarboxamido)pyridin-3-yl)-N-(6-(4-methylpiperazin-1-yl)pyridin-3-yl)-1H-indazole-3-carboxamide 38

White solid (39 mg, 0.08 mmol, 61% yield). $^1$H NMR (DMSO-d$_6$) δ ppm 0.83-0.90 (m, 4H), 1.80-1.86 (m, 1H), 2.25 (brs, 3H), 2.45 (brs, 4H), 3.45 (brs, 4H), 6.86 (d, J=9 Hz, 1H), 7.79 (d, J=1 Hz, 1H), 8.04 (dd, J=9 Hz, J=3 Hz, 1H), 8.42 (t, J=2 Hz, 1H), 8.46 (s, 1H), 8.60 (dd, J=10 Hz, J=3 Hz, 2H), 8.76 (d, J=2 Hz, 1H), 10.34 (s, 1H), 10.56 (s, 1H), 13.90 (s, 1H); ESIMS found for C$_{27}$H$_{27}$N$_8$O$_2$ m/z 497.4 (M+H).

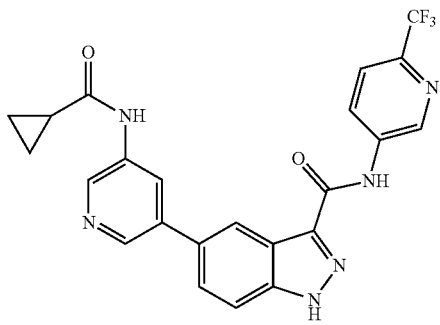

5-(5-(Cyclopropanecarboxamido)pyridin-3-yl)-N-(6-(trifluoromethyl) pyridin-3-yl)-1H-indazole-3-carboxamide 39

White solid (128 mg, 0.27 mmol, 45% yield). $^1$H NMR (DMSO-d$_6$) δ ppm 0.82-0.90 (m, 4H), 1.80-1.86 (m, 1H), 7.84 (s, 2H0, 7.92 (d, J=9 Hz, 1H), 8.43 (d, J=2 Hz, 1H), 8.48 (s, 1H), 8.61-8.65 (m, 2H), 8.77 (d, J=2 Hz, 1H), 9.27 (d, J=2 Hz, 1H), 10.57 (s, 1H), 11.11 (s, 1H), 14.11 (s, 1H); ESIMS found for C$_{23}$H$_{17}$F$_3$N$_6$O$_2$ m/z 467.1 (M+H).

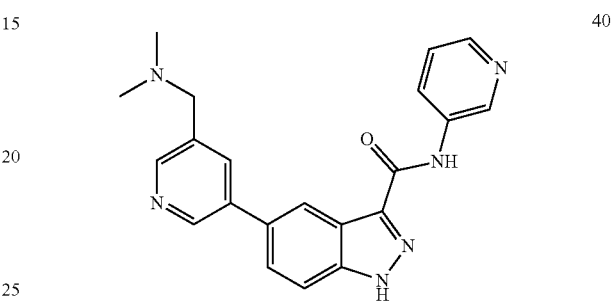

5-(5-((Dimethylamino)methyl)pyridin-3-yl)-N-(pyridin-3-yl)-1H-indazole-3-carboxamide 40

White solid (312 mg, 0.84 mmol, 77% yield). $^1$H NMR (DMSO-d$_6$) δ ppm 2.21 (s, 6H), 3.53 (s, 2H), 7.40 (dd, J=8 Hz, J=5 Hz, 1H), 7.83 (d/Abq, J=9 Hz, J=2 Hz, 2H), 8.01 (t, J=2 Hz, 1H), 8.29-8.34 (m, 2H), 8.48 (dd, J=4 Hz, J=1 Hz, 1H), 8.83 (d, J=2 Hz, 1H), 9.08 (d, J=3 Hz, 1H), 10.70 (s, 1H), 13.99 (brs, 1H); ESIMS found for C$_{21}$H$_{20}$N$_6$O m/z 373.0 (M+H).

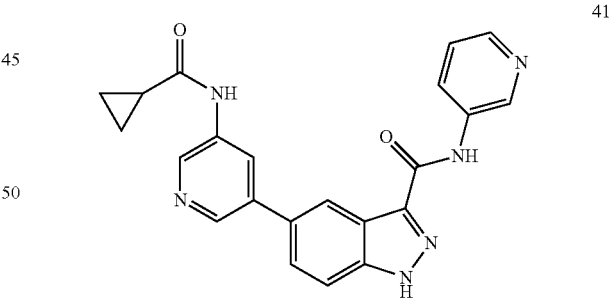

5-(5-(Cyclopropanecarboxamido)pyridin-3-yl)-N-(pyridin-3-yl)-1H-indazole-3-carboxamide 41

White solid (148 mg, 0.37 mmol, 71% yield). $^1$H NMR (DMSO-d$_6$) δ ppm 0.83-0.90 (m, 4H), 1.80-1.87 (m, 1H), 7.40 (dd, J=8 Hz, J=5 Hz, 1H), 7.82 (d, J=1 Hz, 1H), 8.29-8.34 (m, 2H), 8.43 (t, J=2 Hz, 1H), 8.47 (s, 1H), 8.62 (d, J=2 Hz, 1H), 8.76 (d, J=2 Hz, 1H), 9.08 (d, J=2 Hz, 1H), 10.57 (s, 1H), 10.70 (s, 1H), 14.01 (s, 1H); ESIMS found for C$_{22}$H$_{18}$N$_6$O$_2$ m/z 399.0 (M+H).

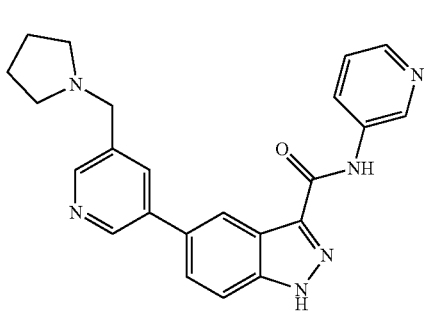

N-(Pyridin-3-yl)-5-(5-(pyrrolidin-1-ylmethyl)pyridin-3-yl)-1H-indazole-3-carboxamide 43

White solid (157 mg, 0.39 mmol, 76% yield). $^1$H NMR (DMSO-d$_6$) δ ppm 1.70-1.74 (m, 4H), 2.46-2.52 (m, 4H), 3.71 (s, 2H), 7.40 (dd, J=8 Hz, J=5 Hz, 1H), 7.83 (d/Abq, J=9 Hz, J=2 Hz, 2H), 8.02 (t, J=2 Hz, 1H), 8.29-8.34 (m, 2H), 8.48 (s, 1H), 8.51 (d, J=2 Hz, 1H), 8.82 (d, J=2 Hz, 1H), 9.08 (d, J=2 Hz, 1H), 10.70 (s, 1H), 14.00 (s, 1H); ESIMS found for C$_{23}$H$_{22}$N$_6$O m/z 399.0 (M+H).

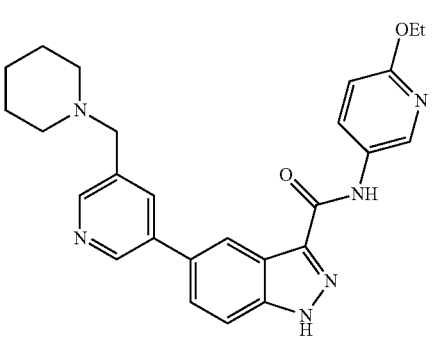

N-(6-Ethoxypyridin-3-yl)-5-(5-(piperidin-1-ylmethyl)pyridin-3-yl)-1H-indazole-3-carboxamide 45

White solid (98 mg, 0.21 mmol, 44% yield). $^1$H NMR (DMSO-d$_6$) δ ppm 1.32 (t, J=7 Hz, 3H), 1.34-1.42 (m, 2H), 1.47-1.53 (m, 4H), 2.38 (brs, 4H), 3.56 (s, 2H), 4.29 (q, J=7 Hz, 2H), 6.81 (d, J=9 Hz, 1H), 7.81 (d/Abq, J=9 Hz, J=2 Hz, 2H), 7.99 (t, J=2 Hz, 1H), 8.16 (dd, J=9 Hz, J=3 Hz, 1H), 8.46 (d, J=1 Hz, 1H), 8.49 (d, J=2 Hz, 1H), 8.63 (d, J=2 Hz, 1H), 8.81 (d, J=2 Hz, 1H), 10.51 (s, 1H), 13.92 (brs, 1H); ESIMS found for C$_{26}$H$_{28}$N$_6$O$_2$ m/z 457.3 (M+H).

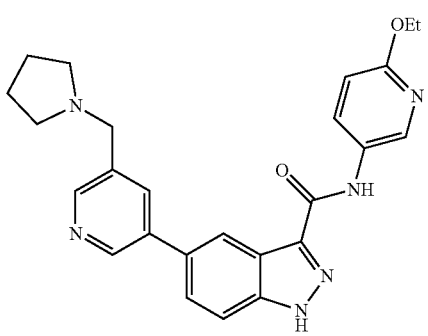

N-(6-Ethoxypyridin-3-yl)-5-(5-(pyrrolidin-1-ylmethyl)pyridin-3-yl)-1H-indazole-3-carboxamide 44

White solid (62 mg, 0.14 mmol, 39% yield). $^1$H NMR (DMSO-d$_6$) δ ppm 1.32 (t, J=7 Hz, 3H), 1.70-1.74 (m, 4H), 2.47-2.52 (m, 4H), 3.71 (s, 2H), 4.29 (q, J=7 Hz, 2H), 6.81 (d, J=9 Hz, 1H), 7.82 (d/Abq, J=9 Hz, J=2 Hz, 2H), 8.01 (t, J=2 Hz, 1H), 8.16 (dd, J=9 Hz, J=3 Hz, 1H), 8.46 (s, 1H), 8.51 (d, J=2 Hz, 1H), 8.63 (d, J=2 Hz, 1H), 8.81 (d, J=2 Hz, 1H), 10.51 (s, 1H), 13.94 (brs, 1H); ESIMS found for C$_{25}$H$_{26}$N$_6$O$_2$ m/z 443.4 (M+H).

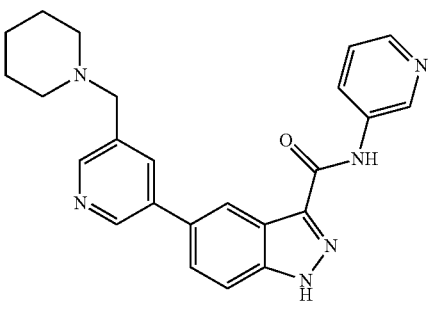

5-(5-(Piperidin-1-ylmethyl)pyridin-3-yl)-N-(pyridin-3-yl)-1H-indazole-3-carboxamide 46

White solid (126 mg, 0.31 mmol, 52% yield). $^1$H NMR (DMSO-d$_6$) δ ppm 1.36-1.42 (m, 2H), 1.48-1.55 (m, 4H), 2.39 (brs, 4H), 3.57 (s, 2H), 7.40 (dd, J=8 Hz, J=5 Hz, 1H), 7.83 (d/Abq, J=9 Hz, J=2 Hz, 2H), 7.99 (t, J=2 Hz, 1H), 8.30-8.34 (m, 2H), 8.48 (d, J=1 Hz, 1H), 8.49 (d, J=2 Hz, 1H), 8.82 (d, J=2 Hz, 1H), 9.08 (d, J=2 Hz, 1H), 10.70 (s, 1H), 14.00 (brs, 1H); ESIMS found for C$_{24}$H$_{24}$N$_6$O m/z 413.0 (M+H).

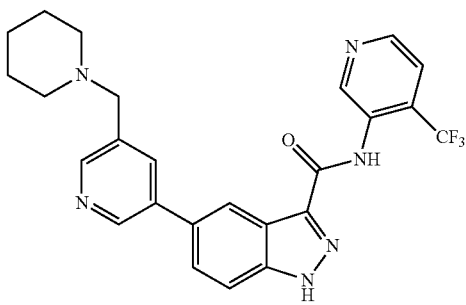

5-(5-(Piperidin-1-ylmethyl)pyridin-3-yl)-N-(4-(trifluoromethyl) pyridin yl)-1H-indazole-3-carboxamide 47

White solid (150 mg, 0.31 mmol, 71% yield). NMR (DMSO-$d_6$) δ ppm 1.34-1.42 (m, 2H), 1.46-1.53 (m, 4H), 2.37 (brs, 4H), 3.55 (s, 2H), 7.81-7.87 (m, 3H), 7.98 (s, 1H), 8.41 (s, 1H), 8.48 (d, J=2 Hz, 1H), 8.75 (d, J=5 Hz, 1H), 8.80 (d, J=2 Hz, 1H), 9.07 (s, 1H), 10.22 (s, 1H), 14.06 (brs, 1H); ESIMS found for $C_{25}H_{23}F_3N_6O$ m/z 481.0 (M+H).

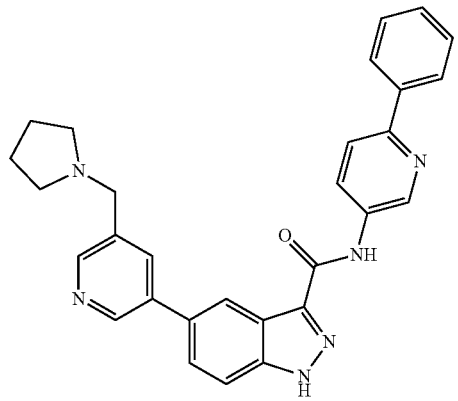

N-(6-Phenylpyridin-3-yl)-5-(5-(pyrrolidin-1-ylmethyl)pyridin-3-yl)-1H-indazole-3-carboxamide 50

Tan flaky solid (61.3 mg, 0.13 mmol, 74% yield). $^1$H NMR (DMSO-$d_6$) δ ppm 1.71-1.72 (m, 4H), 3.72 (s, 2H), 7.39-7.42 (m, 1H), 7.47-7.50 (m, 2H), 7.81-7.86 (m, 2H), 8.00 (d, J=9 Hz, 1H), 8.02-8.03 (m, 1H), 8.08-8.10 (m, 2H), 8.45 (dd, J=9 Hz, J=3 Hz, 1H), 8.49-8.50 (m, 1H), 8.51 (d, J=2 Hz, 1H), 8.83 (d, J=2 Hz, 1H), 9.18 (d, J=3 Hz, 1H), 10.81 (s, 1H), 14.03 (s, 1H); ESIMS found for $C_{29}H_{26}N_6O$ m/z 475 (M+H).

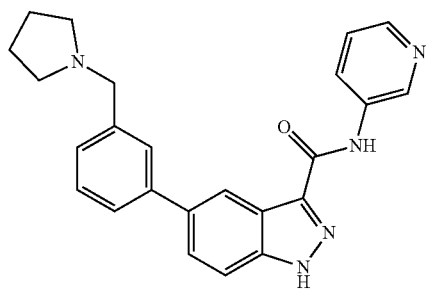

N-(Pyridin-3-yl)-5-(3-(pyrrolidin-1-ylmethyl)phenyl)-1H-indazole-3-carboxamide 49

Tan amorphous solid (53.4 mg, 0.13 mmol, 72% yield). NMR (DMSO-$d_6$) δ ppm 1.70-1.71 (m, 4H), 2.47-2.49 (m, 4H), 3.67 (s, 2H), 7.31 (d, J=8 Hz, 1H), 7.40 (dd, J=8 Hz, J=5 Hz, 1H), 7.44 (t, J=8 Hz, 1H), 7.58-7.60 (m, 1H), 7.63-7.64 (m, 1H), 7.76-7.78 (m, 2H), 8.30-8.34 (m, 2H), 8.44 (s, 1H), 9.08 (d, J=2 Hz, 1H), 10.68 (s, 1H), 13.93 (s, 1H); ESIMS found for $C_{24}H_{23}N_5O$ m/z 398 (M+H).

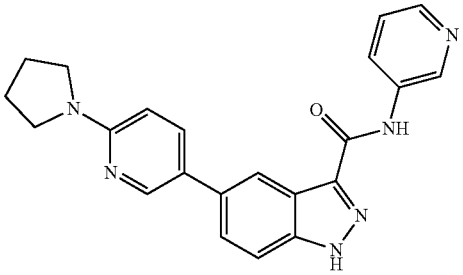

N-(Pyridin-3-yl)-5-(6-(pyrrolidin-1-yl)pyridin-3-yl)-1H-indazole-3-carboxamide 51

Yellow solid (32 mg, 0.08 mmol. 37.8% yield). $^1$H NMR (DMSO-$d_6$) δ ppm 1.94-2.01 (m, 4H), 3.42-3.48 (m, 4H), 6.57 (d, J=9 Hz, 1H), 7.40 (dd, J=8 Hz, J=5 Hz, 1H), 7.72 (d, J=1 Hz, 2H), 7.85 (dd, J=9 Hz, J=3 Hz, 1H), 8.29-8.34 (m, 3H), 8.43 (d, J=2 Hz, 1H), 9.08 (d, J=2 Hz, 1H), 10.63 (s, 1H), 13.87 (s, 1H); ESIMS found for $C_{22}H_{20}N_6O$ m/z 385.0 (M+H).

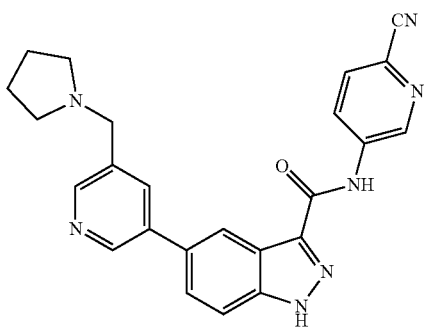

N-(6-Cyanopyridin-3-yl)-5-(5-(pyrrolidin-1-ylmethyl)pyridin-3-yl)-1H-indazole-3-carboxamide 52

Beige solid (52 mg, 0.12 mmol, 49.1% yield). $^1$H NMR (DMSO-$d_6$) δ ppm 1.70-1.75 (m, 4H), 3.31-3.36 (m, 4H), 7.85 (dq, J=9 Hz, J=2 Hz, 2H), 8.02 (s, 1H), 8.05 (d, J=9 Hz, 1H), 8.47 (s, 1H), 8.52 (d, J=2 Hz, 1H), 8.58 (dd, J=9 Hz, J=3 Hz, 1H), 8.82 (d, J=2 Hz, 1H), 9.28 (d, J=2 Hz, 1H), 11.18 (s, 1H), 14.13 (brs, 1H); ESIMS found for $C_{24}H_{21}N_7O$ m/z 424.3 (M+H).

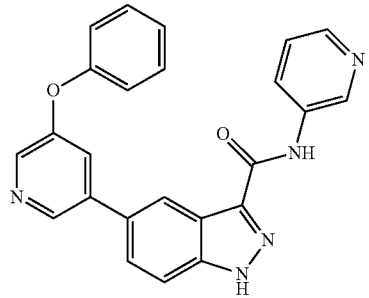

5-(6-Methoxypyridin-3-yl)-N-(pyridin-3-yl)-1H-indazole-3-carboxamide 54

White solid (79.7 mg, 0.23 mmol, 44.2% yield). $^1$H NMR (DMSO-$d_6$) δ ppm 3.91 (s, 3H), 6.95 (d, J=9 Hz, 1H), 7.40 (dd, J=9 Hz, J=5 Hz, 1H), 7.78 (dd, J=11 Hz, J=2 Hz, 2H), 8.06 (dd, J=9 Hz, J=3 Hz, 1H), 8.29-8.34 (m, 2H), 8.39 (s, 1H), 8.51 (d, J=2 Hz, 1H), 9.08 (d, J=3 Hz, 1H), 10.67 (s, 1H), 13.91 (brs, 1H); ESIMS found for $C_{19}H_{15}N_5O_2$ m/z 346.0 (M+H).

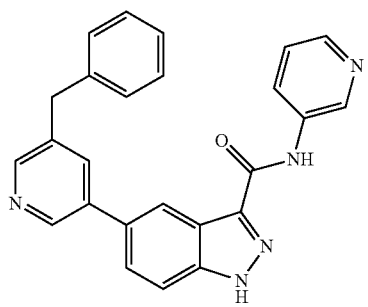

5-(5-Benzylpyridin-3-yl)-N-(pyridin-3-yl)-1H-indazole-3-carboxamide 55

Yellow solid (101.9 mg, 0.25 mmol, 76% yield). $^1$H NMR (DMSO-$d_6$) δ ppm 4.09 (s, 2H), 7.19-7.23 (m, 1H), 7.30-7.35 (m, 4H), 7.39-7.41 (m, 1H), 7.78-7.82 (m, 2H), 7.99 (t, J=2 Hz, 1H), 8.31-8.33 (m, 2H), 8.45 (s, 1H), 8.51 (d, J=2 Hz, 1H), 8.76 (d, J=2 Hz, 1H), 9.08 (d, J=2 Hz, 1H), 10.69 (s, 1H), 14.00 (s, 1H); ESIMS found for $C_{25}H_{19}N_5O$ m/z 406 (M+H).

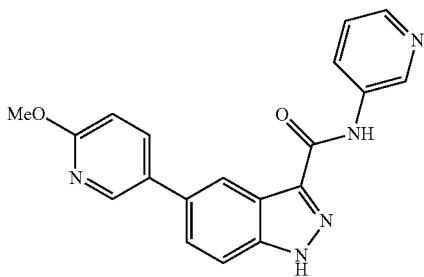

5-(5-Phenoxypyridin-3-yl)-N-(pyridin-3-yl)-1H-indazole-3-carboxamide 56

White solid (73.6 mg, 0.18 mmol, 75% yield). $^1$H NMR (DMSO-$d_6$) δ ppm 7.17-7.18 (m, 2H), 7.22-7.23 (m, 1H), 7.38-7.41 (m, 1H), 7.44-7.47 (m, 2H), 7.72-7.73 (m, 1H), 7.80-7.81 (m, 2H), 8.29-8.31 (m, 2H), 8.37-8.38 (m, 1H), 8.44-8.45 (m, 1H), 8.74 (d, J=2 Hz, 1H), 9.06 (d, J=2 Hz, 1H), 10.69 (s, 1H), 14.00 (s, 1H); ESIMS found for $C_{24}H_{17}N_5O_2$ m/z 408 (M+H).

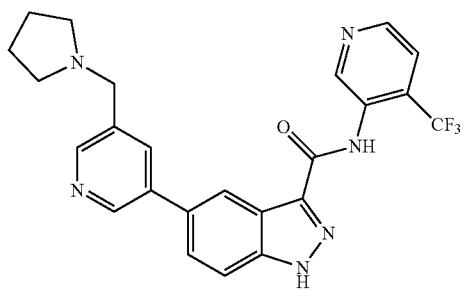

5-(5-(Pyrrolidin-1-ylmethyl)pyridin-3-yl)-N-(4-(trifluoromethyl) pyridin yl)-1H-indazole-3-carboxamide 57

White solid (64 mg, 0.14 mmol, 35.2% yield). $^1$H NMR (DMSO-$d_6$) δ ppm 1.67-1.74 (m, 4H), 2.44-2.52 (m, 4H), 3.70 (s, 2H), 7.81-7.88 (m, 3H), 8.00 (d, J=2 Hz, 1H), 8.41 (s, 1H), 8.50 (d, J=2 Hz, 1H), 8.75 (d, J=5 Hz, 1H), 8.81 (d, J=2 Hz, 1H), 9.07 (s, 1H), 10.22 (s, 1H), 14.01 (brs, 1H); ESIMS found for $C_{24}H_{21}F_3N_6O$ m/z 467.3 (M+H).

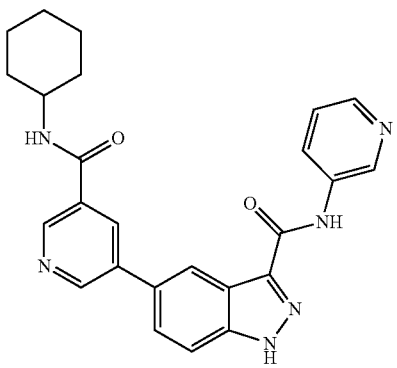

5-(5-(Cyclohexylcarbamoyl)pyridin-3-yl)-N-(pyridin-3-yl)-1H-indazole-3-carboxamide 59

Light brown solid (117 mg, 0.27 mmol, 49.7% yield). $^1$H NMR (DMSO-d$_6$) δ ppm 1.10-1.21 (m, 1H), 1.28-1.39 (m, 4H), 1.63 (d, J=12 Hz, 1H), 1.72-1.78 (m, 2H), 1.86-1.91 (m, 2H), 3.77-3.87 (m, 1H), 7.41 (dd, J=8 Hz, J=5 Hz, 1H), 7.84 (d, J=8 Hz, 1H), 7.91 (d, J=9 Hz, 1H), 8.30-8.36 (m, 2H), 8.48 (t, J=2 Hz, 1H), 8.55 (s, 1H), 8.59 (d, J=8 Hz, 1H), 8.99 (d, J=2 Hz, 1H), 9.04 (d, J=2 Hz, 1H), 9.09 (d, J=2 Hz, 1H), 10.72 (s, 1H), 14.04 (s, 1H); ESIMS found for C$_{25}$H$_{24}$N$_6$O$_2$ m/z 441.0 (M+H).

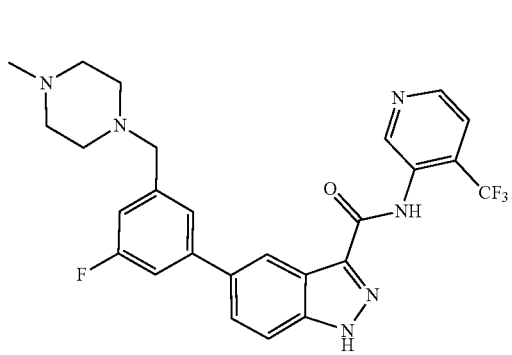

5-(3-Fluoro-5-((4-methylpiperazin-1-yl)methyl)phenyl)-N-(4-(trifluoromethyl)pyridin-3-yl)-1H-indazole-3-carboxamide 60

White solid (43 mg, 0.08 mmol, 76.3% yield). $^1$H NMR (DMSO-d$_6$) δ ppm 1.23 (s, 3H), 2.22-2.50 (m, 8H), 3.56 (s, 2H), 7.12 (d, J=9 Hz, 1H), 7.42 (dd, J=8 Hz, J=2 Hz, 1H), 7.47 (s, 1H), 7.80 (d, J=1 Hz, 2H), 7.85 (d, J=5 Hz, 1H), 8.39 (s, 1H), 8.75 (d, J=5 Hz, 1H), 9.08 (s, 1H), 10.22 (s, 1H), 14.02 (brs, 1H); ESIMS found for C$_{26}$H$_{24}$F$_4$N$_6$O m/z 513.3 (M+H).

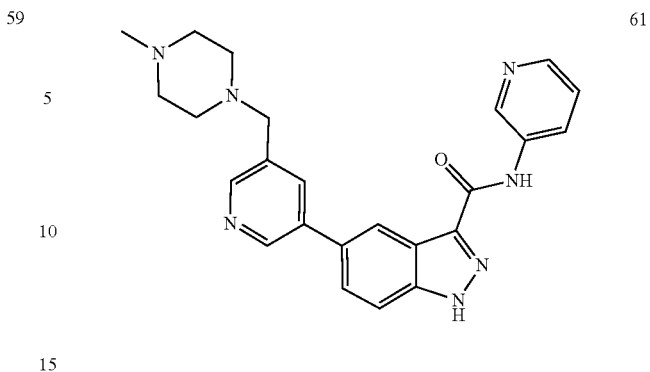

5-(5-((4-Methylpiperazin-1-yl)methyl)pyridin-3-yl)-N-(pyridin-3-yl)-1H-indazole-3-carboxamide 61

White solid (81.6 mg, 0.19 mmol, 55% yield). $^1$H NMR (DMSO-d$_6$) δ ppm 2.14 (s, 3H), 2.33-2.42 (m, 8H), 3.60 (s, 2H), 7.39-7.41 (m, 1H), 7.81-7.85 (m, 2H), 8.00-8.01 (m, 1H), 8.31-8.33 (m, 2H), 8.47-8.48 (m, 1H), 8.49 (d, J=2 Hz, 1H), 8.82 (d, J=2 Hz, 1H), 9.08 (d, J=3 Hz, 1H), 10.74 (s, 1H), 14.00 (s, 1H); ESIMS found for C$_{24}$H$_{25}$N$_7$O m/z 427.8 (M+H).

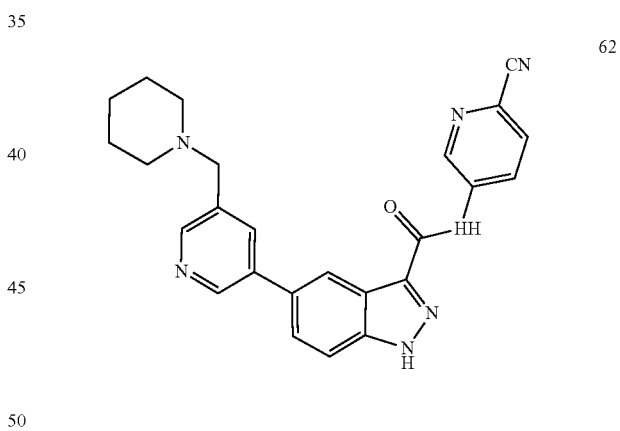

N-(6-Cyanopyridin-3-yl)-5-(5-(piperidin-1-ylmethyl)pyridin-3-yl)-1H-indazole-3-carboxamide 62

Off-white solid (42 mg, 0.10 mmol, 36.9% yield). $^1$H NMR (DMSO-d$_6$) δ ppm 1.36-1.42 (m, 2H), 1.47-1.54 (m, 4H), 2.38 (brs, 4H), 3.57 (s, 2H), 7.85 (d, J=1 Hz, 2H), 8.00 (t, J=2 Hz, 1H), 8.05 (d, J=9 Hz, 1H), 8.47 (d, J=1 Hz, 1H), 8.50 (d, J=2 Hz, 1H), 8.58 (dd, J=9 Hz, J=3 Hz, 1H), 8.82 (d, J=2 Hz, 1H), 9.28 (d, J=2 Hz, 1H), 11.18 (s, 1H), 14.12 (brs, 1H); ESIMS found for C$_{25}$H$_{23}$N$_7$O m/z 438.1 (M+H).

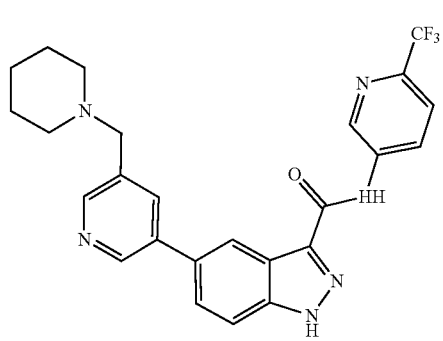

5-(5-(Piperidin-1-ylmethyl)pyridin-3-yl)-N-(6-(trifluoromethyl) pyridin yl)-1H-indazole-3-carboxamide 63

White solid (78 mg, 0.16 mmol, 49% yield). $^1$H NMR (DMSO-d$_6$) δ ppm 1.35-1.44 (m, 2H), 1.46-1.57 (m, 4H), 2.40 (brs, 4H), 3.59 (brs, 2H), 7.85 (s, 2H), 7.93 (d, J=9 Hz, 1H), 8.01 (s, 1H), 8.48 (s, 1H), 8.50 (s, 1H), 8.63 (d, J=8 Hz, 1H), 8.83 (s, 1H), 9.27 (s, 1H), 11.11 (s, 1H), 14.11 (brs, 1H); ESIMS found for C$_{25}$H$_{23}$F$_3$N$_6$O m/z 481.1 (M+H).

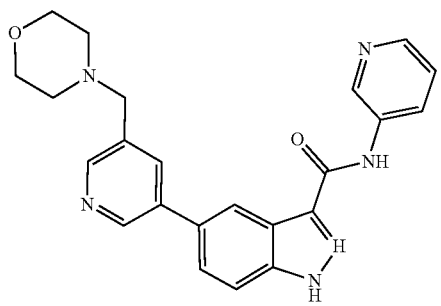

5-(5-(Morpholinomethyl)pyridin-3-yl)-N-(pyridin-3-yl)-1H-indazole-3-carboxamide 64

White solid (77 mg, 0.19 mmol, 66% yield). $^1$H NMR (DMSO-d$_6$) δ ppm 2.41-2.43 (m, 4H), 3.58-3.60 (m, 4H), 3.61 (s, 2H), 7.39-7.41 (m, 1H), 7.81-7.85 (m, 2H), 8.02-8.03 (m, 1H), 8.31-8.33 (m, 2H), 8.47-8.48 (m, 1H), 8.51 (d, J=2 Hz, 1H), 8.83 (d, J=2 Hz, 1H), 9.08 (d, J=2 Hz, 1H), 10.70 (s, 1H), 14.00 (s, 1H); ESIMS found for C$_{23}$H$_{22}$N$_6$O$_2$ m/z 415 (M+H).

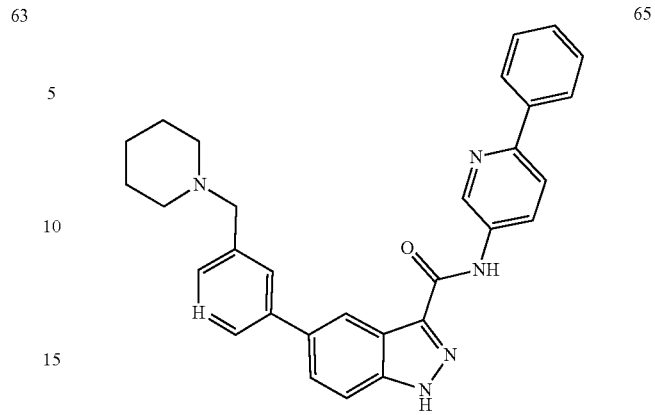

N-(6-Phenylpyridin-3-yl)-5-(5-(piperidin-1-ylmethyl)pyridin-3-yl)-1H-indazole-3-carboxamide 65

White solid (61.5 mg, 0.13 mmol, 68% yield). $^1$H NMR (DMSO-d$_6$) δ ppm 1.39-1.40 (m, 2H), 1.49-1.53 (m, 4H), 2.38-2.39 (m, 4H), 3.57 (s, 2H), 7.39-7.43 (m, 1H), 7.47-7.50 (m, 2H), 7.82-7.86 (m, 2H), 7.99-8.01 (m, 2H), 8.08-8.10 (m, 2H), 8.44 (dd, J=9 Hz, J=3 Hz, 1H), 8.50-8.51 (m, 2H), 8.83 (d, J=2 Hz, 1H), 9.18 (d, J=3 Hz, 1H), 10.81 (s, 1H), 14.02 (s, 1H); ESIMS found for C$_{30}$H$_{28}$N$_6$O m/z 489 (M+H).

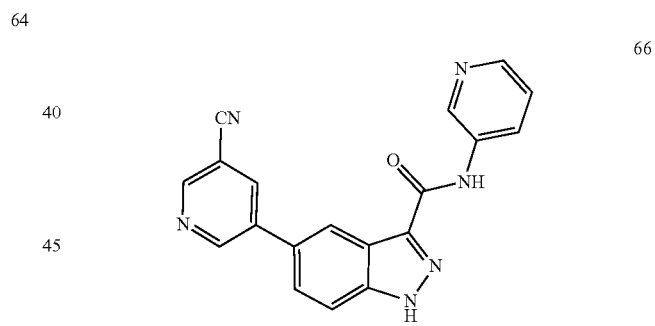

5-(5-Cyanopyridin-3-yl)-N-(pyridin-3-yl)-1H-indazole-3-carboxamide 66

Beige solid (107 mg, 0.31 mmol, 66.7% yield). $^1$H NMR (DMSO-d$_6$) δ ppm 7.40 (dd, J=8 Hz, J=4 Hz, 1H), 7.84 (d, J=8 Hz, 1H), 7.91 (dd, J=9 Hz, J=2 Hz, 1H), 8.30-8.34 (m, 2H), 8.57 (s, 1H), 8.72 (t, J=2 Hz, 1H), 9.03 (d, J=2 Hz, 1H), 9.09 (d, J=2 Hz, 1H), 9.23 (d, J=2 Hz, 1H), 10.72 (s, 1H), 14.06 (s, 1H); ESIMS found for C$_{19}$H$_{12}$N$_6$O m/z 340.8 (M+H).

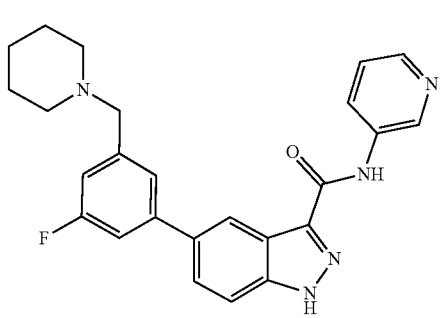

5-(3-Fluoro-5-(piperidin-1-ylmethyl)phenyl)-N-(pyridin-3-yl)-1H-indazole-3-carboxamide 67

Yellow solid (84 mg, 0.20 mmol, 66% yield). $^1$H NMR (DMSO-d$_6$) δ ppm 1.37-1.39 (m, 2H), 1.49-1.54 (m, 4H), 2.37-2.38 (m, 4H), 3.54 (s, 2H), 7.12-7.13 (m, 1H), 7.39-7.43 (m, 2H), 7.47-7.48 (m, 1H), 7.77-7.81 (m, 2H), 8.31-8.33 (m, 2H), 8.44-8.45 (m, 1H), 9.08 (d, J=2 Hz, 1H), 10.69 (s, 1H), 13.97 (s, 1H); ESIMS found for C$_{25}$H$_{24}$FN$_{5O}$ m/z 430 (M+H).

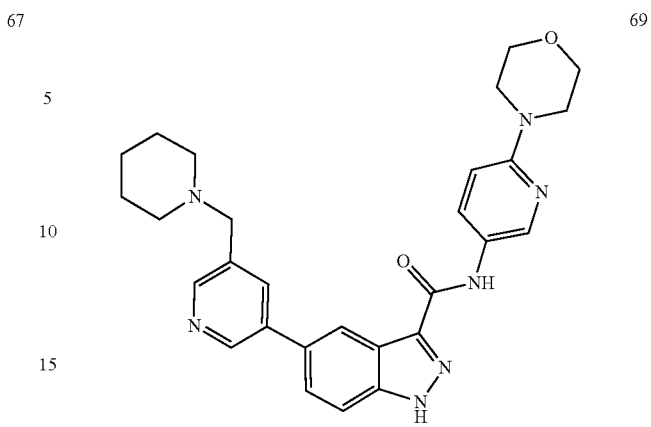

N-(6-Morpholinopyridin-3-yl)-5-(5-(piperidin-1-ylmethyl)pyridin-3-yl)-1H-indazole-3-carboxamide 69

Light yellow solid (58 mg, 0.12 mmol, 36.4% yield). $^1$H NMR (DMSO-d$_6$) δ ppm 1.37-1.44 (m, 2H), 1.51 (quin, J=5 Hz, 4H), 2.33-2.40 (m, 4H), 3.40 (t, J=5 Hz, 4H), 3.56 (s, 2H), 3.71 (t, 5 Hz, 4H), 6.89 (d, J=9 Hz, 1H), 7.78 (d, J=8 Hz, 1H), 7.81 (d, J=9 Hz, 1H), 7.97 (t, J=2 Hz, 1H), 8.06 (dd, J=9 Hz, J=2 Hz, 1H), 8.46 (d, J=10 Hz, 1H), 8.60 (d, J=2 Hz, 1H), 8.79 (d, J=2 Hz, 1H), 10.35 (s, 1H), 13.90 (brs, 1H); ESIMS found for C$_{28}$H$_{31}$N$_7$O$_2$ m/z 498.0 (M+H).

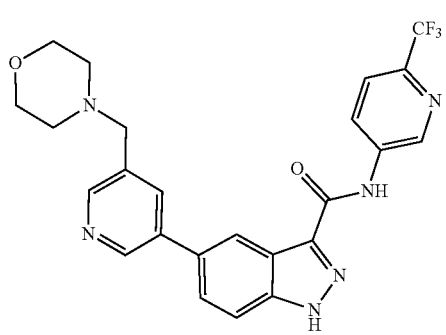

5-(5-(Morpholinomethyl)pyridin-3-yl)-N-(6-(trifluoromethyl)pyridin-3-yl)-1H-indazole-3-carboxamide 68

White solid (72 mg, 0.15 mmol, 30.5% yield). $^1$H NMR (DMSO-d$_6$) δ ppm 2.43 (brs, 4H), 3.56-3.63 (m, 4H), 3.62 (s, 2H), 7.85 (Abq, J=9 Hz, 2H), 7.93 (d, J=9 Hz, 1H), 8.04 (s, 1H), 8.49 (s, 1H), 8.52 (d, J=1 Hz, 1H), 8.63 (dd, J=9 Hz, J=3 Hz, 1H), 8.84 (d, J=2 Hz, 1H), 9.27 (d, J=2 Hz, 1H), 11.11 (s, 1H), 14.11 (brs, 1H); ESIMS found for C$_{24}$H$_{21}$F$_3$N$_6$O$_2$ m/z 483.3 (M+H).

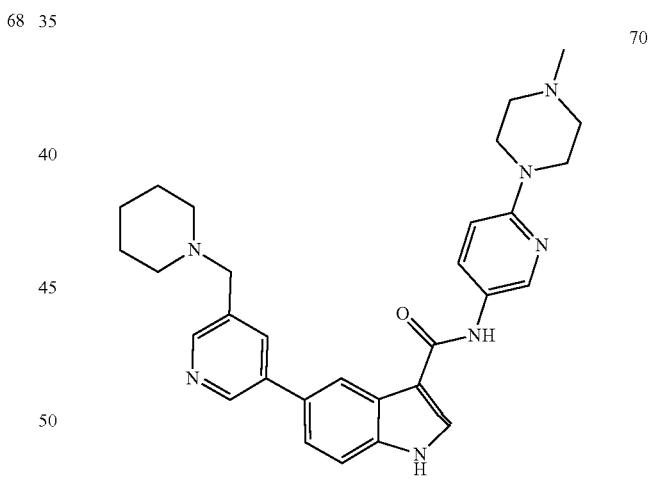

N-(6-(4-Methylpiperazin-1-yl)pyridin-3-yl)-5-(5-(piperidin-1-ylmethyl)pyridin-3-yl)-1H-indazole-3-carboxamide 70

Light yellow solid (37 mg, 0.07 mmol, 39.2% yield). $^1$H NMR (DMSO-d$_6$) δ ppm 1.37-1.44 (m, 2H), 1.51 (quin, J=5 Hz, 4H), 2.22 (s, 3H), 2.35-2.42 (m, 8H), 3.44 (t, J=5 Hz, 4H), 3.56 (s, 2H), 6.86 (d, J=9 Hz, 1H), 7.79 (d, J=9 Hz, 1H), 7.82 (d, J=10 Hz, 1H), 7.98 (d, J=2 Hz, 1H), 8.03 (dd, J=9 Hz, J=3 Hz, 1H), 8.48 (d, J=11 Hz, 1H), 8.58 (d, J=3 Hz, 1H), 8.81 (d, J=3 Hz, 1H), 10.34 (s, 1H), 13.89 (brs, 1H); ESIMS found for C$_{29}$H$_{34}$N$_8$O m/z 511.5 (M+H).

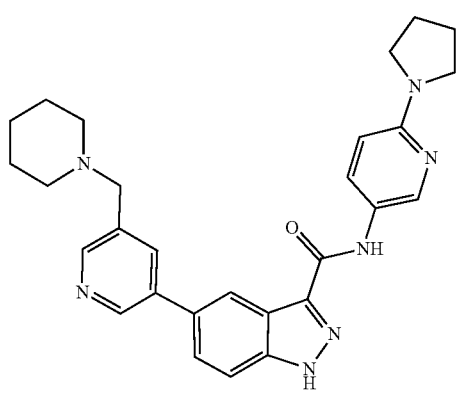

71

5-(5-(Piperidin-1-ylmethyl)pyridin-3-yl)-N-(6-(pyr-rolidin-1-yl) pyridin-3-yl)-1H-indazole-3-carboxam-ide 71

Tan solid (53.9 mg, 0.11 mmol, 53% yield). $^1$H NMR (DMSO-$d_6$) δ ppm 1.38-1.39 (m, 2H), 1.51-1.52 (m, 4H), 1.93-1.96 (m, 4H), 2.36-2.38 (m, 4H), 3.36-3.39 (m, 4H), 3.56 (s, 2H), 6.46 (d, J=9 Hz, 1H), 7.78-7.83 (m, 2H), 7.96 (dd, J=9 Hz, J=3 Hz, 1H), 7.98-7.99 (m, 1H), 8.46-8.47 (m, 2H), 8.49 (, d, J=3 Hz, 1H), 8.80-8.81 (m, 1H), 10.23 (s, 1H), 13.87 (s, 1H); ESIMS found for $C_{28}H_{31}N_7O$ m/z 482 (M+H).

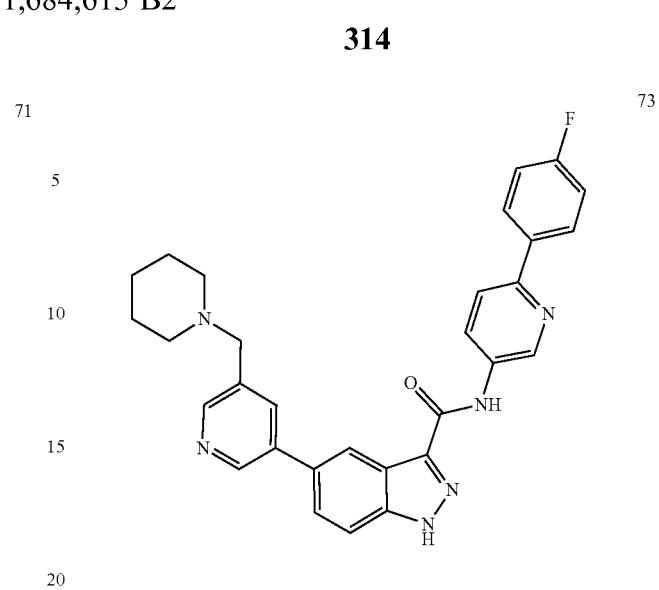

73

N-(6-(4-Fluorophenyl)pyridin-3-yl)-5-(5-(piperidin-1-ylmethyl) pyridin-3-yl)-1H-indazole-3-carboxam-ide 73

White solid (50.8 mg, 0.10 mmol, 55% yield). $^1$H NMR (DMSO-$d_6$) δ ppm 1.39-1.40 (m, 2H), 1.49-1.53 (m, 4H), 2.36-2.39 (m, 4H), 3.57 (s, 2H), 7.29-7.32 (m, 2H), 7.82-7.86 (m, 2H), 7.98-8.01 (m, 2H), 8.12-8.15 (m, 2H), 8.43 (dd, J=9 Hz, J=3 Hz, 1H), 8.49 (s, 2H), 8.82 (d, J=2 Hz, 1H), 9.17 (d, J=3 Hz, 1H), 10.81 (s, 1H), 14.02 (s, 1H); ESIMS found for $C_{30}H_{27}FN_6O$ m/z 507 (M+H).

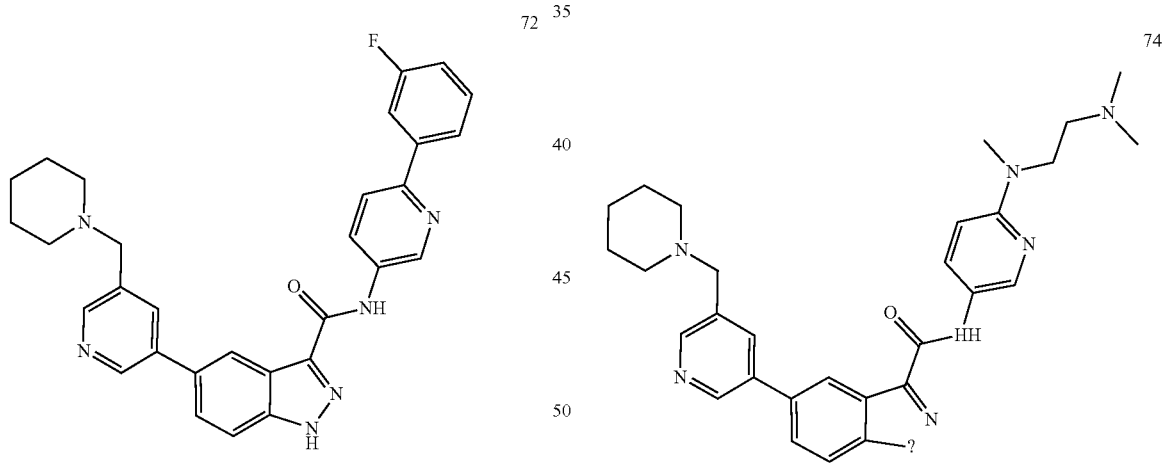

72

N-(6-(3-Fluorophenyl)pyridin-3-yl)-5-(5-(piperidin-1-ylmethyl) pyridin-3-yl)-1H-indazole-3-carboxamide 72

White solid (54.8 mg, 0.11 mmol, 64% yield). $^1$H NMR (DMSO-$d_6$) δ ppm 1.39-1.40 (m, 2H), 1.50-1.54 (m, 4H), 2.38-2.39 (m, 4H), 3.57 (s, 2H), 7.22-7.26 (m, 1H), 7.51-7.55 (m, 1H), 7.82-7.86 (m, 2H), 7.88-7.91 (m, 1H), 7.94-7.96 (m, 1H), 8.00-8.01 (m, 1H), 8.06 (d, J=9 Hz, 1H), 8.46 (dd, J=9 Hz, J=3 Hz, 1H), 8.50 (s, 2H), 8.82 (d, J=2 Hz, 1H), 9.20 (d, J=2 Hz, 1H), 10.86 (s, 1H), 14.03 (s, 1H); ESIMS found for $C_{30}H_{27}FN_6O$ m/z 507 (M+H).

74

N-(6-((2-(Dimethylamino)ethyl)(methyl)amino)pyri-din-3-yl)-5-(5-(piperidin-1-ylmethyl)pyridin-3-yl)-1H-indazole-3-carboxamide 74

Light yellow solid (88.5 mg, 0.17 mmol, 61.7% yield). $^1$H NMR (DMSO-$d_6$) δ ppm 1.38-1.42 (m, 2H), 1.51 (quin, J=5 Hz, 4H), 2.18 (s, 6H), 2.34-2.40 (m, 6H), 2.99 (s, 3H), 3.56 (s, 2H), 3.61 (t, J=7 Hz, 2H), 6.61 (d, J=9 Hz, 1H), 7.79 (d, J=9 Hz, 1H), 7.81 (d, J=9 Hz, 1H), 7.95 (dd, J=9 Hz, J=3 Hz, 1H), 7.98 (t, J=2 Hz, 1H), 8.46 (s, 1H), 8.48 (d, J=2 Hz, 2H), 8.81 (d, J=2 Hz, 1H), 10.24 (s, 1H), 13.84 (brs, 1H); ESIMS found for $C_{29}H_{36}N_8O$ m/z 513.5 (M+H).

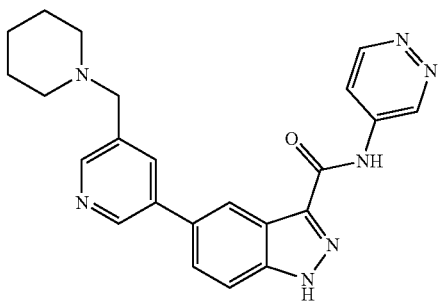

5-(5-(Piperidin-1-ylmethyl)pyridin-3-yl)-N-(pyridazin-4-yl)-1H-indazole-3-carboxamide 75

White solid (53 mg, 0.13 mmol, 33.7% yield). $^1$H NMR (DMSO-$d_6$) δ ppm 1.36-1.43 (m, 2H), 1.47-1.54 (m, 4H), 2.33-2.42 (m, 4H), 3.57 (s, 2H), 7.85 (s, 2H), 8.00 (t, J=2 Hz, 1H), 8.25 (dd, J=6 Hz, J=3 Hz, 1H), 8.47 (t, J=1 Hz, 1H), 8.50 (d, J=2 Hz, 1H), 8.82 (d, J=2 Hz, 1H), 9.09 (d, J=6 Hz, 1H), 9.71 (dd, J=3 Hz, J=1 Hz, 1H), 11.16 (s, 1H), 14.16 (brs, 1H); ESIMS found for $C_{23}H_{23}N_7O$ m/z 414.1 (M+H).

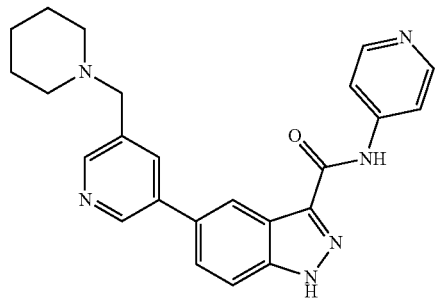

5-(5-(Piperidin-1-ylmethyl)pyridin-3-yl)-N-(pyridin-3-ylmethyl)-1H-indazole-3-carboxamide 76

White solid (26.8 mg, 0.06 mmol, 27% yield). $^1$H NMR (DMSO-$d_6$) δ ppm 1.38-1.39 (m, 2H), 1.49-1.51 (m, 4H), 2.36-2.37 (m, 4H), 3.55 (s, 2H), 4.53 (d, J=6 Hz, 2H), 7.35 (dd, J=8 Hz, J=5 Hz, 1H), 7.74-7.80 (m, 3H), 7.95-7.96 (m, 1H), 8.41-8.42 (m, 1H), 8.45-8.46 (m, 1H), 8.48-8.49 (m, 1H), 8.58-8.59 (m, 1H), 8.78 (d, J=2 Hz, 1H), 9.17 (t, J=6 Hz, 1H), 13.77 (s, 1H); ESIMS found for $C_{25}H_{26}N_6O$ m/z 427 (M+H).

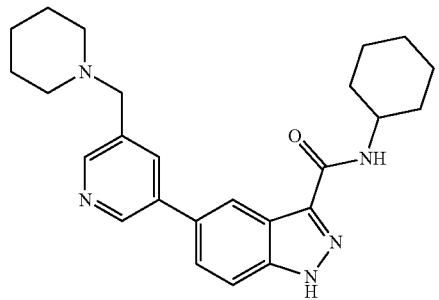

N-Cyclohexyl-5-(5-(piperidin-1-ylmethyl)pyridin-3-yl)-1H-indazole carboxamide 77

White solid (50.4 mg, 0.12 mmol, 72.5% yield). $^1$H NMR (DMSO-$d_6$) δ ppm 1.12-1.47 (m, 7H), 1.50-1.53 (m, 4H), 1.60-1.63 (m, 1H). 1.73-1.75 (m, 2H), 1.83-1.84 (m, 2H), 2.37-2.38 (m, 4H), 3.55 (s, 2H), 3.81-3.87 (m, 1H), 7.73-7.78 (m, 2H), 7.95-7.96 (m, 1H), 8.14 (d, J=8 Hz, 1H), 8.41-8.42 (m, 1H). 8.47 (d, J=2 Hz, 1H), 8.78 (d, J=2 Hz, 1H), 13.67 (s, 1H); ESIMS found for $C_{25}H_{31}N_5O$ m/z 418 (M+H).

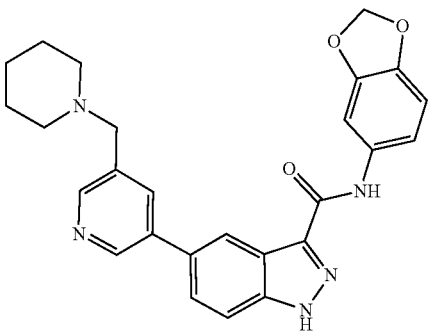

N-(Benzo[d][1,3]dioxol-5-yl)-5-(5-(piperidin-1-ylmethyl)pyridin-3-yl)-1H-indazole-3-carboxamide 78

White solid (48.6 mg, 0.11 mmol, 22.1% yield). $^1$H NMR (DMSO-$d_6$) δ ppm 1.37-1.43 (m, 2H), 1.51 (quin, J=5 Hz, 4H), 2.36-2.42 (m, 4H), 3.56 (s, 2H), 6.01 (s, 2H), 6.90 (d, J=9 Hz, 1H), 7.37 (dd, J=9 Hz, J=2 Hz, 1H), 7.57 (d, J=2 Hz, 1H), 7.91 (dd, J=9 Hz, J=Hz, 1H), 7.82 (dd, J=9 Hz, J=1 Hz, 1H), 7.99 (t, J=2 Hz, 1H), 8.47 (dd, J=12 Hz, J=2 Hz, 1H), 8.81 (d, J=2 Hz, 1H), 10.34 (s, 1H), 13.89 (s, 1H); ESIMS found for $C_{26}H_{25}N_5O_3$ m/z 456.0 (M+H).

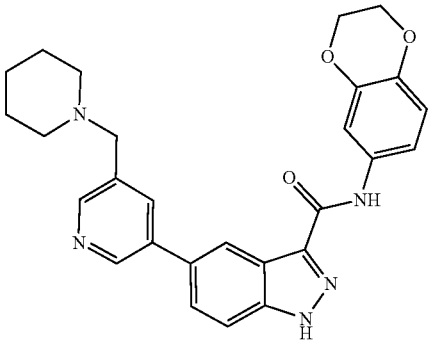

N-(2,3-Dihydrobenzo[b][1,4]dioxin-6-yl)-5-(5-(piperidin-1-ylmethyl) pyridin-3-yl)-1H-indazole-3-carboxamide 79

White solid (98.4 mg, 0.21 mmol, 38.7% yield). $^1$H NMR (DMSO-$d_6$) δ ppm 1.36-1.42 (m, 2H), 1.51 (quin, J=5 Hz, 4H), 2.34-2.41 (m, 4H), 3.56 (s, 2H), 4.20-4.27 (m, 4H), 6.82 (d, J=9 Hz, 1H), 7.35 (dd, J=9 Hz, J=3 Hz, 1H), 7.51 (d, J=3 Hz, 1H), 7.78 (dd, J=9 Hz, J=1 Hz, 1H), 7.81 (dd, J=9 Hz, J=1 Hz, 1H), 7.98 (t, J=2 Hz, 1H), 8.47 (dd, J=12 Hz, J=2 Hz, 1H), 8.81 (d, J=2 Hz, 1H), 10.26 (s, 1H), 13.87 (brs, 1H); ESIMS found for $C_{27}H_{27}N_5O_3$ m/z 470.4 (M+H).

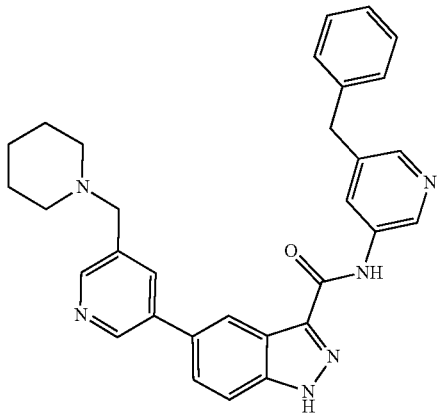

N-(5-Benzylpyridin-3-yl)-5-(5-(piperidin-1-ylmethyl)pyridin-3-yl)-1H-indazole-3-carboxamide 80

White solid (81.9 mg, 0.16 mmol, 59% yield). NMR (DMSO-$d_6$) δ ppm 1.39-1.41 (m, 2H), 1.49-1.53 (m, 4H), 2.37-2.39 (m, 4H), 3.56 (s, 2H), 4.00 (s, 2H), 7.20-7.23 (m, 1H), 7.28-7.34 (m, 4H), 7.79-7.84 (m, 2H), 7.98-7.99 (m, 1H), 8.23-8.24 (m, 1H), 8.25 (d, J=2 Hz, 1H), 8.45-8.46 (m, 1H), 8.49 (d, J=2 Hz, 1H), 8.81 (d, J=2 Hz, 1H), 8.89 (d, J=2 Hz, 1H), 10.65 (s, 1H), 13.97 (s, 1H); ESIMS found for $C_{31}H_{30}N_6O$ m/z 503 (M+H).

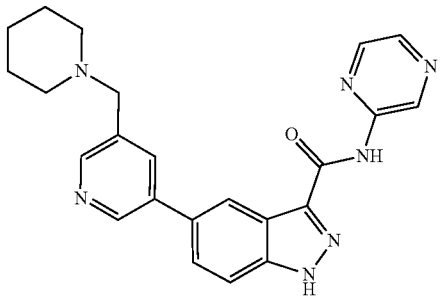

5-(5-(Piperidin-1-ylmethyl)pyridin-3-yl)-N-(pyrazin-2-yl)-1H-indazole-3-carboxamide 81

White solid (104 mg, 0.25 mmol, 41.7% yield). $^1$H NMR (DMSO-$d_6$) δ ppm 1.35-1.42 (m, 2H), 1.51 (quin, J=5 Hz, 4H), 2.33-2.42 (m, 4H), 3.57 (s, 2H), 7.83 (d, J=9 Hz, 1H), 7.85 (d, J=9 Hz, 1H), 8.00 (s, 1H), 8.45 (d, J=2 Hz, 1H), 8.46 (s, 1H), 8.50 (s, 1H), 8.83 (d, J=2 Hz, 1H), 9.50 (s, 1H), 10.36 (s, 1H), 14.11 (brs, 1H); ESIMS found for $C_{23}H_{23}N_7O$ m/z 413.9 (M+H).

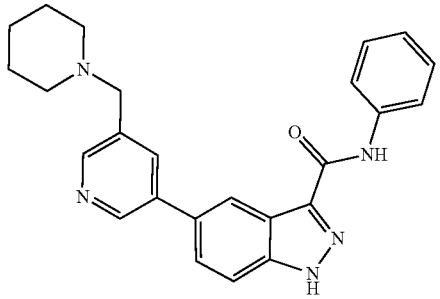

N-Phenyl-5-(5-(piperidin-1-ylmethyl)pyridin-3-yl)-1H-indazole-3-carboxamide 82

White solid (97.8 mg, 0.24 mmol, 81% yield). $^1$H NMR (DMSO-$d_6$) δ ppm 1.39-1.40 (m, 2H), 1.49-1.53 (m, 4H), 2.37-2.39 (m, 4H), 3.57 (s, 2H), 7.09-7.12 (m, 1H), 7.34-7.37 (m, 2H), 7.80 (d, J=9 Hz, 1H), 7.83 (dd, J=9 Hz, 2 Hz, 1H), 7.90-7.92 (m, 2H), 7.99-8.00 (m, 1H), 8.47-8.48 (m, 1H), 8.49 (d, 1H), 8.81 (d, J=2 Hz, 1H), 10.40 (s, 1H), 13.92 (s, 1H); ESIMS found for $C_{25}H_{25}N_5O$ m/z 412 (M+H).

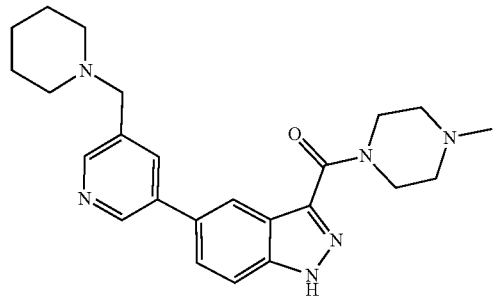

(4-Methylpiperazin-1-yl)(5-(5-(piperidin-1-ylmethyl)pyridin-3-yl)-1H-indazol-3-yl)methanone 83

Light yellow amorphous solid (74.6 mg, 0.18 mmol, 93% yield). NMR (DMSO-$d_6$) δ ppm 1.38-1.39 (m, 2H), 1.48-1.53 (m, 4H), 2.22 (s, 3H), 2.36-2.41 (m, 8H), 3.55 (s, 2H), 3.72-3.73 (m, 2H), 4.01-4.02 (m, 2H), 7.73 (d, J=9 Hz, 1H), 7.79 (dd, J=9 Hz, J=2 Hz, 1H), 7.95-7.96 (m, 1H), 8.22 (d, J=1 Hz, 1H), 8.46 (d, J=2 Hz, 1H), 8.78 (d, J=2 Hz, 1H), 13.64 (s, 1H); ESIMS found for $C_{24}H_{30}N_6O$ m/z 419 (M+H).

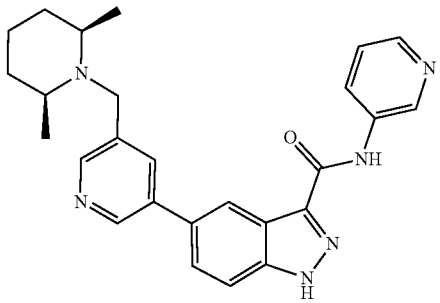

5-(5-(((2R,6S)-2,6-Dimethylpiperidin-1-yl)methyl) pyridin-3-yl)-N-(pyridin-3-yl)-1H-indazole-3-carboxamide 84

Beige solid (76.5 mg, 0.17 mmol, 75.5% yield). $^1$H NMR (DMSO-$d_6$) δ ppm 1.00 (d, J=6 Hz, 6H), 1.21-1.35 (m, 3H), 1.55 (d, J=11 Hz, 2H), 1.60-1.65 (m, 1H), 2.45-2.53 (m, 2H), 3.84 (s, 1H), 7.40 (dd, J=7 Hz, 3 Hz, 1H), 7.79 (dd, J=9 Hz, J=2 Hz, 1H), 7.83 (dd, J=9 Hz, J=1 Hz, 1H), 8.04 (s, 1H), 8.29-8.35 (m, 2H), 8.46 (s, 1H), 8.60 (d, J=2 Hz, 1H), 8.73 (d, J=2 Hz, 1H), 9.08 (d, J=3 Hz, 1H), 10.70 (s, 1H), 14.00 (brs, 1H); ESIMS found for $C_{26}H_{28}N_6O$ m/z 441.3 (M+H).

N-(1-Methylpiperidin-4-yl)-5-(5-(piperidin-1-ylmethyl)pyridin-3-yl)-1H-indazole-3-carboxamide 87

White amorphous solid (18.2 mg, 0.04 mmol, 59.8% yield). $^1$H NMR (DMSO-$d_6$) δ ppm 1.39-1.40 (m, 2H), 1.49-1.53 (m, 4H), 1.66-1.75 (m, 4H), 1.95-2.00 (m, 2H), 2.18 (s, 3H), 2.37-2.38 (m, 4H), 2.77 (d, J=11 Hz, 2H), 3.55 (s, 2H), 3.81-3.83 (m, 1H), 7.73-7.75 (m, 1H), 7.77-7.79 (m, 1H), 7.95-7.96 (m, 1H), 8.25 (d, J=8 Hz, 1H), 8.41-8.42 (m, 1H), 8.47 (d, J=2 Hz, 1H), 8.78 (d, J=2 Hz, 1H), 13.70 (s, 1H); ESIMS found for $C_{25}H_{32}N_6O$ m/z 433 (M+H).

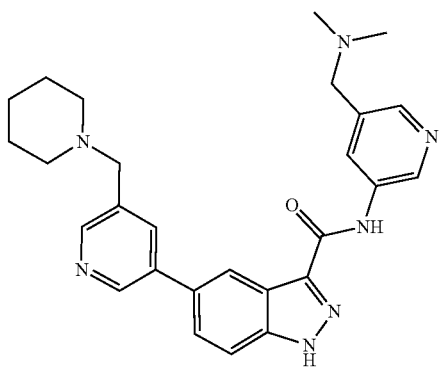

N-(5-((Dimethylamino)methyl)pyridin-3-yl)-5-(5-(piperidin-1-ylmethyl)pyridin-3-yl)-1H-indazole-3-carboxamide 86

White solid (41.5 mg, 0.09 mmol, 72% yield). $^1$H NMR (DMSO-$d_6$) δ ppm 1.39-1.40 (m, 2H), 1.49-1.54 (m, 4H), 2.19 (s, 6H), 2.36-2.39 (m, 4H), 3.44 (s, 2H), 3.58 (s, 2H), 7.81 (d, J=9 Hz, 1H), 7.85 (dd, J=9 Hz, J=2 Hz, 1H), 8.00-8.01 (m, 1H), 8.21 (d, 1H), 8.37-8.38 (m, 1H), 8.49-8.50 (m, 2H), 8.83 (d, J=2 Hz, 1H), 8.91 (d, J=2 Hz, 1H), 10.69 (s, 1H), 14.01 (brs, 1H); ESIMS found for $C_{27}H_{31}N_7O$ m/z 470 (M+H).

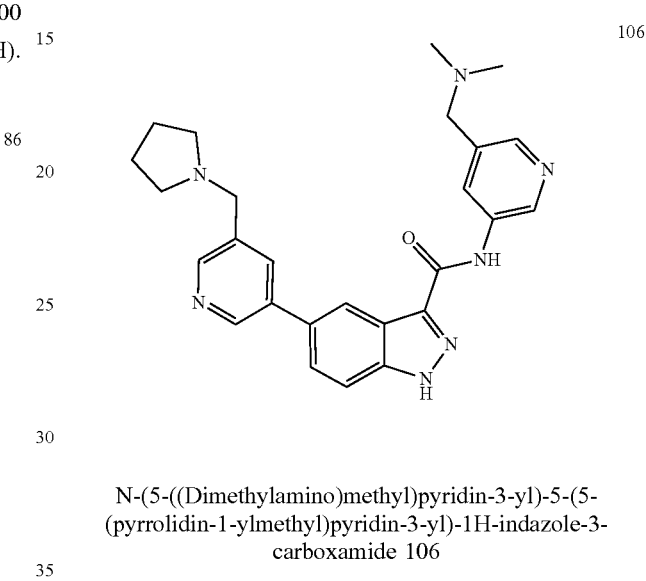

N-(5-((Dimethylamino)methyl)pyridin-3-yl)-5-(5-(pyrrolidin-1-ylmethyl)pyridin-3-yl)-1H-indazole-3-carboxamide 106

White solid (39.4 mg, 0.09 mmol, 74% yield). $^1$H NMR (DMSO-$d_6$) δ ppm 1.71-1.73 (m, 4H), 2.49-2.50 (m, 4H), 2.18 (s, 6H), 3.43 (s, 2H), 3.71 (s, 2H), 7.81 (d, J=9 Hz, 1H), 7.84 (ABq, J=9 Hz, 1H), 8.02-8.03 (m, 1H), 8.21 (d, J=2 Hz, 1H), 8.37-8.38 (m, 1H), 8.48-8.49 (m, 1H), 8.51 (d, J=2 Hz, 1H), 8.83 (d, J=2 Hz, 1H), 8.91 (d, J=2 Hz, 1H), 10.68 (s, 1H), 13.98 (s, 1H); ESIMS found for $C_{26}H_{29}N_7O$ m/z 456 (M+H).

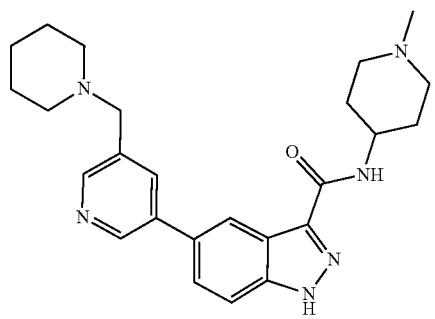

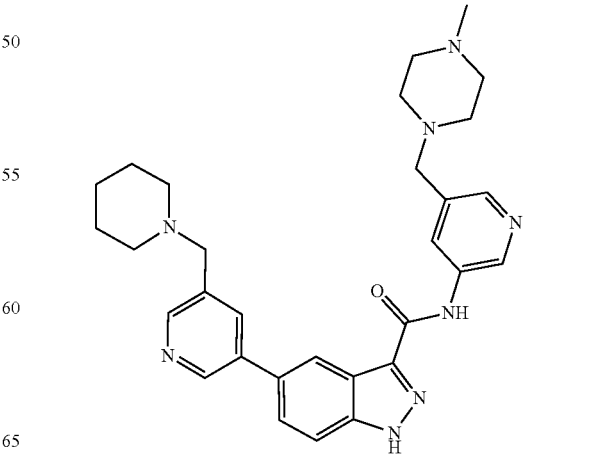

321

N-(5-((4-Methylpiperazin-1-yl)methyl)pyridin-3-yl)-5-(5-(piperidin-1-ylmethyl)pyridin-3-yl)-1H-indazole-3-carboxamide 124

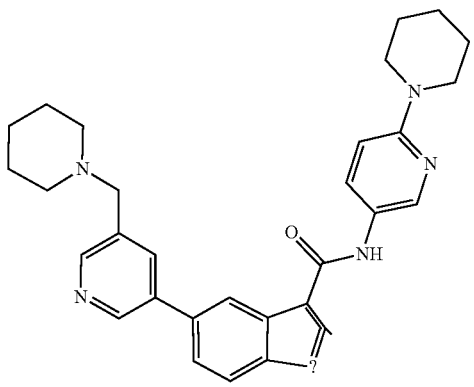

N-(6-(Piperidin-1-yl)pyridin-3-yl)-5-(5-(piperidin-1-ylmethyl)pyridin-3-yl)-1H-indazole-3-carboxamide 126

Grey solid (92.7 mg, 0.19 mmol, 29.0% yield). NMR (DMSO-$d_6$) δ ppm 1.48-1.64 (m, 12H), 2.32-2.43 (m, 4H), 3.48 (t, J=4.5 Hz, 4H), 3.56 (s, 2H), 6.83 (d, J=9 Hz, 1H), 7.80 (ABq, J=10 Hz, 2H), 7.98 (s, 1H), 8.00 (d, J=2.4 Hz, 1H), 8.47 (d, J=10 Hz, 2H), 8.55 (d, J=2.5 Hz, 1H), 8.81 (d, J=2 Hz, 1H), 10.27 (s, 1H), 13.86 (s, 1H); ESIMS found for $C_{29}H_{33}N_7O$ m/z 496.5 (M+H).

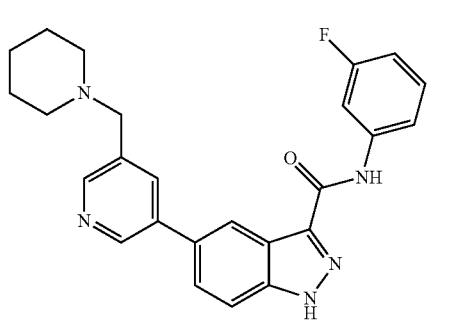

N-(3-Fluorophenyl)-5-(5-(piperidin-1-ylmethyl)pyridin-3-yl)-1H-indazole-3-carboxamide 162

White solid (176 mg, 0.41 mmol, 56.8% yield). $^1$H NMR (DMSO-$d_6$) δ ppm 1.36-1.43 (m, 2H), 1.47-1.55 (m, 4H), 2.38 (brs, 4H), 3.56 (s, 2H), 6.93 (dt, J=9 Hz, J=3 Hz, 1H), 7.39 (q, J=8 Hz, 1H), 7.75 (dd, J=8 Hz, J=1 Hz, 1H), 7.82 (d/Abq, J=9 Hz, J=1 Hz, 2H), 7.89 (td, J=12 Hz, J=2 Hz, 1H), 7.99 (t, J=2 Hz, 1H), 8.47 (s, 1H), 8.49 (d, J=2 Hz, 1H), 8.82 (d, J=2 Hz, 1H), 10.66 (s, 1H), 13.97 (brs, 1H); ESIMS found for $C_{25}H_{24}FN_5O$ m/z 430.0 (M+H).

322

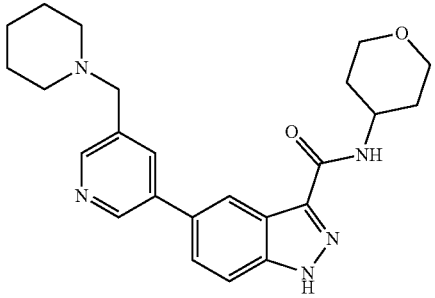

5-(5-(Piperidin-1-ylmethyl)pyridin-3-yl)-N-(tetrahydro-2H-pyran-4-yl)-1H-indazole-3-carboxamide 163

Tan amorphous solid (88 mg, 0.21 mmol, 88% yield). $^1$H NMR (DMSO-$d_6$) δ ppm 1.39-1.40 (m, 2H), 1.49-1.53 (m, 4H), 1.69-1.76 (m, 4H), 2.37-2.38 (m, 4H), 3.39-3.42 (m, 2H), 3.56 (s, 2H), 3.88-3.90 (m, 2H), 4.05-4.10 (m, 1H), 7.74 (d, J=9 Hz, 1H), 7.77-7.79 (m, 1H), 7.95-7.96 (m, 1H), 8.37 (d, J=8 Hz, 1H), 8.41-8.42 (m, 1H), 8.47 (d, J=2 Hz, 1H), 8.79 (d, J=2 Hz, 1H), 13.72 (s, 1H); ESIMS found for $C_{24}H_{29}N_5O_2$ m/z 420 (M+H).

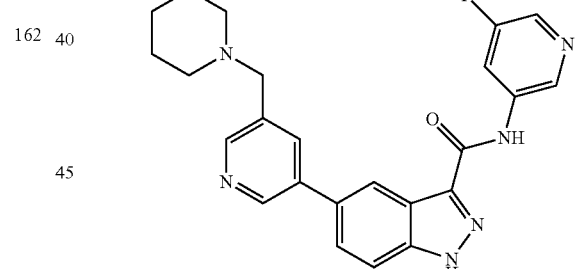

N-(5-Fluoropyridin-3-yl)-5-(5-(piperidin-1-ylmethyl)pyridin-3-yl)-1H-indazole-3-carboxamide 168

White solid (286 mg, 0.66 mmol, 56% yield). $^1$H NMR (DMSO-$d_6$) δ ppm 1.39 (m, 2H), 1.49-1.53 (m, 4H), 2.38 (brs, 4H), 3.56 (s, 2H), 7.81-7.86 (m, 2H), 7.99 (s, 1H), 8.31-8.34 (m, 2H), 8.47 (s, 1H), 8.49 (d, J=1.3 Hz, 1H), 8.82 (d, J=1.7 Hz, 1H), 8.99 (s, 1H), 10.97 (s, 1H), 14.07 (brs, 1H); ESIMS found for $C_{24}H_{23}FN_6O$ m/z 431.4 (M+H).

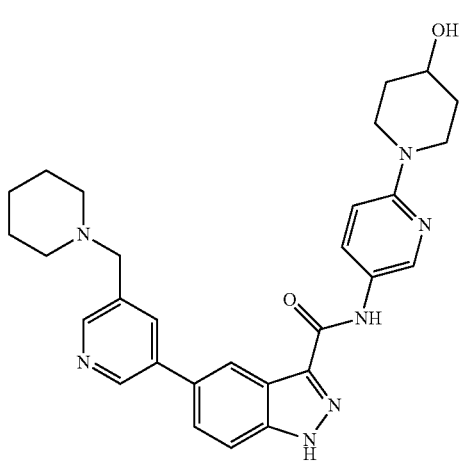

N-(6-(4-Hydroxypiperidin-1-yl)pyridin-3-yl)-5-(5-(piperidin-1-ylmethyl)pyridin-3-yl)-1H-indazole-3-carboxamide 169

Off-white solid (33 mg, 0.06 mmol, 53.8% yield). $^1$H NMR (DMSO-d$_6$) δ ppm 1.32-1.43 (m, 4H), 1.45-1.57 (m, 4H), 1.74-1.83 (m, 2H), 2.33-2.44 (m, 4H), 3.04 (t, J=10 Hz, 2H), 3.56 (s, 2H), 3.63-3.73 (m, 1H), 3.93-4.02 (m, 2H), 4.72 (s, 1H), 6.85 (d, J=9 Hz, 1H), 7.80 (ABq, J=10 Hz, 2H), 7.99 (d, J=7 Hz, 2H), 8.47 (d, J=10 Hz, 2H), 8.54 (s, 1H), 8.81 (s, 1H), 10.28 (s, 1H), 13.87 (s, 1H); ESIMS found for $C_{29}H_{33}N_7O_2$ m/z 512.3 (M+H).

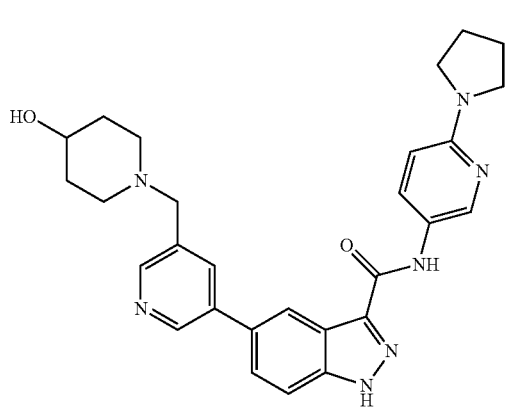

5-(5-((4-Hydroxypiperidin-1-yl)methyl)pyridin-3-yl)-N-(6-(pyrrolidin-1-yl) pyridin-3-yl)-1H-indazole-3-carboxamide 170

Off-white solid (125.4 mg, 0.25 mmol, 73.2% yield). $^1$H NMR (DMSO-d$_6$) δ ppm 1.93-1.96 (m, 4H), 2.09-2.12 (m, 2H), 2.70-2.72 (m, 2H), 3.37-3.39 (m, 4H), 3.46-3.47 (m, 1H), 3.58 (s, 1H), 4.52 (d, J=4 Hz, 1H), 6.46 d, J=9 Hz, 1H), 7.77-7.82 (m, 2H), 7.95-7.98 (m, 2H), 8.44-8.48 (m, 2H), 8.49 (d, J=2.5 Hz, 1H), 8.80 (d, J=2.1 Hz, 1H), 10.20 (s, 1H), 13.85 (s, 1H); ESIMS found for $C_{28}H_{31}N_7O_2$ m/z 498 (M+H).

N-(5-Methyl-6-(pyrrolidin-1-yl)pyridin-3-yl)-5-(5-(piperidin-1-ylmethyl)pyridin-3-yl)-1H-indazole-3-carboxamide 172

Off-white solid (186 mg, 0.38 mmol, 72.2% yield). $^1$H NMR (DMSO-d$_6$) δ ppm 1.34-1.43 (m, 2H), 1.47-1.55 (m, 4H), 1.82-1.89 (m, 4H), 2.30 s, 3H), 2.33-2.42 (m, 4H), 3.43 (t, J=6.6 Hz, 4H), 3.56 (s, 2H), 7.81 (ABq, J=10 Hz, 2H), 7.89 (d, J=2 Hz, 1H), 7.98 (s, 1H), 8.38 (d, J=2 Hz, 1H), 8.47 (d, J=8 Hz, 2H), 8.81 (d, J=2 Hz, 1H), 10.24 (s, 1H), 13.86 (s, 1H); ESIMS found for $C_{29}H_{33}N_7O$ m/z 496.4 (M+H).

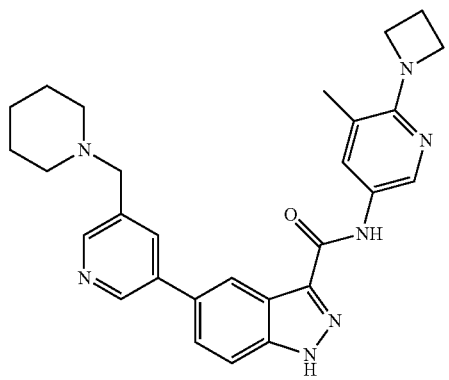

N-(6-(Azetidin-1-yl)-5-methylpyridin-3-yl)-5-(5-(piperidin-1-ylmethyl)pyridin-3-yl)-1H-indazole-3-carboxamide 173

Off-white solid (184 mg, 0.38 mmol, 62.6% yield). NMR (DMSO-d$_6$) δ ppm 1.35-1.43 (m, 2H), 1.47-1.54 (m, 4H), 2.16 (s, 3H), 2.22 (quin, J=7 Hz, 2H), 2.34-2.42 (m, 4H), 3.56 (s, 2H), 4.00 (t, J=7 Hz, 4H), 7.81 (ABq, J=10 Hz, 2H), 7.85 (d, J=2 Hz, 1H), 8.39 (d, J=2 Hz, 1H), 8.47 (d, J=10 Hz, 2H), 8.81 (d, J=2 Hz, 1H), 10.24 (s, 1H), 13.87 (s, 1H); ESIMS found for $C_{28}H_{31}N_7O$ m/z 482.0 (M+H).

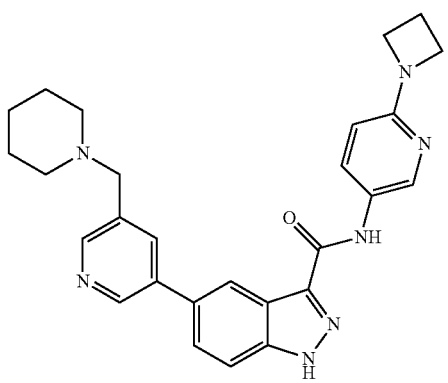

N-(6-(Azetidin-1-yl)pyridin-3-yl)-5-(5-(piperidin-1-ylmethyl)pyridin-3-yl)-1H-indazole-3-carboxamide 174

White solid (14.9 mg, 0.03 mmol, 11.0% yield). $^1$H NMR (DMSO-d$_6$) δ ppm 1.36-1.43 (m, 2H), 1.47-1.54 (m, 4H), 2.32 (quin, J=7 Hz, 2H), 2.35-2.42 (m, 4H), 3.56 (s, 2H), 3.92 (t, J=7 Hz, 4H), 6.39 (d, J=9 Hz, 1H), 7.77-7.83 (m, 2H), 7.98 (dd, J=9 Hz, J=2 Hz, 2H), 8.42-8.53 (m, 3H), 8.78-8.84 (m, 1H), 10.27 (s, 1H), 13.87 (s, 1H). ESIMS found for C$_{27}$H$_{29}$N$_7$O m/z 468.0 (M+H).

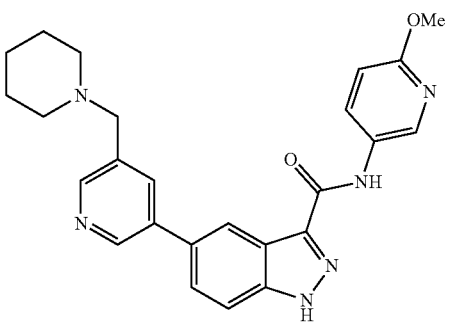

N-(6-Methoxypyridin-3-yl)-5-(5-(piperidin-1-ylmethyl)pyridin-3-yl)-1H-indazole-3-carboxamide 175

White solid (31.2 mg, 0.07 mmol, 25.8% yield). $^1$H NMR (DMSO-d$_6$) δ ppm 1.36-1.43 (m, 2H), 1.47-1.55 (m, 4H), 2.33-2.42 (m, 4H), 3.56 (s, 2H), 3.85 (s, 3H), 6.84 (d, J=9 Hz, 1H), 7.81 (ABq, J=12 Hz, 2H), 7.98 (s, 1H), 8.18 (dd, J=9 Hz, J=2.7 Hz, 1H), 8.47 (dd, J=10 Hz, J=1 Hz, 2H), 8.65 (d, J=2.6 Hz, 1H), 8.81 (d, J=2 Hz, 1H), 10.50 (s, 1H), 13.91 (brs, 1H); ESIMS found for C$_{25}$H$_{26}$N$_6$O$_2$ m/z 443.4 (M+H).

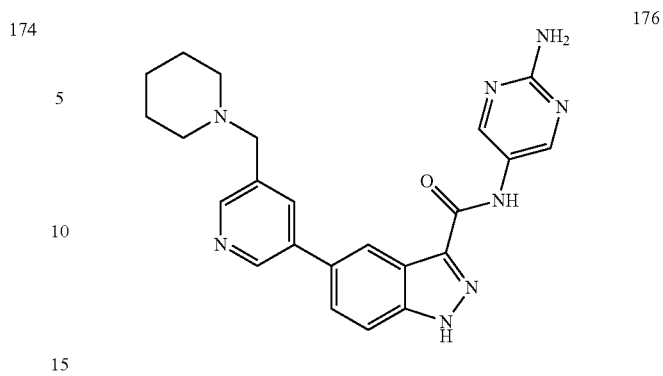

N-(2-Aminopyrimidin-5-yl)-5-(5-(piperidin-1-ylmethyl)pyridin-3-yl)-1H-indazole-3-carboxamide 176

Yellow solid (412 mg, 0.96 mmol, 52.5% yield). $^1$H NMR (DMSO-d$_6$) δ ppm 1.37-1.43 (m, 2H), 1.47-1.54 (m, 4H), 2.35-2.41 (m, 4H), 3.56 (s, 2H), 6.49 (s, 2H), 7.81 (ABq, J=10 Hz, 2H), 7.98 (s, 1H), 8.47 (dd, J=12 Hz, J=2 Hz, 2H), 8.63 (s, 1H), 8.81 (d, J=2 Hz, 1H), 10.32 (s, 1H), 13.91 (s, 1H); ESIMS found for C$_{23}$H$_{24}$N$_8$O m/z 429.3 (M+H).

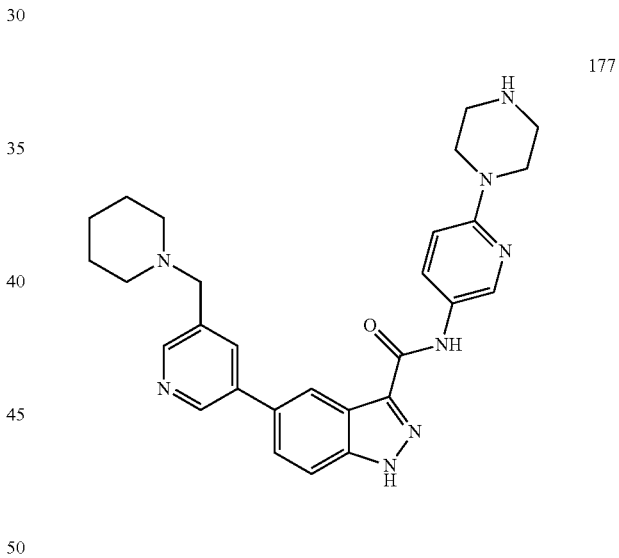

N-(6-(Piperazin-1-yl)pyridin-3-yl)-5-(5-(piperidin-1-ylmethyl)pyridin-3-yl)-1H-indazole-3-carboxamide 177

Tan solid (160 mg, 0.32 mmol, 28.5% yield). $^1$H NMR (DMSO-d$_6$) δ ppm 1.37-1.43 (m, 2H), 1.48-1.54 (m, 4H), 2.34-2.41 (m, 4H), 2.79 (t, J=5 Hz, 4H), 3.36 (t, J=5 Hz, 4H), 3.56 (s, 2H), 6.82 (d, J=9 Hz, 1H), 7.81 (ABq, J=10 Hz, 2H), 7.98 (s, 1H), 8.02 (dd, J=9 Hz, J=2.7 Hz, 1H), 8.47 (dd, J=9 Hz, J=2 Hz, 2H), 8.57 (d, J=2.5 Hz, 1H), 8.81 (d, 1H), 10.29 (s, 1H); ESIMS found for C$_{28}$H$_{32}$N$_8$O m/z 497.1 (M+H).

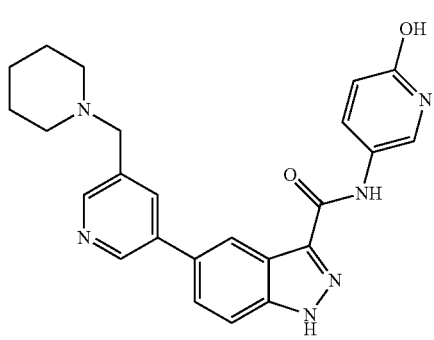

N-(6-Hydroxypyridin-3-yl)-5-(5-(piperidin-1-ylmethyl)pyridin-3-yl)-1H-indazole-3-carboxamide 178

Off-white solid (78.3 mg, 0.18 mmol, 52.4% yield). $^1$H NMR (DMSO-d$_6$) δ ppm 1.36-1.43 (m, 2H), 1.48-1.54 (m, 4H), 2.35-2.42 (m, 4H), 3.56 (s, 2H), 6.38 (d, J=10 Hz, 1H), 7.80 (ABq, J=11 Hz, 2H), 7.83 (dd, J=10 Hz, J=3 Hz, 1H), 7.97 (s, 1H), 8.04 (d, J=2.5 Hz, 1H), 8.44 (s, 1H), 8.48 (d, J=2 Hz, 1H), 8.80 (d, J=2 Hz, 1H), 10.27 (s, 1H), 11.42 (brs, 1H), 13.87 (brs, 1H); ESIMS found for C$_{24}$H$_{24}$N$_6$O$_2$ m/z 429.1 (M+H).

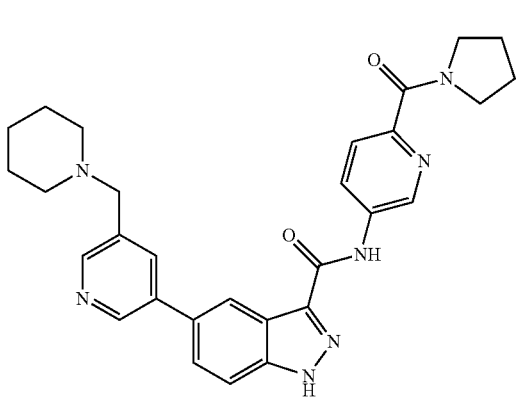

5-(5-(Piperidin-1-ylmethyl)pyridin-3-yl)-N-(6-(pyrrolidine-1-carbonyl)pyridin-3-yl)-1H-indazole-3-carboxamide 179

Light yellow solid (61 mg, 0.12 mmol, 37.8% yield). $^1$H NMR (DMSO-d$_6$) ppm 1.37-1.43 (m, 2H), 1.48-1.55 (m, 4H), 1.82-1.90 (m, 4H), 2.38 (brs, 4H), 3.17 (d, J=5 Hz, 2H), 3.51 (t, J=7 Hz, 2H), 3.57 (s, 2H), 3.70 (t, J=7 Hz, 2H), 7.79 (d, J=9 Hz, 1H), 7.84 (Abq, J=11 Hz, 2H), 8.00 (s, 1H), 8.46 (dd, J=9 Hz, J=2.5 Hz, 1H), 8.48 (dd, J=9 Hz, J=2 Hz, 2H), 8.82 (d, J=2 Hz, 1H), 9.10 (d, J=2 Hz, 1H), 10.91 (s, 1H), 14.05 (brs, 1H); ESIMS found for C$_{29}$H$_{31}$N$_7$O$_2$ m/z 510.6 (M+H).

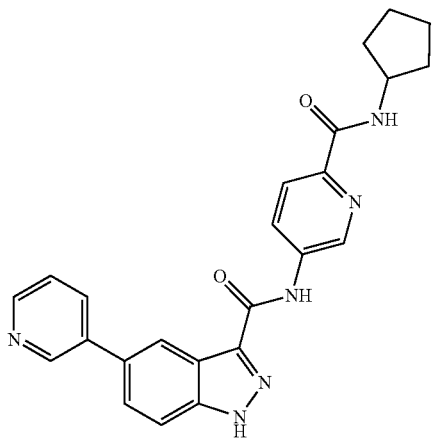

N-(6-(Cyclopentylcarbamoyl)pyridin-3-yl)-5-(pyridin-3-yl)-1H-indazole-3-carboxamide 181

Light yellow solid (18 mg, 0.04 mmol, 16.6% yield). $^1$H NMR (DMSO-d$_6$) ppm 1.50-1.64 (m, 4H), 1.67-1.76 (m, 2H), 1.85-1.94 (m, 4H), 4.24 (quip, J=8 Hz, 1H), 7.53 (dd, J=8 Hz, J=5 Hz, 1H), 7.84 (ABq, 2H), 8.03 (d, J=9 Hz, 1H), 8.14 (d, J=8 Hz, 1H). 8.45 (d, J=8 Hz, 1H), 8.48 (s, 1H), 8.54 (dd, J=9 Hz, J=2.5 Hz, 1H), 8.60 (d, J=4 Hz, 1H), 8.94 (d, J=2 Hz, 1H), 9.16 (d, J=2 Hz, 1H), 10.97 (s, 1H), 14.08 (brs, 1H); ESIMS found for C$_{24}$H$_{22}$N$_6$O$_2$ m/z 427.1 (M+H).

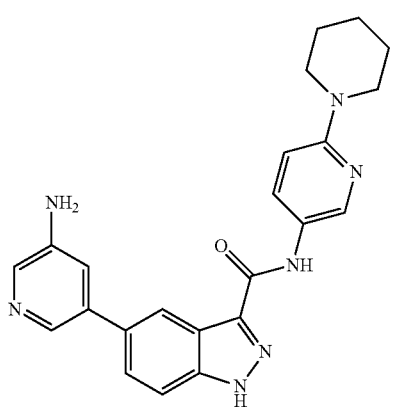

5-(5-Aminopyridin-3-yl)-N-(6-(piperidin-1-yl)pyridin-3-yl)-1H-indazole-3-carboxamide 182

Off-white solid (23.4 mg, 0.06 mmol, 19.4% yield). $^1$H NMR (DMSO-d$_6$) ppm 1.51-1.63 (m, 6H), 3.47 (t, J=5 Hz, 4H), 5.45 (s, 2H), 6.83 (d, J=10 Hz, 1H), 7.24 (t, J=2 Hz, 1H), 7.73 (dq, J=9 Hz, J=2 Hz, 2H), 7.94 (d, J=2.5 Hz, 1H), 8.00 (dd, J=9 Hz, J=2.5 Hz, 1H), 8.08 (d, J=2 Hz, 1H), 8.40 (s, 1H), 8.56 (d, J=2.5 Hz, 1H), 10.27 (s, 1H), 13.84 (s, 1H); ESIMS found for C$_{23}$H$_{23}$N$_7$O m/z 414.3 (M+H).

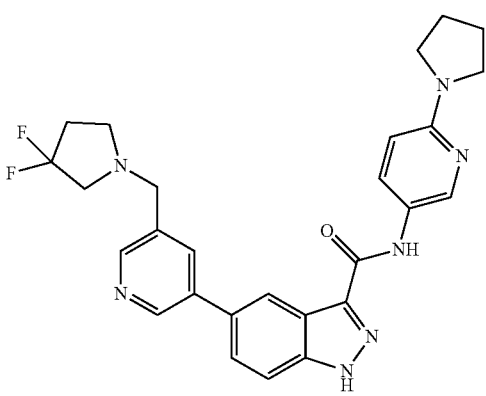

5-(5-((3,3-Difluoropyrrolidin-1-yl)methyl)pyridin-3-yl)-N-(6-(pyrrolidin-1-yl)pyridin-3-yl)-1H-indazole-3-carboxamide 183

Off-white solid (307 mg, 0.61 mmol, 39.6% yield). $^1$H NMR (DMSO-$d_6$) ppm 1.95 (t, J=6.5 Hz, 4H), 2.28 (tt, J=13.5 Hz, J=7 Hz, 2H), 2.76 (t, J=7 Hz, 2H), 2.94 (t, J=13.5 Hz, 2H), 3.38 (t, J=6.5 Hz, 4H), 3.77 (s, 2H), 6.46 (d, J=9 Hz, 1H), 7.81 (dq, J=8.5 Hz, J=1.5 Hz, 2H), 7.97 (dd, J=9 Hz, J=2.5 Hz, 1H), 8.03 (s, 1H), 8.48 (s, 1H), 8.49 (d, J=2.5 Hz, 1H), 8.52 (s, 1H), 8.84 (d, J=2 Hz, 1H), 10.23 (s, 1H), 13.87 (s, 1H); ESIMS found for $C_{27}H_{27}F_2N_7O$ m/z 504.0 (M+H).

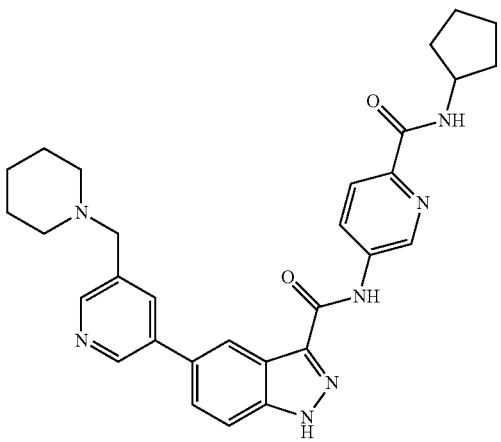

N-(6-(Cyclopentylcarbamoyl)pyridin-3-yl)-5-(5-(piperidin-1-ylmethyl)pyridin-3-yl)-1H-indazole-3-carboxamide 184

White solid (3.2 mg, 0.01 mmol, 18.5% yield). $^1$H NMR (DMSO-$d_6$) δ ppm 1.36-1.43 (m, 2H), 1.43-1.64 (m, 8H), 1.64-1.76 (m, 2H), 1.82-1.93 (m, 2H), 2.38 (brs, 4H), 3.57 (s, 2H), 4.24 (quin, J=7 Hz, 1H), 7.84 (ABq, J=10 Hz, 2H), 8.00 (s, 1H), 8.03 (d, J=9 Hz, 1H), 8.44 (d, J=8 Hz, 1H), 8.48 (dd, J=8 Hz, J=2 Hz, 2H), 8.55 (dd, J=9 Hz, J=2.5 Hz, 1H), 8.82 (d, J=2.5 Hz, 1H), 9.16 (d, J=2.5 Hz, 1H), 10.98 (s, 1H), 14.06 (brs, 1H); ESIMS found for $C_{30}H_{33}N_7O_2$ m/z 524.5 (M+H).

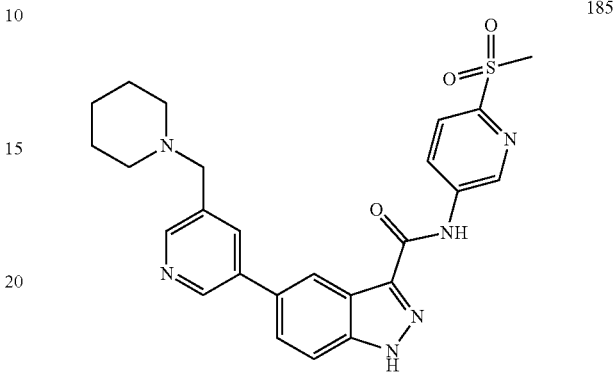

N-(6-(Methylsulfonyl)pyridin-3-yl)-5-(5-(piperidin-1-ylmethyl) pyridin-3-yl)-1H-indazole-3-carboxamide 185

White solid (72 mg, 0.15 mmol, 56.4% yield). $^1$H NMR (DMSO-$d_6$) δ ppm 1.36-1.43 (m, 2H), 1.48-1.55 (m, 4H), 2.39 (brs, 4H), 3.27 (s, 3H), 3.57 (s, 2H), 7.85 (s, 2H), 8.00 (s, 1H), 8.08 (d, J=8.5 Hz, 1H), 8.49 (dd, J=10 Hz, J=1.5 Hz, 2H), 8.83 (d, J=2.5 Hz, 1H), 9.26 (d, J=2.5 Hz, 1H), 11.19 (s, 1H), 14.13 (brs, 1H); ESIMS found for $C_{25}H_{26}N_6O_3S$ m/z 491.1 (M+H).

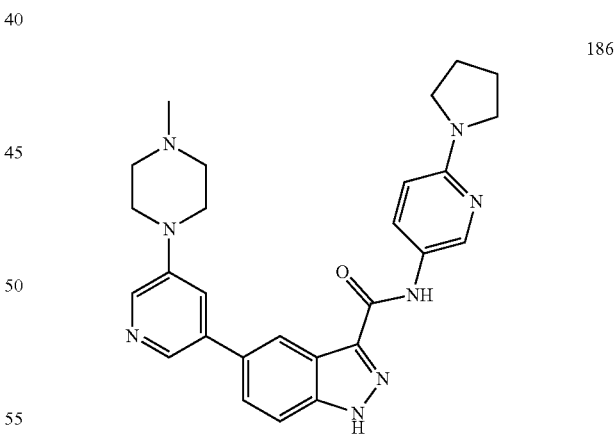

5-(5-(4-Methylpiperazin-1-yl)pyridin-3-yl)-N-(6-(pyrrolidin-1-yl)pyridin-3-yl)-1H-indazole-3-carboxamide 186

Off-white solid (196 mg, 0.41 mmol, 47.8% yield). $^1$H NMR (DMSO-$d_6$) δ ppm 1.89-1.98 (m, 4H), 2.27 (brs, 3H), 3.25-3.42 (m, 12H), 6.45 (d, J=9 Hz, 1H), 7.53 (s, 1H), 7.77 (q, J=8.5 Hz, 2H), 7.96 (d, J=6.5 Hz, 1H), 8.31 (d, J=5.5 Hz, 2H), 8.43 (s, 1H), 8.48 (s, 1H), 10.21 (s, 1H), 13.83 (s, 1H); ESIMS found for $C_{27}H_{30}N_8O$ m/z 483.4 (M+H).

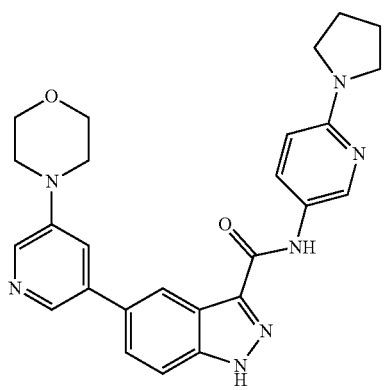

187

5-(5-Morpholinopyridin-3-yl)-N-(6-(pyrrolidin-1-yl)pyridin-3-yl)-1H-indazole-3-carboxamide 187

White solid (92 mg, 0.20 mmol, 43.5% yield). $^1$H NMR (DMSO-d$_6$) δ ppm 1.94 (t, J=6.5 Hz, 4H), 3.28 (t, J=4.5 Hz, 4H), 3.38 (t, J=6.5 Hz, 4H), 3.78 (t, J=4.5 Hz, 4H), 6.45 (d, J=9 Hz, 1H), 7.55 (s, 1H), 7.77 (dq, J=8.5 Hz, J=1.5 Hz, 2H), 7.96 (dd, J=9 Hz, J=2.5 Hz 1H), 8.33 (dd, J=6.5 Hz, J=3 Hz, 2H), 8.44 (s, 1H), 8.49 (d, J=2.5 Hz, 1H), 10.21 (s, 1H), 13.83 (s, 1H); ESIMS found for C$_{26}$H$_{27}$N$_7$O$_2$ m/z 470.5 (M+H).

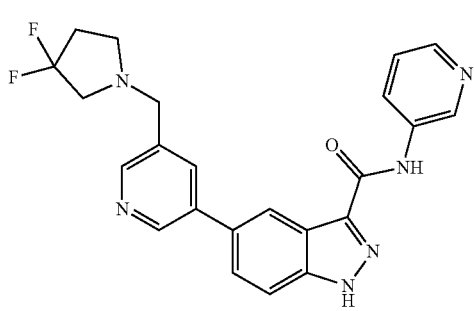

188

5-(5-((3,3-Difluoropyrrolidin-1-yl)methyl)pyridin-3-yl)-N-(pyridin-3-yl)-1H-indazole-3-carboxamide 188

White solid (209 mg, 0.48 mmol, 56.6% yield). $^1$H NMR (DMSO-d$_6$) δ ppm 2.23-2.32 (m, 2H), 2.76 (t, J=7 Hz, 2H), 2.94 (t, J=13.5 Hz, 2H), 3.77 (s, 2H), 7.40 (q, J=8 Hz, 1H), 7.83 (dq, J=8 Hz, J=2 Hz, 2H), 8.04 (s, 1H), 8.31-8.34 (m, 2H), 8.49 (s, 1H), 8.53 (d, J=2 Hz, 1H), 8.85 (d, J=2.5 Hz, 1H), 9.08 (d, J=2 Hz, 1H), 10.70 (s, 1H), 14.01 (brs, 1H); ESIMS found for C$_{23}$H$_{20}$F$_2$N$_6$O m/z 435.2 (M+H).

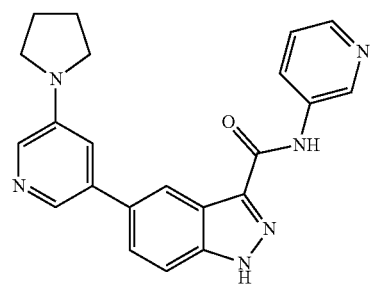

189

N-(Pyridin-3-yl)-5-(5-(pyrrolidin-1-yl)pyridin-3-yl)-1H-indazole-3-carboxamide 189

White solid (30 mg, 0.08 mmol, 26.0% yield). $^1$H NMR (DMSO-d$_6$) δ ppm 1.91-2.05 (m, 4H), 3.33-3.39 (m, 4H), 7.09 (s, 1H), 7.40 (q, J=8 Hz, 1H), 7.79 (s, 2H), 7.96 (d, J=2.5 Hz, 1H), 8.14 (s, 1H), 8.30-8.34 (m, 2H), 8.44 (s, 1H), 9.07 (d, J=2 Hz, 1H), 10.68 (s, 1H), 13.97 (brs, 1H); ESIMS found for C$_{22}$H$_{20}$N$_6$O m/z 385.2 (M+H).

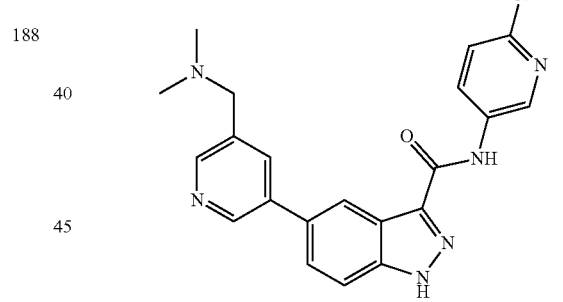

190

5-(5-((Dimethylamino)methyl)pyridin-3-yl)-N-(6-(pyrrolidin-1-yl)pyridin-3-yl)-1H-indazole-3-carboxamide 190

White solid (142 mg, 0.32 mmol, 39.7% yield). $^1$H NMR (DMSO-d$_6$) δ ppm 1.92-1.97 (m, 4H), 2.20 (s, 6H), 3.35-3.40 (m, 4H), 3.53 (s, 2H), 6.46 (d, J=9 Hz, 1H), 7.80 (dq, J=9 Hz, J=1.5 Hz, 2H), 7.97 (dd, J=9 Hz, J=3 Hz, 1H), 8.00 (s, 1H), 8.46-8.50 (m, 3H), 8.82 (d, J=2.5 Hz, 1H), 10.22 (s, 1H), 13.86 (brs, 1H); ESIMS found for C$_{25}$H$_{27}$N$_7$O m/z 442.4 (M+H).

Example 6
Preparation of N-(6-(2-fluorophenoxy)pyridin-3-yl)-5-(pyridin-3-yl)-1H-indazole-3-carboxamide (18) is Depicted Below in Scheme 32
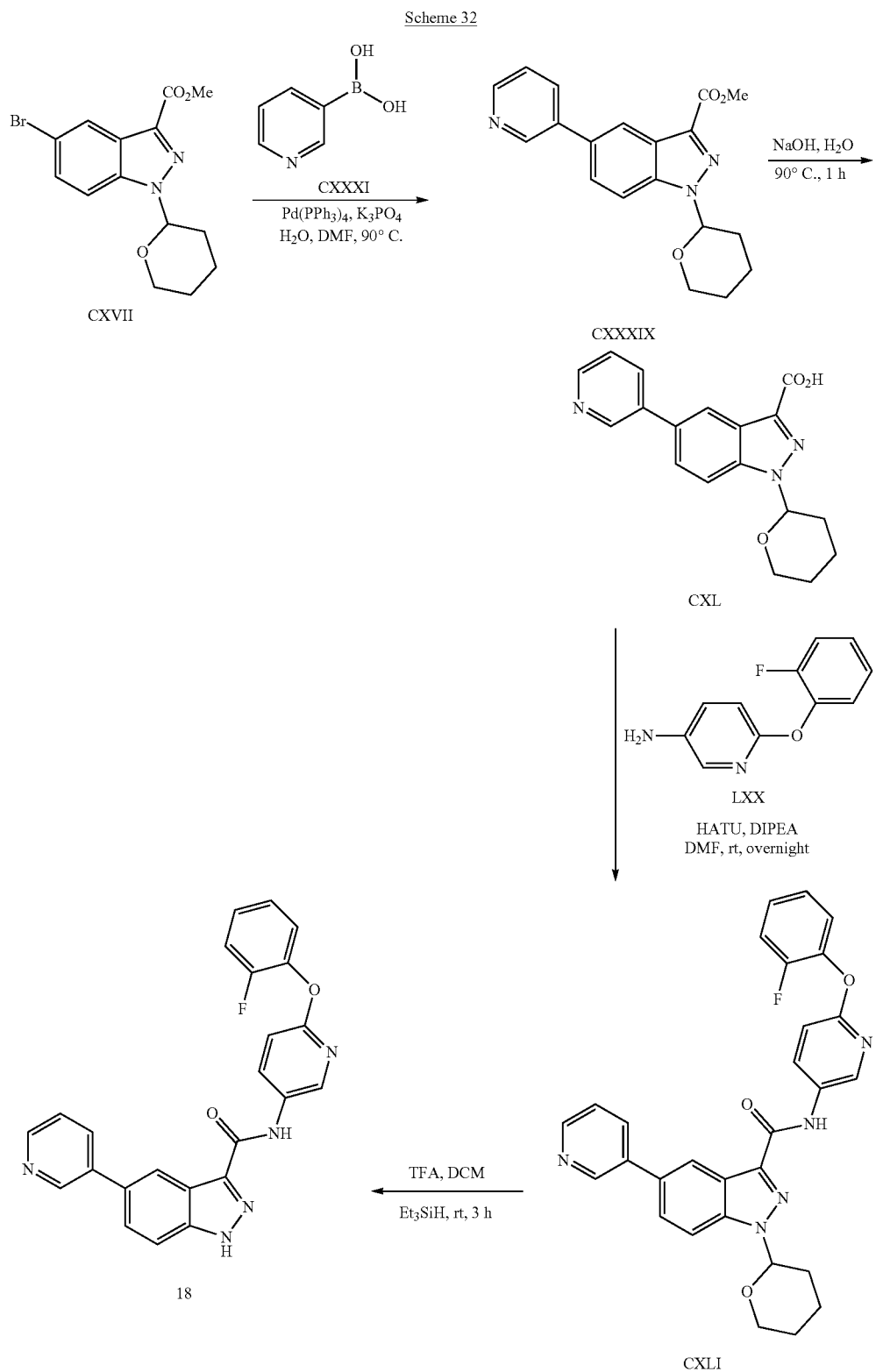

Step 1

To a solution of methyl 5-bromo-1-(tetrahydro-2H-pyran-2-yl)-1H-indazole-3-carboxylate (CXVII) (7.0 g, 20.6 mmol) in DMF (80 mL) and water (16 mL) was added K$_3$PO$_4$ (6.56 g, 30.9 mmol), pyridin-3-ylboronic acid (CXXXI) (2.79 g, 22.7 mmol), Pd(PPh$_3$)$_4$ (1.19 g, 1.03 mmol) and. The solution was purged with argon and heated at 90° C. for 3 h. The solution was cooled to room temperature and then concentrated under reduced pressure. The residue was dissolved in DCM and washed with water, dried over MgSO$_4$, filtered and then evaporated under vacuum. The residue was purified on a silica gel column (100% DCM→1.5:98.5 MeOH:DCM) to give methyl 5-(pyridin-3-yl)-1-(tetrahydro-2H-pyran-2-yl)-1H-indazole-3-carboxylate (CXXXIX) as an orange oil which solidified at rt (6.28 g, 18.6 mmol, 90% yield). ESIMS found for C$_{19}$H$_{19}$N$_3$O$_3$ m/z 338.0 (M+H).

Step 2

Preparation of intermediate 5-(pyridin-3-yl)-1-(tetrahydro-2H-pyran-2-yl)-1H-indazole-3-carboxylic acid (CXL) was performed following the procedure listed in Scheme 25, Step 4. White solid (900 mg, 2.78 mmol, 15% yield). ESIMS found for C$_{18}$H$_{17}$N$_3$O$_3$ m/z 324.1 (M+H).

Step 3

Preparation of intermediate N-(6-(2-fluorophenoxy)pyridin-3-yl)-5-(pyridin-3-yl)-1-(tetrahydro-2H-pyran-2-yl)-1H-indazole-3-carboxamide (CXLI) was performed following the procedure listed in Scheme 28, Step 3. Off-white solid (207 mg, 0.41 mmol, 66% yield). $^1$H NMR (DMSO-d$_6$) δ ppm 1.60-1.69 (m, 2H), 1.76-1.87 (m, 1H), 2.03-2.13 (m, 2H), 2.56-2.65 (m, 1H), 3.84 (dt, J=11 Hz, J=4 Hz, 1H), 3.99 (t, J=11 Hz, 1H), 6.07 (dd, J=10 Hz, J=2 Hz, 1H), 6.98 (dd, J=3 Hz, J=2 Hz, 1H), 7.03-7.08 (m, 2H), 7.14 (d, J=9 Hz, 1H), 7.46 (t, J=7 Hz, 1H), 7.61 (dd, J=8 Hz, J=5 Hz, 1H), 7.91 (dd, J=9 Hz, J=2 Hz, 1H), 8.05 (d, J=9 Hz, 1H), 8.25 (d, J=8 Hz, 1H), 8.37 (dd, J=9 Hz, J=3 Hz, 1H), 8.49 (s, 1H), 8.64 (dd, J=5 Hz, J=2 Hz, 1H), 8.66 (d, J=3 Hz, 1H), 9.00 (d, J=2 Hz, 1H), 10.59 (s, 1H); ESIMS found for C$_{29}$H$_{24}$FN$_5$O$_3$ m/z 509.2 (M+H).

Step 4

Preparation of N-(6-(2-fluorophenoxy)pyridin-3-yl)-5-(pyridin-3-yl)-1H-indazole-3-carboxamide (18) was performed following the procedure listed in Scheme 28, Step 4. White solid (128 mg, 0.30 mmol, 54.7% yield). $^1$H NMR (DMSO-d$_6$) δ ppm 7.16 (d, J=9 Hz, 1H), 7.23-7.39 (m, 4H), 7.52 (dd, J=8 Hz, J=5 Hz, 11-1), 7.79-7.85 (m, 2H), 8.13 (td, J=8 Hz, J=2 Hz, 1H), 8.38 (dd, J=9 Hz, J=3 Hz, 1H), 8.46 (s, 1H), 8.56 (d, J=3 Hz, 1H), 8.59 (dd, J=5 Hz, J=1 Hz, 1H), 8.93 (d, J=2 Hz, 1H), 10.65 (s, 1H), 13.96 (brs, 1H); ESIMS found for C$_{24}$H$_{16}$FN$_5$O$_2$ m/z 426.0 (M+H).

The following compounds were prepared in accordance with the procedure described in the above Example 6.

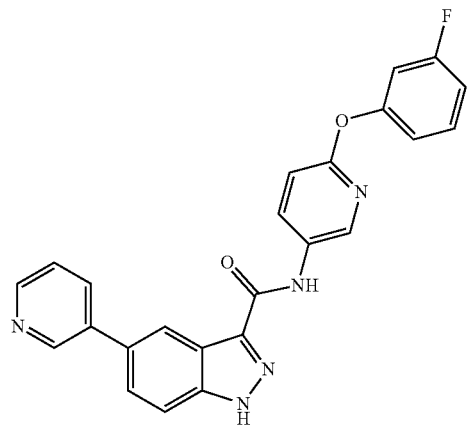

N-(6-(3-Fluorophenoxy)pyridin-3-yl)-5-(pyridin-3-yl)-1H-indazole-3-carboxamide 19

Off-white solid (148 mg, 0.35 mmol, 89.3% yield). $^1$H NMR (DMSO-d$_6$) δ ppm 6.98 (dd, J=8 Hz, J=2 Hz, 1H), 7.01-7.06 (m, 2H), 7.13 (d, J=9 Hz, 1H), 7.44 (q, J=7 Hz, 1H), 7.53 (dd, J=8 Hz, J=5 Hz, 1H), 7.80-7.85 (m, 2H), 8.14 (td, J=6 Hz, J=2 Hz, 1H), 8.40 (dd, J=9 Hz, J=3 Hz, 1H), 8.47 (s, 1H), 8.60 (dd, J=5 Hz, J=1 Hz, 1H), 8.69 (d, J=3 Hz, 1H), 8.93 (d, J=2 Hz, 1H), 10.71 (s, 1H), 13.99 (s, 1H); ESIMS found for C$_{24}$H$_{16}$FN$_5$O$_2$ m/z 426.0 (M+H).

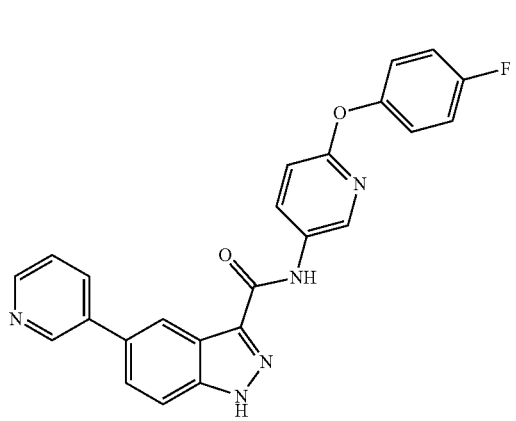

N-(6-(4-Fluorophenoxy)pyridin-3-yl)-5-(pyridin-3-yl)-1H-indazole-3-carboxamide 20

White solid (82 mg, 0.19 mmol, 91.8% yield). $^1$H NMR (DMSO-d$_6$) δ ppm 7.08 (d, J=9 Hz, 1H), 7.15-7.21 (m, 2H), 7.22-7.27 (m, 2H), 7.67 (dd, J=8 Hz, J=5 Hz, 1H), 7.81-7.88 (m, 2H), 8.31 (d, J=8 Hz, 1H), 8.36 (dd, J=9 Hz, J=3 Hz, 1H), 8.51 (s, 1H), 8.63 (d, J=3 Hz, 1H), 8.66 (dd, J=5 Hz, J=1 Hz, 1H), 9.02 (d, 2 Hz, 1H), 10.67 (s, 1H), 14.00 (s, 1H); ESIMS found for C$_{24}$H$_{16}$FN$_5$O$_2$ m/z 426.0 (M+H).

Example 7

Preparation of N-(6-carbamoylpyridin-3-yl)-5-(5-(piperidin-1-ylmethyl)pyridin-3-yl)-1H-indazole-3-carboxamide (180) is Depicted Below in Scheme 33

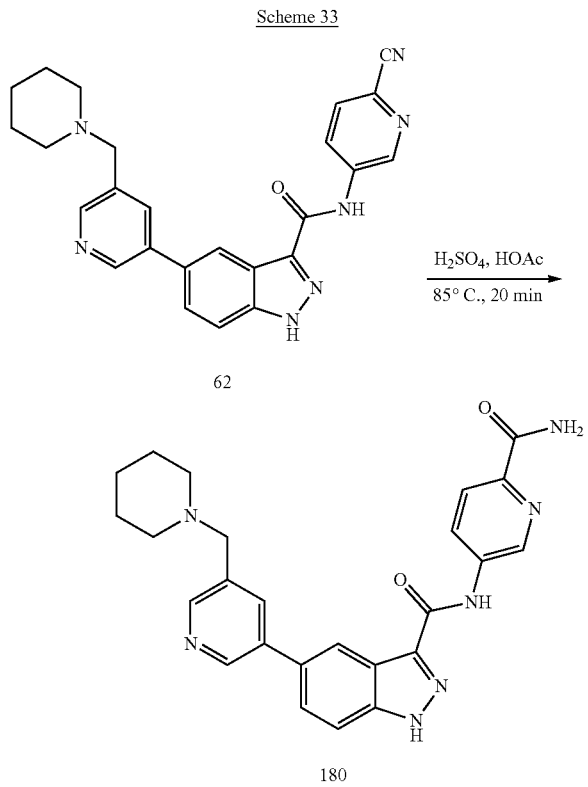

Step 1

To a solution of N-(6-cyanopyridin-3-yl)-5-(5-(piperidin-1-ylmethyl)pyridin-3-yl)-1H-indazole-3-carboxamide (62) (200 mg, 0.45 mmol) in glacial acetic acid (2 mL) heated at 85° C. was carefully added dropwise sulfuric acid (2 mL). The reaction was heated at 85° C. for another 20 minutes before pouring into ice. The solution was basified with cold 5N NH$_4$OH. The solids formed were filtered, washed with cold washed and dried under vacuum. The dry solid was suspended in DCM and a few drops of MeOH were added. The insoluble solids were filtered and discarded. The filtrate was concentrated and suspended again in DCM, boiled for 15 minutes and filtered. The solid was dried under vacuum to give N-(6-carbamoylpyridin-3-yl)-5-(5-(piperidin-1-ylmethyl)pyridin-3-yl)-1H-indazole-3-carboxamide (180) as a white solid (192 mg, 0.42 mmol, 93.7% yield). $^1$H NMR (DMSO-d$_6$) δ ppm 1.36-1.42 (m, 2H), 1.48-1.55 (m, 4H), 2.38 (brs, 4H), 3.56 (s, 2H), 7.49 (s, 1H), 7.65 (d, J=9 Hz, 1H), 7.80 (d, J=9 Hz, 1H), 7.97 (s, 1H), 8.03 (s, 2H), 8.41 (s, 1H), 8.45 (d, J=2 Hz, 1H), 8.54 (dd, J=9 Hz, J=2.5 Hz, 1H), 8.80 (d, J=2 Hz, 1H), 9.15 (d, J=2 Hz, 1H), 10.83 (brs, 1H); ESIMS found for C$_{25}$H$_{25}$N$_7$O$_2$ m/z 456.4 (M+H).

Administration and Pharmaceutical Compositions

Some embodiments include administration of the compounds described herein as pharmaceutical compositions comprising: (a) a safe and therapeutically effective amount of the indazole-3-carboxamide, or its corresponding enantiomer, diastereoisomer or tautomer, or pharmaceutically acceptable salt; and (b) a pharmaceutically acceptable carrier.

In some embodiments, the methods described herein further include administering the compounds of this invention in combination (administered together or sequentially) with other known agents.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, ontologically, neuro-otologically, intraocularly, subconjuctivally, via anterior eye chamber injection, intravitreally, intraperitoneally, intrathecally, intracystically, intrapleurally, via wound irrigation, intrabuccally, intra-abdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic devices. Oral and parenteral administrations are customary in treating the indications.

Compounds of the invention intended for pharmaceutical use may be administered as crystalline or amorphous products. Pharmaceutically acceptable compositions may include solid, semi-solid, liquid, solutions, colloidal, liposomes, emulsions, suspensions, complexes, coacervates and aerosols. Dosage forms, such as, e.g., tablets, capsules, powders, liquids, suspensions, suppositories, aerosols, implants, controlled release or the like. They may be obtained, for example, as solid plugs, powders, or films by methods such as precipitation, crystallization, milling, grinding, supercritical fluid processing, coacervation, complex coacervation, encapsulation, emulsification, complexation, freeze drying, spray drying, or evaporative drying. Microwave or radio frequency drying may be used for this purpose. The compounds can also be administered in sustained or controlled release dosage forms, including depot injections, osmotic pumps, pills (tablets and or capsules), transdermal (including electrotransport) patches, implants and the like, for prolonged and/or timed, pulsed administration at a predetermined rate.

The compounds can be administered either alone or more typically in combination with a conventional pharmaceutical carrier, excipient or the like. The term "excipient" is used herein to describe any ingredient other than the compound(s) of the invention. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human scrum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-b-cyclodextrins, or other solubilized derivatives can also be advantageously used to enhance delivery of compounds of the formulae described herein. Dosage forms or compositions containing a compound as described herein in the range of 0.005% to 100% with the balance made up from non-toxic carrier may be prepared. The contemplated compositions may contain 0.001%-100% active ingredient, in one embodiment 0.1-95%, in another embodiment 75-85%, in a further embodiment 20-80%, Actual methods of preparing such dosage forms are known, or will be apparent, to those skilled in this art; for example, see *Remington: The Science and Practice of Pharmacy,* 21st Edition (Lippincott Williams & Wilkins. 2005).

In one preferred embodiment, the compositions will take the form of a unit dosage form such as a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which the two active ingredients are physically separated are also contemplated; e.g., capsules with granules (or tablets in a capsule) of each drug; two-layer tablets; two-compartment gel caps, etc. Enteric coated or delayed release oral dosage forms are also contemplated.

Liquid pharmaceutically administrable compositions can, for example, be prepared by dissolving, dispersing, etc. an active compound as defined above and optional pharmaceutical adjuvants in a carrier (e.g., water, saline, aqueous dextrose, glycerol, glycols, ethanol or the like) to form a solution, colloid, liposome, emulsion, complexes, coacervate or suspension. If desired, the pharmaceutical composition can also contain minor amounts of nontoxic auxiliary substances such as wetting agents, emulsifying agents, co-solvents, solubilizing agents, pH buffering agents and the like (e.g., sodium acetate, sodium citrate, cyclodextrin derivatives, sorbitan monolaurate, triethanolamine acetate, triethanolamine oleate, and the like).

In some embodiments, the unit dosage of compounds of Formula (I) is 0.25 mg/Kg to 50 mg/Kg in humans.

In some embodiments, the unit dosage of compounds of Formula (I) is 0.25 mg/Kg to 20 mg/Kg in humans.

In some embodiments, the unit dosage of compounds of Formula (I) is 0.50 mg/Kg to 19 mg/Kg in humans.

In some embodiments, the unit dosage of compounds of Formula (I) is 0.75 mg/Kg to 18 mg/Kg in humans.

In some embodiments, the unit dosage of compounds of Formula (I) is 1.0 mg/Kg to 17 mg/Kg in humans.

In some embodiments, the unit dosage of compounds of Formula (I) is 1.25 mg/Kg to 16 mg/Kg in humans.

In some embodiments, the unit dosage of compounds of Formula (I) is 1.50 mg/Kg to 15 mg/Kg in humans.

In some embodiments, the unit dosage of compounds of Formula (I) is 1.75 mg/Kg to 14 mg/Kg in humans.

In some embodiments, the unit dosage of compounds of Formula (I) is 2.0 mg/Kg to 13 mg/Kg in humans.

In some embodiments, the unit dosage of compounds of Formula (I) is 3.0 mg/Kg to 12 mg/Kg in humans.

In some embodiments, the unit dosage of compounds of Formula (I) is 4.0 mg/Kg to 11 mg/Kg in humans.

In some embodiments, the unit dosage of compounds of Formula (I) is 5.0 mg/Kg to 10 mg/Kg in humans.

In some embodiments, the compositions are provided in unit dosage forms suitable for single administration of a precise dose.

In some embodiments, the compositions are provided in unit dosage forms suitable for twice a day administration of a precise dose.

In some embodiments, the compositions are provided in unit dosage forms suitable for three times a day administration of a precise dose.

Injectables can be prepared in conventional forms, either as liquid solutions, colloid, liposomes, complexes, coacervate or suspensions, as emulsions, or in solid forms suitable for reconstitution in liquid prior to injection. The percentage of active compound contained in such parenteral compositions is highly dependent on the specific nature thereof, as well as the activity of the compound and the needs of the subject. However, percentages of active ingredient of 0.01% to 10% in solution are employable, and could be higher if the composition is a solid or suspension, which could be subsequently diluted to the above percentages.

In some embodiments, the injection can be an intratendon injection.

In some embodiments, the composition will comprise 0.1-10% of the active agent in solution.

In some embodiments, the composition will comprise 0.1-5% of the active agent in solution.

In some embodiments, the composition will comprise 0.1-4% of the active agent in solution.

In some embodiments, the composition will comprise 0.15-3% of the active agent in solution.

In some embodiments, the composition will comprise 0.2-2% of the active agent in solution.

In some embodiments, the compositions are provided in dosage forms suitable for continuous dosage by intravenous infusion over a period of 1-96 hours.

In some embodiments, the compositions are provided in dosage forms suitable for continuous dosage by intravenous infusion over a period of 1-72 hours.

In some embodiments, the compositions are provided in dosage forms suitable for continuous dosage by intravenous infusion over a period of 1-48 hours.

In some embodiments, the compositions are provided in dosage forms suitable for continuous dosage by intravenous infusion over a period of 1-24 hours.

In some embodiments, the compositions are provided in dosage forms suitable for continuous dosage by intravenous infusion over a period of 1-12 hours.

In some embodiments, the compositions are provided in dosage forms suitable for continuous dosage by intravenous infusion over a period of 1-6 hours.

In some embodiments, these compositions can be administered by intravenous infusion to humans at doses of 5 mg/m$^2$ to 300 mg/m$^2$.

In some embodiments, these compositions can be administered by intravenous infusion to humans at doses of 5 mg/m$^2$ to 200 mg/m$^2$.

In some embodiments, these compositions can be administered by intravenous infusion to humans at doses of 5 mg/m$^2$ to 100 mg/m$^2$.

In some embodiments, these compositions can be administered by intravenous infusion to humans at doses of 10 mg/m$^2$ to 50 mg/m$^2$.

In some embodiments, these compositions can be administered by intravenous infusion to humans at doses of 50 mg/m$^2$ to 200 mg/m$^2$.

In some embodiments, these compositions can be administered by intravenous infusion to humans at doses of 75 mg/m$^2$ to 175 mg/m$^2$.

In some embodiments, these compositions can be administered by intravenous infusion to humans at doses of 100 mg/m$^2$ to 150 mg/m$^2$.

In one preferred embodiment, the compositions can be administered to the respiratory tract (including nasal and pulmonary) e.g., through a nebulizer, metered-dose inhalers, atomizer, mister, aerosol, dry powder inhaler, insufflator, liquid instillation or other suitable device or technique.

In some embodiments, aerosols intended for delivery to the nasal mucosa are provided for inhalation through the nose. For optimal delivery to the nasal cavities, inhaled particle sizes of about 5 to about 100 microns are useful, with particle sizes of about 10 to about 60 microns being preferred. For nasal delivery, a larger inhaled particle size is desired to maximize impaction on the nasal mucosa and to minimize or prevent pulmonary deposition of the administered formulation. In some embodiments, aerosols intended for delivery to the lung are provided for inhalation through the nose or the mouth. For optimal delivery to the lung, inhaled aerodynamic particle sizes of equal or less than 10 μm are useful, with an aerodynamic particle size of about 0.1 to 10 microns being preferred. Inhaled particles may be defined as liquid droplets containing dissolved drug, liquid droplets containing suspended drug particles (in cases where the drug is insoluble in the suspending medium), dry particles of pure drug substance, drug substance incorporated with excipients, liposomes, emulsions, colloidal systems, coacervates, aggregates of drug nanoparticles, or dry particles of a diluent which contain embedded drug nanoparticles.

In some embodiments, compounds of Formula (I) disclosed herein intended for respiratory delivery (either systemic or local) can be administered as aqueous formulations, as non-aqueous solutions or suspensions, as suspensions or solutions in halogenated hydrocarbon propellants with or without alcohol, as a colloidal system, as emulsions, coacervates or as dry powders. Aqueous formulations may be aerosolized by liquid nebulizers employing either hydraulic or ultrasonic atomization or by modified micropump systems (like the soft mist inhalers, the Aerodose® or the AERx® systems). Propellant-based systems may use suitable pressurized metered-dose inhalers (pMDIs). Dry powders may use dry powder inhaler devices (DPIs), which are capable of dispersing the drug substance effectively. A desired particle size and distribution may be obtained by choosing an appropriate device.

In some embodiments, the compositions of Formula (I) disclosed herein can be administered to the car by various methods. For example, a round window catheter (e.g., U.S. Pat. Nos. 6,440,102 and 6,648,873) can be used.

Alternatively, formulations can be incorporated into a wick for use between the outer and middle ear (e.g., U.S. Pat. No. 6,120,484) or absorbed to collagen sponge or other solid support (e.g., U.S. Pat. No. 4,164,559).

If desired, formulations of the invention can be incorporated into a gel formulation (e.g., U.S. Pat. Nos. 4,474,752 and 6,911,211).

In some embodiments, compounds of Formula (I) disclosed herein intended for delivery to the ear can be administered via an implanted pump and delivery system through a needle directly into the middle or inner ear (cochlea) or through a cochlear implant stylet electrode channel or alternative prepared drug delivery channel such as but not limited to a needle through temporal bone into the cochlea.

Other options include delivery via a pump through a thin film coated onto a multichannel electrode or electrode with a specially imbedded drug delivery channel (pathways) carved into the thin film for this purpose. In other embodiments the acidic or basic solid gacyclidine can be delivered from the reservoir of an external or internal implanted pumping system.

Formulations of the invention also can be administered to the ear by intratympanic injection into the middle ear, inner ear, or cochlea (e.g., U.S. Pat. No. 6,377,849 and Ser. No. 11/337,815).

Intratympanic injection of therapeutic agents is the technique of injecting a therapeutic agent behind the tympanic membrane into the middle and/or inner car. In one embodiment, the formulations described herein are administered directly onto the round window membrane via transtympanic injection. In another embodiment, the ion channel modulating agent auris-acceptable formulations described herein are administered onto the round window membrane via a non-transtympanic approach to the inner ear. In additional embodiments, the formulation described herein is administered onto the round window membrane via a surgical approach to the round window membrane comprising modification of the crista fenestrae cochleae.

In some embodiments, the compounds of Formula (I) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG (like PEG ointments), and the like. In suppository forms of the compositions, a low-melting wax such as, but not limited to, a mixture of fatty acid glycerides, optionally in combination with cocoa butter is first melted.

Suppositories for rectal administration of the drug (either as a solution, colloid, suspension or a complex) can be prepared by mixing the drug with a suitable non-irritating excipient that is solid at ordinary temperatures but liquid at the rectal temperature and will therefore melt or erode/dissolve in the rectum and release the drug. Such materials include cocoa butter, glycerinated gelatin, hydrogenated vegetable oils, poloxamers, mixtures of polyethylene glycols of various molecular weights and fatty acid esters of polyethylene glycol.

In some embodiments, the compositions can be administered by transdermal patch.

Other modes of deliveries include using biodegradable or non-biodegradable scaffolds.

It is to be noted that concentrations and dosage values may also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Solid compositions can be provided in various different types of dosage forms, depending on the physicochemical properties of the drug, the desired dissolution rate, cost considerations, and other criteria. In one of the embodiments, the solid composition is a single unit. This implies that one-unit dose of the drug is comprised in a single, physically shaped solid form or article. In other words, the solid composition is coherent, which is in contrast to a multiple unit dosage form, in which the units are incoherent.

Examples of single units which may be used as dosage forms for the solid composition include tablets, such as compressed tablets, film-like units, foil-like units, wafers, lyophilized matrix units, and the like. In a preferred embodiment, the solid composition is a highly porous lyophilized form. Such lyophilizates, sometimes also called wafers or lyophilized tablets, are particularly useful for their rapid disintegration, which also enables the rapid dissolution of the active compound.

On the other hand, for some applications the solid composition may also be formed as a multiple unit dosage form as defined above. Examples of multiple units are powders, granules, microparticles, pellets, mini-tablets, beads, lyophilized powders, and the like. In one embodiment, the solid composition is a lyophilized powder. Such a dispersed lyophilized system comprises a multitude of powder particles, and due to the lyophilization process used in the formation of the powder, each particle has an irregular, porous microstructure through which the powder is capable of absorbing water very rapidly, resulting in quick dissolution. Effervescent compositions are also contemplated to aid the quick dispersion and absorption of the compound.

Another type of multiparticulate system which is also capable of achieving rapid drug dissolution is that of powders, granules, or pellets from water-soluble excipients which are coated with the drug, so that the drug is located at the outer surface of the individual particles. In this type of system, the water-soluble low molecular weight excipient is useful for preparing the cores of such coated particles, which can be subsequently coated with a coating composition comprising the drug and, preferably, one or more additional excipients, such as a binder, a pore former, a saccharide, a sugar alcohol, a film-forming polymer, a plasticizer, or other excipients used in pharmaceutical coating compositions.

Also provided herein are kits. Typically, a kit includes one or more compounds or compositions as described herein. In certain embodiments, a kit can include one or more delivery systems, e.g., for delivering or administering a compound as provided above, and directions for use of the kit (e.g., instructions for treating a patient). In another embodiment, the kit can include a compound or composition as described herein and a label that indicates that the contents are to be administered to a patient with cancer. In another embodiment, the kit can include a compound or composition as described herein and a label that indicates that the contents are to be administered to a patient with one or more diseases or conditions independently selected from the group consisting of a tendinopathy, dermatitis, psoriasis, morphea, ichthyosis, Raynaud's syndrome, and Darier's disease; and/or for promoting wound healing.

The actual dose of the active compounds of the present invention depends on the specific compound, and on the condition to be treated; the selection of the appropriate dose is well within the knowledge of the skilled artisan.

Methods of Treatment

The compounds and compositions provided herein can be used as inhibitors and/or modulators of one or more components of the Wnt pathway, which may include one or more Wnt proteins, and thus can be used to treat a variety of disorders and diseases in which aberrant Wnt signaling is implicated. Non-limiting examples include one or more diseases or conditions independently selected from the group consisting of a tendinopathy, dermatitis, psoriasis, morphea, ichthyosis, Raynaud's syndrome, and Darier's disease. In certain embodiments, the compounds and compositions provided herein can be used for promoting wound healing.

In some embodiments, the methods further include administering to a patient in need of such treatment an effective amount of one or more of the compounds of Formula (I), in combination (simultaneously or sequentially) with at least one other agent.

In some embodiments, the methods further include administering a pharmaceutical composition that includes a therapeutically effective amount of a compound of Formula (I), or a pharmaceutically acceptable salt thereof, and a pharmaceutically acceptable excipient and optionally at least one other agent.

In some embodiments, the one or more diseases or conditions is a tendinopathy. In certain embodiments, the tendinopathy is tendinosis. In certain embodiments, the tendinopathy is tendinitis. In certain embodiments, the tendinopathy is tenosynovitis.

A tendon is a band of fibrous connective tissue that usually connects muscle to bone. Healthy tendons include parallel arrays of type I collagen fibers closely packed together, but also include a small amount of elastin and of proteoglycans. Tendons can be slow to heal if injured, and sometimes do not regain their original strength. Partial tears heal by the rapid production of disorganized type-III collagen, which is weaker than normal tendon. Recurrence of injury in the damaged region of tendon is common.

Tendons which may be treated by the methods of the invention include any tendon of the human or mammalian body. Non-limiting examples of tendons include the patellar tendon, the anterior tibialis tendon, the Achilles tendon, the hamstring tendon, the semitendinosus tendon, the gracilis tendon, the abductor tendon, the adductor tendon, the supraspinatus tendon, the infraspinatus tendon, the subscapularis tendon, the teres minor tendon, the flexor tendon, the rectus femoris tendon, the tibialis posterior tendon, and the quadriceps femoris tendon.

In some embodiments, the tendon is a tendon of the foot or ankle; e.g., the extensor hallucis longus, the flexor hallucis longus, the extensor digitorum longus, the extensor digitorum brevis, the peroneus longus, the peroneus brevis, the flexor hallucis brevis, the flexor digitorum longus, the posterior tibialis, the Achilles tendon, and the plantar fascia.

In some embodiments, the tendon is a tendon of the leg; e.g., the patellar tendon, the anterior tibialis tendon, the Achilles tendon, the hamstring tendon, the semitendinosus tendon, the gracilis tendon, the abductor tendon, the adductor tendon, the flexor tendon, the rectus femoris tendon, the tibialis posterior tendon, and the quadriceps femoris tendon.

In some embodiments, the tendon is a tendon of the shoulder; e.g., the supraspinatus tendon, the infraspinatus tendon, the subscapularis tendon, and the teres minor tendon (rotator cuff complex).

In some embodiments, the tendon is a tendon of the elbow; e.g., the biceps tendon, the triceps tendon, the extensor carpi radialis brevis, the common extensor tendon, the extensor digitorum, the extensor digiti minimi, the extensor carpi ulnaris, the supinator, the common flexor tendon, the pronator teres, the flexor carpi radialis, the palmaris longus, the flexor carpi ulnaris and the digitorum superficialis. In some embodiments, the tendon is a tendon of the wrist. In some embodiments, the tendon of the wrist is selected from the group consisting of biceps tendon, the triceps tendon, the extensor carpi radialis brevis, the common extensor tendon, the extensor digitorum, the extensor digiti minimi, the extensor carpi ulnaris, the supinator, the common flexor tendon, the pronator teres, the flexor carpi radialis, the palmaris longus, the flexor carpi ulnaris, the digitorum superficialis, the flexor pollicis brevis, the flexor pollicis longus, the abductor pollicis brevis, the abductor pollicis longus, the flexor digitorum profundus, the flexor digitorum superficialis, the extensor pollicis brevis, and the extensor pollicis longus. In some embodiments, the tendon is a tendon of the hand. In some embodiments, the tendon of the hand is selected from the group consisting of the flexor pollicis brevis, the flexor pollicis longus, the abductor pollicis brevis, the abductor pollicis longus, the flexor digitorum profundus, the flexor digitorum superficialis, the extensor pollicis brevis, and the extensor pollicis longus.

Non-limiting examples of tendinopathies include: clavicular or patellar tendinopathy, patellar tendonitis; medial tibial stress syndrome; Achilles tendinopathy, lateral epicondylitis or "tennis elbow;" medial epicondylitis or "golfer's elbow;" plantar fasciitis; and rotator cuff tendinopathy.

In some embodiments, the tendinopathy is rotator cuff tendinopathy; e.g., supraspinatus tendinopathy, infraspinatus tendinopathy, subscapularis tendinopathy, and teres minor tendinopathy.

In some embodiments, the tendinopathy is lateral epicondylitis or "tennis elbow" at the extensor muscle group origin at the lateral humeral condyle insertion, principally in the extensor carpi radialis brevis (ECRB) tendon. In some embodiments, the tendinopathy is medial epicondylitis or "golfer's elbow" at the interface between the pronator teres and flexor carpi radialis origin of the medial humeral condyle.

In some embodiments, the tendinopathy is patellar tendinopathy. In some embodiments, the tendinopathy is Achilles tendinopathy. In some embodiments, the tendinopathy is plantar fasciitis. In some embodiments, the tendinopathy is medial plantar fasciitis. In some embodiments, the tendinopathy is lateral plantar fasciitis.

In some embodiments, the tendinopathy is tendinosis. In some embodiments, the tendinosis is selected from the group consisting of extensor hallucis longus tendinosis, flexor hallucis longus tendinosis, extensor digitorum longus tendinosis, extensor digitorum brevis tendinosis, peroneus longus tendinosis, peroneus brevis tendinosis, flexor hallucis brevis tendinosis, flexor digitorum longus tendinosis, posterior tibialis tendinosis, Achilles tendon tendinosis, and plantar fascia tendinosis. In some embodiments, the tendinosis is selected from the group consisting of patellar tendinosis, the anterior tibialis tendinosis, the hamstring tendinosis, semitendinosus tendinosis, gracilis tendinosis, abductor tendinosis, and adductor tendinosis. In some embodiments, the tendinosis is selected from the group consisting of flexor tendinosis, rectus femoris tendinosis, tibialis posterior tendinosis, and quadriceps femoris tendinosis. In some embodiments, the tendinosis is selected from the group consisting of supraspinatus tendinosis, infraspinatus tendinosis, subscapularis tendinosis, and teres minor tendinosis.

In some embodiments, the tendinosis is selected from the group consisting of biceps tendinosis, triceps tendinosis, extensor carpi radialis brevis tendinosis, common extensor tendinosis, extensor digitorum tendinosis, extensor digiti minimi tendinosis, extensor carpi ulnaris tendinosis, supinator tendinosis, common flexor tendinosis, pronator teres tendinosis, flexor carpi radialis tendinosis, palmaris longus tendinosis, flexor carpi ulnaris tendinosis and digitorum superficialis tendinosis. In some embodiments, the tendinosis is selected from the group consisting of biceps tendinosis, triceps tendinosis, extensor carpi radialis brevis tendinosis, common extensor tendinosis, extensor digitorum tendinosis, extensor digiti minimi tendinosis, extensor carpi ulnaris tendinosis, supinator tendinosis, common flexor tendinosis, pronator teres tendinosis, flexor carpi radialis tendinosis, palmaris longus tendinosis, flexor carpi ulnaris tendinosis, digitorum superficialis tendinosis, flexor pollicis brevis tendinosis, flexor pollicis longus tendinosis, abductor pollicis brevis tendinosis, abductor pollicis longus tendinosis, flexor digitorum profundus tendinosis, flexor digitorum superficialis tendinosis, extensor pollicis brevis tendinosis, and extensor pollicis longus tendinosis. In some embodiments, the tendinosis is selected from the group consisting of flexor pollicis brevis tendinosis, flexor pollicis longus tendinosis, abductor pollicis brevis tendinosis, abductor pollicis longus tendinosis, flexor digitorum profundus tendinosis, flexor digitorum superficialis tendinosis, extensor pollicis brevis tendinosis, and extensor pollicis longus tendinosis.

In some embodiments, the tendinopathy is tendinitis. In some embodiments, the tendinitis is selected from the group consisting of extensor hallucis longus tendinitis, flexor hallucis longus tendinitis, extensor digitorum longus tendinitis, extensor digitorum brevis tendinitis, peroneus longus tendinitis, peroneus brevis tendinitis, flexor hallucis brevis tendinitis, flexor digitorum longus tendinitis, posterior tibialis tendinitis, Achilles tendon tendinitis, and plantar fascia tendinitis. In some embodiments, the tendinitis is selected from the group consisting of patellar tendinitis, the anterior tibialis tendinitis, the hamstring tendinitis, semitendinosus tendinitis, gracilis tendinitis, abductor tendinitis, and adductor tendinitis. In some embodiments, the tendinitis is selected from the group consisting of flexor tendinitis, rectus femoris tendinitis, tibialis posterior tendinitis, and quadriceps femoris tendinitis. In some embodiments, the tendinitis is selected from the group consisting of supraspinatus tendinitis, infraspinatus tendinitis, subscapularis tendinitis, and teres minor tendinitis.

In some embodiments, the tendinitis is selected from the group consisting of biceps tendinitis, triceps tendinitis, extensor carpi radialis brevis tendinitis, common extensor tendinitis, extensor digitorum tendinitis, extensor digiti minimi tendinitis, extensor carpi ulnaris tendinitis, supinator tendinitis, common flexor tendinitis, pronator teres tendinitis, flexor carpi radialis tendinitis, palmaris longus tendinitis, flexor carpi ulnaris tendinitis and digitorum superficialis tendinitis. In some embodiments, the tendinitis is selected from the group consisting of biceps tendinitis, triceps tendinitis, extensor carpi radialis brevis tendinitis, common extensor tendinitis, extensor digitorum tendinitis, extensor digiti minimi tendinitis, extensor carpi ulnaris tendinitis, supinator tendinitis, common flexor tendinitis, pronator teres tendinitis, flexor carpi radialis tendinitis, palmaris longus tendinitis, flexor carpi ulnaris tendinitis, digitorum superficialis tendinitis, flexor pollicis brevis tendinitis, flexor pollicis longus tendinitis, abductor pollicis brevis tendinitis, abductor pollicis longus tendinitis, flexor digitorum profundus tendinitis, flexor digitorum superficialis tendinitis, extensor pollicis brevis tendinitis, and extensor pollicis longus tendinitis. In some embodiments, the tendinitis is selected from the group consisting of flexor pollicis brevis tendinitis, flexor pollicis longus tendinitis, abductor pollicis brevis tendinitis, abductor pollicis longus tendinitis, flexor digitorum profundus tendinitis, flexor digitorum superficialis tendinitis, extensor pollicis brevis tendinitis, calcific tendinitis, and extensor pollicis longus tendinitis.

In some embodiments, the tendinitis is caused by chronic overuse injuries of tendon failed healing.

In some embodiments, the injury or damage is localized very near the muscle-tendon junction (myotendinous junction).

In some embodiments, the tendinitis leads to scarring and fibrosis.

The methods of the invention may result in improvement in one or more of the following: decreasing pain of the affected joint or limb, decreasing stiffness of the affected joint or limb, increasing mobility of the affected joint or limb, increasing strength of the affected joint or limb, decreasing the rate of tendinopathy progression, decreasing inflammation, increasing the strength of the tendon, or improving the rate of tendon strength recovery. Various methods for measuring effectiveness of the treatment include, but are not limited to: Disabilities of the Arm, Shoulder and Hand Score (DASH), Visual Analog Score (VAS), and grip strength testing.

In some embodiments, the treatment results in increased strength of the tendon. In some embodiments, the treatment results in a more rapid rate of tendon strength recovery. In some embodiments, the treatment results in an increase in tendon strength of about 30%, about 40%, about 50%, about 60%, about 70%, about 80%, about 90% within about 1, 2, 3, 4, 5, 6, 7, 8, 9, 10, 11, 12, 13, 14, 15, 16, 17, 18, 19, 20, or 21 days of administration of a compound of the invention, as compared to baseline.

The methods of the invention may include preventive treatments.

In some embodiments, the administering is by direct injection to the affected site. In some embodiments, the direct injection is accomplished using the "peppering technique" with or without ultrasound guidance. The "peppering technique" is an injection method whereby after the needle is inserted into the tender area, multiple small injections are performed by withdrawing, redirecting and reinserting the needle without emerging from the skin.

In some embodiments, the methods can further include administering one or more other therapeutic regimens and/or agents effective for treating a tendinopathy, e.g., palliative care, with treatment focusing on anti-inflammatory measures, including treatment with nonsteroidal anti-inflammatory drugs (NSAIDs), steroid injections, cortisone injections, platelet rich plasma (PRP) injections, physical therapy, shock wave therapy, low-level laser therapy (phototherapy), cell therapy, and sclerotherapy.

In some embodiments, the one or more diseases or conditions is psoriasis. Non-limiting examples include: psoriasis vulgaris (including nummular psoriasis and plaque psoriasis); generalized pustular psoriasis (including impetigo herpetiformis and von Zumbusch's disease); acrodermatitis continua; pustulosis palmaris et plantaris; guttate psoriasis; arthropathic psoriasis; other psoriasis (including inverse psoriasis).

In some embodiments, the one or more diseases or conditions is dermatitis.

Non-limiting examples include: atopic dermatitis, contact dermatitis (e.g., allergic contact dermatitis, irritant contact dermatitis), stasis dermatitis, dermatitis that led up to steroid dermatitis, steroid-resistant dermatitis, dermatitis to which tacrolimus is not applicable, chronic dermatitis, erythroderma (e.g., erythroderma posteczematosa and erythroderma secondary to dermatoses, toxic erythroderma, infantile desquamative erythroderma, and paraneoplastic erythroderma), eczema, nummular eczema, dyshidrotic eczema, astcatotic eczema, seborrheic dermatitis, autosensitization dermatitis, stasis dermatitis, urticaria, drug eruption, dermal vasculitis, prurigo, pruritus cutaneus, erythema (e.g. nodosum or multiforme), rosacea, rosacea-like dermatitis, lichen planus, photo-induced dermatitis, or follicular keratosis. In certain embodiments, the dermatitis is contact dermatitis, e.g., allergic contact dermatitis, e.g., resulting from direct skin contact with a substance such as poison ivy, poison oak, or poison sumac.

In some embodiments, the one or more diseases or conditions is morphea.

In some embodiments, the one or more diseases or conditions is ichthyosis.

In some embodiments, the one or more diseases or conditions is Darier's disease.

In some embodiments, the methods can further include administering one or more other therapeutic regimens and/or agents effective in treating a skin disorder described herein, e.g., corticosteroids, immune modulators, vitamin D3 and its analogs, retinoic acids and their pharmaceutically active derivatives, or combinations thereof. Specific non-limiting examples of drugs include betamethasone dipropionate, clobetasol propionate, halobetasol propionate, diflorasone diacetate, amcinonide, desoximethasone, fluocinonide, halcinonide, mometasone furoate, betamethasone valerate, fluocinonide, fluticasone propionate, triamcinolone acetonide, fluocinolone acetonide, flurandrenolide, desonide, hydrocortisone butyrate, hydrocortisone valerate, alclometasone dipropionate, flumethasone pivolate, hydrocortisone, hydrocortisone acetate, prednisone, Benadryl, tacrolimus, picrolimus, tazarotene, isotretinoin, cyclosporin, anthralin, vitamin D3, cholecalciferol, calcitriol, calcipotriol, tacalcitol, calcipotriene, Gossypol, 4-hydroxyestradiol, 2-hydroxyestradiol, 2-hydroxyestrone, 2-benzimidazolylthioacetamide-N-ethyl-2-benzyl (KH7.102), an antibody, a nucleic acid, or combinations thereof.

In some embodiments, the one or more diseases or conditions is Raynaud's syndrome.

In some embodiments, the patient is a human.

In some embodiments, the compound of Formula (I) inhibits one or more proteins in the Wnt pathway.

In some embodiments, the compound of Formula (I) inhibits signaling induced by one or more Wnt proteins.

In some embodiments, the Wnt proteins are chosen from: WNT1, WNT2, WNT2B, WNT3, WNT3A, WNT4, WNT5A, WNT5B, WNT6, WNT7A, WNT7B, WNT8A, WNT8B, WNT9A, WNT9B, WNT10A, WNT10B, WNT11, and WNT16.

In some embodiments, the compound of Formula (I) inhibits a kinase activity.

In some embodiments, the compound of Formula (I) inhibits one or more Wnt proteins.

Evaluation of Biological Activity

The biological activity of the compounds described herein can be tested using any suitable assay known to those of skill in the art, e.g., WO 2001/053268 or WO 2005/009997. For example, the activity of a compound may be tested using one or more of the test methods outlined below.

In another example, one may utilize in vitro assays for Wnt biological activity, e.g. stabilization of β-catenin and promoting growth of stem cells. Assays for biological activity of Wnt include stabilization of β-catenin, which can be measured, for example, by serial dilutions of a candidate inhibitor composition. An exemplary assay for Wnt biological activity contacts a Wnt composition in the presence of a candidate inhibitor with cells, e.g. mouse L cells. The cells are cultured for a period of time sufficient to stabilize β-catenin, usually at least about 1 hour, and lysed. The cell lysate is resolved by SDS PAGE, then transferred to nitrocellulose and probed with antibodies specific for β-catenin.

In a further example, the activity of a candidate compound can be measured in a *Xenopus* secondary axis bioassay (Leyns, L. et al. *Cell* (1997), 88(6), 747-756).

Example 8

Another screening assay for Wnt activity is described as follows. Reporter cell lines can be generated by stably transducing cells of cancer cell lines (e.g., colon cancer) with a lentiviral construct that include a Wnt-responsive promoter driving expression of the firefly luciferase gene.

Lentiviral constructs can be made in which the SP5 promoter, a promoter having eight TCF/LEF binding sites derived from the SP5 promoter, is linked upstream of the firefly luciferase gene. The lentiviral constructs can also include a hygromycin resistance gene as a selectable marker. The SP5 promoter construct can be used to transduce SW480 cells, a colon cancer cell line having a mutated APC gene that generates a truncated APC protein, leading to de-regulated accumulation of β-catenin. A control cell line can be generated using another lentiviral construct containing the luciferase gene under the control of the SV40 promoter which does not require β-catenin for activation.

Cultured SW480 cells bearing a reporter construct can be distributed at approximately 10,000 cells per well into 96 well or 384 well plates. Compounds from a small molecule compound library can then be added to the wells in half-log dilutions using a ten micromolar top concentration. A series of control wells for each cell type receive only buffer and compound solvent. Twenty-four to forty hours after the addition of compound, reporter activity for luciferase can be assayed, for example, by addition of the BrightGlo luminescence reagent (Promega) and the Victor3 plate reader (Perkin Elmer). Readings can be normalized to DMSO only treated cells, and normalized activities can then be used in the $EC_{50}$ calculations. Table 2 shows the activity of selected indazole-3-carboxamide analogs.

TABLE 2

| Compound | $EC_{50}$ (nM) | Compound | $EC_{50}$ (nM) |
|---|---|---|---|
| 1 | 175 nM | 2 | 5,000 nM |
| 3 | 200 nM | 4 | 160 nM |
| 5 | 10,000 nM | 6 | 270 nM |
| 7 | 110 nM | 8 | 130 nM |
| 9 | 10,000 nM | 11 | 10,000 nM |
| 12 | 63 nM | 13 | 1,250 nM |
| 14 | 106 nM | 15 | 37 nM |
| 16 | 10,000 nM | 18 | 122 nM |
| 19 | 107 nM | 20 | 118 nM |
| 23 | 120 nM | 26 | 210 nM |
| 32 | 1,250 nM | 36 | 275 nM |
| 37 | 1,120 nM | 38 | 120 nM |
| 39 | 65 nM | 40 | 65 nM |
| 41 | 67 nM | 42 | 500 nM |
| 43 | 63 nM | 44 | 158 nM |
| 45 | 110 nM | 46 | 15 nM |
| 47 | 71 nM | 48 | 10,000 nM |
| 49 | 57 nM | 50 | 71 nM |
| 51 | 26 nM | 52 | 57 nM |
| 53 | 63 nM | 54 | 158 nM |
| 55 | 44 nM | 56 | 160 nM |
| 57 | 10,000 nM | 58 | 71 nM |
| 59 | 3,100 nM | 60 | 10,000 nM |
| 61 | 239 nM | 62 | 16 nM |
| 63 | 100 nM | 64 | 6 nM |
| 65 | 101 nM | 66 | 10,000 nM |
| 67 | 10,000 nM | 68 | 48 nM |
| 69 | 50 nM | 70 | 41 nM |
| 71 | 25 nM | 72 | 215 nM |
| 73 | 322 nM | 74 | 65 nM |

TABLE 2-continued

| Compound | $EC_{50}$ (nM) | Compound | $EC_{50}$ (nM) |
|---|---|---|---|
| 75 | 40 nM | 76 | 850 nM |
| 77 | 2,650 nM | 78 | 239 nM |
| 79 | 123 nM | 80 | 158 nM |
| 81 | 77-142 nM | 82 | 143-188 nM |
| 83 | 2,500-3,400 nM | 84 | 822-898 nM |
| 86 | 66 nM | 87 | 2,440 nM |
| 106 | 33 nM | 124 | 67 nM |
| 126 | 22 nM | 162 | 426 nM |
| 163 | 15,400 nM | 168 | 66 nM |
| 169 | 49 nM | 170 | 43 nM |
| 172 | 60 nM | 173 | 36 nM |
| 174 | 48 nM | 175 | 25 nM |
| 176 | 30 nM | 177 | 183 nM |
| 178 | 297 nM | 179 | 30 nM |
| 180 | 13 nM | 181 | 38 nM |
| 182 | 35 nM | 183 | 49 nM |
| 184 | 40 nM | 185 | 27 nM |
| 186 | 460 nM | 187 | 215 nM |
| 188 | 9 nM | 189 | 85 nM |
| 190 | 1,200 nM | | |

Example 9.

Representative compounds were screened using primary human mesenchymal stem cells (hMSCs) to determine their ability to induce tenocyte differentiation (process by which tendon is developed).

Human Mesenchymal Stem Cell Culture: Primary human mesenchymal stem cells (hMSCs) were purchased from Lonza (Walkersville, Md.) and expanded in Mesenchymal Stem Cell Growth Media (Lonza). Cells between passage 3 and 6 were used for the experiments.

Compound Screening: Each compound was dissolved in DMSO as a 10 mM stock and used to prepare compound source plates. For the tenocyte differentiation assay, serial dilution (1:2, 10-point dose-response curves from 10 μM to 19.5 nM) and compound transfer was performed using the ECHO 550 (Labcyte, Sunnyvale, Calif.) into 384-well black clear bottom assay plates (Greiner Bio-One) with appropriate DMSO backfill for a final DMSO concentration of 0.17%. hMSCs were plated at 3,000 cells/well in 70 4/well Dulbecco's modified Eagle's medium (DMEM, Life Technologies, Carlsbad, Calif.) with 1% Fetal Bovine Serum (FBS, Life Technologies). Bone Morphogenic Factor (BMP) and Fetal Growth Factor (FGF) (10 ng/ml each, Peprotech, Inc., Rocky Hill, N.J.) were used as a positive-controls for differentiation while negative control wells were treated with 120 nL DMSO for normalization and calculating $EC_{50}$ values. Cells were incubated at 37° C. and 5% $CO_2$ for 4 days. Cells were fixed using 4% formaldehyde (Electron Microscopy Sciences), and stained with anti-Sclerasis (anti-SCXA) antibodies (Abgent, San Diego, Calif.) [Webb S., et.al., Retinoic acid receptor signaling preserves tendon stem cell characteristics and prevents spontaneous differentiation in vitro, *Stem Cell Research & Therapy* 2016, 7:45] overnight at 4° C. The cells were washed with Phosphate Buffered Saline (PBS, Life Technologies) and incubated with anti-rabbit Alexa-flor 647 secondary antibodies (Life Technologies) and DAPI (Life Technologies) for 1 hour at room temperature. Cells were washed using PBS, and imaged using the CellInsight CX5 (Life Technologies, 594/633 nm filter). Number of cells positive for SCXA in each well was quantified using the CellInsight CX5. Data was normalized to the average of 12 DMSO treated wells on the same plate using Dotmatics Studies module. The normalized averages (fold change over DMSO) of 3 replicate wells for each compound concentration were calculated. Due to solubility limitations of some of the compounds, values for higher doses were manually corrected and curve fitting and $EC_{50}$ determinations were performed using Dotmatics Studies.

$EC_{50}$ for each compound is reported. Table 3 shows the measured activity for representative compounds of Formula I as described herein.

TABLE 3

| Compound | $EC_{50}$ (μM) |
| --- | --- |
| 1 | >100 uM |
| 2 | >100 uM |
| 3 | >100 uM |
| 4 | 4.552 |
| 5 | >100 uM |
| 6 | 92.468 |
| 7 | 6.942 |
| 8 | 4.983 |
| 9 | >100 uM |
| 11 | >100 uM |
| 12 | 4.998 |
| 13 | >100 uM |
| 14 | 50.395 |
| 15 | 4.804 |
| 16 | 35.772 |
| 18 | 5.378 |
| 19 | >100 uM |
| 20 | 11.982 |
| 23 | >100 uM |
| 26 | >100 uM |
| 32 | >100 uM |
| 36 | >100 uM |
| 37 | >100 uM |
| 38 | 2.839 |
| 39 | >100 uM |
| 40 | 5.174 |
| 41 | 8.118 |
| 42 | 5.137 |
| 43 | 5.019 |
| 44 | 25.061 |
| 45 | 9.750 |
| 46 | 5.056 |
| 47 | >100 uM |
| 48 | >100 uM |
| 49 | >100 uM |
| 50 | >100 uM |
| 51 | >100 uM |
| 52 | >100 uM |
| 53 | >100 uM |
| 54 | >100 uM |
| 55 | >100 uM |
| 56 | 0.625 |
| 57 | >100 uM |
| 58 | >100 uM |
| 59 | 14.560 |
| 60 | >100 uM |
| 61 | 12.268 |
| 62 | >100 uM |
| 63 | 10.243 |
| 64 | 7.661 |
| 65 | >100 uM |
| 66 | >100 uM |
| 67 | >100 uM |
| 68 | 4.613 |
| 69 | 12.481 |
| 70 | 10.850 |
| 71 | >100 uM |
| 72 | >100 uM |
| 73 | >100 uM |
| 74 | 10.180 |
| 75 | 12.373 |
| 76 | 2.667 |
| 77 | 6.075 |
| 78 | >100 uM |
| 79 | >100 uM |
| 80 | >100 uM |
| 81 | >100 uM |
| 82 | >100 uM |
| 83 | >100 uM |
| 84 | >100 uM |
| 86 | 5.273 |
| 87 | 1.584 |
| 106 | 5.545 |
| 124 | >100 uM |
| 126 | 5.537 |
| 162 | >100 uM |
| 163 | 5.086 |
| 168 | >100 uM |
| 169 | 4.905 |
| 170 | >100 uM |
| 172 | >100 uM |
| 173 | >100 uM |
| 174 | 5.539 |
| 175 | 10.377 |
| 176 | 4.654 |
| 177 | 5.174 |
| 178 | >100 uM |
| 179 | 1.115 |
| 180 | >100 uM |
| 181 | >100 uM |
| 182 | 8.039 |
| 183 | >100 uM |
| 184 | >100 uM |
| 185 | 6.442 |
| 186 | >100 uM |
| 187 | >100 uM |
| 188 | 1.212 |
| 189 | >100 uM |
| 190 | >100 uM |

Example 10

Wnt Signaling Inhibition

Cell Culture. SW480 cells (ATCC) were cultured in Dulbecco's modified Eagle's medium (DMEM, ThermoFisher) with 1% Glutamax (Life Technologies), 1% Penicillin-Streptomycin (Life Technologies), 150 ug/ml Hygromycin (Life Technologies) with 10% fetal bovine serum (FBS) (Hyclone) at 37° C., 5% $CO_2$.

Wnt Reporter Assay. Human colorectal cancer cell line SW480, stably expressing the Wnt responsive promoter linked to luciferase gene, was plated overnight at $4 \times 10e^4$ cells/well in DMEM, high glucose, no glutamine, no phenol red (Life Technologies), 1% Glutamax (Life Technologies), 1% Sodium Pyruvate (Life Technologies), 1% Penicillin-Streptomycin (Life Technologies) with 1% Fetal Bovine Serum (Hyclone). Cells were then treated with DMSO (vehicle control) or COMPOUND 175 at 10 μM top concentration and half a log dilution up to 10 concentrations (10, 3, 1, 0.3, 0.1, 0.03, 0.01, 0.003, 0.001 and 0.0003 μM). Cells were incubated for 48 hours at 37° C. 15 μl of Bright-Glo (Bright-Glo™ Luciferase Assay System, Promega) was added to the cells and luminescence was measured using the Cytation 3 plate reader (Biotek). Data was normalized using the DMSO control and inhibition profile and $EC_{50}$ was calculated using Prism 4 (GraphPad Software Inc, La Jolla, Calif., USA). Prism 4.0 was used to calculate the $EC_{50}$ of the Wnt reporter inhibition assay.

Exposure of the SW480 cells to compound 175 at concentrations of 10, 3, 1, 0.3, 0.1, 0.03, 0.01, 0.003, 0.001 and 0.0003 μM showed that compound 175 inhibited Wnt pathway activity in these cells in a dose-dependent manner with $EC_{50}$ of ~152.9 nM (see FIG. 1).

Example 11

Tendon Differentiation Cell Culture. Primary human mesenchymal stem cells (hMSCs; Lonza Inc) were cultured in MSCGM™ Mesenchymal Stem Cell Growth Medium, with 10% FBS (Lonza) 10% fetal bovine serum (FBS) (Hyclone) at 37° C., 5% $CO_2$. hMSCs were used between passage 2 and 6 and were never allowed to reach confluence to maintain a naive state.

Tenocyte Differentiation Assay. For tenocyte differentiation, hMSCs were plated in 384-well plates at $1 \times 10^4$ cells/well in Dulbecco's modified Eagle's medium (DMEM, ThermoFisher) with 1% fetal bovine serum (FBS) (Hyclone). Cells were then treated with DMSO (vehicle control) or compound 175 at 750 nM top concentration and 2-fold dilution up to 8 concentrations (750, 333.3, 166.6, 83.3, 41.7, 21.7, 10.8 and 5.8 nM) and incubated for 7 days at 37° C. A combination of BMP and FGF (10 ng/ml each, Peprotech, Inc.) was used as a positive control. At the end of 7 days, cells were fixed using 4% methanol-free formaldehyde (Electron Microscopy Sciences) for 10 min, washed with phosphate buffered saline (PBS) 3 times, permeabilized with PBS containing 0.3% triton X-100 (Sigma) for 5 min, blocked with PBST (PBS containing 0.3% triton X-100) with 3% bovine serum albumin (BSA; Sigma) for 1 h at room temperature, followed by incubation with primary antibodies in PBST+BSA overnight at 4° C. Cells were rinsed 3 times with PBS and incubated with fluorophore-conjugated secondary antibody in PBST+BSA and DAPI for 1 h at room temperature and washed with PBS 3 times. Plates were imaged using a CX5 high-content imager (ThermoFisher) and the % of cells stained positive were determined using a cell scoring algorithm (ThermoFisher). Data was plotted and $EC_{50}$ was calculated using Prism 5 (GraphPad Software Inc, La Jolla, Calif., USA). Prism 5.0 was used to calculate the $EC_{50}$ of the Tenocyte differentiation assay.

Exposure of the hMSCs to compound 175 at concentrations of 750, 333.3, 166.6, 83.3, 41.7, 21.7, 10.8 and 5.8 nM showed that COMPOUND 175 induced the expression of SCXA, TenacinC and Tenomodulin, in a dose-dependent manner with an EC50 between 139-189 nM (see FIGS. 2A-C and 3), indicating a differentiation of hMSC into tenocytes.

Anti-Inflammation

Cell Culture. THP-1 cells (Catalog #TIB-202, ATCC, Manassas, Va.) were cultured in Roswell Park Memorial Institute (RPMI) 1640 Medium (Catalog #21870-100, Buffalo, N.Y.) with 1% L-glutamine, 1% HEPES, 1% Sodium Pyruvate, 2% Sodium Bicarbonate supplemented with 100 units/mL penicillin, 50 µg/mL streptomycin, 2-mercaptoethanol (0.05 mM) [basal medium] and 10% fetal bovine serum (Catalog #16140089, Life Technologies, Carlsbad, Calif.) at 37° C. and 5% $CO_2$.

Cytokine Production Assay. THP-1 cells were cultured in basal media with 1% FBS for 24 hours before the start of the assay. THP-1 cells were plated at $6 \times 10e^4$ cells/well and treated with DMSO (vehicle control) or compound 175 at 10 µM highest test concentration and 2 to 3.5-fold serial dilutions up to 8 concentrations (10, 3.5, 1, 0.5, 0.1, 0.035, 0.01, 0.005 µM). For the TNFα assay, 50 ng/mL of LPS was added to the wells after 2 hours to induce cytokine production, and cells were incubated for 5 hours at 37° C. For the IL6 assay, 500 ng/ml of LPS was added after 2 hours and cells were incubated for 22 hours at 37° C. Plates were spun in a centrifuge for 1 minute at 10,000 rpm and supernatants were collected for ELISA. Supernatants were diluted 1:1 for the TNFα assay and 1:4 for the IL6 assay using the assay medium. ELISA was performed using Human TNF-α ELISA MAX™ Deluxe (Catalog #430204, Biolegend, San Diego, Calif.) and Human IL-6 ELISA MAX™ Deluxe (Catalog #430504, Biolegend, San Diego, Calif.) kits. Briefly, 96-well plates were coated with the appropriate capture antibody overnight and washed to remove excess antibody. Blocking buffer was added and incubated for 1 hour to prevent non-specific binding. Diluted supernatants were incubated in the coated plates for 2 hours at room temperature. Following washes to remove unbound proteins, biotinylated detection antibody was added and incubated for 30 mins at room temperature, followed by washes to remove unbound excess antibody. Avidin-HRP was then added and incubated for 30 mins at room temperature. Following several washes to remove unbound avidin-HRP, the TMB substrate was added and the plates were read on the Cytation 3 plate reader (Biotek Inc., Winooski, Vt.) at an absorbance of 450 nm with correction at 570 nm. All samples were processed in triplicate. Inhibition profile and $EC_{50}$ was calculated using Prism 5 (GraphPad Software Inc, La Jolla, Calif., USA). Prism 5.0 was used to calculate the $EC_{50}$ of the TNFα and IL6 inhibition assays.

Figure 4A:
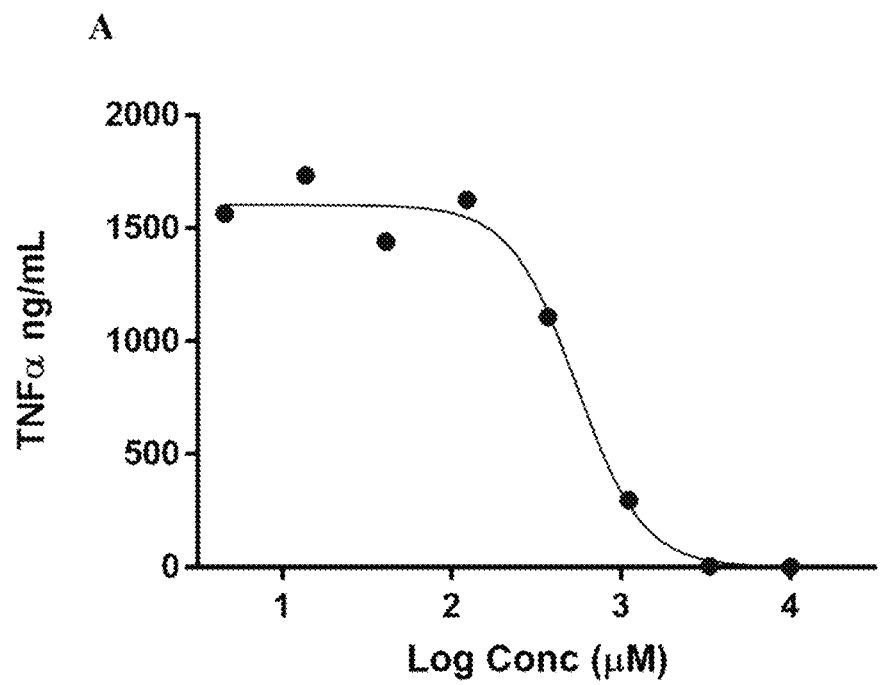
FIGS. 4A-B depict plots of tumor necrosis factor alpha concentration in THP-1 cells vs. the logarithm of the concentration of compound 175 the THP-1 cells were exposed to, and interleukin-6 concentration in THP-1 cells vs. the logarithm of the concentration of compound 175 the THP-1 cells were exposed to, respectively. THP-1 cells, a human monocyte cell line (6×10c$^4$ cells/well in a 96-well plate) were treated with DMSO (vehicle) or compound 175 at concentrations of 10, 3.5, 1, 0.5, 0.1, 0.035, 0.01, 0.005 μM. After 2 hours, treated cells were stimulated with LPS (50 ng/mL for 5 hours [TNFα] and 500 ng/ml for 22 hours [IL6] at 37° C. to induce production of the cytokines. Supernatants (diluted 1:1 or 1:4) were collected and analyzed for TNFα and IL6 levels using the TNFα and IL6 ELISA kits. Inhibition profile and EC$_{50}$ was calculated using Prism 5. Representative images indicate that exposure of the cells to compound 175 inhibited the production of INFα (4A) and IL6 (4B) in THP-1 cells in a dose-dependent manner, with an average EC$_{50}$ of 342-547 nM for TNFα and 356-629 nM for IL6 (2 independent assays and 3 replicates per assay).
Figure 4B:
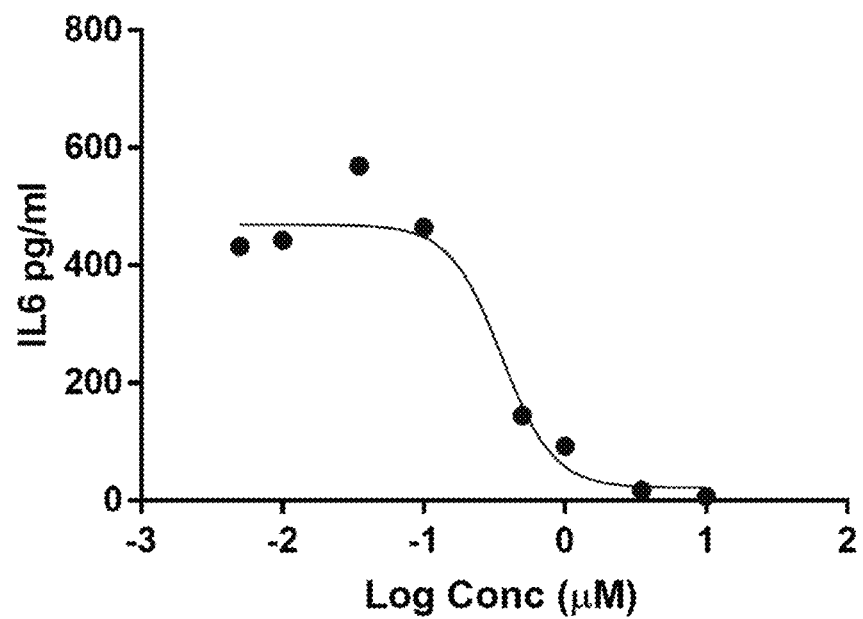

Exposure of THP-1 cells to LPS induced the production of both TNFα and IL6. Compound 175 treatment inhibited the LPS-induced cytokine production in these cells in a dose-dependent manner with average EC50 ranging from 342-547 nM for TNFα and 356-629 nM for IL6 (see FIGS. 4A-B), with results generated from two independent assays and three replicates per assay.

Example 12

Rat Tendinopathy Model (1)

Rat Model of Collagenase-induced Tendonitis. Fifty (50 µl) of Collagenase Type IA (10 mg/ml in PBS, pH 7.4, approximately 469 units/mg) (Catalog #C5138, Sigma, St. Louis, Mo.) was injected into the Achilles tendon of both ankles near the osteotendinous junction of male Sprague Dawley CD®IGS rats (CRL, Inc.), using insulin syringes with 28.5 G needle.

Delivery of compound 175 by Topical Application. Rats were divided into 6 groups with 5 animals per group: Group 1 (sham injection); Group 2 (Collagenase-Vehicle); Group 3 (Collagenase-compound 175 10 mg/mL with 1% BA) and Group 4 (Collagenase-COMPOUND 175 10 mg/mL with 0.5% Tween 80). COMPOUND 175, formulated in 1% HPMC 40-0101/20% PG/1% BA or 1% HPMC 40-0101/20% PG/0.5% Tween 80, or vehicle (1% HPMC 40-0101/20% PG/1% BA) was applied at a dose volume of 30 µL/cm² to cover a 2 cm² dose area to the skin near the Achilles tendon region of both ankles of the collagenase-injected rats using an applicator and rubbed into the skin for 10 seconds. All rats were periodically observed for any pain, illnesses or abnormalities. At various time points, blood was collected for plasma in lithium heparin coated tubes by saphenous vein bleeding. For histology, rats were euthanized using isoflurane, tendons were isolated (n=6 tendons/group), fixed in 10% buffered formalin (Catalog #SF93-4, Fisher, Pittsburgh Pa.) and H & E histology staining was performed at a secondary site (Pacific Pathology, San Diego, Calif.). For biochemical analysis, tendons were isolated (n=4 tendons/group), flash frozen in liquid nitrogen and then stored at −80° C. for subsequent biochemical analysis (not reported).

Histology Scoring of Tendons. There is biological variability in response to collagenase when injected directly into the tendons. This results in varying degrees of severity and location of inflammation as well as tendon degeneration (Urdzikova et al., Human multipotent mesenchymal stem cells improve healing after collagenase tendon injury in the rat. *Biomed Eng Online.* 2014 Apr. 9; 13:42). Therefore, the entire tendon was isolated and placed in a tissue cassette and embedded in paraffin. Five (5) μm sections were generated and an average of 3 sections were fixed on one slide, with a minimum of eight (8) slides per tendon and subjected to Hematoxylin & Eosin (H&E) staining. Slides were viewed under an upright light microscope (EVOS AMEX-1200) at a 10× magnification and scored blinded using a 1-4 scoring system of severity: 1—representing severe damage and 4—representing normal tendon, for Linearity of the fiber structure, Shape of the tendon cells, Density of the tendon cells, Inflammation, and Hemorrhage for a total score of twenty (20) using a modification of that described previously (Urdzikova et al., 2014—see Table 3). After the analysis was completed, the scorer was unblinded and scores for each criterion was annotated, totaled and total scores from each section were averaged together to generate a final score for each rat followed by averaging of scores for a given treatment group.

Biomarker Assays in Plasma. Following manufacturer's instructions, KC/GRO plasma levels were determined using the KC/GRO Immunoassay kit (Catalog #900-K57, Pepro-tech, Rocky Hill, N.J.). Briefly, 96-well plates were coated with the anti-rat KC/GRO capture antibody overnight and washed to remove excess antibody. Plasma samples were incubated in the coated plates for 2 hours at room temperature. Following washes to remove unbound proteins, biotinylated anti-rat KC/GRO detection antibody was added and incubated for 30 mins at room temperature. Following washes to remove unbound excess antibody, avidin-HRP was added and incubated for 30 mins at room temperature. Following washes to remove unbound Avidin-HRP, the ABTS substrate was added and the plates were read on the Cytation 3 plate reader (Biotek Inc., Winooski, Vt.) at an absorbance of 525 nm with correction at 450 nm. All samples were processed in triplicate.

Data Analysis. For tendon scoring, each section was analyzed following a 1-4 point scoring system as previously described (Urdzikova et al., 2014) with the exclusion of one variable, the Thickness of the epitenon, due to the difficulty in discerning the epitenon layer in histology sections. Table 4 below briefly summarizes the scoring system.

TABLE 4

| Variable[a] | Score and Criteria |
|---|---|
| Linearity of the fiber structure | 1 = no linear areas<br>2 = 20-50% linear<br>3 = >50% linear<br>4 = linear (normal) |
| Shape of the tendon cells | 1 = predominantly round<br>2 = moderately round<br>3 = slightly oval<br>4 = linear (normal) |
| Density of the tendon cells | 1 = sheets of cells<br>2 = moderate increase<br>3 = slight increase<br>4 = sparse (normal) |
| Inflammation | 1 = severe increase<br>2 = moderate increase<br>3 = slight increase<br>4 = none |
| Hemorrhage | 1 = predominant hemorrhage<br>2 = multiply areas in each field<br>3 = sparse or patchy<br>4 = none |

[a]Histology Scoring was modified by Samumed to exclude one variable, Thickness of the epitenon.

In this study, a total of 64 sections were scored for Group 1 (sham injection group) and approximately 96 sections each for Group 2 (Collagenase-Vehicle), Group 3 (Collagenase-compound 175 with BA preservative) group and Group 4 (Collagenase-compound 175 without preservative). To determine statistical significance between groups, student's t-test was performed with p<0.05 considered as significant for histology scoring and biomarker assay.

Compound 175 Ameliorates Collagenase-Induced Tendinopathy. Collagenase induced Tendonitis in rats recapitulates acute tendon injury in humans with inflammation resulting within a few hours (Urdzikova et al., 2014). Using an interventional approach, topical formulation of compound 175 was administered 24 hours post collagenase injection into the Achilles tendon. The Collagenase-injected rats were dosed with vehicle alone or compound 175 (10 mg/mL) formulated with or without BA as a preservative for 21 consecutive days. Group 1 rats that received sham injections served as a control for no disease induction.

Figure 5:
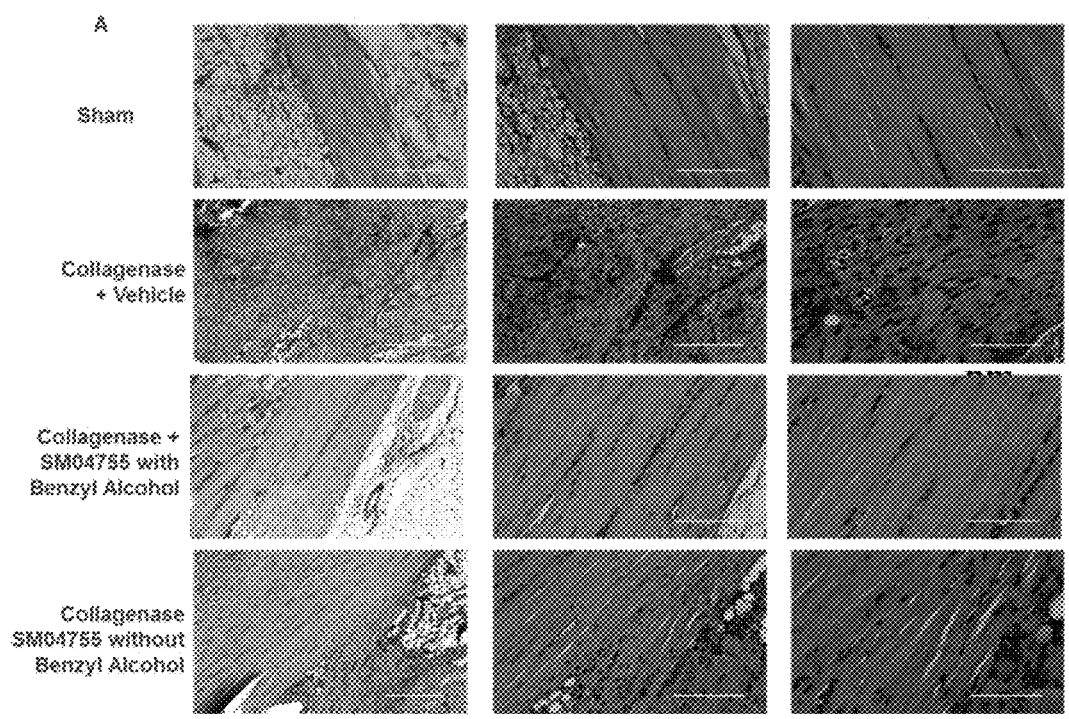
FIG. 5 is a grid of images of a rat Achilles tendon; a rat Achilles tendon treated with a collagenase with a vehicle; a rat Achilles tendon treated with a collagenase, compound 175, and benzyl alcohol; and a rat Achilles tendon treated with a collagenase and compound 175. Tendinopathy in rats was induced by injecting collagenase (50 μl, 10 mg/ml Type IA in PBS, pH 7.4, ~469 units/mg) or sham needle puncture for control in the Achilles tendon. After 1 day, rats were dosed once daily for 21 days via topical application with vehicle control or compound 175 (10 mg/ml). 24 hours after the last dose, tendons were isolated, fixed with 10% buffered formalin, sectioned and stained with H&E. Group 1 (sham injection), Group 2 (Collagenase-Vehicle), Group 3 (Collagenase-compound 175 with 1% BA) and Group 4 (Collagenase-compound 175 with 0.5% Tween 80, without BA).
Figure 6:
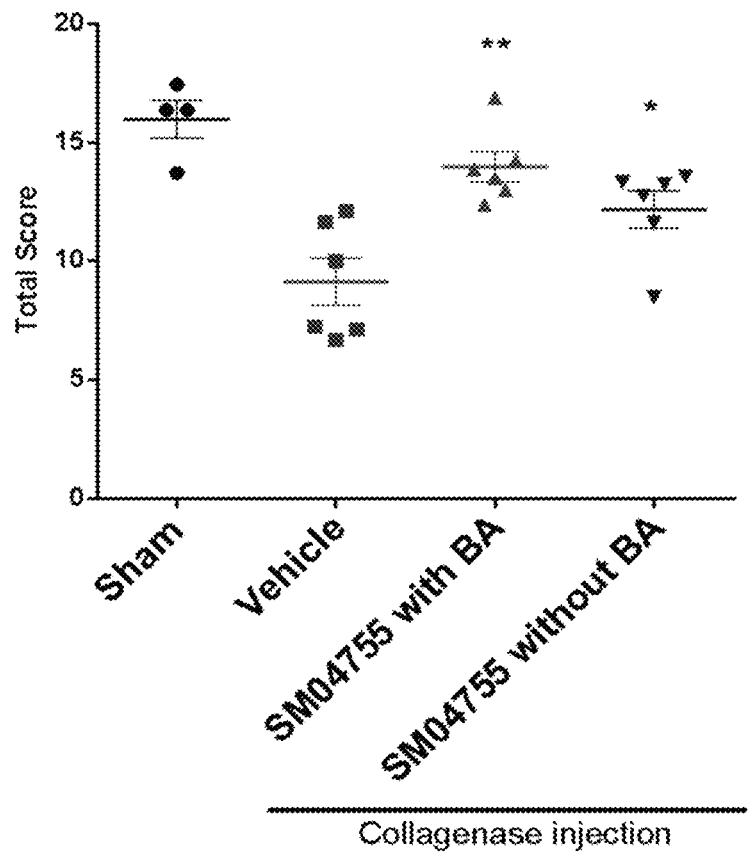
FIG. 6 is a plot of tendon histology scores of rat Achilles tendon; a rat Achilles tendon treated with a collagenase with a vehicle; a rat Achilles tendon treated with a collagenase, compound 175, and benzyl alcohol; and a rat Achilles tendon treated with a collagenase and compound 175. Tendinopathy in rats was induced by injecting collagenase (50 µl, 10 mg/ml Type IA in PBS, pH 7.4, ~469 units/mg) or sham needle puncture for control in the Achilles tendon. After 1 day, rats were dosed once daily for 21 days via topical application with vehicle control or compound 175 (10 mg/ml). 24 hours after the last dose, tendons were isolated, fixed with 10% buffered formalin, sectioned and stained with H&E. Group 1 (sham injection), Group 2 (Collagenase-Vehicle), Group 3 (Collagenase-compound 175 with 1% BA) and Group 4 (Collagenase-compound 175 with 0.5% Tween 80, without BA). Blinded histology scoring of tendon injury and inflammation indicated that compound 175 with or without BA preservative significantly ameliorated collagenase-induced tendinopathy (**$p<0.01$ and *$p<0.05$ respectively) by student's t test. For this study, a total of 64 sections were scored for Group 1 and ~96 sections each for Group 2-4.

As shown in FIG. 5, a significant presence of inflammatory cells was evident in the Collagenase-vehicle group. Consequently, there was evidence of tendon degeneration and damage in the Collagenase-vehicle group compared to normal tendons found in the sham control group. Amelioration of inflammation as well as tendon degeneration by compound 175 is demonstrated in FIG. 5. The histopathology of the tendon from the treatment groups revealed tendons with decreased inflammation as well as improved structure of the fibers and tendon cells with respect to linearity, shape and density. This observation was further confirmed by blinded Histology scoring. As shown in FIG. 6, upon topical treatment with compound 175, both compound 175 treatment groups demonstrated statistically significant increases in the tendon scores, achieving a score of 14.0 (±0.217) in Group 3 (Collagenase-compound 175 with BA) and a score of 12.2 (±0.284) in Group 4 (Collagenase-compound 175 without BA), compared to a score of 9.14 (±2.43) in Group 2 (Collagenase-vehicle), with a p-value of <0.01 and <0.05, respectively by student's t test.

Figure 7:
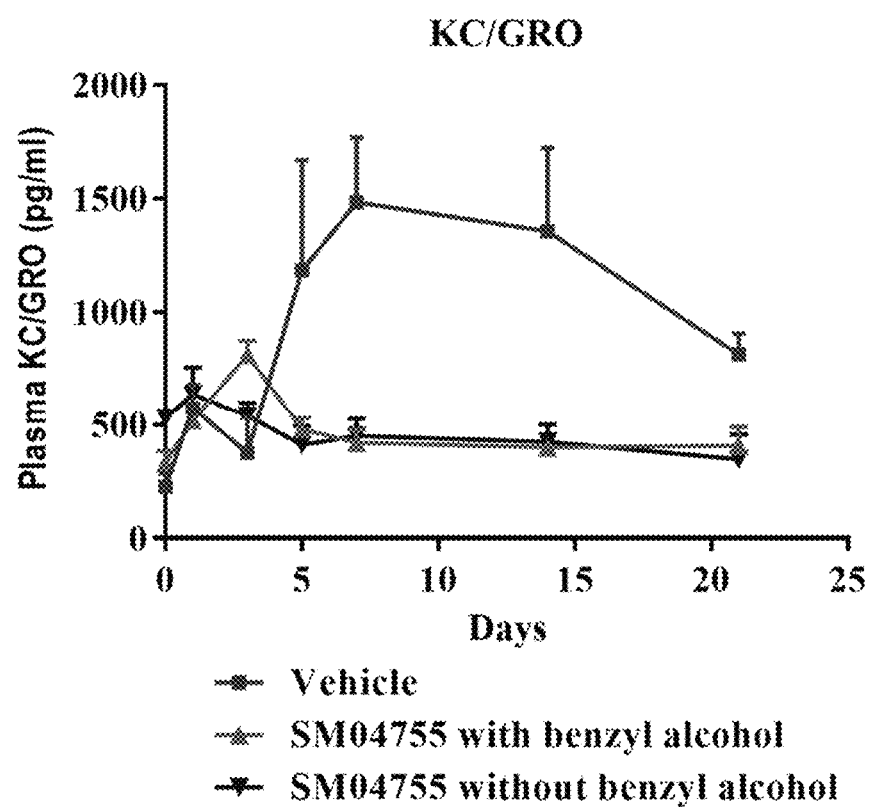
FIG. 7 is series of plots of plasma concentrations of KC/GRO in rats vs. the number of days elapsed after administration of a vehicle, compound 175 with benzyl alcohol, and compound 175. Tendinopathy in rats was induced by injecting collagenase (50 µl, 10 mg/ml Type IA in PBS, pH 7.4, ~469 units/mg) in the Achilles tendon. After 1 day, rats were dosed once daily for 21 days via topical application with vehicle control or compound 175 (10 mg/ml). Blood was collected at various timepoints and plasma was analyzed for KC/GRO by ELISA. Measurement of inflammatory cytokine KC/GRO in the plasma of rats from Group 2 (Collagenase-Vehicle), Group 3 (Collagenase-compound 175 10 mg/mL with 1% BA) and Group 4 (Collagenase-compound 175 10 mg/mL without BA, with 0.5% Tween 80). Compound 175 with or without BA preservative significantly decreased the levels of KC/GRO in plasma ($p<0.05$, student's t test as indicated in Table 3, indicating an anti-inflammatory effect of compound 175. These data were generated from 3 replicates per timepoint per group (n=3).

Compound 175 Reduces Plasma Biomarker KC/GRO in the Collagenase-induced Tendon Injury Model. KC/GRO is an inflammatory biomarker reported to be associated with the development of tendonitis. In this study, plasma concentrations of KC/GRO were investigated at various timepoints of the study. As shown in Table 4 and FIG. 7, KC/GRO levels were elevated in the Group 2 (Collagenase-vehicle) on Days 5-21, ranging from 814-1483 pg/mL, while both the COMPOUND 175-treated groups, with or without BA, had lower levels of KC/GRO in plasma, ranging from 400-480 pg/mL and 347-451 pg/mL, respectively. Both compound 175-treated groups (Groups 3 and 4) demonstrated a statistically significant decrease in plasma KC/GRO levels compared to Collagenase-vehicle control on Days 7 and 21 (p<0.05 by student's t test, Table 5). Overall, the decrease of a plasma biomarker of inflammation corroborates the ability of compound 175 to ameliorate tendonitis.

TABLE 5

Plasma KC/GRO Concentration (pg/mL)

| Day | Group 2<br>Vehicle<br>(0 mg/mL) | Group 3<br>Compound 175<br>(10 mg/mL with<br>0.5% BA) | Group 4<br>Compound 175<br>(10 mg/mL without BA,<br>with 0.5% Tween 80) |
|---|---|---|---|
| 0 | 228 ± 57.4 | 332 ± 51.3 | 530 ± 31.4 |
| 1 | 574 ± 106 | 521 ± 23.9 | 637 ± 120 |
| 3 | 376 ± 156 | 813 ± 61.4 | 541 ± 58.9 |
| 5 | 1185 ± 485[1)] | 480 ± 48.7 | 410 ± 86.0 |
| 7 | 1483 ± 286[a] | 421 ± 57.2* | 451 ± 76.6* |

TABLE 5-continued

Plasma KC/GRO Concentration (pg/mL)

| Day | Group 2 Vehicle (0 mg/mL) | Group 3 Compound 175 (10 mg/mL with 0.5% BA) | Group 4 Compound 175 (10 mg/mL without BA, with 0.5% Tween 80) |
|---|---|---|---|
| 14 | 1356 ± 367[a] | 400 ± 10.3 | 424 ± 76.2 |
| 21 | 814 ± 92.4[a] | 408 ± 83.3* | 347 ± 111* |

[a]Mean values were above quantitation limit (AQL > 1000 pg/mL) and are reported as estimated.
*p < 0.05 (student's t test) in Compound 175-treated groups (Groups 3 and 4) as compared to Group 2 (Vehicle) on Days 7 and 21.

Tendinopathy is an acute injury of the tendon that involves inflammation and tendon damage. If left untreated, repeated injury can lead to tendon ruptures and require surgery. The presence or absence of the preservative benzyl alcohol has no effect on the efficacy of compound 175. Treatment with compound 175 ameliorates tendinopathy as assessed by blinded histological scoring of the tendon. To further confirm this finding, it has shown that compound 175 also results in a decrease of an inflammatory plasma biomarker, KC/GRO.

Example 13

Rat Tendinopathy Model (2)

Fifty (50 µl) of Collagenase Type IA (10 mg/ml in PBS, pH 7.4, approximately 469 units/mg) (Catalog #C5138, Sigma, St. Louis, Mo.) was injected into the Achilles tendon of both ankles near the osteotendinous junction of male Sprague Dawley CD®IGS rats (CRL, Inc.), using insulin syringes with 28.5 G needle.

Delivery of compound 175 by Topical Application. Rats were divided into 6 groups, with 6 animals per group except 8 animals in Group 2: Group 1 (sham injection), Group 2 (Collagenase-Vehicle with 0.5% Phx), Group 3 (Collagenase-compound 175 3 mg/mL with 0.5% BA), Group 4 (Collagenase-compound 175 10 mg/mL with 0.5% BA), Group 5 (Collagenase-compound 175 3 mg/mL with 0.5% Phx) and Group 6 (Collagenase-compound 175 10 mg/mL with 0.5% Phx). COMPOUND 175, either at 3 or 10 mg/ml, prepared in either 1% HPMC 40-0101/20% PG/0.5% BA or 1% HPMC 40-0101/20% PG/0.5% Phx or vehicle (1% HPMC 40-0101/20% PG/0.5% Phx) was applied at 30 µL/cm² over a 2 cm² area to the skin near the Achilles tendon region of both ankles of the collagenase-injected rats using an applicator, and rubbed into the skin for 10 seconds. All rats were periodically observed for any pain, illnesses or abnormalities. At various time points, blood was collected for plasma in lithium heparin coated tubes by saphenous vein bleeding. For histology, rats were euthanized using isoflurane, tendons were isolated (n=8 tendons/group), fixed in 10% buffered formalin (Catalog #SF93-4, Fisher, Pittsburgh, Pa.) and H & E histology staining was performed at a secondary site (Pacific Pathology, San Diego, Calif.). For biochemical analysis, tendons were isolated (n=4 tendons/group), flash frozen in liquid nitrogen and then stored at −80° C. for subsequent biochemical analysis (not reported). Additionally, one (1) day after collagenase injection, 4 tendons were collected from Group 2 (vehicle) to observe the induction of inflammation (not reported).

There is biological variability in response to collagenase when injected directly into the tendons. This results in varying degrees of severity and location of inflammation as well as tendon degeneration (Urdzikova et al., 2014). Therefore, the entire tendon was isolated and placed in a tissue cassette and embedded in paraffin. Five (5) µm sections were generated with an average of 3 sections being fixed on one slide with a minimum of eight (8) slides per tendon and subjected to Hematoxylin & Eosin (H&E) staining. Slides were viewed under an upright light microscope (EVOS AMEX-1200) at a 10× magnification and scored blinded using a 1-4 scoring system of severity: 1—representing severe damage and 4—representing normal tendon, for Linearity of the fiber structure, Shape of the tendon cells, Density of the tendon cells, Inflammation, and Hemorrhage for a total score of twenty (20) using a modification of that described previously (Urdzikova et al., 2014— see Table 3). After the analysis was completed, the scorer was unblinded and scores for each criterion was annotated, totaled and total scores from each section were averaged together to generate a final score for each rat followed by averaging of scores for a given treatment group.

Biomarker Assays in Plasma. Following manufacturer's instructions, KC/GRO plasma levels were determined using the KC/GRO Immunoassay kit (Cat #900-K57, Peprotech, Rocky Hill, N.J.). Briefly, 96-well plates were coated with the anti-rat KC/GRO capture antibody overnight and washed to remove excess antibody. Plasma samples were incubated in the coated plates for 2 hours at room temperature. Following washes to remove unbound proteins, biotinylated anti-rat KC/GRO detection antibody was added and incubated for 30 mins at room temperature. Following washes to remove unbound excess antibody, avidin-HRP was added and incubated for 30 mins at room temperature. Following washes to remove unbound avidin-HRP, the ABTS substrate was added and the plates were read on the Cytation 3 plate reader (Biotek Inc., Winooski, Vt.) at an absorbance of 525 nm with correction at 450 nm. All samples were processed in triplicate.

Data Analysis. For tendon scoring, each section was analyzed following a 1-4 point scoring system as previously described (Urdzikova et al., 2014) with the exclusion of one variable, Thickness of the epitenon, due to difficulty in discerning the epitenon layer in the histology sections. Table 2 below briefly summarizes the scoring system. In this study, a total of 94 sections were scored for Group 1 (sham injection, control group) and between 92-116 sections for Group 2 (Collagenase-Vehicle with 0.5% Phx); Group 3 (Collagenase-compound 175 3 mg/mL with 0.5% BA), Group 4 (Collagenase-compound 175 10 mg/mL with 0.5% BA), Group 5 (Collagenase-compound 175 3 mg/mL with 0.5% Phx) and Group 6 (Collagenase-compound 175 10 mg/mL with 0.5% Phx).

Compound 175 Ameliorates Collagenase-Induced Tendinopathy. Collagenase-induced tendonitis in rats recapitulates acute tendon injury in humans with inflammation resulting within a few hours (Urdzikova et al., 2014). Using an interventional approach, topical formulation of compound 175 was administered one day (~24 hours) after the injection of collagenase into the Achilles tendon. The collagenase-injected rats were dosed with vehicle alone (containing 0.5% Phx) or compound 175 (3 or 10 mg/mL) formulated with either 0.5% BA or 0.5% Phx as a preservative for twenty-one (21) consecutive days. Group 1 rats (sham injections) served as control animals for no disease induction.

Figure 8:
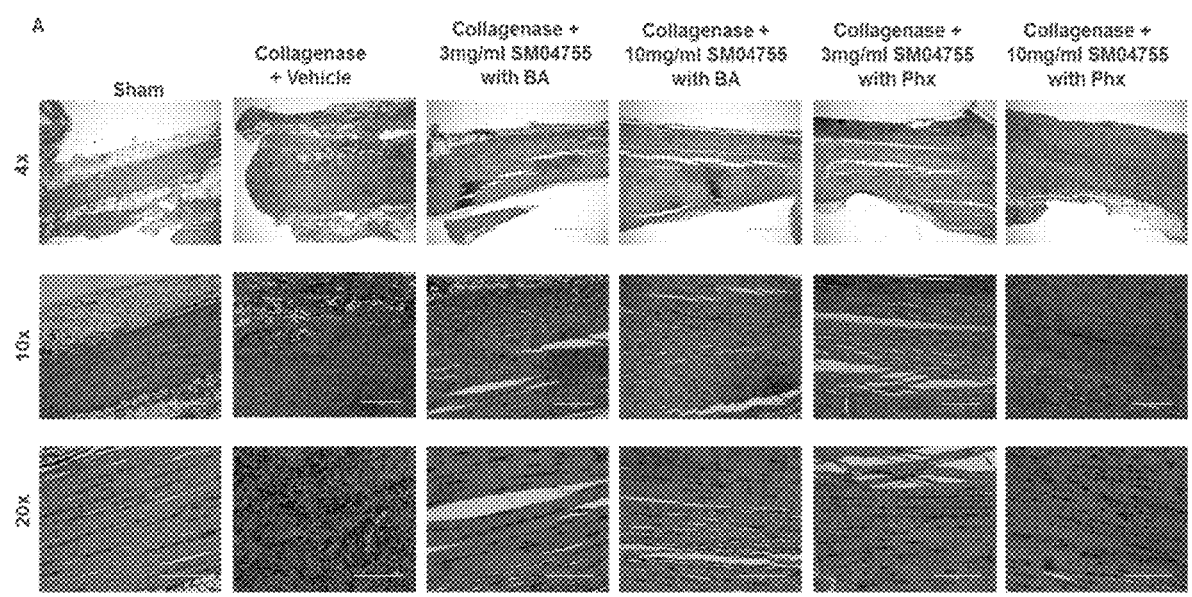
FIG. 8 is a grid of images of a rat Achilles tendon; a rat Achilles tendon treated with a collagenase with a vehicle; a rat Achilles tendon treated with a collagenase, 3 mg/ml compound 175, and benzyl alcohol; a rat Achilles tendon treated with a collagenase, 10 mg/ml compound 175 and benzyl alcohol; a rat Achilles tendon treated with a collagenase, 3 mg/ml compound 175, and Phx; and a rat Achilles tendon treated with a collagenase, 10 mg/ml compound 175, and Phx. Tendinopathy in rats was induced by injecting collagenase (50 µl, 10 mg/ml Type IA in PBS, pH 7.4, ~469 units/mg) or sham needle puncture for control in the Achilles tendon. After 1 day, rats were dosed once daily for 21 days via topical application with vehicle or compound 175 topical formulations. 24 hours after the last dose, tendons were isolated, fixed with 10% buffered formalin, sectioned and stained with H&E. Group 1 (sham injection), Group 2 (Collagenase-Vehicle with 0.5% Phx), Group 3 (Collagenase-compound 175 3 mg/ml with 0.5% BA), Group 4 (Collagenase-compound 175 10 mg/ml with 0.5% BA), Group 5 (Collagenase-compound 175 3 mg/ml with 0.5% Phx) and Group 6 (Collagenase-COMPOUND 175 10 mg/ml with 0.5% Phx).
Figure 9:
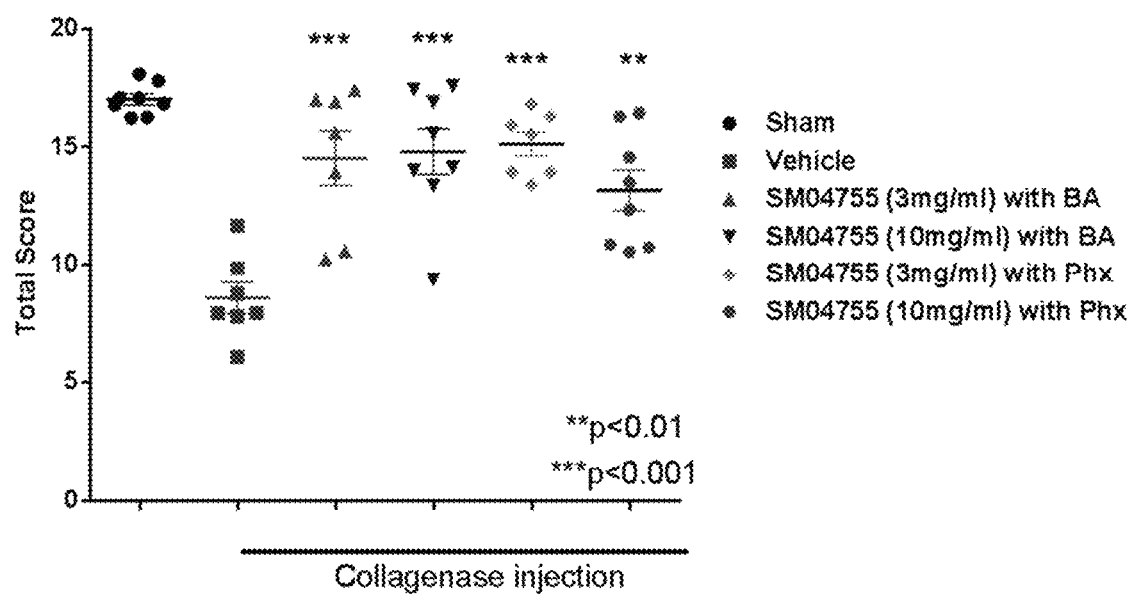
FIG. 9 is a plot of tendon histology scores of a rat Achilles tendon; a rat Achilles tendon treated with a collagenase with a vehicle; a rat Achilles tendon treated with a collagenase, 3 mg/ml compound 175, and benzyl alcohol; a rat Achilles tendon treated with a collagenase, 10 mg/ml compound 175, and benzyl alcohol; a rat Achilles tendon treated with a collagenase, 3 mg/ml compound 175, and Phx; and a rat Achilles tendon treated with a collagenase, 10 mg/ml compound 175, and Phx. Tendinopathy in rats was induced by injecting collagenase (50 µl, 10 mg/ml Type IA in PBS, pH 7.4, ~469 units/mg) or sham needle puncture for control in the Achilles tendon. After 1 day, rats were dosed once daily for 21 days via topical application with vehicle or COMPOUND 175 topical formulations. 24 hours after the last dose, tendons were isolated, fixed with 10% buffered formalin, sectioned and stained with H&E. Group 1 (sham injection), Group 2 (Collagenase-Vehicle with 0.5% Phx), Group 3 (Collagenase-compound 175 3 mg/ml with 0.5% BA), Group 4 (Collagenase-compound 175 10 mg/ml with 0.5% BA), Group 5 (Collagenase-compound 175 3 mg/ml with 0.5% Phx) and Group 6 (Collagenase-compound 175 10 mg/ml with 0.5% Phx). Blinded histology scoring of tendon injury and inflammation indicates that compound 175 at both 3 and 10 mg/mL, with either BA or Phx as a preservative, significantly ameliorated collagenase-induced tendinopathy ($p<0.01$ and *$p<0.001$) by student's t test. For this study, a total of 94 sections were scored for Group 1 and 92-116 sections for Groups 2-6.

As shown in FIG. 8, a significant presence of inflammatory cells was evident in the Collagenase-vehicle group (Group 2). Consequently, there was evidence of tendon degeneration and damage in the Collagenase-vehicle group compared to normal tendons found in the sham control group (Group 1). Amelioration of inflammation as well as tendon degeneration by compound 175 is demonstrated in FIG. 8. The histopathology of the tendon from the compound 175-treated groups revealed tendons with decreased inflammation as well as improved structure of the fibers and tendon cells with respect to linearity, shape and density. This observation was further confirmed by blinded Histology scoring. As shown in FIG. 9, upon topical treatment with compound 175, all four (4) compound 175-treated groups demonstrated statistically significant increases in the tendon scores, achieving a score of 14.5 (±1.15) in Group 3 (Collagenase-compound 175 3 mg/mL with 0.5% BA), a score of 14.8 (±0.968) in Group 4 (Collagenase-compound 175 10 mg/mL with 0.5% BA), a score of 15.1 (±0.506) in Group 5 (Collagenase-compound 175 3 mg/mL with 0.5% Phx) and a score of 13.2 (±0.855) in Group 6 (Collagenase-compound 175 10 mg/mL with 0.5% Phx), compared to a score of 8.57 (±0.672) in Group 2 (Collagenase-vehicle), with p-values of <0.001 (Groups 3, 4 and 5) and <0.01 (Group 6) versus Group 2, by student's t test.

Figure 10:
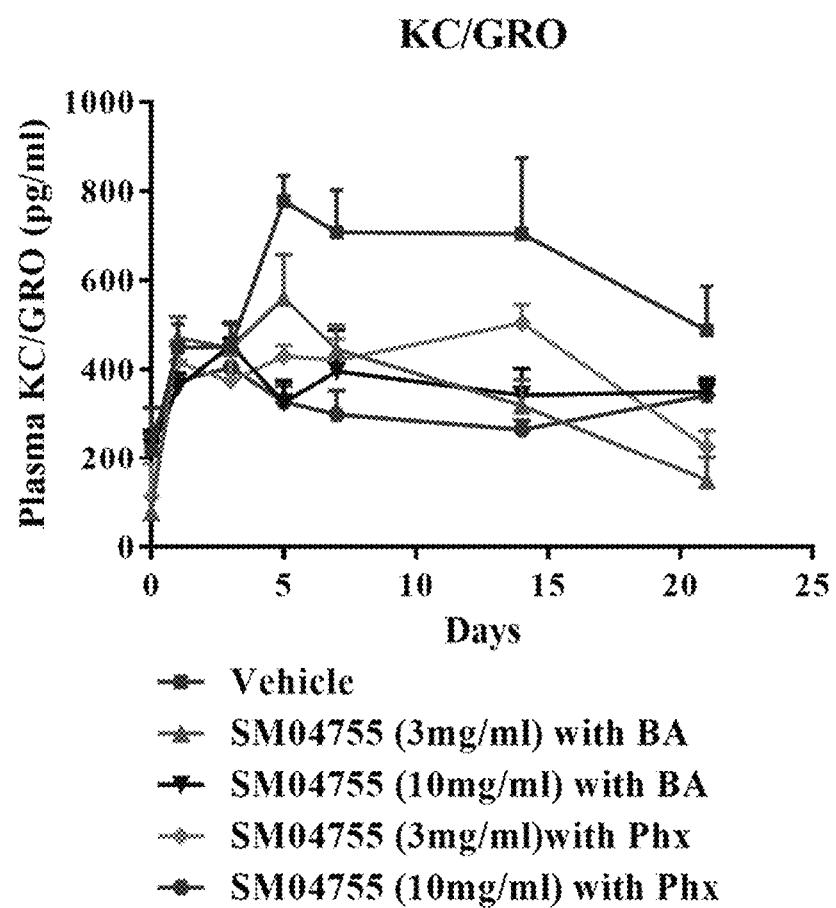
FIG. 10 is series of plots of plasma concentrations of KC/GRO in rats vs. the number of days elapsed after administration of a vehicle, 3 mg/ml COMPOUND 175 with benzyl alcohol, 10 mg/ml COMPOUND 175 with benzyl alcohol, 3 mg/ml COMPOUND 175 with Phx, and 10 mg/ml compound 175 with Phx. Tendinopathy in rats was induced by injecting collagenase (50 µl, 10 mg/ml Type IA in PBS, pH 7.4, ~469 units/mg) in the Achilles tendon. After 1 day, rats were dosed once daily for 21 days via topical application with vehicle control or topical compound 175. Blood was collected at various timepoints and plasma was analyzed for KC/GRO by ELISA. Measurement of inflammatory cytokine KC/GRO in the plasma of rats from Group 2 (Collagenase-Vehicle containing 0.5% Phx), Group 3 (Collagenase-compound 175 3 mg/mL with 0.5% BA), Group 4 (Collagenase-compound 175 10 mg/mL with 0.5% BA), Group 5 (Collagenase—compound 175 3 mg/mL with 0.5% Phx) and Group 6 (Collagenase-compound 175 10 mg/mL with 0.5% Phx). Compound 175 at both 3 and 10 mg/mL dose concentrations, with either BA or Phx as preservative significantly decreased the levels of KC/GRO in plasma compared to vehicle ($p<0.05$ and $p<0.01$, student's t test as indicated in Table 5), indicating an anti-inflammatory effect of compound 175. These data were generated from 3 replicates per timepoint per group (n=3).

Compound 175 Reduces Plasma Biomarker KC/GRO in the Collagenase-induced Tendon Injury Model. KC/GRO is an inflammatory biomarker reported to be associated with the development of tendonitis. In this study, plasma concentrations of KC/GRO were investigated at various timepoints of the study. As shown in Table 5 and FIG. 10, KC/GRO levels were elevated in Group 2 (Collagenase-vehicle with 0.5% Phx) on Days 5-21, ranging from 488-778 pg/mL, while all four compound 175-treated groups had decreased levels of KC/GRO in plasma, ranging from 150-561 pg/mL. Compound 175 at both 3 and 10 mg/mL dose concentrations, with either BA or Phx as preservative (Groups 3-6), demonstrated a statistically significant decrease in plasma KC/GRO levels compared to vehicle control (Group 2) on Days 5, 7 and 21 (p<0.05, by student's t test) as indicated in Table 6. Overall, the decrease of a plasma biomarker of inflammation corroborates the ability of compound 175 to ameliorate tendonitis.

TABLE 6

| | Plasma KC/GRO Concentration (pg/mL) | | | | |
|---|---|---|---|---|---|
| | Vehicle | Compound 175-Treated Groups | | | |
| Day | Group 2<br>0<br>0.5% Phx | Group 3<br>3 mg/mL<br>0.5% BA | Group 4<br>10 mg/mL<br> | Group 5<br>3 mg/mL<br>0.5% Phx | Group 6<br>10 mg/mL<br> |
| 0 | 219 ± 94.9 | 78.2 ± 14.9 | 224 ± 40.1 | 112 ± 74.0 | 254 ± 60.6 |
| 1 | 450 ± 53.1 | 472 ± 47.2 | 360 ± 31.4 | 416 ± 47.9 | 375 ± 44.4 |

TABLE 6-continued

| | Plasma KC/GRO Concentration (pg/mL) | | | | |
|---|---|---|---|---|---|
| | Vehicle | Compound 175-Treated Groups | | | |
| Day | Group 2<br>0<br>0.5% Phx | Group 3<br>3 mg/mL<br>0.5% BA | Group 4<br>10 mg/mL<br> | Group 5<br>3 mg/mL<br>0.5% Phx | Group 6<br>10 mg/mL<br> |
| 3 | 451 ± 50.2 | 449 ± 53.9 | 454 ± 52.2 | 374 ± 89.1 | 405 ± 42.1 |
| 5 | 778 ± 56.9 | 561 ± 97.2 | 327 ± 49.9** | 431 ± 24.5** | 328 ± 37.1** |
| 7 | 708 ± 95.5 | 445 ± 54.5 | 396 ± 92.4 | 422 ± 47.9 | 299 ± 53.9* |
| 14 | 704 ± 170 | 319 ± 57.7 | 343 ± 59.4 | 505 ± 41.0 | 265 ± 20.8 |
| 21 | 488 ± 98.8 | 150 ± 53.8* | 350 ± 25.6 | 226 ± 37.3 | 342 ± 39.7 |

*p < 0.05 (student's t test) on Day 7 (Group 6) and on Day 21 (Group 3) compared to Group 2 (Vehicle) on Days 7 and 21.
**p < 0.01 (student's t test) on Day 5 compound 175-treated groups (Groups 4, 5 and 6) compared to Group 2 (Vehicle).

Tendinopathy is an acute injury of the tendon that involves inflammation and tendon damage. If left untreated, repeated injury can lead to tendon ruptures and require surgery. Both doses of compound 175 (3 and 10 mg/ml with either BA or Phx preservatives) were efficacious in the rat tendonitis model. Based on the foregoing results, neither preservative, BA or Phx, appeared to improve the efficacy of compound 175. The results demonstrate that treatment with compound 175 ameliorated tendinopathy as assessed by blinded histological scoring of the tendon. To further confirm this finding, it has been shown that compound 175 also results in a decrease of an inflammatory plasma biomarker, KC/GRO.

Example 14

Pharmacokinetics

Thirty (30) naïve male Sprague Dawley rats were divided into three dose groups (Groups 1-3; 10 animals/group). compound 175 was formulated in 1% hydroxypropyl methylcellulose (HPMC) 40-0101/20% propylene glycol at 1 or 10 mg/mL containing 1% benzyl alcohol (BA) as preservative (Groups 1 and 2) or at 10 mg/mL containing 0.5% Tween 80 (used in earlier rat studies) without BA preservative (Group 3). The compound 175 formulation was applied once topically to each ankle of the hind leg of each animal at 60 μL volume (30 μL/cm²×2 cm²) over the area of the Achilles tendon. The study design is presented in Table 7 below.

TABLE 7

| | | | | Left and Right Hind limb[a] | | | |
|---|---|---|---|---|---|---|---|
| Group | N/Sex | Cmpd. 175<br>Conc.<br>(mg/mL) | Preservative[b] | Dose<br>Volume<br>(μL/cm²) | Dose<br>Area<br>(cm²) | Dose per<br>Unit Area<br>(mg/cm²) | Total Dose<br>Volume<br>(μL) |
| 1 | 10/M | 1 | BA | 30 | 2 | 0.03 | 60 |
| 2 | 10/M | 10 | | | | 0.3 | |
| 3 | 10/M | 10 | No preservative | | | 0.3 | |

[a]Topical application to left and right ankles of the hind limbs over the area of the Achilles tendon

[b]Compound 175 topical formulations: 1% HPMC 40-0101/20% propylene glycol containing 1% benzyl alcohol (BA) as preservative (Groups 1 and 2), and without BA preservative but with 0.5% Tween 80 (Group 3).

Blood Sample Collection. Blood samples (~0.5 mL) were collected via cardiac puncture, into tubes containing $K_2EDTA$ as anticoagulant, at 1, 2, 4, 7 and 24 hours post-dose from 2 animals per timepoint (n=2). Plasma was harvested and frozen at −80° C. for bioanalysis.

Tissue Sample Collection. The Achilles tendons from both ankles were collected following euthanasia at 1, 2, 4, 7 and 24 hours post-dose from 2 animals per timepoint (n=4) from all groups. Skin tissue samples were collected from the dose-site at 7 and 24 hours post-dose from 2 animals per timepoint (n=4) in Group 2. Tissues were frozen at −80° C. for bioanalysis. Blood and tissue collection schedule is outlined in Table 8 below.

TABLE 8

| Group | Cmpd. 175 Conc. (mg/mL) | Preservative | Blood Collection Timepoints (h)[1] | Tendon Collection Timepoints (h)[b] | Skin Collection Timepoints (h)[b] |
|---|---|---|---|---|---|
| 1 | 1 | BA | 1, 2, 4, 7 and 24 | 1, 2, 4, 7 and 24 | NS |
| 2 | 10 | | | | 7 and 24 |
| 3 | 10 | No preservative | | | NS |

NS = No samples collected.
[1]n = 2/timepoint/group for blood collection.
[b]n = 4/timepoint/group for tendon and skin collection (2 animals per timepoint × 2 ankles).

Experimental Procedures. Skin tissue samples were processed using the following procedures: 1) Weigh tissue and homogenize using cryoPrep (Covaris); 2) Add 9×volume of Acetonitrile:Methanol (70:30) and vortex for one hour; 3) Aliquot 100 μL of tissue homogenate into 96 microtube polypropylene plate; 4) Add 10 μL of working standard to each standard; 5) Add 10 μL of methanol in all samples and blanks; 6) Add 10 μL of internal standard (IS) to all tubes except blanks; 7) Spin in centrifuge at 3000 rpm for 10 minutes; and 8) Transfer 100 μL of supernatant into 96-well plate containing 150 μL of water. Cap and vortex for LC/MS/MS analysis.

Bioanalytical and Pharmacokinetic Analysis. The chromatograms of the samples were integrated and calibrated using Analyst 1.6.2 (AB Sciex, Redwood City, Calif.). Linear regression with $1/x^2$ weighting and internal standardization was used for standard calibration, with an acceptance criterion of ±30% of nominal standard concentration. The lower limit of quantitation (LLOQ) was 2.00 ng/mL (plasma), 6.00 ng/g (tendon) and 25.0 ng/g (skin). Pharmacokinetic parameters were estimated by noncompartmental analysis from individual concentration versus time profiles using Pheonix WinNonlin version 6.3 (Certara, Inc., Princeton, N.J.). The time to maximum concentration ($t_{max}$) and the maximum concentration ($C_{max}$) were determined based on measured plasma and tissue concentrations. The area under the curve ($AUC_{0-last}$) was calculated using the linear trapezoidal rule.

Systemic Exposure. Systemic exposure to compound 175 was low compared to tendon and skin tissues after a single topical administration of a 1 or 10 mg/mL formulation, with either BA or Tween 80. Plasma exposure in Groups 1 and 2 (1 and 10 mg/mL formulation containing BA) were: 1.30 and 10.6 ng/mL Cmax and 0.650 and 36.1 h·ng/mL AUC (0-last), respectively, showing a dose-proportional increase in Cmax and greater than dose-proportional increase in total exposure (AUC(0-last)). Exposure in Group 3 (10 mg/mL formulation without BA but containing Tween 80) was 1.94 ng/mL Cmax and 6.79 h·ng/mL AUC(0-last), which was ~0.2× of Group 2 (10 mg/mL with BA).

Tendon Exposure. Compound 175 Achilles tendon exposure in Groups 1 and 2 (1 and 10 mg/mL formulation containing BA) was 519 and 1930 ng/g $C_{max}$ and 2164 and 7270 h·ng/g $AUC_{(0-last)}$, respectively, indicating a less than dose-proportional increase in exposure: 3.4×increase in $AUC_{(0-last)}$ for a 10× dose-increment. Group 3 (10 mg/mL without BA) tendon exposure was 7053 ng/g $C_{max}$ and 28077 h·ng/g $AUC_{(0-last)}$, which was ~4× of Group 2 (10 mg/mL with BA). Tendon to plasma ratios ($AUC_{(0-last)}$) were 3329 and 202 in Groups 1 and 2 (1 and 10 mg/mL formulations containing BA) and 4135 in Group 3 (10 mg/mL without BA).

Figure 11:
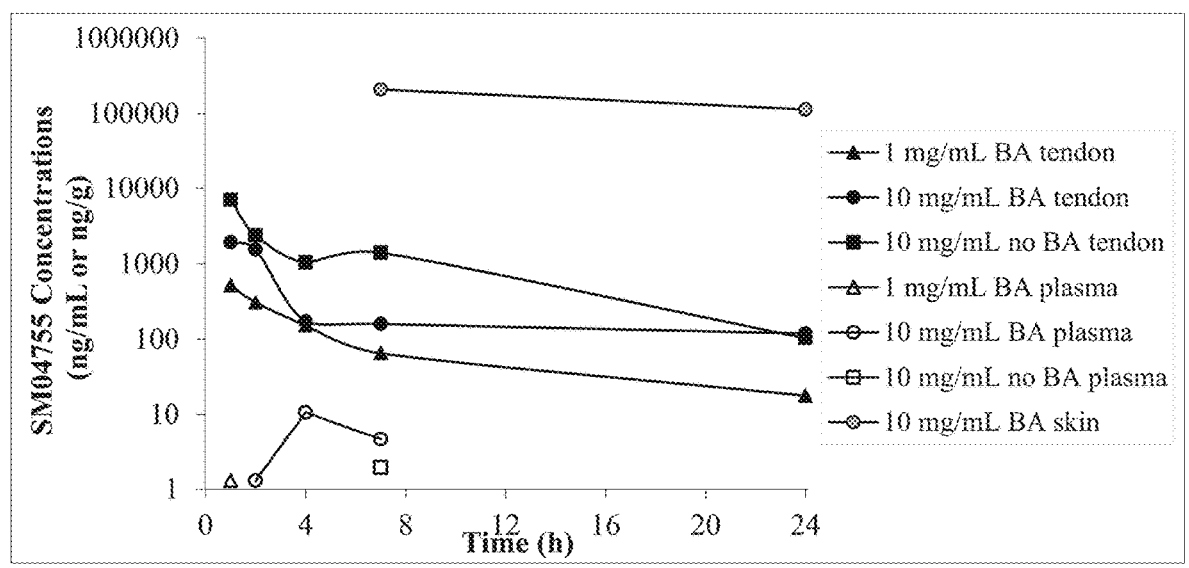
FIG. 11 is a series of plots of compound 175 concentrations vs. time in Sprague-Dawley rat tendons, plasma, and skin after a topical application of 1 mg/mL compound 175 and benzyl alcohol, 10 mg/mL compound 175 and benzyl alcohol, and 10 mg/mL compound 175.

Skin concentrations in Group 2 (10 mg/mL containing BA) were reported as estimated as all values were above quantitation limit (AQL>25000 ng/g). Mean skin concentrations at 7 and 24 hours post-dose were 208600 and 113375 ng/g, roughly 1000×tendon concentrations at these timepoints. Plasma, Tendon and Skin PK parameters are presented below in Table 9 and concentration-time profiles are displayed in FIG. 11.

TABLE 9

| Group | Dose Conc. (mg/mL) | Preservative | Tissue | $t_{max}$ (h) | $C_{max}$ (ng/g or ng/mL) | $last$ (h) | $AUC_{(0-last)}$ (h · ng/g or h · ng/mL) | Tissue/Plasma AUC Ratio |
|---|---|---|---|---|---|---|---|---|
| 1 | 1 | 1% BA | Plasma | 1.00 | 1.30 | 1.00 | 0.650 | 3329 |
| | | | Tendon | 1.00 | 519 | 24.0 | 2164 | |
| 2 | 10 | 1% BA | Plasma | 4.00 | 10.6 | 7.00 | 36.1 | 202 |
| | | | Tendon | 1.00 | 1930 | 24.0 | 7270 | |
| | | | Skin | 7.00 | 208600[1] | 24.0 | NC | NC |
| 3 | 10 | No preservative | Plasma | 7.00 | 1.94 | 7.00 | 6.79 | 4135 |
| | | | Tendon | 1.00 | 7053 | 24.0 | 28077 | |

Total dose volume = 60 μL/ankle of hind limb;
n = 2 (plasma),
n = 4 (tendon, skin; 2).
NC = not calculated due to lack of sufficient timepoints for AUC calculation.
[1]Above quantitation limit (AQL > 25000 ng/g)—value reported as estimated.

Systemic exposure to compound 175 in rats after a single topical administration was low in all dose groups compared to tendon exposure, with tendon to plasma ratios ranging from 202 to 4135 across groups. A dose dependent increase in plasma and tendon exposure was seen between the 1 and 10 mg/mL formulations containing BA. While the 10 mg/mL formulation without BA (containing Tween 80)

showed lower systemic exposures (0.2×) compared to the formulation containing BA, the tendon exposure was 4 fold higher than the 10 mg/mL formulation containing BA.

The term "comprising" as used herein is synonymous with "including," "containing," or "characterized by," and is inclusive or open-ended and does not exclude additional, unrecited elements or method steps.

What is claimed is:

1. A method of treating tendinosis the method comprising administering to a subject a compound or pharmaceutically acceptable salt thereof having the structure of Formula I:

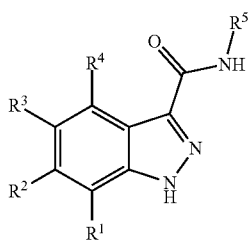

wherein:
$R^1$, $R^2$ and $R^4$ are independently selected from the group consisting of H, $C_{1-9}$ alkyl, halide, —N($R^{10}$)$_2$, —X$R^{10}$, CN, —OCF$_3$ and —CF$_3$;
$R^3$ is selected from the group consisting of carbocyclyl$R^6$, heterocyclyl$R^6$, aryl$R^6$ and heteroaryl$R^6$;
$R^5$ is selected from the group consisting of —($C_{1-9}$ alkyl)$_n$carbocyclyl$R^7$, —($C_{1-9}$ alkyl)$_n$heterocyclyl$R^7$, —($C_{1-9}$ alkyl)$_n$aryl$R^7$ and —($C_{1-9}$ alkyl)$_n$heteroaryl$R^7$;
each $R^6$ is 1-5 substituents each selected from the group consisting of H, $C_{1-9}$ alkyl, halide, amino, —OCF$_3$, —CF$_3$, —CN, —X$R^{10}$, —($C_{1-9}$ alkyl)$_n$carbocyclyl$R^8$, —($C_{1-9}$ alkyl)$_n$heterocyclyl$R^8$, —($C_{1-9}$ alkyl)$_n$aryl$R^8$, —($C_{1-9}$ alkyl)$_n$heteroaryl$R^8$, —C(=O)$R^{11}$, —N($R^{10}$)C(=O)$R^{11}$, —($C_{1-9}$)alkyl)$_n$N($R^{10}$)$_2$, —($C_{1-9}$alkyl)$_n$N($R^{10}$)SO$_2$$R^{11}$ and —SO$_2$$R^{11}$;
each $R^7$ is 1-5 substituents each selected from the group consisting of H, $C_{1-9}$ alkyl, halide, amino, —OCF$_3$, —CF$_3$, —CN, —X$R^{10}$, —($C_{1-9}$ alkyl)$_n$carbocyclyl$R^9$, —($C_{1-9}$ alkyl)$_n$heterocyclyl$R^9$, —($C_{1-9}$ alkyl)$_n$aryl$R^9$, —($C_{1-9}$ alkyl)$_n$heteroaryl$R^9$, —C(=O)$R^{11}$, —N($R^{10}$)C(=O)$R^{11}$, —($C_{1-9}$)alkyl)$_n$N($R^{10}$)$_2$, —($C_{1-9}$)alkyl)$_n$N($R^{10}$)SO$_2$$R^{11}$ and —SO$_2$$R^{11}$;
each $R^8$ is 1-5 substituents each selected from the group consisting of H, $C_{1-3}$ alkyl, halide, amino, OCF$_3$, —CF$_3$—CN, —X$R^{12}$, —C(=O)$R^{13}$, —N($R^{12}$)C(=O)$R^{13}$, —($C_{1-9}$ alkyl)$_n$N($R^{12}$)$_2$, —($C_{1-9}$ alkyl)$_n$N($R^{12}$)SO$_2$$R^{13}$ and —SO$_2$$R^{13}$;
each $R^9$ is 1-5 substituents each selected from the group consisting of H, $C_{1-3}$ alkyl, halide, amino, —OCF$_3$, —CF$_3$—CN, —X$R^{12}$, —C(=O)$R^{13}$, —N($R^{12}$)C(=O)$R^{13}$, —($C_{1-9}$ alkyl)$_n$N($R^{12}$)$_2$, —($C_{1-9}$ alkyl)$_n$N($R^{12}$)SO$_2$$R^{13}$ and —SO$_2$$R^{13}$;
each $R^{10}$ is independently selected from the group consisting of H, $C_{1-9}$ alkyl, —($C_{1-9}$ alkyl)$_n$N($R^{14}$)$_2$, —($C_{1-9}$ alkyl)$_n$carbocyclyl$R^8$, —($C_{1-9}$ alkyl)$_n$heterocyclyl$R^8$, —($C_{1-9}$ alkyl)$_n$aryl$R^8$ and —($C_{1-9}$ alkyl)$_n$heteroaryl$R^8$;
each $R^{11}$ is independently selected from the group consisting of $C_{1-9}$ alkyl, —N($R^{14}$)$_2$, —($C_{1-9}$ alkyl)$_n$carbocyclyl$R^8$, —($C_{1-9}$ alkyl)$_n$heterocyclyl$R^8$, —($C_{1-9}$ alkyl)$_n$ aryl$R^8$ and —($C_{1-9}$ alkyl)$_n$heteroaryl$R^8$;
each $R^{12}$ is independently selected from the group consisting of H, $C_{1-9}$ alkyl, —($C_{1-9}$ alkyl)$_n$N($R^{14}$)$_2$, —($C_{1-9}$ alkyl)$_n$carbocyclyl, —($C_{1-9}$ alkyl)$_n$heterocyclyl, —($C_{1-9}$ alkyl)$_n$aryl and —($C_{1-9}$ alkyl)$_n$heteroaryl;
each $R^{13}$ is independently selected from the group consisting of $C_{1-9}$ alkyl, —N($R^{14}$)$_2$, —($C_{1-9}$ alkyl)$_n$carbocyclyl, —($C_{1-9}$ alkyl)$_n$heterocyclyl, —($C_{1-9}$ alkyl)$_n$aryl and —($C_{1-9}$ alkyl)$_n$heteroaryl;
each $R^{14}$ is independently selected from the group consisting of H, $C_{1-3}$ alkyl, carbocyclyl and aryl;
each X is selected from the group consisting of a bond, —O— and —S—; and
each n is 0 or 1.

2. The method of claim 1, wherein $R^1$, $R^2$ and $R^4$ are H.

3. The method of claim 2, wherein $R^3$ is 3-pyridyl$R^6$.

4. The method of claim 2, wherein $R^3$ is 5-pyrimidinyl$R^6$.

5. The method of claim 2, wherein $R^3$ is 4-pyridazinyl$R^6$.

6. The method of claim 3, wherein $R^6$ is one substituent and is —N($R^9$)C(=O)$R^{10}$.

7. The method of claim 3, wherein $R^6$ is one substituent and is —(CH$_2$)heterocyclyl$R^8$.

8. The method of claim 7, wherein the $R^6$ heterocyclyl is independently selected from the group consisting of azetidinyl$R^8$, pyrrolidinyl$R^8$, piperidinyl$R^8$, piperazinyl$R^8$, and morpholinyl$R^8$.

9. The method of claim 2, wherein $R^5$ is 3-pyridyl$R^7$.

10. The method of claim 3, wherein $R^5$ is 3-pyridyl$R^7$.

11. The method of claim 2, wherein $R^5$ is 5-pyrimidinyl$R^7$.

12. The method of claim 2, wherein $R^5$ is 4-pyridazinyl$R^7$.

13. The method of claim 9, wherein $R^7$ is one substituent and is selected from the group consisting of halide, —OCF$_3$, —CF$_3$, —($C_{1-9}$)alkyl)$_n$N($R^{10}$)$_2$, —($C_{1-9}$) alkyl)$_n$N($R^{10}$)SO$_2$$R^{11}$ and —N($R^{10}$)C(=O)$R^{11}$.

14. The method of claim 10, wherein $R^7$ is one substituent and is selected from the group consisting of halide, —OCF$_3$, —CF$_3$, —($C_{1-9}$ alkyl)$_n$N($R^{10}$)$_2$, —($C_{1-9}$ alkyl)$_n$N($R^{10}$)SO$_2$$R^{11}$ and —N($R^{10}$)C(=O)$R^{11}$.

15. The method of claim 9, wherein $R^7$ is one substituent and is selected from the group consisting of —O$R^{10}$ and —C(=O)$R^{11}$ where $R^{11}$ is —N($R^{10}$)$_2$, and each $R^{10}$ is independently selected from the group consisting of H, methyl and —($C_{1-9}$ alkyl)$_n$carbocyclyl$R^8$ where n is 0 and each $R^8$ is 1-2 substituents independently selected from H or halide.

16. The method of claim 10, wherein $R^7$ is one substituent and is selected from the group consisting of —O$R^{10}$ and —C(=O)$R^{11}$ where $R^{11}$ is —N($R^{10}$)$_2$, and each $R^{10}$ is independently selected from the group consisting of H, methyl and —($C_{1-9}$ alkyl)$_n$carbocyclyl$R^8$ where n is 0 and each $R^8$ is 1-2 substituents independently selected from H or halide.

17. The method of claim 1, the compound having a structure selected from the group consisting of:

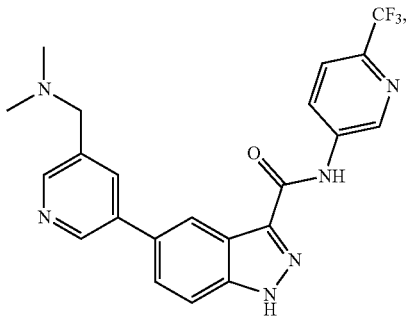

-continued
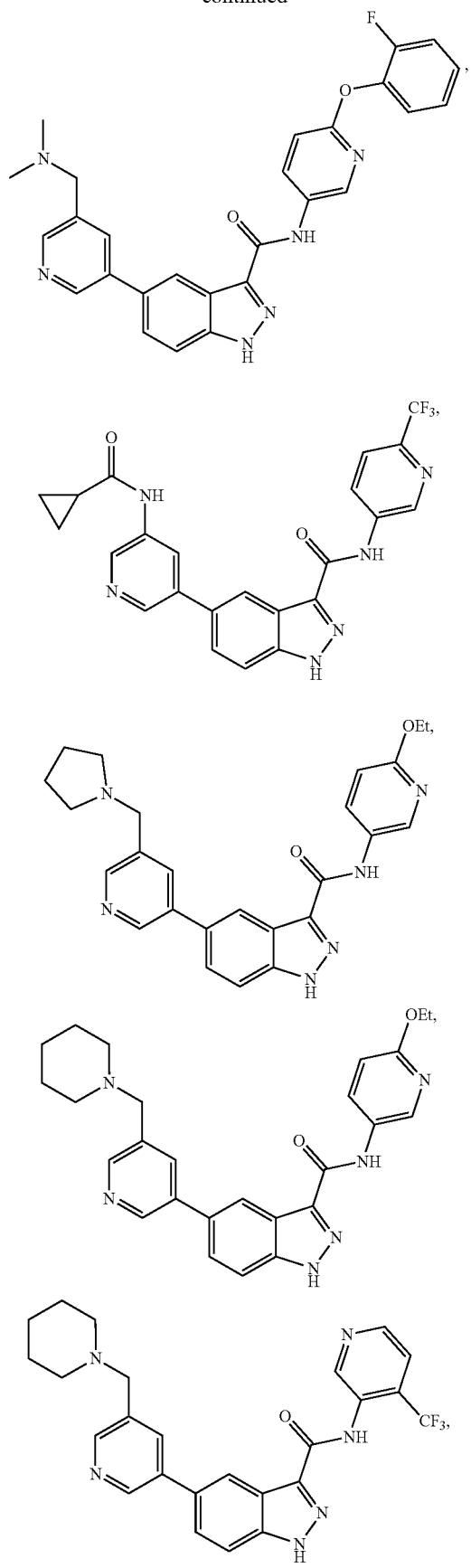
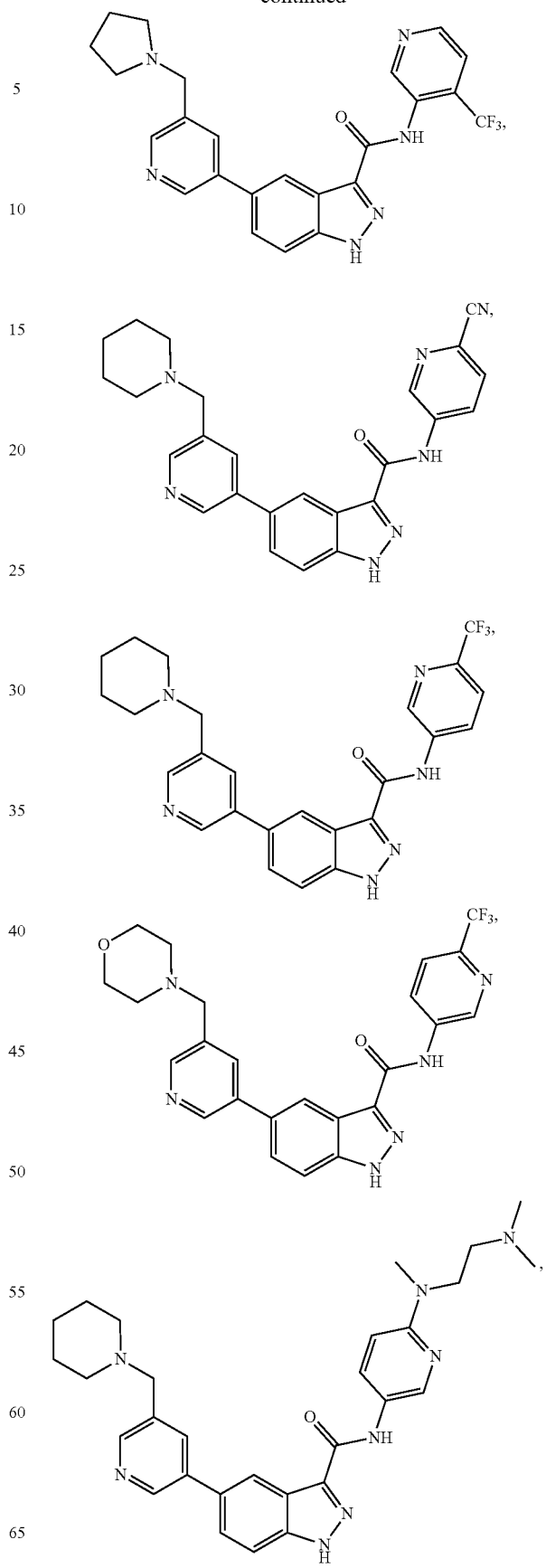

367
-continued
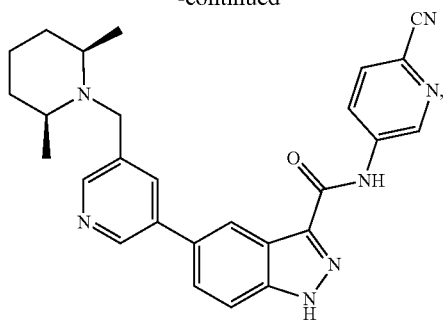
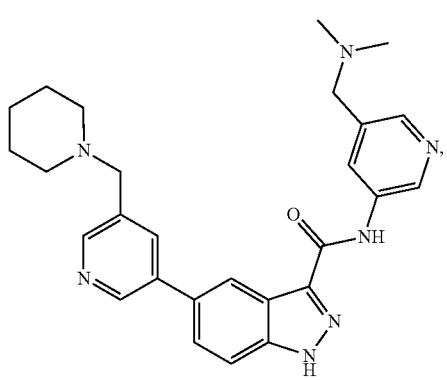
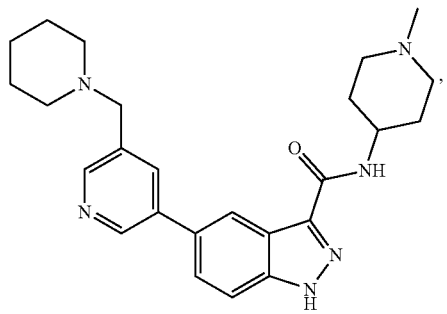
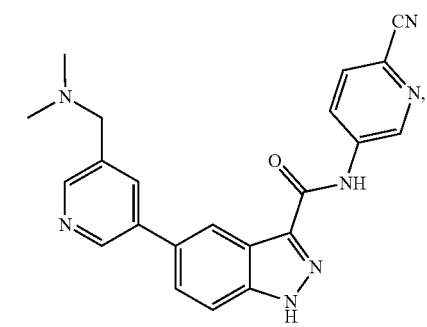
368
-continued
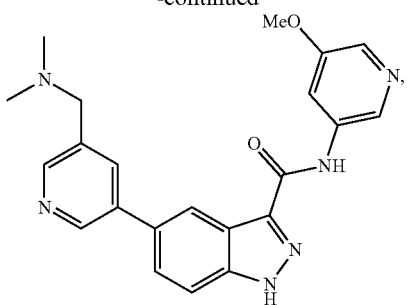
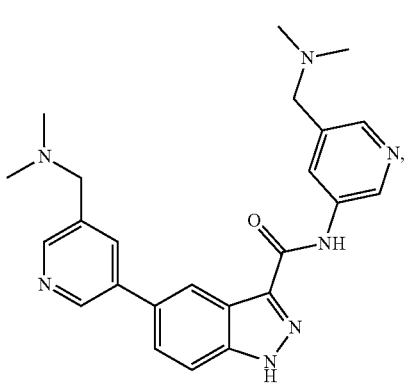
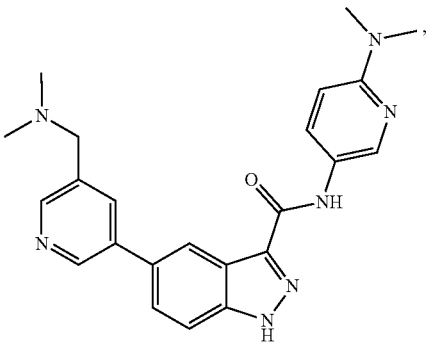
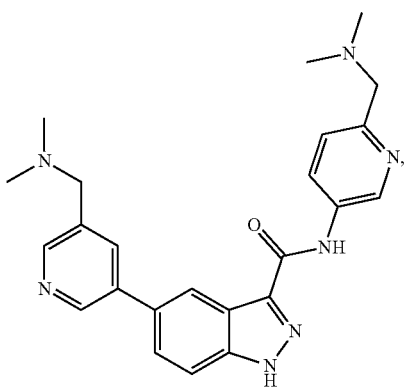

369 -continued
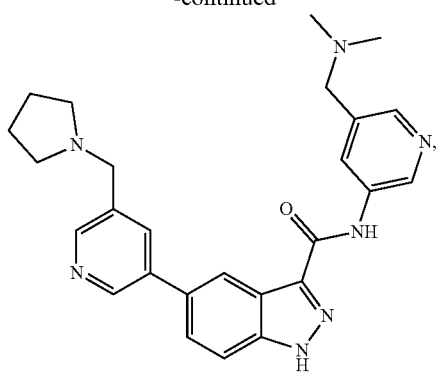
370 -continued
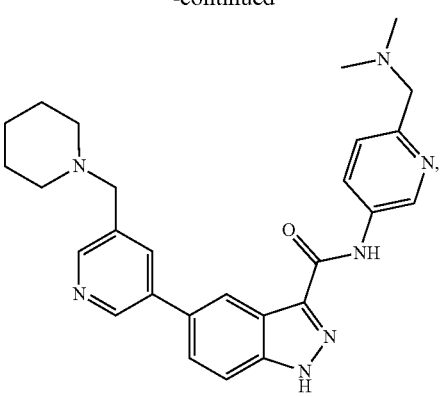

371
-continued
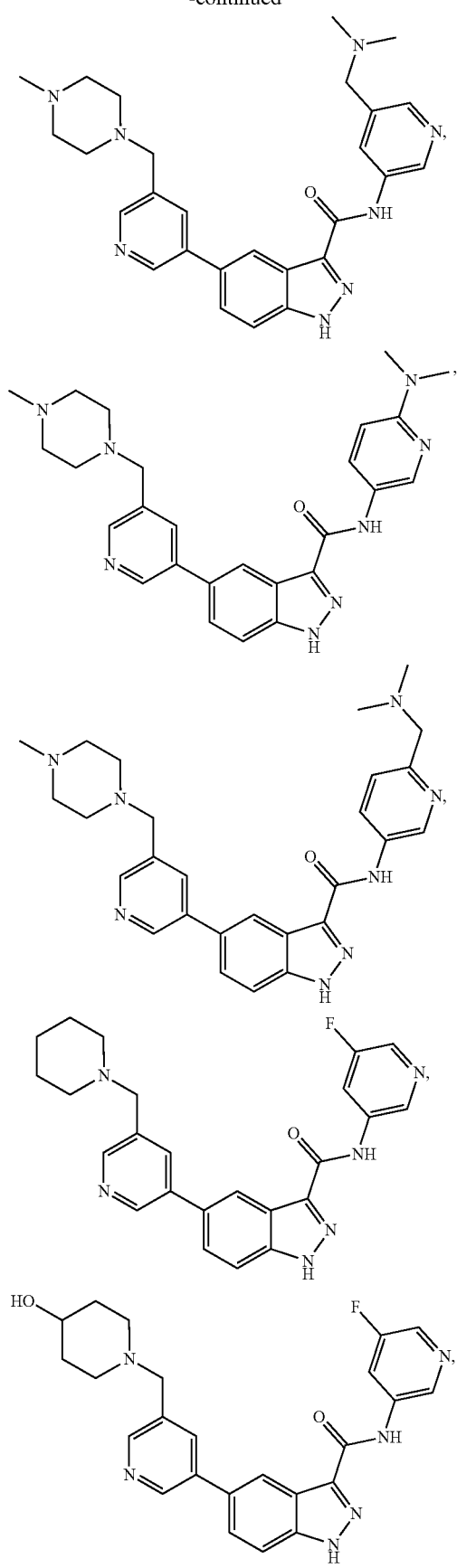
372
-continued
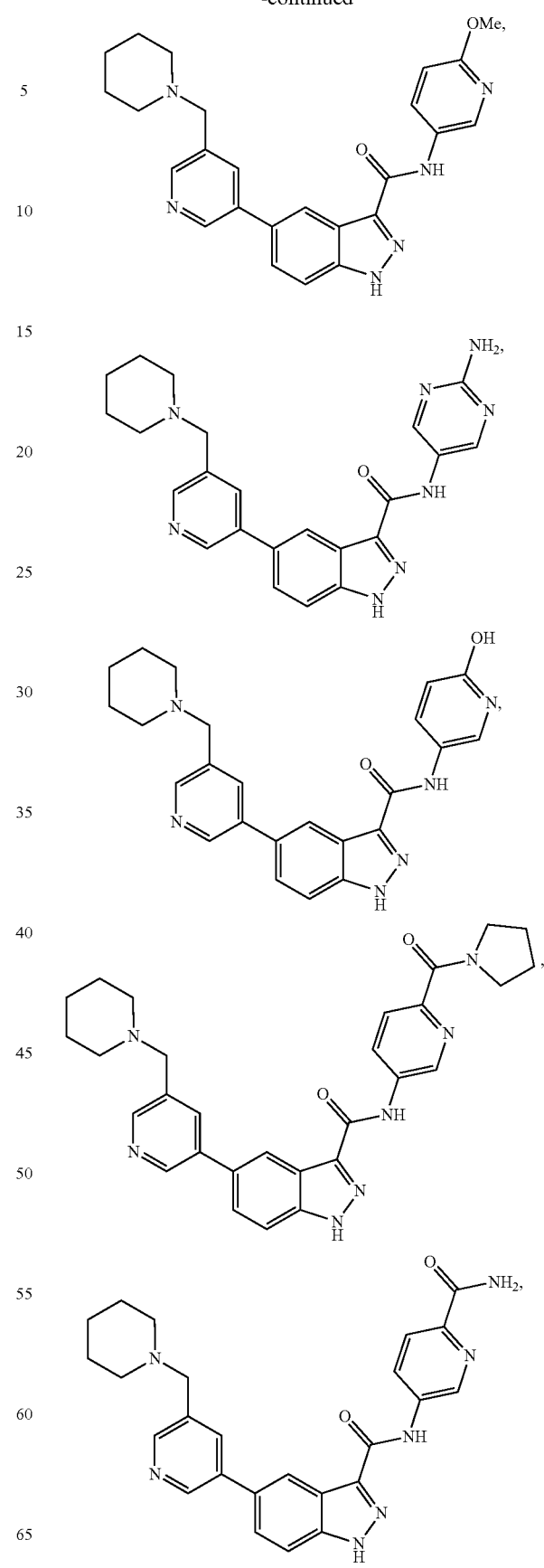

373
-continued
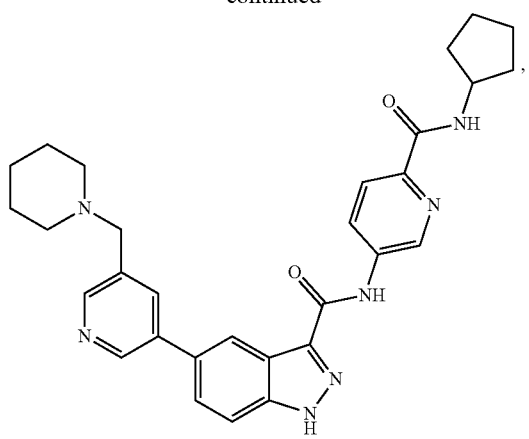
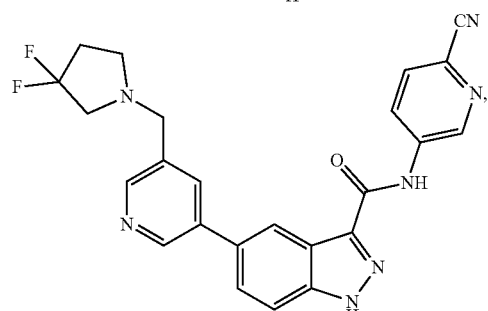
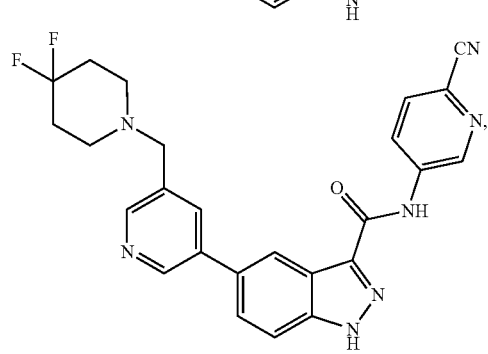
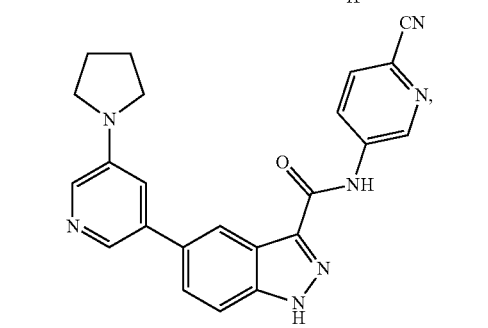
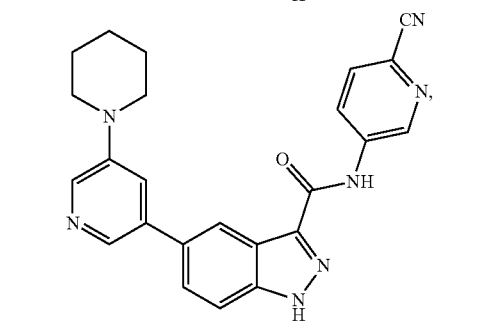
374
-continued
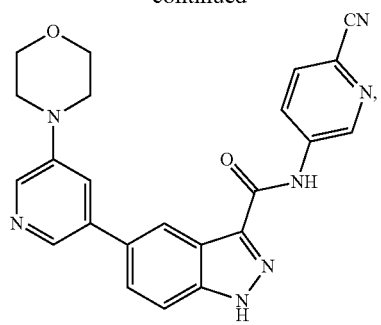
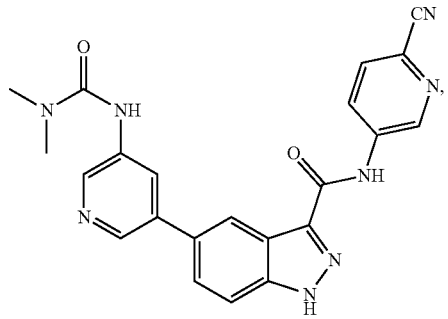
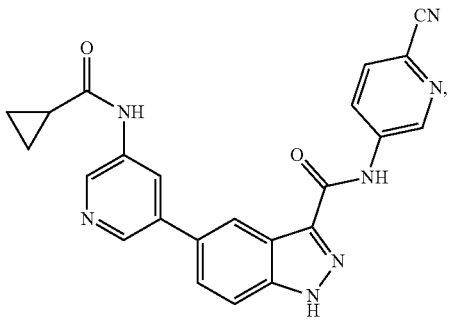
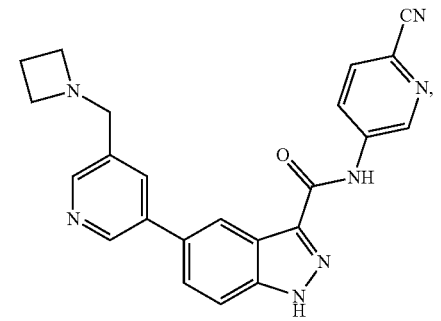
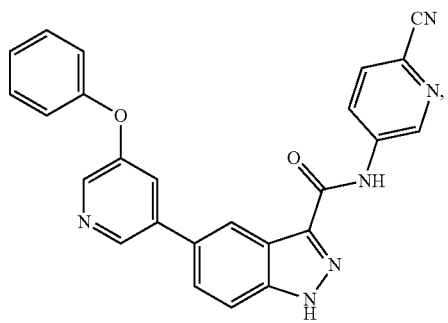

375
-continued
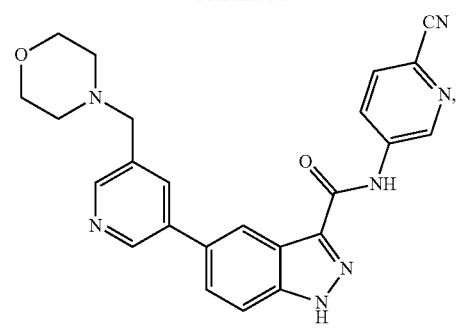
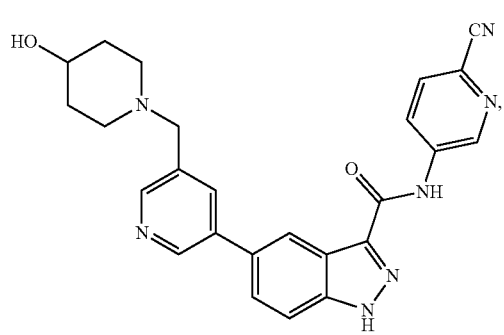
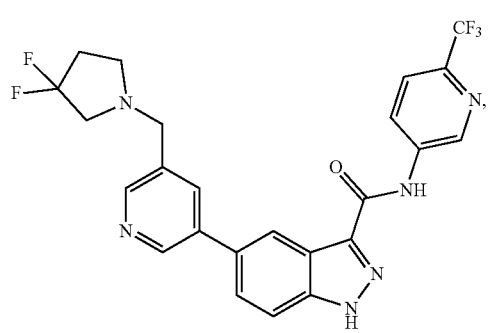
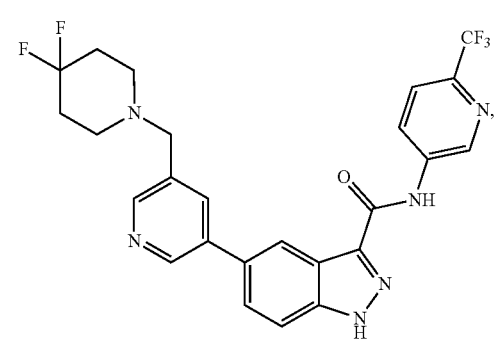
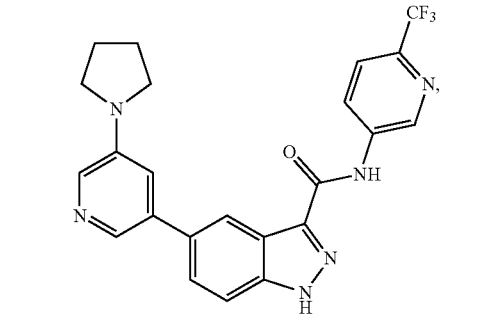
376
-continued
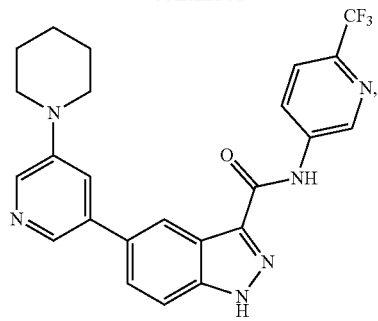
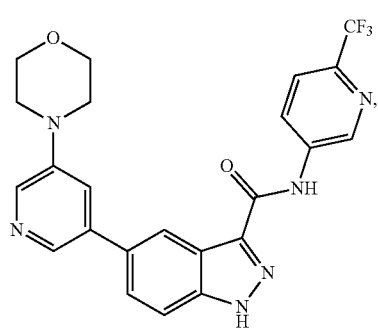
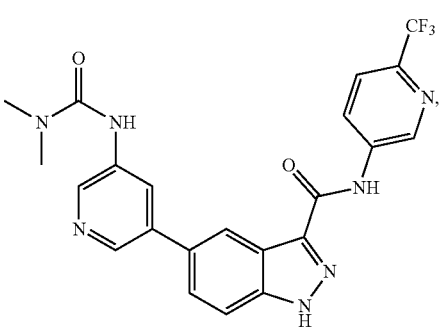
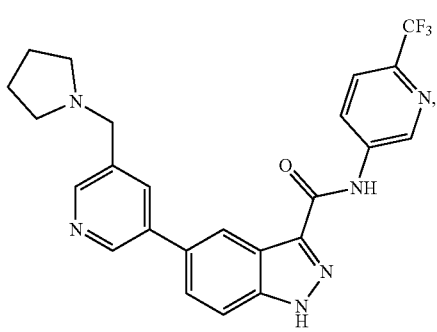
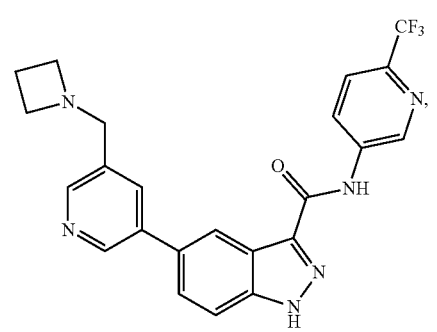

377
-continued
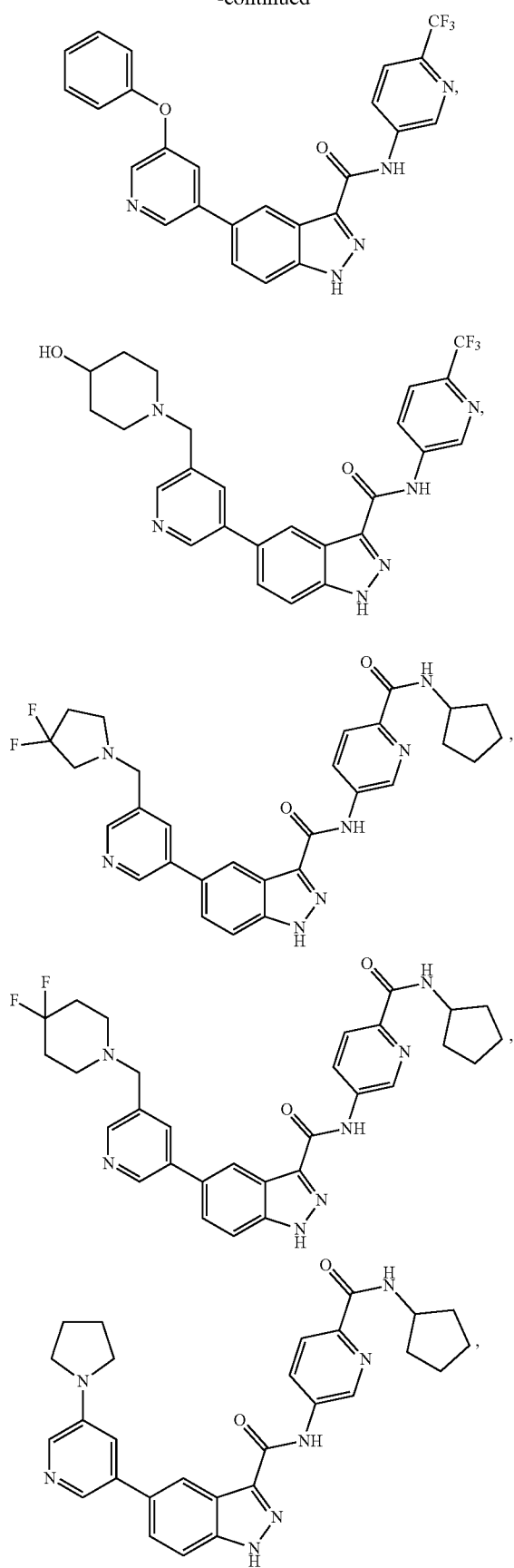
378
-continued
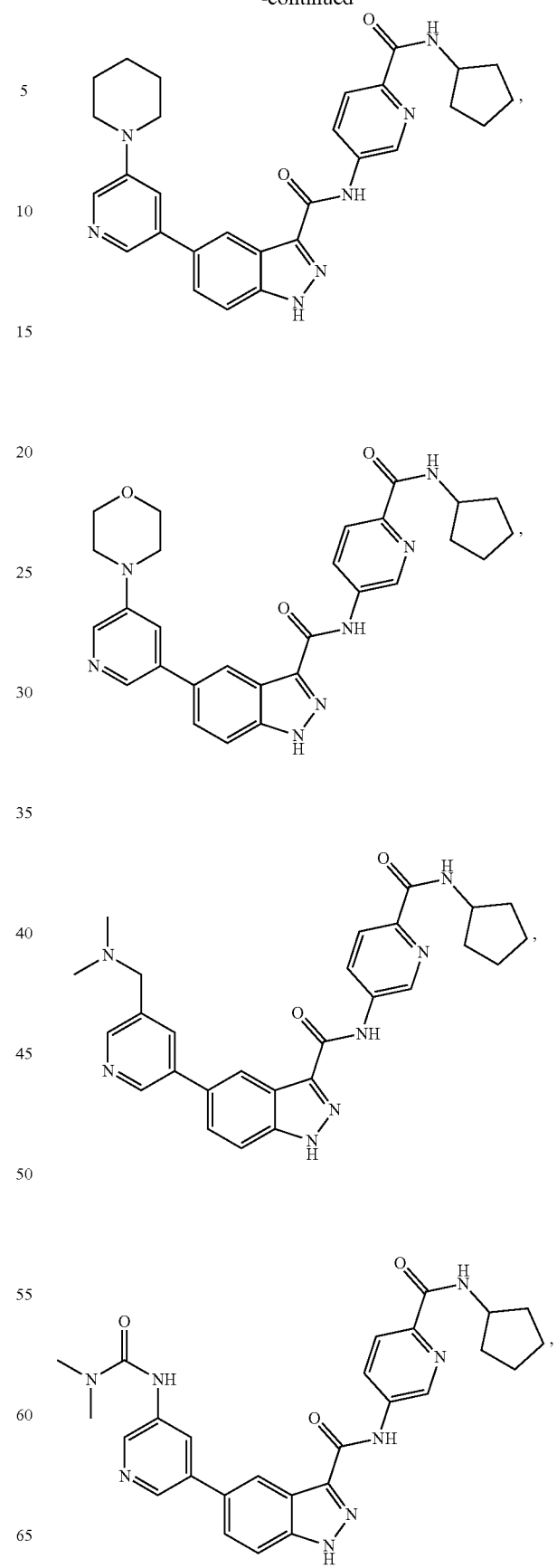

379
-continued
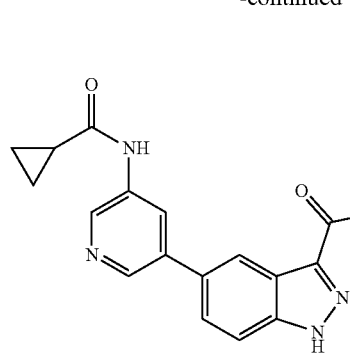
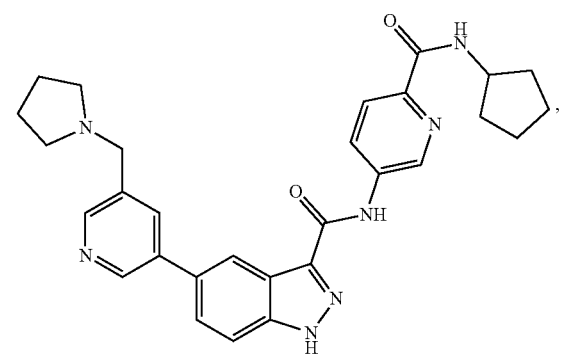
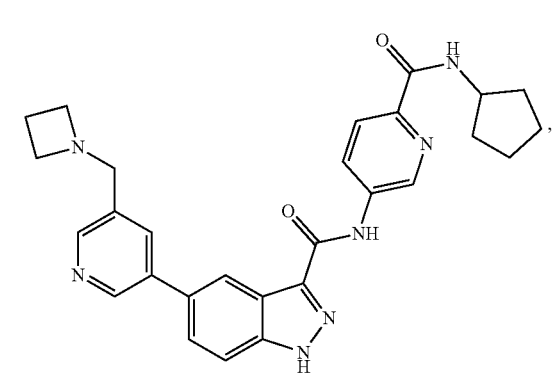
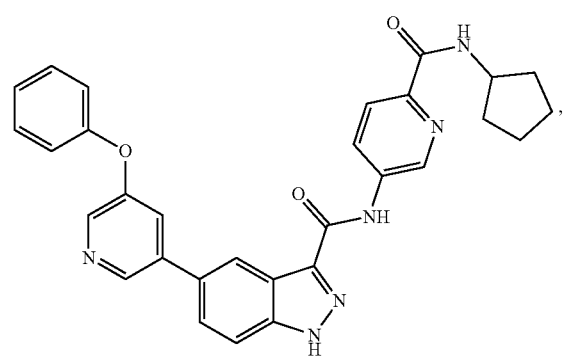
380
-continued
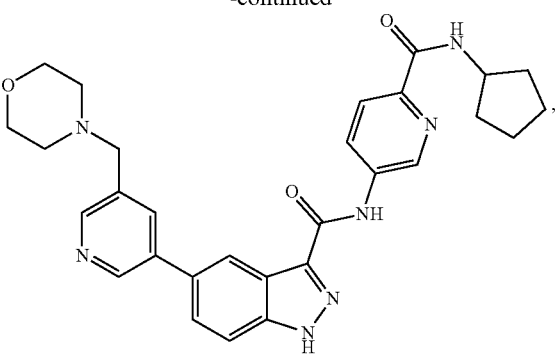
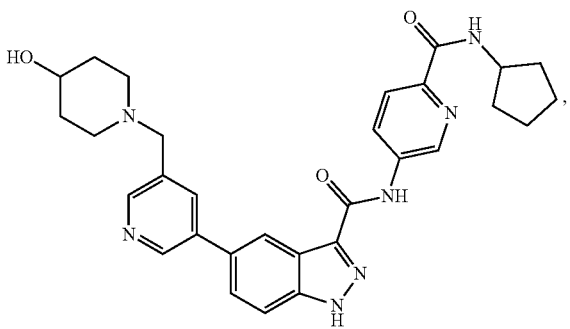
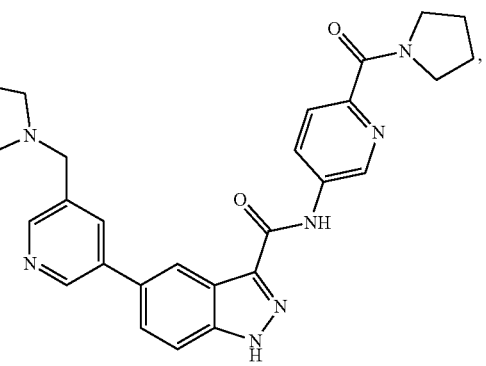
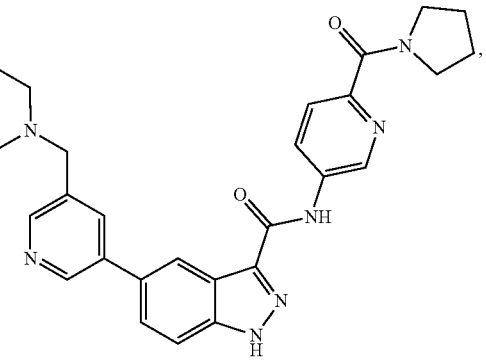

381
-continued
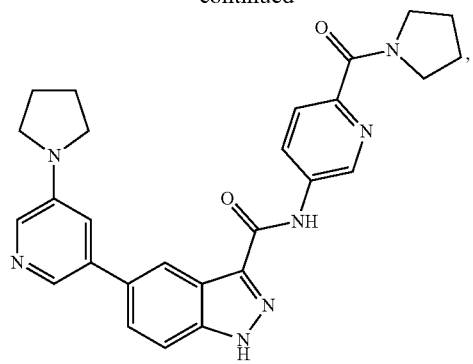
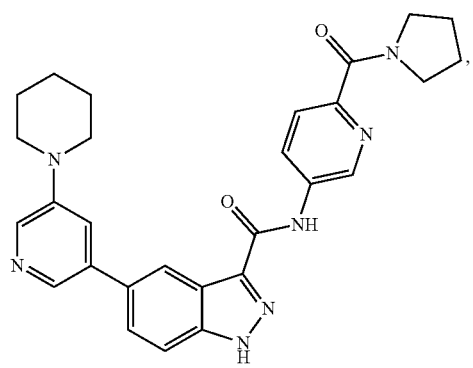
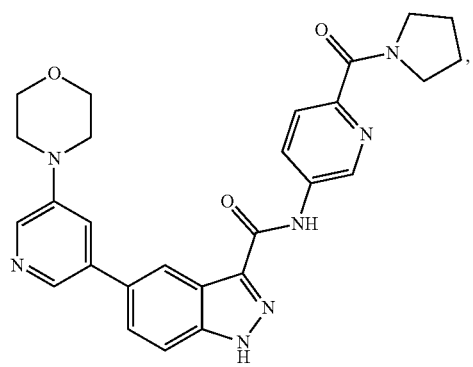
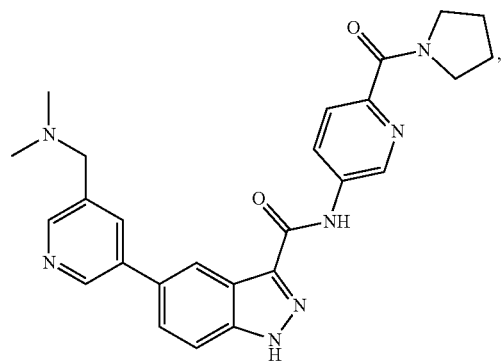
382
-continued
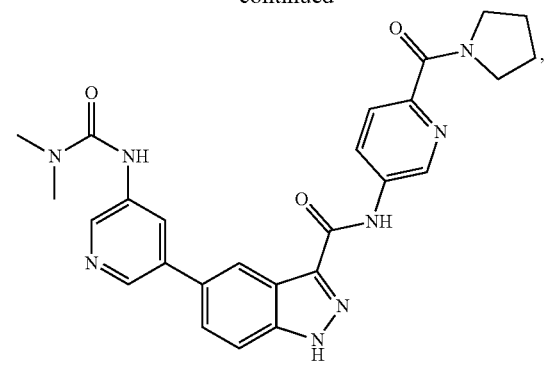
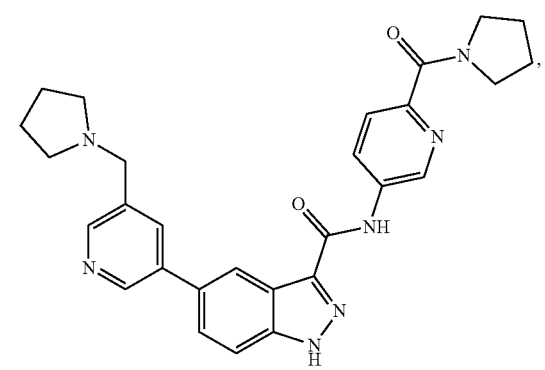
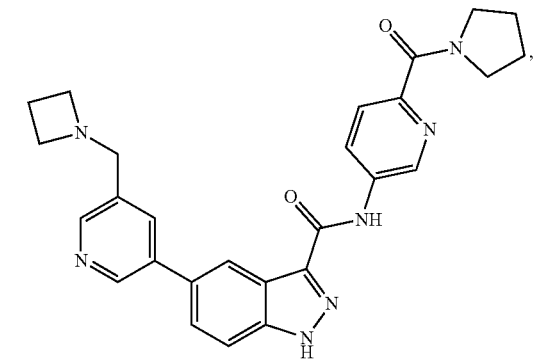

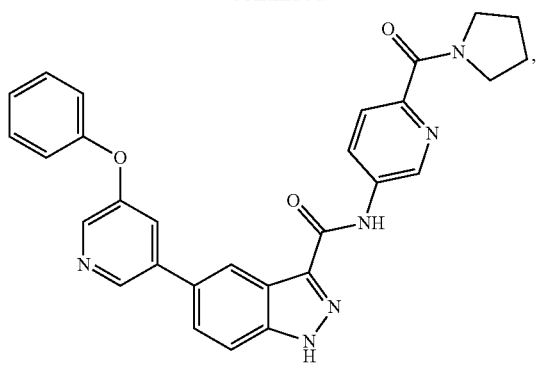
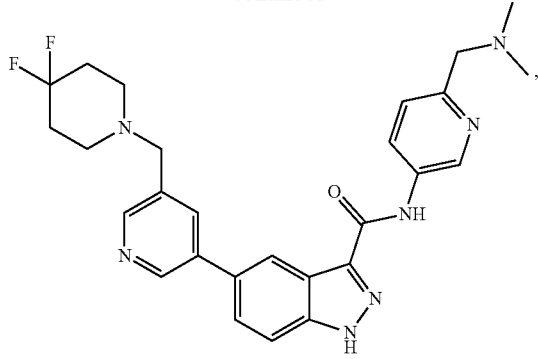
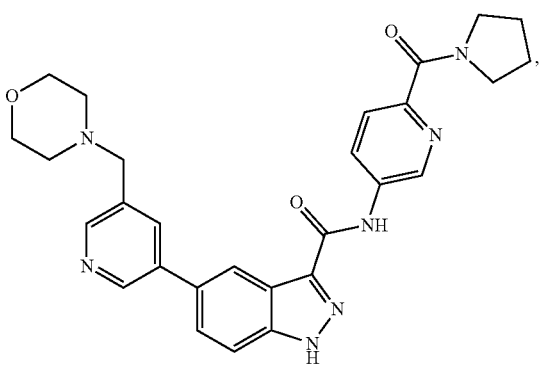
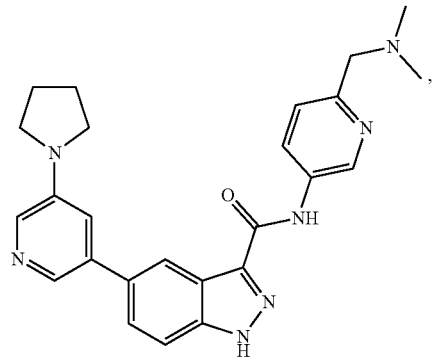
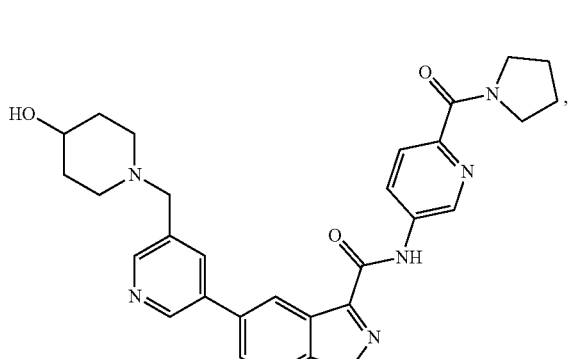
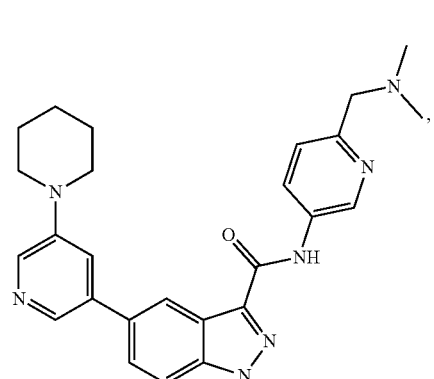
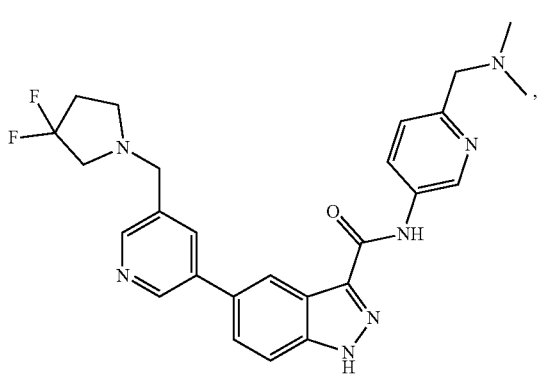
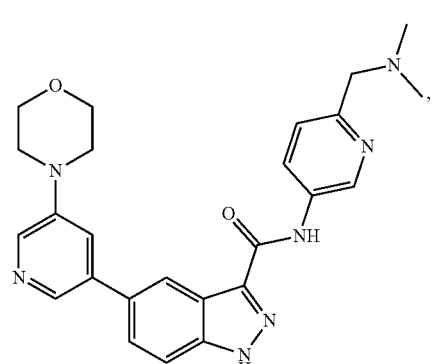

385
-continued
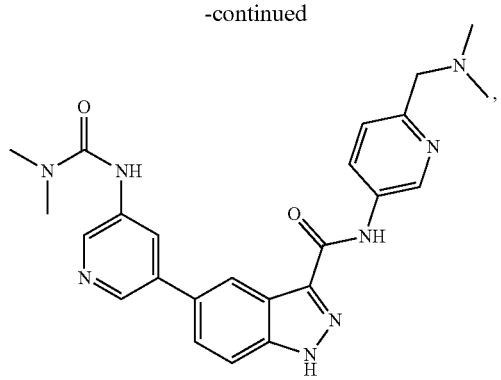
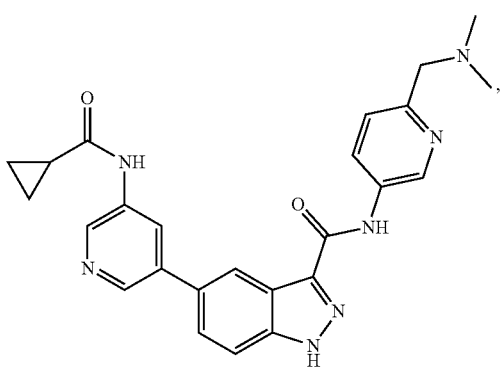
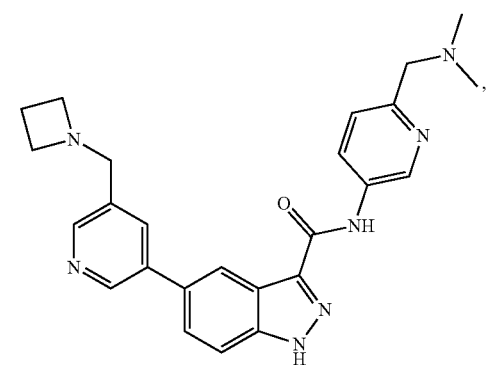
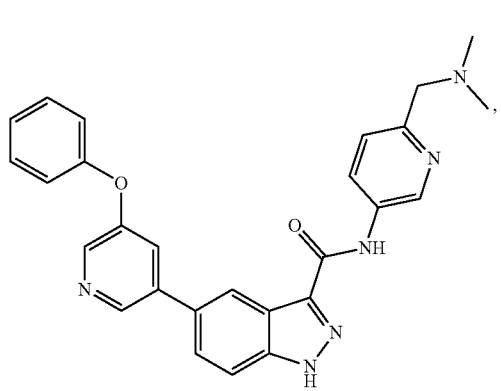
386
-continued
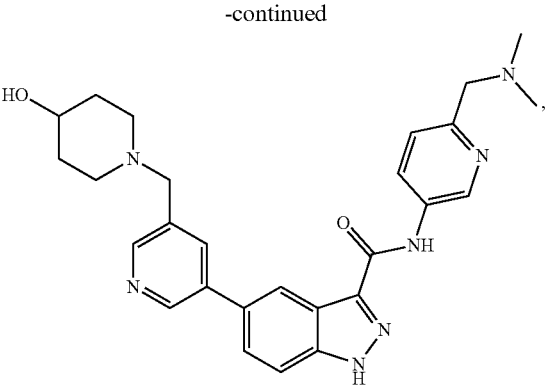
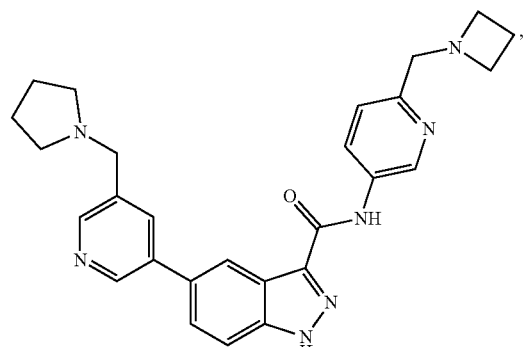
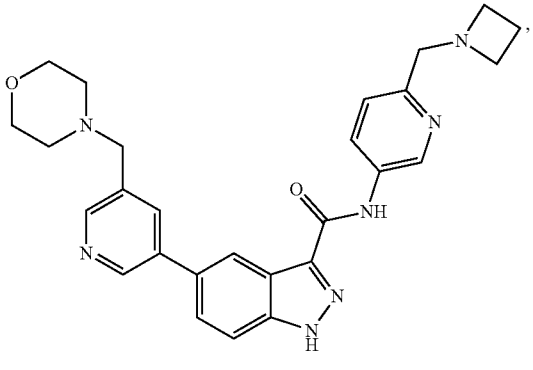
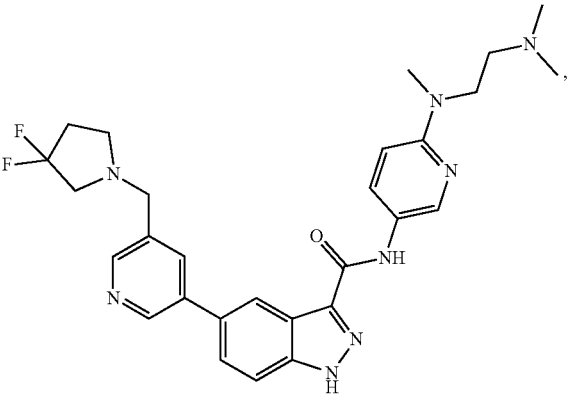

387
-continued
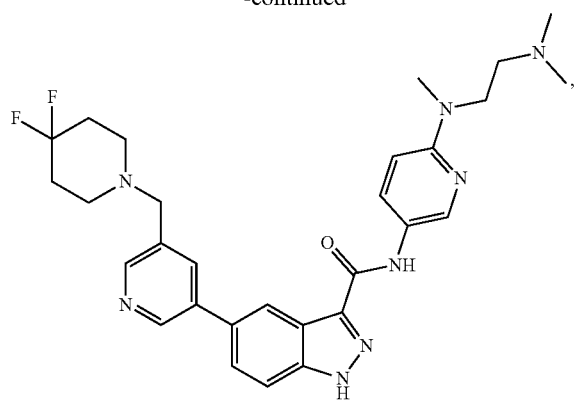
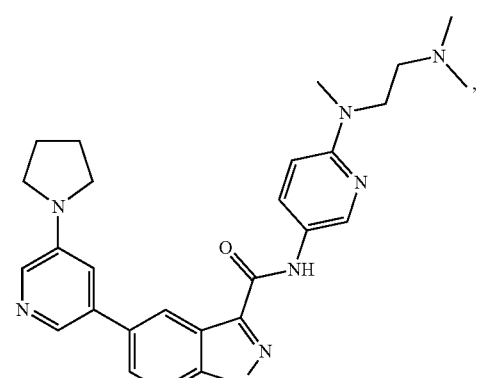
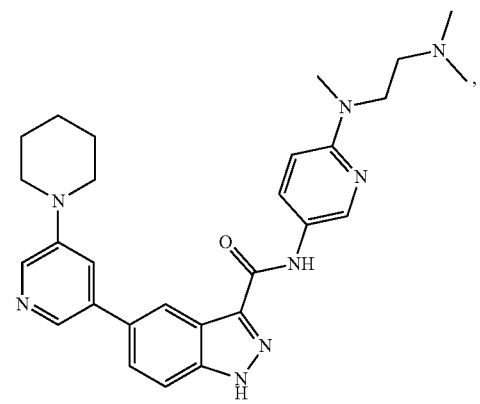
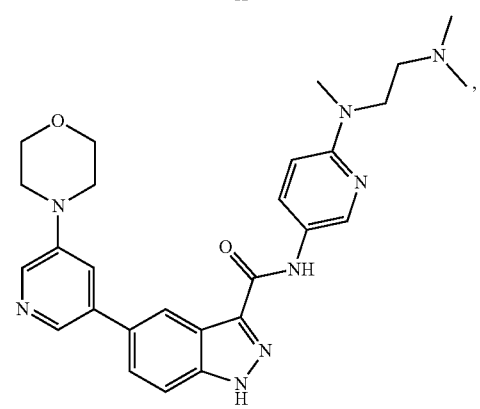
388
-continued
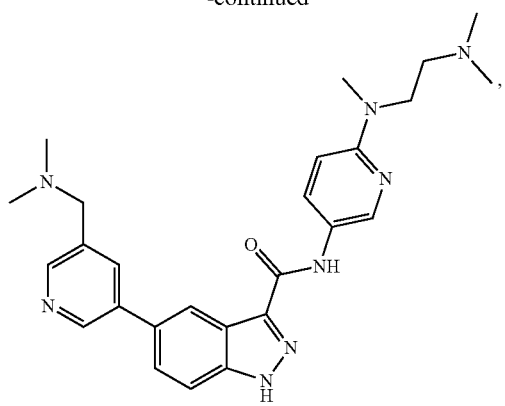
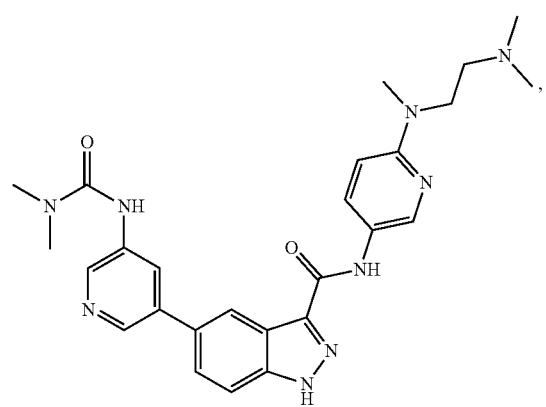
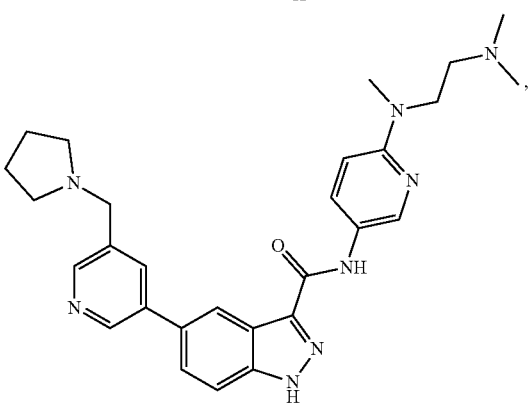

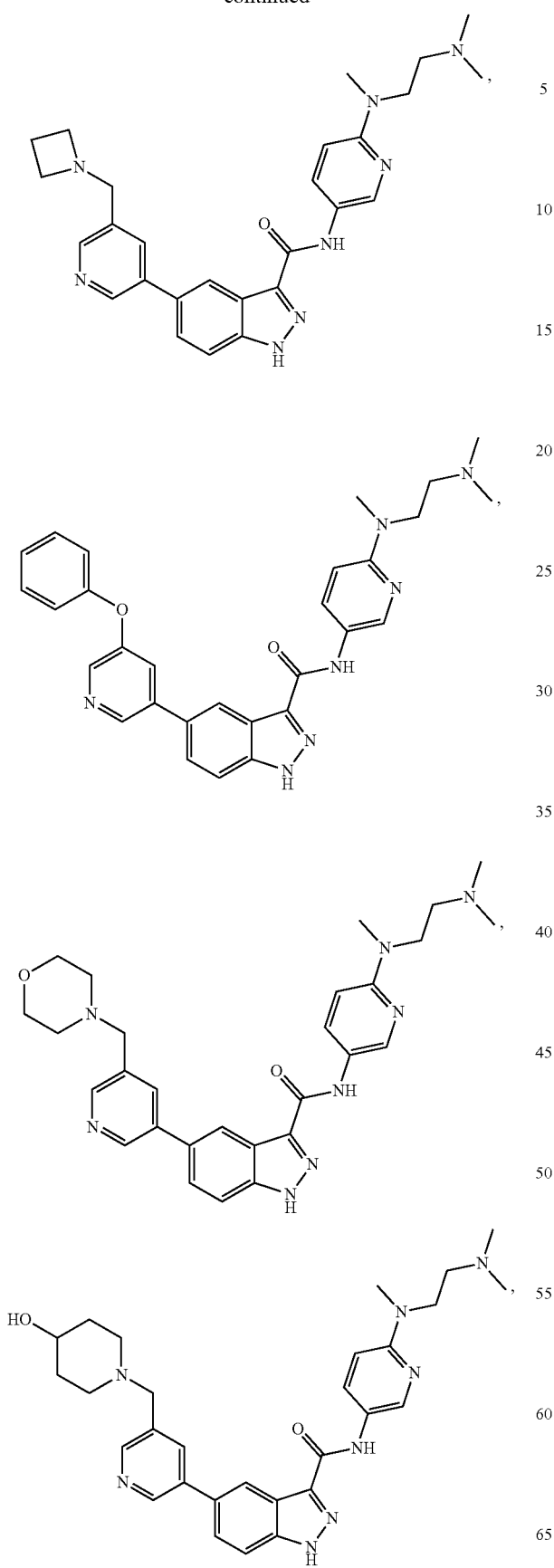
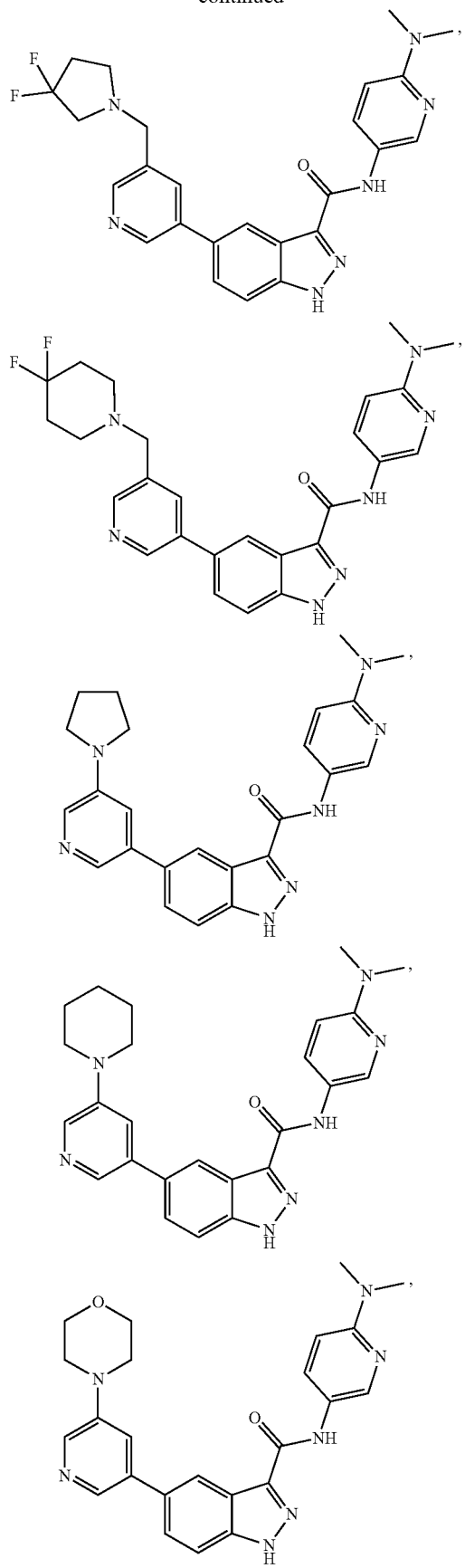

391
-continued
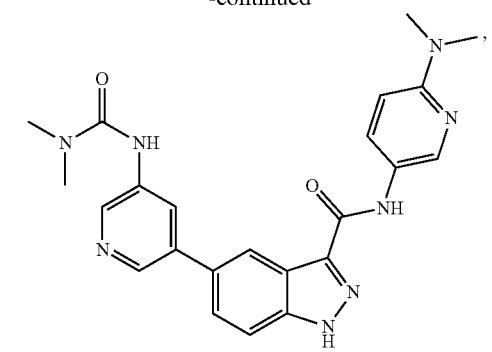
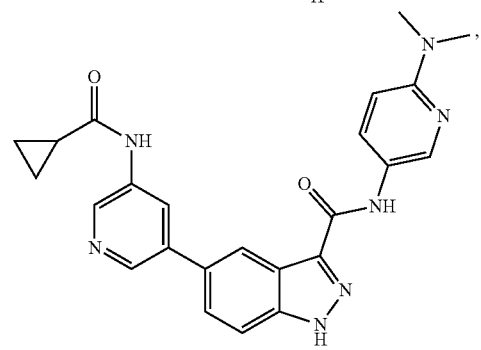
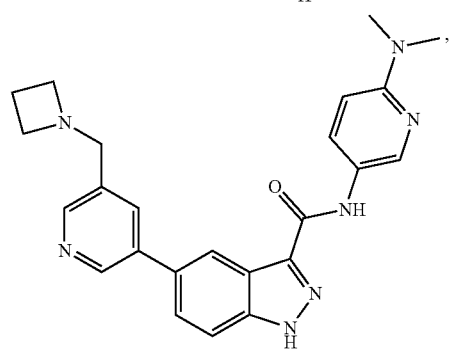
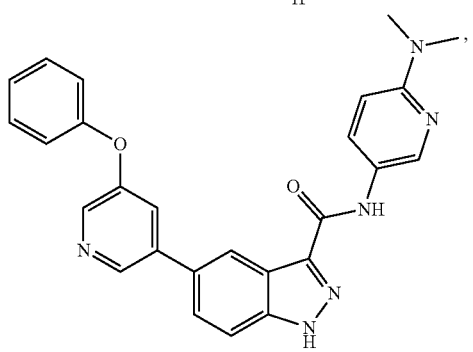
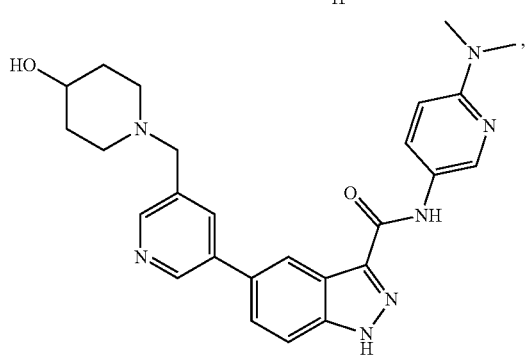
392
-continued
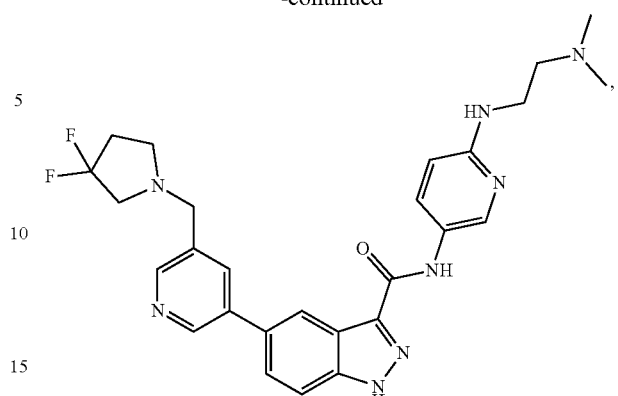
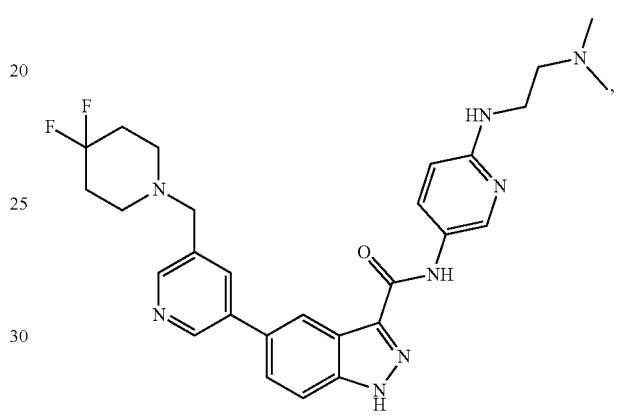
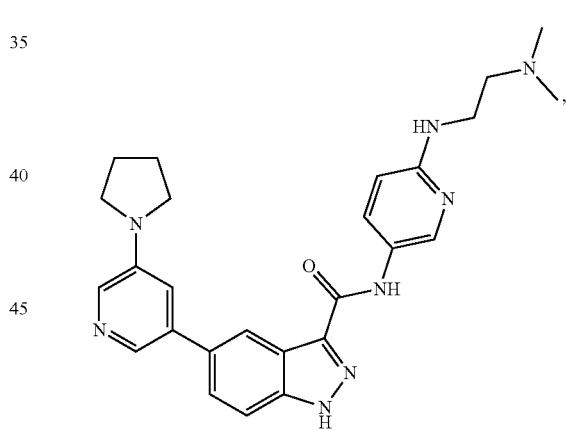
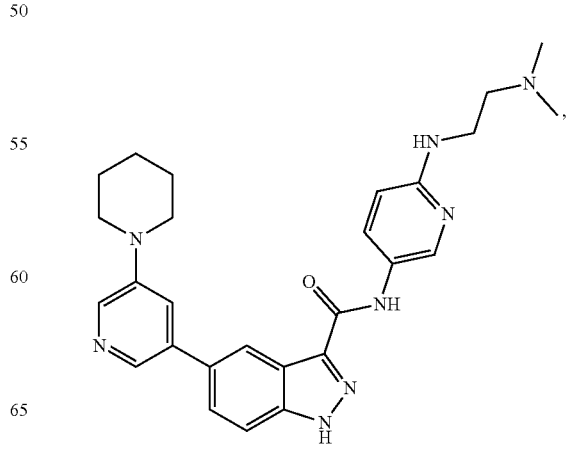

393
-continued
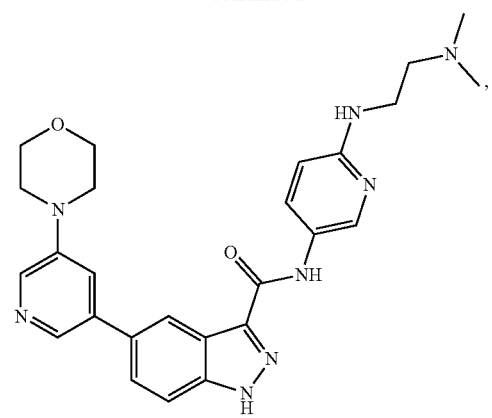
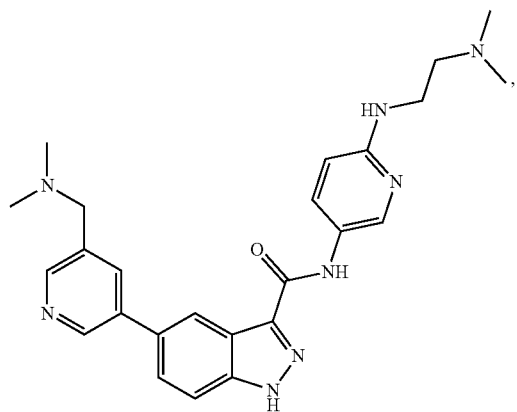
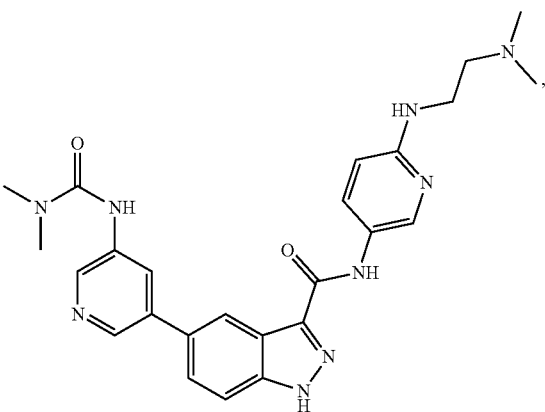
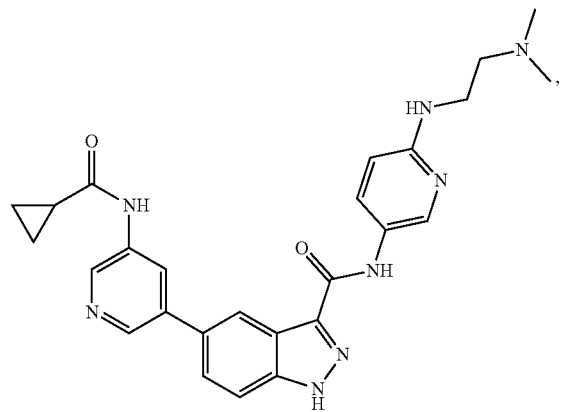
394
-continued
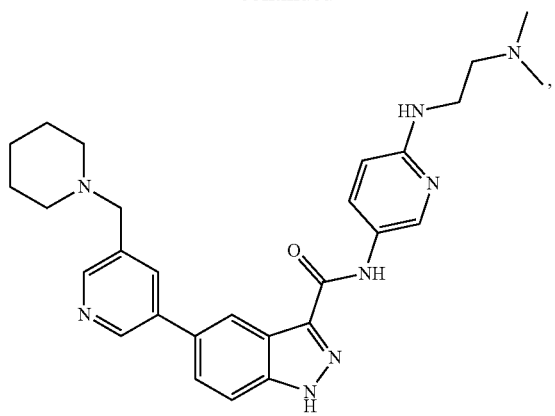
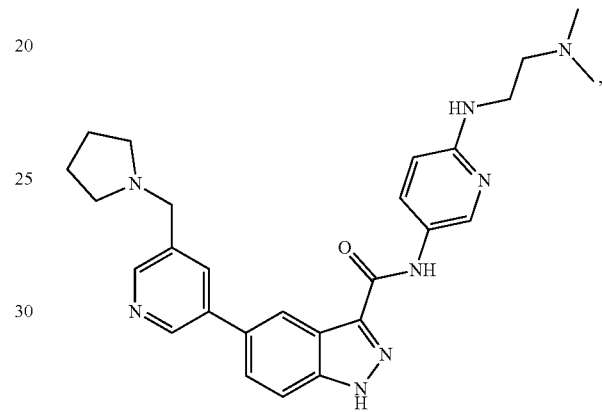
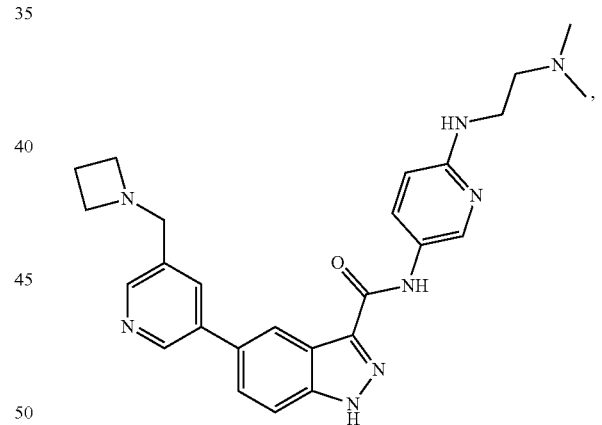
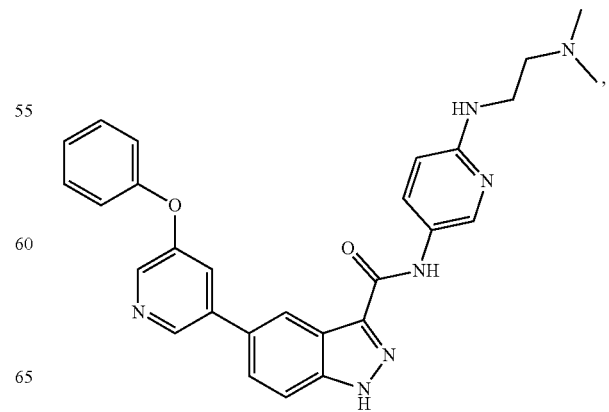

395
-continued
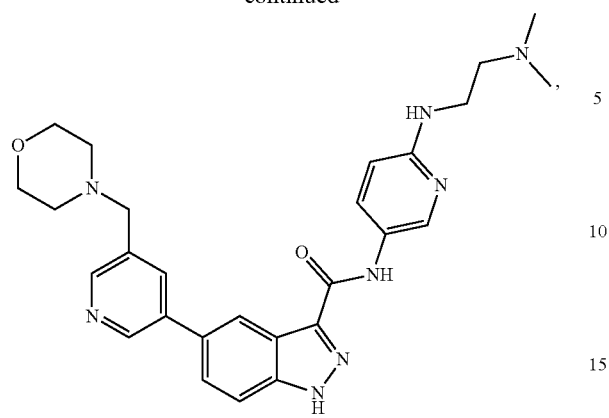
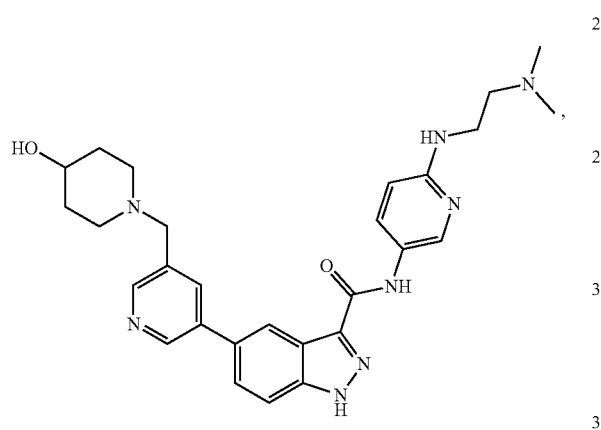
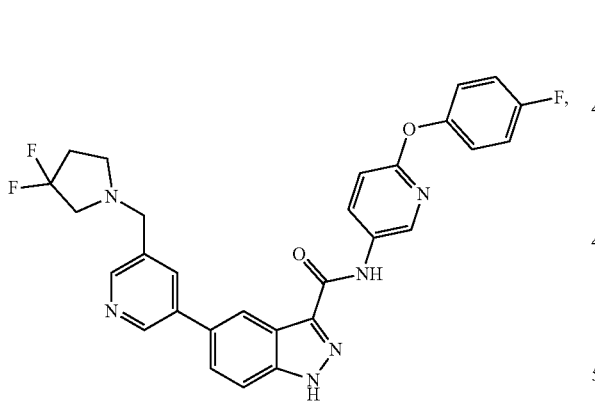
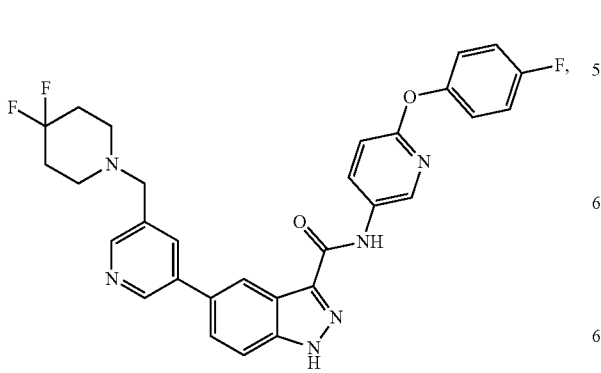
396
-continued
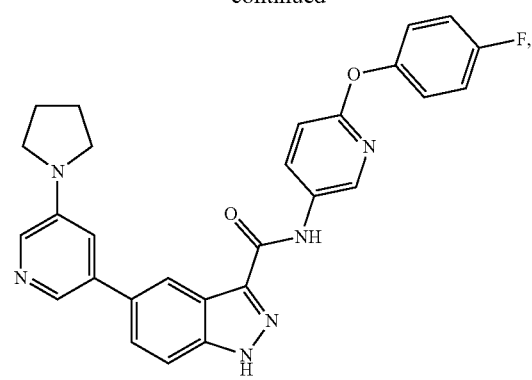
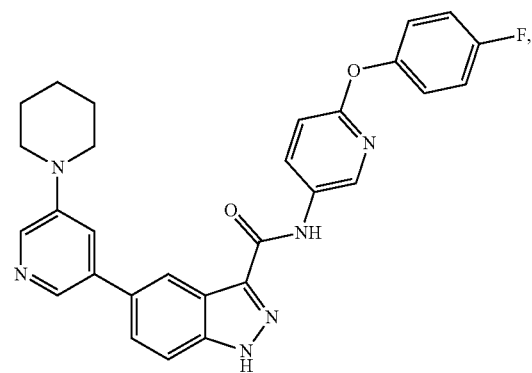
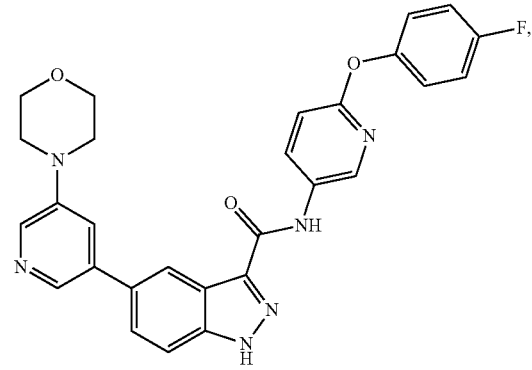
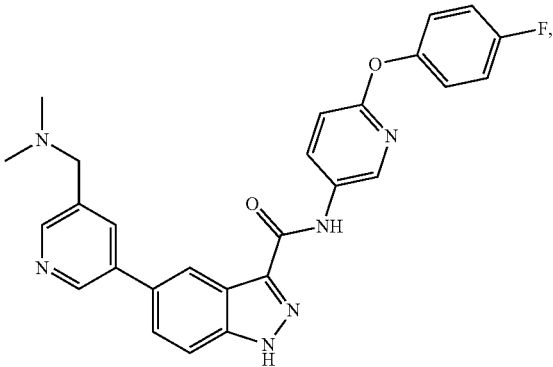

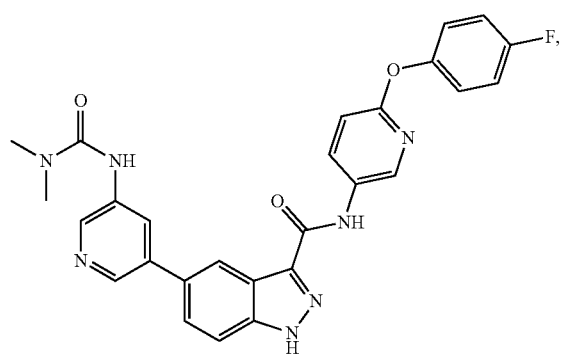
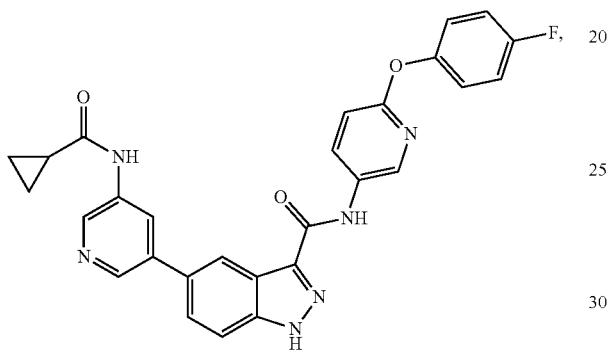
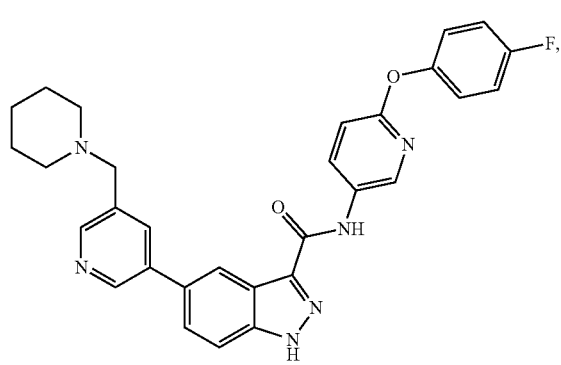
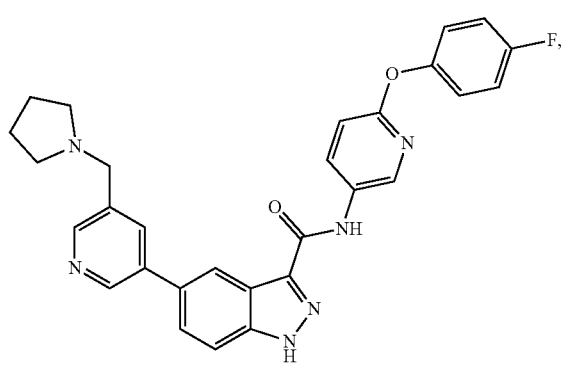
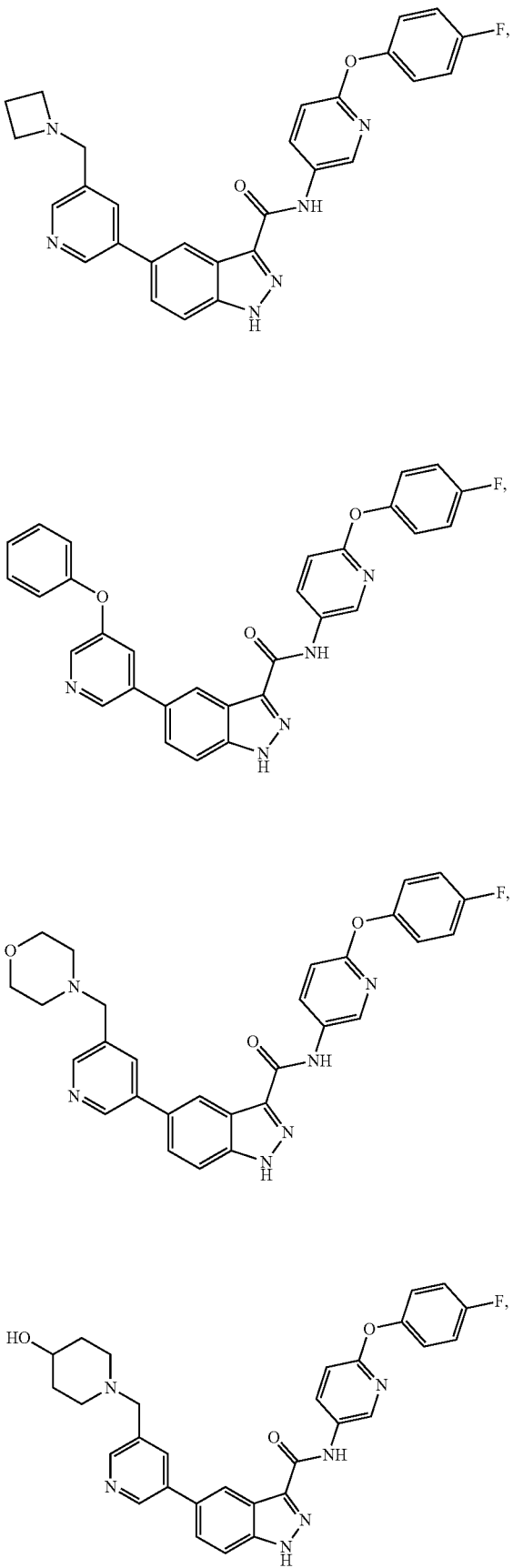

399
-continued
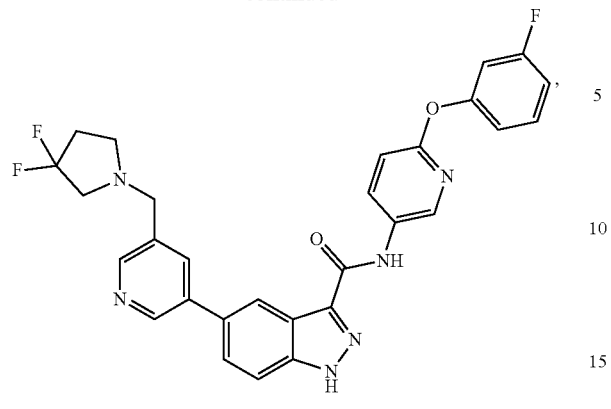
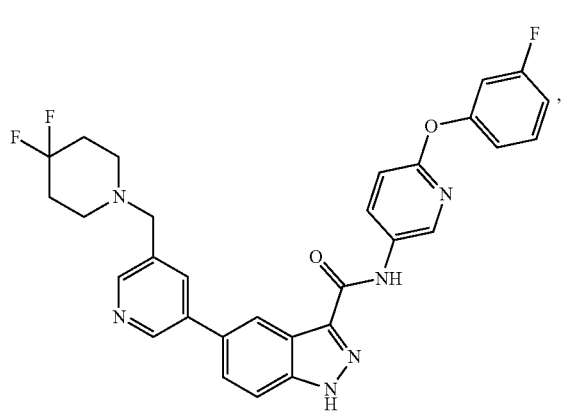
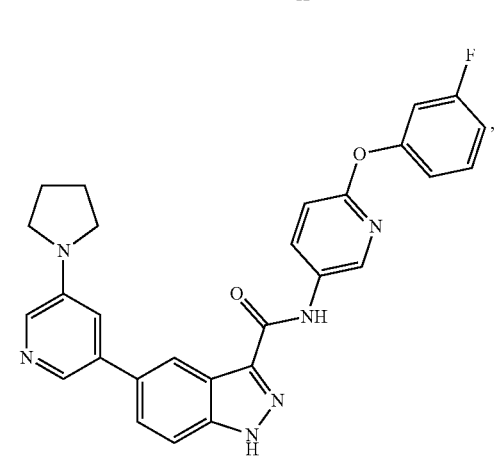
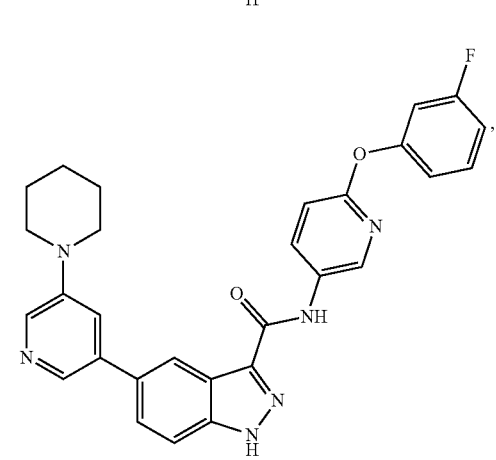
400
-continued
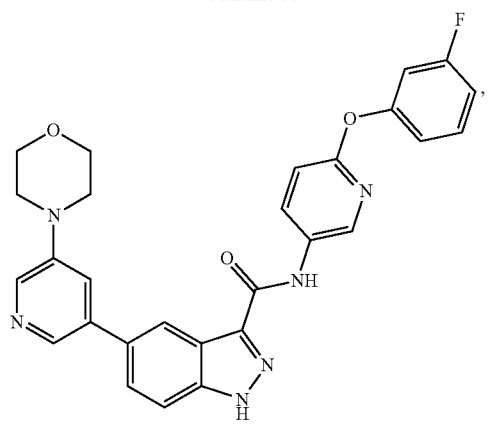
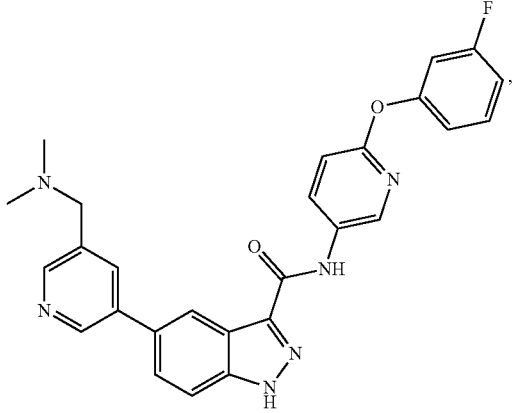
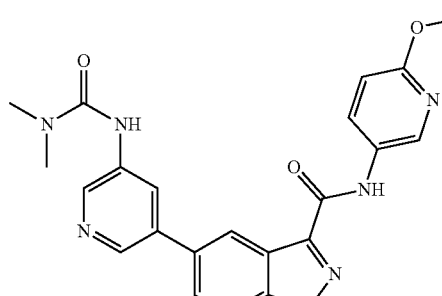
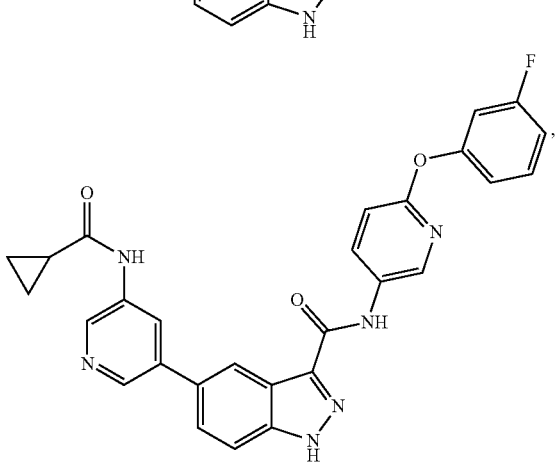

401
-continued
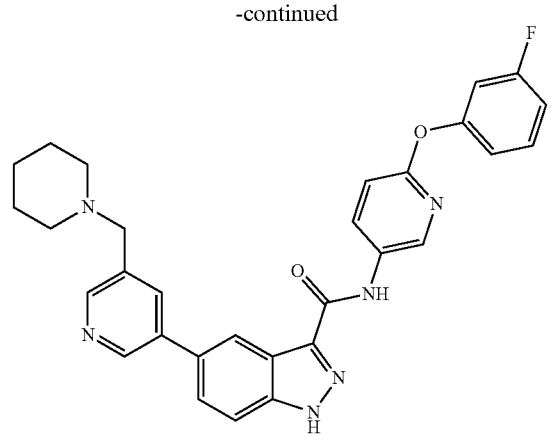
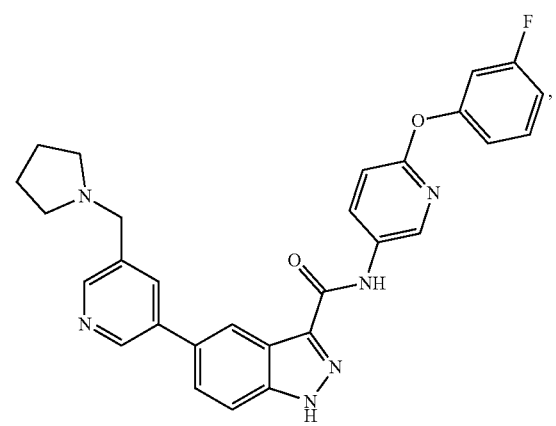
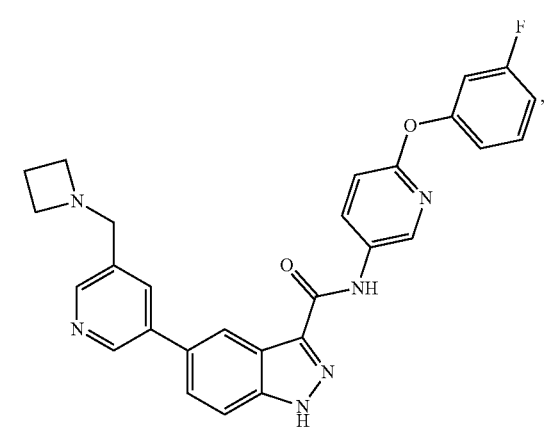
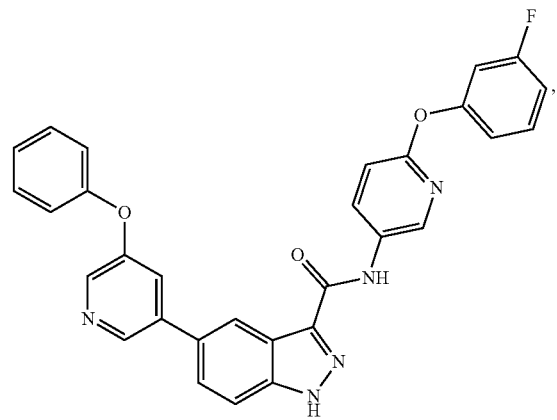
402
-continued
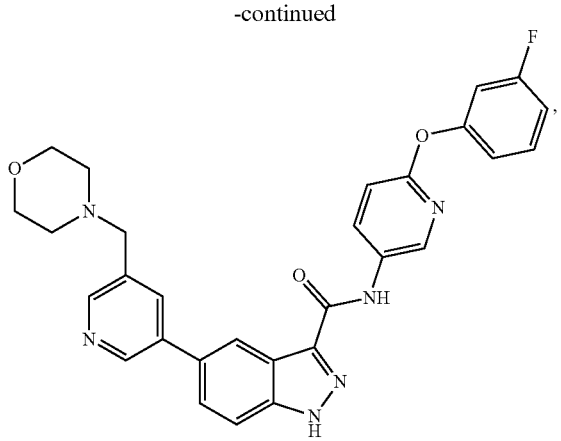

403
-continued
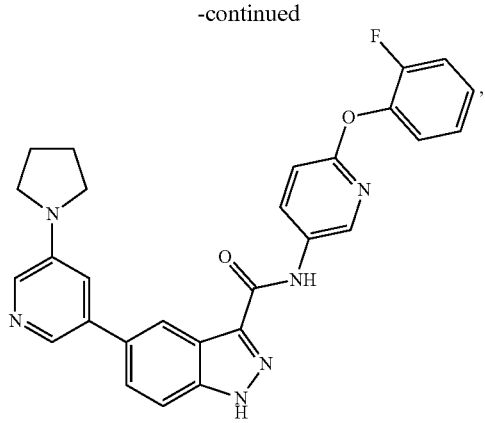
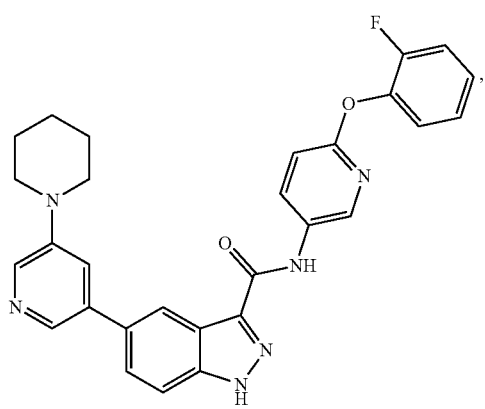
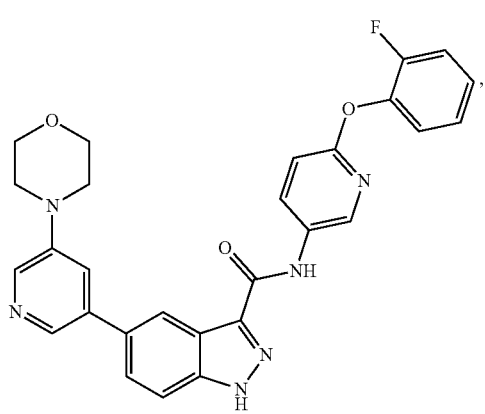
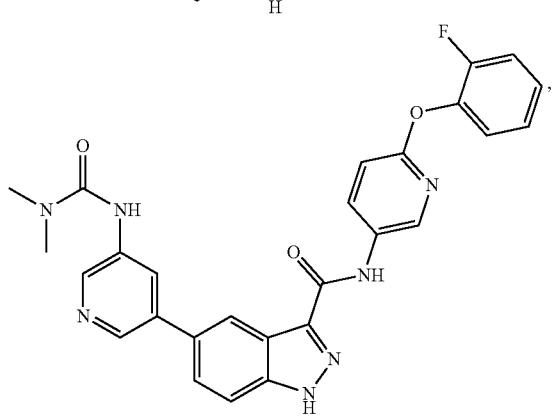
404
-continued
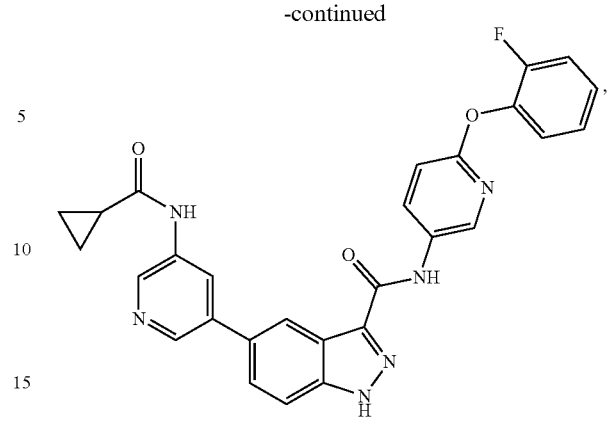
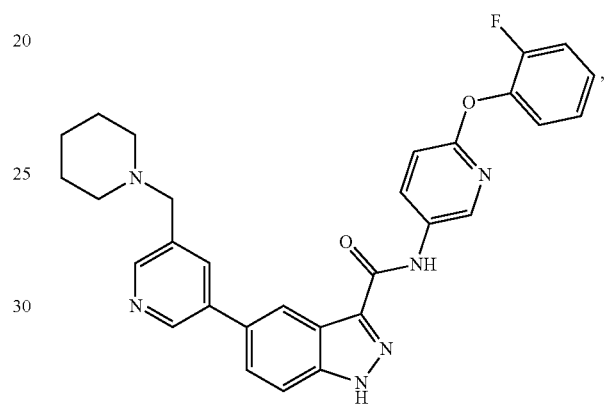
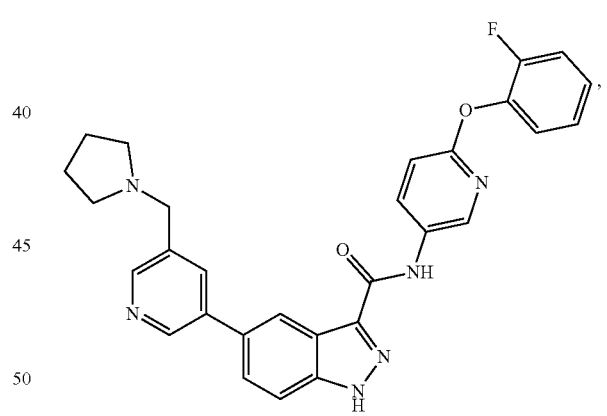
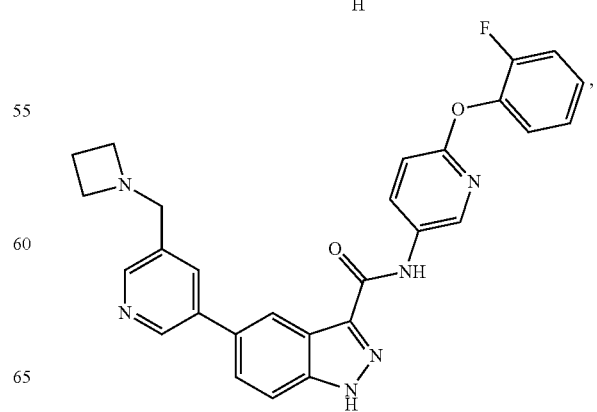

405
-continued
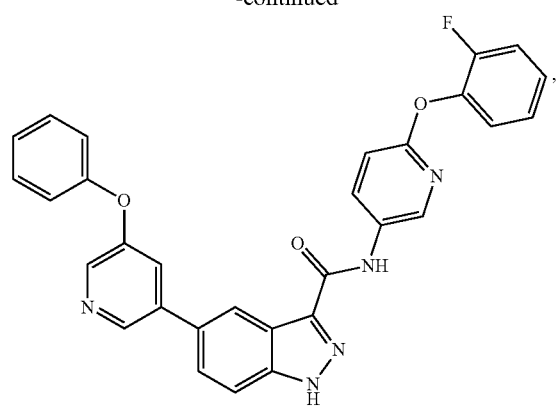
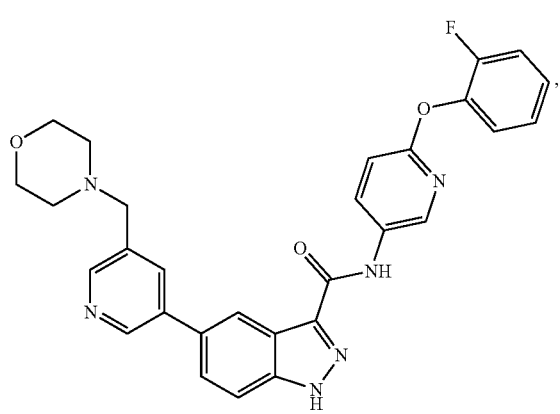
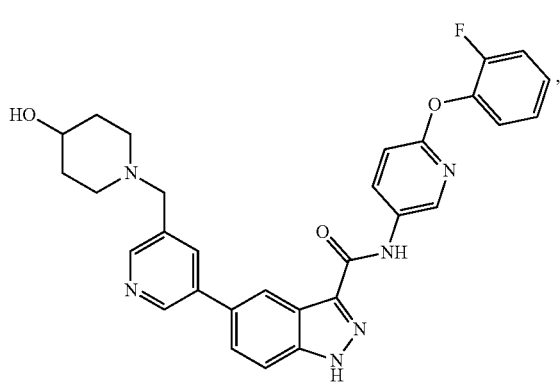
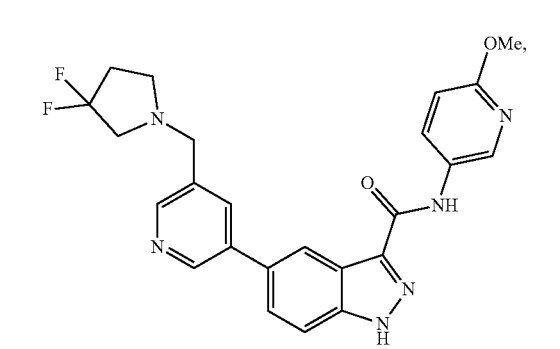
406
-continued
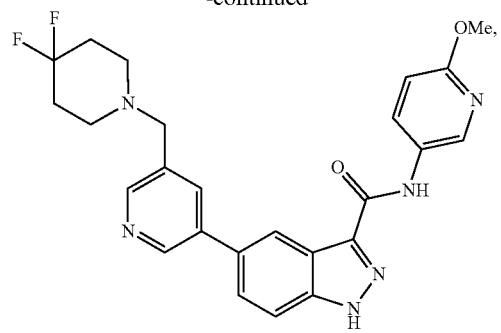
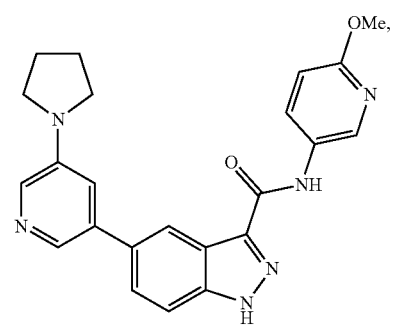
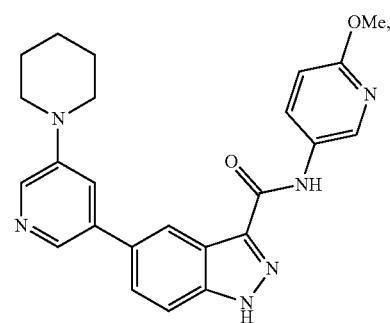
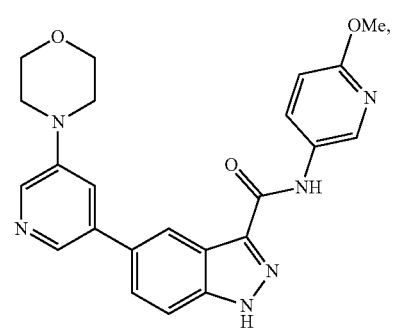
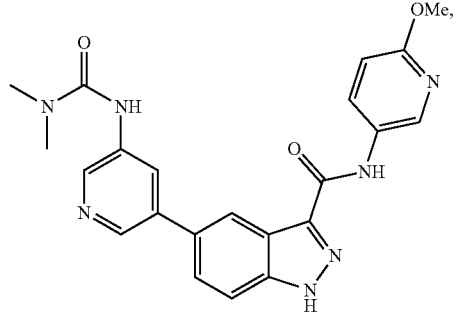

407
-continued
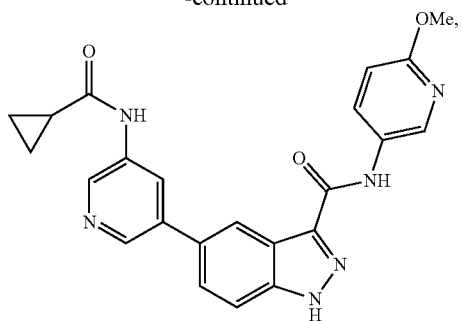
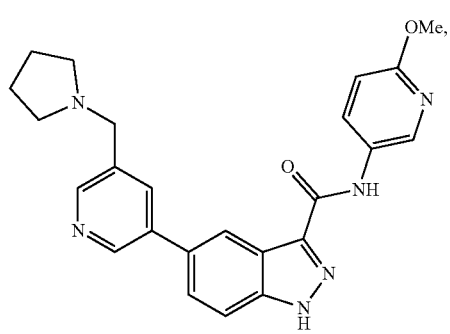
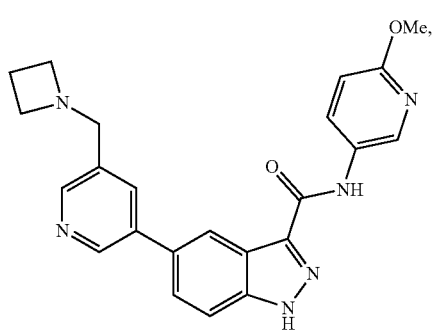
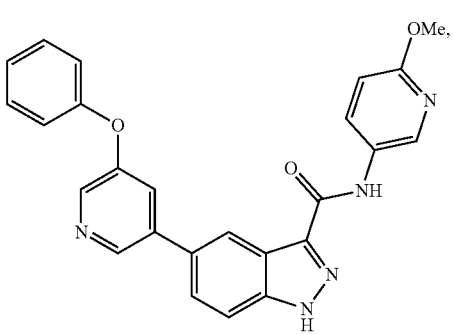
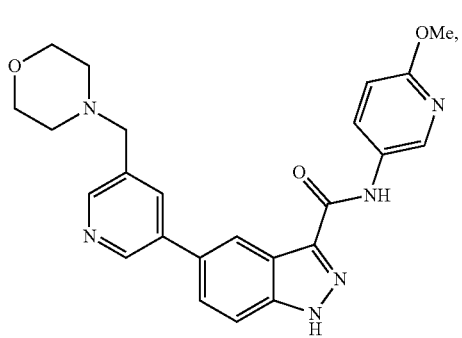
408
-continued
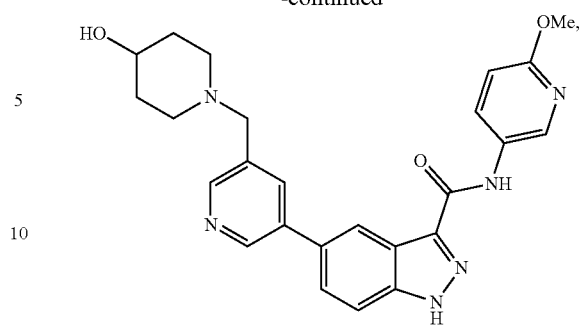
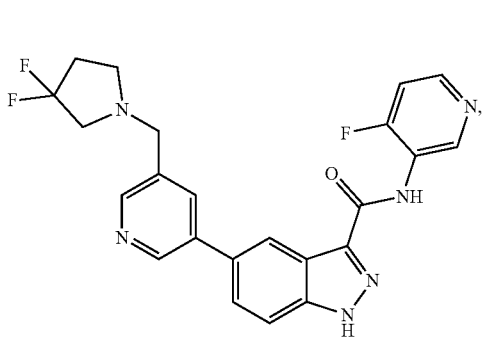
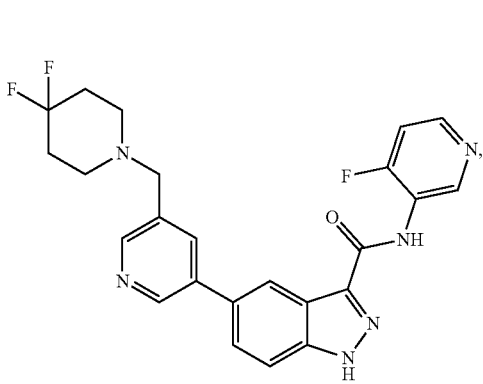
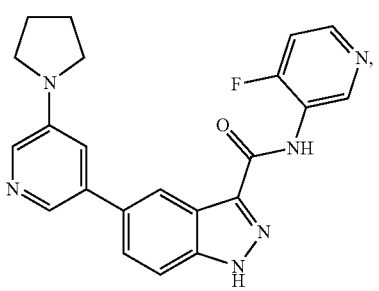
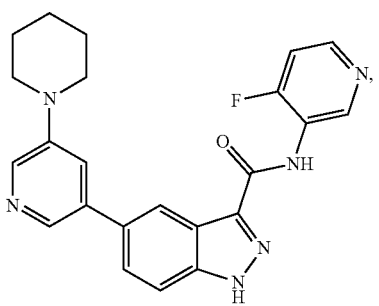

409
-continued
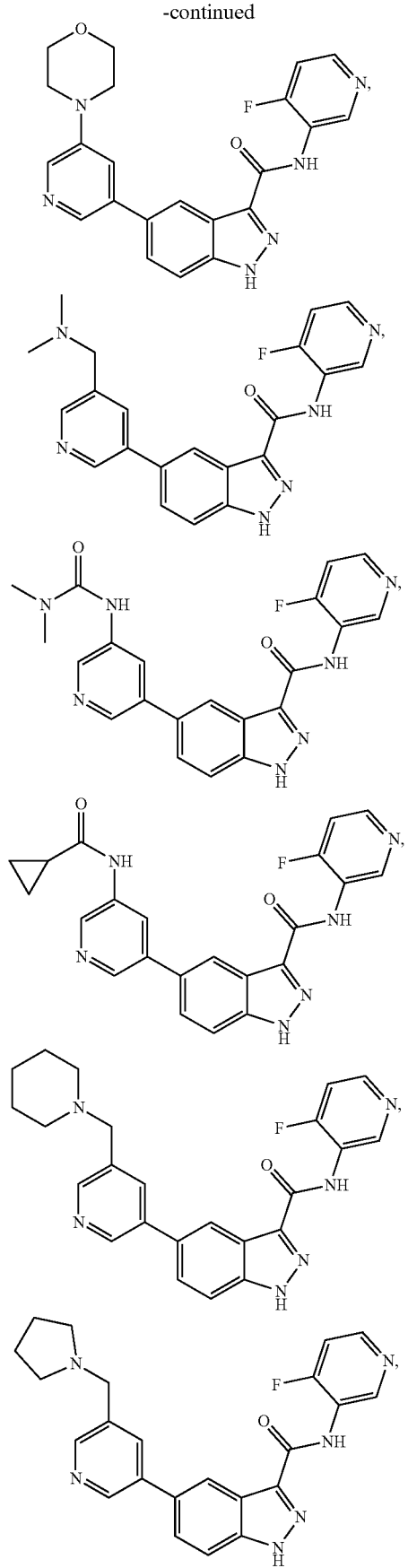
410
-continued
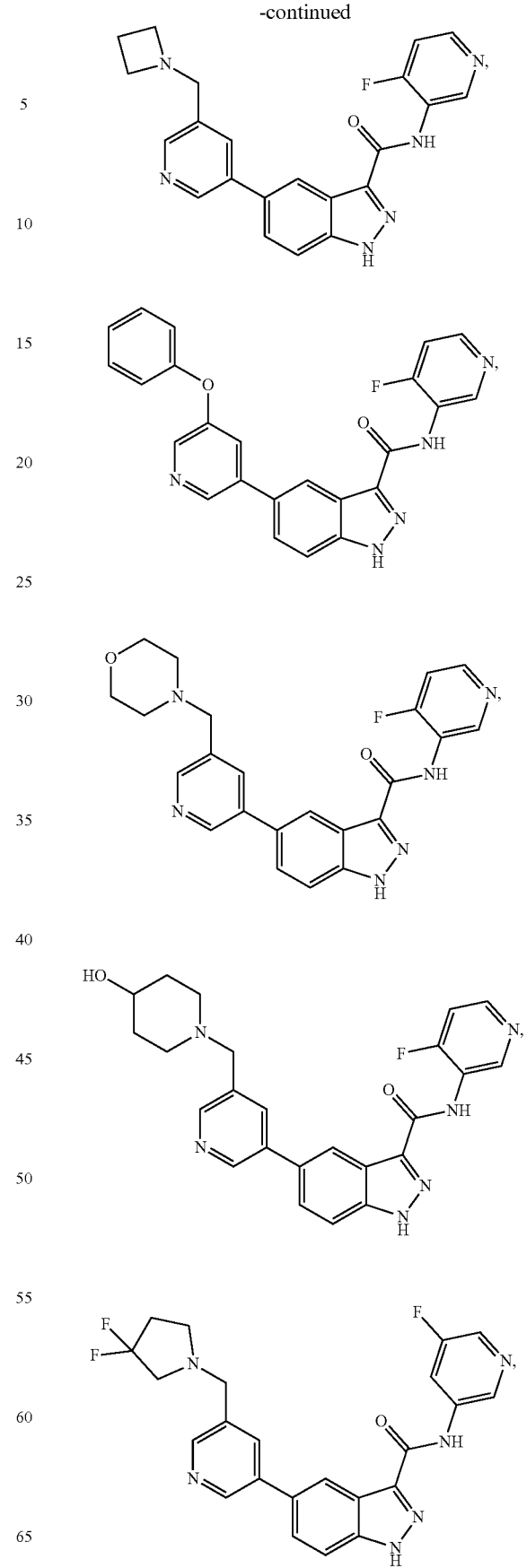

411
-continued
412
-continued
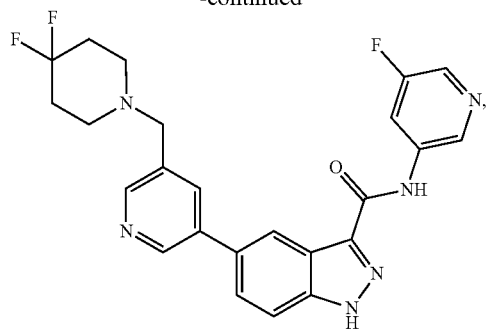
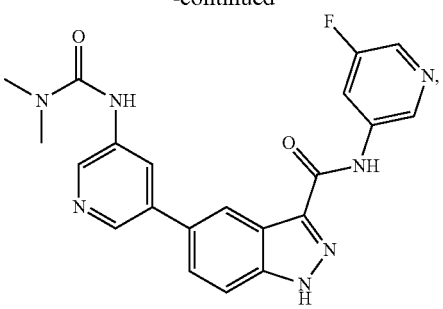
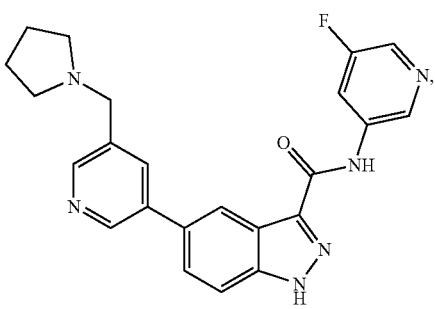
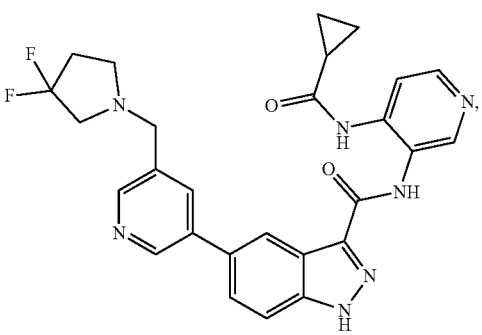

413
-continued
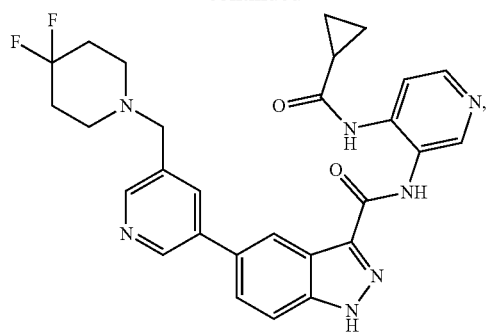
414
-continued
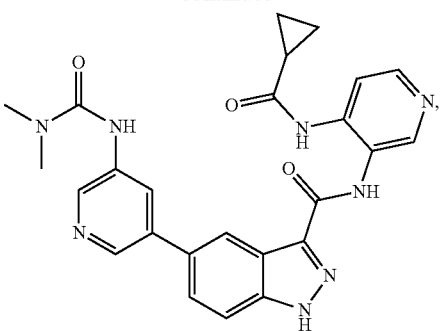
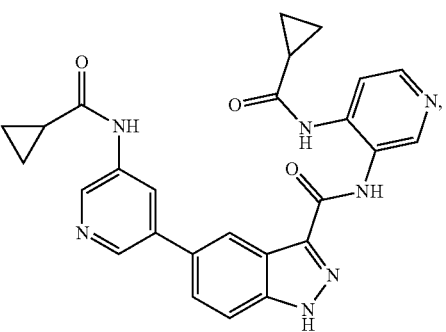
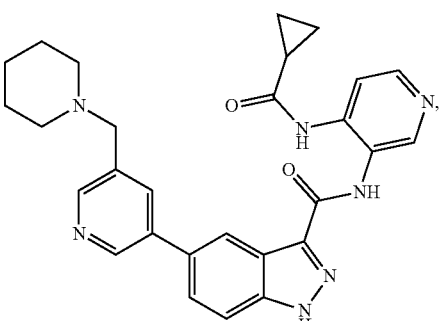
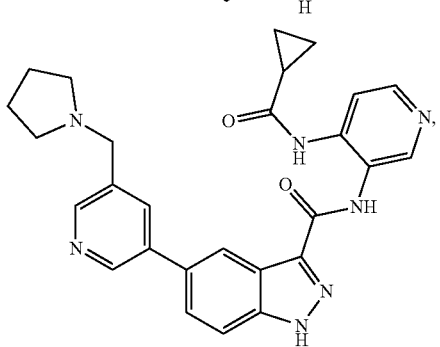
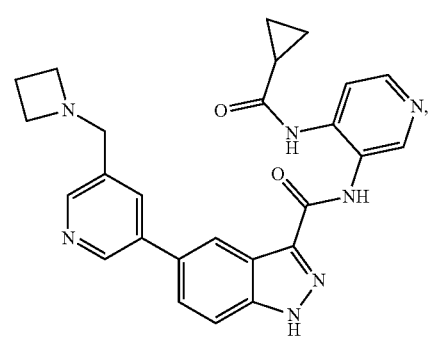

415
-continued
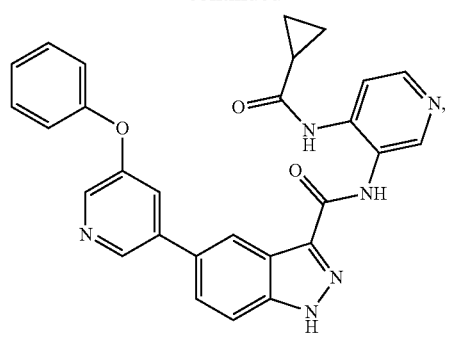
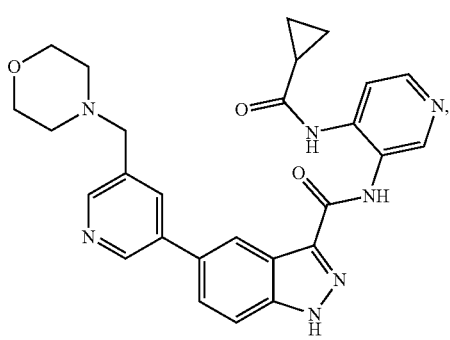
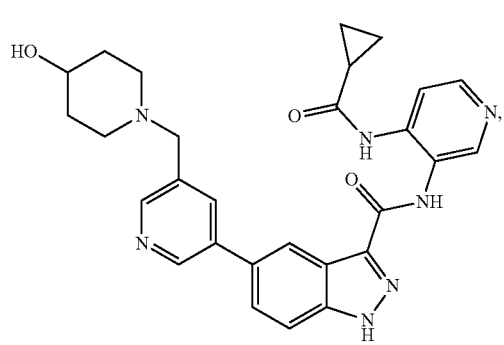
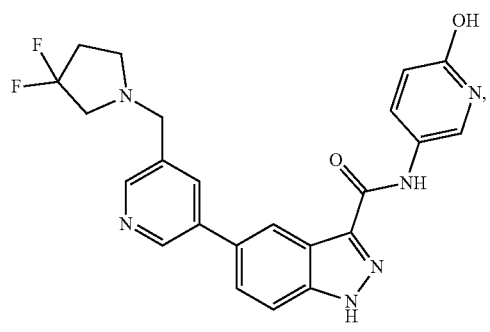
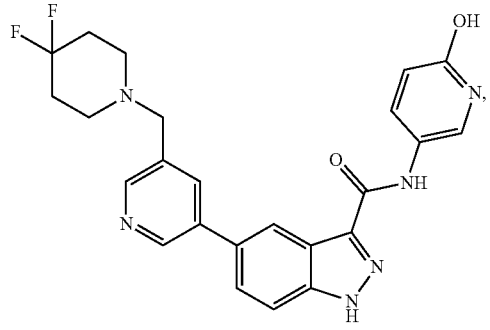
416
-continued
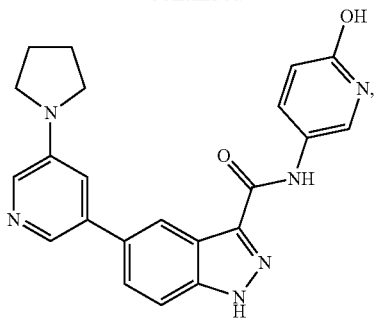
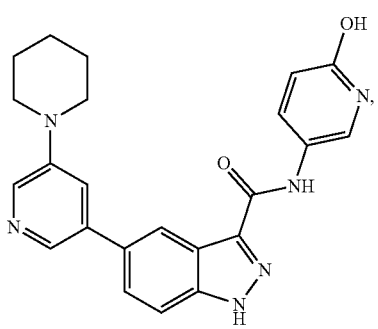
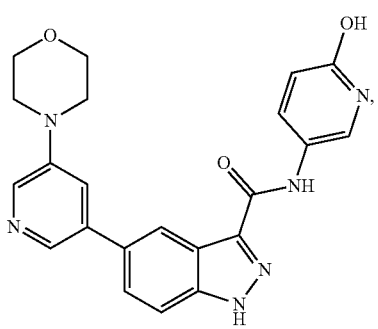
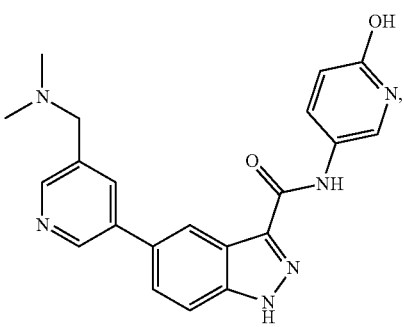
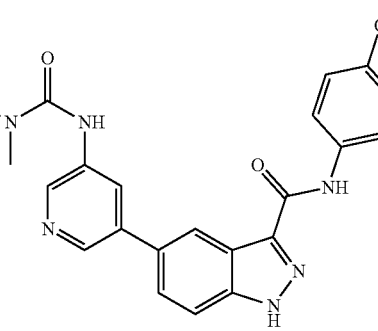

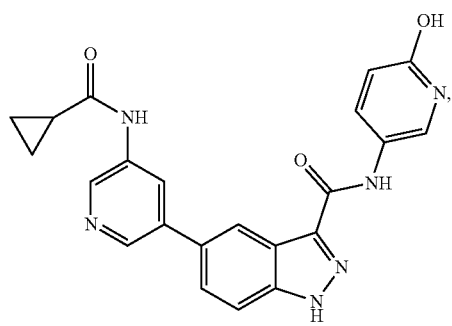
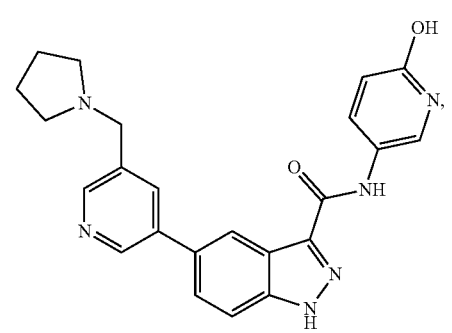
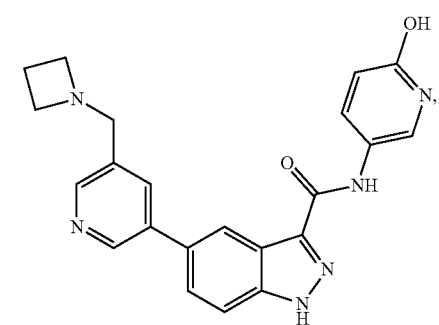
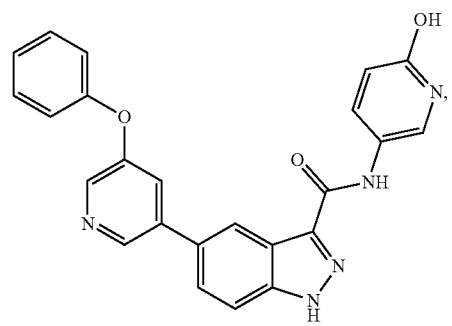
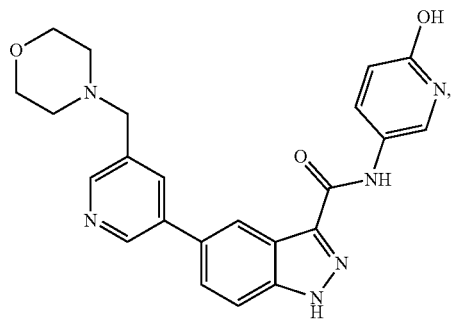
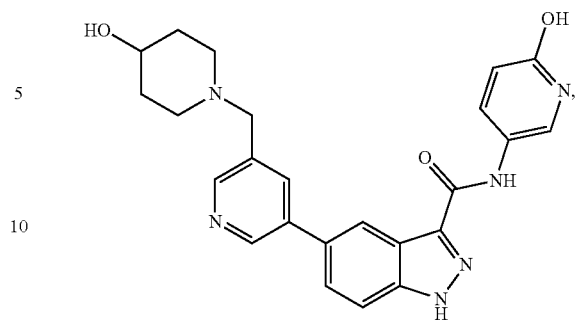
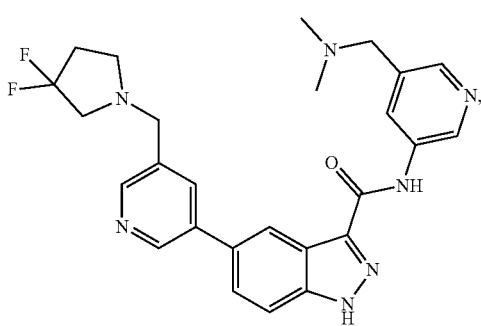
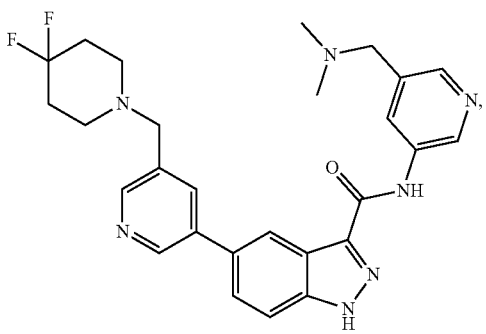
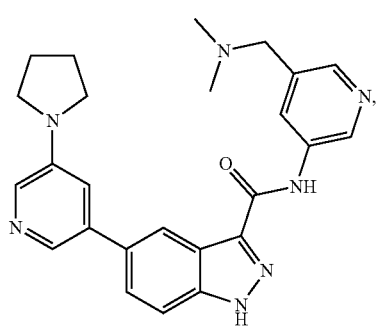
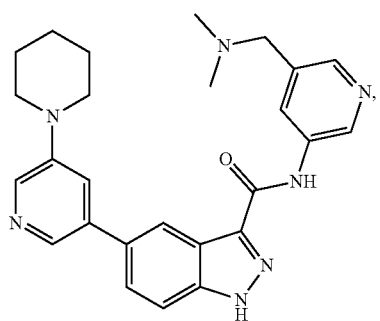

419
-continued
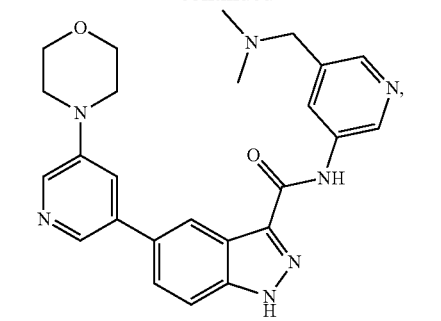
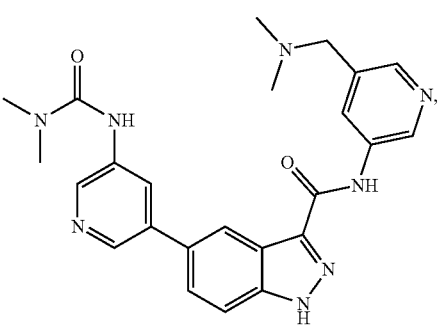
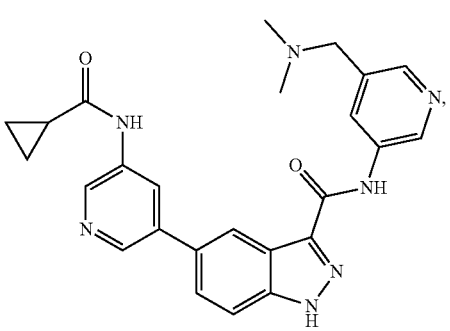
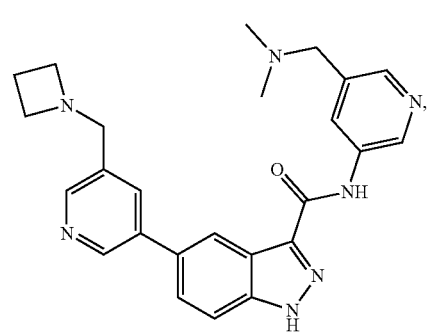
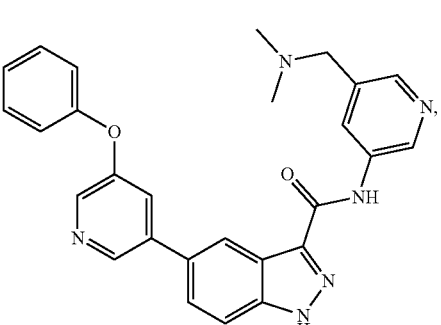
420
-continued
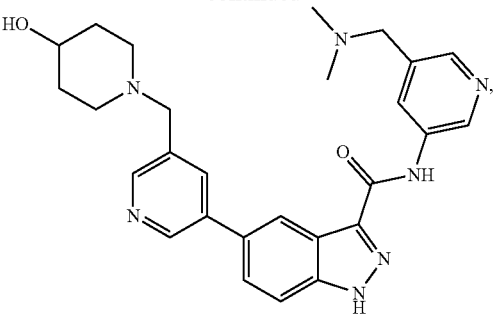
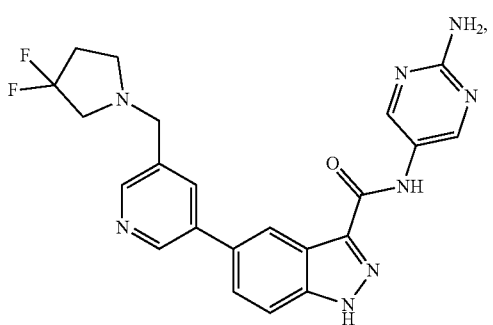
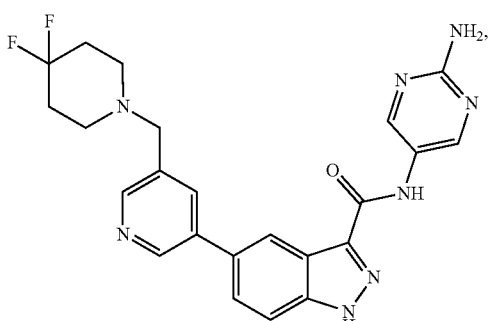
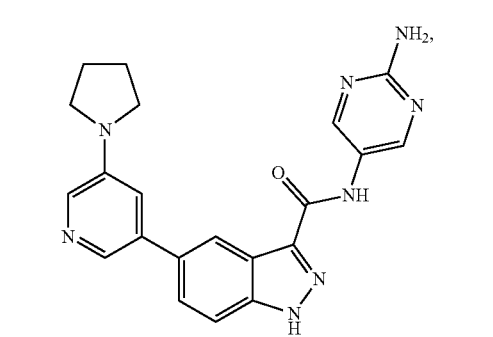
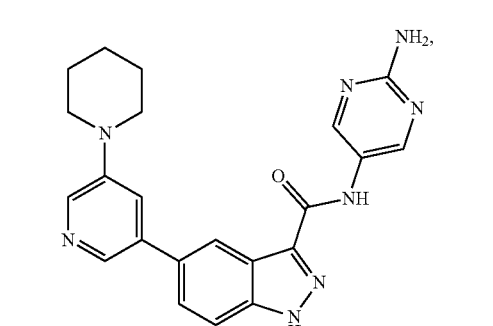

421
-continued
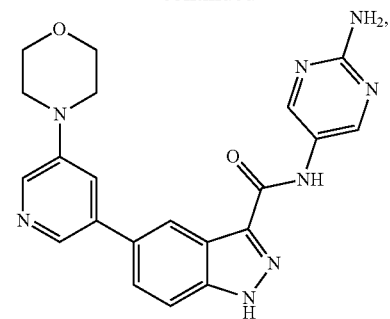
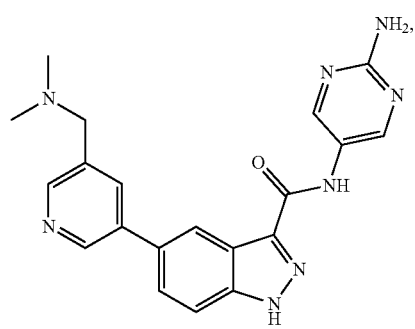
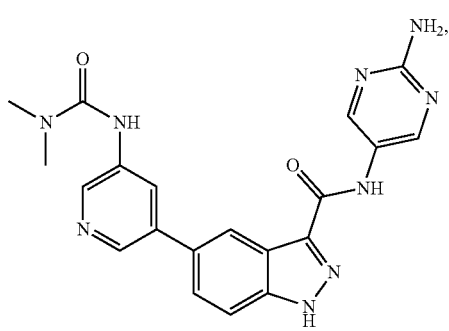
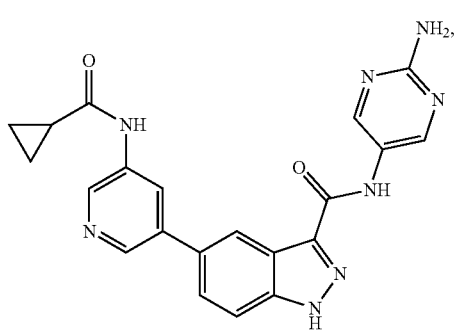
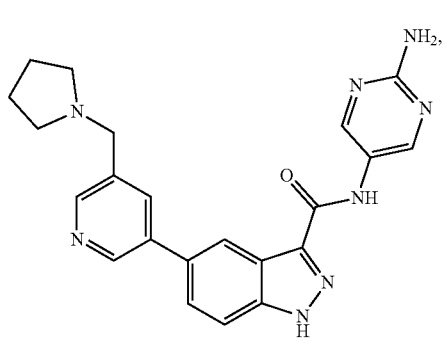
422
-continued
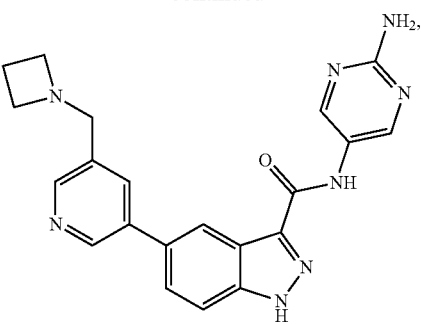
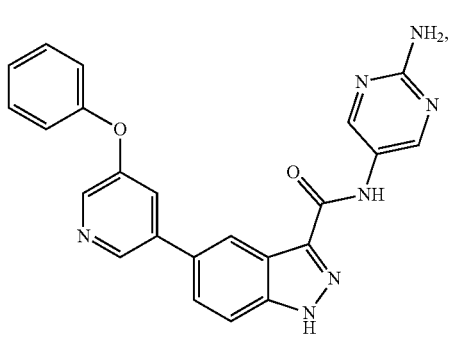
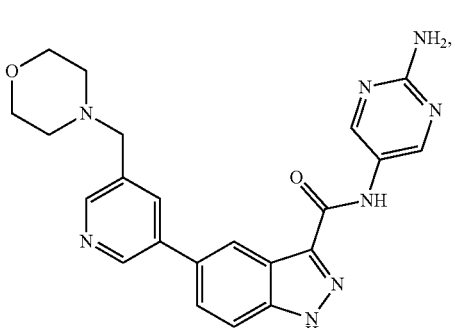
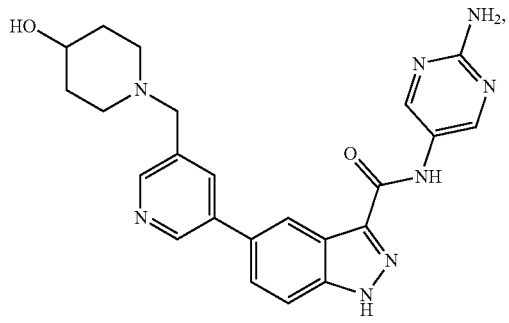
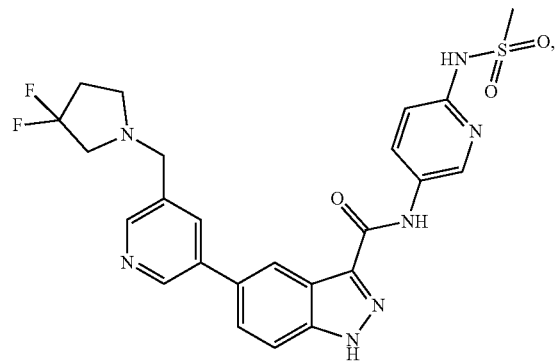

423
-continued
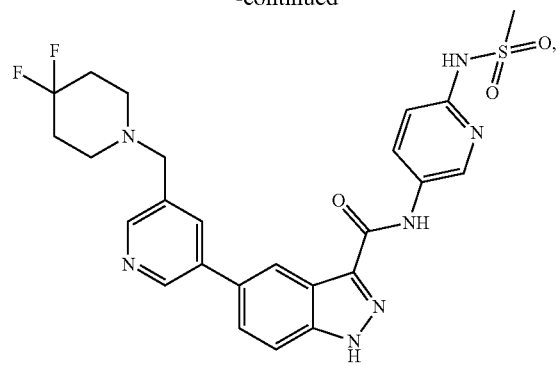
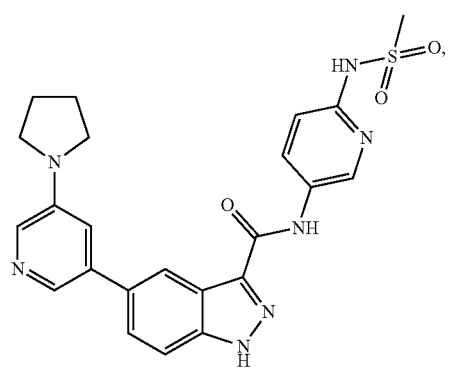
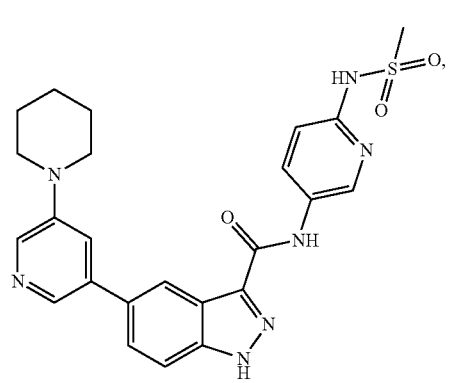
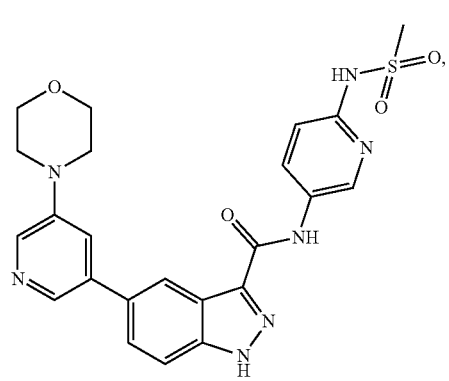
424
-continued
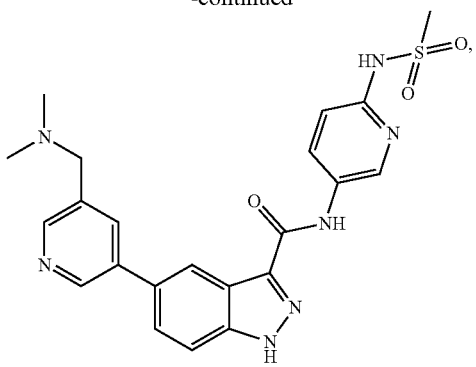
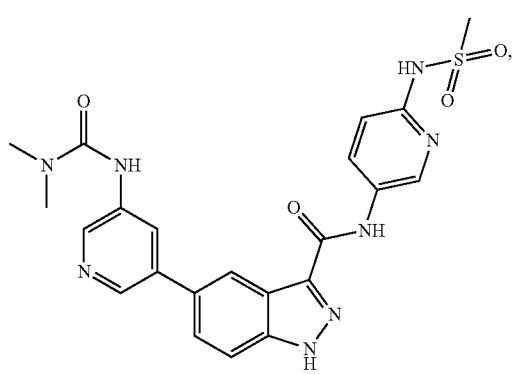
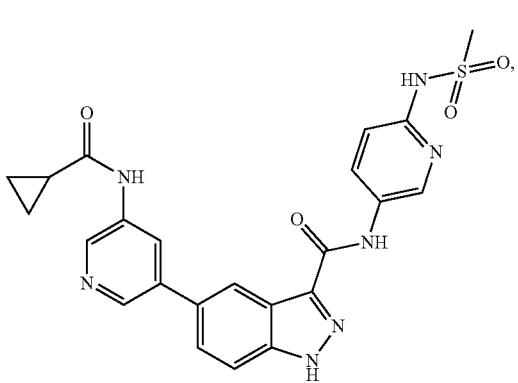
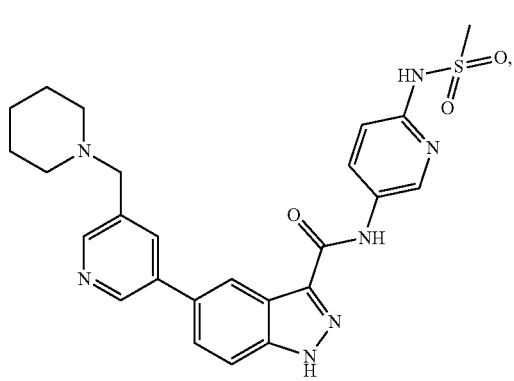

425
-continued
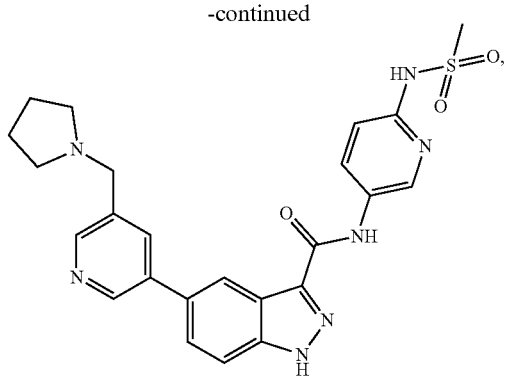
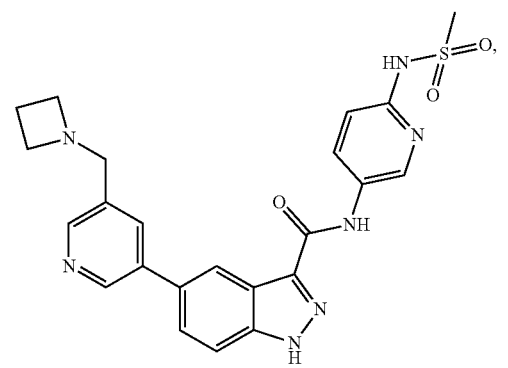
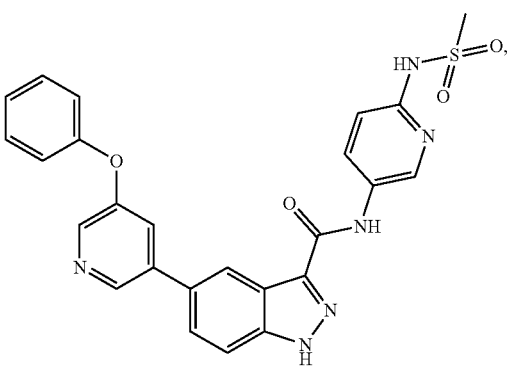
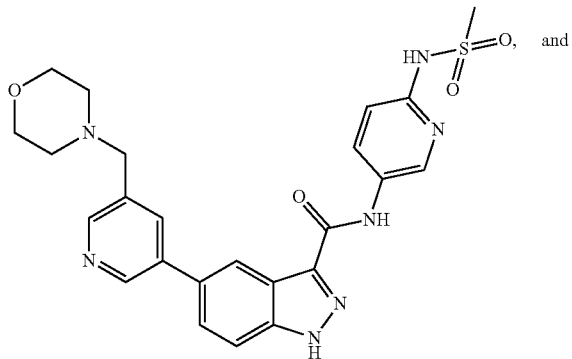
426
-continued
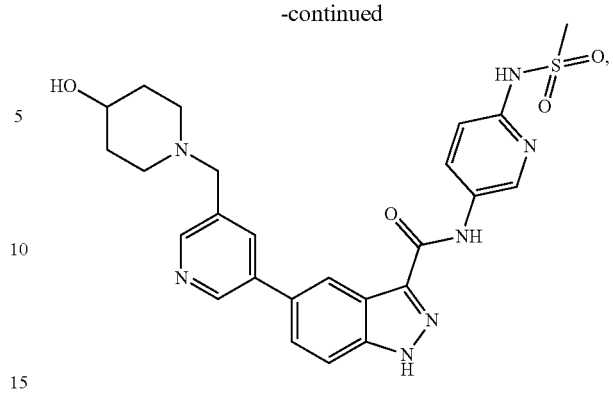
and or a pharmaceutically acceptable salt thereof.
18. The method of claim 17, the compound having a structure selected from the group consisting of:
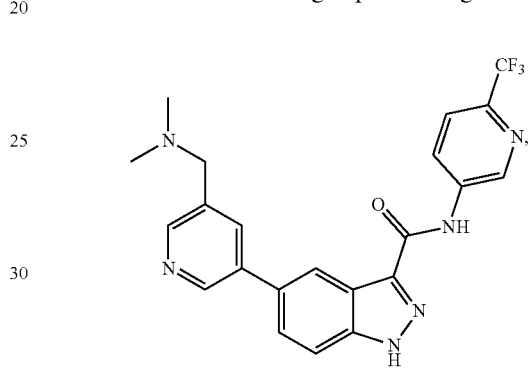
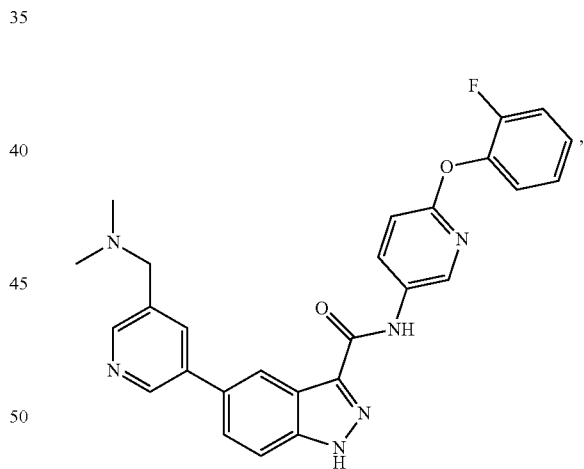
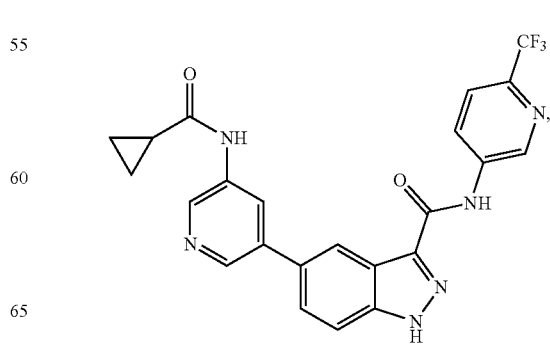

427
-continued
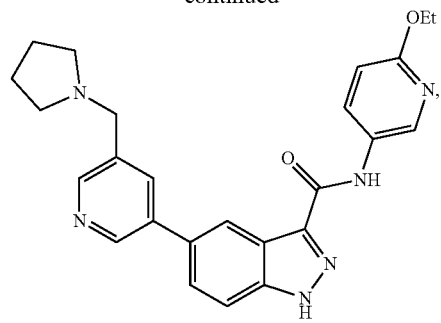
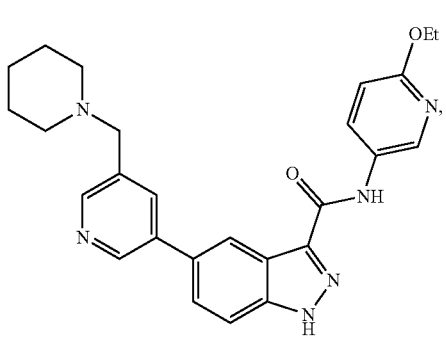
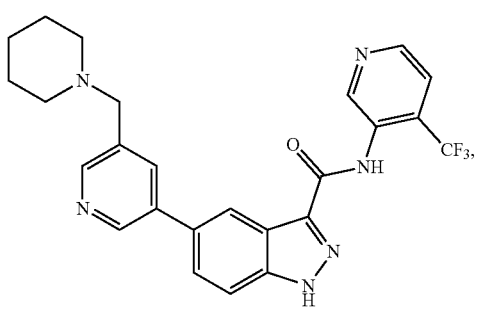
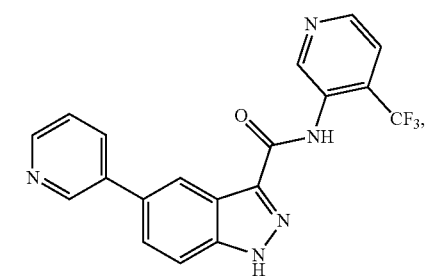
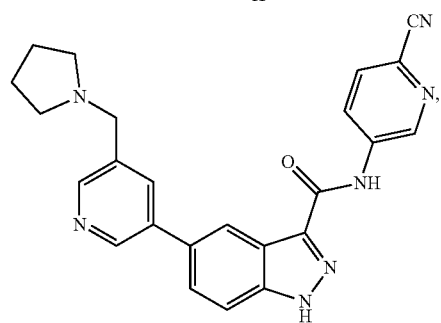
428
-continued
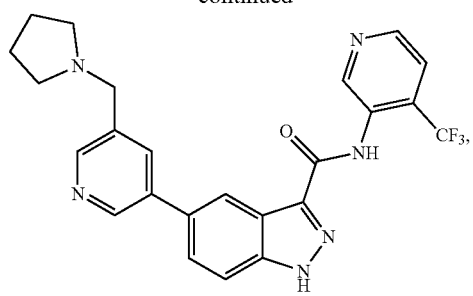
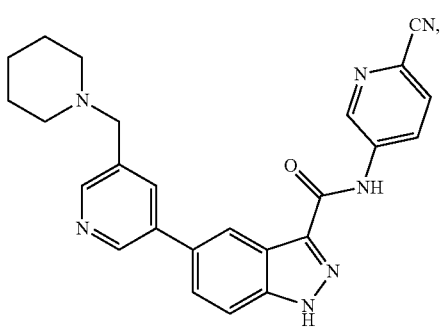
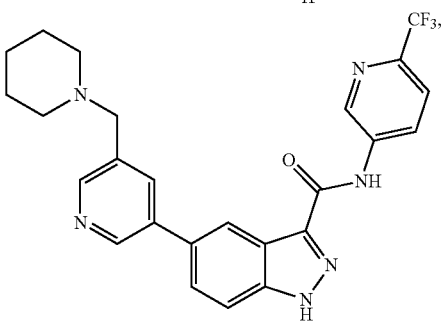
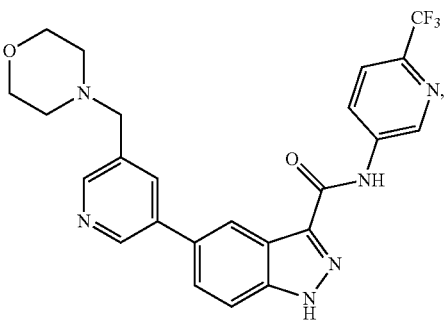
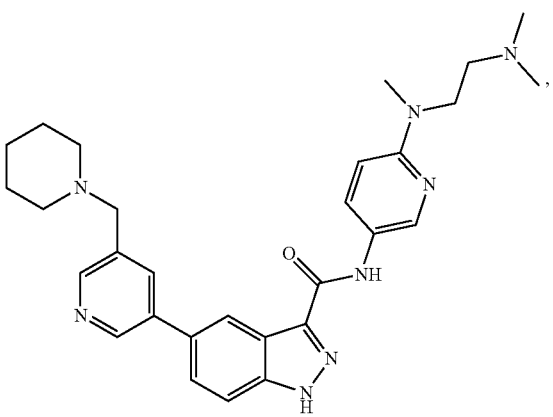

429
-continued
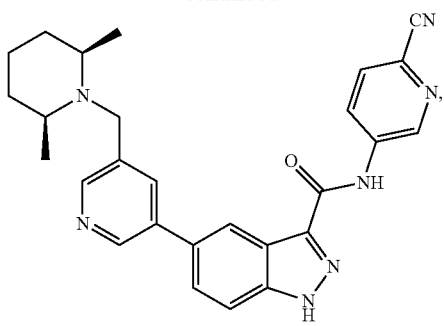
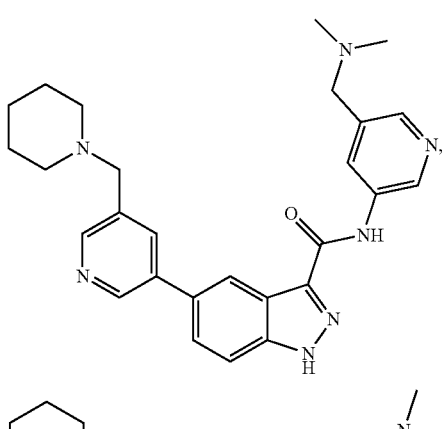
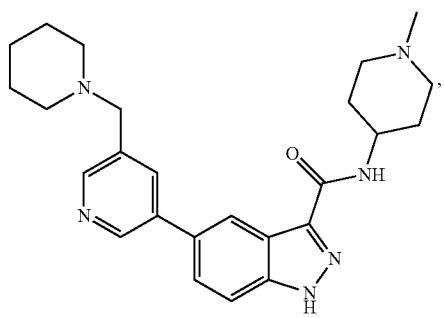
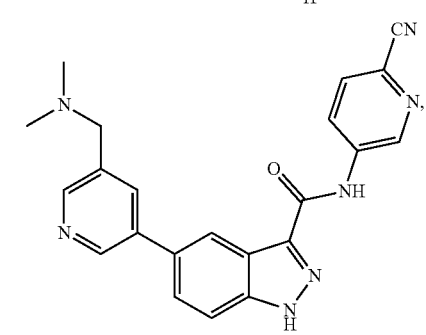
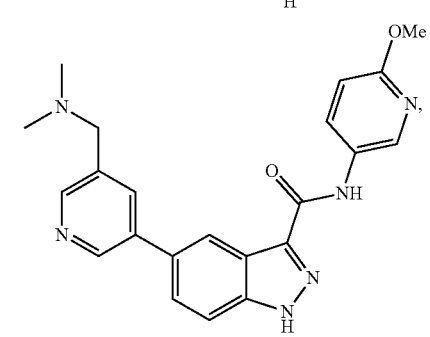
430
-continued
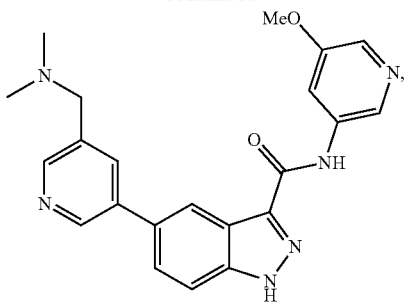
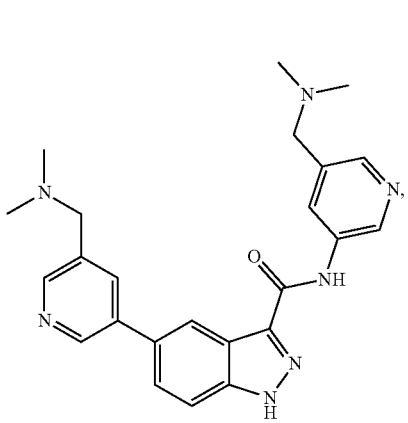
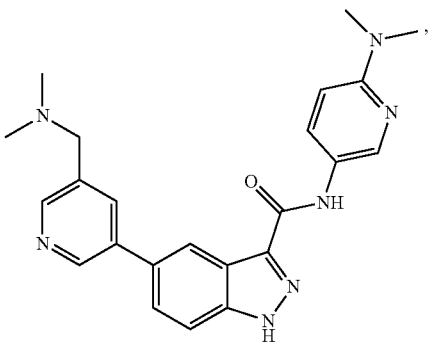
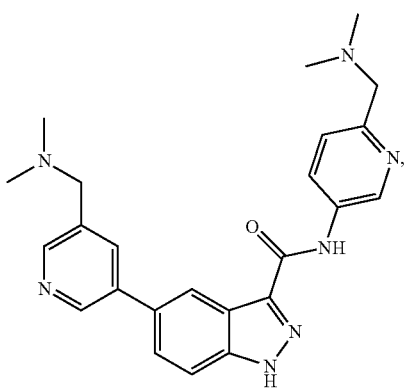

-continued
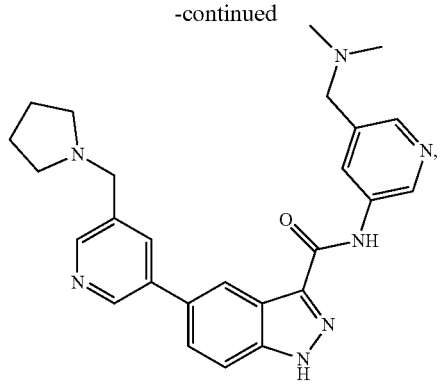
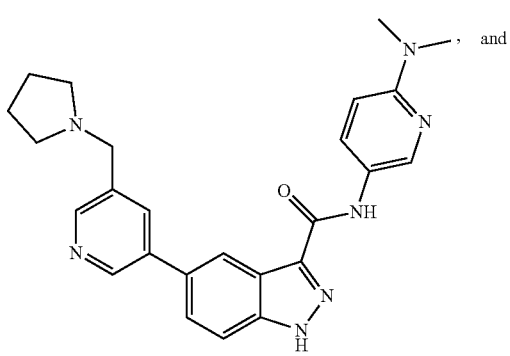
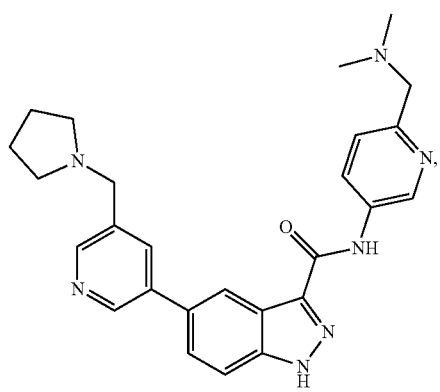 [SMILES: CN(C)Cc1ccc(NC(=O)c2n[nH]c3ccc(-c4cncc(CN5CCCC5)c4)cc23)cn1]
or a pharmaceutically acceptable salt thereof.
19. The method of claim 17, the compound having a structure selected from the group consisting of:
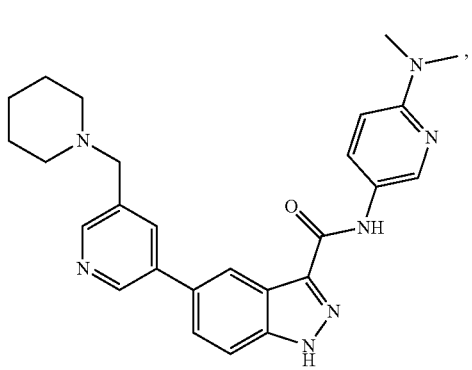
-continued
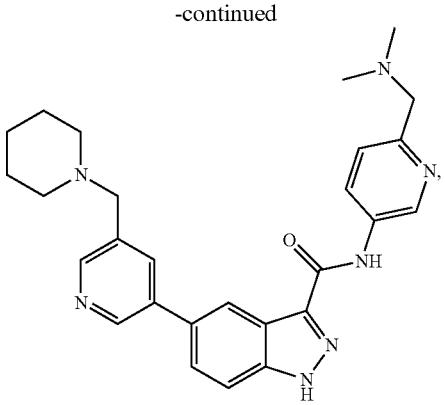
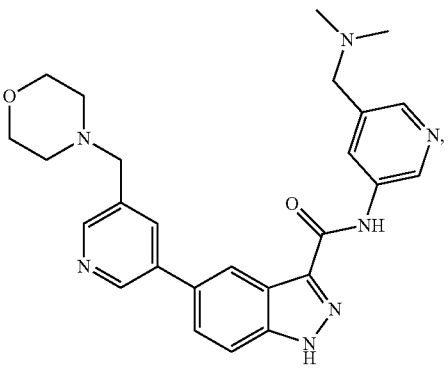
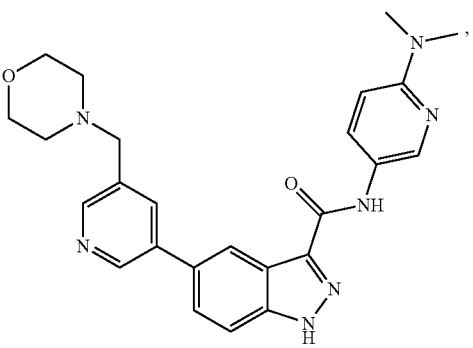
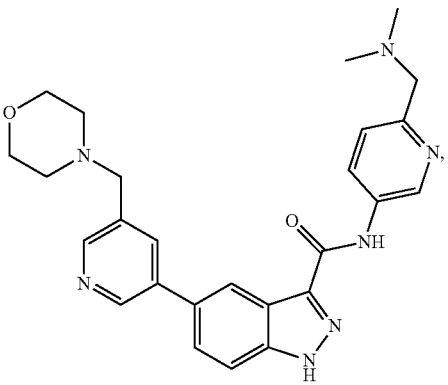

433
-continued
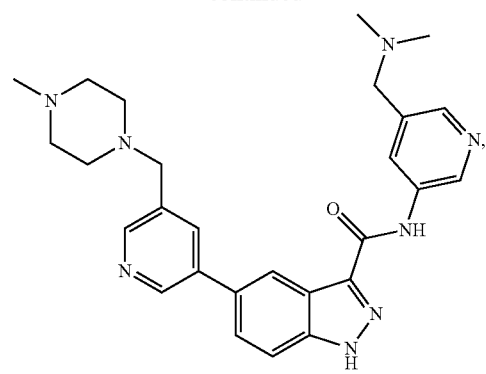
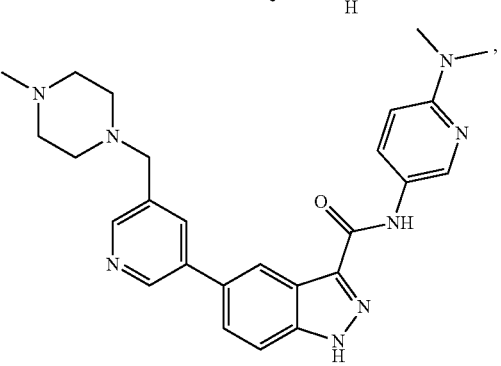
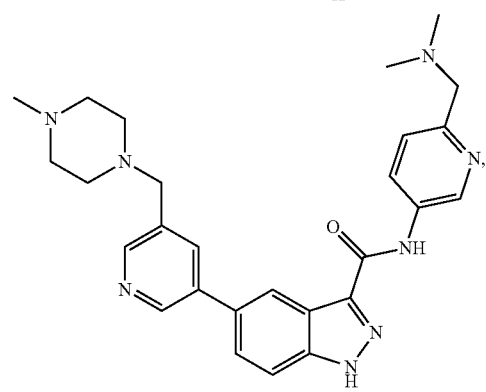
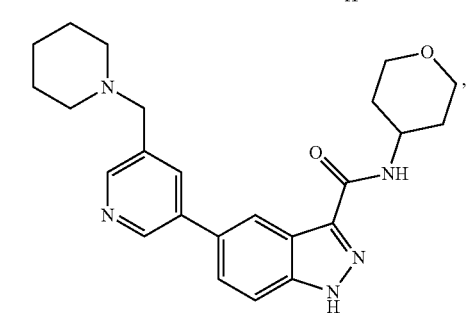
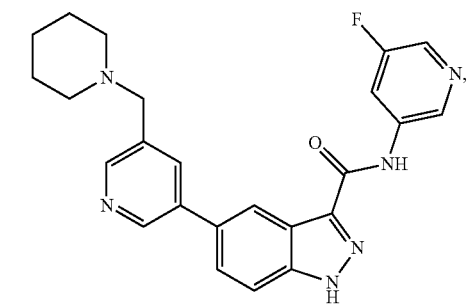
434
-continued
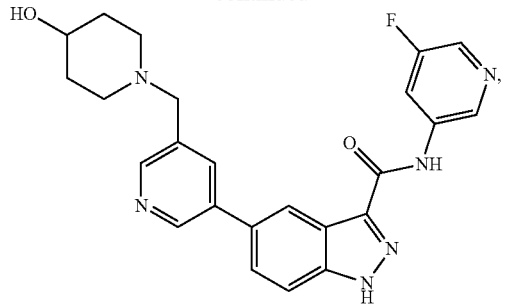
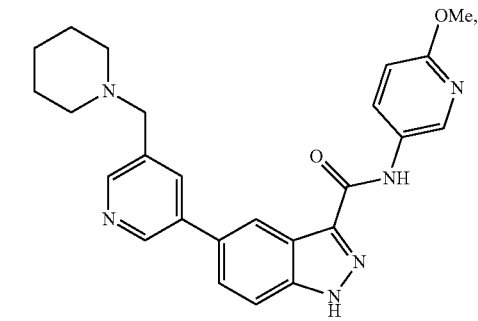
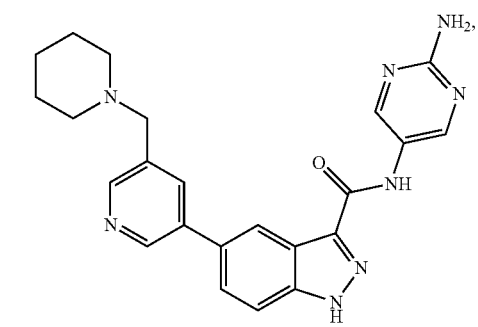
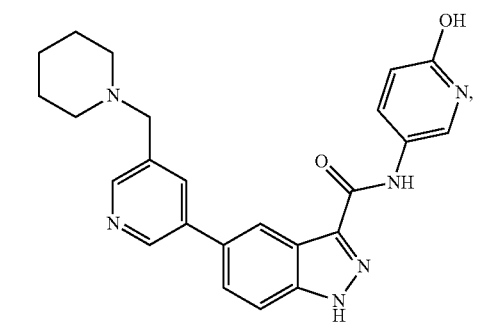
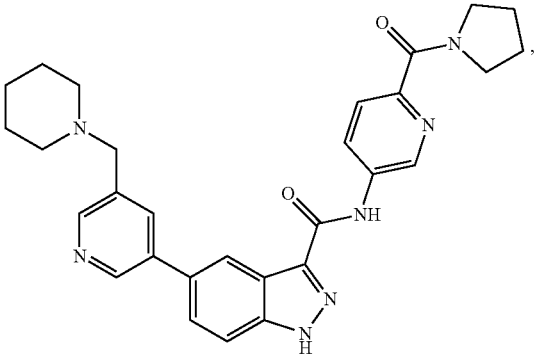

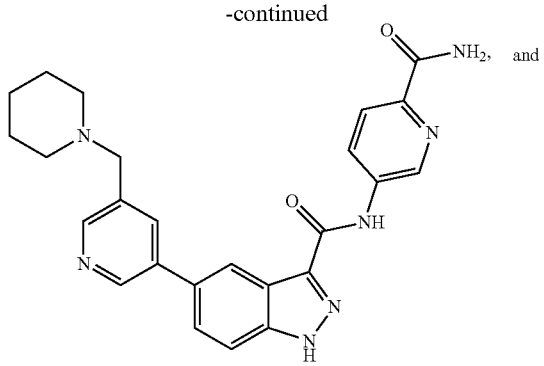
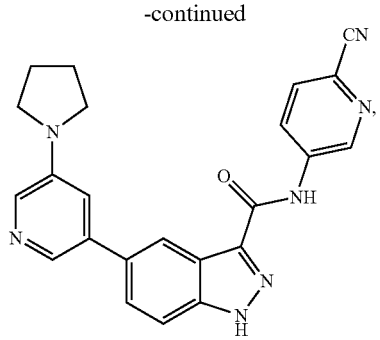
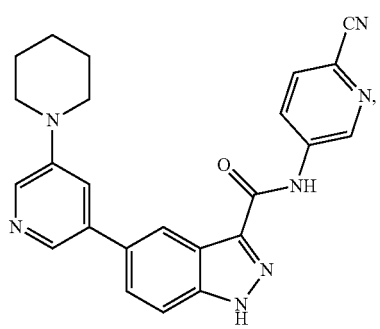
or a pharmaceutically acceptable salt thereof.
20. The method of claim 17, the compound having a structure selected from the group consisting of:

437
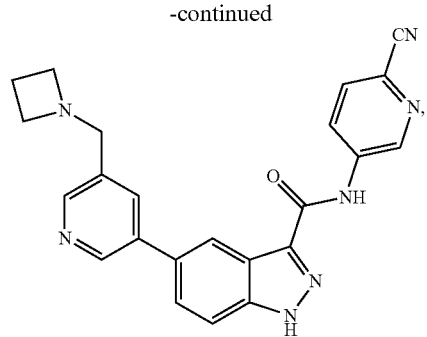
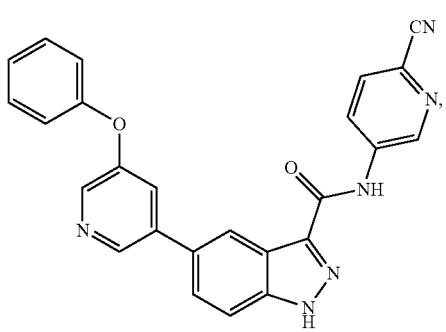
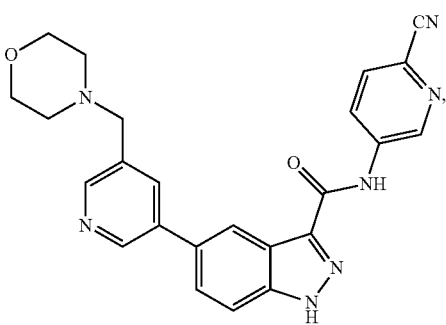
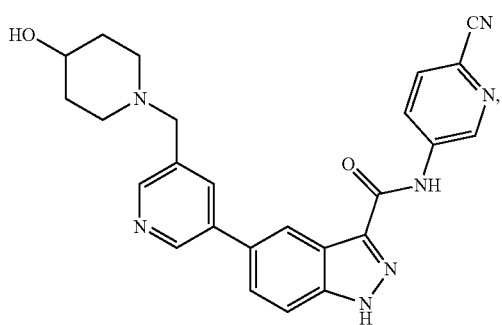
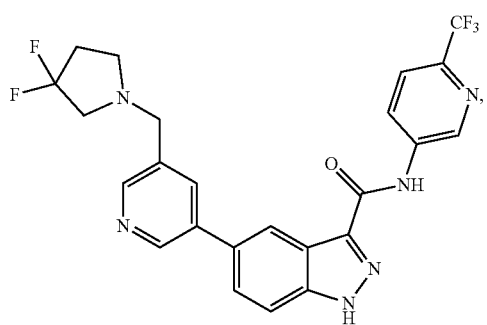
438
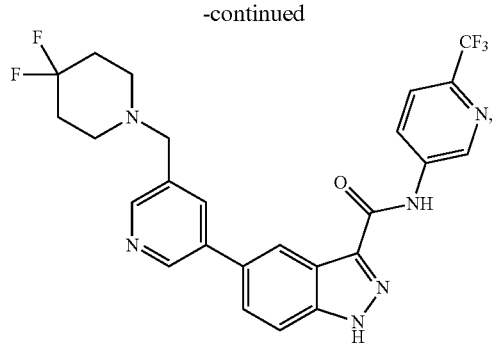
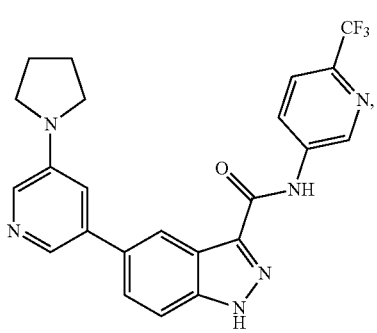
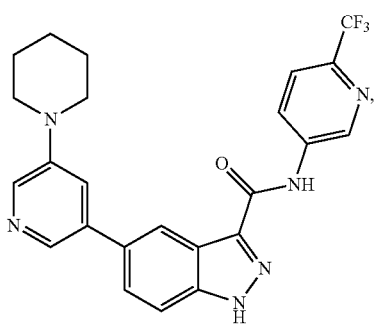
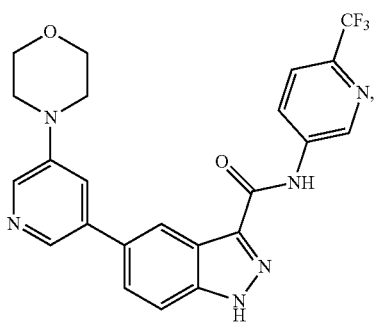
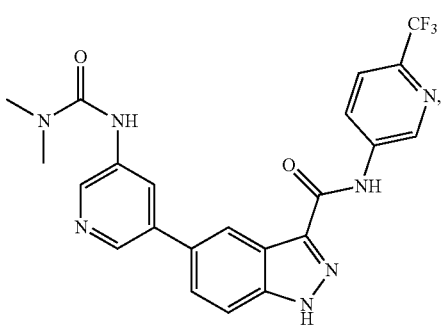

439
-continued
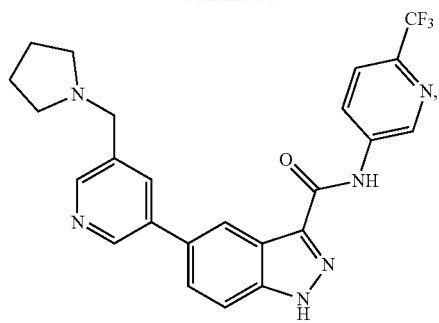
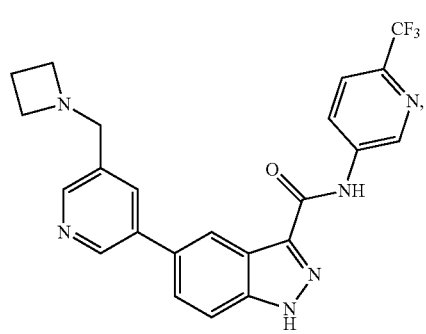
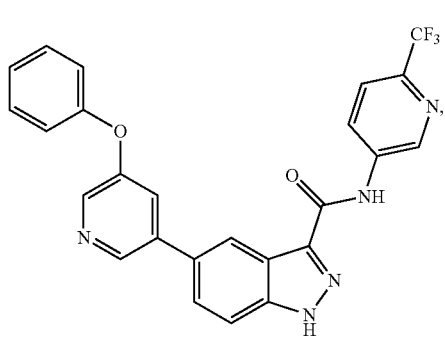
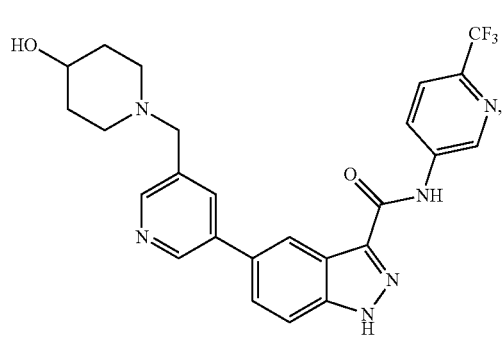
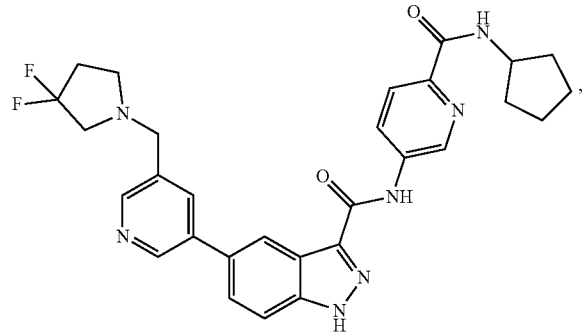
440
-continued
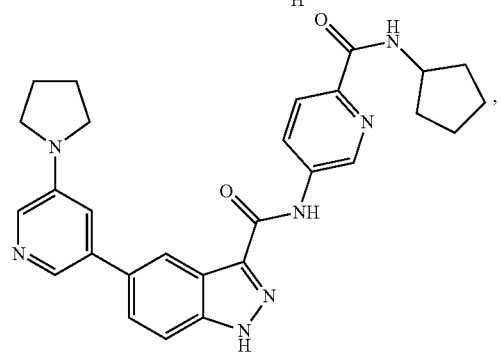
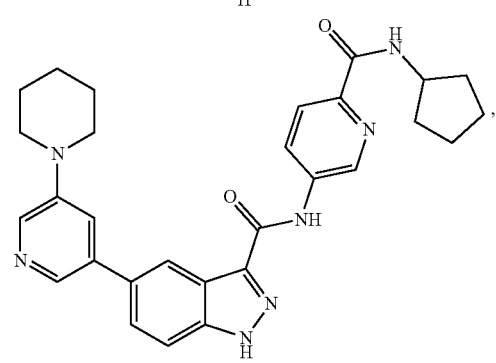
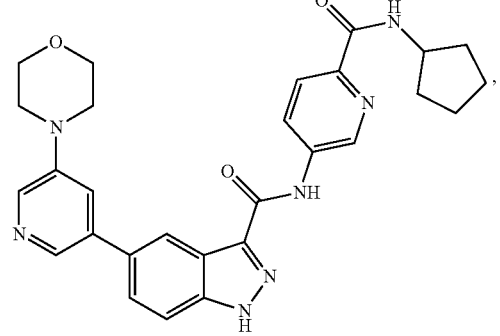
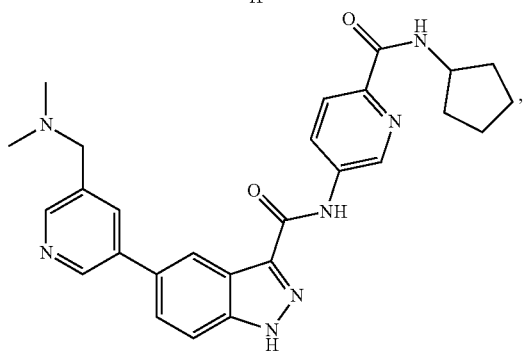

441
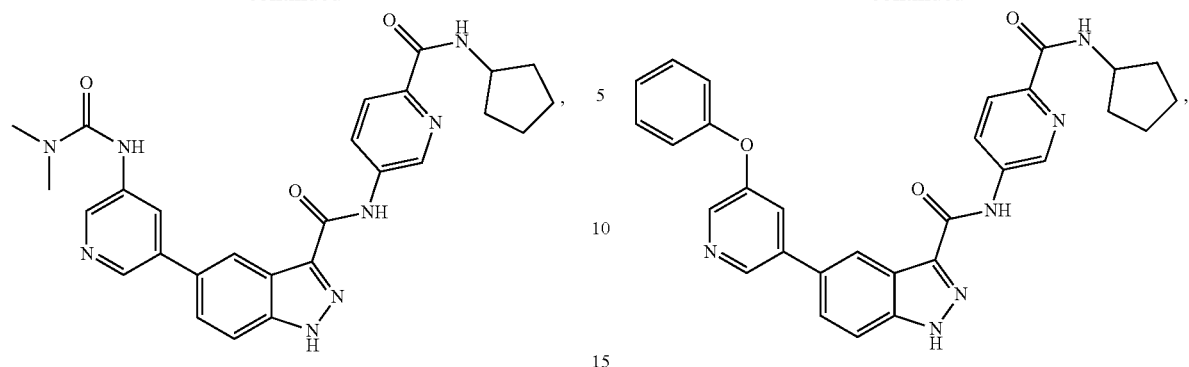
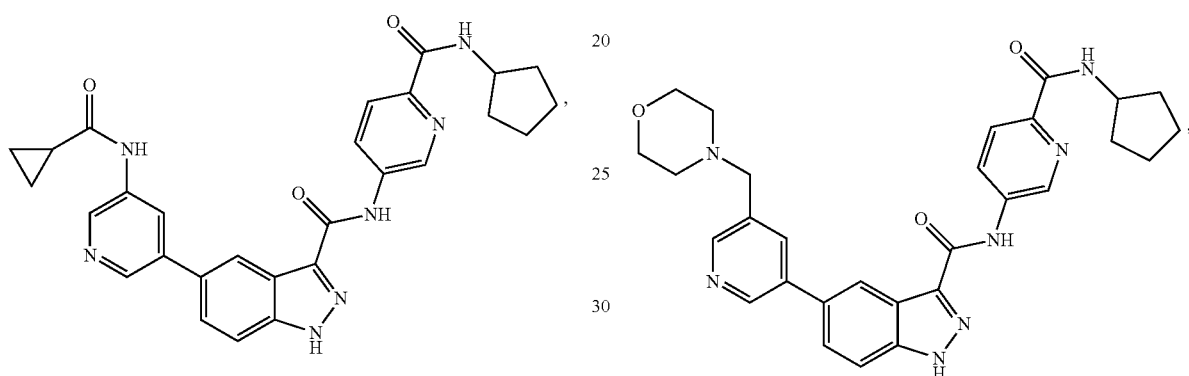
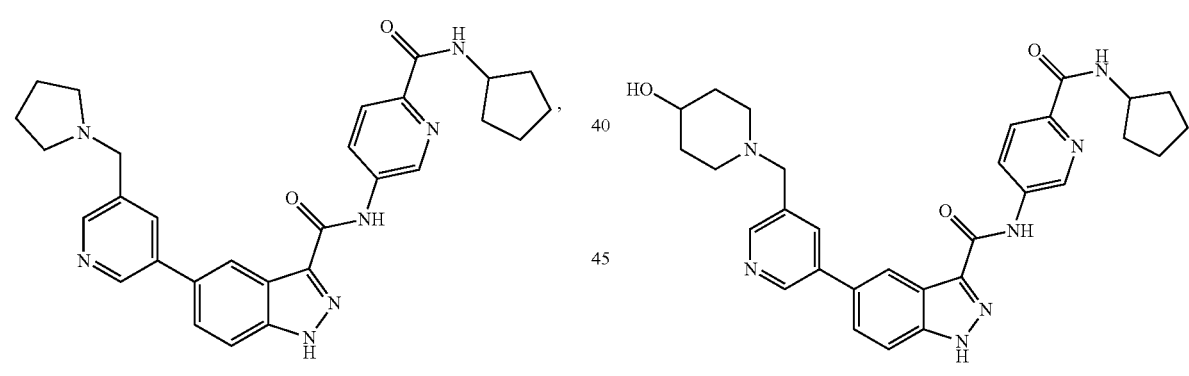
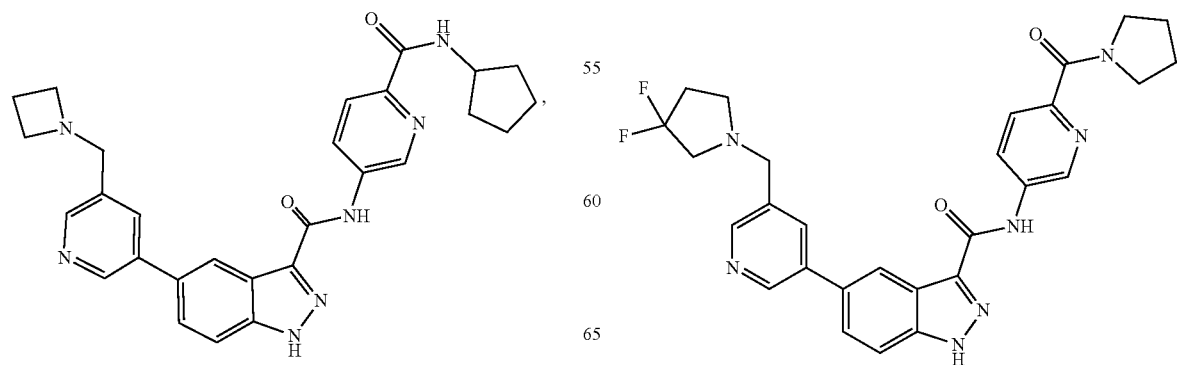
442
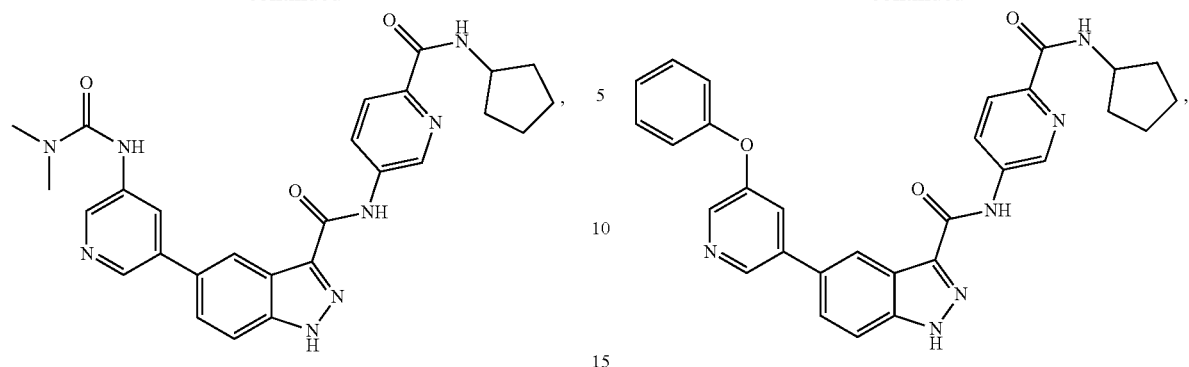
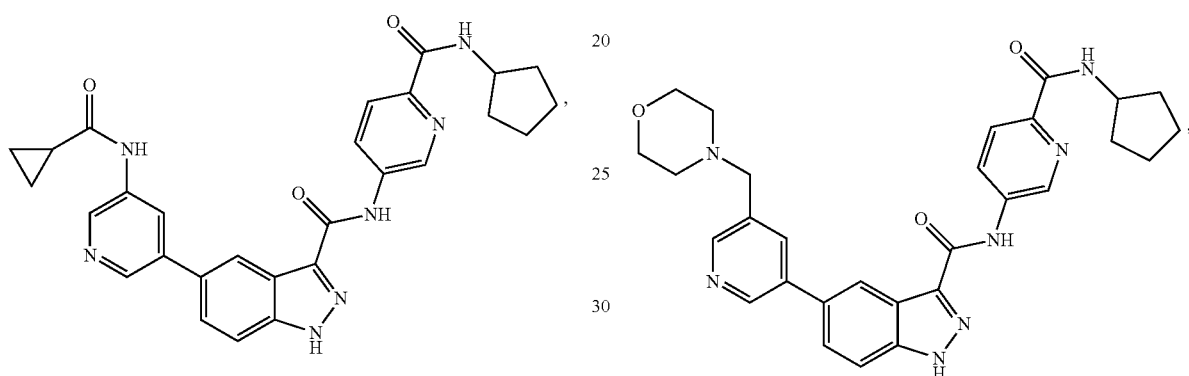
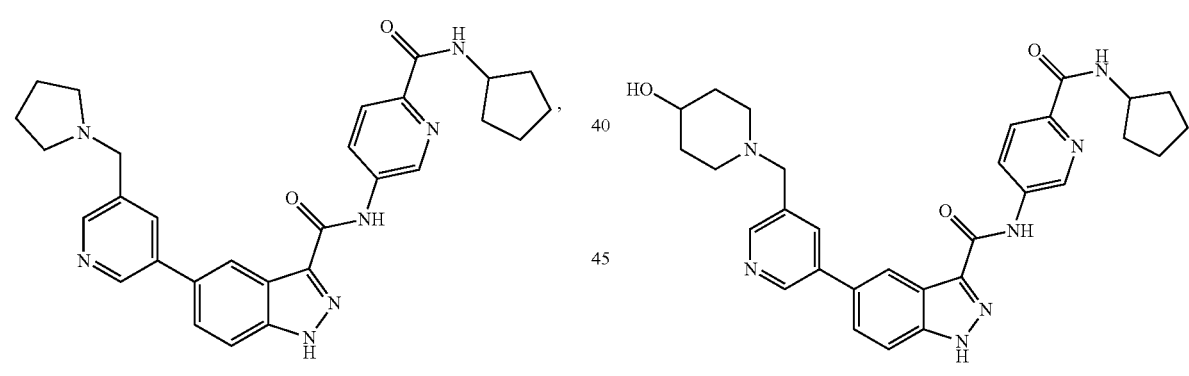
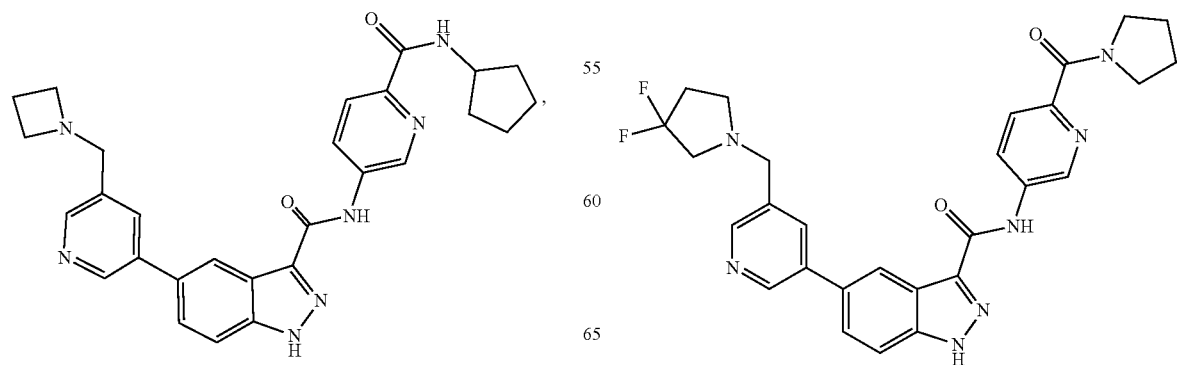

443
-continued
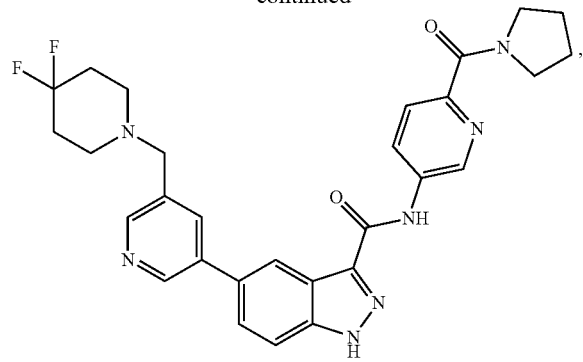
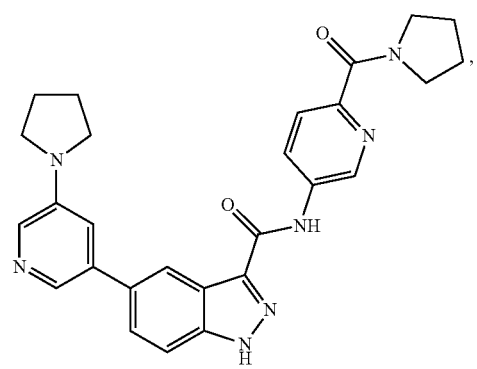
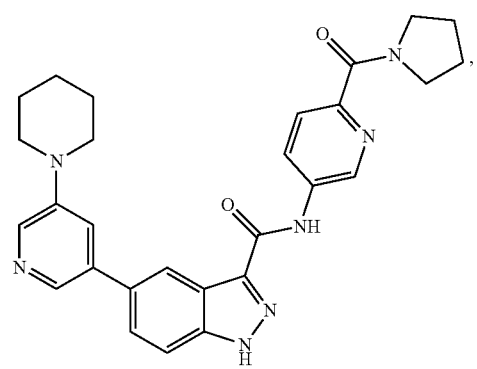
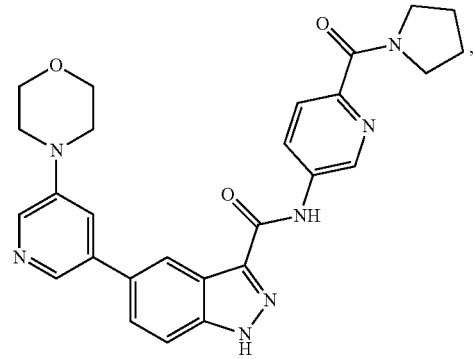
444
-continued
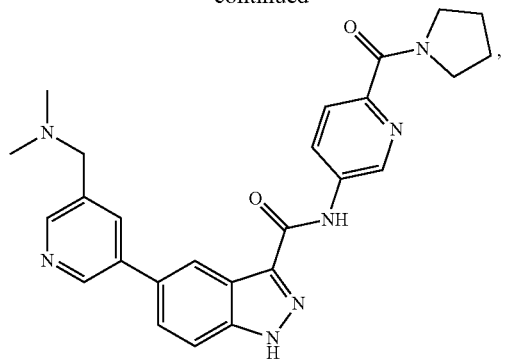
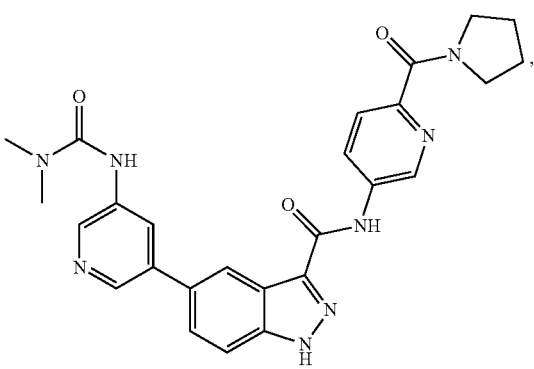
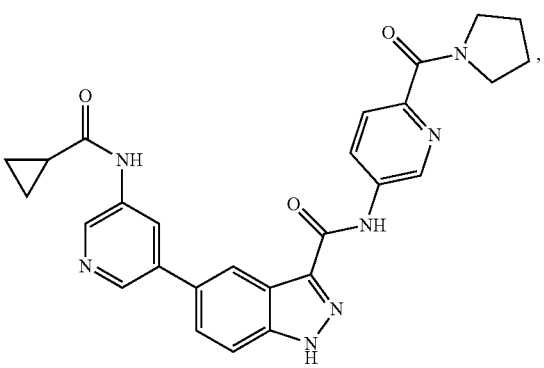
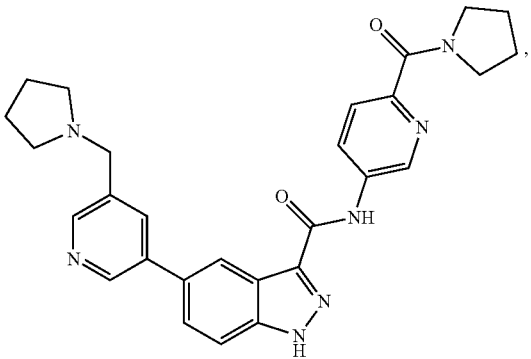

-continued
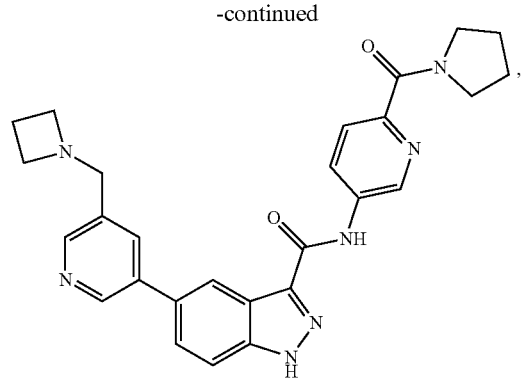
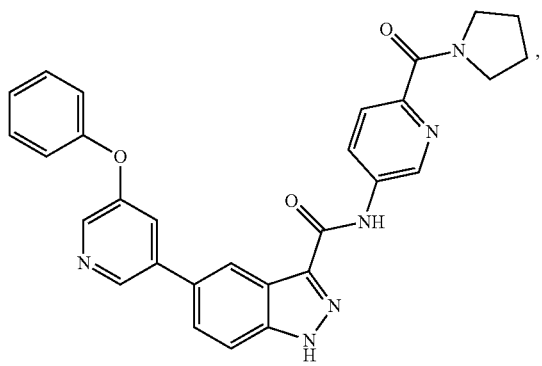
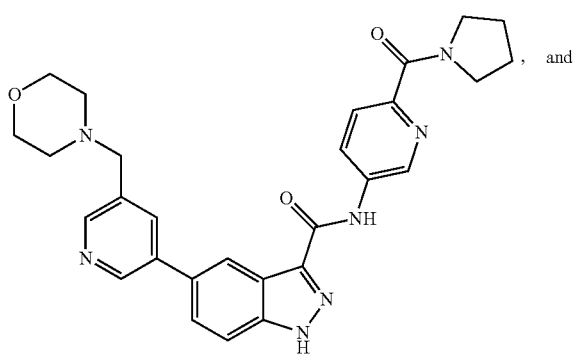
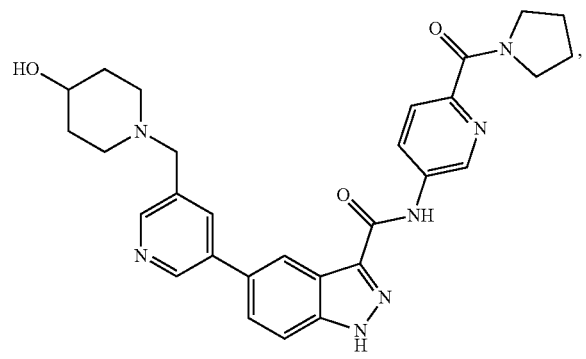
or a pharmaceutically acceptable salt thereof.
21. The method of claim 17, the compound having a structure selected from the group consisting of:
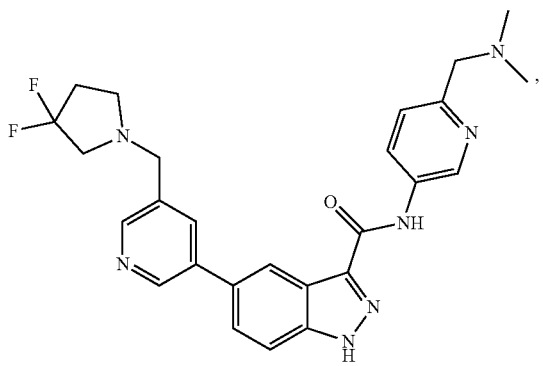
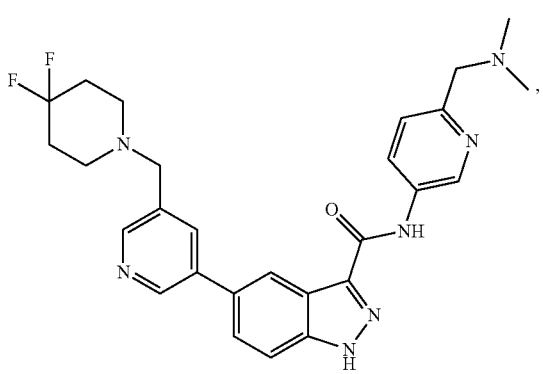
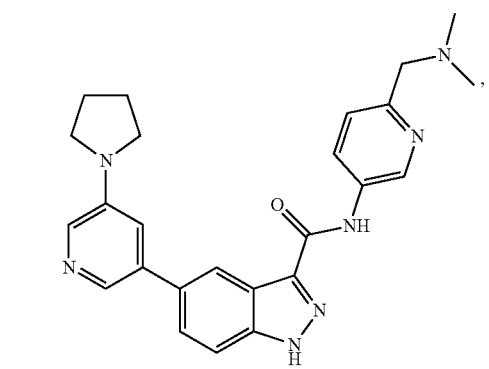
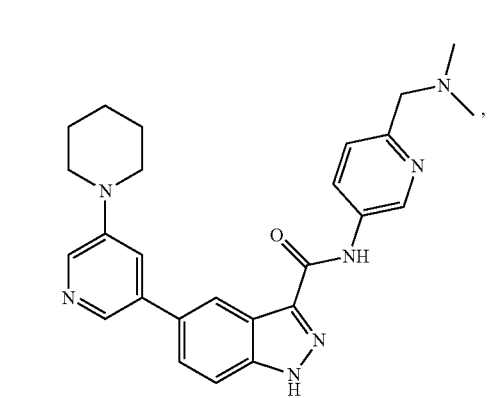

447
-continued
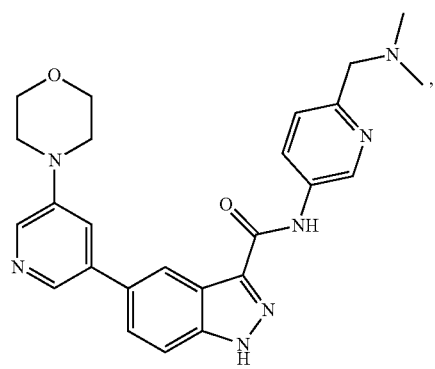
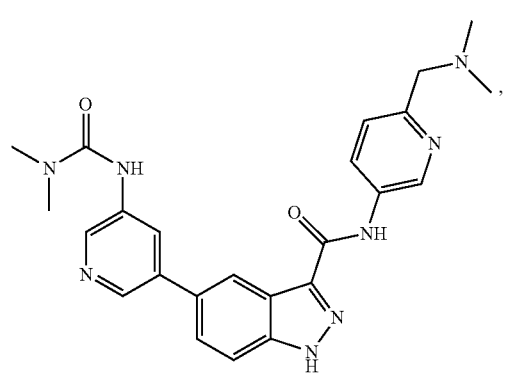
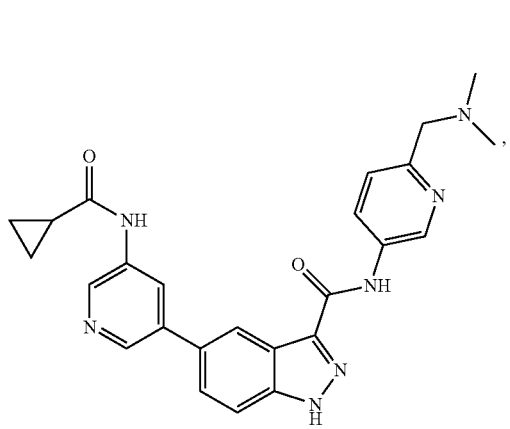
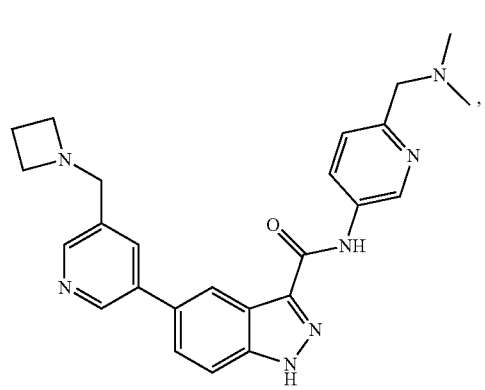
448
-continued
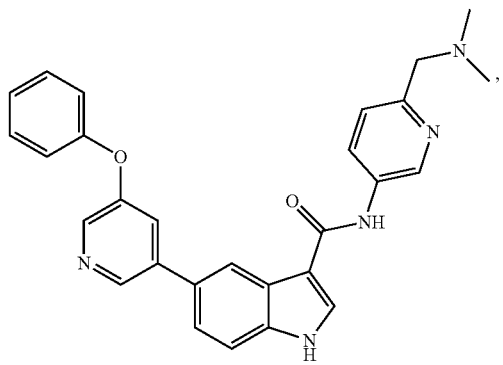
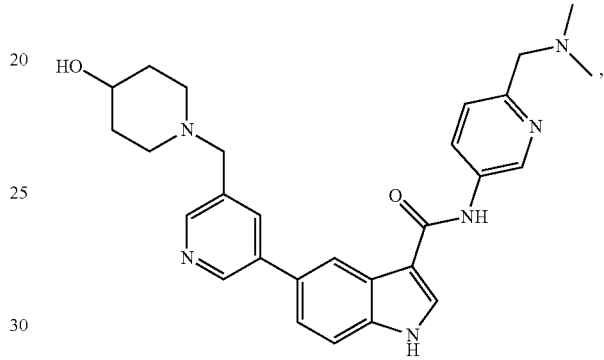
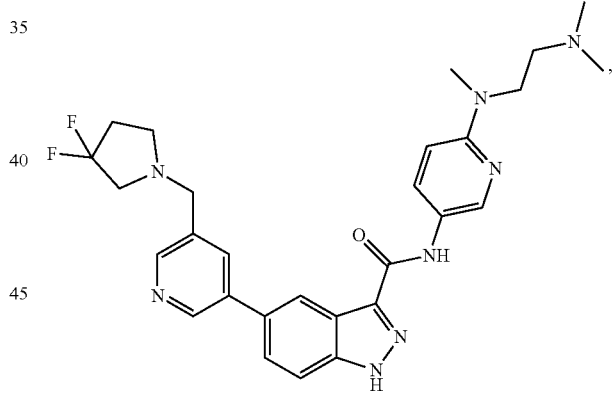
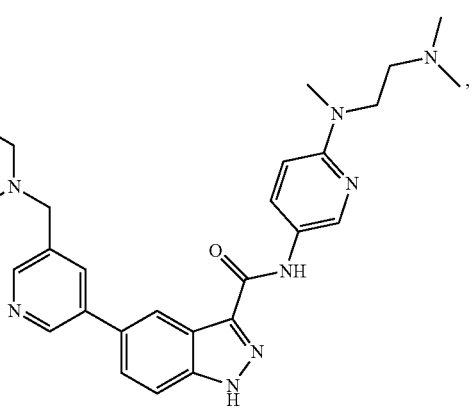

449
-continued
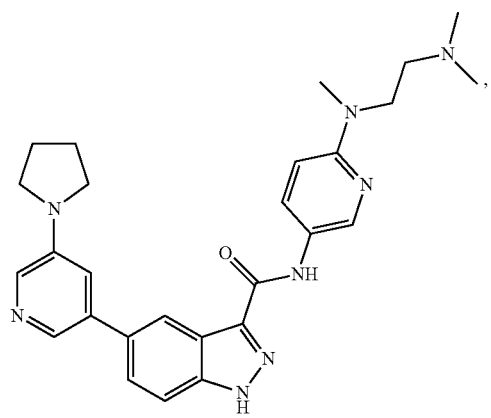
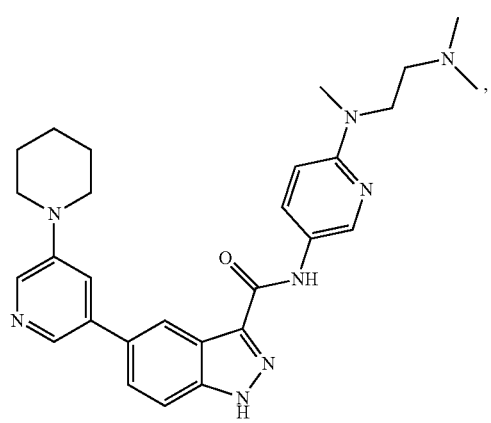
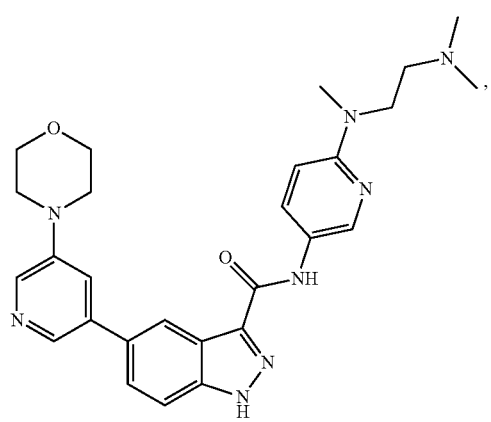
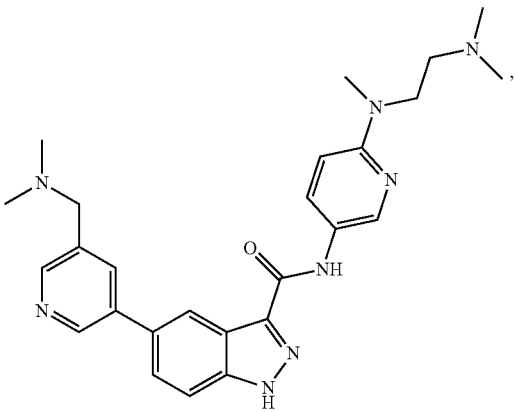
450
-continued
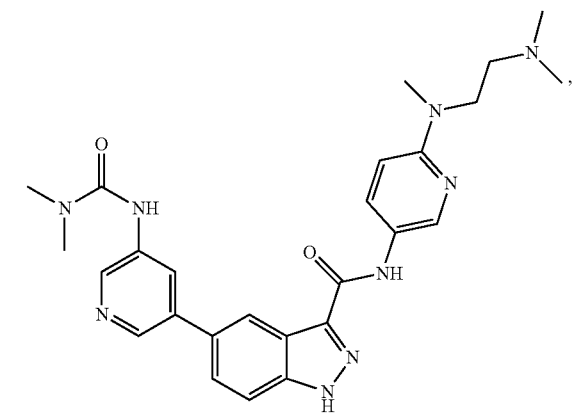
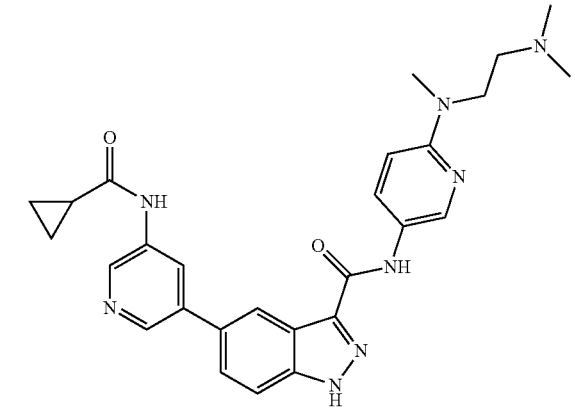
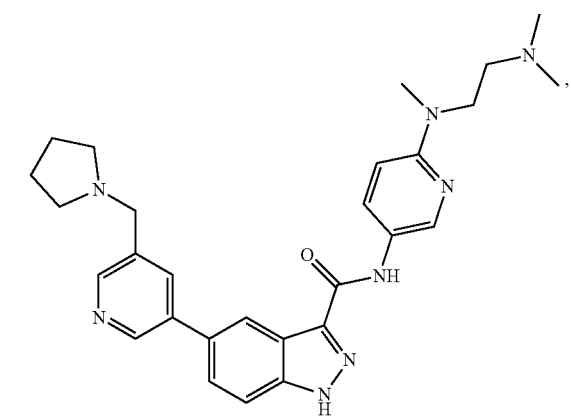
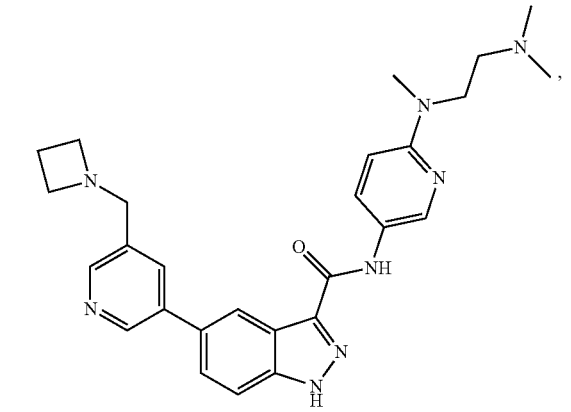

451
-continued
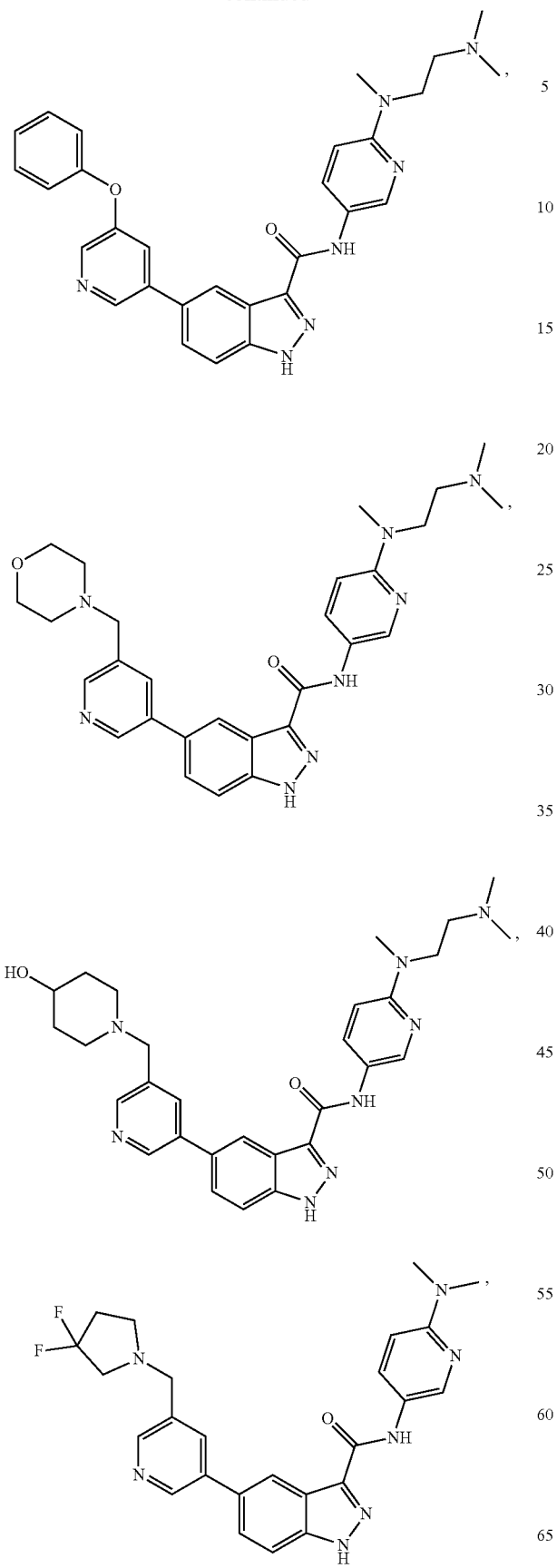
452
-continued
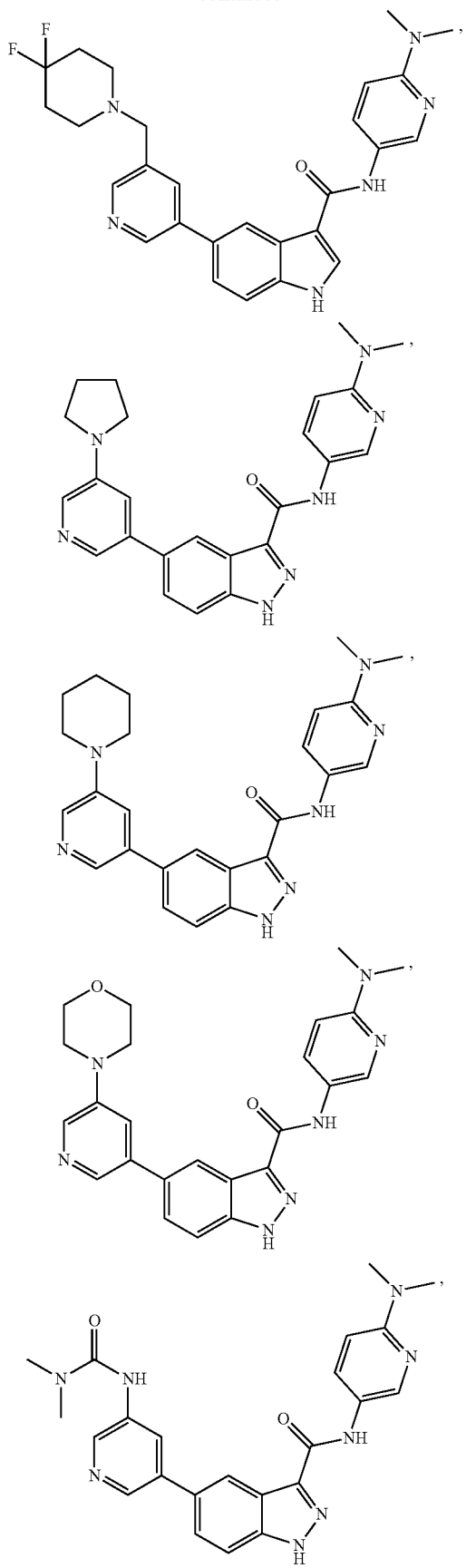

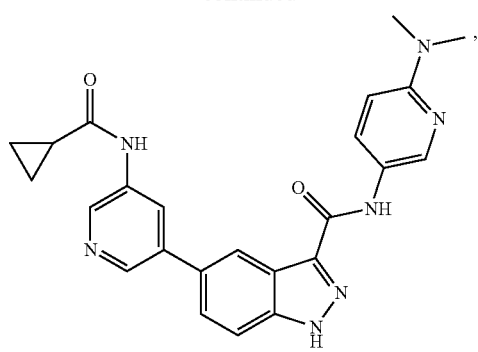
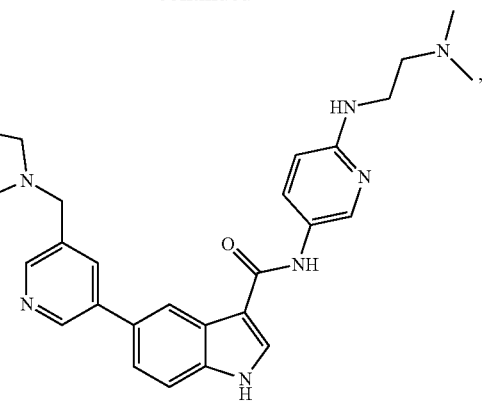
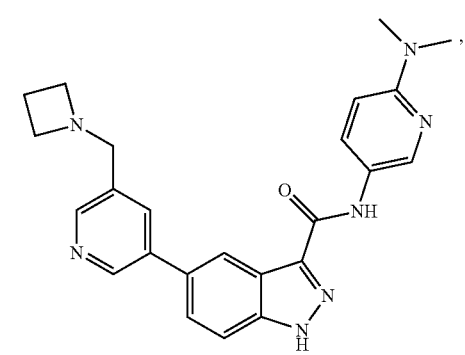
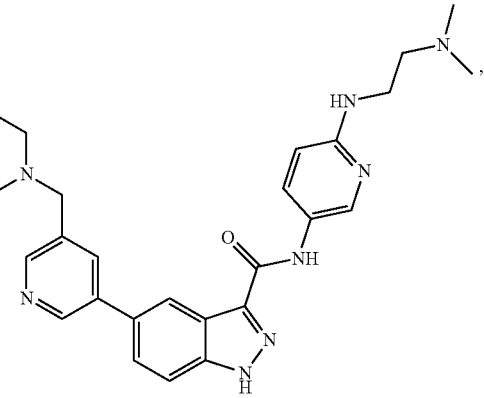
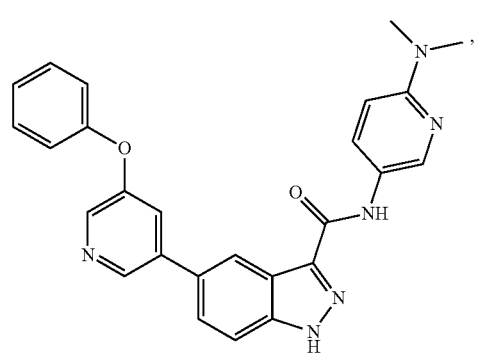
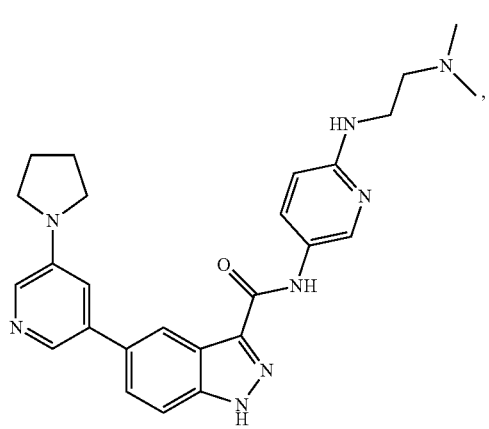
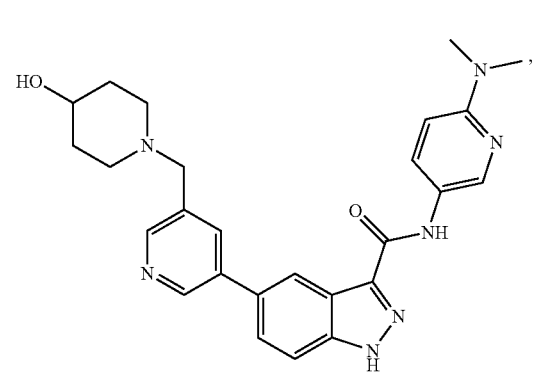
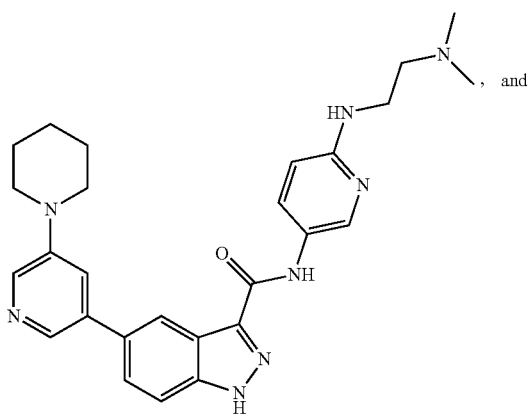

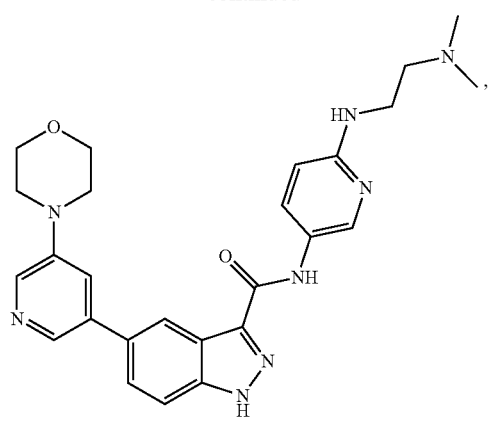
or a pharmaceutically acceptable salt thereof.
22. The method of claim 17, the compound having a structure selected from the group consisting of:
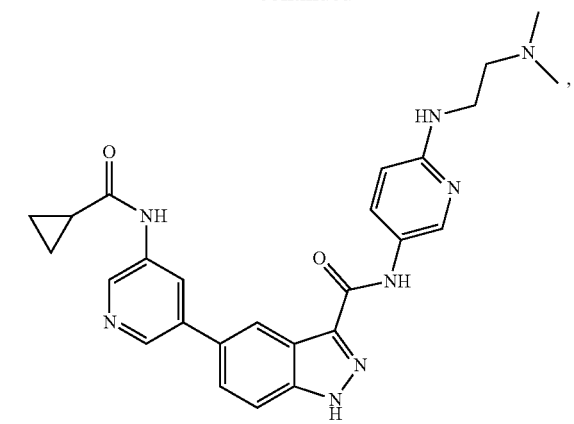
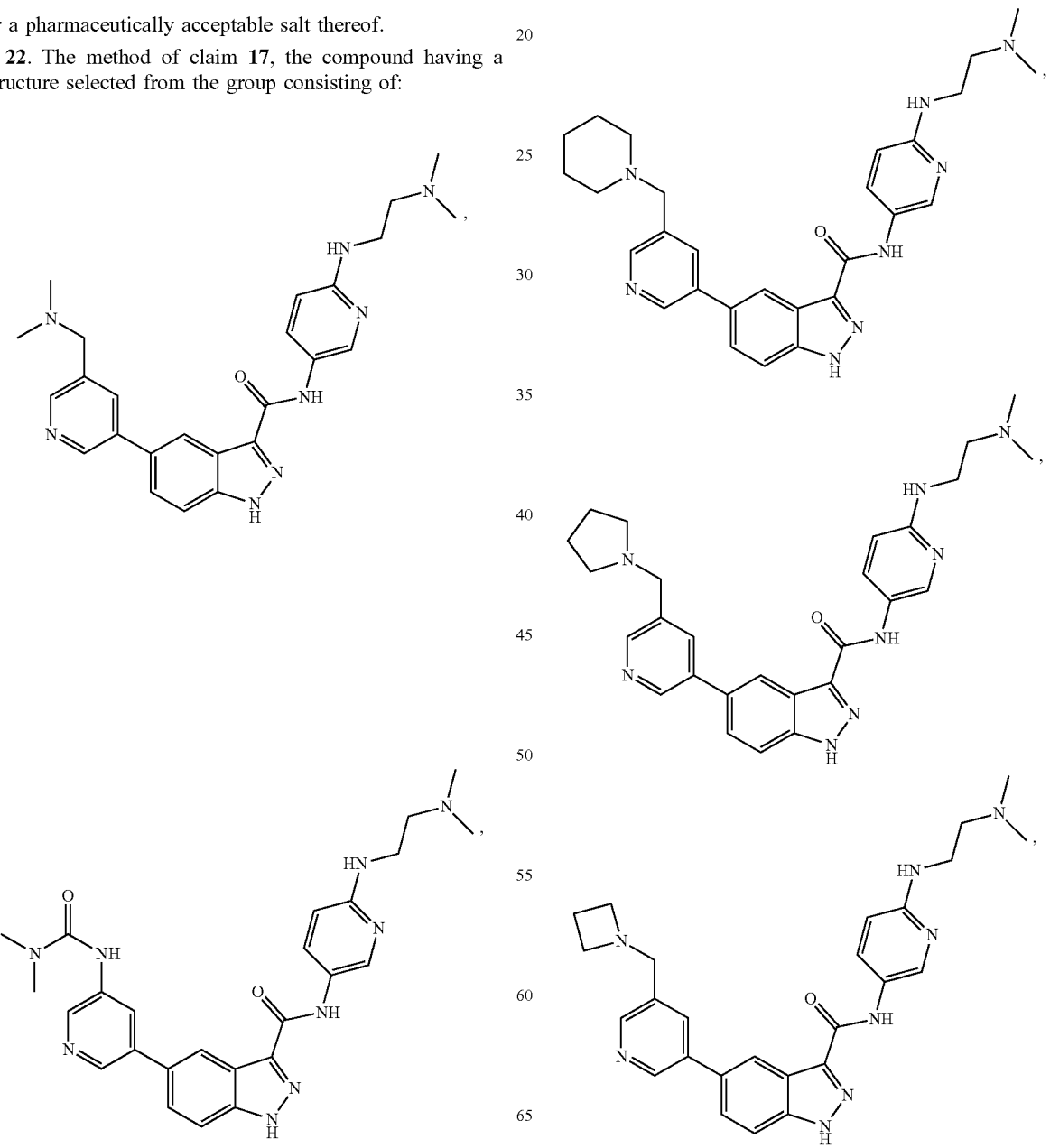

457
-continued
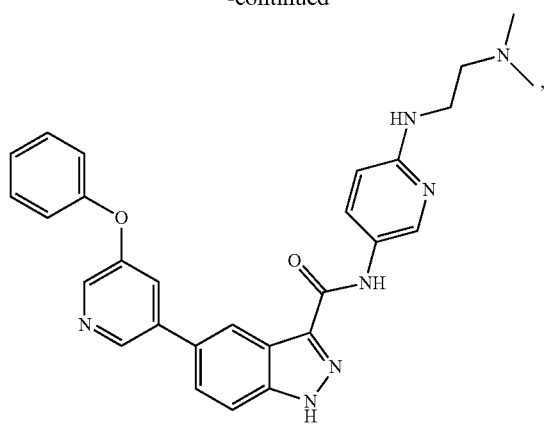
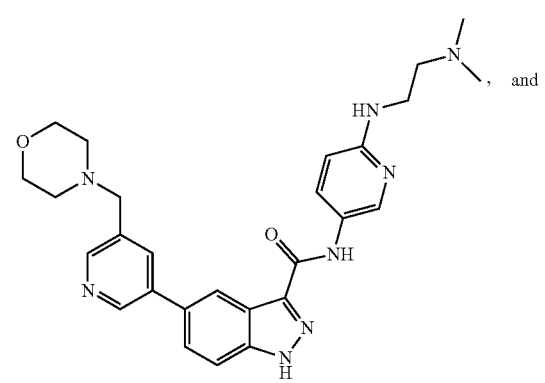
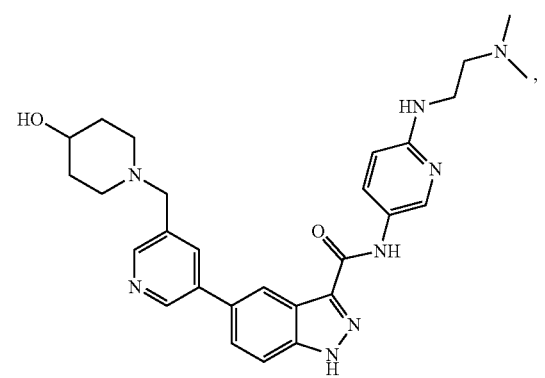 [SMILES: CN(C)CCNc1ccc(NC(=O)c2n[nH]c3ccc(-c4cncc(CN5CCC(O)CC5)c4)cc23)cn1]
or a pharmaceutically acceptable salt thereof.
23. The method of claim 17, the compound having a structure selected from the group consisting of:
458
-continued
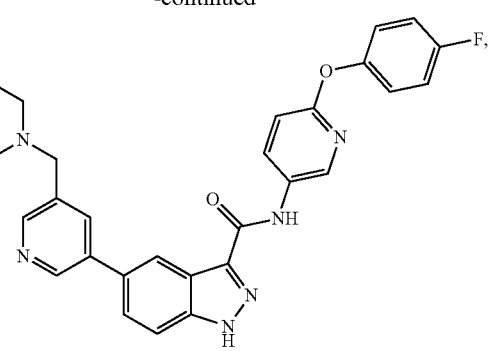
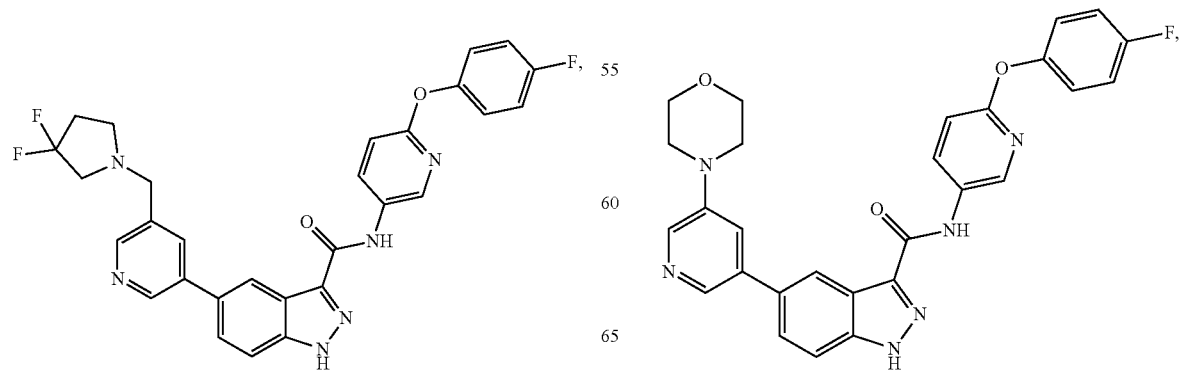

459
-continued
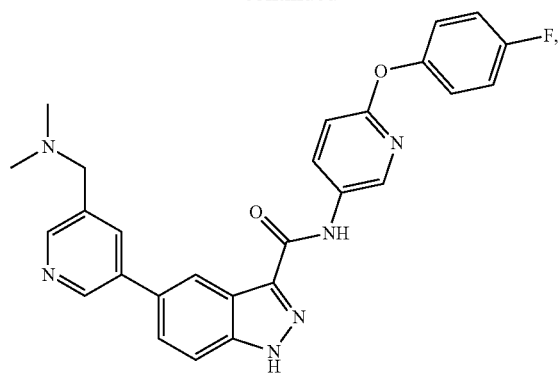
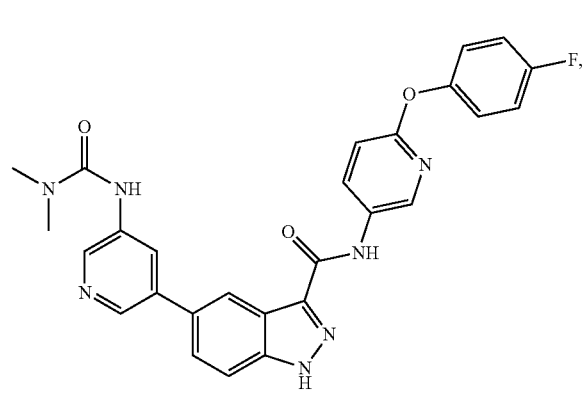
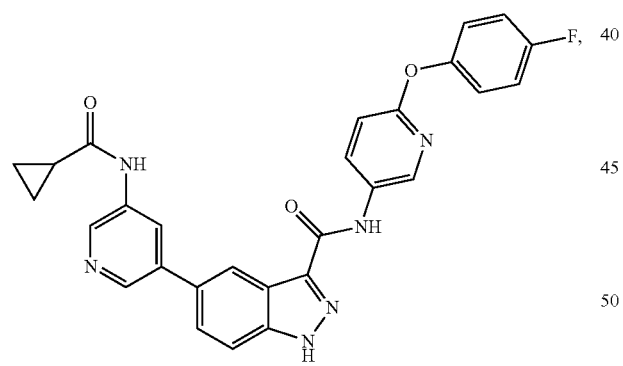
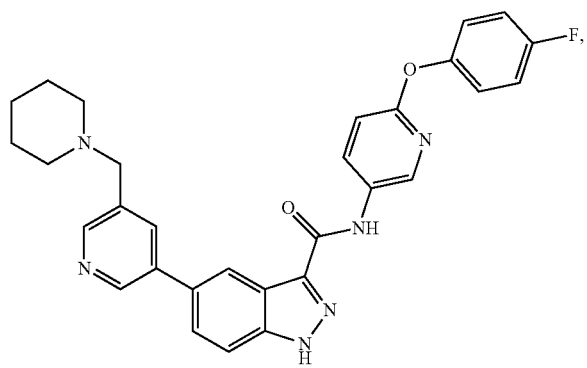
460
-continued
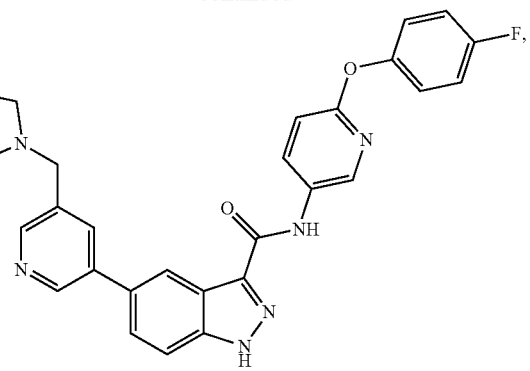
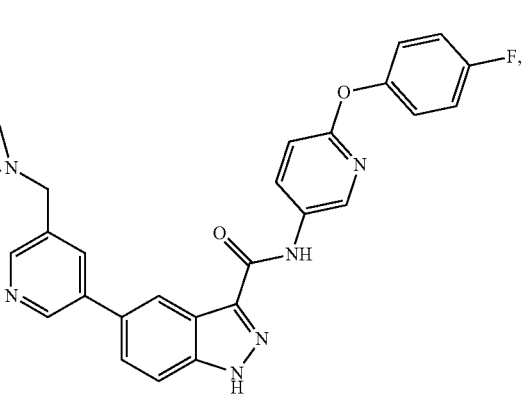
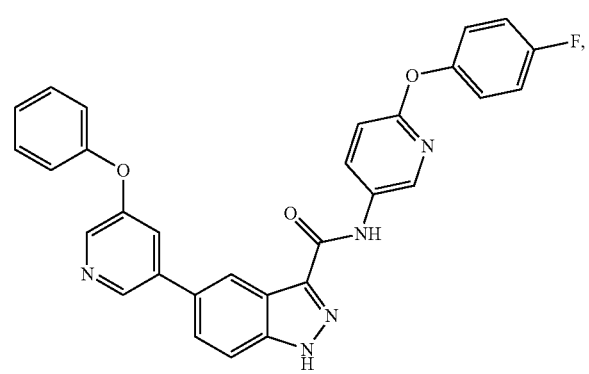
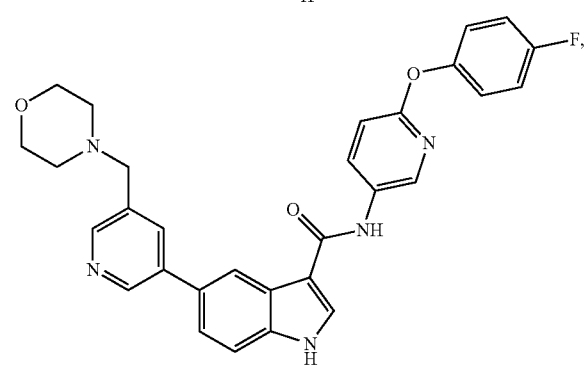

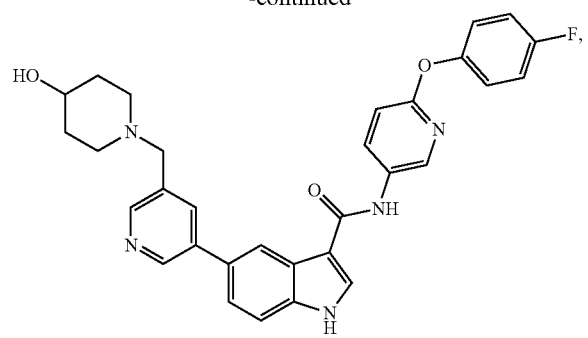
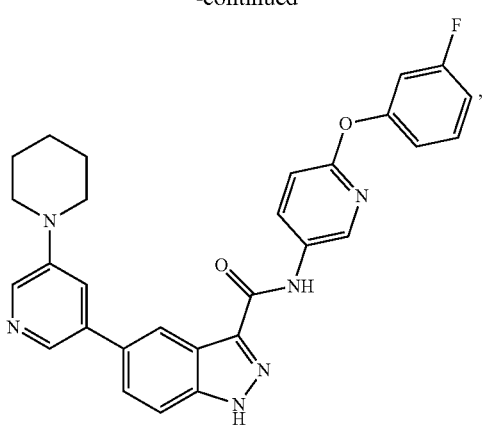
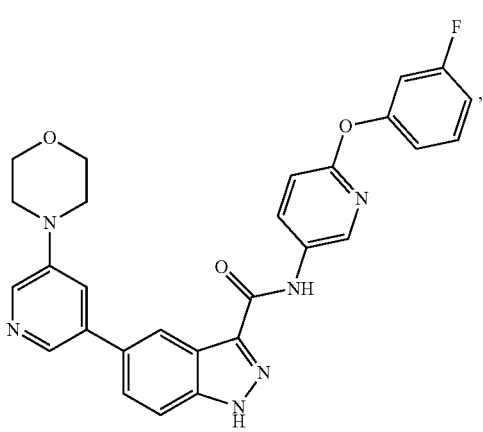
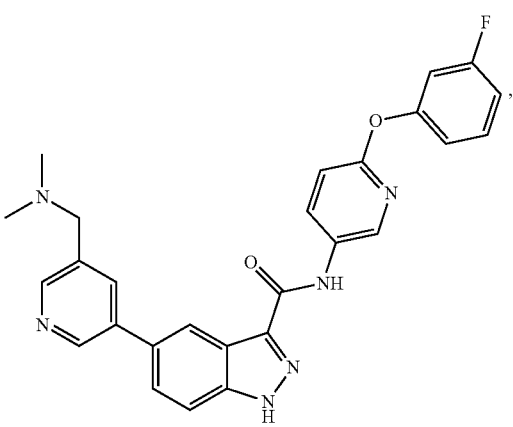
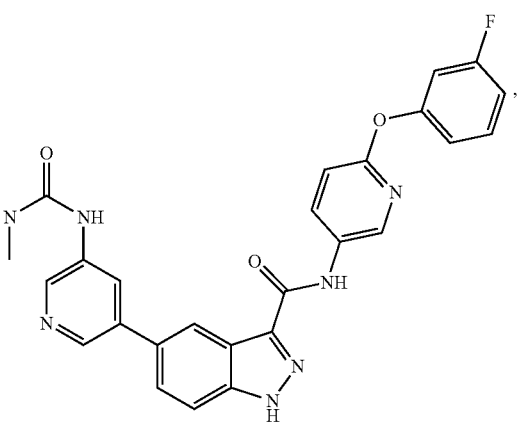

463
-continued
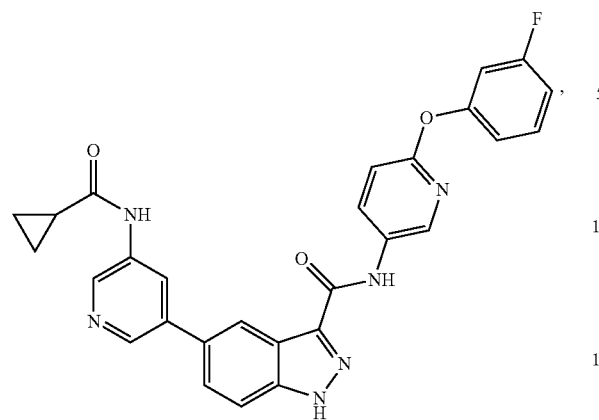
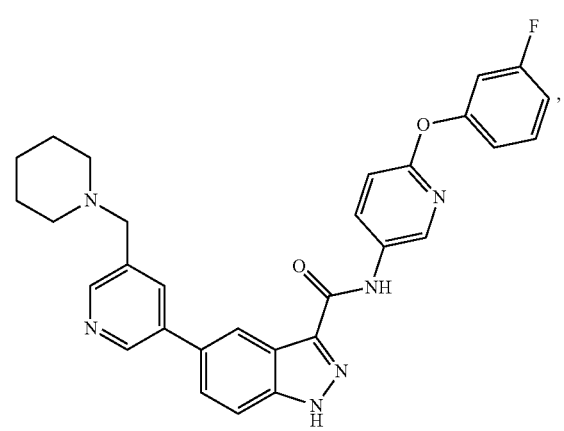
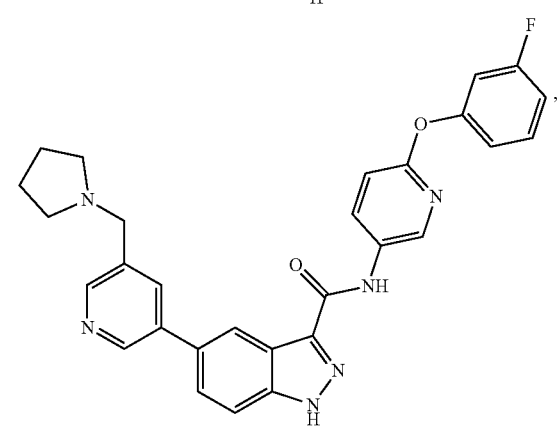
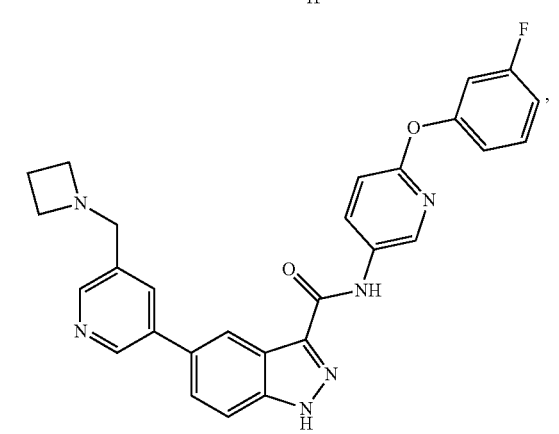
464
-continued
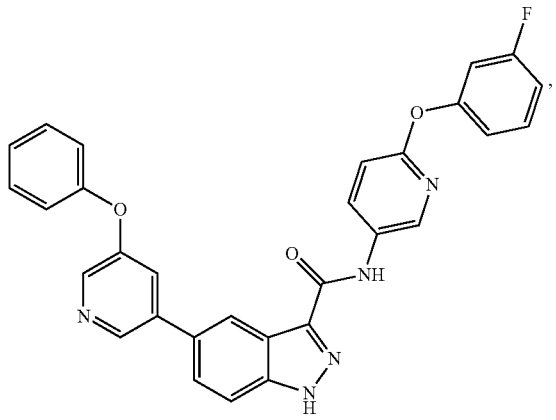
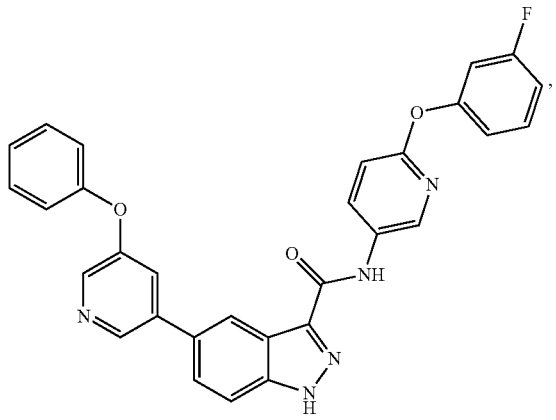
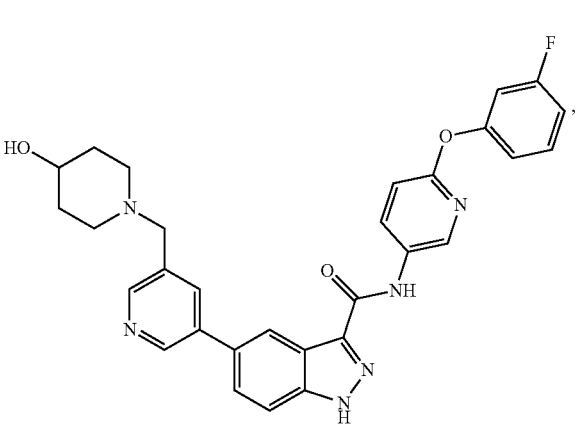

465 -continued
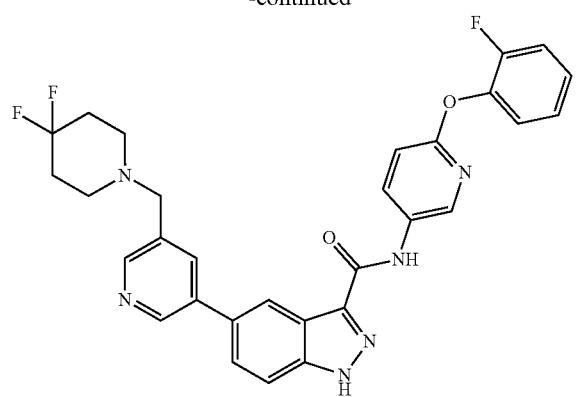
466 -continued
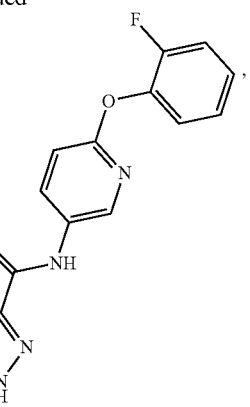
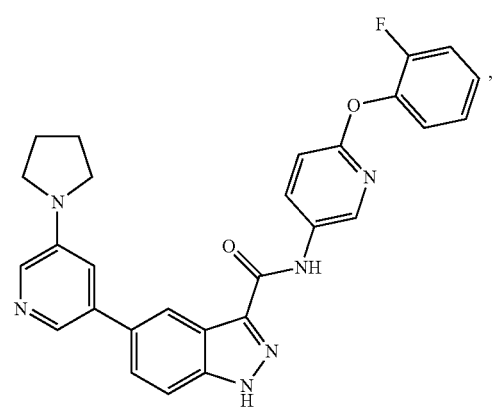
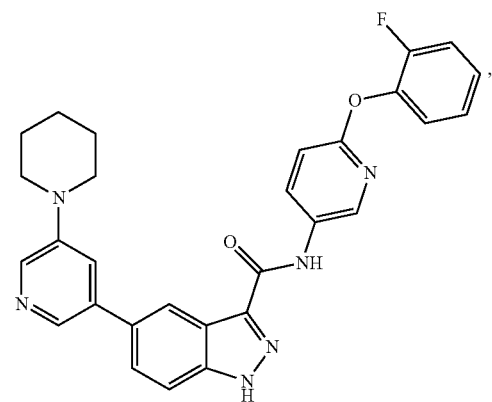
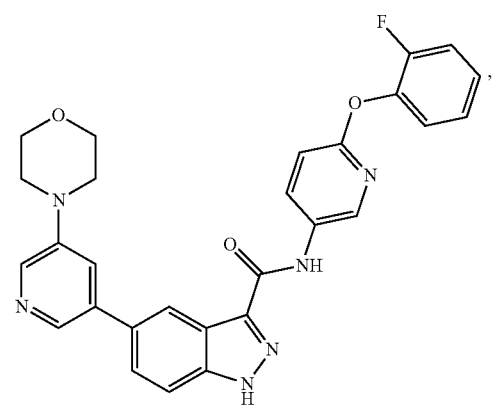

467
-continued
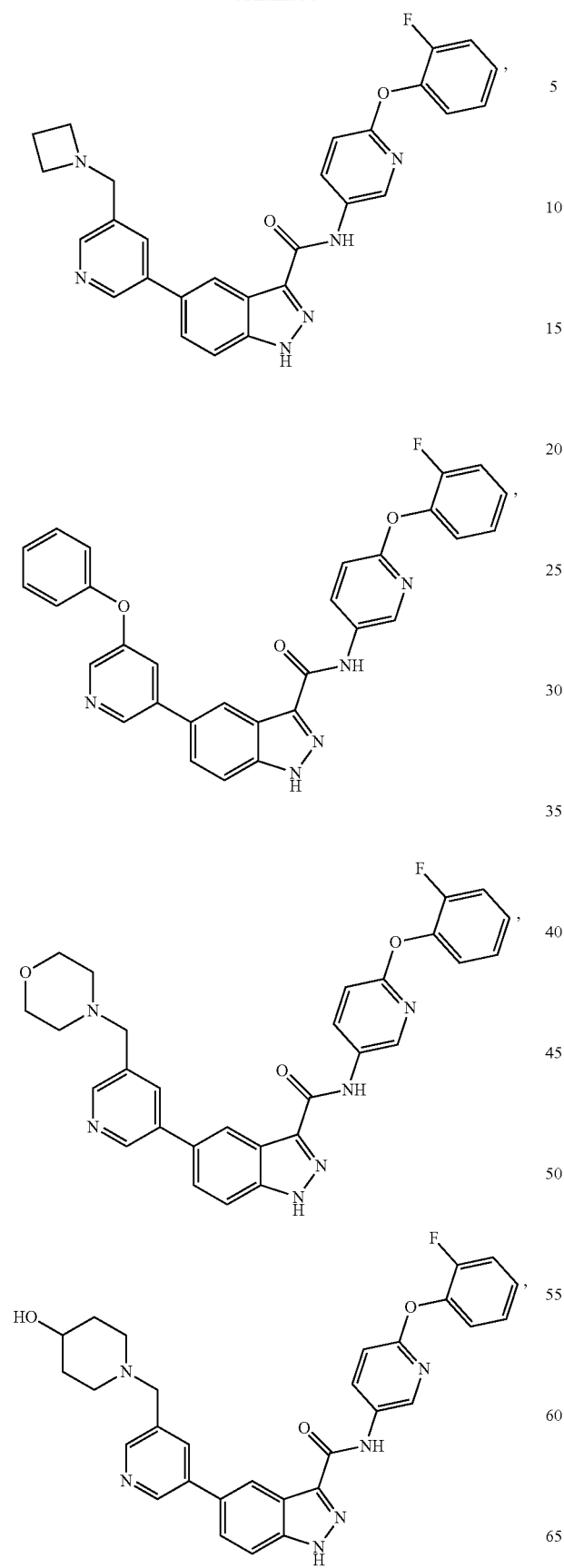
468
-continued
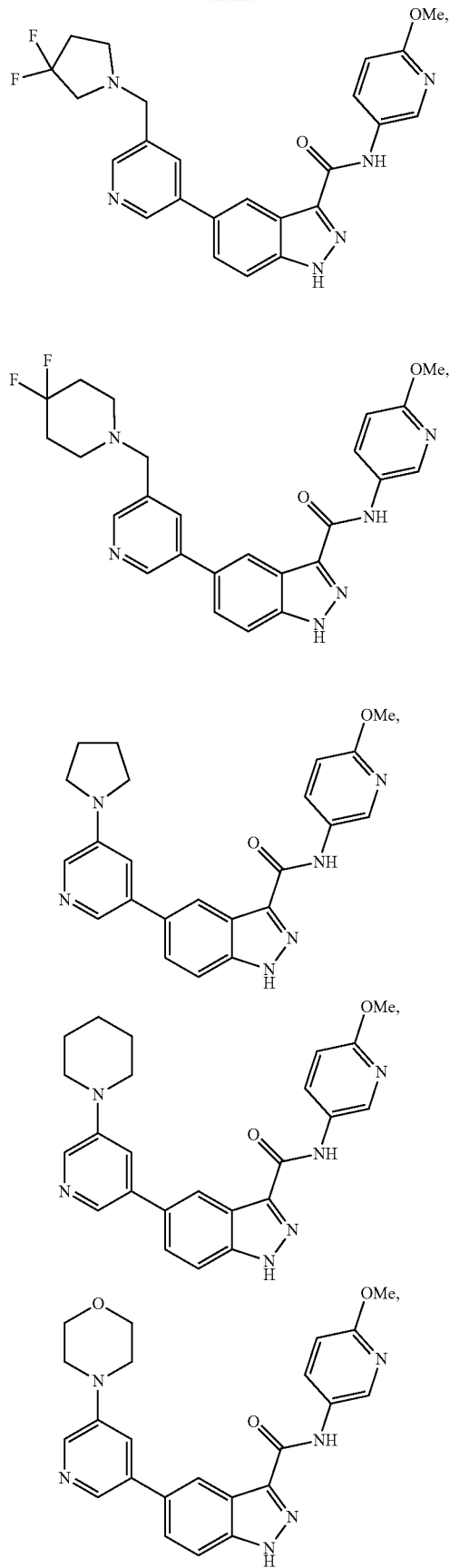

-continued
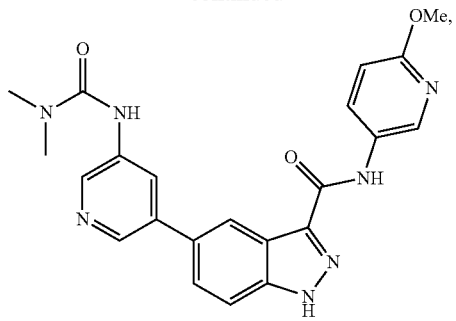
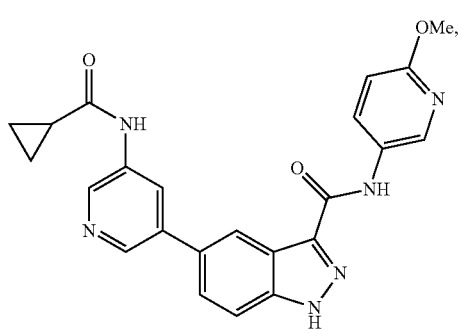
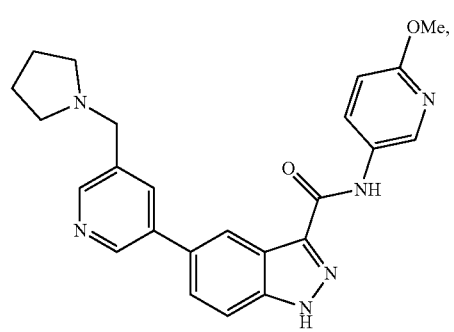
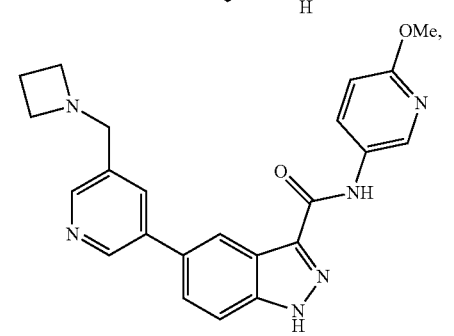
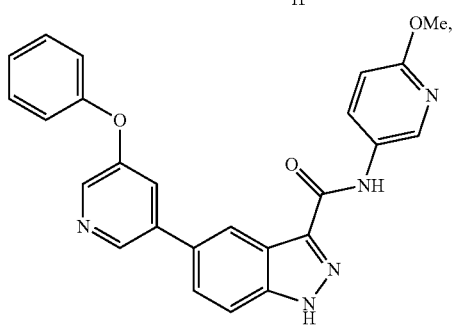
-continued
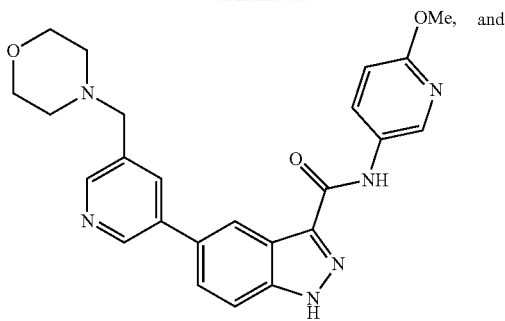
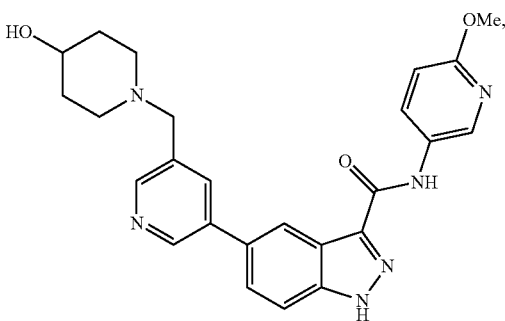 [SMILES: COc1ccc(NC(=O)c2n[nH]c3ccc(-c4cncc(CN5CCC(O)CC5)c4)cc23)cn1]
or a pharmaceutically acceptable salt thereof.
24. The method of claim 17, the compound having a structure selected from the group consisting of:
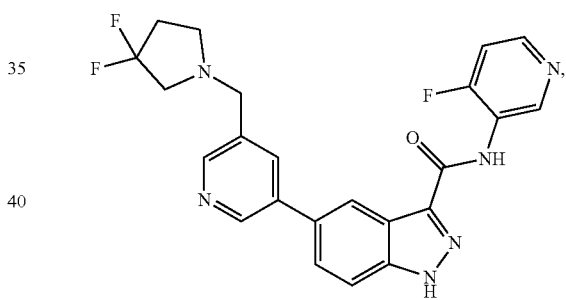
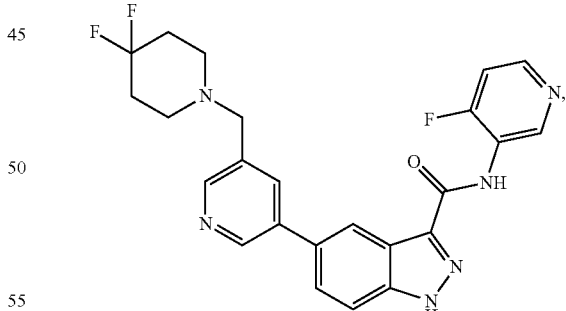
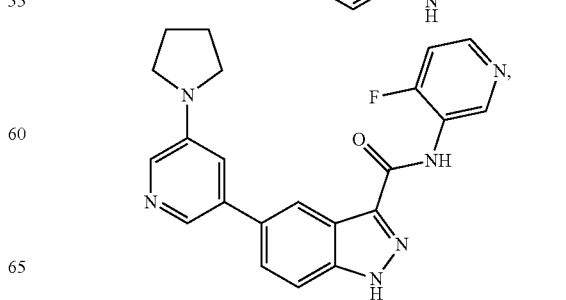

471
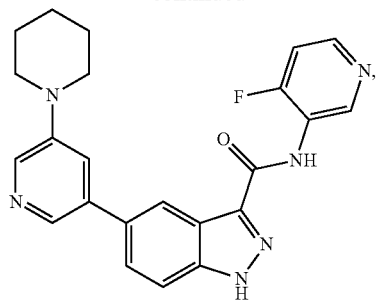
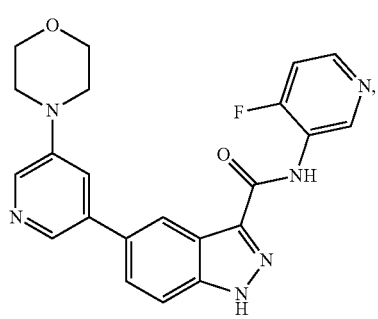
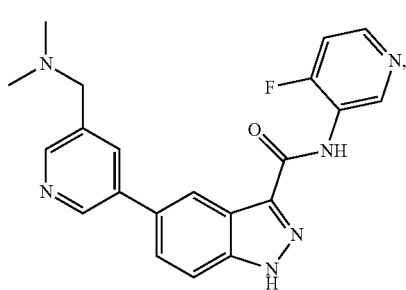
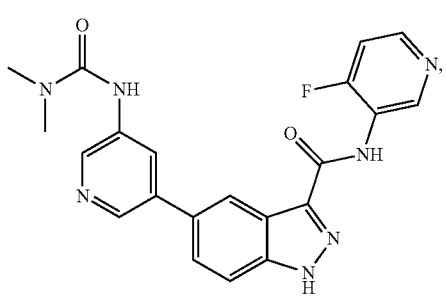
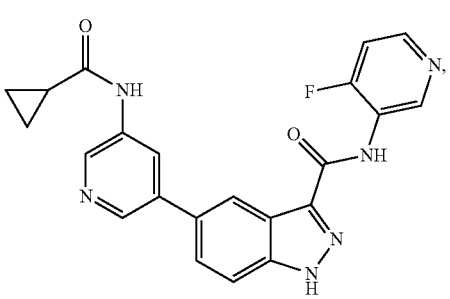
472
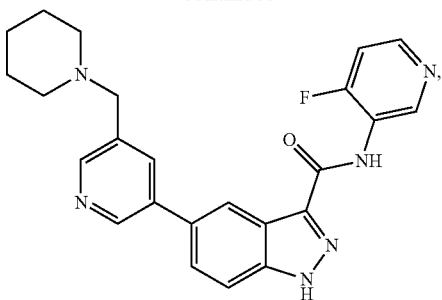
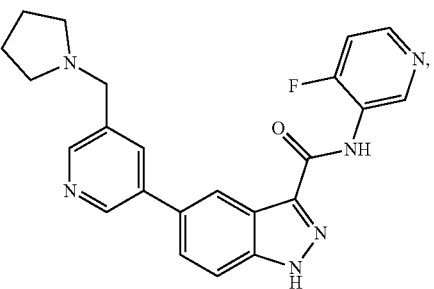
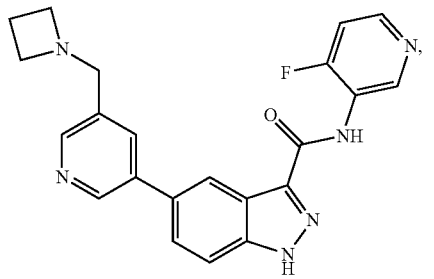
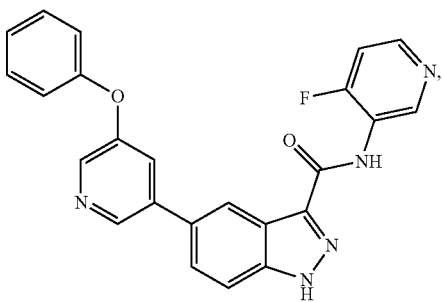
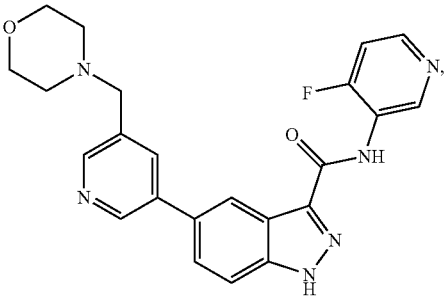

473
-continued
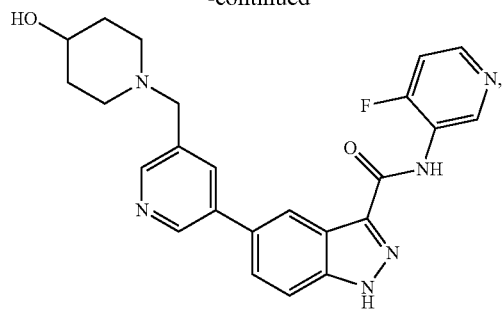
474
-continued
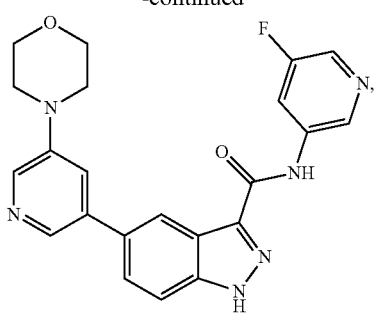
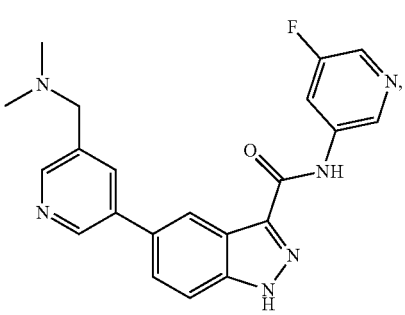
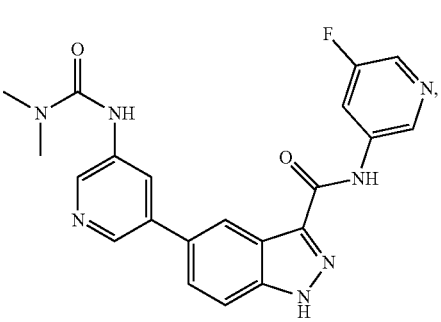
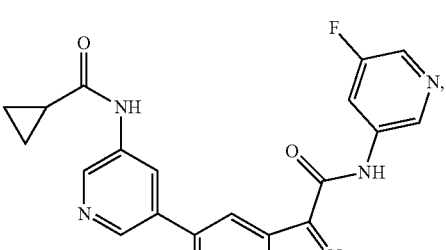
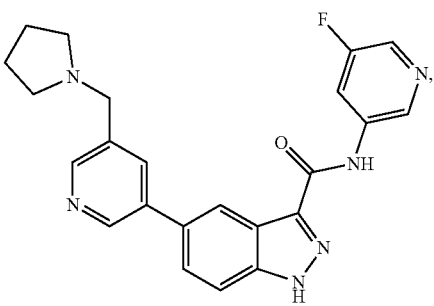

475
-continued
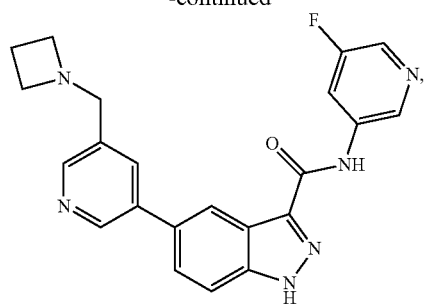
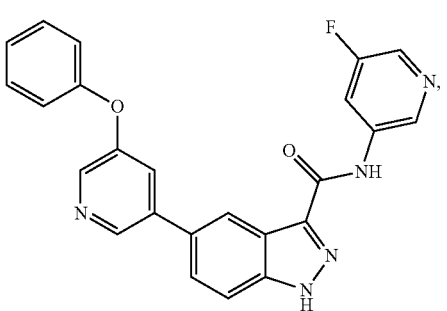
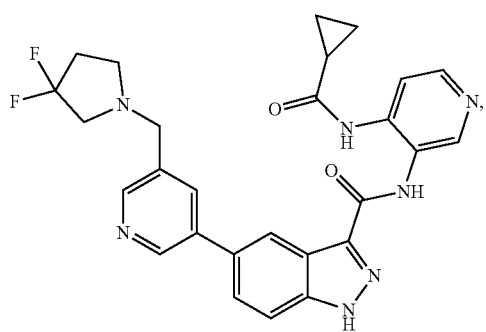
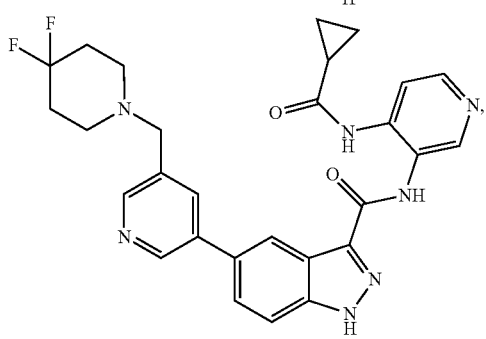
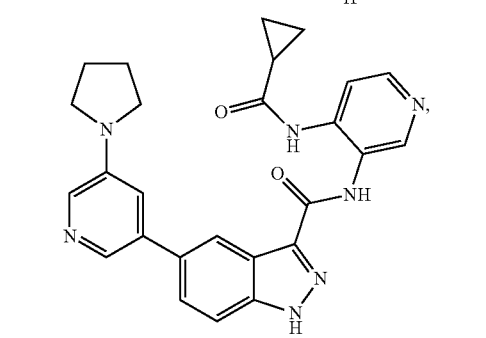
476
-continued
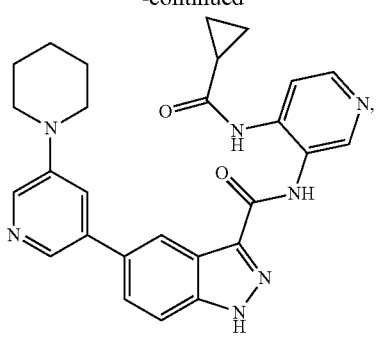
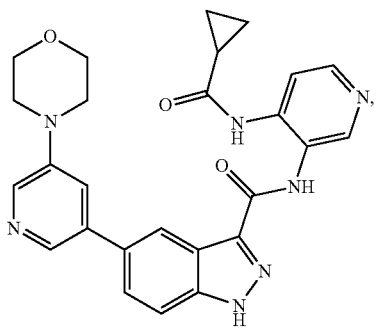
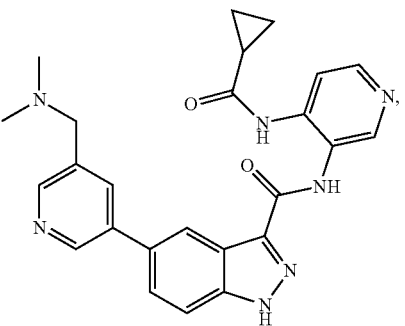
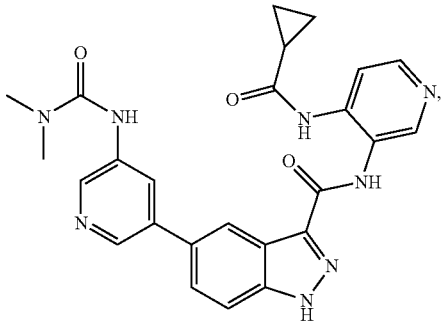
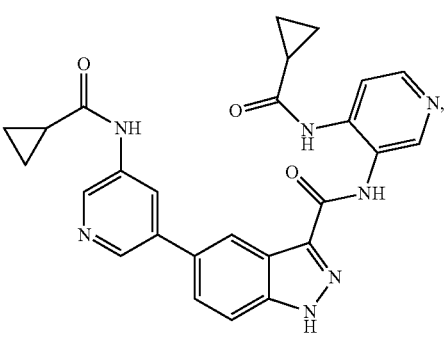

477
-continued
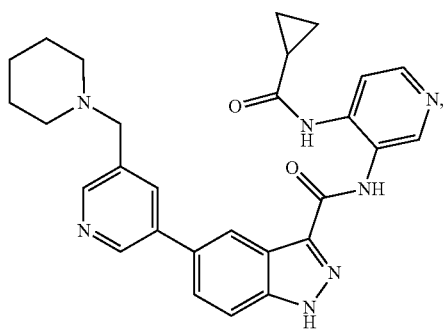
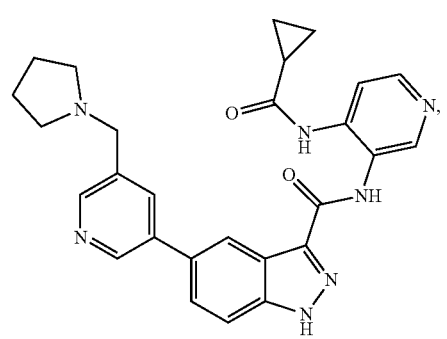
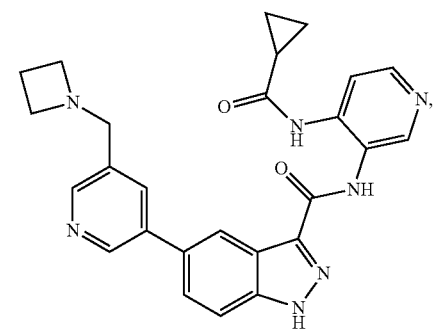
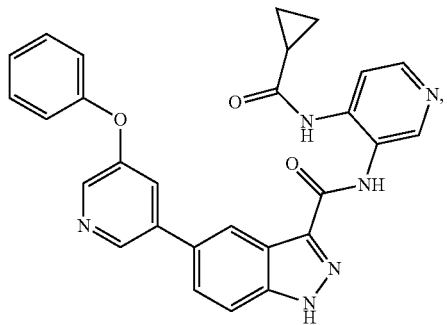
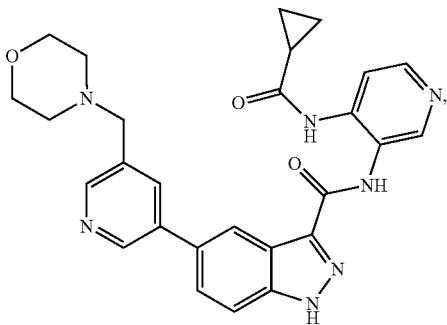
478
-continued
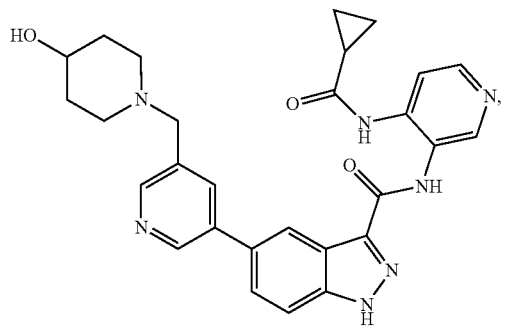
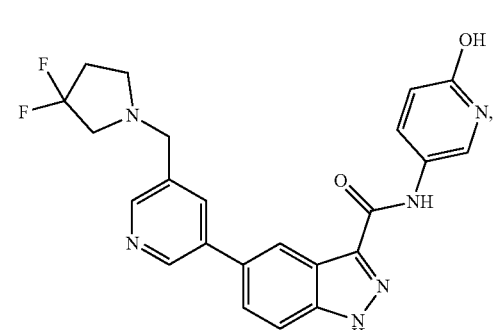
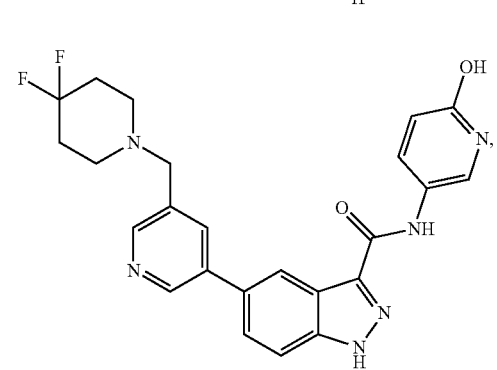
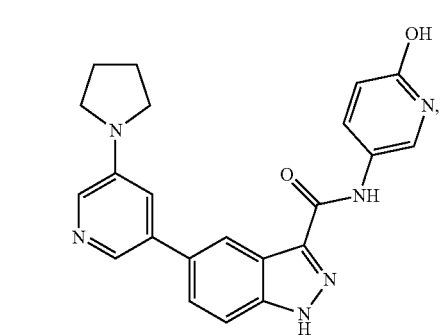
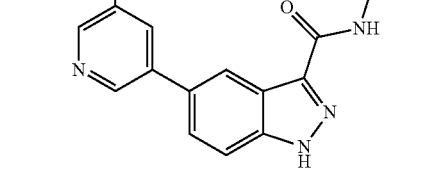

479
-continued
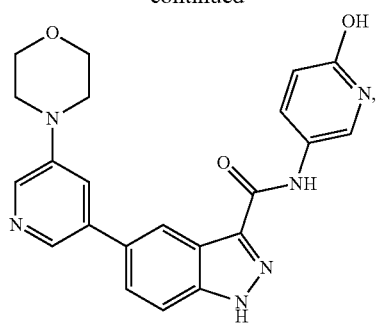
and
or a pharmaceutically acceptable salt thereof.
25. The method of claim 17, the compound having a structure selected from the group consisting of:
480
-continued
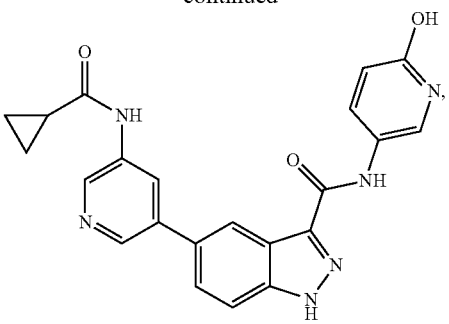

481
-continued
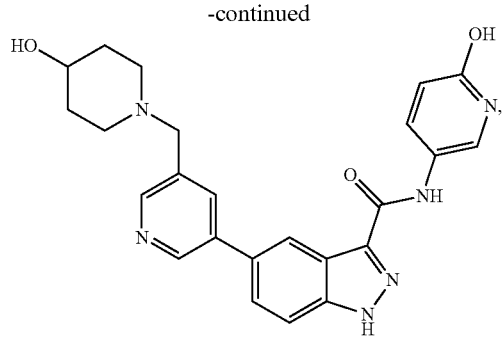
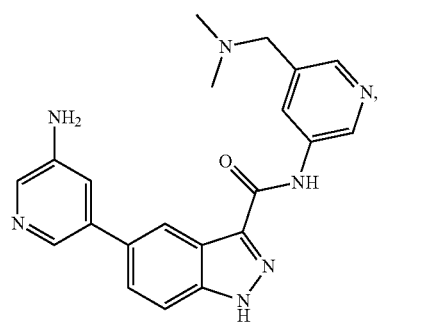
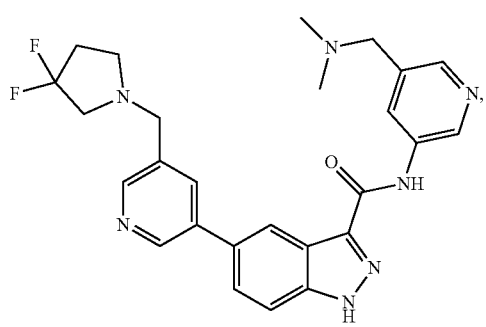
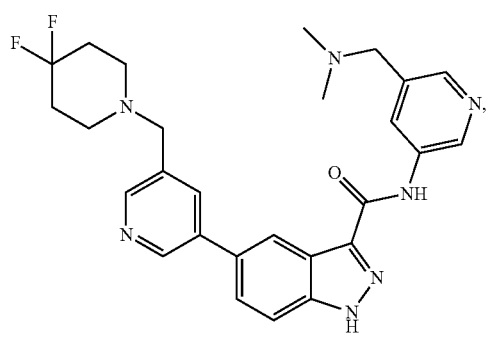
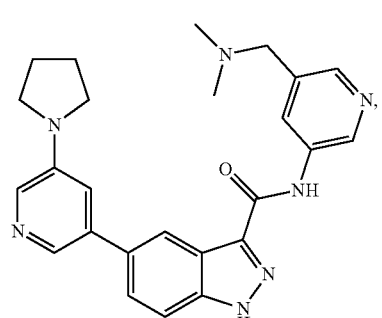
482
-continued
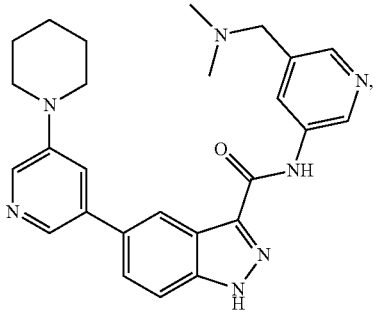
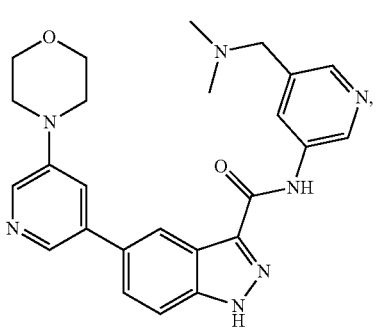
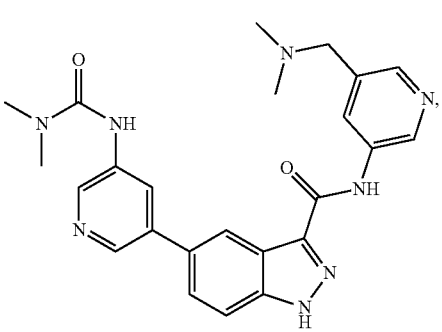
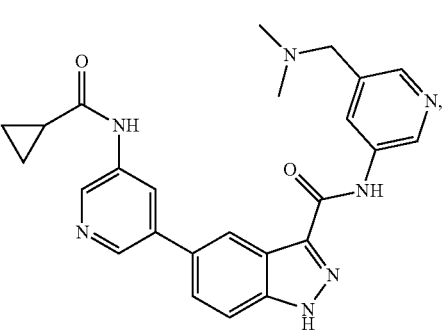
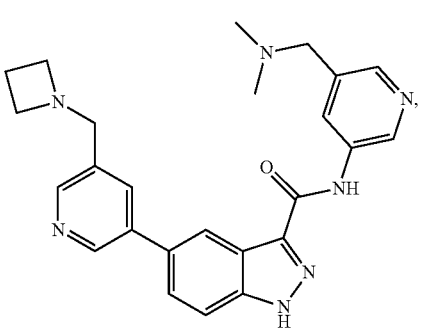

| 483 -continued | 484 -continued |
|---|---|
| 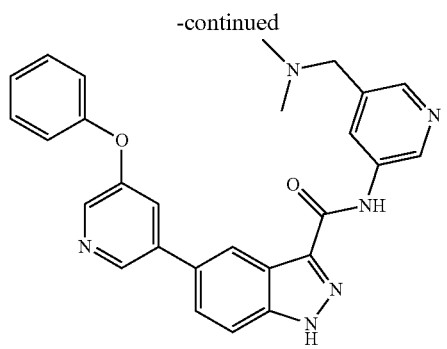 | 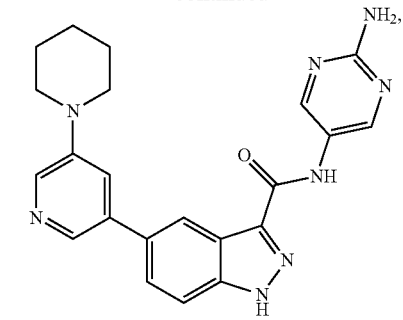 |
| 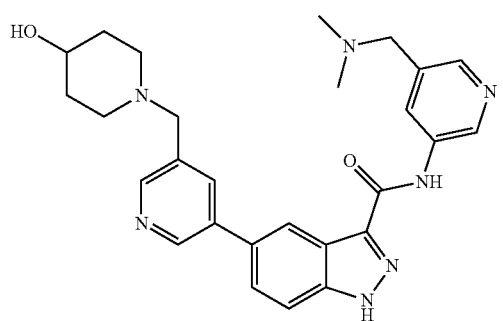 | 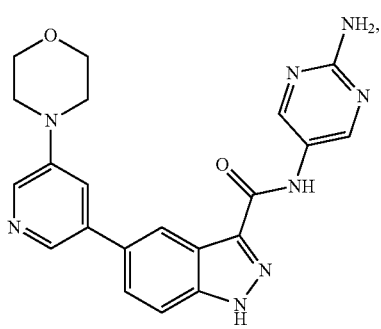 |
| 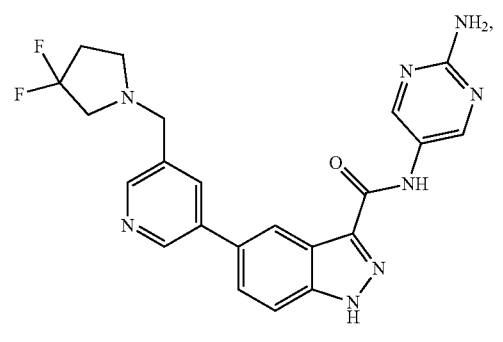 | 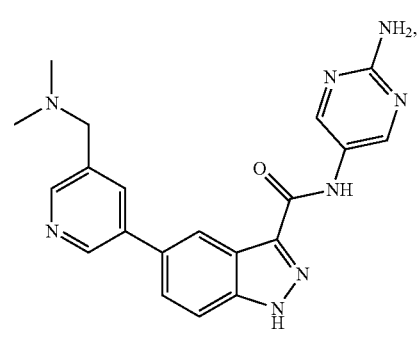 |
| 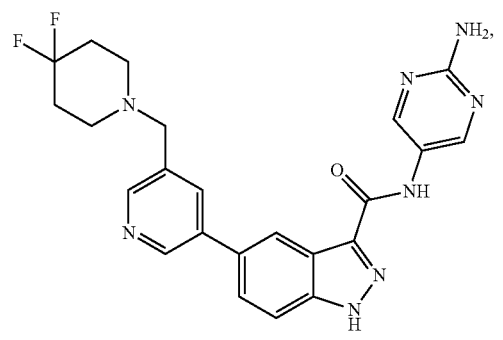 | 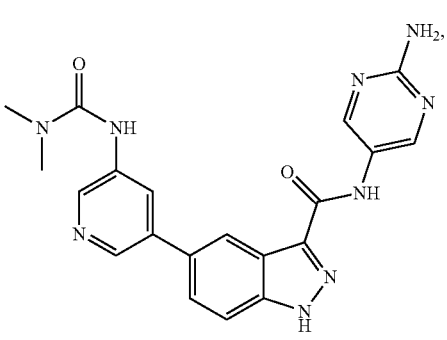 |
| 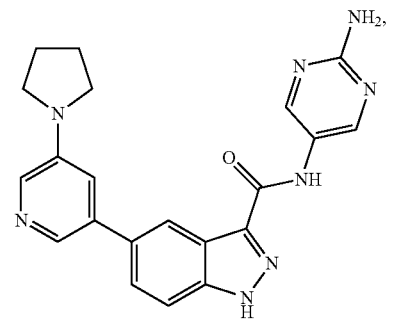 | 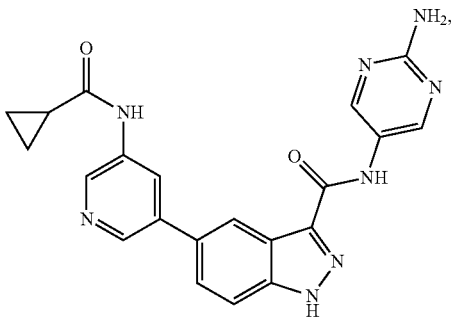 |

485
-continued
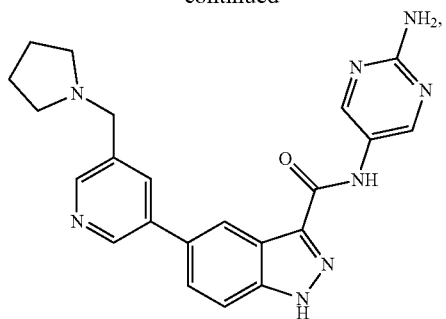
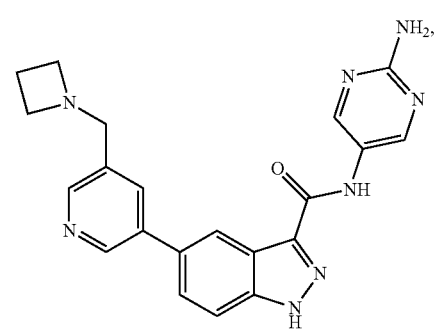
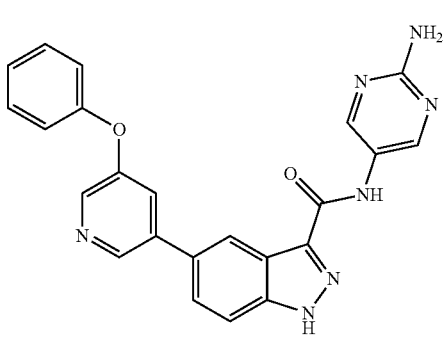
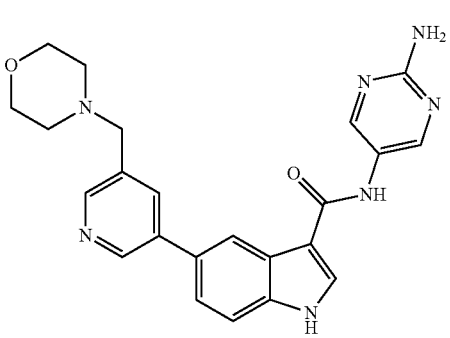
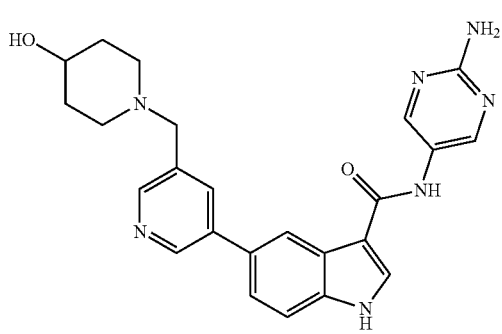
486
-continued
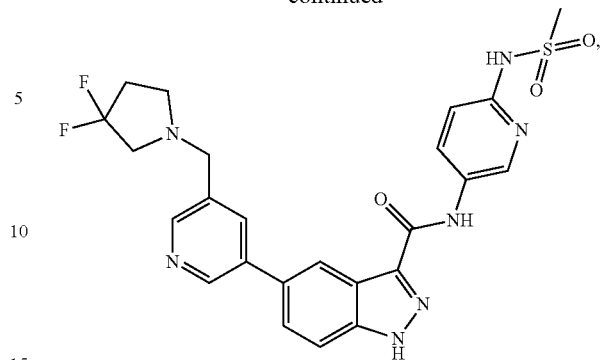
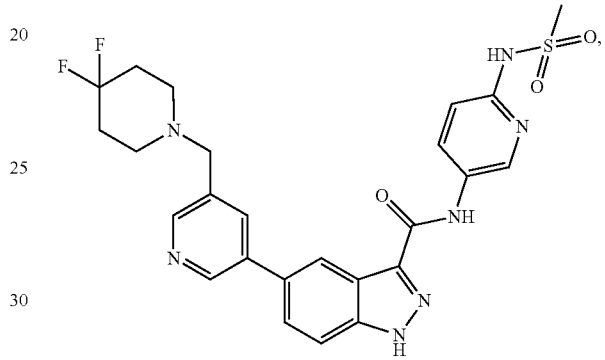
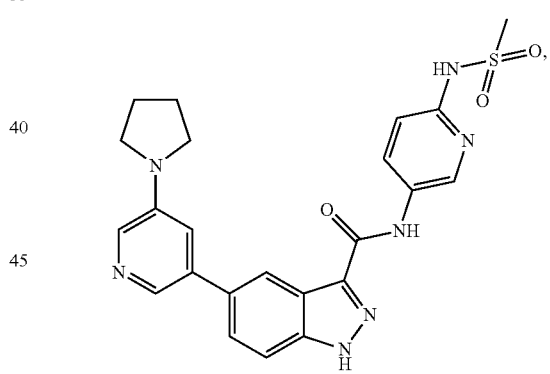
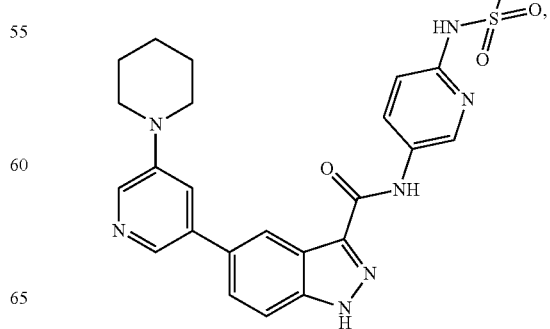

487
-continued
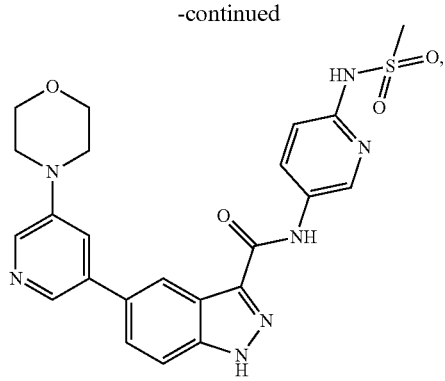
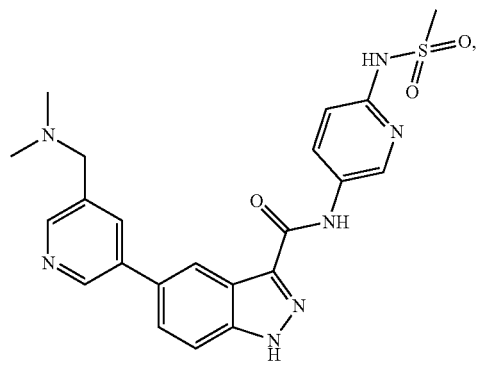
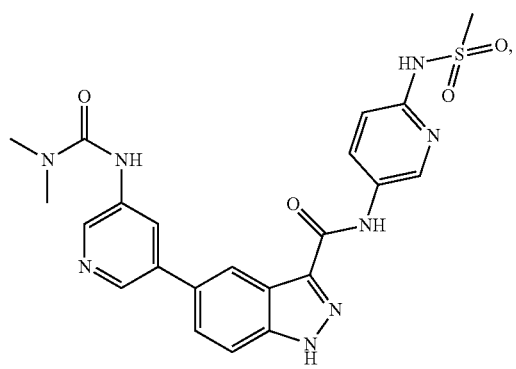
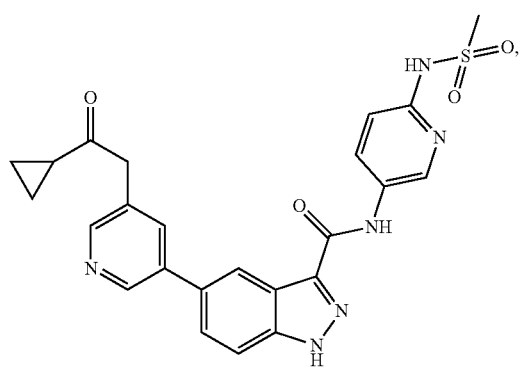
488
-continued
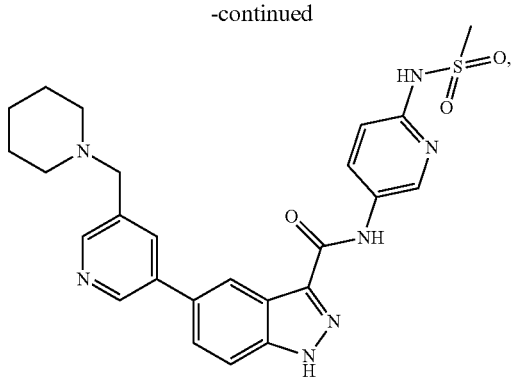
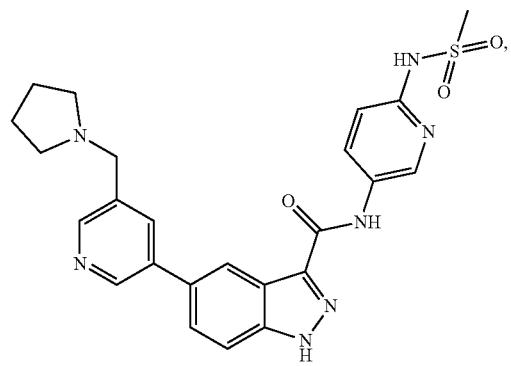
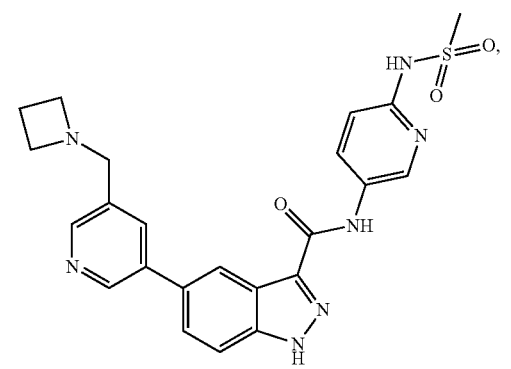
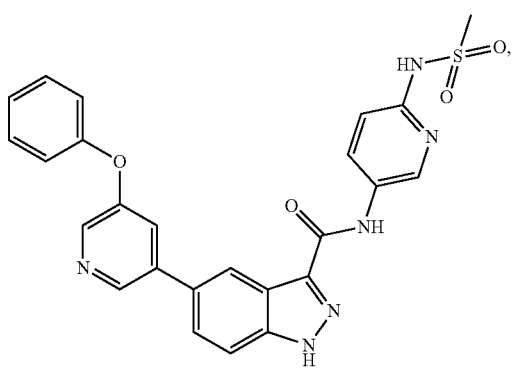

-continued

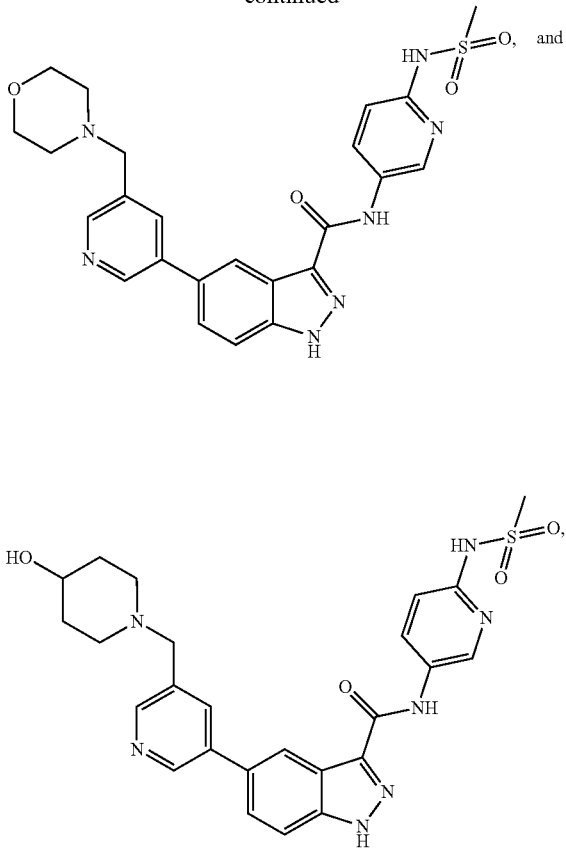

or a pharmaceutically acceptable salt thereof.

26. A method of treating tendinosis the method comprising administering to a subject a compound or pharmaceutically acceptable salt thereof having the structure of Formula Ia:

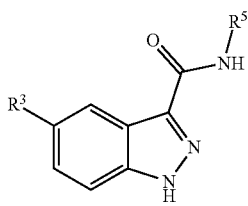

wherein:
R$^3$ is 3-pyridylR$^6$;
R$^5$ is selected from the group consisting of pyridylR$^7$, -pyrimidinylR$^7$, and -pyridazinylR$^7$;
R$^6$ is —CH$_2$heterocyclylR$^8$;
R$^7$ is 1-2 substituents each independently selected from the group consisting of H, F, methyl, —NH$_2$, —CF$_3$, —CN, —OMe, —SO$_2$Me,

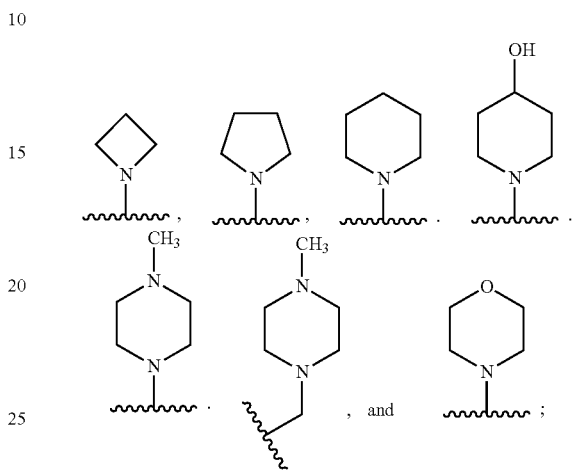

and
R$^8$ is 1-2 substituents each independently selected from the group consisting of H and halide.

27. The method of claim 26, wherein the R$^6$ heterocyclyl is selected from the group consisting of azetidinylR$^8$, pyrrolidinylR$^8$, piperidinylR$^8$, piperazinylR$^8$, and morpholinylR$^8$.

28. The method of claim 26, wherein R$^6$ is —CH$_2$piperidinylR$^8$.

29. The method of claim 26, wherein R$^7$ is selected from the group consisting of H, —CF$_3$, —OMe, —CN,

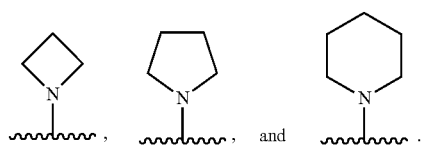 [SMILES: *N1CCC1 ; *N1CCCC1 ; *N1CCCCC1]

30. The method of claim 27, wherein R$^8$ is H.
31. The method of claim 28, wherein R$^8$ is H.

* * * * *

UNITED STATES PATENT AND TRADEMARK OFFICE
CERTIFICATE OF CORRECTION

PATENT NO. : 11,684,615 B2
APPLICATION NO. : 16/915316
DATED : June 27, 2023
INVENTOR(S) : Vishal Deshmukh et al.

Page 1 of 5

It is certified that error appears in the above-identified patent and that said Letters Patent is hereby corrected as shown below:

In the Claims

Column 363, Approximately Line 10, In Claim 1, delete "tendinosis" and insert -- tendinosis, --.

Column 363, Line 41, In Claim 1, delete "—$(C_{1-9})$alkyl$)_n$N$(R^{10})_2$,—$(C_{1-9}$alkyl$)_n$N" and insert -- —$(C_{1-9}$ alkyl$)_n$N$(R^{10})_2$, —$(C_{1-9}$ alkyl$)_n$N --.

Column 363, Line 48, In Claim 1, delete "—$(C_{1-9})$alkyl$)_n$N$(R^{10})_2$,—$(C_{1-9}$alkyl$)_n$N" and insert -- —$(C_{1-9}$ alkyl$)_n$N$(R^{10})_2$, —$(C_{1-9}$ alkyl$)_n$N --.

Column 363, Line 52, In Claim 1, delete "—$CF_3$—CN," and insert -- —$CF_3$, —CN, --.

Column 363, Line 57, In Claim 1, delete "—$CF_3$—CN," and insert -- —$CF_3$, —CN, --.

Column 363, Line 67, In Claim 1, delete "alkyl$)_n$ aryl$R^8$" and insert -- alkyl$)_n$aryl$R^8$ --.

Column 364, Approximately Line 31, In Claim 13, delete "—$(C_{1-9})$alkyl$)_n$N$(R^{10})_2$, —$(C_{1-9})$alkyl$)_n$" and insert -- —$(C_{1-9}$ alkyl$)_n$N$(R^{10})_2$, —$(C_{1-9}$ alkyl$)_n$ --.

Column 411, Approximately Lines 29-40, In Claim 17, delete " 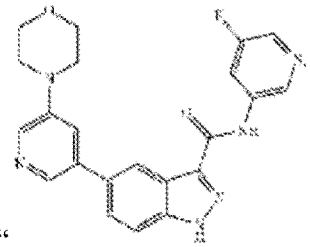 " and insert Signed and Sealed this
Third Day of October, 2023

Katherine Kelly Vidal
*Director of the United States Patent and Trademark Office*

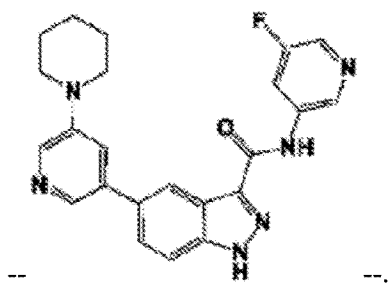
-- --.
Column 426, Approximately Line 17, In Claim 17, delete "and or" and insert -- or --.
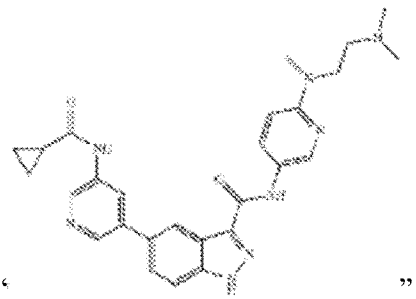
Column 450, Approximately Lines 20-35, In Claim 21, after " " insert -- , --.
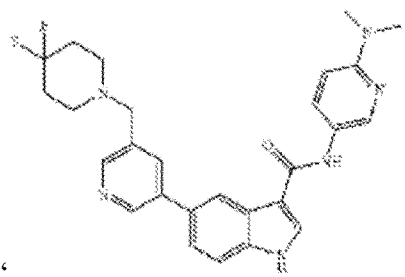
Column 450, Approximately Lines 1-15, In Claim 21, delete " " and
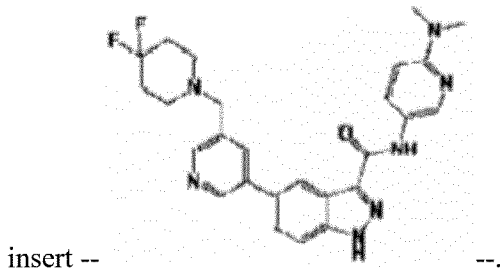
insert -- --.

CERTIFICATE OF CORRECTION (continued) Page 3 of 5
U.S. Pat. No. 11,684,615 B2

Column 454, Approximately Lines 1-15, In Claim 21, delete " 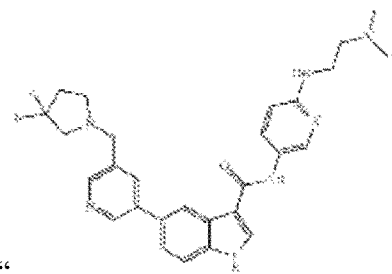 " and insert -- 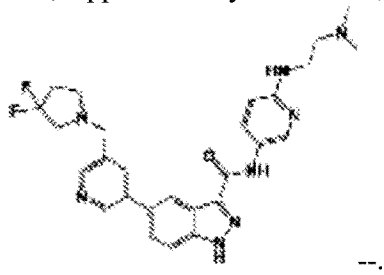 --.

Column 458, Approximately Lines 17-30, In Claim 23, delete " 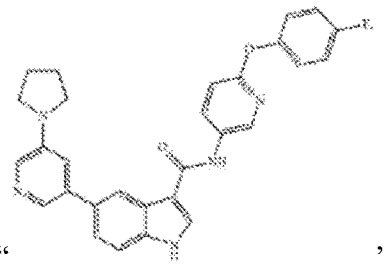 " and insert -- 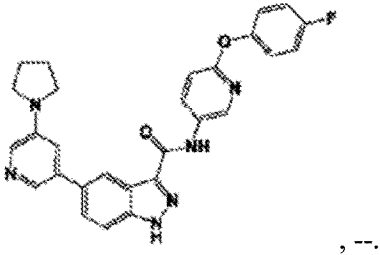 , --.

Column 460, Approximately Lines 54-67, In Claim 23, delete " 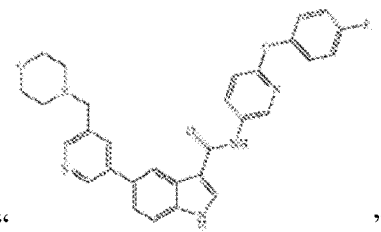 " and insert -- 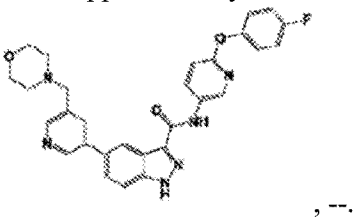 , --.

CERTIFICATE OF CORRECTION (continued)
U.S. Pat. No. 11,684,615 B2

Column 461, Approximately Lines 1-13, In Claim 23, delete " 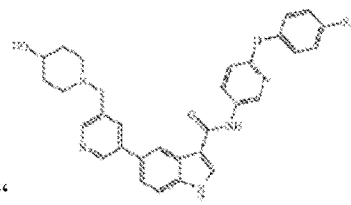 " and insert -- 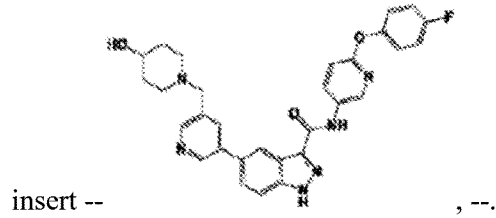 , --.

Column 483, Approximately Lines 1-14, In Claim 25, after " 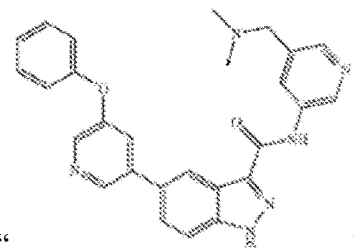 " insert -- , --.

Column 483, Approximately Lines 15-26, In Claim 25, after " 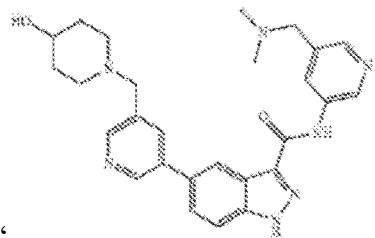 " insert -- , --.

Column 485, Approximately Lines 27-39, In Claim 25, after " 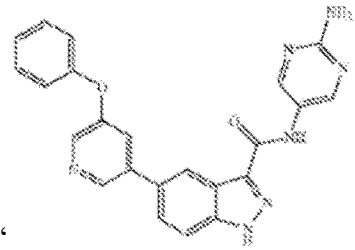 " insert -- , --.

Column 485, Approximately Lines 41-54, In Claim 25, delete " 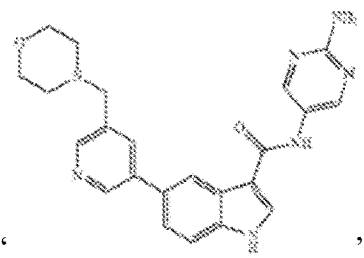 " and
insert -- 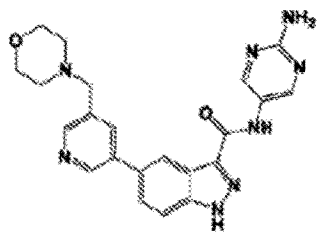 , --.
Column 485, Approximately Lines 55-66, In Claim 25, delete " 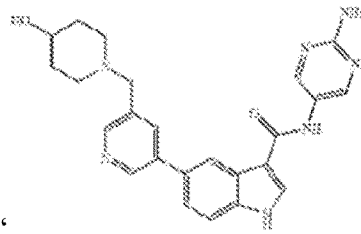 " and
insert -- 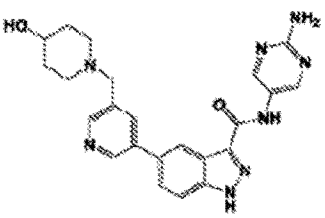 , --.
Column 487, Approximately Lines 54-66, In Claim 25, delete " 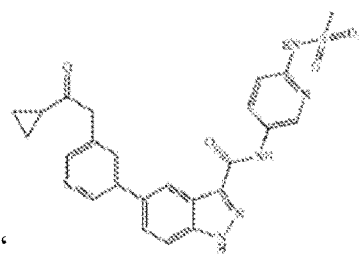 " and
insert -- 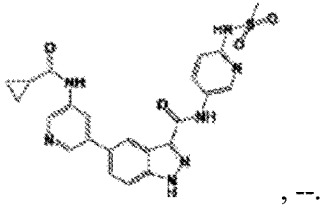 , --.
Column 489, Line 36, In Claim 26, delete "tendinosis" and insert -- tendinosis, --.